US011786607B2

(12) United States Patent
Hoge et al.

(10) Patent No.: US 11,786,607 B2
(45) Date of Patent: Oct. 17, 2023

(54) RNA FORMULATIONS

(71) Applicant: ModernaTX, Inc., Cambridge, MA (US)

(72) Inventors: Stephen Hoge, Brookline, MA (US); Joseph Schariter, Waltham, MA (US); Charles Bowerman, Waltham, MA (US); Michael H. Smith, Needham, MA (US); Yan Xia, Natick, MA (US)

(73) Assignee: ModernaTX, Inc., Cambridge, MA (US)

( * ) Notice: Subject to any disclaimer, the term of this patent is extended or adjusted under 35 U.S.C. 154(b) by 86 days.

(21) Appl. No.: 16/623,069

(22) PCT Filed: Jun. 15, 2018

(86) PCT No.: PCT/US2018/037922
§ 371 (c)(1),
(2) Date: Dec. 16, 2019

(87) PCT Pub. No.: WO2018/232357
PCT Pub. Date: Dec. 20, 2018

(65) Prior Publication Data
US 2021/0145982 A1 May 20, 2021

Related U.S. Application Data

(60) Provisional application No. 62/590,200, filed on Nov. 22, 2017, provisional application No. 62/520,530, filed on Jun. 15, 2017.

(51) Int. Cl.
*A61K 47/69* (2017.01)
*A61K 47/54* (2017.01)
*A61K 31/7105* (2006.01)

(52) U.S. Cl.
CPC ...... *A61K 47/6931* (2017.08); *A61K 31/7105* (2013.01); *A61K 47/543* (2017.08)

(58) Field of Classification Search
CPC ............ A61K 47/6931; A61K 47/5431; A61K 31/7105
See application file for complete search history.

(56) References Cited

U.S. PATENT DOCUMENTS

| | | |
|---|---|---|
| 4,737,323 A | 4/1988 | Martin et al. |
| 4,857,319 A | 8/1989 | Crowe et al. |
| 4,946,683 A | 8/1990 | Forssen et al. |
| 5,049,392 A | 9/1991 | Weiner et al. |
| 5,194,654 A | 3/1993 | Hostetler et al. |
| 5,223,263 A | 6/1993 | Hostetler et al. |
| 5,256,555 A | 10/1993 | Milburn et al. |
| 5,750,114 A | 5/1998 | Burke et al. |
| 6,303,378 B1 | 10/2001 | Bridenbaugh et al. |
| 6,696,038 B1 | 2/2004 | Mahala et al. |
| 7,094,423 B1 | 8/2006 | Maurer et al. |
| 7,371,404 B2 | 5/2008 | Panzner et al. |
| 8,058,069 B2 | 11/2011 | Yaworski et al. |
| 8,158,601 B2 | 4/2012 | Chen et al. |
| 8,420,123 B2 | 4/2013 | Troiano et al. |
| 8,460,696 B2 | 6/2013 | Slobodkin et al. |
| 8,466,122 B2 | 6/2013 | Heyes et al. |
| 8,563,041 B2 | 10/2013 | Grayson et al. |
| 8,569,256 B2 | 10/2013 | Heyes et al. |
| 8,603,499 B2 | 12/2013 | Zale et al. |
| 8,603,500 B2 | 12/2013 | Zale et al. |
| 8,603,501 B2 | 12/2013 | Zale et al. |
| 8,603,534 B2 | 12/2013 | Zale et al. |
| 8,603,535 B2 | 12/2013 | Troiano et al. |
| 8,613,951 B2 | 12/2013 | Zale et al. |
| 8,628,801 B2 | 1/2014 | Garreta et al. |
| 8,642,076 B2 | 2/2014 | Manoharan et al. |
| 8,663,599 B1 | 3/2014 | Sung et al. |
| 8,663,700 B2 | 3/2014 | Troiano et al. |
| 8,691,750 B2 | 4/2014 | Constein et al. |
| 8,691,966 B2 | 4/2014 | Kariko et al. |
| 8,697,098 B2 | 4/2014 | Perumal et al. |
| 8,709,483 B2 | 4/2014 | Farokhzad et al. |
| 8,710,200 B2 | 4/2014 | Schrum et al. |
| 8,734,853 B2 | 5/2014 | Sood et al. |
| 8,754,062 B2 | 6/2014 | De Fougerolles et al. |
| 8,822,663 B2 | 9/2014 | Schrum et al. |
| 8,980,864 B2 | 3/2015 | Hoge et al. |
| 8,999,380 B2 | 4/2015 | Bancel et al. |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,364,433 B2 | 6/2016 | Andersson et al. |

(Continued)

FOREIGN PATENT DOCUMENTS

| | | |
|---|---|---|
| AU | 652831 B2 | 9/1994 |
| CN | 102068701 A | 5/2011 |

(Continued)

OTHER PUBLICATIONS

Espacenet_search_1-26-22_joseph_schariter.pdf (Year: 2022).*
Lipid_nanoparticles_RNA_PEG-lipid_shell_core_-_Google_Scholar_2-4-22.pdf (Year: 2022).*
Alex K. K. Leung, Yuen Yi C. Tam, Sam Chen, Ismail M. Hafez, and Pieter R. Cullis. "Microfluidic Mixing: A General Method for Encapsulating Macromolecules in Lipid Nanoparticle Systems,"J. Phys. Chem. B, 2015, 119, 8698-8706. (Year: 2015).*
U.S. Appl. No. 15/748,782, filed Jan. 30, 2018, Mousavi et al.
U.S. Appl. No. 16/853,973, filed Apr. 21, 2020, Ciaramella et al.

(Continued)

*Primary Examiner* — Michael P Cohen
(74) *Attorney, Agent, or Firm* — Wolf, Greenfield & Sacks, P.C.

(57) ABSTRACT

This disclosure provides improved lipid-based compositions, including lipid nanoparticle compositions, and methods of use thereof for delivering agents in vivo including nucleic acids and proteins.

22 Claims, 13 Drawing Sheets

Specification includes a Sequence Listing.

(56) References Cited

U.S. PATENT DOCUMENTS

| | | |
|---|---|---|
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,572,896 B2 | 2/2017 | Bancel et al. |
| 9,597,380 B2 | 3/2017 | Chakraborty et al. |
| 9,675,668 B2 | 6/2017 | Bancel et al. |
| 9,693,958 B2 | 7/2017 | Zhu et al. |
| 9,803,199 B2 | 10/2017 | Koizumi et al. |
| 9,868,691 B2 | 1/2018 | Benenato et al. |
| 9,872,900 B2 | 1/2018 | Ciaramella et al. |
| 10,023,626 B2 | 7/2018 | Bolen et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,027,025 B2 | 6/2021 | Hoge et al. |
| 11,045,540 B2 | 6/2021 | Ciaramella |
| 11,103,578 B2 | 8/2021 | Ciaramella et al. |
| 11,351,242 B1 | 6/2022 | Lori et al. |
| 11,384,352 B2 | 7/2022 | Miracco |
| 11,406,703 B2 | 8/2022 | Kramarczyk et al. |
| 11,464,848 B2 | 10/2022 | Ciaramella et al. |
| 11,485,960 B2 | 11/2022 | Dousis et al. |
| 11,497,807 B2 | 11/2022 | Ciaramella et al. |
| 11,564,893 B2 | 1/2023 | Smith |
| 11,576,961 B2 | 2/2023 | Ciaramella et al. |
| 11,643,441 B1 | 5/2023 | Ciaramella et al. |
| 2003/0073619 A1 | 4/2003 | Mahato et al. |
| 2003/0092653 A1 | 5/2003 | Kisich et al. |
| 2003/0135040 A1 | 7/2003 | Eritja et al. |
| 2003/0165849 A1 | 9/2003 | Zhang et al. |
| 2004/0132683 A1 | 7/2004 | Feigner et al. |
| 2004/0142474 A1 | 7/2004 | Mahala et al. |
| 2005/0079212 A1 | 4/2005 | Wheeler et al. |
| 2005/0143336 A1 | 6/2005 | Ramesh et al. |
| 2005/0287540 A1 | 12/2005 | Murphy et al. |
| 2006/0008910 A1 | 1/2006 | Maclachlan et al. |
| 2006/0083780 A1 | 4/2006 | Heyes et al. |
| 2007/0252295 A1 | 11/2007 | Panzner et al. |
| 2009/0042825 A1 | 2/2009 | Matar et al. |
| 2009/0042829 A1 | 2/2009 | Matar et al. |
| 2009/0098162 A1 | 4/2009 | Freiman et al. |
| 2010/0068226 A1 | 3/2010 | Taylor et al. |
| 2010/0112042 A1 | 5/2010 | Polisky et al. |
| 2010/0130588 A1 | 5/2010 | Yaworski et al. |
| 2010/0267806 A1 | 10/2010 | Bumcrot et al. |
| 2011/0200582 A1 | 8/2011 | Baryza et al. |
| 2011/0244026 A1 | 10/2011 | Guild et al. |
| 2012/0101148 A1 | 4/2012 | Aking et al. |
| 2012/0177724 A1 | 7/2012 | Irvine et al. |
| 2012/0178702 A1 | 7/2012 | Huang |
| 2012/0201872 A1 | 8/2012 | Huang et al. |
| 2012/0295832 A1 | 11/2012 | Constien et al. |
| 2013/0017223 A1 | 1/2013 | Hope et al. |
| 2013/0064894 A1 | 3/2013 | Martin et al. |
| 2013/0065942 A1 | 3/2013 | Matar et al. |
| 2013/0090372 A1 | 4/2013 | Budzik et al. |
| 2013/0102034 A1 | 4/2013 | Schrum et al. |
| 2013/0115274 A1 | 5/2013 | Knopov et al. |
| 2013/0116307 A1 | 5/2013 | Heyes et al. |
| 2013/0122104 A1 | 5/2013 | Yaworski et al. |
| 2013/0123338 A1 | 5/2013 | Heyes et al. |
| 2013/0129785 A1 | 5/2013 | Manoharan et al. |
| 2013/0150625 A1 | 6/2013 | Budzik et al. |
| 2013/0156845 A1 | 6/2013 | Manoharan et al. |
| 2013/0158021 A1 | 6/2013 | Dong et al. |
| 2013/0164400 A1 | 6/2013 | Knopov et al. |
| 2013/0172406 A1 | 7/2013 | Zale et al. |
| 2013/0178541 A1 | 7/2013 | Stanton et al. |
| 2013/0183244 A1 | 7/2013 | Hanes et al. |
| 2013/0183355 A1 | 7/2013 | Jain et al. |
| 2013/0189351 A1 | 7/2013 | Geall |
| 2013/0195759 A1 | 8/2013 | Mirkin et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236500 A1 | 9/2013 | Zale et al. |
| 2013/0236533 A1 | 9/2013 | Von Andrian et al. |
| 2013/0236968 A1 | 9/2013 | Manoharan et al. |
| 2013/0236974 A1 | 9/2013 | De Fougerolles |
| 2013/0243848 A1 | 9/2013 | Lobovkina et al. |
| 2013/0245103 A1 | 9/2013 | de Fougerolles et al. |
| 2013/0245107 A1 | 9/2013 | de Fougerolles et al. |
| 2013/0251766 A1 | 9/2013 | Zale et al. |
| 2013/0251816 A1 | 9/2013 | Zale et al. |
| 2013/0251817 A1 | 9/2013 | Zale et al. |
| 2013/0259923 A1* | 10/2013 | Bancel ............... A61K 38/177 530/358 |
| 2013/0274504 A1 | 10/2013 | Colletti et al. |
| 2013/0274523 A1 | 10/2013 | Bawiec, III et al. |
| 2013/0302432 A1 | 11/2013 | Zale et al. |
| 2013/0330401 A1 | 12/2013 | Payne et al. |
| 2013/0338210 A1 | 12/2013 | Manoharan et al. |
| 2013/0344158 A1 | 12/2013 | Zale et al. |
| 2014/0037573 A1 | 2/2014 | Eliasof et al. |
| 2014/0037660 A1 | 2/2014 | Folin-Mleczek et al. |
| 2014/0037714 A1 | 2/2014 | Quay et al. |
| 2014/0039032 A1 | 2/2014 | Kumboyama et al. |
| 2014/0044772 A1 | 2/2014 | Maclachlan et al. |
| 2014/0044791 A1 | 2/2014 | Basilion et al. |
| 2014/0045913 A1 | 2/2014 | Kumboyama et al. |
| 2014/0050775 A1 | 2/2014 | Slobodkin et al. |
| 2014/0065228 A1 | 3/2014 | Yarowoski et al. |
| 2014/0079774 A1 | 3/2014 | Brinker et al. |
| 2014/0141070 A1 | 5/2014 | Geall et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0206753 A1 | 7/2014 | Guild et al. |
| 2014/0255472 A1 | 9/2014 | Geall et al. |
| 2014/0308304 A1 | 10/2014 | Manoharan et al. |
| 2014/0328825 A1 | 11/2014 | Meis et al. |
| 2014/0343139 A1 | 11/2014 | Lippard et al. |
| 2014/0378538 A1 | 12/2014 | Bancel |
| 2015/0030622 A1 | 1/2015 | Marshall et al. |
| 2015/0051268 A1 | 2/2015 | Bancel et al. |
| 2015/0056253 A1 | 2/2015 | Bancel et al. |
| 2015/0064242 A1 | 3/2015 | Heyes et al. |
| 2015/0079121 A1 | 3/2015 | Weiner et al. |
| 2015/0110857 A1 | 4/2015 | DeRosa et al. |
| 2015/0118183 A1 | 4/2015 | Baumhof et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2015/0376115 A1 | 12/2015 | Ansell et al. |
| 2016/0022580 A1 | 1/2016 | Ramsay et al. |
| 2016/0024140 A1 | 1/2016 | Issa et al. |
| 2016/0024141 A1 | 1/2016 | Issa et al. |
| 2016/0151284 A1 | 1/2016 | Heyes et al. |
| 2016/0032273 A1 | 2/2016 | Shahrokh et al. |
| 2016/0038612 A1 | 2/2016 | Hoge et al. |
| 2016/0243220 A1 | 8/2016 | Hoge et al. |
| 2016/0367638 A1 | 12/2016 | Byers et al. |
| 2016/0376224 A1* | 12/2016 | Du ...................... A61K 47/24 514/44 A |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0210697 A1 | 7/2017 | Benenato et al. |

(56) References Cited

U.S. PATENT DOCUMENTS

| | | |
|---|---|---|
| 2017/0239371 A1 | 8/2017 | Guild et al. |
| 2017/0130255 A1 | 10/2017 | Wang et al. |
| 2018/0000953 A1 | 1/2018 | Almarsson et al. |
| 2018/0002393 A1 | 1/2018 | Bancel et al. |
| 2018/0214537 A1 | 8/2018 | Mutzke et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0022004 A1 | 1/2019 | Kan et al. |
| 2019/0085368 A1 | 3/2019 | Bancel et al. |
| 2019/0125839 A1 | 5/2019 | Frederick et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0216843 A1 | 7/2019 | Derosa et al. |
| 2019/0241633 A1 | 8/2019 | Fotin-Mleczek et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0336452 A1 | 11/2019 | Brader |
| 2019/0351040 A1 | 11/2019 | Valiante et al. |
| 2019/0351047 A1 | 11/2019 | Jasny et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129445 A1 | 4/2020 | Patel et al. |
| 2020/0129608 A1 | 4/2020 | Ciaramella et al. |
| 2020/0129615 A1 | 4/2020 | Ciaramella et al. |
| 2020/0163878 A1 | 5/2020 | Baumhof et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0306191 A1 | 10/2020 | Schariter et al. |
| 2020/0338004 A1 | 10/2020 | Hansson et al. |
| 2020/0368162 A1 | 11/2020 | Martini |
| 2021/0046173 A1 | 2/2021 | Ciaramella et al. |
| 2021/0087135 A1 | 3/2021 | Benenato et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0309976 A1 | 10/2021 | Dousis et al. |
| 2021/0378980 A1 | 12/2021 | Horhota et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062175 A1 | 3/2022 | Smith et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |
| 2023/0000970 A1 | 1/2023 | Nachbagauer et al. |
| 2023/0142529 A1 | 5/2023 | White et al. |

FOREIGN PATENT DOCUMENTS

| | | |
|---|---|---|
| CN | 102204920 A | 10/2011 |
| CN | 102813929 A | 12/2012 |
| CN | 104644555 A | 5/2015 |
| EP | 0737750 A2 | 10/1996 |
| EP | 1873180 A1 | 1/2008 |
| EP | 2092064 B1 | 9/2010 |
| EP | 2476430 A1 | 7/2012 |
| EP | 2548960 A1 | 1/2013 |
| EP | 2620161 A1 | 7/2013 |
| EP | 2073848 B1 | 8/2013 |
| EP | 1404860 B1 | 11/2013 |
| EP | 2732825 A1 | 5/2014 |
| EP | 3269395 A1 | 1/2018 |
| EP | 3452101 A2 | 3/2019 |
| WO | WO 2016/037053 A1 | 1/1900 |
| WO | WO 1993/003709 A1 | 3/1993 |
| WO | WO 1993/14778 A1 | 8/1993 |
| WO | WO 1996/17086 A1 | 6/1996 |
| WO | WO 1997/30064 A1 | 8/1997 |
| WO | WO 1999/14346 A2 | 3/1999 |
| WO | WO 1999/52503 A2 | 10/1999 |
| WO | WO 2001/005373 A1 | 1/2001 |
| WO | WO 03/086280 A2 | 10/2003 |
| WO | WO 2005/034979 A2 | 4/2005 |
| WO | WO 2005/118857 A2 | 12/2005 |
| WO | WO 2005/120152 A2 | 12/2005 |
| WO | WO 2005/121348 A1 | 12/2005 |
| WO | WO 2006/044456 A1 | 4/2006 |
| WO | WO 2006/044503 A2 | 4/2006 |
| WO | WO 2006/044505 A2 | 4/2006 |
| WO | WO 2006/044682 A1 | 4/2006 |
| WO | WO 2006/058088 A2 | 6/2006 |
| WO | WO 2006/063249 A2 | 6/2006 |
| WO | WO 2006/065479 A2 | 6/2006 |
| WO | WO 2006/065480 A2 | 6/2006 |
| WO | WO 2007/069068 A2 | 6/2007 |
| WO | WO 2008/014979 A2 | 2/2008 |
| WO | WO 2008/042973 A2 | 4/2008 |
| WO | WO 2008/068631 A2 | 6/2008 |
| WO | WO 2008/077592 A1 | 7/2008 |
| WO | WO 2008/103276 A2 | 8/2008 |
| WO | WO 2009/024599 A1 | 2/2009 |
| WO | WO 2009/068649 A2 | 6/2009 |
| WO | WO 2009/095226 A2 | 8/2009 |
| WO | WO 2009/127060 A1 | 10/2009 |
| WO | WO 2010/033906 A2 | 3/2010 |
| WO | WO 2010/042877 A1 | 4/2010 |
| WO | WO 2010/045512 A2 | 4/2010 |
| WO | WO 2010/053572 A2 | 5/2010 |
| WO | WO 2010/054401 A1 | 5/2010 |
| WO | WO 2010/054406 A1 | 5/2010 |
| WO | WO 2010/088537 A3 | 8/2010 |
| WO | WO 2010/111290 A1 | 9/2010 |
| WO | WO 2010/129709 A1 | 11/2010 |
| WO | WO 2011/026641 A1 | 3/2011 |
| WO | WO 2011/062965 A2 | 5/2011 |
| WO | WO 2023/081311 A1 | 5/2011 |
| WO | WO 2011/068810 A1 | 6/2011 |
| WO | WO 2011/071931 A2 | 6/2011 |
| WO | WO 2011/119058 A2 | 9/2011 |
| WO | WO 2011/120053 A1 | 9/2011 |
| WO | WO 2011/127255 A1 | 10/2011 |
| WO | WO 2011/140627 A1 | 11/2011 |
| WO | WO 2012/006376 A2 | 1/2012 |
| WO | WO 2012/006378 A1 | 1/2012 |
| WO | WO 2012/030901 A1 | 3/2012 |
| WO | WO 2012/031043 A1 | 3/2012 |
| WO | WO 2012/031046 A2 | 3/2012 |

(56) References Cited

FOREIGN PATENT DOCUMENTS

| | | |
|---|---|---|
| WO | WO 2012/094304 A1 | 7/2012 |
| WO | WO 2012/099755 A1 | 7/2012 |
| WO | WO 2012/129483 A1 | 9/2012 |
| WO | WO 2012/135025 A2 | 10/2012 |
| WO | WO 2012/149252 A2 | 11/2012 |
| WO | WO 2012/149255 A2 | 11/2012 |
| WO | WO 2012/149265 A2 | 11/2012 |
| WO | WO 2012/149282 A2 | 11/2012 |
| WO | WO 2012/149301 A2 | 11/2012 |
| WO | WO 2012/149376 A2 | 11/2012 |
| WO | WO 2012/149393 A2 | 11/2012 |
| WO | WO 2012/152910 A1 | 11/2012 |
| WO | WO 2012/153297 A1 | 11/2012 |
| WO | WO 2012/153338 A2 | 11/2012 |
| WO | WO 2012/159643 A1 | 11/2012 |
| WO | WO 2012/166241 A1 | 12/2012 |
| WO | WO 2012/168491 A1 | 12/2012 |
| WO | WO 2012/170607 A2 | 12/2012 |
| WO | WO 2012/170889 A1 | 12/2012 |
| WO | WO 2012/170930 A1 | 12/2012 |
| WO | WO 2012/170952 A2 | 12/2012 |
| WO | WO 2013/006825 A1 | 1/2013 |
| WO | WO 2013/006834 A1 | 1/2013 |
| WO | WO 2013/006837 A1 | 1/2013 |
| WO | WO 2013/006838 A1 | 1/2013 |
| WO | WO 2013/006842 A2 | 1/2013 |
| WO | WO 2013/012476 A2 | 1/2013 |
| WO | WO 2013/032829 A1 | 3/2013 |
| WO | WO 2013/033438 A2 | 3/2013 |
| WO | WO 2013/033563 A1 | 3/2013 |
| WO | WO 2013/033620 A1 | 3/2013 |
| WO | WO 2012/045075 A1 | 4/2013 |
| WO | WO 2013/049328 A1 | 4/2013 |
| WO | WO 2013/052167 A2 | 4/2013 |
| WO | WO 2013/056132 A2 | 4/2013 |
| WO | WO 2013/057715 A1 | 4/2013 |
| WO | WO 2013/059496 A1 | 4/2013 |
| WO | WO 2013/059922 A1 | 5/2013 |
| WO | WO 2013/063468 A1 | 5/2013 |
| WO | WO 2013/064911 A2 | 5/2013 |
| WO | WO 2013/066274 A1 | 5/2013 |
| WO | WO 2013/066903 A1 | 5/2013 |
| WO | WO 2013/067537 A1 | 5/2013 |
| WO | WO 2013/070872 A1 | 5/2013 |
| WO | WO 2013/072929 A2 | 5/2013 |
| WO | WO 2013/082529 A1 | 6/2013 |
| WO | WO 2013/086322 A1 | 6/2013 |
| WO | WO 2013/086354 A1 | 6/2013 |
| WO | WO 2013/086373 A1 | 6/2013 |
| WO | WO 2013/086526 A1 | 6/2013 |
| WO | WO 2013/087083 A1 | 6/2013 |
| WO | WO 2013/087791 A1 | 6/2013 |
| WO | WO 2013/090601 A2 | 6/2013 |
| WO | WO 2013/093648 A2 | 6/2013 |
| WO | WO 2013/112778 A1 | 8/2013 |
| WO | WO 2013/112780 A1 | 8/2013 |
| WO | WO 2013/113501 A1 | 8/2013 |
| WO | WO 2013/113736 A1 | 8/2013 |
| WO | WO 2013/135359 A1 | 9/2013 |
| WO | WO 2013/138343 A1 | 9/2013 |
| WO | WO 2013/138346 A1 | 9/2013 |
| WO | WO 2013/143555 A1 | 10/2013 |
| WO | WO 2013/143683 A1 | 10/2013 |
| WO | WO 2013/143699 A1 | 10/2013 |
| WO | WO 2013/148186 A1 | 10/2013 |
| WO | WO 2013/148541 A1 | 10/2013 |
| WO | WO 2013/149141 A1 | 10/2013 |
| WO | WO 2013/151650 A1 | 10/2013 |
| WO | WO 2013/151666 A2 | 10/2013 |
| WO | WO 2013/151736 A2 | 10/2013 |
| WO | WO 2013/154774 A1 | 10/2013 |
| WO | WO 2013/155487 A1 | 10/2013 |
| WO | WO 2013/155493 A1 | 10/2013 |
| WO | WO 2013/158127 A1 | 10/2013 |
| WO | WO 2013/158579 A1 | 10/2013 |
| WO | WO 2013/166498 A1 | 11/2013 |
| WO | WO 2013/173693 A1 | 11/2013 |
| WO | WO 2013/174409 A1 | 11/2013 |
| WO | WO 2013/177421 A2 | 11/2013 |
| WO | WO 2013/185069 A1 | 12/2013 |
| WO | WO 2014/008334 A1 | 1/2014 |
| WO | WO 2014/024193 A1 | 2/2014 |
| WO | WO 2014/025795 A1 | 2/2014 |
| WO | WO 2014/026284 A1 | 2/2014 |
| WO | WO 2014/028487 A1 | 2/2014 |
| WO | WO 2014/028763 A1 | 2/2014 |
| WO | WO 2014/042920 A1 | 3/2014 |
| WO | WO 2014/043618 A1 | 3/2014 |
| WO | WO 2014/047649 A1 | 3/2014 |
| WO | WO 2014/052634 A1 | 4/2014 |
| WO | WO 2014/053622 A1 | 4/2014 |
| WO | WO 2014/053624 A1 | 4/2014 |
| WO | WO 2014/053628 A1 | 4/2014 |
| WO | WO 2014/053629 A1 | 4/2014 |
| WO | WO 2014/053879 A1 | 4/2014 |
| WO | WO 2014/053880 A1 | 4/2014 |
| WO | WO 2014/053881 A1 | 4/2014 |
| WO | WO 2014/053882 A1 | 4/2014 |
| WO | WO 2014/054026 A1 | 4/2014 |
| WO | WO 2014/062697 A2 | 4/2014 |
| WO | WO 2014/064258 A1 | 5/2014 |
| WO | WO 2014/064687 A1 | 5/2014 |
| WO | WO 2014/066811 A1 | 5/2014 |
| WO | WO 2014/066898 A9 | 5/2014 |
| WO | WO 2014/071072 A2 | 5/2014 |
| WO | WO 2014/072468 A1 | 5/2014 |
| WO | WO 2014/072997 A1 | 5/2014 |
| WO | WO 2014/074218 A1 | 5/2014 |
| WO | WO 2014/074289 A1 | 5/2014 |
| WO | WO 2014/074299 A1 | 5/2014 |
| WO | WO 2014/074823 A1 | 5/2014 |
| WO | WO 2014/078399 A1 | 5/2014 |
| WO | WO 2014/081299 A1 | 5/2014 |
| WO | WO 2014/081300 A1 | 5/2014 |
| WO | WO 2014/081303 A1 | 5/2014 |
| WO | WO 2014/081849 A1 | 5/2014 |
| WO | WO 2014/089239 A1 | 6/2014 |
| WO | WO 2014/089486 A1 | 6/2014 |
| WO | WO 2014/108515 A1 | 7/2014 |
| WO | WO 2014/127917 A1 | 8/2014 |
| WO | WO 2014/140211 A1 | 9/2014 |
| WO | WO 2014/144196 A1 | 9/2014 |
| WO | WO 2014/152200 A1 | 9/2014 |
| WO | WO 2014/152966 A1 | 9/2014 |
| WO | WO 2014/159813 A1 | 10/2014 |
| WO | WO 2014/160243 A1 | 10/2014 |
| WO | WO 2014/168874 A2 | 10/2014 |
| WO | WO 2014/172045 A1 | 10/2014 |
| WO | WO 2014/182661 A2 | 11/2014 |
| WO | WO 2014/210356 A1 | 12/2014 |
| WO | WO 2015/095351 A1 | 12/2014 |
| WO | WO 2015/023461 A1 | 2/2015 |
| WO | WO 2015/061491 A1 | 4/2015 |
| WO | WO 2015/082080 A1 | 6/2015 |
| WO | WO 2015/095340 A1 | 6/2015 |
| WO | WO 2015/095346 A1 | 6/2015 |
| WO | WO 2015/110957 A2 | 7/2015 |
| WO | WO 2015/130584 A2 | 9/2015 |
| WO | WO 2015/134332 A2 | 9/2015 |
| WO | WO 2015/135558 A1 | 9/2015 |
| WO | WO 2015/199952 A1 | 12/2015 |
| WO | WO 2016/123864 A1 | 8/2016 |
| WO | WO 2016/164762 A1 | 10/2016 |
| WO | WO 2016/201377 A1 | 12/2016 |
| WO | WO 2017/011773 A2 | 1/2017 |
| WO | WO 2017/015457 A1 | 1/2017 |
| WO | WO 2017/034991 A1 | 3/2017 |
| WO | WO 2017/049245 A2 | 3/2017 |
| WO | WO 2017/066789 A1 | 4/2017 |
| WO | WO 2017/070601 A1 | 4/2017 |
| WO | WO 2017/070618 A1 | 4/2017 |
| WO | WO 2017/070622 A1 | 4/2017 |
| WO | WO 2017/075038 A1 | 5/2017 |
| WO | WO 2017/099823 A1 | 6/2017 |

(56) References Cited

FOREIGN PATENT DOCUMENTS

| | | |
|---|---|---|
| WO | WO 2017/112865 A1 | 6/2017 |
| WO | WO 2017/127750 A1 | 7/2017 |
| WO | WO 2017/191274 A2 | 11/2017 |
| WO | WO 2017/201328 A1 | 11/2017 |
| WO | WO 2017/201333 A1 | 11/2017 |
| WO | WO 2017/218704 A1 | 12/2017 |
| WO | WO 2017/219033 A1 | 12/2017 |
| WO | WO 2018/006052 A1 | 1/2018 |
| WO | WO 2018/039131 A1 | 3/2018 |
| WO | WO 2018/089540 A1 | 5/2018 |
| WO | WO 2018/089790 A1 | 5/2018 |
| WO | WO 2018/089801 A1 | 5/2018 |
| WO | WO 2018/157009 A1 | 8/2018 |
| WO | WO 2018/170245 A1 | 9/2018 |
| WO | WO 2018/170306 A1 | 9/2018 |
| WO | WO 2018/170336 A1 | 9/2018 |
| WO | WO 2018/232120 A1 | 12/2018 |
| WO | WO 2018/232355 A1 | 12/2018 |
| WO | WO 2018/232357 A1 | 12/2018 |
| WO | WO 2019/036683 A1 | 2/2019 |
| WO | WO 2019/036685 A1 | 2/2019 |
| WO | WO 2019/089818 A1 | 5/2019 |
| WO | WO 2009/120247 A2 | 10/2019 |
| WO | WO 2019/202035 A1 | 10/2019 |
| WO | WO 2020/002540 A1 | 1/2020 |
| WO | WO 2020/006242 A1 | 1/2020 |
| WO | WO 2020/047061 A1 | 3/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/061457 A1 | 3/2020 |
| WO | WO 2020/077007 A1 | 4/2020 |
| WO | WO 2020/081933 A1 | 4/2020 |
| WO | WO 2020/097291 A1 | 5/2020 |
| WO | WO 2020/160397 A1 | 8/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/232276 A1 | 11/2020 |
| WO | WO 2020/243561 A1 | 12/2020 |
| WO | WO 2021/016430 A1 | 1/2021 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/155274 A1 | 8/2021 |
| WO | WO 2021/159040 A2 | 8/2021 |
| WO | WO 2021/159130 A2 | 8/2021 |
| WO | WO 2021/204175 A1 | 10/2021 |
| WO | WO 2021/211343 A1 | 10/2021 |
| WO | WO 2021/222304 A1 | 11/2021 |
| WO | WO 2021/231929 A1 | 11/2021 |
| WO | WO 2021/231963 A1 | 11/2021 |
| WO | WO 2021/237084 A1 | 11/2021 |
| WO | WO 2021/247817 A1 | 12/2021 |
| WO | WO 2022/067010 A1 | 3/2022 |
| WO | WO 2022/150717 A1 | 7/2022 |
| WO | WO 2022/155524 A1 | 7/2022 |
| WO | WO 2022/155530 A1 | 7/2022 |
| WO | WO 2022/187698 A1 | 9/2022 |
| WO | WO 2022/204491 A1 | 9/2022 |
| WO | WO 2022/212191 A1 | 10/2022 |
| WO | WO 2022/212442 A1 | 10/2022 |
| WO | WO 2022/212711 A2 | 10/2022 |
| WO | WO 2022/221335 A1 | 10/2022 |
| WO | WO 2022/221336 A1 | 10/2022 |
| WO | WO 2022/221359 A1 | 10/2022 |
| WO | WO 2022/221440 A1 | 10/2022 |
| WO | WO 2022/232585 A1 | 11/2022 |
| WO | WO 2022/241103 A1 | 11/2022 |
| WO | WO 2022/266010 A1 | 12/2022 |
| WO | WO 2022/266012 A1 | 12/2022 |
| WO | WO 2022/266389 A1 | 12/2022 |
| WO | WO 2023/283642 A2 | 1/2023 |
| WO | WO 2023/283645 A1 | 1/2023 |
| WO | WO 2023/283651 A1 | 1/2023 |
| WO | WO 2023/018773 A1 | 2/2023 |
| WO | WO 2023/018923 A1 | 2/2023 |
| WO | WO 2023/019181 A1 | 2/2023 |
| WO | WO 20230/014649 A1 | 2/2023 |
| WO | WO 2023/056401 A1 | 4/2023 |
| WO | WO 2023/069625 A1 | 4/2023 |
| WO | WO 2023/069895 A1 | 4/2023 |
| WO | WO 2023/069900 A1 | 4/2023 |
| WO | WO 2023/076358 A1 | 5/2023 |

OTHER PUBLICATIONS

U.S. Appl. No. 16/850,519, filed Apr. 16, 2020, Ciaramella et al.
U.S. Appl. No. 15/746,286, filed Jan. 19, 2018, Ciaramella et al.
U.S. Appl. No. 16/898,268, filed Jun. 10, 2020, Ciaramella et al.
U.S. Appl. No. 16/599,661, filed Oct. 11, 2019, Besin et al.
U.S. Appl. No. 16/333,330, filed Mar. 14, 2019, Hoge et al.
U.S. Appl. No. 16/864,566, filed May 1, 2020, Ciaramella et al.
U.S. Appl. No. 16/468,838, filed Jun. 12, 2019, Miracco.
U.S. Appl. No. 16/467,142, filed Jun. 6, 2019, Ciaramella et al.
U.S. Appl. No. 16/657,122, filed Oct. 18, 2019, Rabideau et al.
U.S. Appl. No. 16/494,162, filed Sep. 13, 2019, Ciaramella.
U.S. Appl. No. 16/848,318, filed Apr. 14, 2020, Ciaramella et al.
U.S. Appl. No. 16/788,182, filed Feb. 11, 2020, Panther et al.
U.S. Appl. No. 17/000,201, filed Aug. 21, 2020, Stewart-Jones et al.
U.S. Appl. No. 17/000,215, filed Aug. 21, 2020, Stewart-Jones et al.
PCT/US2018/037922, Sep. 13, 2018, International Search Report and Written Opinion.
International Search Report and Written Opinion for Application No. PCT/US2018/037922, dated Sep. 13, 2018.
[No Author Listed], MEGAscript Kit Product Manual, Oct. 27, 2009. Ambion/lnvitrogen website: http://lools.invitrogen.com/contenl/sfs/manuals/ cms_072987.pdf, (last accessed Mar. 17, 2013).
[No Author Listed], NEB RNase H (https://www.neb.com/products/m0297-rnase-h) Downloaded Mar. 30, 2020.
[No Author Listed], Oligotex Handbook, Qiagen, Jun. 2012 [retrieved from internet on Sep. 22, 2020] https://www.qiagen.com/au/resources/resourcedetail?id=f9fa1d98-d54d-47e7-a20b-8b0cb8975009&lang=en.
[No Author Listed], User Guide for mMessage mMachine T7 Kit from Ambion. 2012. p. 1-36.
Abu Lila et al., Application of polyglycerol coating to plasmid DNA lipoplex for the evasion of the accelerated blood clearance phenomenon in nucleic acid delivery. J Pharm Sci. Feb. 2014;103(2):557-66. doi: 10.1002/jps.23823. Epub Dec. 17, 2013.
Abu Lila et al., Use of polyglycerol (PG), instead of polyethylene glycol (PEG), prevents induction of the accelerated blood clearance phenomenon against long-circulating liposomes upon repeated administration. Int J Pharm. Nov. 1, 2013;456(1):235-42. doi: 10.1016/j.ijpharm.2013.07.059. Epub Aug. 5, 2013.
Adamiak, et al. glycoprotein E [Human alphaherpesvirus 2]. GenBank: ABU45436.1. Pub. Nov. 29, 2007.
Adney et al., Efficacy of an Adjuvanted Middle East Respiratory Syndrome Coronavirus Spike Protein Vaccine in Dromedary Camels and Alpacas. Viruses. Mar. 2, 2019;11(3). pii: E212. doi: 10.3390/v11030212.
Agadjanyan, Prototype Alzheimer's Disease Vaccine Using the lmmunodominant B Cell Type from Beta-Amyloid and Promiscuous T Cell Epitope Pan HLA DR-Binding Peptide. J Immunol. Feb. 1, 2005;174(3):1580-6.
Agrawal et al., Immunization with inactivated Middle East Respiratory Syndrome coronavirus vaccine leads to lung immunopathology on challenge with live virus. Hum Vaccin Immunother. Sep. 2016;12(9):2351-6. doi:10.1080/21645515.2016.1177688. Epub Jun. 7, 2016.
Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.
Al Kahlout et al., Comparative Serological Study for the Prevalence of Anti-MERS Coronavirus Antibodies in High- and Low-Risk

(56) References Cited

OTHER PUBLICATIONS

Groups in Qatar. J Immunol Res. Feb. 18, 2019;2019:1386740. doi: 10.1155/2019/1386740. eCollection 2019.

Aleku et al., Atu027, a liposomal small interfering RNA formulation targeting protein kinase N3, inhibits cancer progression. Cancer Res. 2008; 68: 9788-9798.

Alexander et al., The long view: a selective review of 40 years of Newcastle disease research. Avian Pathol. 2012;41(4):329-35. doi: 10.1080/03079457.2012.697991.

Anderson et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.

Andreakos et al., Amphoteric liposomes enable systemic antigen-presenting cell-directed delivery of CD40 antisense and are therapeutically effective in experimental arthritis. Arthritis Rheum. Apr. 2009;60(4):994-1005. doi: 10.1002/art.24434.

Andrews-Pfannkoch et al., Hydroxyapatite-mediated separation of double-stranded DNA, single-stranded DNA, and RNA genomes from natural viral assemblages. Appl Environ Microbiol. Aug. 2010;76(15):5039-45. Epub Jun. 11, 2010.

Andries et al., Comparison of the gene transfer efficiency of mRNA/GL67 and pDNA/GL67 complexes in respiratory cells. Mal Pharmaceutics. 2012; 9: 2136-2145.

Ausar et al., High-throughput screening of stabilizers for respiratory syncytial virus: identification of stabilizers and their effects on the conformational thermostability of viral particles. Hum Vaccin. May-Jun. 2007;3(3):94-103. Epub May 15, 2007.

Awasthi et al., Immunization With a Vaccine Combining Herpes Simplex Virus 2 (HSV-2) Glycoprotein C (gC) and gD Subunits Improves the Protection of Dorsal Root Ganglia in Mice and Reduces the Frequency of Recurrent Vaginal Shedding of HSV-2 DNA in Guinea Pigs Compared to Immunization With gD Alone. J Virol. Oct. 2011;85(20):10472-86. doi: 10.1128/JVI.00849-11. Epub Aug. 3, 2011.

Baars et al., A Phase II Study of Active Specific Immunotherapy and 5-FU/Leucovorin as Adjuvant Therapy for Stage III Colon Carcinoma, British Journal of Cancer, 2002, vol. 86, No. 8, pp. 1230-1234.

Badawi et al., Immune Modulating Peptide for the Treatment and Suppression of Multiple Sclerosis. Clin Immunol. Aug. 2012;144(2):127-138. Author manuscript, 22 pages.

Bag, Recovery of normal protein synthesis in heat-shocked chicken myotubes by liposome-mediated transfer of mRNAs. Can. J. Biochem. Cell Biol. 1985; 63(3): 231-235.

Belliveau et al., Microfluidic synthesis of highly potent limit-size lipid nanoparticles for in vivo delivery of siRNA. Mol Ther Nucleic Acids. Aug. 2012; 1(8): e37.

Betker et al., Nonadditive Effects of Repetitive Administration of Lipoplexes in Immunocompetent Mice. J Pharm Sci. Mar. 2017;106(3):872-881. doi: 10.1016/j.xphs.2016.11.013. Epub Nov. 22, 2016.

Bettinger et al., Peptide-mediated RNA delivery: a novel approach for enhanced transfection of primary and post-mitotic cells. Nucleic Acids Res. Sep. 15, 2001;29(18):3882-91.

Blenke, Intracellular delivery of RNA therapeutics with lipid nanoparticles, publicly available on Jan. 25, 2017, Department of Pharmaceutics, Utrecht Institute for Pharmaceutical Sciences (UIPS), Faculty of Science, University of Utrecht, Netherlands.

Bolhassani et al., Improvement of Different Vaccine Delivery Systems for Cancer Therapy. Mol Cancer. Jan. 7, 2011;10:3. 20 pages. doi: 10.1186/1476-4598-10-3.

Bonehill et al., Single-step antigen loading and activation of dendritic cells by mRNA electroporation for the purpose of therapeutic vaccination in melanoma patients. Clin Cancer Res. May 2009; 15(10): 3366-3375.

Bonham et al., An assessment of the antisense properties of RNase H-competent and steric-blocking oligomers. Nucleic Acids Res. Apr. 11, 1995; 23(7): 1197-1203.

Borghaei et al., Phase I Dose Escalation, Pharmacokinetic and Pharmacodynamic Study of Naptumomab Estafenatox Alone in Patients With Advanced Cancer and With Docetaxel in Patients With Advanced Non-Small-Cell Lung Cancer. J Clin Oncol. Sep. 1, 2009;27(25):4116-23. doi: 10.1200/JCO.2008.20.2515. Epub Jul. 27, 2009.

Bose et al., Influence of cationic lipid concentration on properties of lipid-polymer hybrid nanospheres for gene delivery. Int J Nanomedicine. Sep. 2, 2015;10:5367-82. doi: 10.2147/IJN.S87120. eCollection 2015.

Bouxsein et al., Structure and gene silencing activities of monovalent and pentavalent cationic lipid vectors complexed with siRNA. Biochem. 2007; 46(16): 4785-4792.

Boyer-Di Ponio et al., Biological function of mutant forms of JAGGED1 proteins in Alagille syndrome: inhibitory effect on Notch signaling. Hum Mol Genet. Nov. 15, 2007;16(22):2683-92. Epub Aug. 24, 2007.

Brennan, Ribonucleoside triphosphate concentration-dependent termination of bacteriophage SP01 transcription in vitro by *Bacillus subtilis* RNA polymerase. Virology. Jun. 1984;135(2):555-60. doi: 10.1016/0042-6822(84)90211-3.

Brito et al., A cationic nanoemulsion for the delivery of next-generation RNA vaccines. Mol Ther. Dec. 2014;22(12):1-12. doi: 10.1038/mt.2014.133. Epub Jul. 16, 2014.

Brito et al., Self-amplifying mRNA vaccines. Adv Genet. 2015;89:179-233. doi: 10.1016/bs.adgen.2014.10.005. Epub Dec. 4, 2014.

Brown, Genomes. 2002. 2nd Edition. Oxford:Wiley-Liss, p. 1-20.

Burke et al., Formulation, stability, and delivery of live attenuated vaccines for human use. Crit Rev Ther Drug Carrier Syst. 1999;16(1):1-83.

Byoung-Shik et al., Intranasal immunization with plasmid DNA encoding spike protein of SARS-coronavirus/polyethylenimine nanoparticles elicits antigen-specific humoral and cellular immune responses.BMC Immunol. Dec. 31, 2010;11:65. doi: 10.1186/1471-2172-11-65.

Cao et al. 'MDR3/ABCB4 mRNA Therapy for Treating Progressive Familial Intrahepatic Cholestasis 3 (PFIC3)', Abstract No. 768, Molecular Therapy Apr. 22, 2019, vol. 27, No. 4, Suppl 1 pp. 358-359.

Carnahan et al., Epratuzumab, a Humanized Monoclonal Antibody Targeting CD22 Characterization of in Vitro Properties Clin Cancer Res. Sep. 1, 2003;9(10 Pt 2):3982S-90S.

Chamberlain et al., Recurrent lymphomatous meningitis treated with intra-CSF rituximab and liposomal ara-C. J Neurooncol. Feb. 2009;91(3):271-7. doi: 10.1007/s11060-008-9707-1. Epub Sep. 27, 2008.

Chattopadhyay et al., A chimeric vesiculo/alphavirus is an effective alphavirus vaccine. J Virol. Jan. 2013;87(1):395-402. doi: 10.1128/JVI.01860-12. Epub Oct. 17, 2012.

Chen et al., Human monoclonal antibodies targeting the haemagglutinin glycoprotein can neutralize H7N9 influenza virus. Nat Commun. Mar. 30, 2015;6:6714. doi: 10.1038/ncomms7714.

Chen et al., Influence of Particle Size on the in Vivo Potency of Lipid Nanoparticle Formulations of siRNA. J Control Release. Aug. 10, 2016;235:236-244. doi: 10.1016/j.jconrel.2016.05.059. Epub May 26, 2016.

Chen et al., Molecular evolution and epidemiology of four serotypes of dengue virus in Thailand from 1973 to 2007. Epidemiol Infect. Feb. 2013;141(2):419-24. doi: 10.1017/S0950268812000908. Epub May 14, 2012.

Chen et al., Rapid discovery of potent siRNA-containing lipid nanoparticles enabled by controlled microfluidic formulation. J Am Chem Soc. 2012; 134: 6948-6951.

Chudley et al., Harmonisation of short-term in vitro culture for the expansion of antigen-specific CD8(+) T cells with detection by ELISPOT and HLA-multimer staining. Cancer Immunol Immunother. 2014;63(11):1199-1211.

Corazzelli et al., Biweekly rituximab, cyclophosphamide, vincristine, non-pegylated liposome-encapsulated doxorubicin and prednisone (R-COMP-14) in elderly patients with poor-risk diffuse large B-cell lymphoma and moderate to high 'life threat' impact cardiopathy. Br J Haematol. Sep. 2011;154(5):579-89. doi: 10.1111/j.1365-2141. 2011.08786.x. Epub Jun. 28, 2011.

(56) References Cited

OTHER PUBLICATIONS

Cribbs et al., Adjuvant-dependent Modulation of Th1 and Th2 Responses to Immunization with beta-amyloid, International Immunology. Apr. 2003;15(4):505-14. doi: 10.1093/intimm/dxg049.

Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.

Cun, Don GM El, et al., Preparation and characterization of poly(DL-lactide-co-glycolide) nanoparticles for siRNA delivery. International Journal of Pharmaceutics 390 (2010) 70-75.

Cunnigham, The herpes zoster subunit vaccine. Expert Opin Biol Ther. 2016;16(2):265-71. doi: 10.1517/14712598.2016.1134481.

Dahlman et al., In vivo endothelial siRNA delivery using polymeric nanoparticles with low molecular weight. Nat Nanotechnol. 2014;9(8):1-8. doi:10.1038/nnano.2014.84. Epub May 11, 2014.

Davtyan et al., lmmunogenicity, Efficacy, Safety, and Mechanism of Action of Epitope Vaccine (Lu AF20513) for Alzheimer's Disease: Prelude to a Clinical Trial. The Journal of Neuroscience : the Official Journal of the Society for Neuroscience. Mar. 2013;33(11):4923-4934. DOI: 10.1523/jneurosci.4672-12.2013.

Delehanty et al., Peptides for specific intracellular delivery and targeting of nanoparticles: implications for developing nanoparticle-mediated drug delivery. Ther Deliv. Sep. 2010;1(3):411-33. doi: 10.4155/tde.10.27.

Depledge et al., Deep Sequencing of Distinct Preparations of the Live Attenuated Varicella-Zoster Virus Vaccine Reveals a Conserved Core of Attenuating Single-Nucleotide Polymorphisms. J Viral. Sep. 12, 2016;90(19):8698-704.

Deshayes et al., Cell-penetrating peptides: tools for intracellular delivery of therapeutics. Cell Mal Life Sci. Aug. 2005;62(16):1839-49.

Dharap et al., Tumor-specific Targeting of an Anticancer Drug Delivery System by LHRH Peptide. PNAS. 2005 102(36):12962-7.

Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.

Dong et al., Poly(d,1-laclide-co-glycolide)/montmorillonite nanoparticles for oral delivery of anticancer drugs. Biomaterials. Oct. 2005;26(30):6068-76.

Dropulic et al., The challenge of developing a herpes simplex virus 2 vaccine. Expert Rev Vaccines. Dec. 2012;11(12):1429-40. doi:10.1586/erv.12.129. Author's Manuscript, 21 pages.

Du et al., Arginine-rich cell-penetrating peptide dramatically enhances AMO-mediated ATM aberrant splicing correction and enables delivery to brain and cerebellum. Hum Mol Genet. Aug. 15, 2011;20(16):3151-60. doi: 10.1093/hmg/ddr217. Epub May 16, 2011.

Du et al., Recombinant adeno-associated virus expressing the receptor-binding domain of severe acute respiratory syndrome coronavirus S protein elicits neutralizing antibodies: Implication for developing SARS vaccines. Virology. Sep. 15, 2006;353(1):6-16. doi: 10.1016/j.virol.2006.03.049. Epub Jun. 21, 2006.

Durbin et al., RNAs Containing Modified Nucleotides Fail to Trigger RIG-I Conformational Changes for Innate Immune Signaling. mBio. Sep. 20, 2016;7(5):e00833-16. doi: 10.1128/mBio.00833-16.

Easton et al., Rapid, nondenaturing RNA purification using weak anion-exchange fast performance liquid chromatography. RNA. Mar. 2010;16(3):647-53. Epub Jan. 25, 2010.

El Ouahabi et al., Double long-chain amidine liposome-mediated self replicating RNA transfection. FEBS Letters. Feb. 1996; 380(1-2): 108-112.

Espeseth et al., Modified mRNA/lipid nanoparticle-based vaccines expressing respiratory syncytial virus F protein variants are immunogenic and protective in rodent models of RSV infection. NPJ Vaccines. Feb. 14, 2020;5:16. doi: 10.1038/s41541-020-0163-z. eCollection 2020.

Ewert et al., Cationic liposome-nucleic acid complexes for gene delivery and silencing: pathways and mechanisms for plasmid DNA and siRNA. Top Curr Chem. 2010;296:191-226. Author's Manuscript, 40 pages.

Ezzat et al. PepFect 14, a Novel Cell-penetrating Peptide for Oligonucleotide Deliver in Solution and as Solid Formulation. Nucleic Acids Research. 2011;39(12):5284-5298.

Fang et al., A Novel Cell-Penetrating Peptide Derived from Human Eosinophil Cationic Protein. PLOS One. 2013;8(3):e57318.(pp. 1-13).

Felgner et al., Lipofection: a highly efficient, lipid-mediated DNA-transfection procedure. Proc Natl Acad Sci USA. Nov. 1987;84(21):7413-7.

Felgner, Cationic lipid/polynucleotide condensates for in vitro and in vivo polynucleotide delivery—the cytofectins. J. of Liposome Research. 1993;3(1):3-16.

Felgner, Particulate systems and polymers for in vitro and in vivo delivery of polynucleotides. Adv. Drug Delivery Rev. 1990;5(3):163-187.

Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.

Freer et al., Varicella-zoster virus infection: natural history, clinical manifestations, immunity and current and future vaccination strategies. New Microbiol. Apr. 2018;41(2):95-105. Epub Mar. 2, 2018.

Furie et al., A Phase 111, Randomized, Placebo-Controlled Study of Belimumab, a Monoclonal Antibody That Inhibits B Lymphocyte Stimulator, in Patients With Systemic Lupus Erythematosus. Arthritis & Rheumatism. 2011;63(12):3918-3930.

Furuichi, Caps on Eukaryotic mRNAs. eLS. John Wiley & Sons. Jul. 2014. 12 pages.

Gao et al., Nonviral gene delivery: what we know and what is next. AAPS J. Mar. 23, 2007;9(1):E92-104.

Geall et al., Nonviral delivery of self-amplifying RNA vaccines. Proc Natl Acad Sci USA. Sep. 4, 2012;109(36): 14604-9. doi:10.1073/pnas.1209367109. Epub Aug. 20, 2012.

GENBANK Submission; NIH/NCBI, Accession No. ADG45118.1. Schmidt-Chanasit et al., Jun. 24, 2010. 2 pages.

GENBANK Submission; NIH/NCBI, Accession No. NM_172138.2. Zakaria et al., Jan. 13, 2020. 4 pages.

GENBANK Submission; NIH/NCBI, Accession No. YP009137218.1. Davidson. May 16, 2016. 2 Pages.

Genini et al., Serum Antibody Response to the gH/gL/pUL128-131 Five-Protein Complex of Human Cytomegalovirus (HCMV) in Primary and Reactivated HCMV Infections. J Clin Virol. Oct. 2011;52(2):113-8. doi: 10.1016/j.jcv.2011.06.018. Epub Aug. 4, 2011.

Georgopoulos et al., Use of high-performance liquid chromatographic fractionation of large RNA molecules in the assay of group I intron ribozyme activity. J Chromatogr A. Jan. 28, 2000;868(1):109-14.

Giblin et al., Selective Targeting of E. coli Heat-stable Enterotoxin Analogs to Human Colon Cancer Cells. Anticancer Research. 2006;26:3243-51.

Giljohann et al., Gene regulation with polyvalent siRNA-nanoparticle conjugates. J Am Chem Soc. Feb. 2009; 131 (6): 2072-2073. _Author's Manuscript, 7 pages.

Gilkeson et al., Induction of cross-reactive anti-dsDNA antibodies in preautoimmune NZB/NZW mice by immunization with bacterial DNA. J Clin Invest. Mar. 1995;95(3):1398-402.

Gjetting et al., In vitro and in vivo effects of polyethylene glycol (PEG)-modified lipid in DOTAP/cholesterol-mediated gene transfection. Int J Nanomedicine. Aug. 9, 2010;5:371-83.

Gluzman et al., Esterification of stearic acid with polyethylene glycols. Zhurnal Prikladnoi Khimii, Maik Nauka: Rossiiskaya Akademiya Nauk. Jan. 1, 1968;41(1):167-170.

Grabbe et al., Translating nanoparticulate-personalized cancer vaccines into clinical applications: case study with RNA-lipoplexes for the treatment of melanoma. Nanomedicine (Lond). Oct. 2016;11(20):2723-2734.

(56) References Cited

OTHER PUBLICATIONS

Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.

Hartmaier et al., Genomic analysis of 63,220 tumors reveals insights into tumor uniqueness and targeted cancer immunotherapy strategies. Genome Med. Feb. 24, 2017;9(1):16. doi: 10.1186/s13073-017-0408-2.

Hartmann et al., Handbook of RNA Biochemistry, Second Edition, "Part I RNA Synthesis and Detection." 2014. pp. 1-27.

Hashimoto et al., Relationship between the concentration of anti-polyethylene glycol (PEG) immunoglobulin M (IgM) and the intensity of the accelerated blood clearance (ABC) phenomenon against PEGylated liposomes in mice. Biol Pharm Bull. 2015;38(3):417-24. doi: 10.1248/bpb.b14-00653.

Hassett et al., Optimization of Lipid Nanoparticles for Intramuscular Administration of mRNA Vaccines. Mol Ther Nucleic Acids. Apr. 2019;15:1-11. Epub Feb. 7, 2019.

He et al., Synthesis and Separation of Diastereomers of Ribonucleoside 5'-(alpha-P-Borano)triphosphates. J Org Chem. Aug. 21, 1998;63(17):5769-5773.

Hecker et al., Non-Viral DNA and mRNA Gene Delivery to the CNS Pre-Operatively for Neuroprotection and Following Neurotrauma. Molecular Therapy. 2004; 9, S258.

Hecker, Nonviral, cationic lipid-mediated delivery of mRNA. Methods Mol Biol. 2013;969:73-88. doi: 10.1007/978-1-62703-260-5_5.

Heesch et al., Abstract CT020: MERIT: introducing individualized cancer vaccines for the treatment of TNBC—a phase I trial, [abstract]. In: Proceedings of the 107th Annual Meeting of the American Association for Cancer Research; Apr. 16-20, 2016; New Orleans, LA. Philadelphia (PA): AACR; Cancer Res 2016; 76 (14 Suppl).

Heyes et al., Cationic lipid saturation influences intracellular delivery of encapsulated nucleic acids. J Control Release. Oct. 3, 2005;107(2):276-87.

Hoerr et al., In vivo application of RNA leads to induction of specific cytotoxic T lymphocytes and antibodies. Eur. J. lmmunol. Jan. 2000;30(1):1-7.

Hsu et al., Cationic lipid nanoparticles for therapeutic delivery of siRNA and miRNA to murine liver tumor. Nanomedicine. Nov. 2013;9(8):1169-80. doi: 10.1016/j.nano.2013.05.007. Epub May 30, 2013.

Huber et al., Analysis of nucleic acids by on-line liquid chromatography-Mass spectrometry (Mass Spectrometry Reviews 2001, 20, pp. 310-343).

Hussein et al., Synthesis, Quantum Chemical Calculations and Properties of Nonionic and Nonionic-Anionic Surfactants Based on Fatty Alkyl Succinate. Journal of Surfactants and Detergents vol. 17, pp. 615-627(2014).

Ivanovska et al., Immunization with a DNA chimeric molecule encoding a hemagglutinin peptide and a scFv CD21-specific antibody fragment induces long-lasting lgM and CTL responses to influenza virus. Vaccine. Mar. 10, 2006;24(11):1830-7. Epub Nov. 2, 2005.

Jachertz et al., Treatment of P815 mastocytoma in DBA/2 mice with RNA. J Immunogen. 1974; 1: 355-362.

Janeway et al., lmmunobiology: the immune system in health and disease. Garland Publishing, Inc., London. 1997. 3$^{rd}$ Edition. Chapter 13:12-21.

Jia et al., Kinetic mechanism of GTP binding and RNA synthesis during transcription initiation by bacteriophage T7 RNA polymerase. J Biol Chem. Nov. 28, 1997;272(48):30147-53. doi: 10.1074/jbc.272.48.30147.

John et al., Multi-antigenic human cytomegalovirus mRNA vaccines that elicit potent humoral and cell-mediated immunity. Vaccine. Mar. 14, 2018;36(12):1689-1699. doi:10.1016/j.vaccine.2018.01.029. Epub Feb. 15, 2018.

Juliano et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.

Kalantari-Dehagi et al., Discovery of Potential Diagnostic and Vaccine Antigens in Herpes Simplex Virus 1 and 2 by Proteome-Wide Antibody Profiling. J Virol. Apr. 2012;86(8):4328-39. doi: 10.1128/JVI.05194-11. Epub Feb. 8, 2012.

Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.

Kallen et al., A novel, disruptive vaccination technology: self-adjuvanted RNActive® vaccines. Hum Vaccin Immunother. Oct. 2013;9(10):2263-76. doi: 10.4161/hv.25181. Epub Jun. 4, 2013. Review.

Kanapathipillai, et al., Nanoparticle targeting of anti-cancer drugs that alter intracellular signaling or influence the tumor microenvironment. Adv. Drug Deliv. Rev. Dec. 2014;79-80. 12 pages.

Kang et al., Inhibition of MDR1 Gene Expression by Chimeric HNA Antisense Oligonucleotides. Nucleic Acids Research. 2004;32(14):4411-19. doi: 10.1093/nar/gkh775.

Kariko et al., Generating the optimal mRNA for therapy: HPLC purification eliminates immune activation and improves translation of nucleoside-modified, protein-encoding mRNA. Nucleic Acids Res. Nov. 2011;39(21):e142(pp. 1-10).

Kariko et al., In vivo protein expression from mRNA delivered into adult rat brain. J. of Neuroscience Methods. Jan. 2001; 105(1): 77-86.

Kariko et al., Incorporation of pseudouridine into mRNA yields superior nonimmunogenic vector with increased translational capacity and biological stability. Molecular Therapy. Nov. 2008;16(11):1833-1840. doi: 10.1038/mt.2008.200. Author Manuscript, 18 pages.

Kariko et al., Phosphate-enhanced transfection of cationic lipid-complexed mRNA and plasmid DNA. Biochim Biophys Acta. Mar. 2, 1998;1369(2):320-34.

Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.

Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.

Keown et al., [41] Methods for Introducing DNA into Mammalian Cells. Methods in Enzymology, 1990, 185:527-37.

Keshwara et al., Rabies-based vaccine induces potent immune responses against Nipah virus. NPJ Vaccines. Apr. 15, 2019;4:15. Erratum in: NPJ Vaccines. May 13, 2019;4:18.

Kingston, 'Preparation of poly (A)+ RNA', Current protocols in molecular biology. 1993;21(1):4.5.1-4.5.3.

Kirchdoerfer et al., Stabilized coronavirus spikes are resistant to conformational changes induced by receptor recognition or proteolysis. Sci Rep. Oct. 24, 2018;8(1):15701. doi: 10.1038/s41598-018-34171-7.

Kirpotin et al., Antibody targeting of long-circulating lipidic nanoparticles does not increase tumor localization but does increase internalization in animal models. Cancer Res. 2006; 66: 6732-6740.

Klinman et al., DNA vaccines: safety and efficacy issues. Springer Semin lmmunopathol. 1997;19(2):245-56.

Knudsen et al., Antisense properties of duplex- and triplex-forming PNAs. Nucleic Acids Res. Feb. 1, 1996; 24(3): 494 500.

Koch et al., Quantitative Studies on the lnfectivity of ribonucleic acid from partially purified and highly purified poliovirus preparations. Virology. Mar. 1960; 10(3): 329-343.

Kowalski et al., Delivering the Messenger: Advances in Technologies for Therapeutic mRNA Delivery. Molecular Therapy. Apr. 4, 2019;27(4):710-28.

Kozielski et al., Bioreducible cationic polymer-based nanoparticles for efficient and environmentally triggered cytoplasmic siRNA delivery to primary human brain cancer cells. ACS Nano. Apr. 22, 2014;8(4):3232-41. doi: 10.1021/nn500704t. Epub Apr. 3, 2014.

(56) References Cited

OTHER PUBLICATIONS

Krause et al., Prevention of the hemodynamic effects of iopromide-carrying liposomes in rats and pigs. Invest Radiol. Aug. 2000;35(8):493-503.

Kulkarni et al., Lipid Nanoparticles Enabling Gene Therapies: From Concepts to Clinical Utility. Nucleic Acid Ther. Jun. 2018;28(3):146-157. doi: 10.1089/nat.2018.0721. Epub Apr. 23, 2018.

Kumar et al., Shielding of Lipid Nanoparticles for siRNA Delivery: Impact on Physicochemical Properties, Cytokine Induction, and Efficacy. Mol Ther Nucleic Acids. Nov. 18, 2014;3(11):e210. doi: 10.1038/mtna.2014.61.

Kussie et al., A single engineered amino acid substitution changes antibody fine specificity. J Immunol. Jan. 1, 1994;152(1):146-52.

Kutchko et al., Transcending the Prediction Paradigm: Novel Applications of SHAPE to RNA Function and Evolution. Wiley Interdiscip Rev RNA. Jan. 2017;8(1):e1374. doi: 10.1002/wrna.1374. Epub Jul. 10, 2016.

Laakkonen et al., Homing Peptides as Targeted Delivery Vehicles. Interactive Biology. Jul. 2010;2:326-337. doi: 10.1039/c0ib00013b.

Lai et al., Mucus-penetrating nanoparticles for drug and gene delivery to mucosal tissues. Adv Drug Deliv Rev. Feb. 27, 2009 61(2):158-171. Author's Manuscript, 36 pages.

Lai et al., Rapid transport of large polymeric nanoparticles in fresh undiluted human mucus. PNAS. Jan. 30, 2007; 04(5):1482-1487.

Leader et al., Protein therapeutics: a summary and pharmacological classification. Nat Rev Drug Discov. Jan. 2008;7(1):21-39.

Lee et al., Lipid Nanoparticle siRNA Systems for Silencing the Androgen Receptor in Human Prostate Cancer in Vivo. International Journal of Cancer. 2012;131:E781-E790.

Lee et al., Separation and determination of polyethylene glycol fatty acid esters in cosmetics by a reversed-phase HPLC/ELSD. Talanta. Feb. 15, 2008;74(5):1615-20. doi: 10.1016/j.talanta.2007.10.020. Epub Oct. 18, 2007.

Lehto et al., Cell-penetrating peptides for the delivery of nucleic acids. Expert Opin. Drug Deliv. Jul. 2012; 9(7): 823-836.

Leung et al., Microfluidic Mixing: A General Method for Encapsulating Macromolecules in Lipid Nanoparticle Systems. J Phys Chem B. Jul. 16, 2015;119(28):8698-706. doi: 10.1021/acs.jpcb.5b02891. Epub Jul. 7, 2015.

Lewandowski et al., Separation of the infectious ribonucleic acid of potato spindle tuber virus from double-stranded ribonucleic acid of plant tissue extracts. J Virol. Nov. 1971;8(5):809-12.

Lewis., Dynamic Poly conjugates (DPC) Technology: An elegant solution to the siRNA delivery problem. Arrowhead Research Corp (NASDAQ: ARWR). Nov. 2011; 6 pages.

Li et al., Alagille syndrome is caused by mutations in human Jagged1, which encodes a ligand for Notch1. Nat Genet. Jul. 1997;16(3):243-51.

Li et al., Overcoming obstacles to develop effective and safe siRNA therapeutics. Expert Opin Biol Ther. May 2009; 9(5): 609-19.

Li et al., Preparation and gene delivery of alkaline amino acids-based cationic liposomes. Arch Pharm Res. Jul. 2008;31(7):924-31. Epub Aug. 14, 2008.

Lian et al., Trends and developments in liposome drug delivery systems. J Pharm Sci. Jun. 2001;90(6):667-80.

Lo et al., Hepatocellular Carcinoma Cell-Specific Peptide Ligand for Targeted Drug Delivery. Molecular Cancer Therapeutics. 2008;7(3):579-589.

Lopez-Berestein et al., Treatment of systemic fungal infections with liposomal amphotericin B. Arch Intern Med. Nov. 1989;149(11):2533-6.

Lu et al., Bat-to-human: spike features determining 'host jump' of coronaviruses SARS-CoV, MERS-CoV, and beyond. Trends Microbiol. Aug. 2015;23(8):468-78. doi: 10.1016/j.tim.2015.06.003. Epub Jul. 21, 2015.

Lu et al., IFNL3 mRNA structure is remodeled by a functional non-coding polymorphism associated with hepatitis C virus clearance. Sci Rep. 2015;5:16037.

Lu et al., Targeted Drug Delivery Systems Mediated by a Novel Peptide in Breast Cancer Therapy and Imaging. PLOS One. Jun. 2013;8(6). 13 pages.

Luo et al., Synthetic DNA delivery systems. Nat Biotechnol. Jan. 2000;18(1):33-7.

MacLachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97bld2/MacLachlan_mRNA_Conf_2013.pdf. 32 pages, [last accessed Dec. 22, 2016].

Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.

Magee et al., Marked stimulation of lymphocyte-mediated attack on tumor cells by target-directed liposomes containing immune RNA, Cancer Res., 1978, 38(4):1173-6.

Maier et al., Biodegradable Lipids Enabling Rapidly Eliminated Lipid Nanoparticles for Systemic Delivery of RNAi Therapeutics. Mol Ther. Aug. 2013; 21(8): 1570-1578.

Malone et al., Cationic liposome-mediated RNA transfection. Proc Natl Acad Sci U SA. Aug. 1989;86(16):6077-81.

Marć et al., Nucleic acid vaccination strategies against infectious diseases. Expert Opin Drug Deliv. 2015;12(12):1851-65. doi: 10.1517/17425247.2015.1077559. Epub Sep. 12, 2015.

Marina et al., Dose escalation and pharmacokinetics of pegylated liposomal doxorubicin (Doxil) in children with solid tumors: a pediatric oncology group study. Clin Cancer Res. Feb. 2002;8(2):413-8.

Mas et al., Engineering, Structure and Immunogenicity of the Human Metapneumovirus F Protein in the Postfusion Conformation. PLoS Pathog. Sep. 9, 2016;12(9):e1005859. doi:10.1371/journal.ppat.1005859. eCollection Sep. 2016.

Mateo et al., Vaccines inducing immunity to Lassa virus glycoprotein and nucleoprotein protect macaques after a single shot. Sci Transl Med. Oct. 2, 2019;11(512):eaaw3163. doi: 10.1126/scitranslmed.aaw3163.

Maurer et al., Spontaneous entrapment of polynucleotides upon electrostatic interaction with ethanol-destabilized cationic liposomes. Biophys J. May 2001; 80(5): 2310-2326.

McCormack et al., Activation of the T-cell oncogene LM02 after gene therapy for X-linked severe combined immunodeficiency. N Engl J Med. Feb. 2004; 350: 913-922.

Mellits et al., Removal of double-stranded contaminants from RNA transcripts: synthesis of adenovirus VA RNAI from a T7 vector. Nucleic Acids Res. Sep. 25, 1990;18(18):5401-6.

Middleton et al., Hendra virus vaccine, a one health approach to protecting horse, human, and environmental health. Emerg Infect Dis. Mar. 2014;20(3):372-9. doi: 10.3201/eid2003.131159.

Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.

Mishra et al., Improved leishmanicidal effect of phosphorothioate antisense oligonucleotides by LDL-mediated delivery. Biochim Biophys Acta. Nov. 7, 1995;1264(2):229-37.

Mishra et al., Induction by RNA of inositol independence in Neurospora crassa. Proc. Natl Acad. Sci. U.S.A., 1975, 72(2):642-5.

Morello et al., Immunization With Herpes Simplex Virus 2 (HSV-2) Genes Plus Inactivated HSV-2 Is Highly Protective Against Acute and Recurrent HSV-2 Disease. J Virol. Apr. 2011;85(7):3461-72. doi: 10.1128/JVI.02521-10. Epub Jan. 26, 2011.

Muller et al., Transfection of dendritic cells with RNA induces CD4- and COB-mediated T cell immunity against breast carcinomas and reveals the immunodominance of presented T cell epitopes. J Immunol. Jun. 15, 2003;170(12):5892-6.

Nair et al., Soluble proteins delivered to dendritic cells via pH-sensitive liposomes induce primary cytotoxic T lymphocyte responses in vitro. J Exp Med. Feb. 1, 1992;175(2):609-12.

(56) References Cited

OTHER PUBLICATIONS

Nakamura et al., Antigen restricted hybridization between antigen primed macrophage and thymic RNA. lmmunol Commun. 1981;10(4-5):367-82.

NCT02410733—Evaluation of the Safety and Tolerability of i.v. Administration of a Cancer Vaccine in Patients With Advanced Melanoma (Lipo-MERIT), ClinicalTrials.gov, Jul. 17, 2019, (Online), Viewed online Jan. 2, 2020, <URL: https://www.clinicaltrials.gov/ct2/show/record/NCT02410733?term=NCT02410733&draw=2&rank=1>.

Nielsen et al. Toward Personalized Lymphoma Immunotherapy: Identification of Common Driver Mutations Recognized by Patient CD8+ T Cells. Clin Cancer Res. 2016;22(9):2226-2236.

Niu et al., Poly(A)-attached RNA as activator in embryonic differentiation. Proc Soc Exp Biol Med. Oct. 1974;147 (1):318-22.

Oda et al., Mutations in the human Jagged1 gene are responsible for Alagille syndrome. Nat Genet. Jul. 1997;16(3):235-42.

Oja et al., Doxorubicin entrapped within liposome-associated antigens results in a selective inhibition of the antibody response to the linked antigen. Biochim Biophys Acta. Sep. 29, 2000;1468(1-2):31-40.

Okumura et al., Bax mRNA therapy using cationic liposomes for human malignant melanoma. J Gene Med. 2008; 10: 910-917.

Oster et al. Comparative study of DNA encapsulation into PLGA microparticles using modified double emulsion methods and spray drying techniques. Journal of Microencapsulation, May 2005; 22(3): 235-244.

Pallesen et al., Immunogenicity and structures of a rationally designed prefusion MERS-CoV spike antigen. Proc Natl Acad Sci U S A. Aug. 29, 2017;114(35):E7348-E7357. doi: 10.1073/pnas.1707304114. Epub Aug. 14, 2017.

Pangburn et al., Peptide-and Aptamer-Functionalized Nanovectors for Targeted Delivery of Therapeutics. Journal of Biomedical Engineering. Jul. 2009;131. 20 pages.

Pardi et al., Developing an influenza vaccine using lipid nanoparticle-encapsulated nucleoside-modified mRNA. Eur. J. Immunol. Aug. 2016.;46(Sl):1232-1233. Abstract 1349.

Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015. Author's Manuscript, 18 pages.

Pardi et al., Nucleoside-modified mRNA vaccines induce potent T follicular helper and germinal center B cell responses. J Exp Med. Jun. 4, 2018;215(6):1571-1588. doi: 10.1084/jem.20171450. Epub May 8, 2018.

Parker et al., Targeting of Polyelectrolyte RNA Complexes to Cell Surface lntegrins as an Efficient, Cytoplasmic Transfection Mechanism. Journal of Bioactive and Compatible Polymers. Jul. 2002;17(4). 10 pages.

Petro et al., Herpes simplex type 2 virus deleted in glycoprotein D protects against vaginal, skin and neural disease. Elife. Mar. 10, 2015;4:e06054. doi: 10.7554/eLife.06054.

Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.

Phelan et al., lntercellular Delivery of Functional p53 by the Herpesvirus Protein VP22. Nature Biotechnology. 1998;16: 440-443.

Pollard et al., Type I IFN counteracts the induction of antigen-specific immune responses by lipid-based delivery of mRNA vaccines. Mol Ther. Jan. 2013; 21 (1): 251-259.

Popov et al., Multivalent rituximab lipid nanoparticles as improved lymphoma therapies: indirect mechanisms of action and in vivo activity. nNanomedicine (Lond). Nov. 2011;6(9):1575-91. doi: 10.2217/nnm.11.50. Epub Oct. 20, 2011.

Porteous et al., Evidence for safety and efficacy of DOTAP cationic liposome mediated CFTR gene transfer to the nasal epithelium of patients with cystic fibrosis. Gene Ther. Mar. 1997;4(3):210-8.

Poveda et al., Establishing Preferred Product Characterization for the Evaluation of RNA Vaccine Antigens. Vaccines (Basel). Sep. 27, 2019;7(4):131. doi: 10.3390/vaccines7040131.

Rajasagi et al., Systematic identification of personal tumor-specific neoantigens in chronic lymphocytic leukemia. Blood. 2014;124(3):453-462.

Ramamoorth et al., Non viral vectors in gene therapy—an overview. J Clin Diagn Res. Jan. 2015; 9(1): GE01-GE06.

Rammensee et al., Cancer Vaccines: Some Basic Considerations. Genomic and Personalized Medicine. 2009;573-589.

Read et al., A versatile reducible polycation-based system for efficient delivery of a broad range of nucleic acids. Nucleic Acids Res. 2005; 33(9): e86.

Regberg et al., Applications of Cell-Penetrating Peptides for Tumor Targeting and Future Cancer Therapies. Pharmaceuticals. 2012;5:991-1007.

Reichmuth et al., mRNA Vaccine Delivery Using Lipid Nanoparticles. Ther Deliv. 2016;7(5):319-34. doi: 10.4155/tde-2016-0006.

Riccardi et al., "Dressing up" an Old Drug: An Aminoacyl Lipid for the Functionalization of Ru(III)-Based Anticancer Agents. ACS Biomater. Sci. Eng. 2018, 4, 1, 163-174.

Riley et al., Simple repeat evolution includes dramatic primary sequence changes that conserve folding potential. Biochem Biophys Res Commun. Apr. 13, 2007;355(3):619-25. Epub Feb. 15, 2007.

Rodriguez et al., Minimal self peptides that inhibit phagocytic clearance and enhance delivery of nanoparticles. Science. Feb. 22, 2013; 339(6122): 971-975.

Rohloffet al., DU ROS® Technology delivers peptides and proteins at consistent rate continuously for 3 to 12 months. J Diabetes Sci Technol. May 2008; 2(3): 461-467.

Romano et al., Inter- and intra-host viral diversity in a large seasonal DENV2 outbreak. PLoS One. Aug. 2, 2013;8(8):e70318. doi: 10.1371/journal.pone.0070318. Print 2013.

Sabnis et al., A Novel Amino Lipid Series for mRNA Delivery: Improved Endosomal Escape and Sustained Pharmacology and Safety in Non-human Primates. Mol Ther. Jun. 6, 2018;26(6):1509-1519. doi: 10.1016/j.ymthe.2018.03.010. Epub Mar. 14, 2018.

Sahin et al., Personalized RNA mutanome vaccines mobilize poly-specific therapeutic immunity against cancer. Nature. Jul. 1, 20173;547(7662):222-226. doi: 10.1038/nature23003. Epub Jul. 5, 2017.

Saito et al., Distribution of liposomes into brain and rat brain tumor models by convection-enhanced delivery monitored with magnetic resonance imaging. Cancer Res. Apr. 2004; 64: 2572-2579.

Sakuma et al., Mucoadhesion of polystyrene nanoparticles having surface hydrophilic polymeric chains in the gastrointestinal tract. Int J Pharm. Jan. 25, 1999;177(2):161-72.

Schirrmacher et al., Intra-pinna anti-tumor vaccination with self-replicating infectious RNA or with DNA encoding a model tumor antigen and a cytokine. Gene Ther. Jul. 2000;7(13):1137-47.

Schleiss, Cyotmegalovirus vaccines under clinical development. J Virus Erad. Oct. 5, 2016;2(4):198-207.

Schmidt et al., Progress in the development of human parainfluenza virus vaccines. Expert Rev Respir Med. Aug. 2011;5(4):515-26. doi: 10.1586/ers.11.32. Author's Manuscript, 20 pages.

Schott et al., Viral and non-viral approaches for transient delivery of mRNA and proteins. Current Gene Ther. 2011; 11 (5): 382-398.

Schwendener, Liposomes as vaccine delivery systems: a review of the recent advances. Ther Adv Vaccines. Nov. 2014;2(6):159-82. doi: 10.1177/2051013614541440.

Semple et al., Rational design of cationic lipids for siRNA delivery. Nat Biotechnol. Feb. 2010; 28(2): 172-176.

Shah et al., Shingrix for Herpes Zoster: A Review. Skin Therapy Lett. Jul. 2019;24(4):5-7.

Shea et al., Synthesis, hybridization properties and antiviral activity of lipid-oligodeoxynucleotide conjugates. Nucleic Acids Res.Jul. 11, 1990;18(13):3777-83.

Shimizu et al., Transport of PEGylated liposomes from the splenic marginal zone to the follicle in the induction phase of the accelerated blood clearance phenomenon. Immunobiology. May 2013;218(5):725-32. doi: 10.1016/j.imbio.2012.08.274. Epub Aug. 23, 2012.

(56) References Cited

OTHER PUBLICATIONS

Shinu et al., Multi-antigenic Human Cytomegalovirus mRNA Vaccines That Elicit Potent Humoral and Cell-Mediated Immunity. Vaccine. Mar. 14, 2018;36(12):1689-1699. doi: 10.1016/j.vaccine. 2018.01.029. Epub Feb. 15, 2018.

Sieber et al., The Definition of Open Reading Frame Revisited. Trends Genet. Mar. 2018;34(3):167-170. doi: 10.1016/j.tig.2017. 12.009. Epub Jan. 30, 2018.

Slater, The purification of poly(a)-containing RNA by affinity chromatography. Methods MolBiol. 1985;2:117-20. doi: 10.1385/0-89603-064-4:117.

Srivastava, Progressive Familial Intrahepatic Cholestasis. Journal of Clinical and Experimental Hepatology. Mar. 2014;4(1):25-36.

Stiles et al., Widespread suppression of huntingtin with convection-enhanced delivery of siRNA. Experimental Neurology. Jan. 2012; 233(1): 463-471.

Strobel et al., Human dendritic cells transfected with either RNA or DNA encoding influenza matrix protein M1 differ in their ability to stimulate cytotoxic T lymphocytes. Gene Ther. Dec. 2000; 7(23): 2028-2035.

Svinarchuk et al., Inhibition of HIV proliferation in MT-4 cells by antisense oligonucleotide conjugated to lipophilic groups. Biochimie. 1993;75(1-2):49-54.

Taguchi et al., Effect of Repeated Injections of Adenosine Diphosphate-Encapsulated Liposomes Coated with a Fibrinogen γ-Chain Dodecapeptide Developed as a Synthetic Platelet Substitute on Accelerated Blood Clearance in a Healthy and an Anticancer Drug-Induced Thrombocytopenia Rat Model. J Pharm Sci. Sep. 2015;104(9):3084-91. doi: 10.1002/jps.24418. Epub Mar. 9, 2015.

Taguchi et al., Hemoglobin vesicles, polyethylene glycol (PEG)ylated liposomes developed as a red blood cell substitute, do not induce the accelerated blood clearance phenomenon in mice. Drug Metab Dispos. Nov. 2009;37(11):2197-203. doi: 10.1124/dmd.109. 028852. Epub Aug. 13, 2009.

Tanaka et al., Inhibition of heart transplant injury and graft coronary artery disease after prolonged organ ischemia by selective protein kinase C regulators. J Thorac Cardiovasc Surg. May 2005;129(5):1160-7.

Tang et al., Genetic immunization is a simple method for eliciting an immune response. Nature. Mar. 12, 1992;356(6365):152-4.

Tavernier et al., mRNA as gene therapeutic: How to control protein expression. J. of Controlled Release. Mar. 2011; 150(3): 238-247.

Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015. 103. Epub Jun. 8, 2015.

Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 11, 2014.

Tracy, Progress in the Development of LNP Delivery for siRNA Advancing LNPs to the Clinic. International Liposome Research Days Meeting. Aug. 2010. Alnylam Pharmaceuticals. 52 pages.

Treat et al., in Liposomes in the Therapy of Infectious Disease and Cancer, Lopez-Berestein and Fidler (eds.), Liss, New York, 1989. 353-65.

Tripathy et al., Long-term expression of erythropoietin in the systemic circulation of mice after intramuscular injection of a plasmid DNA vector, Proc. Natl. Acad. Sci. USA. Oct. 1996;93:10876-10880.

UNIPROT; NIH/NCBI, Accession No. P06475.1. Swain et al., Jan. 1, 2015. 3 pages.

UNIPROT; NIH/NCBI, Accession No. P06764.1. Hodgman et al., Jan. 7, 2015. 1 page.

Uzgun et al., PEGylation improves nanoparticle formation and transfection efficiency of messenger RNA. Pharm Res. Sep. 2011; 28(9); 2223-2232.

Van Tendeloo et al., Highly efficient gene delivery by mRNA electroporation in human hematopoietic cells: superiority to lipofection and passive pulsing of mRNA and to electroporation of plasmid cDNA for tumor antigen loading of dendritic cells. Blood. Jul. 1, 2001;98(1):49-56.

Viklund et al., Enzymatic synthesis of surfactants based on polyethylene glycol and stearic or 12-hydroxystearic acid. Journal of Molecular Catalysis B Enzymatic 27(2):51-53 • Feb. 2004.

Wang et al., Enhanced bioavailability and efficiency of curcumin for the treatment of asthma by its formulation in solid lipid nanoparticles. Int J Nanomedicine. 2012;7:3667-77. doi: 10.2147/IJN.S30428. Epub Jul. 17, 2012.

Wang et al., Purification of the messenger ribonucleic acid for the lipoprotein of the *Escherichia coli* outer membrane. Biochemistry. Oct. 2, 1979;18(20):4270-7.

Wang et al., Structural Definition of a Neutralization-sensitive Epitope on the MERS-CoV S1-NTD. Cell Rep. Sep. 24, 2019;28(13):3395-3405.e6. doi: 10.1016/j.celrep.2019.08.052. Author's Manuscript, 29 pages.

Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.

Weaver., Molecular Biology. 1999. WCB/McGraw-Hill. Chapter 15:456. 5 pages.

Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.

Weissman et al., HPLC purification of in vitro transcribed long RNA. Methods Mol Biol. 2013;969:43-54. doi: 10.1007/978-1-62703-260-5_3.

WHO Drug Information, International Nonproprietary Names for Pharmaceutical Substances (INN). 1993;7(4):1-16.

Wilson et al., Real time measurement of PEG shedding from lipid nanoparticles in serum via NMR spectroscopy. Mol Pharm. Feb. 2, 2015;12(2):386-92. doi: 10.1021/mp500400k. Epub Jan. 12, 2015.

Woodward et al., Varicella Virus Vaccine Live: A 22-Year Review of Postmarketing Safety Data. Open Forum Infect Dis. Aug. 1, 2019 ;6(8):ofz295.

Wrapp et al., Cryo-EM structure of the 2019-nCoV spike in the prefusion conformation. Science. Feb. 19, 2020. pii: eabb2507. doi: 10.1126/science.abb2507.

Wussow et al., Human cytomegalovirus vaccine based on the envelope gH/gL pentamer complex. PLoS Pathog. Nov. 20, 2014;10(11):e1004524. doi: 10.1371/journal.ppat. 1004524. eCollection Nov. 2014.

Yadav et al., Predicting Immunogenic Tumour Mutations by Combining Mass Spectrometry and Exome Sequencing. Nature. Nov. 27, 2014;515(7528):572-6. doi: 10.1038/nature14001.

Yamamoto et al., Current prospects for mRNA gene delivery. Eur J Pharm Biopharm. Mar. 2009;71(3):484-9. doi: 10.1016/j.ejpb.2008. 09.016. Epub Oct. 10, 2008.

Yang et al., Effect of CD44 Binding Peptide Conjugated to an Engineered Inert Matrix on Maintenance of Breast Cancer Stem Cells and Tumorsphere Formation. PLOS One. 2013;8(3):1-15.

Yu et al., Anti-GD2 Antibody with GM-CSF, lnterleukin-2, and lsotretinoin for Neuroblastoma. The New England Journal of Medicine. Sep. 2010;363(14):, vol. 363;1324-1334.

Yuan et al., Cryo-EM structures of MERS-CoV and SARS-CoV spike glycoproteins reveal the dynamic receptor binding domains. Nat Commun. Apr. 10, 2017;8:15092. doi: 10.1038/ncomms15092.

Yuan et al., Human Jagged 1 mutants cause liver defect in Alagille syndrome by overexpression of hepatocyte growth factor. J Mol Biol. Feb. 24, 2006;356(3):559-68. Epub Dec. 20, 2005.

Zhang et al., Personalized cancer vaccines: Targeting the cancer mutanome. Vaccine. Feb. 15, 2017;35(7):1094-1100. doi: 10.1016/j.vaccine.2016.05.073. Epub Jul. 20, 2016. Author's Manuscript, 16 pages.

Zhao et al., A frustrating problem: accelerated blood clearance of PEGylated solid lipid nanoparticles following subcutaneous injection in rats. Eur J Pharm Biopharm. Aug. 2012;81(3):506-13. doi: 10.1016/j.ejpb.2012.04.023. Epub May 11, 2012.

Zhao et al., Chapter Two: Lipid Nanoparticles for Gene Delivery. Book: Advances in Genetics. Elsevier, 2014. 24 pages.

(56) References Cited

OTHER PUBLICATIONS

Zhigaltsev et al., Bottom-Up design and synthesis of limit size lipid nanoparticle systems with aqueous and triglyceride cores using millisecond microfluidic mixing. Langmuir. Feb. 21, 2012; 28(7): 3633-3640.
Zimmermann et al., Electrolyte- and pH-stabilities of aqueous solid lipid nanoparticle (SLN™) dispersions in artificial gastrointestinal media. Eur J Pharm Biopharm. Sep. 2001;52(2):203-10.
Zohra et al., Drastic effect of nanoapatite particles on liposome-mediated mRNA delivery to mammalian cells. Analytical Biochem. Oct. 2005; 345(1): 164-166.
Zohra et al., Effective delivery with enhanced translational activity synergistically accelerates mRNA-based transfection. Biochem Biophys Res Comm. Jun. 2007; 358(1 ): 373-378.
Zou et al., Cell-Penetrating Peptide-Mediated Therapeutic Molecule Delivery Into the Central Nervous System. Current Neuropharmacology. 2013;11(2):197-208.
Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010. Author's Manuscript, 26 pages.
[No Author Listed] Programme of the 1st International mRNA Health Conference, Germany; Oct. 2013. 32 pages.
Dickman et al., Ion Pair Reverse-Phase Chromatography: A Versatile Platform for the Analysis of RNA. Chromatography Today. 2011; 22-26.
Michel et al., Cationic Nanoliposomes Meet mRNA: Efficient Delivery of Modified mRNA Using Hemocompatible and Stable Vectors for Therapeutic Applications. Mol Ther Nucleic Acids. Sep. 15, 2017;8:459-468. doi: 10.1016/j.omtn.2017.07.013. Epub Jul. 25, 2017.
Shin et al., Recent Advances in RNA Therapeutics and RNA Delivery Systems Based on Nanoparticles. Adv. Therap., Nov. 2018;1(7):1800065. Review.
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir. 0c03039. Epub Jan. 13, 2021.
Wang et al., Chapter 3: Lipid Nanoparticles for the Delivery of Nucleic Acids. Book: Nanoparticulate Drug Delivery Systems: Strategies, Technologies, and Applications. 2013. 29 pages.
U.S. Appl. No. 16/833,409, filed Mar. 27, 2020, Ciaramella.
U.S. Appl. No. 17/548,172, filed Dec. 10, 2021, Ciaramella et al.
U.S. Appl. No. 16/496,135, filed Sep. 20, 2019, Narayanan et al.
U.S. Appl. No. 16/494,103, filed Sep. 13, 2019, Ciaramella et al.
U.S. Appl. No. 17/155,592, filed Jan. 22, 2021, Ciaramella et al.
U.S. Appl. No. 17/325,883, filed May 20, 2021, Dousis et al.
U.S. Appl. No. 17/518,542, filed Nov. 3, 2021, Metkar et al.
U.S. Appl. No. 17/796,208, filed Jul. 28, 2022, Stewart-Jones et al.
U.S. Appl. No. 17/797,784, U.S. Appl. No. 17/797,784, Stewart-Jones et al.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/204,801, filed Mar. 17, 2021, Ciaramella et al.
U.S. Appl. No. 17/683,171, filed Feb. 28, 2022, Ciaramella et al.
U.S. Appl. No. 15/748,773, filed Jan. 30, 2018, Ciaramella et al.
U.S. Appl. No. 17/554,182, filed Dec. 17, 2021, Ciaramella et al.
U.S. Appl. No. 15/753,293, filed Feb. 17, 2018, Smith.
U.S. Appl. No. 15/767,587, filed Apr. 11, 2018, Ciaramella.
U.S. Appl. No. 17/819,414, filed Aug. 12, 2022, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 17/737,532, filed May 5, 2022, Ciaramella et al.
U.S. Appl. No. 17/583,674, filed Jan. 25, 2022, Besin et al.
U.S. Appl. No. 17/523,034, filed Nov. 10, 2021, Hoge et al.
U.S. Appl. No. 17/523,060, filed Nov. 10, 2021, Hoge et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 16/001,765, filed Jun. 6, 2018, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/483,012, filed Aug. 1, 2019, Mauger et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 18/055,193, filed Nov. 14, 2022, Ciaramella et al.
U.S. Appl. No. 16/494,130, filed Sep. 13, 2019, Ciaramella et al.
U.S. Appl. No. 17/823,255, filed Aug. 30, 2022, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 17/938,823, filed Oct. 7, 2022, Ciaramella et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/291,947, filed May 6, 2021, Ashburn et al.
U.S. Appl. No. 17/439,198, filed Sep. 14, 2021, Lusso et al.
U.S. Appl. No. 17/737,581, filed May 5, 2022, Panther et al.
U.S. Appl. No. 16/794,318, filed Feb. 19, 2020, Mauger et al.
U.S. Appl. No. 17/615,202, filed Nov. 30, 2021, Hopson.
U.S. Appl. No. 17/641,967, filed Mar. 10, 2022, John et al.
U.S. Appl. No. 17/840,478, filed Jun. 14, 2022, Kramarczyk et al.
U.S. Appl. No. 17/796,401, filed Jul. 29, 2022, Shaw et al.
U.S. Appl. No. 17/797,784, filed Aug. 5, 2022, Stewart-Jones et al.
U.S. Appl. No. 17/572,465, filed Jan. 10, 2022, Nachbagauer et al.
Danaei et al., Impact of Particle Size and Polydispersity Index on the Clinical Applications of Lipidic Nanocarrier Systems. Pharmaceutics. May 18, 2018;10(2):57. doi: 10.3390/pharmaceutics10020057.
Jayaraman et al., Maximizing the potency of siRNA lipid nanoparticles for hepatic gene silencing in vivo. Angew Chem Int Ed Engl. Aug. 20, 2012;51(34):8529-33. Epub Jul. 10, 2012. doi: 10.1002/anie. 201203263.
Li et al., Lipid-based nanoparticles for nucleic acid delivery. Pharm Res. Mar. 2007;24(3):438-49. doi: 10.1007/s11095-006-9180-5.
[No Author Listed], DMG-PEG 2000. Sigma-Aldrich. Accessed at https://www.sigmaaldrich.com/catalog/product/avanti/880151p?lang=en&region=us on Jan. 4, 2021, pp. 1-2. (Year: 2021).
Garcia-Manyes et al., Nanomechanics of lipid bilayers: heads or tails? J Am Chem Soc. Sep. 22, 2010;132(37):12874-86. doi: 10.1021/ja1002185.
Hoarau et al., Novel long-circulating lipid nanocapsules. Pharm Res. Oct. 2004;21(10):1783- 9. doi: 10.1023/b:pham.0000045229. 87844.21.
Iden et al., In vitro and in vivo comparison of immunoliposomes made by conventional coupling techniques with those made by a new post-insertion approach. Biochim Biophys Acta. Aug. 6, 2001;1513(2):207-16. doi: 10.1016/s0005-2736(01)00357-1.
Ishida et al., A combinatorial approach to producing sterically stabilized (Stealth) immunoliposomal drugs. FEBS Lett. Oct. 22, 1999;460(1):129-33. doi: 10.1016/s0014- 5793(99)01320-4.
Machlachlan, Chapter 9 Liposomal Formulations for Nucleic Acid Delivery. Retrieved from the Internet on Aug. 10, 2020 from http://arbutusbio.com/docs/Liposome_Formulations_Proof_for_Distribution.pdf; originally published 2007, pp. 237-270.
Perouzel et al., Synthesis and formulation of neoglycolipids for the functionalization of liposomes and lipoplexes. Bioconjug Chem. Sep.-Oct. 2003;14(5):884-98. doi: 10.1021/bc034068q.
Perrier et al., Post-insertion into Lipid NanoCapsules (LNCs): From experimental aspects to mechanisms. Int J Pharm. Aug. 30, 2010;396(1-2):204-9. doi: 10.1016/j.ijpharm.2010.06.019.Epub Jun. 1, 20109.
Santos et al., Design of peptide-targeted liposomes containing nucleic acids. Biochim Biophys Acta. Mar. 2010;1798(3):433-41. doi: 10.1016/j.bbamem.2009.12.001. Epub Dec. 11, 2009.

(56) References Cited

OTHER PUBLICATIONS

Sugiyama et al., Change in the character of liposomes as a drug carrier by modifying various polyethyleneglycol-lipids. Biol Pharm Bull. 2013;36(6):900-6. doi: 10.1248/bpb.b13-00084.
Wang et al., Delivery of oligonucleotides with lipid nanoparticles. Adv Drug Deliv Rev. Jun. 29, 2015;87:68-80. doi: 10.1016/j.addr. 2015.02.007. Epub Feb. 2, 20157.
Wang et al., Encapsulating protein into preformed liposomes by ethanol-destabilized method. Artif Cells Blood Substit Immobil Biotechnol. Aug. 2003;31(3):303-12. doi: 10.1081/bio-120023160.
Xu et al., Enhanced pH-Responsiveness, Cellular Trafficking, Cytotoxicity and Long-circulation of PEGylated Liposomes with Post-insertion Technique Using Gemcitabine as a Model Drug. Pharm Res. Jul. 2015;32(7):2428-38. doi: 10.1007/s11095-015-1635-0. Epub Feb. 6, 2015.
U.S. Appl. No. 18/161,857, filed Jan. 30, 2023, Smith.
U.S. Appl. No. 17/253,034, filed Nov. 10, 2021, Hoge et al.
U.S. Appl. No. 17/253,060, filed Nov. 10, 2021, Hoge et al.
U.S. Appl. No. 17/830,742, filed Jun. 2, 2022, Miracco.
U.S. Appl. No. 17/852,974, filed Jun. 29, 2022, Marquardt et al.
U.S. Appl. No. 16/483,012, filed Aug. 1, 2019, Manger et al.
U.S. Appl. No. 18/093,119, filed Jan. 4, 2023, Mauger et al.
U.S. Appl. No. 17/350,662, filed Jun. 17, 2021, Rabideau et al.
U.S. Appl. No. 16/639,265, filed Feb. 14, 2020, Issa et al.
U.S. Appl. No. 16/639,305, filed Feb. 14, 2020 Issa et al.
U.S. Appl. No. 16/639,403, filed Feb. 14, 2020, Hoge et al.
U.S. Appl. No. 17/438,049, filed Sep. 10, 2021, Elich et al.
U.S. Appl. No. 17/634,939, filed Feb. 11, 2022, Shamashkin et al.
U.S. Appl. No. 17/816,696, filed Aug. 1, 2022, Dousis et al.
U.S. Appl. No. 16/974,318, filed Feb. 19, 2020, Mauger et al.
U.S. Appl. No. 17/761,420, filed Mar. 17, 2022, Amato et al.
U.S. Appl. No. 17/145,164, filed Jan. 8, 2021, Giessel et al.
U.S. Appl. No. 18/008,139, filed Dec. 2, 2022, Smith et al.
U.S. Appl. No. 17/926,353, filed Nov. 18, 2022, Brader et al.
U.S. Appl. No. 17/925,114, filed Nov. 14, 2022, White et al.
U.S. Appl. No. 17/726,971, filed Apr. 22, 2022, Hennessy.
U.S. Appl. No. 17/925,125, filed Nov. 14, 2022, White et al.
U.S. Appl. No. 18/085,457, filed Dec. 20, 2022, Joyal et al.
Erik Oude Blenke Intracellular delivery of RNA therapeutics with lipid nanoparticles 2017 Utrecht Insitute for Pharmaceutical Sciences (UIPS), Utrecht, the Netherlands.†
Blenke, Intracellular delivery of RNA therapeutics with lipid nanoparticles, Publicly available as of Jan. 2017 by Department of Pharmaceutics, Utrecht Insitute for Pharmaceutical Sciences (UIPS), Faculty of Science, Utrecht, the Netherlands.†

\* cited by examiner
† cited by third party

SEQUENCE LISTING

```
<160> NUMBER OF SEQ ID NOS: 66

<210> SEQ ID NO 1
<211> LENGTH: 47
<212> TYPE: RNA
<213> ORGANISM: Artificial Sequence
<220> FEATURE:
```

<223> OTHER INFORMATION: Synthetic Polynucleotide

<400> SEQUENCE: 1
gggaaauaag agagaaaaga agaguaagaa gaaauauaag agccacc    47

<210> SEQ ID NO 2
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 2
gggagaucag agagaaaaga agaguaagaa gaaauauaag agccacc    47

<210> SEQ ID NO 3
<211> LENGTH: 114
<212> TYPE: RNA
<213> ORGANISM: Artificial Sequence
<220> FEATURE:
<223> OTHER INFORMATION: Synthetic Polynucleotide

<400> SEQUENCE: 3
acaaacgaau cucaagcaau caagcauucu acuucuauug cagcaauuua aaucauuucu    60
uuuaaagcaa aagcaauuuu cugaaaauuu ucaccauuua cgaacgauag caac    114

<210> SEQ ID NO 4
<211> LENGTH: 42
<212> TYPE: RNA
<213> ORGANISM: Artificial Sequence
<220> FEATURE:
<223> OTHER INFORMATION: Synthetic Polynucleotide

<400> SEQUENCE: 4
gggagacaag cuuggcauuc cgguacuguu gguaaagcca cc    42

<210> SEQ ID NO 5
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 5
gggagaucag agagaaaaga agaguaagaa gaaauauaag agccacc    47

<210> SEQ ID NO 6
<211> LENGTH: 145
<212> TYPE: RNA
<213> ORGANISM: Artificial Sequence
<220> FEATURE:
<223> OTHER INFORMATION: Synthetic Polynucleotide

<400> SEQUENCE: 6
ggaauaaaag ucucaacaca acauauacaa aacaaacgaa ucucaagcaa ucaagcauuc    60
uacuucuauu gcagcaauuu aaaucauuuc uuuuaaagca aaagcaauuu ucugaaaauu    120
uucaccauuu acgaacgaua gcaac    145

<210> SEQ ID NO 7
<211> LENGTH: 42
<212> TYPE: RNA
<213> ORGANISM: Artificial Sequence
<220> FEATURE:
<223> OTHER INFORMATION: Synthetic Polynucleotide

```
<400> SEQUENCE: 7
gggagacaag cuuggcauuc cgguacuguu gguaaagcca cc                    42

<210> SEQ ID NO 8
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 8
gggaauuaac agagaaaaga agaguaagaa gaaauauaag agccacc               47

<210> SEQ ID NO 9
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 9
gggaaauuag acagaaaaga agaguaagaa gaaauauaag agccacc               47

<210> SEQ ID NO 10
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 10
gggaaauaag agaguaaaga acaguaagaa gaaauauaag agccacc               47

<210> SEQ ID NO 11
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 11
gggaaaaaag agagaaaaga agacuaagaa gaaauauaag agccacc               47

<210> SEQ ID NO 12
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 12
gggaaauaag agagaaaaga agaguaagaa gauauauaag agccacc               47

<210> SEQ ID NO 13
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 13
gggaaauaag agacaaaaca agaguaagaa gaaauauaag agccacc               47

<210> SEQ ID NO 14
```

```
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 14
gggaaauuag agaguaaaga acaguaagua gaauuaaaag agccacc          47

<210> SEQ ID NO 15
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 15
gggaaauaag agagaauaga agaguaagaa gaaauauaag agccacc          47

<210> SEQ ID NO 16
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 16
gggaaauaag agagaaaaga agaguaagaa gaaaauuaag agccacc          47

<210> SEQ ID NO 17
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 17
gggaaauaag agagaaaaga agaguaagaa gaaauuuaag agccacc          47

<210> SEQ ID NO 18
<211> LENGTH: 92
<212> TYPE: RNA
<213> ORGANISM: Artificial Sequence
<220> FEATURE:
<223> OTHER INFORMATION: Synthetic Polynucleotide

<400> SEQUENCE: 18
ucaagcuuuu ggacccucgu acagaagcua auacgacuca cuauagggaa auaagagaga    60
aaagaagagu aagaagaaau auaagagcca cc                                 92

<210> SEQ ID NO 19
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 19
ugauaauagu ccauaaagua ggaaacacua cagcuggagc cucgguggcc augcuucuug    60
ccccuugggc cuccccccag ccccuccucc ccuuccugca cccguacccc cguggucuuu   120
gaauaaaguc ugaguggggcg gc                                           142

<210> SEQ ID NO 20
<211> LENGTH: 142
```

```
<212> TYPE: RNA
<213> ORGANISM: Artificial Sequence
<220> FEATURE:
<223> OTHER INFORMATION: Synthetic Polynucleotide

<400> SEQUENCE: 20
ugauaauagg cuggagccuc gguggcucca uaaaguagga aacacuacac augcuucuug      60
ccccuugggc ucccccccag ccccuccucc ccuuccugca cccguacccc cguggucuuu     120
gaauaaaguc ugagugggcg gc                                              142

<210> SEQ ID NO 21
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 21
ugauaauagg cuggagccuc gguggccaug cuucuugccc cuuccauaaa guaggaaaca      60
cuacaugggc ucccccccag ccccuccucc ccuuccugca cccguacccc cguggucuuu     120
gaauaaaguc ugagugggcg gc                                              142

<210> SEQ ID NO 22
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 22
ugauaauagg cuggagccuc gguggccaug cuucuugccc cuugggccuc ccccagucc       60 auaaaguagg aaacacuaca ccccuccucc ccuuccugca cccguacccc cguggucuuu     120
gaauaaaguc ugagugggcg gc                                              142

<210> SEQ ID NO 23
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 23
ugauaauagg cuggagccuc gguggccaug cuucuugccc cuugggccuc ccccagccc       60 cucccccccu ucccauaaa guaggaaaca cuacacugca cccguacccc cguggucuuu      120
gaauaaaguc ugagugggcg gc                                              142

<210> SEQ ID NO 24
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 24
ugauaauagg cuggagccuc gguggccaug cuucuugccc cuugggccuc ccccagccc       60 cucccccccu uccugcaccc guaccccuc cauaaaguag gaaacacuac aguggucuuu      120
gaauaaaguc ugagugggcg gc                                              142

<210> SEQ ID NO 25
```

```
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 25
ugauaauagg cuggagccuc gguggccaug cuucuugccc cuugggccuc ccccagccc      60 cuccucccu uccugcaccc guaccccgu ggucuuugaa uaaaguucca uaaaguagga     120
aacacuacac ugagugggcg gc                                            142

<210> SEQ ID NO 26
<211> LENGTH: 371
<212> TYPE: RNA
<213> ORGANISM: Artificial Sequence
<220> FEATURE:
<223> OTHER INFORMATION: Synthetic Polynucleotide

<400> SEQUENCE: 26
gcgccugccc accugccacc gacugcugga acccagccag ugggagggcc uggcccacca      60
gaguccugcu cccucacucc ucgccccgcc cccuguccca gaguccccacc uggggggcucu  120 cuccacccuu cucagaguuc caguuucaac cagaguucca accaaugggc uccauccucu    180
ggauucuggc caaugaaaua ucucccuggc agguccucu ucuuuuccca gagcuccacc    240
ccaaccagga gcucuaguua auggagagcu cccagcacac ucggagcuug gcuuugucu     300 ccacgcaaag cgauaaauaa aagcauuggu ggccuuuggu cuugaauaa agccugagua    360 ggaagucuag a                                                         371

<210> SEQ ID NO 27
<211> LENGTH: 568
<212> TYPE: RNA
<213> ORGANISM: Artificial Sequence
<220> FEATURE:
<223> OTHER INFORMATION: Synthetic Polynucleotide

<400> SEQUENCE: 27
gccccugccg cucccacccc cacccaucug ggccccgggu caagagaga gcggggucug      60 aucucgugua gccauauaga guuugcuucu gagugucugc uuuguuuagu agaggugggc   120
aggaggagcu gaggggcugg ggcuggggug uugaaguugg cuugcaugc ccagcgaugc    180 gccucccugu gggaugucau cacccuggga accgggagug gcccuuggcu cacuguguuc   240
ugcaugguuu ggaucugaau uaauugccu uucuucuaaa ucccaaccga acuucuucca    300
accuccaaac uggcuguaac cccaaauccca agccauuaac uacaccugac aguagcaauu  360
gucugauuaa ucacuggccc cuugaagaca gcagaaaugc ccuuugcaau gaggaggaga   420
ucugggcugg gcgggccagc ugggagagca uuugacuauc uggaacuugu gugugccucc   480
ucagguaugg cagugacuca ccugguuuua auaaacaac cugcaacauc caugucucuu    540
ugaauaaagc cugaguagga agucuaga                                      568

<210> SEQ ID NO 28
<211> LENGTH: 289
<212> TYPE: RNA
<213> ORGANISM: Artificial Sequence
<220> FEATURE:
<223> OTHER INFORMATION: Synthetic Polynucleotide

<400> SEQUENCE: 28
acacacucca ccuccagcac gcgacuucuc aggacgacga aucuucucaa ugggggggcg      60
```

```
gcugagcucc agccaccccg cagucacuuu cuuuguaaca acuuccguug cugccaucgu    120
aaacugacac aguguuuaua acguguacau acauuaaccu auuaccucau uuuguuauuu    180
uucgaaacaa agcccugugg aagaaaaugg aaaacuugaa gaagcauuaa agucauucug    240
uuaagcugcg uaaauggucu uugaauaaag ccgaguuagg aagucuaga                289
```

<210> SEQ ID NO 29
<211> LENGTH: 379
<212> TYPE: RNA
<213> ORGANISM: Artificial Sequence
<220> FEATURE:
<223> OTHER INFORMATION: Synthetic Polynucleotide

<400> SEQUENCE: 29

```
caucacauuu aaaagcaucu cagccuacca ugagaauaag agaaagaaaa ugaagaucaa    60
aagcuuauuc aucuguuuuu cuuuuucguu ggucuaaagc caacacccug ucuaaaaaac   120
auaaauuucu uuaaucauuu ugccucuuuu cucugugcuu caauuaauaa aaaauggaaa   180
gaaucuaaua gaguggauca gcacuguuau uuucaaaga uguguugcua uccugaaaau    240
ucuuaagguu cuguggaagu uccaguguuc ucucuuauuc cacuucggua gaggauuucu    300
aguuucuugu gggcuaauua aauaaaucau uaauacucuu cuaauggucu uugaauaaag    360
ccgaguuagg aagucuaga                                                  379
```

<210> SEQ ID NO 30
<211> LENGTH: 118
<212> TYPE: RNA
<213> ORGANISM: Artificial Sequence
<220> FEATURE:
<223> OTHER INFORMATION: Synthetic Polynucleotide

<400> SEQUENCE: 30

```
gcugccuucu gcggggcuug ccuucuggcc augcccuucu ucucucccuu gcaccuguac    60
cucuuggucu uugaauaaag ccgaguuagg aaggcggccg cucgagcaug caucuaga     118
```

<210> SEQ ID NO 31
<211> LENGTH: 908
<212> TYPE: RNA
<213> ORGANISM: Artificial Sequence
<220> FEATURE:
<223> OTHER INFORMATION: Synthetic Polynucleotide

<400> SEQUENCE: 31

```
gccaagcccu ccccauccca uguauuuauc ucuauuuaau auuuaugucu auuuaagccu    60
cauauuuaaa gacagggaag agcagaacgg agccccaggc cucuguqucc uucccugcau   120 uucugaguuu cauucuccug ccguagcag ugagaaaaag cuccuguccu cccauccccu    180
ggacugggag guagauaggu aaauaccaag uauuuauuac uaugacugcu ccccagcccu    240
ggcucugcaa ugggcacugg gaugagccgc ugugagcccc ugguccugag ggucccaccu    300
ugggacccuu gagaguauca ggucucccac guggagaca agaaauccccu guuuaauauu    360 uaaacagcag uguuccccau cugggucccuu gcaccccuca cucuggccuc agccgacugc    420
acagcggccc cugcaucccc uuggcuguga ggccccugga caagcagagg uggcagagc    480 ugggaggcau ggcccugggg ucccacgaau uugcugggga aucucguuuu ucuucuuaag    540
acuuuuggga caugguuuga cucccgaaca ucaccgacgc gucuccuguu uuucggggug    600
gccucgggac accugcccug cccccacgag ggucaggacu gugacucuuu uuaagggccag    660
```

| | |
|---|---|
| gcaggugccu ggacauuugc cuugcuggac ggggacuggg gaugugggag ggagcagaca | 720 |
| ggaggaauca ugucaggccu gugugugaaa ggaagcucca cugucacccu ccaccucuuc | 780 |
| accccccacu caccaguguc ccuccacug ucacauugua acugaacuuc aggauaauaa | 840 |
| aguguuugcc uccauggucu uugaauaaag ccugaguagg aaggcggccg cucgagcaug | 900 |
| caucuaga | 908 |

<210> SEQ ID NO 32
<211> LENGTH: 835
<212> TYPE: RNA
<213> ORGANISM: Artificial Sequence
<220> FEATURE:
<223> OTHER INFORMATION: Synthetic Polynucleotide

<400> SEQUENCE: 32

| | |
|---|---|
| acucaaucua aauuaaaaaa gaaagaaauu ugaaaaaacu uucucuuugc cauuucuucu | 60 |
| ucuucuuuuu uaacugaaag cugaauccuu ccauuucuuc ugcacaucua cuugcuuaaa | 120 |
| uuguggggcaa aagagaaaaa gaaggauuga ucagagcauu gugcaauaca guuucauuaa | 180 |
| cuccuucccc cgcuccccca aaaauuugaa uuuuuuuuuc aacacucuua caccuguuau | 240 |
| ggaaaauguc aaccuuugua agaaaaccaa aauaaaaauu gaaaaauaaa aaccauaaac | 300 |
| auuugcacca cuuguggcuu uugaauaucu uccacagagg gaaguuuaaa acccaaacuu | 360 |
| ccaaagguuu aaacuaccuc aaaacacuuu cccaugagug uauccacau uguuaggugc | 420 |
| ugaccuagac agagaugaac ugagguccuu guuuguuuu guucauaaua caaaggugcu | 480 |
| aauuaauagu auuucagaua cuugaagaau guugauggu cuagaagaau uugagaagaa | 540 |
| auacuccugu auugaguugu aucguguggu guauuuuua aaaauuuga uuuagcauuc | 600 |
| auauuuucca ucuuauuccc aauuaaaagu augcagauua uuugcccaaa ucuucuucag | 660 |
| auucagcauu uguucuuugc cagucucauu uucaucuucu uccauggguuc cacagaagcu | 720 |
| uuguuucuug ggcaagcaga aaaauuaaau uguaccuauu uuguauaugu gagauguuua | 780 |
| aauaaauugu gaaaaaaaug aaauaaagca uguugguuu uccaaaagaa cauau | 835 |

<210> SEQ ID NO 33
<211> LENGTH: 297
<212> TYPE: RNA
<213> ORGANISM: Artificial Sequence
<220> FEATURE:
<223> OTHER INFORMATION: Synthetic Polynucleotide

<400> SEQUENCE: 33

| | |
|---|---|
| cgccgccgcc cgggccccgc agucgagggu cgugagccca ccccguccau ggugcuaagc | 60 |
| gggcccgggu cccacacggc cagcaccgcu gcucacucgg acgacgcccu gggccugcac | 120 |
| cucuccagcu ccucccacgg ggucccgua gccccggccc ccgcccagcc ccaggucucc | 180 |
| ccaggcccuc cgcaggcugc ccggccuccc ucccccugca gccaucccaa ggcuccugac | 240 |
| cuaccuggcc ccugagcucu ggagcaagcc cugacccaau aaaggcuuug aacccau | 297 |

<210> SEQ ID NO 34
<211> LENGTH: 602
<212> TYPE: RNA
<213> ORGANISM: Artificial Sequence
<220> FEATURE:
<223> OTHER INFORMATION: Synthetic Polynucleotide

<400> SEQUENCE: 34

| | |
|---|---|
| ggggcuagag cccucuccgc acagcgugga gacggggcaa ggagggggu uauuaggauu | 60 |

| | |
|---|---:|
| ggugguuuug uuuugcuuug uuuaaagccg ugggaaaaug gcacaacuuu accucugugg | 120 |
| gagaugcaac acugagagcc aaggggguggg aguugggaua auuuuauau aaagaaguu | 180 |
| uuuccacuuu gaauugcuaa aaguggcauu uuccuaugu gcagcacuc cucucauuuc | 240 |
| uaaaauaggg acguggccag gcacgguggc ucaugccugu aaucccagca cuuugggagg | 300 |
| ccgaggcagg cggcucacga ggucaggaga ucgagacuau ccuggcuaac acgguaaaac | 360 |
| ccugucucua cuaaaaguac aaaaaauuag cugggcgugg ugugggcac cuguagcccc | 420 |
| agcuacucgg gaggcugagg caggagaaag gcaugaaucc aagaggcaga gcuugcagug | 480 |
| agcugagauc acgccauugc acuccagccu gggcaacagu guuaagacuc ugucucaaau | 540 |
| auaaauaaau aaauaaauaa auaaauaaau aaauaaaaau aaagcgagau guugcccuca | 600 |
| aa | 602 |

<210> SEQ ID NO 35
<211> LENGTH: 785
<212> TYPE: RNA
<213> ORGANISM: Artificial Sequence
<220> FEATURE:
<223> OTHER INFORMATION: Synthetic Polynucleotide

<400> SEQUENCE: 35

| | |
|---|---:|
| ggcccugccc cgucggacug cccccagaaa gccuccugcc cccugccagu gaagucccuuc | 60 |
| agugagcccc ucccagcca gcccuuccccu ggccccgccg gauguauaaa uguaaaaaug | 120 |
| aaggaauuac auuuauaug ugagcgagca agccggcaag cgagcacagu auuauuucuc | 180 |
| caucccccucc cugccugcuc cuuggcaccc ccaugcugcc uucagggaga caggcaggga | 240 |
| gggcuugggg cugcacccucc uacccuccca ccagaacgca ccccacuggg agagcuggug | 300 |
| gugcagccuu ccccucccug uauaagacac uuugccaagg cucuccccuc ucgcccccauc | 360 |
| ccugcuugcc cgcucccaca gcuuccugag ggcuaauucu gggaagggag aguucuuugc | 420 |
| ugccccuguc uggaagacgu ggcucugggu gagguaggcg ggaaaggaug gaguguuuua | 480 |
| guucuugggg gaggccacccc caaacccccag ccccaacucc aggggcaccu augagauggc | 540 |
| caugcucaac ccccccuccca gacaggcccu cccugucccc agggccccca ccgagguucc | 600 |
| cagggcugga gacuuccucu gguaaacauu ccuccagccu cccucccccu ggggacgcca | 660 |
| aggaggugggg ccacacccag gaagggaaag cgggcagccc cguuuugggg acgugaacgu | 720 |
| uuuaauaauu uuugcugaau uccuuuacaa cuaaauaaca cagauauugu uauaauaaa | 780 |
| auugu | 785 |

<210> SEQ ID NO 36
<211> LENGTH: 3001
<212> TYPE: RNA
<213> ORGANISM: Artificial Sequence
<220> FEATURE:
<223> OTHER INFORMATION: Synthetic Polynucleotide

<400> SEQUENCE: 36

| | |
|---|---:|
| auauuaagga ucaagcuguu agcuaauauu gccaccucug caguuuuggg aacaggcaaa | 60 |
| uaaaguauca guauacaugg ugauacau cuguagcaaa gcucuggag aaaaugaaga | 120 |
| cugaagaaag caaagcaaaa acuguauaga gagauuuuuc aaaagcagua auccccucaau | 180 |
| uuuaaaaag gauugaaaau ucuaaaugu uuucugugca uauuuuugu guuaggaauc | 240 |
| aaaaguauuu uauaaaagga gaaagaacag ccucauuuua gauguagucc uguuggauuu | 300 |

```
uuuaugccuc cucaguaacc agaaauguuu uaaaaaacua aguguuuagg auuucaagac    360
aacauuauac auggcucuga aauaucugac acaauguaaa cauugcaggc accugcauuu    420
uauguuuuuu uuuucaacaa augugacuaa uuugaaacuu uaugaacuu cugagcuguc    480
cccuugcaau ucaaccgcag uuugaauuaa ucauaucaaa ucaguuuaa uuuuuaaau     540
uguacuucag agucuauauu ucaagggcac auuuucucac uacuauuuua auacauuaaa   600
ggacuaaaua aucuuucaga gaugcuggaa acaaacauu ugcuuauau guuucauuag     660
aauaccaaug aaacauacaa cuugaaaauu aguaauagua uuuugaaga ucccauuucu    720
aauuggagau cucuuuaauu ucgaucaacu uauaaugugu aguacuauau uaagugcacu   780
ugagguggaau ucaacauuug acuaauaaaa ugaguucauc auguuggcaa gugaugguggc 840
aauuaucucu ggugacaaaa gaguaaaauc aaauauuucu gccguuaca aauaucaagg   900
aagaccugcu acuaugaaau agaugacauu aaucugucuu cacguuuau aauacggaug   960
gauuuuuuuu caaaucagug uguguuuuga ggucuuaugu aauugaugac auuugagaga  1020
aauggugcu uuuuuuagcu accucuuugu ucauuuaagc accaguaaag aucaugucuu   1080
uuuauagaag uguagauuuu cuuugugacu ugcuaucgu gccuaaagcu cuaaauauag   1140
gugaaugugu gaugaauacu caguuauuu gucucucuau auaauuaguu ugguacuaag   1200
uuucucaaaa aauuauuaac acaugaaaga caaucucuaa accagaaaaa gaaguaguac  1260
aaauuuuguu acuguaaugc ucgcguuuag ugaguuuaaa acacacagua ucuuuuggu    1320
uuauaaucag uuucuauuu gcugugccug agauuaagau cuguguaugu guguguguguu  1380
gugugugcgu uugugguuua agcagaaaaa gacuuuuuua aaaguuuuaa gugauaaaug   1440
caauuuguua auugaucuua gaucacuagu aaacucaggg cugaauuaua ccauguauau  1500
ucuauuagaa gaaaguaaac accaucuuua uccugcccu uuuucuucuc ucaaaguagu   1560
uguaguuaua ucuagaaaga agcaauuuug auuucuugaa aagguaguuc cugcacucag  1620
uuuaaacuaa aaauaaucau acuuggauuu auuuauuuu ugucauagua aaauuuuaa    1680
uuuauauaua uuuuuauuua guauuaucuu auucuuugcu auuugccaau ccuuugucau  1740
caauugugu aaaugaauug aaaauucaug cccuguucau uuuauuuuac uuuauugguu  1800
aggauauuua aaggauuuuu guauauauaa uuucuuaaau uaauauucca aaagguuagu  1860
ggacuuagau uauaaauuau ggcaaaaauc uaaaaacaac aaaaaugauu uuuauacauu  1920
cuauuucauu auccucuuu uuccaauaag ucauacaauu gguagauaug acuuauuuua   1980
uuuuuguauu auucacuaua ucuuuaugau auuuaaguau aaauaauuaa aaaaauuuau  2040
uguaccuuau agucugucac caaaaaaaaa aaauuaucug uagguaguga aaugcuaaug  2100
uugauuuguc uuuaagggcu uguuaacuau ccuuuauuuu ucacuuuguc uuaaauuagg  2160
aguuugguguu uaauuacuc aucuaagcaa aaaauguaua uaaaucccau acuggguau   2220
auacccaaag gauuauaaau caugcugcua uaaagacaca ugcacgcua uguuauugc    2280
agcacuauuc acaauagcaa agacuuggaa ccaacccaaa uguccaucaa ugauagacuu  2340
gauuaagaaa augugcacau auacaccaug gaauacuaug cagccauaaa aaaggaugag   2400
uucaugcccu uuguagggac auggauaaag cuggaaacca ucauucgag caaacuauug    2460
caaggacaga aaaccaaaca cugcauguuc ucacucauag ugggaauug aacaaugaga    2520
acacuuggac acaaggugg gaacaccaca caccagggcc ugucaugggg uggggggagu   2580
gggagggau agcauuagga gauauaccua auguaaauga ugaguaaaug ggucagcac    2640
accaacaugg cacauguaua cauauguagc aaaccugcac guugugcaca uguacccuag  2700
```

-continued

```
aacuuaaagu auaauuaaaa aaaaaaagaa aacagaagcu auuuauaaag aaguuauuug    2760
cugaaauaaa ugugaucuuu cccauuaaaa aauaaagaa auuuggggu aaaaaaacac      2820 aauauauugu auucuugaaa aauucuaaga gaguggaugu gaaguguucu caccacaaaa    2880
gugauaacua auugagguaa ugcacauauu aauuagaaag auuuugucau uccacaaugu    2940
auauauacuu aaaaauaugu uauacacaau aaauacauac auuaaaaaau aaguaaaugu    3000
a                                                                    3001
```

<210> SEQ ID NO 37
<211> LENGTH: 1037
<212> TYPE: RNA
<213> ORGANISM: Artificial Sequence
<220> FEATURE:
<223> OTHER INFORMATION: Synthetic Polynucleotide

<400> SEQUENCE: 37

```
cccacccugc acgccggcac caaacccugu ccucccaccc cuccccacuc aucacuaaac      60
agaguaaaau gugaugcgaa uuuucccgac caaccugauu cgcuagauuu uuuuuaagga    120
aaagcuugga aagccaggac acaacgcugc ugccugcuuu gugcagggdc uccggggcu      180 cagcccugag uuggcaucac cugcgcaggg cccucgggg cucagcccug agcuagloguc    240 accugcacag ggcccucuga ggcucagccc ugagcuggcg ucaccugugc agggcccucu    300
ggggcucagc ccugagcugg ccucaccugg guucccacc ccgggcucuc cugcccugcc    360
cuccugcccg cccucccucc ugccugcgca gcuccuuccc uaggcaccuc ugugcugcau    420
cccaccagcc ugagcaagac gcccucucgg ggccugugcc gcacuagccu cccucuccuc    480 ugucccccaua gcugguuuuu cccaccaauc cucaccuaac aguuacuuua caauuaaacu    540
caaagcaagc ucuucuccuc agcuuggggc agccauuggc cucugucucg uuuugggaaa    600
ccaaggucag gaggccguug cagacauaaa ucucggcgac ucggccccgu ucccugaggg    660
uccugcuggu gaccggccug gaccuuggcc cuacagcccu ggaggccgcu gcugaccagc    720
acugaccccg accucagaga guacucgcag gggcgcuggc ugcacucaag acccucgaga    780
uuaacggugc uaaccccguc ugcuccuccc ucccgcagag acuggggccu ggacuggaca    840
ugagagccCC uugggugcca agagggcugu gucuuacuag aaacaacgca aaccucuccu    900
uccucagaau agugaugugu ucgacguuuu aucaaaggcc cccuuucuau guucauguua    960
guuuugcucc uucuguguuu uuucgaac cauauccaug uugcugacuu uccaaauaa     1020 agguuuucac uccucuc                                                  1037
```

<210> SEQ ID NO 38
<211> LENGTH: 577
<212> TYPE: RNA
<213> ORGANISM: Artificial Sequence
<220> FEATURE:
<223> OTHER INFORMATION: Synthetic Polynucleotide

<400> SEQUENCE: 38

```
agaggccugc cuccagggcu ggacugaggc cugagcgcuc cugccgcaga gcuggccgcg      60
ccaaauaaug ucucugugag acucgagaac uuucauuuuu uuccaggcug guucggauuu    120
gggguggauu uugguuugu ucccccuccuc cacucuccc caccccucc ccgcccuuuu      180 uuuuuuuuu uuuuaaacug guauuuuauc uuugauucuc cuucagcccu caccccuggu    240
ucucaucuuu cuugaucaac aucuuuucuu gccucugucc ccuucucuca ucucuuagcu    300
```

| | |
|---|---|
| cccccuccaac cugggggggca guggugugga gaagccacag gccugagauu ucaucugcuc | 360 |
| uccuuccugg agcccagagg agggcagcag aaggggggugg ugucuccaac cccccagcac | 420 |
| ugaggaagaa cggggcucuu cucauuucac cccucccuuu ucccccugcc cccaggacug | 480 |
| ggccacuucu ggguggggca guggguccca gauuggcuca cacugagaau guaagaacua | 540 |
| caaacaaaau uucuauuaaa uuaaauuuug ugucucc | 577 |

<210> SEQ ID NO 39
<211> LENGTH: 2212
<212> TYPE: RNA
<213> ORGANISM: Artificial Sequence
<220> FEATURE:
<223> OTHER INFORMATION: Synthetic Polynucleotide

<400> SEQUENCE: 39

| | |
|---|---|
| cucccuccau cccaaccugg cucccuccca cccaaccaac uucccccca acccggaaac | 60 |
| agacaagcaa cccaaacuga acccccucaa aagccaaaaa augggagaca auuucacaug | 120 |
| gacuuuggaa aauauuuuuu uccuuugcau ucaucucuca aacuuaguuu uuaucuuga | 180 |
| ccaaccgaac augaccaaaa accaaaagug cauucaaccu uaccaaaaaa aaaaaaaaaa | 240 |
| aaagaauaaa uaaauaacuu uuuaaaaaag gaagcuuggu ccacugcuu gaagacccau | 300 |
| gcggggguaa gucccuuucu gcccguuggg cuuaugaaac cccaaugcug cccuuucugc | 360 |
| uccuuucucc acaccccccu uggggccucc ccuccacucc uucccaaauc uguccccca | 420 |
| gaagacacag gaaacaaugu auugucugcc cagcaaucaa aggcaaugcu caaacaccca | 480 |
| aguggccccc acccucagcc cgcuccugcc cgcccagcac cccaggcccc uggggggaccu | 540 |
| ggggguucuca gacugccaaa gaagccuugc caucuggcgc ucccauggcu cuugcaacau | 600 |
| cuccccuucg uuuuugaggg ggucaugccg ggggagccac cagccccuca cuggguucgg | 660 |
| aggagaguca ggaagggcca cgacaaagca gaaacaucgg auuuggggaa cgcgugucaa | 720 |
| ucccuugugc cgcagggcug ggcgggagag acuguucugu ccuugugua acuguguugc | 780 |
| ugaaagacua ccucguucuu gucuugaugu gucaccgggg caacugccug ggggcgggga | 840 |
| uggggggcagg guggaagcgg cuccccauuu uauaccaaag gugcuacauc uaugugaugg | 900 |
| guggggugggg gagggaauca cuggugcuau agaaauugag augccccccc aggccagcaa | 960 |
| auguuccuuu uuguucaaag ucuauuuuua uccuugaua uuuuucuuuu uuuuuuuuu | 1020 |
| uuuuugugga uggggacuug ugaauuuuuc uaaaggugcu auuaacaug ggaggagagc | 1080 |
| gugugcggcu ccagcccagc ccgcugcuca cuuccacccc ucuccaccc ugccucuggc | 1140 |
| uucucaggcc ucugcucucc gaccucucuc cucugaaacc cucuccaca gcugcagccc | 1200 |
| auccucccgg cucccuccua gucuguccug cguccucugu cccgggguuu cagagacaac | 1260 |
| ucccaaagc acaaagcagu uuucccccu agggguggga ggaagcaaaa gacucuguac | 1320 |
| cuauuuugua uguguauaau aauuugagau guuuuuaauu auuuugauug cuggaauaaa | 1380 |
| gcauguggaa augacccaaa cauaauccgc aguggccucc uaauuccuu cuuuggaguu | 1440 |
| gggggagggg uagacauggg gaaggggcuu uggggugaug ggcuugccuu ccauuccugc | 1500 |
| ccuuucccuc cccacuauuc ucuucuagau cccuccauaa ccccacuccc cuuucucuca | 1560 |
| cccuucuuau accgcaaacc uuucuacuuc cuuucauu uucuauucuu gcaauuuccu | 1620 |
| ugcaccuuuu ccaaauccuc uucccccug caauaccaua caggcaaucc acgugcacaa | 1680 |
| cacacacaca cacucuucac aucuggggu guccaaaccu cauacccacu ccccuucaag | 1740 |
| cccauccacu cuccaccccc uggaugcccu gcacuuggug gcgguggau gcucauggau | 1800 |

| | |
|---|---|
| acugggaggg ugaggggagu ggaacccgug aggaggaccu ggggccucu ccuugaacug | 1860 |
| acaugaaggg ucaucuggcc ucugucccu ucucacccac gcugacccc ugccgaagga | 1920 |
| gcaacgcaac aggagagggg ucugcugagc cuggcgaggg ucuggaggg accaggagga | 1980 |
| aggcgugcuc ccugcucgcu guccggccc uggggagug agggagacag acaccuggga | 2040 |
| gagcugugg gaaggcacuc gcaccgugcu cugggaagg aaggagaccu ggcccugcuc | 2100 |
| accacggacu gggugccucg accuccugaa uccccagaac acaaccccc ugggcugggg | 2160 |
| uggucugggg aaccaucgug cccccgccuc cgccuacuc cuuuuaagc uu | 2212 |

<210> SEQ ID NO 40
<211> LENGTH: 729
<212> TYPE: RNA
<213> ORGANISM: Artificial Sequence
<220> FEATURE:
<223> OTHER INFORMATION: Synthetic Polynucleotide

<400> SEQUENCE: 40

| | |
|---|---|
| uuggccaggc cugacccucu uggaccuuuc uucuugccg acaaccacug cccagcagcc | 60 |
| ucugggaccu cggggucca gggaaccag uccagccucc uggcuguuga cuucccauug | 120 |
| cucuuggagc caccaaucaa agagauucaa agagauuccu gcaggccaga ggcggaacac | 180 |
| accuuuaugg cuggggcucu ccguggugu cuggacccag ccccuggaga caccauucac | 240 |
| uuuuacugcu uguagugac ucgugcucuc caaccugucu uccugaaaaa ccaaggcccc | 300 |
| cuucccccac cucuuccaug ggugagacu ugagcagaac aggggcuucc ccaaguugcc | 360 |
| cagaaagacu gucuggguga aagccaugg ccagagcuuc cccaggcac aggugugca | 420 |
| ccagggacuu cugcuucaag uuugggua aagacaccug gaucagacuc caagggcugc | 480 |
| ccugagucug ggacuucugc cuccauggcu ggucaugaga gcaaaccgua uccccugga | 540 |
| gacagcgacu ccagagaacc ucuugggaga cagaagaggc aucgugcac agcucgaucu | 600 |
| ucuacuugcc cugggggagg ggagugacag guccacacac cacacugggu cacccugucc | 660 |
| uggaugccuc ugaagagagg gacagaccgu cagaaacugg agaguucua uuaaagguca | 720 |
| uuuaaaccaa | 729 |

<210> SEQ ID NO 41
<211> LENGTH: 847
<212> TYPE: RNA
<213> ORGANISM: Artificial Sequence
<220> FEATURE:
<223> OTHER INFORMATION: Synthetic Polynucleotide

<400> SEQUENCE: 41

| | |
|---|---|
| uccuccggga ccccagcccu caggauuccu gaugcuccaa ggcgacugau gggcgcugga | 60 |
| ugaagugcca cagucagcuu cccuggggc uggugcaug uugggcuccu ggggcggggg | 120 |
| cacggccugg cauuucacgc auugcugcca ccccaggucc accugucucc acuuucacag | 180 |
| ccuccaaguc uguggcucuu cccuucuguc cuccgagggg cuugccuucu cucgugucca | 240 |
| gugaggugcu cagugaucgg cuuaacuuag agaagcccgc ccccucccu ucuccgucug | 300 |
| ucccaagagg gucugcucug agccugcguu ccuaggugcc ucggcucag cugccuggu | 360 |
| uguggccgcc cuagcauccu guaugcccac agcuacugga auccccgcug cugcuccggg | 420 |
| ccaagcuucu gguugauuaa ugagggcaug ggguggucc ucaagaccuu ccccuaccuu | 480 |
| uuguggaacc agugaugccu caaagacagu gucccucca cagcugggug ccaggggcag | 540 |

```
gggauccuca guauagccgg ugaacccuga uaccaggagc cugggccucc cugaaccccu    600
ggcuuccagc caucucaucg ccagccuccu ccuggaccuc uuggccccca gcccuuccc     660 cacacagccc cagaagggu c ccagagcuga ccccacucca ggaccuaggc ccagcccuc    720 agccucaucu ggagcccug aagaccaguc ccaccaccu uucugccuc aucgacacu        780 gcuccgcauc cugcugugug uccguuucca uguucgguu ccauccaaau acacuuucug     840
gaacaaa                                                              847
```

<210> SEQ ID NO 42
<211> LENGTH: 110
<212> TYPE: RNA
<213> ORGANISM: Artificial Sequence
<220> FEATURE:
<223> OTHER INFORMATION: Synthetic Polynucleotide

<400> SEQUENCE: 42

```
gcuggagccu cgguggccau gcuucuugcc ccuugggccu cccccagccc cuccuccccc    60
uuccugcacc cguaccccccg uggucuuuga auaaagcucg agugggcggc              110
```

<210> SEQ ID NO 43
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 43

```
ugauaauagg cuggagccuc gguggccuag cuucuugccc cuugggccuc ccccagccc     60 cuccuccccu uccugcaccc guaccccgu ggucuuugaa uaaagucuga gugggcggc     119
```

<210> SEQ ID NO 44
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 44

```
ugauaauagg cuggagccuc gguggccuag cuucuugccc cuugggccuc ccccagccc     60 cuccuccccu uccugcaccc guaccccccuc cauaaaguag gaaacacuac aguggucuuu   120
gaauaaaguc ugagugggcg gc                                            142
```

<210> SEQ ID NO 45
<211> LENGTH: 141
<212> TYPE: RNA
<213> ORGANISM: Artificial Sequence
<220> FEATURE:
<223> OTHER INFORMATION: Synthetic Polynucleotide

<400> SEQUENCE: 45

```
ugauaauagg cuggagccuc gguggccuag cuucuugccc cuugggccuc ccccagccc     60 cuccuccccu uccugcaccc guaccccccg cauuauuacu cacgguacga guggucuuug    120
aauaaagucu gagugggcgg c                                             141
```

<210> SEQ ID NO 46
<211> LENGTH: 164
<212> TYPE: RNA
<213> ORGANISM: Artificial Sequence
<220> FEATURE:
<223> OTHER INFORMATION: Synthetic Polynucleotide

<400> SEQUENCE: 46
ugauaauagu ccauaaagua ggaaacacua cagcuggagc cucgguggcc uagcuucuug    60
ccccuugggc ucccccccag ccccuccucc ccuuccugca cccguacccc ccgcauuauu    120
acucacggua cgaguggucu uugaauaaag ucgaguggg cggc    164

<210> SEQ ID NO 47
<211> LENGTH: 188
<212> TYPE: RNA
<213> ORGANISM: Artificial Sequence
<220> FEATURE:
<223> OTHER INFORMATION: Synthetic Polynucleotide

<400> SEQUENCE: 47
ugauaauagu ccauaaagua ggaaacacua cagcuggagc cucgguggcc uagcuucuug    60
ccccuugggc cuccauaaag uaggaaacac uacauccccc cagccccucc uccccuuccu    120
gcacccguac ccccuccaua aaguaggaaa cacuacagug ucuuugaau aaagucugag    180 ugggcggc    188

<210> SEQ ID NO 48
<211> LENGTH: 140
<212> TYPE: RNA
<213> ORGANISM: Artificial Sequence
<220> FEATURE:
<223> OTHER INFORMATION: Synthetic Polynucleotide

<400> SEQUENCE: 48
ugauaauagg cuggagccuc gguggccaug cuucuugccc cuugggccuc ccccagccc    60 cucccccu uccugcaccc guaccccag uagugcuuuc uacuuuaugg uggucuuuga    120
auaaagucug agugggcggc    140

<210> SEQ ID NO 49
<211> LENGTH: 181
<212> TYPE: RNA
<213> ORGANISM: Artificial Sequence
<220> FEATURE:
<223> OTHER INFORMATION: Synthetic Polynucleotide

<400> SEQUENCE: 49
ugauaauaga guagugcuuu cuacuuuaug gcuggagccu cgguggccau gcuucuugcc    60
ccuugggcca guagugcuuu cuacuuuaug uccccccagc cccucucccc uuccugcacc    120
cguaccccca guagugcuuu cuacuuuaug guggucuuug aauaaagucu gagugggcgg    180
c    181

<210> SEQ ID NO 50
<211> LENGTH: 184
<212> TYPE: RNA
<213> ORGANISM: Artificial Sequence
<220> FEATURE:
<223> OTHER INFORMATION: Synthetic Polynucleotide

<400> SEQUENCE: 50
ugauaauaga guagugcuuu cuacuuuaug gcuggagccu cgguggccau gcuucuugcc    60
ccuugggccu ccauaaagua ggaaacacua caucccccca gccccuccuc cccuuccugc    120
acccguaccc ccaguagugc uuucuacuuu auggugguucu uugaauaaag ucgagugggg    180
cggc    184

<210> SEQ ID NO 51
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 51
ugauaauagu ccauaaagua ggaaacacua cagcuggagc cucggugggcc uagcuucuug    60 ccccuugggc cuccccccag ccccuccucc ccuuccugca cccguacccc cguggucuuu   120
gaauaaaguc ugagugggcg gc                                             142

<210> SEQ ID NO 52
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 52
ugauaauagg cuggagccuc gguggcucca uaaaguagga aacacuacac uagcuucuug    60
ccccuugggc cuccccccag ccccuccucc ccuuccugca cccguacccc cguggucuuu   120
gaauaaaguc ugagugggcg gc                                             142

<210> SEQ ID NO 53
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 53
ugauaauagg cuggagccuc gguggccuag cuucuugccc cuugggccuc cauaaaguag    60
gaaacacuac auccccccag ccccuccucc ccuuccugca cccguacccc cguggucuuu   120
gaauaaaguc ugagugggcg gc                                             142

<210> SEQ ID NO 54
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 54
ugauaauagg cuggagccuc gguggccuag cuucuugccc cuugggccuc ccccagccc    60 cuccuccccu uccugcaccc guaccccac cccaucaca auuagcauua agugucuuu   120 gaauaaaguc ugagugggcg gc                                             142

<210> SEQ ID NO 55
<211> LENGTH: 188
<212> TYPE: RNA
<213> ORGANISM: Artificial Sequence
<220> FEATURE:
<223> OTHER INFORMATION: Synthetic Polynucleotide

<400> SEQUENCE: 55
ugauaauaga ccccuaucac aauuagcauu aagcuggagc cucggugggcc uagcuucuug    60 ccccuugggc cacccuauc acaauuagca uuaauccccc cagccccucc ucccuuccu   120 gcacccguac ccccaccccu aucacaauua gcauuaagug gucuuugaau aaagucugag   180

```
ugggcggc                                                                188
```

<210> SEQ ID NO 56
<211> LENGTH: 188
<212> TYPE: RNA
<213> ORGANISM: Artificial Sequence
<220> FEATURE:
<223> OTHER INFORMATION: Synthetic Polynucleotide

<400> SEQUENCE: 56

```
ugauaauaga ccccuaucac aauuagcauu aagcuggagc cucgguggcc uagcuucuug         60
ccccuugggc cuccauaaag uaggaaacac uacauccccc cagccccucc ucccuuccu         120 gcacccguac ccccacccccu aucacaauua gcauuaagug gucuuugaau aaagucugag        180
ugggcggc                                                                188
```

<210> SEQ ID NO 57
<211> LENGTH: 10
<212> TYPE: RNA
<213> ORGANISM: Artificial Sequence
<220> FEATURE:
<223> OTHER INFORMATION: Synthetic Polynucleotide

<400> SEQUENCE: 57

```
ccccggcgcc                                                               10
```

<210> SEQ ID NO 58
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 58

```
gggaaataag agagaaaaga agagtaagaa gaaatataag a                            41
```

<210> SEQ ID NO 59
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 59

```
gggaaataag agagaaaaga agagtaagaa gaaatataag accccggcgc cgccacc           57
```

<210> SEQ ID NO 60
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 60

```
gggaaataag agagaaaaga agagtaagaa gaaatataag agccacc                      47
```

<210> SEQ ID NO 61
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 61

```
gggaaataag agagaaaaga agagtaagaa gaaatataag accccggcgc cacc        54
```

```
<210> SEQ ID NO 62
<211> LENGTH: 30
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(30)
<223> OTHER INFORMATION: may be absent

<400> SEQUENCE: 62
ccgccgccgc cgccgccgcc gccgccgccg                                  30

<210> SEQ ID NO 63
<211> LENGTH: 30
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(30)
<223> OTHER INFORMATION: may be absent

<400> SEQUENCE: 63
gccgccgccg ccgccgccgc cgccgccgcc                                  30

<210> SEQ ID NO 64
<211> LENGTH: 15
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(15)
<223> OTHER INFORMATION: may be absent

<400> SEQUENCE: 64
ccgccgccgc cgccg                                                  15

<210> SEQ ID NO 65
<211> LENGTH: 12
<212> TYPE: RNA
<213> ORGANISM: Artificial Sequence
<220> FEATURE:
<223> OTHER INFORMATION: Synthetic Polynucleotide

<400> SEQUENCE: 65
ccgccgccgc cg                                                     12

<210> SEQ ID NO 66
<211> LENGTH: 15
<212> TYPE: RNA
<213> ORGANISM: Artificial Sequence
<220> FEATURE:
<223> OTHER INFORMATION: Synthetic Polynucleotide

<400> SEQUENCE: 66
ccgccgccgc cgccg                                                  15
```

RNA FORMULATIONS

RELATED APPLICATIONS

This application is a national stage filing under 35 U.S.C. § 371 of international PCT application PCT/US2018/037922, filed Jun. 15, 2018, which claims the benefit under 35 U.S.C. § 119(e) of U.S. provisional application No. 62/520,530, filed Jun. 15, 2017 and U.S. provisional application No. 62/590,200, filed Nov. 22, 2017, which are both incorporated by reference herein in their entirety.

FIELD OF INVENTION

The present embodiments relate generally to lipid nanoparticles, and more specifically, to lipid nanoparticles having a certain distribution of one or more components.

BACKGROUND

It is of great interest in the fields of therapeutics, diagnostics, reagents, and for biological assays to be able to control protein expression. Most methods rely upon regulation at the transcriptional level (e.g., from DNA to mRNA), but not at the translational level (e.g., from mRNA to protein). Although attempts have been made to control protein expression on the translational level, the low levels of translation, the immunogenicity, and other delivery issues have hampered the development of mRNA as a therapeutic.

There remains a need in the art to be able to design, synthesize, and deliver a nucleic acid, e.g., a ribonucleic acid (RNA) such as a messenger RNA (mRNA) encoding a peptide or polypeptide of interest inside a cell, whether in vitro, in vivo, in-situ, or ex vivo, so as to effect physiologic outcomes which are beneficial to the cell, tissue or organ and ultimately to an organism.

SUMMARY

Lipid nanoparticles having a certain distribution of one or more components, related compositions, and methods associated therewith are provided. The present disclosure is based, in part, on the discovery that the distribution of certain components within the lipid nanoparticles can influence and/or dictate physical (e.g., stability) and/or biological (e.g., efficacy, intracellular delivery, immunogenicity) properties of the lipid nanoparticles. Inventive lipid nanoparticles having a certain distribution of one or more components may not suffer from one or more limitations of conventional particulate carriers, even though the inventive lipid nanoparticles may contain the same or similar molecules (e.g., at the molar ratios, at the same weight percentages) as the conventional particulate carrier. Compositions comprising inventive lipid nanoparticles may have advantageous biological and physical properties.

Methods for controlling the distribution of components capable of imparting beneficial properties to the lipid nanoparticle have also been discovered. In some cases, these methods may be readily applied to the formulation process using relatively simple techniques.

In one set of embodiments, compositions are provided. In one embodiment, a composition comprises lipid nanoparticles (LNPs) that comprise an ionizable lipid, a PEG lipid, and inaccessible mRNA, and a relatively small amount of accessible mRNA. In such cases, no more than about 50% (e.g., no more than about 45%, 40%, 35%, 30%, 25%, 20%, 15%, 10%, 5%, 3%, or 1%) of mRNA in the composition is accessible mRNA and the half-life time of the PEG lipid in serum is relatively short, e.g., less than or equal to about 3.0 hours (e.g., less than or equal to about 2.75, 2.5, 2.25, 2.0, 175, 1.5, 1.25, 1.0, 0.75, 0.5, or 0.25 hours). In some cases, no more than 30% of mRNA in the composition is accessible mRNA. In certain cases, no more than 5% of mRNA in the composition is accessible mRNA. In some cases, the quantitative value of the amount of accessible mRNA is generated using an ion-exchange chromatography (IEX) assay and/or is not generated using a Ribogreen assay. In some embodiments, the lipid nanoparticles may also comprise a structural lipid and/or a neutral lipid. In some cases, the ionizable lipid is an ionizable amino lipid.

In another embodiment, a composition comprises lipid nanoparticles (LNPs) comprising an ionizable lipid, a PEG lipid, and mRNA and having an exterior region and one or more interior regions. The majority of the mRNA is positioned in the one or more interior regions and the majority of the PEG lipid is positioned within the exterior region. For instance, at least about 60% (e.g., at least about 65%, 70%, 75%, 80%, 85%, 90%, 95%, or 100%) of the mRNA is positioned within the one or more interior regions and at least about 60% (e.g., at least about 65%, 70%, 75%, 80%, 85%, 90%, 95%, or 100%) of the PEG lipid is positioned within the exterior region. In some embodiments, the lipid nanoparticles may also comprise a structural lipid and/or a neutral lipid. In some cases, the ionizable lipid is an ionizable amino lipid. In some embodiments, the composition further comprises a continuous phase. In some such cases, the exterior region is in direct contact with the continuous phase.

In one embodiment, a composition comprises lipid nanoparticles (LNPs) comprising an ionizable lipid, a PEG lipid, and mRNA. The majority of the PEG lipid is surface accessible and the majority of the mRNA in the composition is inaccessible. For instance, at least about 50% (e.g., at least about 55%, 60% 65%, 70%, 75%, 80%, 85%, 90%, 95%, or 100%) of the PEG lipid in the lipid nanoparticles is surface accessible and no more than about 50% of mRNA (e.g., no more than about 45%, 40%, 35%, 30%, 25%, 20%, 15%, 10%, 5%, 3%, 1%, or 0%) in the composition is accessible mRNA. In some embodiments, the lipid nanoparticles may also comprise a structural lipid and/or a neutral lipid. In some cases, the ionizable lipid is an ionizable amino lipid.

In another embodiment, a composition comprises lipid nanoparticles (LNPs) comprising an ionizable lipid, a PEG lipid, and mRNA. The surface polarity of the lipid nanoparticles is relatively low (e.g., lower than a threshold) and the half-life time of the PEG lipid is relatively short. For instance, the half-life time of the PEG lipid in serum is less than or equal to about 3.0 hours (e.g., less than or equal to about 2.75, 2.5, 2.25, 2.0, 175, 1.5, 1.25, 1.0, 0.75, 0.5, or 0.25 hours) and the normalized general polarization of laurdan in the lipid nanoparticles is greater than or equal to about 0.5 (e.g., greater than or equal to about 0.55, 0.6, 0.65, 0.7, 0.75, 0.8, or 0.85). In some cases, the normalized general polarization of laurdan in the lipid nanoparticles is greater than or equal to about 0.5 and less than or equal to about 0.9. In some embodiments, the lipid nanoparticles may also comprise a structural lipid and/or a neutral lipid. In some cases, the ionizable lipid is an ionizable amino lipid.

In one embodiment, a composition comprises lipid nanoparticles (LNPs) comprising an ionizable lipid, a PEG lipid, and mRNA. The surface polarity of the lipid nanoparticles is less than a threshold and the half-life time of the PEG lipid is relatively short. For instance, the half-life time of the PEG lipid in serum is less than or equal to about 3.0 hours (e.g., less than or equal to about 2.75, 2.5, 2.25, 2.0, 175, 1.5, 1.25, 1.0, 0.75, 0.5, or 0.25 hours). In some cases, the surface polarity of the lipid nanoparticles is less than that of a comparative lipid nanoparticle. In some cases, the comparative lipid nanoparticles formed via a nanoprecipitation reaction, wherein the comparative lipid nanoparticles comprise the same ionizable lipid, PEG lipid, and mRNA as the lipid nanoparticles, and wherein greater than about 30% (e.g., greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, 100%) of the PEG lipid nanoparticles in the comparative lipid nanoparticles originated from the nanoprecipitation reaction. In some embodiments, the lipid nanoparticles may also comprise a structural lipid and/or a neutral lipid. In some cases, the ionizable lipid is an ionizable amino lipid.

In another embodiment, a composition comprises lipid nanoparticles (LNPs) comprising an ionizable lipid, a PEG lipid, and mRNA. The majority of the PEG lipid is surface accessible and the surface polarity is relatively low. For instance, greater than about 50% (e.g., at least about 55%, 60% 65%, 70%, 75%, 80%, 85%, 90%, 95%, or 100%) of the PEG lipid in the lipid nanoparticles is surface accessible and the normalized general polarization of laurdan in the lipid nanoparticles is greater than or equal to about 0.5 (e.g., greater than or equal to about 0.55, 0.6, 0.65, 0.7, 0.75, 0.8, or 0.85). In some cases, the normalized general polarization of laurdan in the lipid nanoparticles is greater than or equal to about 0.5 and less than or equal to about 0.9. In some embodiments, the lipid nanoparticles may also comprise a structural lipid and/or a neutral lipid. In some cases, the ionizable lipid is an ionizable amino lipid.

In one embodiment, a composition comprises lipid nanoparticles (LNPs) comprising an ionizable lipid, a PEG lipid, and mRNA. The majority of the PEG lipid is surface accessible and the surface polarity is lower than a threshold. For instance, greater than about 50% (e.g., at least about 55%, 60% 65%, 70%, 75%, 80%, 85%, 90%, 95%, or 100%) of the PEG lipid in the lipid nanoparticles is surface accessible. In some cases, the surface polarity of the lipid nanoparticles is less than that of a comparative lipid nanoparticle. In some cases, the comparative lipid nanoparticles formed via a nanoprecipitation reaction, wherein the comparative lipid nanoparticles comprise the same ionizable lipid, PEG lipid, and mRNA as the lipid nanoparticles, and wherein greater than about 30% (e.g., greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, 100%) of the PEG lipid nanoparticles in the comparative lipid nanoparticles originated from the nanoprecipitation reaction. In some embodiments, the lipid nanoparticles may also comprise a structural lipid and/or a neutral lipid. In some cases, the ionizable lipid is an ionizable amino lipid.

In another embodiment, a composition comprises lipid nanoparticles (LNPs) comprising an ionizable lipid, a PEG lipid, and mRNA and having an exterior region and one or more interior regions. The majority of the PEG lipid is positioned within the exterior region and the surface polarity of the lipid nanoparticles is relatively low. For instance, at least about 60% (e.g., at least about 65%, 70%, 75%, 80%, 85%, 90%, 95%, or 100%) of the PEG lipid is positioned within the exterior region and the normalized general polarization of laurdan in the lipid nanoparticles is greater than or equal to about 0.5 (e.g., greater than or equal to about 0.55, 0.6, 0.65, 0.7, 0.75, 0.8, or 0.85). In some cases, the normalized general polarization of laurdan in the lipid nanoparticles is greater than or equal to about 0.5 and less than or equal to about 0.9. In some embodiments, the lipid nanoparticles may also comprise a structural lipid and/or a neutral lipid. In some cases, the ionizable lipid is an ionizable amino lipid. In some embodiments, the composition further comprises a continuous phase. In some such cases, the exterior region is in direct contact with the continuous phase.

In one embodiment, a composition comprises lipid nanoparticles (LNPs) comprising an ionizable lipid, a PEG lipid, and mRNA and having an exterior region and one or more interior regions. The majority of the PEG lipid is positioned within the exterior region and the surface polarity of the lipid nanoparticles is lower than a threshold. For instance, at least about 60% (e.g., at least about 65%, 70%, 75%, 80%, 85%, 90%, 95%, or 100%) of the PEG lipid is positioned within the exterior region. In some cases, the surface polarity of the lipid nanoparticles is less than that of a comparative lipid nanoparticle. In some cases, the comparative lipid nanoparticles formed via a nanoprecipitation reaction, wherein the comparative lipid nanoparticles comprise the same ionizable lipid, PEG lipid, and mRNA as the lipid nanoparticles, and wherein greater than about 30% (e.g., greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, 100%) of the PEG lipid nanoparticles in the comparative lipid nanoparticles originated from the nanoprecipitation reaction. In some embodiments, the lipid nanoparticles may also comprise a structural lipid and/or a neutral lipid. In some cases, the ionizable lipid is an ionizable amino lipid. In some embodiments, the composition further comprises a continuous phase. In some such cases, the exterior region is in direct contact with the continuous phase.

In another embodiment, a composition comprises lipid nanoparticles (LNPs) comprising an ionizable lipid and inaccessible mRNA, and a relatively small amount of accessible mRNA. In such cases, no more than about 50% (e.g., no more than about 45%, 40%, 35%, 30%, 25%, 20%, 15%, 10%, 5%, 3%, or 1%) of mRNA in the composition is accessible mRNA and the normalized general polarization of laurdan in the lipid nanoparticles is greater than or equal to about 0.5 (e.g., greater than or equal to about 0.55, 0.6, 0.65, 0.7, 0.75, 0.8, or 0.85). In some cases, the normalized general polarization of laurdan in the lipid nanoparticles is greater than or equal to about 0.5 and less than or equal to about 0.9. In some embodiments, the lipid nanoparticles may also comprise a PEG lipid, structural lipid, and/or a neutral lipid. In some cases, the ionizable lipid is an ionizable amino lipid.

In one embodiment, a composition comprises lipid nanoparticles (LNPs) comprising an ionizable lipid and inaccessible mRNA, and a relatively small amount of accessible mRNA. In such cases, no more than about 50% (e.g., no more than about 45%, 40%, 35%, 30%, 25%, 20%, 15%, 10%, 5%, 3%, or 1%) of mRNA in the composition is accessible mRNA and the surface polarity is lower than a threshold. In some cases, the surface polarity of the lipid nanoparticles is less than that of a comparative lipid nanoparticle. In some cases, the comparative lipid nanoparticles formed via a nanoprecipitation reaction, wherein the comparative lipid nanoparticles comprise the same ionizable lipid and mRNA as the lipid nanoparticles, and wherein greater than about 30% (e.g., greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, 100%) of the PEG lipid nanoparticles in the comparative lipid nanoparticles originated from the nanoprecipitation reaction. In some embodiments, the lipid nanoparticles may also comprise a structural lipid, a PEG lipid, and/or a neutral lipid. In some cases, the ionizable lipid is an ionizable amino lipid.

In another embodiment, a composition comprises lipid nanoparticles (LNPs) comprising an ionizable lipid and mRNA and having an exterior region and one or more interior regions. The majority of the mRNA is positioned in the one or more interior regions and the surface polarity of the lipid nanoparticles is relatively low. For instance, at least about 60% (e.g., at least about 65%, 70%, 75%, 80%, 85%, 90%, 95%, or 100%) of the mRNA is positioned within the one or more interior regions and the normalized general polarization of laurdan in the lipid nanoparticles is greater than or equal to about 0.5 (e.g., greater than or equal to about 0.55, 0.6, 0.65, 0.7, 0.75, 0.8, or 0.85). In some cases, the normalized general polarization of laurdan in the lipid nanoparticles is greater than or equal to about 0.5 and less than or equal to about 0.9. In some embodiments, the lipid nanoparticles may also comprise a structural lipid, a PEG lipid, and/or a neutral lipid. In some cases, the ionizable lipid is an ionizable amino lipid. In some embodiments, the composition further comprises a continuous phase. In some such cases, the exterior region is in direct contact with the continuous phase.

In one embodiment, a composition comprises lipid nanoparticles (LNPs) comprising an ionizable lipid and mRNA and having an exterior region and one or more interior regions. The majority of the mRNA is positioned in the one or more interior regions and the surface polarity is lower than a threshold. For instance, at least about 60% (e.g., at least about 65%, 70%, 75%, 80%, 85%, 90%, 95%, or 100%) of the mRNA is positioned within the one or more interior regions. In some cases, the surface polarity of the lipid nanoparticles is less than that of a comparative lipid nanoparticle. In some cases, the comparative lipid nanoparticles formed via a nanoprecipitation reaction, wherein the comparative lipid nanoparticles comprise the same ionizable lipid and mRNA as the lipid nanoparticles, and wherein greater than about 30% (e.g., greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, 100%) of the PEG lipid nanoparticles in the comparative lipid nanoparticles originated from the nanoprecipitation reaction. In some embodiments, the composition further comprises a continuous phase. In some such cases, the exterior region is in direct contact with the continuous phase.

In one embodiment, a composition comprises lipid nanoparticles (LNPs) comprising an ionizable lipid and inaccessible mRNA, and very little accessible mRNA, e.g., no more than about 30% (e.g., no more than about 25%, 20%, 15%, 10%, 5%, 3%, or 1%) of mRNA in the composition is accessible mRNA. In some embodiments, the lipid nanoparticles may also comprise a structural lipid, a PEG lipid, and/or a neutral lipid. In some cases, the ionizable lipid is an ionizable amino lipid.

In another embodiment, a composition comprises lipid nanoparticles (LNPs) comprising an ionizable lipid, a PEG lipid, and mRNA. A substantial amount of the lipid nanoparticles in the composition are enhanced lipid nanoparticles. The enhanced lipid nanoparticles have more inaccessible mRNA than the accessible mRNA. For instance, at least about 50% (e.g., at least about 55%, 60% 65%, 70%, 75%, 80%, 85%, 90%, 95%, or 100%) of the lipid nanoparticles in the composition are enhanced lipid nanoparticles. In some embodiments, the lipid nanoparticles may also comprise a structural lipid and/or a neutral lipid. In some cases, the ionizable lipid is an ionizable amino lipid.

In certain embodiments, at least about 95% of the PEG lipid in the composition is surface accessible. In some embodiments, at least about 95% of the PEG lipid is surface accessible in at least about 95% of the LNPs in the composition. In certain embodiments, at least about 95% of the mRNA in the composition is inaccessible. In some embodiments, at least about 95% of the mRNA is inaccessible in at least about 60% (e.g., at least about 65%, at least about 70%, at least about 75%, at least about 80% at least about 85%, at least about 90%, at least about 95%) of the LNPs in the composition. In some embodiments, at least about 95% of the mRNA is inaccessible in at least about 95%.

In some embodiments, the PEG lipid comprising two or more aliphatic groups that are indirectly attached. In certain cases, the PEG lipid is not a hydroxyl-PEG lipid. In some cases, the PEG lipid is a methoxy-PEGylated lipid. In certain cases, the PEG lipid does not have the following structure:

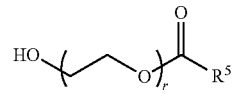

wherein r is 45. In other embodiments, the PEG lipid does have the above structure. In some cases, the PEG-lipid is not Compounds 419, 420, 421, 422, 423, 424, 425, 426, 427, or 428. In other cases, the PEG-lipid is Compounds 419, 420, 421, 422, 423, 424, 425, 426, 427, or 428. In certain cases, the LNPs have a molar ratio of ionizable amino lipid:structural lipid:neutral lipid:PEG-lipid other than 50:38.5:10:1.5. In certain cases, the LNPs have a molar ratio of ionizable amino lipid:structural lipid:neutral lipid:PEG-lipid of 50:38.5:10:1.5. In some cases, the PEG lipid is less than 1.5 in the molar ratio of ionizable amino lipid:structural lipid:neutral lipid:PEG-lipid. In other cases, the PEG lipid is not less than 1.5 in the molar ratio of ionizable amino lipid:structural lipid:neutral lipid:PEG-lipid.

In some embodiments, at least about 50%, at least about 55%, at least about 60%, at least about 65%, at least about 70%, at least about 75%, at least about 80%, at least about 85%, at least about 90%, or at least about 95% of the mRNA in the composition is fully encapsulated. In some cases, the quantitative value of the amount of accessible mRNA and/or fully encapsulated mRNA is generated using an ion-exchange chromatography (IEX) assay and/or is not generated using a Ribogreen assay.

In some embodiments, surface polarity is determined using one or more fluorescent probes. The one or more fluorescent probes may comprise prodan. The one or more fluorescent probes may comprise laurdan.

In general, the compositions may have relatively high in vitro and/or in vivo expression. The composition may have an in vitro expression of mRNA that is greater than a threshold value. The threshold value may be the value from a comparative lipid nanoparticle. In some cases, an in vitro expression of the mRNA in the composition is greater than comparative lipid nanoparticles formed via a nanoprecipitation reaction, wherein the comparative lipid nanoparticles comprise the same ionizable lipid, PEG lipid, and mRNA as the lipid nanoparticles, and wherein greater than 30% of the PEG lipid nanoparticles in the comparative lipid nanoparticles originated from the nanoprecipitation reaction. The composition may have an in vivo expression of mRNA that is greater than a threshold value. The threshold value may be the value from a comparative lipid nanoparticle. In some cases, an in vivo expression of the mRNA is greater than comparative lipid nanoparticles formed via a nanoprecipitation reaction, wherein the comparative lipid nanoparticles comprise the same ionizable lipid, PEG lipid, and mRNA as the lipid nanoparticles, and wherein greater than 30% of the PEG lipid nanoparticles in the comparative lipid nanoparticles originated from the nanoprecipitation reaction.

In one set of embodiments, compositions comprising precursor lipid nanoparticles are provided. In one embodiment, a composition comprises lipid nanoparticles (LNPs) comprising an ionizable lipid, a PEG lipid, and mRNA, wherein at least about 50% of the lipid nanoparticles in the composition are precursor lipid nanoparticles, the precursor lipid nanoparticles have more mRNA associated with the ionizable lipid than the PEG lipid, and the precursor lipid nanoparticles comprise at least about 0.01 mol % and less than or equal to about 1.0 mol % of the PEG lipid. In some cases, at least about 50% (e.g., at least about 60%, 65%, 70%, 75%, 80%, 85%, 90%, or 95%) of the mRNA in the precursor lipid nanoparticles is associated with the ionizable lipid. In some instances, less than about 50% (e.g., less than about 40%, 35%, 30%, 25%, 20%, 15%, 10%, or 5%) of the mRNA in the precursor lipid nanoparticles is associated with the PEG lipid. In certain cases, the ratio of mRNA associated with the ionizable lipid to mRNA associated with the PEG lipid in the precursor lipid nanoparticles is at least about 2:1 (e.g., at least about 3:1, 4:1, or 5:1). In some cases, the composition further comprises an organic solvent (e.g., ethanol). In some instances, the precursor lipid nanoparticles comprise at least about 0.05 mol % (e.g., at least about 0.1 mol %, 0.2 mol %, 0.3 mol %, 0.4 mol %, 0.5 mol %, 0.6 mol %, 0.7 mol %, or 0.8 mol %) of the PEG lipid.

In one aspect, the present disclosure is based, at least in part, on the discoveries that lipid nanoparticles (LNPs) may be designed in order to provide stealth delivery of therapeutic payload without inducing a damaging innate immune response. Components of prior art LNPs, such as phosphatidylcholine, induce the production of natural IgM and/or IgG molecules, which may be mediated by activation of B1 cells, such as B1a and/or B1b cells. These biological mechanisms may contribute to drug responses caused by LNPs, including accelerated blood clearance (ABC) and dose-limiting toxicity such as acute phase response (APR) and complement activation-related pseudoallergy (CARPA). In some embodiments, the LNPs of the invention are designed as a composition having optimal surface properties that avoid immune cell recognition. Highly effective compositions having enriched populations of LNPs that avoid immune activation are provided in aspects of the invention.

In some aspects, the invention is a composition comprising an enriched population of LNPs, wherein the LNPs have an outer shell and an inner core and comprise an ionizable lipid, a phospholipid, a PEG lipid, and optionally a structural lipid, wherein at least about 50% (e.g. 50, 55, 60, 65, 70, 75, 80, 85, 90, 95 or 100%) of the LNPs comprise RNA encapsulated within the inner core and wherein the outer shell comprises at least about 80, 85, 90, 95 or 100% of the PEG lipid. In some aspects, between about 90 and 100% of the LNPs comprise RNA encapsulated within the inner core and the outer shell comprises at least about 95% of the total PEG lipid. In some aspects, between about 95 and 100% of the LNPs comprise RNA encapsulated within the inner core and about 95% of the total PEG lipid in the outer shell.

In some aspects, the invention is a composition comprising an enriched population of lipid nanoparticles (LNPs), wherein the LNPs have an outer shell and an inner core and comprise an ionizable lipid, a phospholipid, a PEG lipid, and optionally a structural lipid, wherein at least 95% of the LNPs comprise RNA encapsulated within the inner core and wherein the outer shell comprises greater than 95% of the total PEG lipid.

In other aspects, the invention is a composition comprising an enriched population of lipid nanoparticles (LNPs) comprising RNA, wherein the LNPs have an outer shell and an inner core and comprise an ionizable lipid, a phospholipid, a PEG lipid, and optionally a structural lipid, wherein at least 95% of the RNA in the composition is encapsulated within the LNPs and wherein the outer shell comprises greater than 95% of the total PEG lipid.

According to other aspects the invention is a composition comprising an enriched population of lipid nanoparticles (LNPs), wherein the LNPs have an outer shell and an inner core and comprise an ionizable lipid, a phospholipid, a PEG lipid, and a structural lipid, wherein at least 50% (e.g. 50, 55, 60, 65, 70, 75, 80, 85, 90, 95 or 100%) of the LNPs have an outer shell fluidity value of greater than a threshold polarization level and wherein RNA is encapsulated within the and wherein the outer shell comprises greater than 95% of the total PEG lipid.

In yet other aspects the invention is a composition comprising an enriched population of lipid nanoparticles (LNPs), wherein the LNPs have an outer shell and an inner core and comprise an ionizable lipid, a phospholipid, a PEG lipid, and a structural lipid, wherein at least 50% (e.g. 50, 55, 60, 65, 70, 75, 80, 85, 90, 95 or 100%) of the LNPs have a ratio of ionizable lipid:phospholipid:structural lipid of 35-50:30-40: 20-30, and wherein the PEG-lipid is a rapidly diffusing PEG-lipid. In yet other aspects the invention is a composition comprising an enriched population of lipid nanoparticles (LNPs), wherein the LNPs have an outer shell and an inner core and comprise an ionizable lipid, a phospholipid, a PEG lipid, and a structural lipid, wherein at least 50% (e.g. 50, 55, 60, 65, 70, 75, 80, 85, 90, 95 or 100%) of the LNPs have a ratio of ionizable lipid:phospholipid:structural lipid of 60:20:20 or 40:30:30 or 50:30:20 or 40:40:20. In yet other aspects the invention is a composition comprising an enriched population of lipid nanoparticles (LNPs), wherein the LNPs have an outer shell and an inner core and comprise an ionizable lipid, a phospholipid, a PEG lipid, and a structural lipid, wherein at least 50% (e.g. 50, 55, 60, 65, 70, 75, 80, 85, 90, 95 or 100%) of the LNPs have a ratio of ionizable lipid:phospholipid:structural lipid of 30-50:30:50: 10-30 or preferably 35-45:35-45:15-25. In such formulations, PEG lipid, e.g., rapidly or fast-diffusing PEG lipid can be about 0.5-3% (for example, replacing a portion of e.g., structural lipid or phospholipid).

In some embodiments, a quantitative value of the amount of RNA encapsulated in the LNP is generated using an ion-exchange chromatography (IEX) assay.

In other embodiments, the LNP is insensitive to accelerated blood clearance upon repeated administration in vivo within 10 days.

In some embodiments, at least 50% (e.g. 50, 55, 60, 65, 70, 75, 80, 85, 90, 95 or 100%) of the LNPs have 1-5 inner shells in some embodiments. In other embodiments, the structural lipid is cholesterol. In yet other embodiments 10-30% of the LNP, exclusive of RNA, is the structural lipid. The outer shell is comprised of 10-30% of the structural lipid in other embodiments.

In some embodiments at least about 50%, at least about 55%, at least about 60%, at least about 65%, at least about 70%, at least about 75%, at least about 80%, at least about 85%, at least about 95%, or at least about 95% of the LNPs in the population have mRNA encapsulated therein, as determined by ion-exchange chromatography (IEX). In some embodiments, the LNPs have an encapsulation efficiency of at least about 50%, at least about 60%, at least about 70%, at least about 80% or at least about 90%, as determined by ion-exchange chromatography (IEX).

In some embodiments at least about 95% of the LNPs in the population have mRNA encapsulated therein, as determined by ion-exchange chromatography (IEX). In some embodiments the LNPs have an encapsulation efficiency of at least about 95%, as determined by ion-exchange chromatography (IEX).

In some embodiments, a composition comprising a population of lipid nanoparticles (LNPs), the LNPs comprise an ionizable amino lipid, a poly(ethylene glycol) (PEG) lipid, a phospholipid, and optionally, a structural lipid, wherein at least about 50%, at least about 60%, at least about 70%, at least about 80% or at least about 90% of the LNPs in the population have mRNA encapsulated therein, as determined by ion-exchange chromatography (IEX) is provided in other aspects of the invention. In some embodiments, at least 95% of the LNPs in the population have mRNA encapsulated therein, as determined by ion-exchange chromatography (IEX).

In some embodiments, a composition comprising a population of lipid nanoparticles (LNPs), the LNPs comprise an ionizable cationic lipid, a poly(ethylene glycol) (PEG) lipid, a phospholipid, and optionally, a structural lipid, wherein the LNPs have an encapsulation efficiency of at least about 50%, at least about 60%, at least about 70%, at least about 80% or at least about 90%, as determined by ion-exchange chromatography (IEX) is provided according to other aspects of the invention. of the LNPs in the population have mRNA encapsulated therein, as determined by ion-exchange chromatography (IEX) In some embodiments, the structural lipid is cholesterol or a cholesterol derivative.

In some embodiments, the composition is enriched for LNPs (a) lacking B1a cell-stimulating phospholipid epitopes, and/or (b) lacking scavenger receptor ligands.

In other embodiments at least about 50%, at least about 60%, at least about 70%, at least about 80% or at least about 90% of the LNPs (a) lack B1a cell-stimulating phospholipid epitopes, and/or (b) lack scavenger receptor ligands.

In other embodiments at least about 95% of the LNPs (a) lack B1a cell-stimulating phospholipid epitopes, and/or (b) lack scavenger receptor ligands.

In other embodiments the composition is enriched for LNPs having a majority of the total phospholipid present is in the outer shell. For instance, at least about 50%, at least about 60%, at least about 70%, at least about 80% or at least about 90% of total phospholipid present is in the outer shell.

At least about 50%, at least about 60%, at least about 70%, at least about 80% or at least about 90% of the LNPs having the majority of the total phospholipid present in the outer LNP shell. In other embodiments the composition is enriched for LNPs having more than 50% of the total phospholipid present on the surface (e.g., in outer LNP layers).

In yet other embodiments at least about 50%, at least about 60%, at least about 70%, at least about 80% or at least about 90% of the LNPs have the more than 50% of the total phospholipid present on the surface.

In other embodiments, at least about 95% of the LNPs have the total amount of phospholipid present is in the outer LNP shell. In other embodiments the composition is enriched for LNPs having more than 95% of the total phospholipid present on the surface (e.g., in one or more outer LNP layers).

In yet other embodiments at least about 95% of the LNPs have more than 95% of the total phospholipid present on the surface.

In one aspect, the present disclosure provides a method of producing a lipid nanoparticle composition, the method comprising: i) mixing a lipid solution comprising a first PEG lipid and an ionizable lipid with a solution comprising a nucleic acid thereby forming a precursor lipid nanoparticle, ii) adding a lipid nanoparticle modifier comprising a modifying agent to the precursor lipid nanoparticle thereby forming a modified lipid nanoparticle, and iii) processing the precursor lipid nanoparticle, the modified lipid nanoparticle, or both thereby forming the lipid nanoparticle composition.

In one embodiment, the precursor lipid nanoparticle is not processed prior to the adding the lipid nanoparticle modifier. In one embodiment, the precursor lipid nanoparticle is processed prior to the adding the lipid nanoparticle modifier.

In one embodiment, the lipid solution further comprises a phospholipid. In one embodiment, the lipid solution further comprises a structural lipid. In one embodiment, the modifying agent is at least one agent selected from the group consisting of a second PEG lipid and a surfactant. In one embodiment, the modifying agent is a second PEG lipid. In one embodiment, the modifying agent is a surfactant. In one embodiment, a molar ratio of the first PEG lipid to the modifying agent is in a range of about 1:100 to about 1:1. In one embodiment, a molar ratio of the first PEG lipid to the modifying agent is in a range of about 1:50 to about 1:1. In one embodiment, a molar ratio of the first PEG lipid to the modifying agent is in a range of about 1:25 to about 1:1.

In one embodiment, a molar ratio of the first PEG lipid to the modifying agent is in a range of about 1:10 to about 1:1. In one embodiment, the mixing comprises turbulent mixing and/or microfluidic mixing. In one embodiment, the processing comprises a filtration. In one embodiment, the processing comprises a tangential flow filtration. In one embodiment, the processing comprises a freezing and/or a lyophilizing. In one embodiment, the method further comprises packing the lipid nanoparticle composition.

In one embodiment, the first PEG lipid and the second PEG lipid are the same. In one embodiment, the first PEG lipid and the second PEG lipid are not the same. In one embodiment, a molar ratio of the second PEG lipid to the first PEG lipid is in a range of from 1:1 to 100:1. In one embodiment, a molar ratio of the second PEG lipid to the first PEG lipid is in a range of from 1:1 to 10:1. In one embodiment, the first PEG lipid and the second PEG lipid are each independently at least one PEG lipid selected from the group consisting of a PEG-modified phosphatidylethanolamine, a PEG-modified phosphatidic acid, a PEG-modified ceramide, a PEG-modified dialkylamine, a PEG-modified diacylglycerol, and a PEG-modified dialkylglycerol.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1A depicts varying encapsulation efficiency based on mRNA formulation buffer conditions. FIG. 1B depicts varying encapsulation efficiency based on mRNA formulation salt concentrations.

DETAILED DESCRIPTION

Figure 1A:
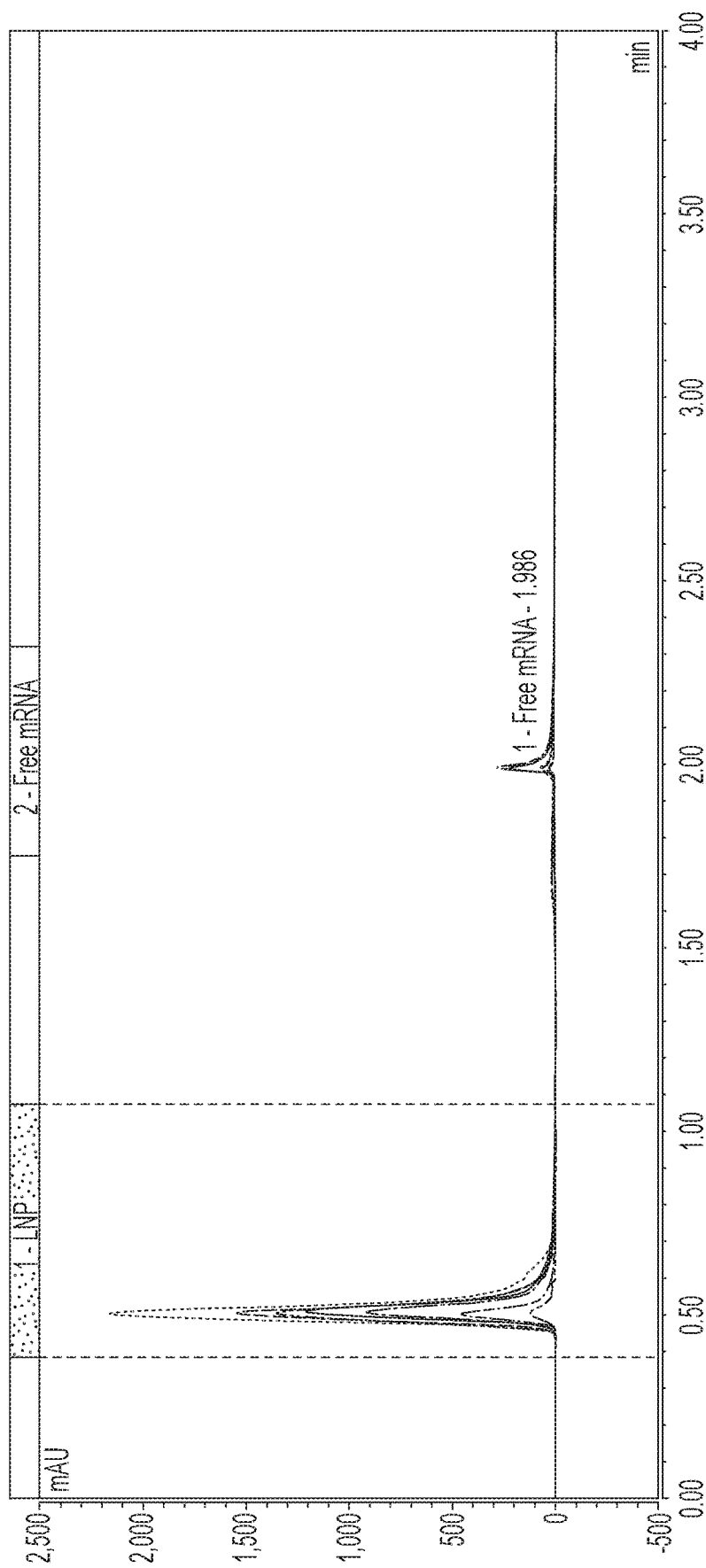
FIG. 1A-1B is a set of graphs depicting separation results demonstrating that LNP elutes in the void and mRNA elutes when gradient changes from low to high salt concentration.

Compositions comprising lipid nanoparticles ("LNPs") are provided. In some embodiments, a lipid nanoparticle may comprise two or more components (e.g., ionizable lipid and nucleic acid, PEG-lipid, phospholipid, cholesterol). For instance, a lipid nanoparticle may comprise an ionizable lipid and a nucleic acid. The distribution of one or more components within the lipid nanoparticle may impart beneficial properties to the lipid nanoparticle and resulting compositions. For instance, certain distributions of the nucleic acid in the lipid nanoparticle may impart advantageous physical and/or biological properties (e.g., protein expression) to the lipid nanoparticle. In some embodiments, a favorable distribution of components within the lipid nanoparticle may be readily achieved during the formulation process using relatively simple techniques. Compositions comprising the lipid nanoparticles, described herein, may be used for a wide variety of applications, including the stealth delivery of therapeutic payloads with minimal adverse innate immune response.

Effective in vivo delivery of nucleic acids represents a continuing medical challenge. External nucleic acids (i.e., originating from outside of a cell) are readily degraded in the body, e.g., by the immune system. Accordingly, effective delivery of nucleic acids to cells often requires the use of a particulate carrier (e.g., lipid nanoparticles). The particulate carrier should be formulated to have minimal particle aggregation, be relatively stable prior to intracellular delivery, effectively deliver nucleic acids intracellularly, and illicit no or minimal immune response. To achieve minimal particle aggregation and pre-delivery stability, many conventional particulate carriers have relied on the presence and/or concentration of certain components (e.g., PEG lipid). However, it has been discovered that certain components and/or concentrations thereof used to promote particle separation and/or pre-delivery stability can adversely affect encapsulation and/or the intracellular delivery of nucleic acids. For instance, polyethylene glycol, which can be used to prevent particle aggregation, may lower nucleic acid encapsulation. The reduced encapsulation may limit the therapeutic efficacy of the particulate carriers. Moreover, it has been found that certain components used to impart stability and prevent aggregation may also induce an immune response (e.g., innate immune response). In some instances, carriers containing such components may not be able to be repeatedly and frequently dosed, for example, over a period of days without loss of activity. The immune response to carrier components may contribute to the drug responses caused by particulate carriers, including accelerated blood clearance (ABC) and dose-limiting toxicity such as acute phase response (APR) and complement activation-related pseudo-allergy (CARPA). Therefore, in many conventional particulate carriers, a tradeoff exists between advantageous physical properties (e.g., stability, aggregation resistance, diameter) and therapeutic efficacy (e.g., expression, immunogenicity, antigenicity). Accordingly, there remains a need for particulate carriers having minimal particle aggregation, pre-delivery stability, effective intracellular delivery of nucleic acids, and/or reduced antigenicity and immunogenicity.

The present disclosure is based, in part, on the discovery that the distribution of certain components within the lipid nanoparticles can influence and/or dictate physical (e.g., stability) and/or biological (e.g., efficacy, intracellular delivery, immunogenicity) properties of the lipid nanoparticles. For instance, the distribution of the nucleic acid within the lipid nanoparticles may significantly affect intercellular delivery and in vivo expression. Lipid nanoparticles having a favorable distribution of the nucleic acid may have enhanced intercellular delivery and in vivo expression compared essentially identical particles having a different distribution. In some embodiments, the distribution of one or more components can be used to mitigate and/or eliminate adverse effects associated with certain components (e.g., components used to prevent aggregation and/or impart stability) in the lipid nanoparticle. For example, certain distributions of molecules comprising polyethylene glycol (e.g., PEG lipid) can be used to mitigate the immunogenicity associated with polyethylene glycol.

In this disclosure, compositions comprising lipid nanoparticles having an advantageous distribution of components and associated methods are described. In some embodiments, the lipid nanoparticles, due at least in part to the distribution of certain components, do not suffer from one or more limitations of conventional carriers, even though the lipid nanoparticles may contain the same or similar molecules (e.g., at the molar ratios, at the same weight percentages) as the conventional carrier.

In some embodiments, lipid nanoparticles having advantageous physical and/or biological properties may have a certain distribution of nucleic acids (e.g., mRNA). In some embodiments, the nucleic acid may be distributed, such that a relatively high percentage (e.g., majority) of the nucleic acid is inaccessible from the surface of the lipid nanoparticles. As used herein, the terms "inaccessible" and "accessible" with respect to a nucleic acid (e.g., inaccessible nucleic acid, accessible nucleic acid) may refer to the association and/or encapsulation state of the nucleic acid (e.g., mRNA). An inaccessible nucleic acid (e.g., inaccessible mRNA) may be unable to associate with certain species (e.g., molecular probe, resin, charged molecule) under certain conditions and/or unable to dissociate from one or more components (e.g., lipid components) under certain conditions. For example, a positively charged resin may be unable to associate with a nucleic acid that is fully encapsulated by one or more components (e.g., ionizable lipid, PEG-lipid) of the lipid nanoparticle. In such cases, the nucleic acid is inaccessible. Conversely, an accessible nucleic acid (e.g., accessible mRNA) may be able to associate with certain species (e.g., molecular probe, resin, charged molecule) under certain conditions and/or able to dissociate from one or more lipid components under certain conditions. For example, a nucleic acid associated with (e.g., via a chemical interaction) the surface of a lipid nanoparticle may be able to associate with a positively charged resin. In such cases, the nucleic acid is accessible.

In some embodiments, the accessibility of the nucleic acid in a lipid nanoparticle and/or a composition comprising lipid nanoparticles may be determined by one or more assays (e.g., in vitro assay). In general, any suitable in vitro assay may be used. Suitable assays are able to distinguish between different encapsulation states of the nucleic acid and/or association states of the nucleic acid with components of the lipid nanoparticle. For example, the accessibility of a nucleic acid may be determined by an ion-exchange chromatography (IEX) assay. In certain embodiments, as described in more detail below, certain conventional assays may not be suitable for determining the accessibility of a nucleic acid. For instance, in some embodiments, a Ribogreen assay is not suitable for determining the accessibility of a nucleic acid (e.g., mRNA). In some embodiments, the in vitro assay may be used to generate a quantitative value of the amount of accessible or inaccessible nucleic acids (e.g., mRNA) in the lipid nanoparticles or composition. For example, an ion-exchange chromatography (IEX) assay may be used to generate a quantitative value of the amount of accessible or inaccessible mRNA in a composition comprising lipid nanoparticles. In general, the amount of inaccessible or accessible nucleic acids may be determined for the total composition and/or a fraction of the composition (e.g., fraction comprising certain lipid nanoparticles).

In some embodiments, the accessibility of the nucleic acid within the lipid nanoparticle may correlate to one or more biological properties of the lipid nanoparticle. In certain embodiments, the accessibility of the nucleic acid within the lipid nanoparticle may correlate with protein expression levels and/or the efficacy of intracellular nucleic acid delivery. For instance, in some embodiments, a relatively high percentage of inaccessible nucleic acid, and accordingly a relatively low percentage of accessible nucleic acid, may produce high levels of protein expression (e.g., in vitro, in vivo). In such cases, a composition having a low percentage of accessible mRNA may have a higher level of mRNA expression than a comparative composition having a higher percentage of accessible mRNA.

A "comparative lipid nanoparticle" as used herein in the context of comparing an inventive lipid nanoparticle possessing a particular feature or produced according to a particular process modification, is a lipid nanoparticle that is substantially identical to the inventive lipid nanoparticle except lacking such specific feature or process modification. For instance, in some embodiments, the comparative lipid nanoparticle comprises the same components (e.g., ionizable lipid, PEG lipid, and mRNA) as the lipid nanoparticle at the same molar ratios and/or same weight percentages, but has a different distribution of at least one component and/or is formed via a different process. For instance, in embodiments in which the lipid nanoparticles comprise an ionizable lipid, a PEG lipid, and mRNA, the comparative lipid nanoparticle may comprise the same ionizable lipid, PEG lipid, and mRNA as the lipid nanoparticle, but be formed via a nanoprecipitation reaction, wherein greater than about 30% (e.g., greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, 100%) of the PEG lipid in the comparative lipid nanoparticles originated from the nanoprecipitation reaction. In some cases in which the lipid nanoparticles and comparative lipid nanoparticles substantially differ only with respect to the formation process, the comparative lipid nanoparticles formation process may lack a post-particle formation (e.g., post-nanoprecipitation reaction) lipid nanoparticle component exposure step. For example, the comparative lipid nanoparticle formation process may not comprise a step after the particle formation step (e.g., after the nanoprecipitation reaction) that comprises exposing the particle to one or more components (e.g., PEG lipid) of the lipid nanoparticle.

It should be noted that in certain cases, the "comparative lipid nanoparticle" may nonetheless be non-conventional and inventive so that a "comparative lipid nanoparticle" is not necessarily a conventional lipid nanoparticle. In other cases, a "comparative lipid nanoparticle" is a conventional lipid nanoparticle.

In some embodiments, the accessibility of the nucleic acid within the lipid nanoparticle may correlate with one or more aspects of the intracellular delivery of the nucleic acid. For instance, in certain embodiments, nucleic acid accessibility may correlate with the ability of the lipid nanoparticle to minimize nucleic acid loss (e.g., release, degradation) during endosomal transport and/or release (e.g., in vitro, in vivo). For instance, a high percentage of inaccessible nucleic acid (e.g., inaccessible mRNA) may result in low levels of mRNA being released and/or degraded in the endosome. Without being bound by theory, it is believed that the inaccessible nucleic acid may be protected from certain biological mechanism (e.g., intracellular mechanisms) that release of the nucleic acid. In some embodiments, the endosomal release characteristics of lipid nanoparticles may be determined by one or more assays (e.g., in vitro assay). In general, any suitable in vitro assay may be used.

In some embodiments, the accessibility of the nucleic acid within the lipid nanoparticle may correlate to one or more physical properties of the lipid nanoparticle. For instance, in some embodiments, the accessibility of the nucleic acid within the lipid nanoparticle may correlate with surface polarity. For instance, in some embodiments, lipid nanoparticles having a relatively low percentage of accessible nucleic acid, and accordingly a relatively high percentage of inaccessible nucleic acid, may have a relatively low surface polarity (i.e., high normalized generalized polarization, N-GP). For example, a composition having a low percentage of accessible mRNA may have a lower surface polarity (i.e. higher N-GP) than a comparative composition having a higher percentage of accessible mRNA. Without being bound by theory, it is believed that the surface polarity of a lipid nanoparticle corresponds to the water concentration in the surface portion of the lipid nanoparticle. A relatively high water content, along with a relatively high surface polarity (i.e. low N-GP), likely correlate with a surface portion having a relatively disordered or loose associations between the components (e.g., lipids, cholesterol) in the surface portion. A relatively low water content, along with a relatively low surface polarity, is believed to correlate with a relatively ordered or close associations between the components (e.g., lipids, cholesterol) within the surface portion. It is also believed that a relatively high water content in the surface portion of a lipid nanoparticle indicates a relatively fluid surface portion, whereas a relatively low water content in the surface portion of a lipid nanoparticle indicates a relatively rigid surface portion.

In general, the surface polarity may be determined using known assays in the art. In some embodiments, the surface polarity of the surface portion of the lipid nanoparticles may be determined using one or more fluorescent probes (e.g., laurdan, prodan). For instance, the surface polarity may be determined using fluorescence spectroscopy using laurdan. An exemplary fluorescence measurement involves dissolving laurdan (6-dodecanoyl-2-dimethyaminonaphthalene) in DMSO (dimethyl sulfoxide) at a concentration of 0.05 mg/mL and then adding 1 μL of Laurdan/DMSO solution (0.05 mg/mL) to 499 μL LNP (0.12 mg/mL lipid concentration). The sample solution is incubated for 3 hours at 25° C. The fluorescence spectra are then recorded at emission wavelengths from 400 to 600 nm, with the excitation wavelength of 340 nm using Fluoromax (Horiba). The generalized polarization (GP) was estimated on the basis of the following equation $$GP = \frac{I_{435} - I_{490}}{I_{435} + I_{490}}$$

where $I_{435}$ and $I_{490}$ are the emission intensities of Laurdan at 435 and 490 nm, respectively. The normalized GP (N-GP) is calculated based on the GP range that has been observed in the LNP systems using the following equation $$N-GP = \frac{GP - GP_{min}}{GP_{max} - GP_{min}},$$

where $GP_{max}$ is 0.6 and $GP_{min}$ is 0.3. Samples with the maximum N-GP (GP=GPmax, thus N-GP=1) and minimum N-GP (GP=GPmin, thus N-GP=0) are considered to have the least polar and most polar surface, respectively. In some embodiments, the normalized general polarization may be greater than a threshold value (e.g., value for a comparative lipid nanoparticle, value for a conventional particulate carrier). In some such embodiments, the surface polarity may be lower than a certain threshold (e.g., lower than the surface polarity of a comparative lipid nanoparticle).

In some embodiments, the surface polarity may be determined using fluorescence spectroscopy using prodan as described in Sanchez et al Biophys J 1991, 60, 179-189. An exemplary polarization measurement is as follows: 2 μL of Prodan (0.1 mg/mL in DMSO) was added into 998 μL LNPs (lipid conc. of 0.12 mg/mL in PBS). The mixtures were incubated at 25° C. for at least 1 hour to allow the partition of the dye into the LNP. The fluorescence spectra of prodan were recorded at emission wavelengths from 400 to 600 nm, with the excitation wavelength of 340 nm. The generalized polarization was estimated using the following equation, $$GP_{340} = \frac{I_b - I_r}{I_b + I_r},$$

where $I_b$ and $I_r$ are the emission intensities of Prodan at blue and red region, respectively. The fractions of the intensities of the blue and red are calculated as $$\frac{I_b}{I_b + I_r} \text{ and } \frac{I_r}{I_b + I_r},$$

respectively. In some embodiments, the normalized general polarization may be greater than a threshold value (e.g., value for a comparative lipid nanoparticle, value for a conventional particulate carrier).

In some embodiments, regardless of the amount of accessible mRNA, lipid nanoparticles having a certain physical arrangement of nucleic acids (e.g., mRNA) may have advantageous physical and/or biological properties, as described herein. Without being bound by theory, it is believed that lipid nanoparticles comprise an exterior region and one or more interior regions. The exterior region may be in direct physical contact with the bulk environment. For instance, in embodiments in which lipid nanoparticles are dispersed in a continuous phase, the exterior regions of the lipid nanoparticles may be in direct physical contact with the bulk continuous phase. In certain embodiments, the exterior region may be and/or comprise at least a portion (e.g., all) of the surface portion of the lipid nanoparticle. In other embodiments, the exterior region may not be the surface portion of the lipid nanoparticle. In some embodiments, at least a portion of an interior region is not in direct physical contact with the bulk continuous phase. In some embodiment, one or more interior regions may be at least partially encapsulated by at least at a portion of the exterior region. In some embodiments, the nucleic acid may be arranged, such that a relatively high percentage (e.g., majority) of the nucleic acids are positioned in the interior region(s).

In some embodiments, the arrangement of the nucleic acid within the lipid nanoparticle may correlate to one or more biological and/or physical properties. In certain embodiments, the arrangement of the nucleic acid within the lipid nanoparticle may correlate with nucleic acid expression levels and/or efficacy of intracellular delivery of nucleic acids. For instance, in some embodiments, lipid nanoparticles having a relatively high percentage of nucleic acids within one or more interior regions, and accordingly a relatively low percentage of nucleic acids within the exterior region, may produce high levels of protein expression (e.g., in vitro, in vivo). In some embodiments, the arrangement of the nucleic acid within the lipid nanoparticle may correlate to one or more physical properties of the lipid nanoparticle. For instance, in some embodiments, the arrangement of the nucleic acid within the lipid nanoparticle may correlate with surface polarity. For instance, in some embodiments, lipid nanoparticles having a relatively high percentage of nucleic acids within one or more interior regions, and accordingly a relatively low percentage of nucleic acids within the exterior region, may have a relatively low surface polarity.

In some embodiments, the distribution of one or more components in the lipid nanoparticle may be dictated, at least in part, by the process by which the components are assembled. For instance, in some embodiments, the distribution (e.g., accessibility, arrangement) of nucleic acid (e.g., mRNA) within the lipid nanoparticle may be controlled, at least in part, by the formulation process. For example, the formulation process may comprise one or more steps that allow the distribution of mRNA to be tailored, as described in more detail below. For example, the formulation process may use a relatively low weight percentage of certain components (e.g., PEG lipid) during the particle formation step (e.g., nanoprecipitation reaction) and/or add certain lipid nanoparticle components after particle formation.

In some embodiments, regardless of the process used, the distribution of one or more components within the lipid nanoparticle may be influenced, at least in part, by the distribution of another component in the lipid nanoparticle. For instance, the distribution of the nucleic acid within the lipid nanoparticle may be dictated, at least in part, by the distribution of another component in the lipid nanoparticle, such as a molecule comprising polyethylene glycol (also referred to as "PEG molecules"). Without being bound by theory, it is believed that certain distributions of PEG molecules promote certain associations that result in a beneficial mRNA distribution. Regardless of whether the distribution of a molecule comprising PEG (e.g., PEG lipid) influences the distribution of mRNA, certain distributions of molecules comprising polyethylene glycol (e.g., PEG lipid) may result in beneficial properties.

As described herein, in some embodiments, lipid nanoparticles having a certain distribution of molecules comprising polyethylene glycol (e.g., PEG lipid) may have advantageous physical and/or biological properties. In some embodiments, a molecule comprising polyethylene glycol (e.g., PEG lipid) may be distributed, such that a relatively high percentage (e.g., majority) of the molecule comprising polyethylene glycol (e.g., PEG-lipid) is accessible from the surface of the lipid nanoparticle. As used herein, the term "accessible" (also referred to as "surface accessible") with respect to a molecule comprising polyethylene glycol (e.g., PEG-lipid) may refer to PEG molecules that are localized at the surface of the lipid nanoparticle and/or PEG molecules that can be readily localized, e.g., through facile reorganization, at the surface of the lipid nanoparticle under certain conditions (e.g., physiological conditions, in serum, in buffer). PEG molecules that are not surface accessible may be referred to as "residual" PEG molecules. In certain embodiments, residual PEG molecules may be positioned in one or more interior regions of the lipid nanoparticles. In certain embodiments, surface accessible PEG molecules may be positioned within the exterior region of the lipid nanoparticles.

In some embodiments, the surface accessibility of PEG molecules may be determined by one or more assays (e.g., in vitro assay). In general, any suitable in vitro assay may be used. In some embodiments, the shedding of PEG molecules from the lipid nanoparticles as assessed via diffusion-ordered spectroscopy (DOSY) NMR may be used to determine the relative percentage of surface accessible and residual PEG molecules in the lipid nanoparticles and/or a composition. PEG shedding and DOSY NMR is further described in Wilson, S. C.; Baryza, J. L.; Reynolds, A. J.; Bowman, K.; Rajan, S.; et al. (2015). Real Time Measurement of PEG Shedding from Lipid Nanoparticles in Serum via NMR Spectroscopy. Molecular Pharmaceutics, 12(2):386-92, which is incorporated by reference in its entirety. In some embodiments, the percentage of surface accessible PEG molecules corresponds to the percentage of PEG molecules shed after a certain period of time (e.g., 6 hours, 24 hours) under certain conditions (e.g., in mouse serum at 25° C.).

In some embodiments, the PEG molecules may distribute in a manner that produces a relatively short half-life time. As used herein, the half-life time of a molecule comprising polyethylene glycol is the time it takes for 50% of the molecule comprising polyethylene glycol to shed from the surface of the lipid nanoparticle under certain conditions (e.g., in mouse serum at 25° C.) as determined by DOSY NMR. In some embodiments, the lipid nanoparticles may have a shorter half-life time than certain comparative lipid nanoparticles.

In some embodiments, the surface accessibility, arrangement, and/or half-life time of PEG molecules may correlate to one or more biological and/or physical properties of the lipid nanoparticles. For example, in certain embodiments, the surface accessibility, arrangement, and/or half-life time of a PEG molecule may correlate with the immunogenicity of the lipid nanoparticles and/or composition. For instance, in some embodiments, a relatively high percentage of surface accessible PEG molecules and/or a relatively short half-life time may correspond to low or no immunogenicity. Certain inventive compositions may have a lower immunogenicity than comparative compositions.

In some embodiments, the surface accessibility, arrangement, and/or half-life time of PEG molecules may correlate to one or more physical properties of the lipid nanoparticles. For example, a relatively high percentage of surface accessible PEG molecules and/or a relatively short half-life time may correspond to higher nucleic acid encapsulation efficiency. As another example, the surface accessibility, arrangement, and/or half-life time of PEG molecules may correlate with surface polarity. For instance, in some embodiments, lipid nanoparticles having a relatively high percentage of surface accessible PEG molecules and/or a relatively short half-life time may have a relatively low surface polarity.

As described herein, in certain embodiments, lipid nanoparticles may have a beneficial distribution of one or more components. In some embodiments, a lipid nanoparticle may have a beneficial distribution of two or more components (e.g., three or more components, four or more components, five or more components). For instance, the lipid nanoparticle may have a having a beneficial distribution of nucleic acid and a beneficial distribution of a PEG molecule. In some such cases, the lipid nanoparticle may have at least some (e.g., all) of the advantageous properties associated with the beneficial distribution of each component.

In some embodiments, compositions are provided. The compositions may comprise the lipid nanoparticles described herein. In some embodiments, a composition may comprise a relatively high percentage of the lipid nanoparticles described herein. In certain embodiments, the lipid nanoparticles, described herein, may have one or more properties that are superior to other lipid nanoparticles in the composition. Such a lipid nanoparticle having one or more superior properties to another lipid nanoparticle in the composition may be referred to as an "enhanced lipid nanoparticle." For example, an enhanced lipid nanoparticle may have more inaccessible mRNA than another lipid nanoparticle (e.g., all other lipid nanoparticles) in a composition. In some instances, an enhanced lipid nanoparticle may have more inaccessible mRNA than accessible mRNA. In certain embodiment, an enhanced lipid nanoparticle may have a relatively high percentage (e.g., at least about 50%, at least about 60%, at least about 70%, at least about 80%, at least about 90%, at least about 95%) of surface accessible PEG molecules. In some embodiments in which the enhanced lipid nanoparticles comprise a relatively high percentage (e.g., at least about 50%, about least about 60%, at least about 70%, about least about 80%, at least about 90%, at least about 95%) of the total lipid nanoparticles in the composition, the composition may be referred to as being enriched in enhanced lipid nanoparticles.

In some embodiments, the lipid nanoparticles and/or composition, described herein, may have a low amount of accessible nucleic acid (e.g., mRNA). For instance, in some embodiments, less than or equal to about 50%, less than or equal to about 45%, less than or equal to about 40%, less than or equal to about 35%, less than or equal to about 30%, less than or equal to about 25%, less than or equal to about 20%, less than or equal to about 15%, less than or equal to about 10%, or less than or equal to about 5% of the total amount of nucleic acid in the lipid nanoparticles and/or a composition is accessible nucleic acid (e.g., mRNA). In certain embodiments, lipid nanoparticles and/or a composition may comprise accessible nucleic acid. In some such embodiments, a lipid nanoparticle and/or a composition may comprise at least about 0.01%, at least about 0.05%, at least about 0.1%, at least about 0.5%, at least about 1%, or at least about 2% of accessible nucleic acid. All combinations of the above referenced ranges are possible (e.g., at least about 0.01% and less than or equal to about 50%).

In some embodiments, a lipid nanoparticle and/or composition, described herein, may have a beneficial amount of inaccessible nucleic acid (e.g., mRNA). For instance, in some embodiments, at least about 50%, at least about 55%, at least about 60%, at least about 65%, at least about 70%, at least about 75%, at least about 80%, at least about 85%, less than or equal to about 90%, or at least about 95% of the total amount of nucleic acid in a lipid nanoparticle and/or a composition is inaccessible nucleic acid (e.g., mRNA).

In some embodiments, a lipid nanoparticle and/or composition, described herein, may have a beneficial amount of nucleic acid (e.g., mRNA) positioned in the one or more interior regions of the lipid nanoparticles. For instance, in some embodiments, at least about 30%, at least about 35%, at least about 40%, at least about 45%, at least about 50%, at least about 55%, at least about 60%, at least about 65%, less than or equal to about 70%, at least about 75%, at least about 80%, at least about 85%, less than or equal to about 90%, or at least about 95% of the total amount of nucleic acid in the lipid nanoparticle and/or a composition is positioned in the interior region(s) of the lipid nanoparticles.

In some embodiments, a lipid nanoparticles and/or composition, described herein, may have a beneficial amount of nucleic acid (e.g., mRNA) that is at least partially (e.g., fully) encapsulated. For instance, in some embodiments, at least about 30%, at least about 35%, at least about 40%, at least about 45%, at least about 50%, at least about 55%, at least about 60%, at least about 65%, less than or equal to about 70%, at least about 75%, at least about 80%, at least about 85%, less than or equal to about 90%, or at least about 95% of the total amount of nucleic acid in the lipid nanoparticle and/or a composition is at least partially (e.g., fully) encapsulated. In certain embodiments, at least about 50%, at least about 55%, at least about 60%, at least about 65%, at least about 70%, at least about 75%, at least about 80%, at least about 85%, at least about 90%, or at least about 95% of the mRNA in the composition is fully encapsulated.

In some embodiments, the percentage of at least partially (e.g., fully) encapsulated nucleic acid may be determined by an in vitro assay (e.g., IEX) as described herein.

In some embodiments, a lipid nanoparticle and/or composition, described herein, may have a beneficial amount of surface accessible PEG molecules (e.g., PEGlipid). For instance, in some embodiments, at least about 50%, at least about 55%, at least about 60%, at least about 65%, at least about 70%, at least about 75%, at least about 80%, at least about 85%, less than or equal to about 90%, or at least about 95% of the total amount of molecules comprising PEG (e.g., PEG lipid) in the lipid nanoparticle and/or composition is surface accessible PEG molecules. In some embodiments, 100% of the total amount of molecules comprising PEG (e.g., PEG lipid) in the lipid nanoparticle and/or composition is surface accessible PEG molecules.

In some embodiments, a lipid nanoparticle and/or composition, described herein, may have a beneficial amount of residual molecules comprising PEG (e.g., PEG lipid). For instance, in some embodiments, less than or equal to about 50%, less than or equal to about 45%, less than or equal to about 40%, less than or equal to about 35%, less than or equal to about 30%, less than or equal to about 25%, less than or equal to about 20%, less than or equal to about 15%, less than or equal to about 10%, or less than or equal to about 5% of the total amount of PEG molecules (e.g., PEG-lipid) in the lipid nanoparticle and/or composition is residual PEG molecules. In certain embodiments, a lipid nanoparticle and/or a composition may comprise residual PEG molecules. In some such embodiments, the lipid nanoparticle and/or composition may comprise at least about 0.01%, at least about 0.05%, at least about 0.1%, at least about 0.5%, at least about 1%, or at least about 2% of residual PEG molecules. All combinations of the above referenced ranges are possible (e.g., at least about 0.01% and less than or equal to about 50%). In some embodiments, the lipid nanoparticle and/or composition may not comprise residual PEG molecules.

In some embodiments, a lipid nanoparticle and/or composition, described herein, may have a beneficial amount of PEG molecules (e.g., PEG lipid) positioned in the exterior region of the lipid nanoparticle(s). For instance, in some embodiments, at least about 30%, at least about 35%, at least about 40%, at least about 45%, at least about 50%, at least about 55%, at least about 60%, at least about 65%, less than or equal to about 70%, at least about 75%, at least about 80%, at least about 85%, less than or equal to about 90%, or at least about 95% of the total amount of PEG molecules (e.g., PEG lipid) in the lipid nanoparticle and/or composition is positioned in the exterior region(s) of the lipid nanoparticle(s). In certain embodiments, at least about 95% or 100% of the PEG lipid is positioned in the exterior region.

In certain embodiments in which the lipid nanoparticles comprise a molecule comprising polyethylene glycol (e.g., PEG-lipid), the half-life time of the molecule comprising polyethylene glycol may be relatively short. For instance, the half-life time may be less than or equal to about 5 hours, less than or equal to about 4.5 hours, less than or equal to about 4 hours, less than or equal to about 3 hours, less than or equal to about 2.75 hours, less than or equal to about 2.5 hours, less than or equal to about 2.25 hours, less than or equal to about 2.0 hours, less than or equal to about 1.75 hours, less than or equal to about 1.5 hours, less than or equal to about 1.25 hours, less than or equal to about 1.0 hours, less than or equal to about 0.75 hours, less than or equal to about 0.5 hours, or less than or equal to about 0.25 hours. In some instances, the half-life time may be at least about 0.01 hours, at least about 0.05 hour, at least about 0.1 hours, at least about 0.5 hours. All combinations of the above-referenced ranges are possible (e.g., at least about 0.01 hours and less than or equal to about 5 hours, at least about 0.01 hours and less than or equal to about 3 hours, at least about 0.5 hours and less than or equal to about 3 hours).

In certain embodiments in which a lipid nanoparticle and/or composition comprises a molecule comprising polyethylene glycol (e.g., PEG-lipid), the mole percentage of PEG molecule in the lipid nanoparticle and/or composition may be relatively small. For instance, in some embodiments, the mole percent of PEG molecule(s) in the lipid nanoparticle and/or composition is less than or equal to about 5%, less than or equal to about 4.5%, less than or equal to about 4.0%, less than or equal to about 3.5%, less than or equal to about 3.0%, less than or equal to about 2.5%, less than or equal to about 2.0%, less than or equal to about 1.5%, less than or equal to about 1.0%, or less than or equal to about 0.5%. In certain embodiments, a lipid nanoparticle and/or composition may comprise PEG molecule(s). In some such embodiments, lipid nanoparticles and/or a composition may comprise at least about 0.01%, at least about 0.05%, at least about 0.1%, at least about 0.5%, at least about 1%, or at least about 2% of mole percent of PEG molecules. All combinations of the above referenced ranges are possible (e.g., at least about 0.01% and less than or equal to about 5.0%). In some embodiments, the mole percentage of the PEG molecules (e.g., PEG lipid) in the lipid nanoparticle and/or composition may be less than the critical micelle concentration of the PEG molecule (e.g., PEG lipid).

In some embodiments, the molecule comprising polyethylene glycol may be a PEG lipid. In some such embodiments, the PEG lipid may comprise one or more aliphatic groups. In some instances, the PEG lipid may comprise two or more aliphatic groups. It should be understood that the two or more aliphatic groups refer to aliphatic groups that are not within the same aliphatic chain. For example, a carbon atom of the first aliphatic group may not form a direct carbon-carbon covalent bond with a carbon atom of second aliphatic group. That is, the two or more aliphatic groups may be indirectly attached to each other.

In some embodiments, the PEG lipid is not a hydroxyl-PEG lipid (PEG-OH). In some embodiments, the PEG lipid is a methoxy-PEG lipid. In other embodiments, the PEG lipid does not have the following structure:

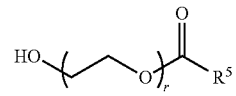

wherein r is 45, as described in more detail below. In other embodiments, the PEG-lipid is not a compound selected from Compounds 419, 420, 421, 422, 423, 424, 425, 426, 427, or 428 as described in more detail below.

In other embodiments, the LNP has a molar ratio of ionizable lipid:structural lipid:neutral lipid:PEG lipid other than 50:38.5:10:1.5. In some embodiments, the PEG lipid is less than 1.5 in the molar ratio of ionizable lipid:structural lipid:neutral lipid:PEG lipid.

In some embodiments, the normalized general polarization of a lipid nanoparticle and/or composition for laurdan may be relatively high. For instance, the normalized general polarization for laurdan may be greater than or equal to about 0.5, greater than or equal to about 0.55, greater than or equal to about 0.6, greater than or equal to about 0.65, greater than or equal to about 0.7, greater than or equal to about 0.75, greater than or equal to about 0.8, or greater than or equal to about 0.85. In some embodiments, the normalized general polarization for laurdan is greater than or equal to about 0.5 and less than or equal to about 0.9 (e.g., greater than or equal to about 0.6 and less than or equal to about 0.9, greater than or equal to about 0.7 and less than or equal to about 0.9, greater than or equal to about 0.75 and less than or equal to about 0.9).

In some embodiments, a lipid nanoparticle and/or composition may produce desirable in vitro and/or in vivo protein expression. In certain embodiments, the protein expression may be greater than a comparative lipid. In some embodiments, the protein expression may be greater than a threshold value (e.g., conventional particulate carrier). In another aspect, precursor lipid nanoparticles are provided. As used herein, a "precursor lipid nanoparticle" refers to a lipid nanoparticle that is a precursor to a lipid nanoparticle, described herein. In some embodiments, a precursor lipid nanoparticle may be formed and/or exist during one or more steps in the particle formulation process. In some embodiments, in which a lipid nanoparticle comprises a PEG molecule, the precursor lipid nanoparticle may comprise a relatively low percentage of PEG molecules (e.g., at least about 0.01 mol % and less than or equal to about 1.0 mol %, at least about 0.05 mol %, at least about 0.1 mol %, at least about 0.2 mol %, at least about 0.3 mol %, at least about 0.4 mol %, at least about 0.5 mol %, at least about 0.6 mol %, at least about 0.7 mol %, or 0.8 mol %). In some embodiments, in which a lipid nanoparticle comprises a PEG molecule, the precursor lipid nanoparticle may have more mRNA associated with the ionizable lipid than the PEG molecule. For instance, at least about 50%, at least about 55%, at least about 60%, at least about 65%, at least about 70%, at least about 75%, at least about 80%, at least about 85%, at least about 90%, or at least about 95% of the mRNA in the precursor lipid nanoparticle is associated with the ionizable lipid. In some such cases, less than about 50%, less than about 45%, less than about 40%, less than about 35%, less than about 30%, less than about 25%, less than about 20%, less than about 15%, less than about 10%, or less than about 5% of the mRNA in the precursor lipid nanoparticle is associated with the PEG molecule (e.g., PEG lipid). In certain embodiments, a ratio of mRNA associated with the ionizable lipid to mRNA associated with the PEG lipid in the precursor lipid nanoparticles is at least about 2:1 (e.g., at least about 3:1, at least about 4:1, at least about 5:1). In some embodiments, a composition comprising precursor lipid nanoparticles may comprise one or more organic solvents (e.g., ethanol). In certain embodiments, the composition may be enriched in precursor lipid nanoparticles. For instance, at least about 50% (e.g., at least about 50%, at least about 55%, at least about 60%, at least about 65%, at least about 70%, at least about 75%, at least about 80%, at least about 85%, at least about 90%, at least about 95%) of the lipid nanoparticles in the composition may be precursor lipid nanoparticles.

The present disclosure provides methods of producing a lipid nanoparticle composition, the method comprising: i) mixing a lipid solution comprising a first PEG lipid and an ionizable lipid with a solution comprising a nucleic acid thereby forming a precursor lipid nanoparticle, ii) adding a lipid nanoparticle modifier comprising a modifying agent to the precursor lipid nanoparticle thereby forming a modified lipid nanoparticle, and iii) processing the precursor lipid nanoparticle, the modified lipid nanoparticle, or both thereby forming the lipid nanoparticle composition.

In certain embodiments, the precursor lipid nanoparticle is not processed prior to the adding the lipid nanoparticle modifier. As used herein, this embodiment may be referred to as a "post insertion" method or process.

In certain embodiments, the precursor lipid nanoparticle is processed prior to adding the lipid nanoparticle modifier. As used herein, this embodiment may be referred to as a "final spike" method or process.

In some embodiments, the modifying agent is at least one selected from the group consisting of a second PEG lipid and a surfactant. In some embodiments, the modifying agent is a second PEG lipid. In some embodiments, the modifying agent is a surfactant.

In some embodiments, the modifying agent is a second PEG lipid. In certain embodiments, the first PEG lipid and the second PEG lipid are the same. In certain embodiments, the first PEG lipid and the second PEG lipid are not the same.

In some embodiments, the molar ratio of the first PEG lipid to the modifying agent is in a range of about 1:100 to about 1:1, preferably about 1:50 to about 1:1, preferably about 1:25 to about 1:1, preferably about 1:10 to about 1:1. In some embodiments, the modifying agent is a second PEG lipid and the molar ratio of the first PEG lipid to the second PEG lipid is in a range of about 1:100 to about 1:1, preferably about 1:50 to about 1:1, preferably about 1:25 to about 1:1, preferably about 1:10 to about 1:1. In some embodiments, the modifying agent is a surfactant and the molar ratio of the first PEG lipid to the surfactant is in a range of about 1:100 to about 1:1, preferably about 1:50 to about 1:1, preferably about 1:25 to about 1:1, preferably about 1:10 to about 1:1.

The lipid mixture can be solubilized in a water miscible organic solvent, preferably absolute ethanol. In certain embodiments, the organic solvent is used in the form in which it is commercially available. In one exemplary embodiment, the mixture of lipids is a mixture of an ionizable lipid and a first PEG lipid are co-solubilized in the organic solvent. In preferred embodiments, the lipid mixture consists essentially of an ionizable lipid and a PEG lipid, and optionally a phospholipid and/or a structural lipid. Preferred molar ranges are between 30 to 60 mol % ionizable lipid and 0.01 to 10 mol % first PEG lipid, preferably 0.01-5 mol %, preferably 0.01-4 mol %, preferably 0.01-3 mol %, preferably 0.01-2 mol %, preferably 0.01-1 mol %, preferably 0.01-0.8 mol %, preferably 0.01-0.6 mol %, preferably 0.01-0.5 mol %, preferably 0.01-0.25 mol % first PEG lipid. The total concentration of lipid is preferably less than 25 mg/ml, preferably less than 5 mg/ml. The lipid mixture may filtered through membrane, e.g. a 0.45 or 0.2 μm filter.

In accordance with the present invention, the lipid mixture may be combined with a nucleic acid solution, preferably in the form of a buffered aqueous solution. The buffered aqueous solution may be a solution in which the buffer has a pH less than the pKa of a protonated lipid in the lipid mixture. Examples of suitable buffers include, but are not limited to, citrate, phosphate, and acetate. A particularly preferred buffer is citrate buffer. Preferred buffers will be in the concentration range of 1-1000 mM of the anion, depending on the chemistry of the nucleic acid being encapsulated, and optimization of buffer concentration may be significant to achieving high loading levels. It may be suitable to add a cryoprotectant, and/or a non-ionic solute, which will balance the osmotic potential across the particle membrane, e.g., when the particles are dialyzed to remove ethanol, increase the pH, or mixed with a pharmaceutically acceptable carrier or diluent. The amount of nucleic acid in buffer is preferably from about 0.01 to 1.0 mg/mL, preferably 0.08 to 0.8 mg/mL At the time of addition of the lipid solution (e.g., ethanol), the temperature of the aqueous nucleic acid solution is 25 to 45° C., preferably 30 to 40° C. In certain embodiments, briefly heating the aqueous nucleic acid solution at elevated temperature may be useful, e.g., 1-2 minutes at 65° C. The lipid solution may be added to the aqueous solution either by spraying on the air-water interface, in a narrow stream, or through a liquid-liquid interface between lipid solution delivered through a tube that is submerged in the aqueous nucleic acid solution.

The organic lipid solution may be added by gravity or by a pump delivering the organic lipid solution to the aqueous nucleic acid solution at a controlled rate, preferably a constant rate. The delivery of the organic lipid solution can be completed in 1 minute to 100 minutes, preferably in 1 to 25 minutes. The organic lipid solution may be added through a single spray or stream, through a tube or nozzle, or through a multi-nozzle system. While the lipid organic solution is added into the nucleic acid aqueous solution, the resulting solution it may be mixed by stirring, shaking, or recirculation. As used herein, "mixing" preferably comprises turbulent mixing (Tmix), microfluidic mixing, or both. The addition/mixing step results in a final concentration that is preferably 25 to 45% ethanol, most preferably 35% ethanol.

Preferably, formation involves either turbulent or microfluidic mixing of solutions to induce precipitation lipids in organic phase with nucleic acid in aqueous phase, or extrusion of an already phase-separated mixture of nucleic acid and lipids through membranes to create LNPs.

In one step of the process a lipid solution comprising a first PEG lipid is mixed with a solution comprising a nucleic acid thereby forming a precursor lipid nanoparticle. In some embodiments, the precursor nucleic provided. In another aspect, precursor lipid nanoparticles are provided. In some embodiments, a precursor lipid nanoparticle may be formed and/or exist during one or more steps in the particle formulation process. In some embodiments, in which a lipid nanoparticle comprises a PEG molecule, the precursor lipid nanoparticle may comprise a relatively low percentage of PEG molecules (e.g., at least about 0.01 mol % and less than or equal to about 1.0 mol %, at least about 0.05 mol %, at least about 0.1 mol %, at least about 0.2 mol %, at least about 0.3 mol %, at least about 0.4 mol %, at least about 0.5 mol %, at least about 0.6 mol %, at least about 0.7 mol %, or 0.8 mol %).

In certain embodiments, all of the nucleic acid in the precursor lipid nanoparticle is associated with the ionizable lipid. In certain embodiments, between about 90% and about 100% of the nucleic acid in the precursor lipid nanoparticle is associated with the ionizable lipid, preferably about 95% to about 100%, preferably about 98% to about 100%, preferably about 99% to about 100%.

In some embodiments, in which a lipid nanoparticle comprises a PEG molecule, the precursor lipid nanoparticle may have more nucleic acid associated with the ionizable lipid than the PEG molecule. For instance, at least about 50%, at least about 60%, at least about 70%, at least about 80%, or at least about 90% of the nucleic acid in the precursor lipid nanoparticle is associated with the ionizable lipid. In some such cases, less than about 50%, less than about 40%, less than about 30%, less than about 20%, or less than about 10% of the nucleic acid in the precursor lipid nanoparticle is associated with the PEG molecule (e.g., PEG lipid). In certain embodiments, a ratio of nucleic acid associated with the ionizable lipid to nucleic acid associated with the PEG lipid in the precursor lipid nanoparticles is at least about 2:1. In some embodiments, a composition comprising precursor lipid nanoparticles may comprise one or more organic solvents (e.g., ethanol). In certain embodiments, the lipid nanoparticle composition may be enriched in precursor lipid nanoparticles. For instance, at least about 50% of the lipid nanoparticles in the lipid nanoparticle composition may be precursor lipid nanoparticles.

In some embodiments, the precursor lipid nanoparticle comprises about 30-60 mol % ionizable lipid; about 0-30 mol % phospholipid; about 15-50 mol % structural lipid; and about 0.01-10 mol % the first PEG lipid. In some embodiments, the precursor lipid nanoparticle comprises about 30-60 mol % ionizable lipid; about 0-30 mol % phospholipid; about 15-50 mol % structural lipid; and about 0.01-1 mol % the first PEG lipid. In some embodiments, the precursor lipid nanoparticle comprises about 40-60 mol % ionizable lipid; about 5-15 mol % phospholipid; about 35-45 mol % structural lipid; and about 0.01-10 mol % the first PEG lipid. In some embodiments, the precursor lipid nanoparticle comprises about 40-60 mol % ionizable lipid; about 5-15 mol % phospholipid; about 35-45 mol % structural lipid; and about 0.01-1 mol % the first PEG lipid. In some embodiments, the precursor lipid nanoparticle comprises about 30-60 mol % ionizable lipid; about 0-30 mol % phospholipid; about 15-50 mol % structural lipid; and about 0.01-0.75 mol % the first PEG lipid. In some embodiments, the precursor lipid nanoparticle comprises about 30-60 mol % ionizable lipid; about 0-30 mol % phospholipid; about 15-50 mol % structural lipid; and about 0.01-0.5 mol % the first PEG lipid.

In certain embodiments, the processing may involve treating to remove an organic solvent (i.e., ethanol), by dialysis or filtration, preferably by diafiltration. As used herein, "processing" includes steps to purify, pH adjust, buffer exchange, and/or concentrate LNPs. In some embodiments, the processing comprises a filtration such as a sterile filtration. In one embodiment, the processing comprises a tangential flow filtration (TFF). While the ethanol is removed, the aqueous solution is converted to a one buffered at a neutral pH, pH 6.5 to 7.8, pH 6.8 to pH 7.5, preferably, pH 7.0 to pH 7.2, for example a phosphate or HEPES buffer. The resulting aqueous solution is preferably sterilized before storage or use, such as, for example by filtration through a 0.22 µm filter.

In certain embodiments, the processing may comprise a freezing and/or lyophilizing. Lyophilizing steps may be carried out in a suitable glass receptacle, preferably a 10 ml, cylindrical glass vial. The glass vial must withstanding extreme changes in temperatures of less than −40° C. and greater than room temperature in short periods of time, and be cut in a uniform shape. The composition comprising the lipid nanoparticle is added to the vial, preferably in a 3 ml volume, and preferably with about 9 mg/ml lipid. The step of lyophilizing may comprise freezing the composition at a temperature of greater than about −40° C., or e.g. less than about −30° C., forming a frozen composition; and drying the frozen composition to form the lyophilized composition. The freezing step preferably results in a linear decrease in temperature to the final over about 6 minutes, preferably at 1° C./minute from 20 to −40° C. More preferably, sucrose at 12-15% may be used, and the drying step is at about 50-150 mTorr, first at a low temperature of about −15 to about −35° C., and thereafter at a higher temperature of room temperature to about 25° C., and is completed in three to seven days. In another embodiment of the present disclosure the drying step is at about 50-100 mTorr, first at a low temperature of about 0 to about −15° C., and then at the higher temperature.

In certain embodiments, the method may further comprise packing the lipid nanoparticle composition. As used herein, "storage" or "packing" may refer to storing drug product in its final state or in-process storage of LNPs before they are placed into final packaging. Modes of storage and/or packing include, but are not limited to refrigeration in sterile bags, refrigerated or frozen formulations in vials, lyophilized formulations in vials and syringes, etc.

In some embodiments, the lipid nanoparticle comprises about 30-60 mol % ionizable lipid; about 0-30 mol % phospholipid; about 15-50 mol % structural lipid; and about 0.01-20 mol % total amount of the first PEG lipid and the second PEG lipid. In some embodiments, the lipid nanoparticle comprises about 30-60 mol % ionizable lipid; about 0-30 mol % phospholipid; about 15-50 mol % structural lipid; and about 0.5-3.0 mol % total amount of the first PEG lipid and the second PEG lipid. In some embodiments, the lipid nanoparticle comprises about 40-60 mol % ionizable lipid; about 5-15 mol % phospholipid; about 35-45 mol % structural lipid; and about 0.01-20 mol % total amount of the first PEG lipid and the second PEG lipid. In some embodiments, the lipid nanoparticle comprises about 40-60 mol % ionizable lipid; about 5-15 mol % phospholipid; about 35-45 mol % structural lipid; and about 0.5-3 mol % total amount of the first PEG lipid and the second PEG lipid. In some embodiments, the lipid nanoparticle comprises about 30-60 mol % ionizable lipid; about 0-30 mol % phospholipid; about 15-50 mol % structural lipid; and about 0.5-2.5 mol % total amount of the first PEG lipid and the second PEG lipid. In some embodiments, the lipid nanoparticle comprises about 30-60 mol % ionizable lipid; about 0-30 mol % phospholipid; about 15-50 mol % structural lipid; and about 0.5-2.25 mol % total amount of the first PEG lipid and the second PEG lipid.

In some embodiments, the concentration of the non-ionic surfactant in the nucleic acid LNP formulation ranges from about 0.00001% w/v to about 1% w/v, e.g., from about 0.00005% w/v to about 0.5% w/v, or from about 0.0001% w/v to about 0.1% w/v.

In some embodiments, the concentration of the non-ionic surfactant in the nucleic acid LNP formulation ranges from about 0.000001 wt % to about 1 wt %, e.g., from about 0.000002 wt % to about 0.8 wt %, or from about 0.000005 wt % to about 0.5 wt %.

In some embodiments, the concentration of the PEG lipid in the stabilized LNP formulation ranges from about 0.01% by molar to about 50% by molar, e.g., from about 0.05% by molar to about 20% by molar, from about 0.07% by molar to about 10% by molar, from about 0.1% by molar to about 8% by molar, from about 0.2% by molar to about 5% by molar, or from about 0.25% by molar to about 3% by molar.

The present disclosure provides methods of stabilizing a lipid nanoparticle (LNP) formulation upon application of stress, by adding modifying agent to the LNP formulation before or when the stress is applied or during its production.

In some embodiments, the stress includes any stress applied to the formulation when producing, purifying, packing, storing, transporting and using the formulation, such as heat, shear, excessive agitation, membrane concentration polarization (change in charge state), dehydration, freezing stress, drying stress, freeze/thaw stress, nebulization stress, etc. For example, the stress can cause one or more undesired property changes to the formulation, such as an increased amount of impurities, of sub-visible particles, or both, an increase in LNP size, a decrease in encapsulation efficiency, in therapeutic efficacy, or both, and a decrease in tolerability (e.g., an increase in immunogenicity).

In some embodiments, the stress applied is from producing a LNP formulation, for example, from mixing lipid components in an organic solvent (e.g., ethanol) to produce an organic phase, from mixing mRNA into an acidic solution to produce an aqueous phase, from adjusting pH values of the aqueous phase, and/or from mixing the organic phase with the aqueous phase to produce the LNP formulation. For example, each said mixing step can comprise turbulent mixing or microfluidic mixing. For example, before mixing the organic with the aqueous phase, each phase may be purified via, e.g., filtration (such as tangential flow filtration or TFF). For example, the stress applied is from such purification.

In some embodiments, the stress applied is from processing LNPs following LNP formation, e.g., downstream purification and concentration by tangential flow filtration (TFF). For example, during a typical TFF process, the LNP dispersion is exposed to a variety of hydrophobic interfaces, shear forces, and turbulence. For example, during a typical TFF process, molecules larger than the membrane pores (i.e., LNPs) accumulate at the membrane surface to form a gel or concentration-polarized layer. For example, the increased concentration of LNPs serve as a destabilizing stress, promoting inter-molecular interactions that may generate larger particulate species.

In some embodiments, the stress applied is from purification of a LNP formulation. Accordingly, the disclosure also features a method of purifying a lipid nanoparticle (LNP) formulation, comprising filtering a first LNP formulation in the presence of an amphiphilic polymer to obtain a second LNP formulation.

In some embodiments, the stress applied is from freezing or lyophilizing a LNP formulation. Accordingly, the disclosure also features a method of freezing or lyophilizing a lipid nanoparticle (LNP) formulation, comprising freezing or lyophilizing a first LNP formulation in the presence of modifying agent.

For example, the modifying agent is present at a concentration ranging between about 0.025% w/v and about 1% w/v (e.g., about 0.025% w/v, about 0.05% w/v, about 0.1% w/v, about 0.5% w/v, about 1% w/v, about 0.025-0.5% w/v, about 0.05-1% w/v, about 0.1-1% w/v, or about 0.1-0.5% w/v). For example, the modifying agent is present at a concentration ranging between about 0.025% w/w and about 1% w/w (e.g., about 0.025% w/w, about 0.05% w/w, about 0.1% w/w, about 0.5% w/w, about 1% w/w, about 0.025-0.5% w/w, about 0.05-1% w/w, about 0.1-1% w/w, or about 0.1-0.5% w/w).

For example, the modifying agent is present at a concentration ranging between about 0.025% w/v and about 1% w/v (e.g., about 0.025% w/v, about 0.05% w/v, about 0.1% w/v, about 0.5% w/v, about 1% w/v, about 0.025-0.5% w/v, about 0.05-1% w/v, about 0.1-1% w/v, or about 0.1-0.5% w/v). For example, the modifying agent is present at a concentration ranging between about 0.025% w/w and about 1% w/w (e.g., about 0.025% w/w, about 0.05% w/w, about 0.1% w/w, about 0.5% w/w, about 1% w/w, about 0.025-0.5% w/w, about 0.05-1% w/w, about 0.1-1% w/w, or about 0.1-0.5% w/w).

For example, the third amphiphilic polymer is present at a concentration ranging between about 0.1% w/v and about 3% w/v (e.g., about 0.1% w/v, about 0.5% w/v, about 1% w/v, about 2% w/v, about 2.5% w/v, about 0.1-2.5% w/v, about 0.1-1% w/v, about 0.1-0.5% w/v, or about 0.1-0.4% w/v). For example, the third amphiphilic polymer is present at a concentration ranging between about 0.1% w/w and about 3% w/w (e.g., about 0.1% w/w, about 0.5% w/w, about 1% w/w, about 2% w/w, about 2.5% w/w, about 0.1-2.5% w/w, about 0.1-1% w/w, about 0.1-0.5% w/w, or about 0.1-0.4% w/w).

For example, the fourth amphiphilic polymer is present at a concentration ranging between about 0.1% w/v and about 3% w/v (e.g., about 0.1% w/v, about 0.5% w/v, about 1% w/v, about 2% w/v, about 0.1-2.5% w/v, about 0.1-1% w/v, about 0.1-0.5% w/v, or about 0.1-0.4% w/v). For example, the fourth amphiphilic polymer is present at a concentration ranging between about 0.1% w/w and about 3% w/w (e.g., about 0.1% w/w, about 0.5% w/w, about 1% w/w, about 2% w/w, about 2.5% w/w, about 0.1-2.5% w/w, about 0.1-1% w/w, about 0.1-0.5% w/w, or about 0.1-0.4% w/w).

For example, the weight ratio between the modifying agent and the nucleic acid is about 0.025:1 to about 100:1.

For example, the modifying agent is added such that the weight ratio between the modifying agent and the LNP is about 0.0004:1 to about 100:1 (e.g., about 0.001:1 to about 10:1, about 0.001:1 to about 5:1, about 0.001:1 to about 0.1:1, about 0.005 to about 0.4:1, or about 0.5:1 to about 4:1, about 0.05:1 to about 5:1, about 0.1:1 to about 5:1 or about 0.05:1 to about 2.5:1, about 1:1 to about 50:1, about 2:1 to about 50:1 or about 1:1 to about 25:1).

In one aspect, the present disclosure is based, at least, in part on the understanding that certain surface properties of lipid nanoparticles (LNPs), in particular, lipid nanoparticles (LNPs) encapsulating nucleic acids, correlate with or dictate several key biological attributes of such LNPs, thus affecting efficacy of LNP-mediated delivery of nucleic acids (e.g., delivery of therapeutic nucleic acids, for example, therapeutic mRNAs). The instant inventors have determined that certain surface properties of LNPs can cause undesirable immunotoxicity (i.e., inflammatory and/or immune responses in response to LNP that result in the protein encoded by the therapeutic nucleic acid, e.g., mRNA, being cleared. Such a phenomenon is described herein and in the art as accelerated blood clearance, or ABC. It is herein described that certain chemical components of the LNP surface, for example, phospholipid and or PEG components, can present on the LNP surface to create epitopes recognized by natural IgGs and/or IgMs, component-specific antibodies (e.g., IgGs, for example, anti-PEG IgGs), as well as ligands recognized by, for example, scavenger receptors.

As such, the surface properties of (LNPs), in particular, lipid nanoparticles (LNPs) encapsulating nucleic acids, can significantly affect in vivo performance of the nucleic acids, e.g., mRNAs, when delivered to subjects via LNP-mediated delivery.

The present disclosure is also based, at least, in part on surprising discovery that traditional methods for determining encapsulation efficiency can produce artificially high values for encapsulation of mRNA in LNPs. Fluorescent dye-based methods (e.g., Ribogreen) are routinely used in the art for the quantitation of RNA e.g., in vitro transcribed RNAs, and are regularly used to determine amount or percentage of RNA encapsulated in LNPs. Unbound (or free) dye exhibits little fluorescence and possesses a negligible absorbance signature, whereas dye bound to nucleic acids fluoresces with high intensity. The fluorescence can be detected by a sensor and the nucleic acid can be quantified. Quantitation of RNA can be used to determine amount or percentage of RNA encapsulated in LNPs indirectly, by determining free RNA remaining post-encapsulation. Such methods assume that bound RNA equates to encapsulated RNA. However, it has been discovered that RNA may exist in bound form(s) other that fully-encapsulated, for example, lipid-associated forms, and such forms can artificially inflate an indirectly determined encapsulation efficiency.

Orthogonal methods are described herein that can be used to more accurately determine encapsulation efficiency. In particular, fractionation technologies, combined with compositional and/or biological analyses can be used to accurately determine mRNA encapsulation within LNPs. Chemical composition of LNPs and production processes, and optionally purification processes, can be improved to enrich LNP populations for particles having desired surface properties as well as enhanced encapsulation efficiencies, ultimately resulting in highly efficacious LNP compositions for use in therapeutic delivery of nucleic acids, e.g., mRNA.

In some aspects, this disclosure provides lipid-comprising compounds and compositions that are not subject to ABC and/or that have reduced toxicity, as well as methods for delivering LNPs to a subject without promoting LNP-related drug responses, including ABC and LNP-induced toxicity.

Lipid-comprising compounds and compositions are compounds and compositions that comprise or are conjugated to one or more lipids. These agents may be referred to herein as lipid-conjugated agents or lipidated agents. Alternatively, such lipids may encapsulate agents such as prophylactic, therapeutic and diagnostic agents. These agents may be referred to herein as lipid-encapsulated agents or lipid nanoparticle (LNP) encapsulated agents.

Thus, it is to be understood that this disclosure provides enriched compositions for delivering highly effective therapeutic agents and avoiding, reducing or eliminating ABC and toxicity upon in vivo administration. Without being bound in theory, it is believed that within a population of LNPs (e.g., LNPs encapsulating mRNA), mRNA can exist in a variety of different encapsulation states, including, for example, fully encapsulated, surface-associated, loosely encapsulated (or other physical states). Art-recognized methods for determining nucleic acid encapsulation efficiency, in particular, the routinely-used Ribogreen assays, fails to differentiate between such physical states (e.g., deos not discern differences in structural characteristics). To exemplify the utility of the IEX method of the invention, a LNP sample population can be subjected to an art-recognized separation technique, for example, size-exclusion chromatography (SEC). This fractionates particles based on size. Fractions can be subjected, for example, to a biological assay, e.g., in vitro protein expression assay. Fractions can likewise be subjected to determination of encapsulation efficiency according to the IEX methods of the invention. It is shown in the Examples that % mRNA accessible or retention on IEX column correlates (inversely) with in vitro protein expression.

The ability to accurately quantify encapsulation efficiency in LNPs has important implications for therapeutic delivery of nucleic acids. Enriched populations of LNPs have more therapeutic cargo (RNA) encapsulated per LNP particle than prior art particles. Such distinctions can now be assessed using the methods described herein. In some embodiments, an enriched population of LNPs have at least 50% of the LNPs comprise RNA encapsulated within the inner core. In embodiments enriched population of LNPs have at least 55%, 60%, 65%, 70%, 75%, 80%, 85%, 90%, 95%, 96%, 97%, 98%, 99% and in some embodiments 100% of the LNPs comprise RNA encapsulated within the inner core. In other embodiments in an enriched population of LNPs at least 50% of the RNA in the composition is encapsulated within the LNPs, relative to RNA in the composition but not associated with complete LNP particles. In other embodiments in an enriched population of LNPs at least at least 55%, 60%, 65%, 70%, 75%, 80%, 85%, 90%, 95%, 96%, 97%, 98%, 99% and in some embodiments 100% of the RNA in the composition is encapsulated within the LNPs.

The LNPs described herein have an outer shell and an inner core. In some embodiments, the structure may have a single outer shell. In other embodiments, the structure may have an outer shell and 1 or more inner shells. The composition of the outer shell is important to stealthness of the particle since the outer shell is initially exposed to the cells of the immune system. In some embodiments, it is desirable to have less than 90% of a nucleic acid material exposed to the exterior of the LNP and presented on the surface. In other embodiments, it is desirable to have no nucleic acid exposed to the exterior of the LNP.

Additionally, the presence of certain phospholipids such as phosphatidylcholine (PC) on the surface of the LNP impart functional properties. In some embodiments, the lipids have minimal amounts of PC on the surface. For example, in some embodiments more than 50% of the phospholipids in the outer shell of the LNP are PC. In other embodiments less than 9%, 8%, 7%, 6%, 5%, 4%, 3%, 2%, or 1% of the phospholipids in the outer shell of the LNP are PC. In other embodiments, the outer shell of the LNP is free of PC. Certain of the LNPs provided herein lack specific phosphatidyl choline lipids such as but not limiting to DSPC. Certain of the LNPs comprise a phosphatidyl choline analog, such analogs comprising modified head groups (e.g., a modified quaternary amine head group), modified core group, and/or modified lipid tail group. Such analogs may comprise a zwitterionic group that is a non-PC zwitterionic group.

The fluidity of the outer shell of the LNP has an effect on the immunogenicity of the LNP. In some embodiments at least 50% (e.g., at least 55%, at least about 60%, at least about 70%, at least about 75%, at least about 80%, at least about 90%, at least about 95%) of the LNPs have an outer shell fluidity value of greater than a threshold polarization level and wherein RNA is encapsulated within the LNP. The polarization value may be measured using known assays in the art. For instance, Sanchez et al Biophys J 1991, 60, 179-189. An exemplary polarization measurement involves: 2 μL of Prodan (0.1 mg/mL in DMSO) was added into 998 μL LNPs (lipid conc. of 0.12 mg/mL in PBS). The mixtures were incubated at 25° C. for at least 1 hour to allow the partition of the dye into the LNP. The fluorescence spectra of prodan were recorded at emission wavelengths from 400 to 600 nm, with the excitation wavelength of 340 nm. The generalized polarization was estimated using the following equation, $$GP_{340} = \frac{I_b - I_r}{I_b + I_r},$$

where $I_b$ and $I_r$ are the emission intensities of Prodan or Laurdan at blue and red region, respectively. The fractions of the intensities of the blue and red are calculated as $$\frac{I_b}{I_b + I_r} \text{ and } \frac{I_r}{I_b + I_r},$$

respectively. The threshold is the level of polarization of an LNP known in the art such an MC3 LNP.

In some embodiments at least about 50%, at least about 60%, at least about 70%, at least about 80% or at least about 90% of the LNPs in the population have mRNA encapsulated therein, as determined by ion-exchange chromatography (IEX). In other embodiments, the LNPs have an encapsulation efficiency of at least about 50%, at least about 60%, at least about 70%, at least about 80% or at least about 90%, as determined by ion-exchange chromatography (IEX).

In some embodiments, the composition is enriched for LNPs (a) lacking B1a cell-stimulating phospholipid epitopes, and/or (b) lacking scavenger receptor ligands. As used herein, the term "phospholipid epitope" refers to a structural arrangement of phospholipids, or phospholipid headgroups, within an LNP, e.g., within an LNP layer (for example, an outer layer or surface layer), wherein the phospholipid is capable of stimulating B1a cells. As used herein, the term "scavenger receptor ligand" refers to a structural arrangement of lipids within an LNP, e.g., within an LNP layer (for example, an outer layer or surface layer), wherein the lipids are capable of binding and/or activating scavenger receptors.

Accelerated Blood Clearance (ABC)

The invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments, the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus, a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments, the reduction is 10-100%, 10-50%, 20-100%, 20-50%, 30-100%, 30-50%, 40%-100%, 40-80%, 50-90%, or 50-100%. Alternatively, the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically, by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case, the LNP is directly or indirectly interacting with the sensors. The sensors may interact directly with one another in response to recognition of the LNP. For instance, many sensors are located in the spleen and can easily interact with one another. Alternatively, one or more of the sensors may interact with LNP in the blood and become activated. The activated sensor may then interact directly with other sensors or indirectly (e.g., through the stimulation or production of a messenger such as a cytokine e.g., IL6).

In some embodiments, the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time, the circulating effectors can interact with newly administered LNPs, triggering those LNPs for clearance by the body. For instance, an effector may recognize and bind to an LNP. The Fc region of the effector may be recognized by and trigger uptake of the decorated LNP entitiesby macrophages. The macrophages are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments, the LNP is designed to limit or block interaction of the LNP with a sensor. For instance, the LNP may have an altered PC and/or PEG to prevent interactions with sensors. Alternatively, or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus, conventional B cells react against the administered agent and contribute to IgM (and eventually IgG) that mediates ABC. The IgM and IgG are typically anti-PEG IgM and anti-PEG IgG.

It is contemplated that in some instances, most of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as "poly-specific" or "poly-reactive", indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments, it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments, these agents block the interaction between B1a/B1b cells and the LNP or platelets or pDC. For instance, the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments, the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively, agents that act on the pDC to block its ability to get activated or on its effectors can be used together with the LNP to avoid ABC.

Platelets may also play an important role in ABC and toxicity. Very quickly after a first dose of LNP is administered to a subject platelets associate with the LNP, aggregate and are activated. In some embodiments, it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively, agents that act on the platelets to block its activity once it is activated or on its effectors can be used together with the LNP to avoid ABC.

Measuring ABC and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments, the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus, administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

B1a or B1b Activation Assay

Certain compositions provided in this disclosure do not activate B cells, such as B1a or B1b cells (CD19+CD5+) and/or conventional B cells (CD19+CD5−. Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments, the terms do not activate and do not induce production are a relative reduction to a reference value or condition. In some embodiments, the reference value or condition is the amount of activation or induction of production of a molecule such as IgM by a standard LNP such as an MC3 LNP. In some embodiments, the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments, the terms do not activate cells such as B cells and do not induce production of a protein such as IgM may refer to an undetectable amount of the active cells or the specific protein.

Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related psudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune cascade for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

In one set of embodiments, lipid nanoparticles (LNPs) are provided. In one embodiment, a lipid nanoparticle comprises lipids including an ionizable lipid, a structural lipid, a phospholipid, and mRNA. Each of the LNPs described herein may be used as a formulation for the mRNA described herein. In one embodiment, a lipid nanoparticle comprises an ionizable lipid, a structural lipid, a phospholipid, and mRNA. In some embodiments, the LNP comprises an ionizable lipid, a PEG-modified lipid, a phospholipid and a structural lipid. In some embodiments, the LNP has a molar ratio of about 20-60% ionizable lipid:about 5-25% phospholipid:about 25-55% structural lipid; and about 0.5-15% PEG-modified lipid. In some embodiments, the LNP comprises a molar ratio of about 50% ionizable lipid, about 1.5% PEG-modified lipid, about 38.5% structural lipid and about 10% phospholipid. In some embodiments, the LNP comprises a molar ratio of about 55% ionizable lipid, about 2.5% PEG lipid, about 32.5% structural lipid and about 10% phospholipid. In some embodiments, the ionizable lipid is an ionizable amino or cationic lipid and the phospholipid is a neutral lipid, and the structural lipid is a cholesterol. In some embodiments, the LNP has a molar ratio of 50:38.5:10:1.5 of ionizable lipid:cholesterol:DSPC:PEG2000-DMG.

a. Ionizable Lipid

The present disclosure provides pharmaceutical compositions with advantageous properties. For example, the lipids described herein (e.g. those having any of Formula (I), (IA), (II), (IIa), (IIb), (IIc), (IId), (IIe), (III), (IV), (V), or (VI) may be advantageously used in lipid nanoparticle compositions for the delivery of therapeutic and/or prophylactic agents to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprises a reference lipid (e.g., MC3, KC2, or DLinDMA) and the same therapeutic or prophylactic agent. In particular, the present application provides pharmaceutical compositions comprising:

(a) a polynucleotide comprising a nucleotide sequence encoding a target polypeptide; and (b) a delivery agent.

In some embodiments, the delivery agent comprises a lipid compound having the Formula (I)

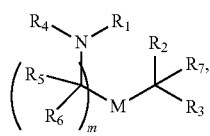

(I)

wherein $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In some embodiments, a subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof, wherein alkyl and alkenyl groups may be linear or branched.

In some embodiments, a subset of compounds of Formula (I) includes those in which when $R_4$ is —$(CH_2)_{in}Q$, —$(CH_2)_n CHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In another embodiment, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n Q$, —$(CH_2)_n CHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_n N(R)_2$, —C(O)OR, —OC(O)R, —$CX_3$, $CX_2H$, $CXH_2$, —CN, —$C(O)N(R)_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In another embodiment, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n Q$, —$(CH_2)_n CHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)$—$N(R)_2$, —C(O)OR, —OC(O)R, —$CX_3$, —$CX_2H$, —$CXH_2$, —CN, —$C(O)N(R)_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, In yet another embodiment, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n Q$, —$(CH_2)_n CHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, (R)$_2$, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)—CHQR in which n is 1, or (iii) R$_4$ is —CHQR, and —CQ(R)$_2$, then Q is either a 5- to 14-membered heteroaryl or 8- to 14-membered heterocycloalkyl;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiment, another subset of compounds of Formula (I) includes those in which R$_1$ is selected from the group consisting of C$_{5-20}$ alkyl, C$_{5-20}$ alkenyl, —R*YR", —YR", and —R"M'R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heterocycle having one or more heteroatoms selected from N, O, and S, —OR, —O(CH$_2$)—N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)$_n$CHQR in which n is 1, or (iii) R$_4$ is —CHQR, and —CQ(R)$_2$, then Q is either a 5- to 14-membered heteroaryl or 8- to 14-membered heterocycloalkyl;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiment, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heteroaryl having one or more heteroatoms selected from N, O, and S, —OR, —O(CH$_2$)—N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiment, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)—N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiment, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —(CH$_2$)$_n$Q or —(CH$_2$)$_n$CHQR, where Q is —N(R)$_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiment, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —(CH$_2$)$_n$Q or —(CH$_2$)$_n$CHQR, where Q is —N(R)$_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group; $R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In certain embodiments, a subset of compounds of Formula (I) includes those of Formula (IA):

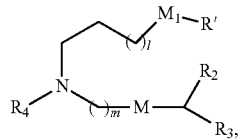

(IA)

or a salt or stereoisomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IA), or a salt or stereoisomer thereof, wherein 1 is selected from 1, 2, 3, 4, and 5; m is selected from 5, 6, 7, 8, and 9;

$M_1$ is a bond or M';

$R_4$ is unsubstituted $C_{1-3}$ alkyl, or —(CH$_2$)$_n$Q, in which Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In certain embodiments, a subset of compounds of Formula (I) includes those of Formula (II):

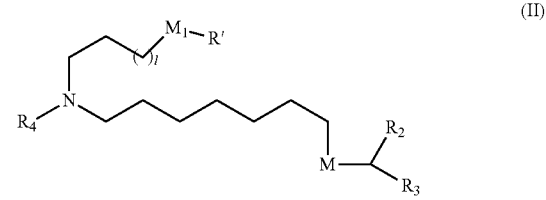

(II)

or a salt or stereoisomer thereof, wherein 1 is selected from 1, 2, 3, 4, and 5; $M_1$ is a bond or M'; $R_4$ is unsubstituted $C_{1-3}$ alkyl, or —(CH$_2$)$_n$Q, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II), or a salt or stereoisomer thereof, wherein 1 is selected from 1, 2, 3, 4, and 5;

$M_1$ is a bond or M';

$R_4$ is unsubstituted $C_{1-3}$ alkyl, or —(CH$_2$)$_n$Q, in which n is 2, 3, or 4, and Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In some embodiments, the compound of formula (I) is of the formula (IIa),

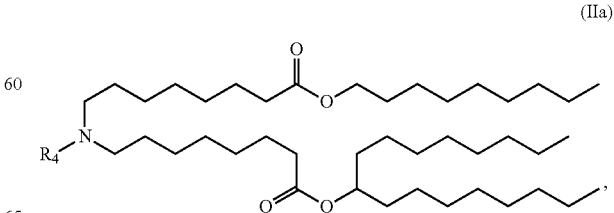

(IIa)

or a salt thereof, wherein $R_4$ is as described above.

In some embodiments, the compound of formula (I) is of the formula (IIb),

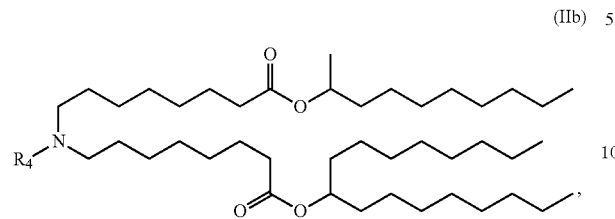
(IIb)

or a salt thereof, wherein R$_4$ is as described above.

In some embodiments, the compound of formula (I) is of the formula (IIc),

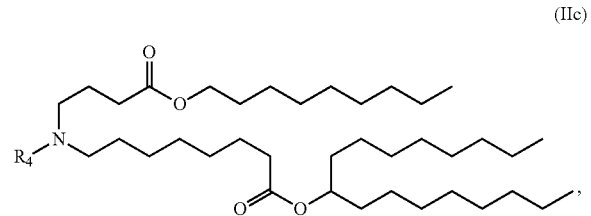
(IIc)

or a salt thereof, wherein R$_4$ is as described above.

In some embodiments, the compound of formula (I) is of the formula (IIe):

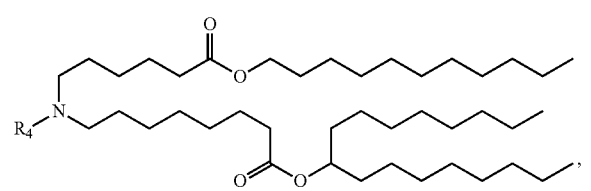
(IIe)

or a salt thereof, wherein R$_4$ is as described above.

In some embodiments, the compound of formula (IIa), (IIb), (IIc), or (IIe) comprises an R$_4$ which is selected from —(CH$_2$)$_n$Q and —(CH$_2$)$_n$CHQR, wherein Q, R and n are as defined above.

In some embodiments, Q is selected from the group consisting of —OR, —OH, —O(CH$_2$)—N(R)$_2$, —OC(O)R, —CX$_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), and a heterocycle, wherein R is as defined above. In some aspects, n is 1 or 2. In some embodiments, Q is OH, —NHC(S)N(R)$_2$, or —NHC(O)N(R)$_2$.

In some embodiments, the compound of formula (I) is of the formula (IId),

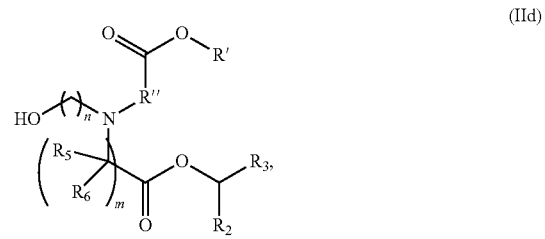
(IId)

or a salt thereof, wherein R$_2$ and R$_3$ are independently selected from the group consisting of C$_{5-14}$ alkyl and C$_{5-14}$ alkenyl, n is selected from 2, 3, and 4, and R', R", R$_5$, R$_6$ and m are as defined above.

In some aspects of the compound of formula (IId), R$_2$ is C$_8$ alkyl. In some aspects of the compound of formula (IId), R$_3$ is C$_5$-C$_9$ alkyl. In some aspects of the compound of formula (IId), m is 5, 7, or 9. In some aspects of the compound of formula (IId), each R$_5$ is H. In some aspects of the compound of formula (IId), each R$_6$ is H.

In another aspect, the present application provides a lipid composition (e.g., a lipid nanoparticle (LNP)) comprising: (1) a compound having the formula (I); (2) optionally a helper lipid (e.g. a phospholipid); (3) optionally a structural lipid (e.g. a sterol); and (4) optionally a lipid conjugate (e.g. a PEG-lipid). In exemplary embodiments, the lipid composition (e.g., LNP) further comprises a polynucleotide encoding a target polypeptide, e.g., a polynucleotide encapsulated therein.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms).

The notation "C$_{1-14}$ alkyl" means a linear or branched, saturated hydrocarbon including 1-14 carbon atoms. An alkyl group can be optionally substituted.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond.

The notation "C$_{2-14}$ alkenyl" means a linear or branched hydrocarbon including 2-14 carbon atoms and at least one double bond. An alkenyl group can include one, two, three, four, or more double bonds. For example, C$_{18}$ alkenyl can include one or more double bonds. A C$_{18}$ alkenyl group including two double bonds can be a linoleyl group. An alkenyl group can be optionally substituted.

As used herein, the term "carbocycle" or "carbocyclic group" means a mono- or multi-cyclic system including one or more rings of carbon atoms. Rings can be three, four, five, six, seven, eight, nine, ten, eleven, twelve, thirteen, fourteen, or fifteen membered rings.

The notation "C$_{3-6}$ carbocycle" means a carbocycle including a single ring having 3-6 carbon atoms. Carbocycles can include one or more double bonds and can be aromatic (e.g., aryl groups). Examples of carbocycles include cyclopropyl, cyclopentyl, cyclohexyl, phenyl, naphthyl, and 1,2-dihydronaphthyl groups. Carbocycles can be optionally substituted.

As used herein, the term "heterocycle" or "heterocyclic group" means a mono- or multi-cyclic system including one or more rings, where at least one ring includes at least one heteroatom. Heteroatoms can be, for example, nitrogen, oxygen, or sulfur atoms. Rings can be three, four, five, six, seven, eight, nine, ten, eleven, or twelve membered rings. Heterocycles can include one or more double bonds and can be aromatic (e.g., heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles can be optionally substituted.

As used herein, a "biodegradable group" is a group that can facilitate faster metabolism of a lipid in a subject. A biodegradable group can be, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group.

As used herein, an "aryl group" is a carbocyclic group including one or more aromatic rings. Examples of aryl groups include phenyl and naphthyl groups.

As used herein, a "heteroaryl group" is a heterocyclic group including one or more aromatic rings. Examples of heteroaryl groups include pyrrolyl, furyl, thiophenyl, imidazolyl, oxazolyl, and thiazolyl. Both aryl and heteroaryl groups can be optionally substituted. For example, M and M' can be selected from the non-limiting group consisting of optionally substituted phenyl, oxazole, and thiazole. In the formulas herein, M and M' can be independently selected from the list of biodegradable groups above.

Alkyl, alkenyl, and cyclyl (e.g., carbocyclyl and heterocyclyl) groups can be optionally substituted unless otherwise specified. Optional substituents can be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C═O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —C(OR)$_2$R"", in which each OR are alkoxy groups that can be the same or different and R"" is an alkyl or alkenyl group), a phosphate (e.g., P(O)$_4^{3-}$), a thiol (e.g., —SH), a sulfoxide (e.g., —S(O)R), a sulfinic acid (e.g., —S(O)OH), a sulfonic acid (e.g., —S(O)$_2$OH), a thial (e.g., —C(S)H), a sulfate (e.g., S(O)$_4^{2-}$), a sulfonyl (e.g., —S(O)$_2$—), an amide (e.g., —C(O)NR$_2$, or —N(R)C(O)R), an azido (e.g., —N$_3$), a nitro (e.g., —NO$_2$), a cyano (e.g., —CN), an isocyano (e.g., —NC), an acyloxy (e.g., —OC(O)R), an amino (e.g., —NR$_2$, —NRH, or —NH$_2$), a carbamoyl (e.g., —OC(O)NR$_2$, —OC(O)NRH, or —OC(O)NH$_2$), a sulfonamide (e.g., —S(O)$_2$NR$_2$, —S(O)$_2$NRH, —S(O)$_2$NH$_2$, —N(R)S(O)$_2$R, —N(H)S(O)$_2$R, —N(R)S(O)$_2$H, or —N(H)S(O)$_2$H), an alkyl group, an alkenyl group, and a cyclyl (e.g., carbocyclyl or heterocyclyl) group.

In any of the preceding, R is an alkyl or alkenyl group, as defined herein. In some embodiments, the substituent groups themselves can be further substituted with, for example, one, two, three, four, five, or six substituents as defined herein. For example, a C$_{1-6}$ alkyl group can be further substituted with one, two, three, four, five, or six substituents as described herein.

The compounds of any one of formulae (I), (IA), (II), (IIa), (IIb), (IIc), (IId), and (IIe) include one or more of the following features when applicable.

In some embodiments, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, 5- to 14-membered aromatic or non-aromatic heterocycle having one or more heteroatoms selected from N, O, S, and P, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5.

In another embodiment, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and a 5- to 14-membered heterocycloalkyl having one or more heteroatoms selected from N, O, and S which is substituted with one or more substituents selected from oxo (═O), OH, amino, and C$_{1-3}$ alkyl, and each n is independently selected from 1, 2, 3, 4, and 5.

In another embodiment, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, a 5- to 14-membered heterocycle having one or more heteroatoms selected from N, O, and S, —OR, —O(CH$_2$)—N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)—CHQR in which n is 1, or (iii) R$_4$ is —CHQR, and —CQ(R)$_2$, then Q is either a 5- to 14-membered heteroaryl or 8- to 14-membered heterocycloalkyl.

In another embodiment, R$_4$ is selected from the group consisting of a C$_{3-6}$ carbocycle, —(CH$_2$)$_n$Q, —(CH$_2$)$_n$CHQR, —CHQR, and —CQ(R)$_2$, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5.

In another embodiment, R$_4$ is unsubstituted C$_{1-4}$ alkyl, e.g., unsubstituted methyl.

In certain embodiments, the disclosure provides a compound having the Formula (I), wherein R$_4$ is —(CH$_2$)$_n$Q or —(CH$_2$)$_n$CHQR, where Q is —N(R)$_2$, and n is selected from 3, 4, and 5.

In certain embodiments, the disclosure provides a compound having the Formula (I), wherein R$_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5.

In certain embodiments, the disclosure provides a compound having the Formula (I), wherein R$_2$ and R$_3$ are independently selected from the group consisting of C$_{2-14}$ alkyl, C$_{2-14}$ alkenyl, —R*YR", —YR", and —R*OR", or R$_2$ and R$_3$, together with the atom to which they are attached, form a heterocycle or carbocycle, and $R_4$ is —$(CH_2)_nQ$ or —$(CH_2)_nCHQR$, where Q is —$N(R)_2$, and n is selected from 3, 4, and 5.

In certain embodiments, $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle.

In some embodiments, $R_1$ is selected from the group consisting of $C_{5-20}$ alkyl and $C_{5-20}$ alkenyl.

In other embodiments, $R_1$ is selected from the group consisting of —R*YR", —YR", and —R"M'R'.

In certain embodiments, $R_1$ is selected from —R*YR" and —YR". In some embodiments, Y is a cyclopropyl group. In some embodiments, R* is $C_8$ alkyl or $C_8$ alkenyl. In certain embodiments, R" is $C_{3-12}$ alkyl. For example, R" can be $C_3$ alkyl. For example, R" can be $C_{4-8}$ alkyl (e.g., $C_4$, $C_5$, $C_6$, $C_7$, or $C_8$ alkyl).

In some embodiments, $R_1$ is $C_{5-20}$ alkyl. In some embodiments, $R_1$ is $C_6$ alkyl. In some embodiments, $R_1$ is $C_8$ alkyl. In other embodiments, $R_1$ is $C_9$ alkyl. In certain embodiments, $R_1$ is $C_{14}$ alkyl. In other embodiments, $R_1$ is $C_{18}$ alkyl.

In some embodiments, $R_1$ is $C_{5-20}$ alkenyl. In certain embodiments, $R_1$ is $C_{18}$ alkenyl. In some embodiments, $R_1$ is linoleyl.

In certain embodiments, $R_1$ is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl, or heptadeca-9-yl). In certain embodiments, $R_1$ is

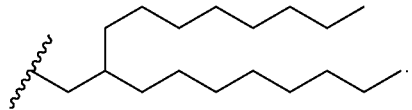 [SMILES: *CC(CCCCCCCC)CCCCCCCC]

In certain embodiments, $R_1$ is unsubstituted $C_{5-20}$ alkyl or $C_{5-20}$ alkenyl. In certain embodiments, R' is substituted $C_{5-20}$ alkyl or $C_{5-20}$ alkenyl (e.g., substituted with a $C_{3-6}$ carbocycle such as 1-cyclopropylnonyl).

In other embodiments, $R_1$ is —R"M'R'.

In some embodiments, R' is selected from —R*YR" and —YR". In some embodiments, Y is $C_{3-8}$ cycloalkyl. In some embodiments, Y is $C_{6-10}$ aryl. In some embodiments, Y is a cyclopropyl group. In some embodiments, Y is a cyclohexyl group. In certain embodiments, R* is $C_1$ alkyl.

In some embodiments, R" is selected from the group consisting of $C_{3-12}$ alkyl and $C_{3-12}$ alkenyl. In some embodiments, R" adjacent to Y is $C_1$ alkyl. In some embodiments, R" adjacent to Y is $C_{4-9}$ alkyl (e.g., $C_4$, $C_5$, $C_6$, $C_7$ or $C_8$ or $C_9$ alkyl).

In some embodiments, R' is selected from $C_4$ alkyl and $C_4$ alkenyl. In certain embodiments, R' is selected from $C_5$ alkyl and $C_5$ alkenyl. In some embodiments, R' is selected from $C_6$ alkyl and $C_6$ alkenyl. In some embodiments, R' is selected from $C_7$ alkyl and $C_7$ alkenyl. In some embodiments, R' is selected from $C_9$ alkyl and $C_9$ alkenyl.

In other embodiments, R' is selected from $C_{ii}$ alkyl and $C_{11}$ alkenyl. In other embodiments, R' is selected from $C_{12}$ alkyl, $C_{12}$ alkenyl, $C_{13}$ alkyl, $C_{13}$ alkenyl, $C_{14}$ alkyl, $C_{14}$ alkenyl, $C_{15}$ alkyl, $C_{15}$ alkenyl, $C_{16}$ alkyl, $C_{16}$ alkenyl, $C_{17}$ alkyl, $C_{17}$ alkenyl, $C_{18}$ alkyl, and $C_{18}$ alkenyl. In certain embodiments, R' is branched (e.g., decan-2-yl, undecan-3-yl, dodecan-4-yl, tridecan-5-yl, tetradecan-6-yl, 2-methyl-undecan-3-yl, 2-methyldecan-2-yl, 3-methylundecan-3-yl, 4-methyldodecan-4-yl or heptadeca-9-yl). In certain embodiments, R' is

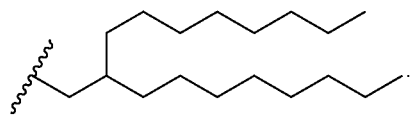 [SMILES: *CC(CCCCCCCC)CCCCCCCC]

In certain embodiments, R' is unsubstituted $C_{1-18}$ alkyl. In certain embodiments, R' is substituted $C_{1-18}$ alkyl (e.g., $C_{1-15}$ alkyl substituted with a $C_{3-6}$ carbocycle such as 1-cyclopropylnonyl).

In some embodiments, R" is selected from the group consisting of $C_{3-14}$ alkyl and $C_{3-14}$ alkenyl. In some embodiments, R" is $C_3$ alkyl, $C_4$ alkyl, $C_5$ alkyl, $C_6$ alkyl, $C_7$ alkyl, or $C_8$ alkyl. In some embodiments, R" is $C_9$ alkyl, $C_{10}$ alkyl, $C_{11}$ alkyl, $C_{12}$ alkyl, $C_{13}$ alkyl, or $C_{14}$ alkyl.

In some embodiments, M' is —C(O)O—. In some embodiments, M' is —OC(O)—.

In other embodiments, M' is an aryl group or heteroaryl group. For example, M' can be selected from the group consisting of phenyl, oxazole, and thiazole.

In some embodiments, M is —C(O)O— In some embodiments, M is —OC(O)—. In some embodiments, M is —C(O)N(R')—. In some embodiments, M is —P(O)(OR')O—.

In other embodiments, M is an aryl group or heteroaryl group. For example, M can be selected from the group consisting of phenyl, oxazole, and thiazole.

In some embodiments, M is the same as M'. In other embodiments, M is different from M'.

In some embodiments, each $R_5$ is H. In certain such embodiments, each $R_6$ is also H.

In some embodiments, $R_7$ is H. In other embodiments, $R_7$ is $C_{1-3}$ alkyl (e.g., methyl, ethyl, propyl, or i-propyl).

In certain embodiments, $R_2$ and $R_3$ are independently $C_{5-14}$ alkyl or $C_{5-14}$ alkenyl.

In some embodiments, $R_2$ and $R_3$ are the same. In some embodiments, $R_2$ and $R_3$ are $C_8$ alkyl. In certain embodiments, $R_2$ and $R_3$ are $C_2$ alkyl. In other embodiments, $R_2$ and $R_3$ are $C_3$ alkyl. In some embodiments, $R_2$ and $R_3$ are $C_4$ alkyl. In certain embodiments, $R_2$ and $R_3$ are $C_5$ alkyl. In other embodiments, $R_2$ and $R_3$ are $C_6$ alkyl. In some embodiments, $R_2$ and $R_3$ are $C_7$ alkyl.

In other embodiments, $R_2$ and $R_3$ are different. In certain embodiments, $R_2$ is $C_8$ alkyl. In some embodiments, $R_3$ is $C_{1-7}$ (e.g., $C_1$, $C_2$, $C_3$, $C_4$, $C_5$, $C_6$, or $C_7$ alkyl) or $C_9$ alkyl.

In some embodiments, $R_7$ and $R_3$ are H.

In certain embodiments, $R_2$ is H.

In certain embodiments, m is 5, 7, or 9.

In some embodiments, $R_4$ is selected from —$(CH_2)_nQ$ and —$(CH_2)_nCHQR$.

In some embodiments, Q is selected from the group consisting of —OR, —OH, —$O(CH_2)_nN(R)_2$, —OC(O)R, —$CX_3$, —CN, —N(R)C(O)R, —N(H)C(O)R, —N(R)S(O)_2R, —N(H)S(O)_2R, —N(R)C(O)N(R)_2, —N(H)C(O)N(R)_2, —N(H)C(O)N(H)(R), —N(R)C(S)N(R)_2, —N(H)C(S)N(R)_2, —N(H)C(S)N(H)(R), —C(R)N(R)_2C(O)OR, a carbocycle, and a heterocycle.

In certain embodiments, Q is —OH.

In certain embodiments, Q is a substituted or unsubstituted 5- to 10-membered heteroaryl, e.g., Q is an imidazole, a pyrimidine, a purine, 2-amino-1,9-dihydro-6H-purin-6-one-9-yl (or guanin-9-yl), adenin-9-yl, cytosin-1-yl, or uracil-1-yl. In certain embodiments, Q is a substituted 5- to 14-membered heterocycloalkyl, e.g., substituted with one or more substituents selected from oxo (=O), OH, amino, and $C_{1-3}$ alkyl. For example, Q is 4-methylpiperazinyl, 4-(4-methoxybenzyl)piperazinyl, or isoindolin-2-yl-1,3-dione.

In certain embodiments, Q is an unsubstituted or substituted $C_{6-10}$ aryl (such as phenyl) or $C_{3-6}$ cycloalkyl.

In some embodiments, n is 1. In other embodiments, n is 2. In further embodiments, n is 3. In certain other embodiments, n is 4. For example, $R_4$ can be —$(CH_2)_2OH$. For example, $R_4$ can be —$(CH_2)_3OH$. For example, $R_4$ can be —$(CH_2)_4OH$. For example, $R_4$ can be benzyl. For example, $R_4$ can be 4-methoxybenzyl.

In some embodiments, $R_4$ is a $C_{3-6}$ carbocycle. In some embodiments, $R_4$ is a $C_{3-6}$ cycloalkyl. For example, $R_4$ can be cyclohexyl optionally substituted with e.g., OH, halo, $C_{1-6}$ alkyl, etc. For example, $R_4$ can be 2-hydroxycyclohexyl.

In some embodiments, R is H.

In some embodiments, R is unsubstituted $C_{1-3}$ alkyl or unsubstituted $C_{2-3}$ alkenyl. For example, $R_4$ can be —$CH_2CH(OH)CH_3$ or —$CH_2CH(OH)CH_2CH_3$.

In some embodiments, R is substituted $C_{1-3}$ alkyl, e.g., $CH_2OH$. For example, $R_4$ can be —$CH_2CH(OH)CH_2OH$.

In some embodiments, $R_2$ and $R_3$, together with the atom to which they are attached, form a heterocycle or carbocycle. In some embodiments, $R_2$ and $R_3$, together with the atom to which they are attached, form a 5- to 14-membered aromatic or non-aromatic heterocycle having one or more heteroatoms selected from N, O, S, and P. In some embodiments, $R_2$ and $R_3$, together with the atom to which they are attached, form an optionally substituted $C_{3-20}$ carbocycle (e.g., $C_{3-18}$ carbocycle, $C_{3-15}$ carbocycle, $C_{3-12}$ carbocycle, or $C_{3-10}$ carbocycle), either aromatic or non-aromatic. In some embodiments, $R_2$ and $R_3$, together with the atom to which they are attached, form a $C_{3-6}$ carbocycle. In other embodiments, $R_2$ and $R_3$, together with the atom to which they are attached, form a $C_6$ carbocycle, such as a cyclohexyl or phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a cyclohexyl or phenyl group bearing one or more $C_5$ alkyl substitutions. In certain embodiments, the heterocycle or $C_{3-6}$ carbocycle formed by $R_2$ and $R_3$, is substituted with a carbocycle groups. For example, $R_2$ and $R_3$, together with the atom to which they are attached, can form a cyclohexyl or phenyl group that is substituted with cyclohexyl. In some embodiments, $R_2$ and $R_3$, together with the atom to which they are attached, form a $C_{7-15}$ carbocycle, such as a cycloheptyl, cyclopentadecanyl, or naphthyl group.

In some embodiments, $R_4$ is selected from —$(CH_2)_nQ$ and —$(CH_2)_nCHQR$. In some embodiments, Q is selected from the group consisting of —OR, —OH, —$O(CH_2)_nN(R)_2$, —OC(O)R, —$CX_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), and a heterocycle. In other embodiments, Q is selected from the group consisting of an imidazole, a pyrimidine, and a purine.

In some embodiments, $R_2$ and $R_3$, together with the atom to which they are attached, form a heterocycle or carbocycle. In some embodiments, $R_2$ and $R_3$, together with the atom to which they are attached, form a $C_{3-6}$ carbocycle, such as a phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a phenyl group bearing one or more $C_5$ alkyl substitutions.

In some embodiments, the pharmaceutical compositions of the present disclosure, the compound of formula (I) is selected from the group consisting of:

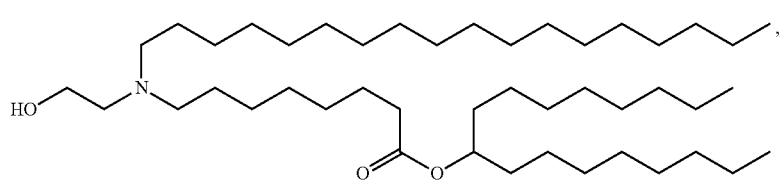

(Compound 1)

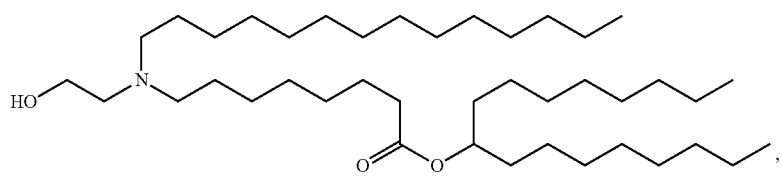

(Compound 2)

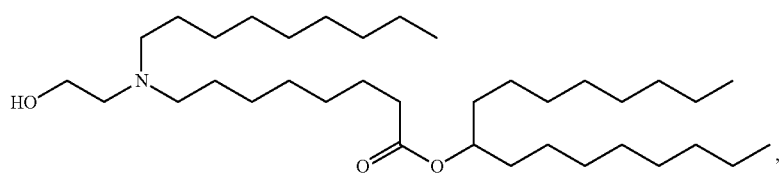

(Compound 3)

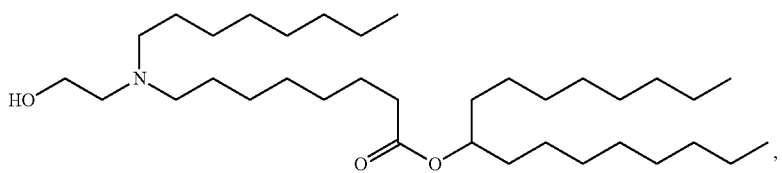
(Compound 4)
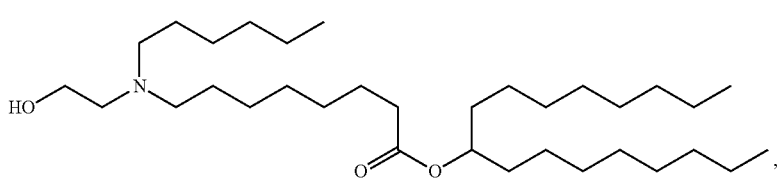
(Compound 5)
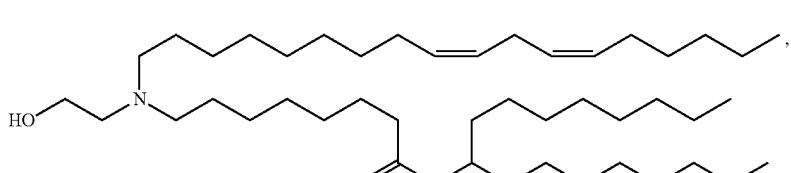
(Compound 6)
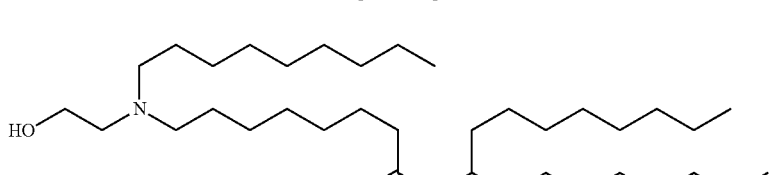
(Compound 7)
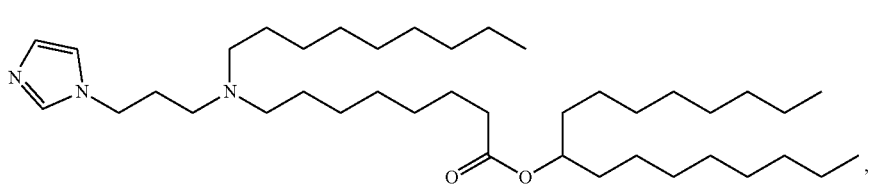
(Compound 8)
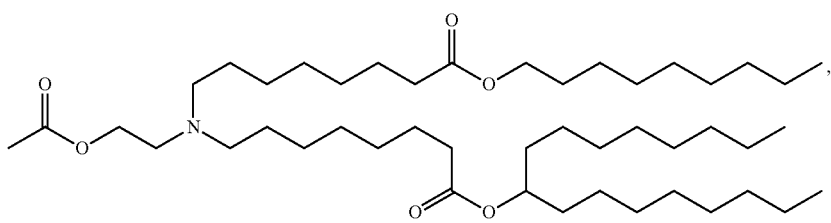
(Compound 9)
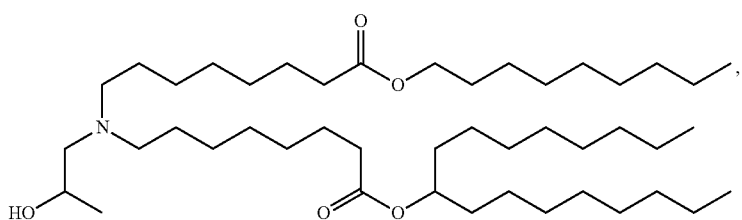
(Compound 10)
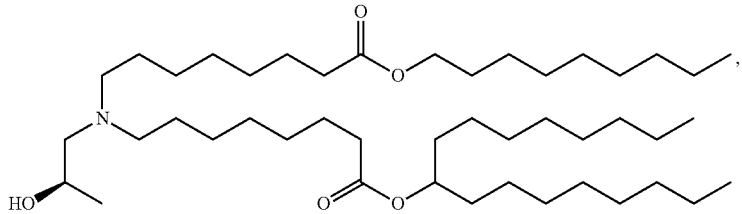
(Compound 11)

(Compound 12)
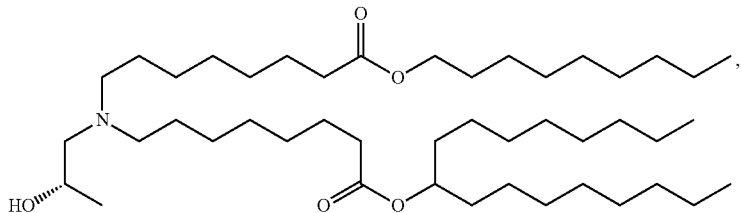
(Compound 13)
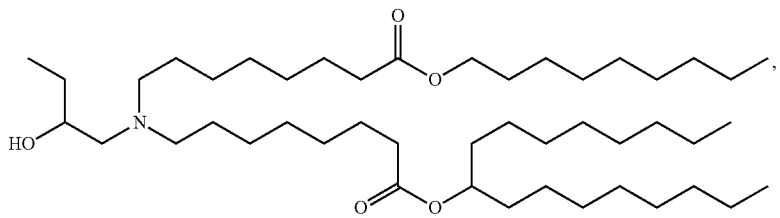
(Compound 14)
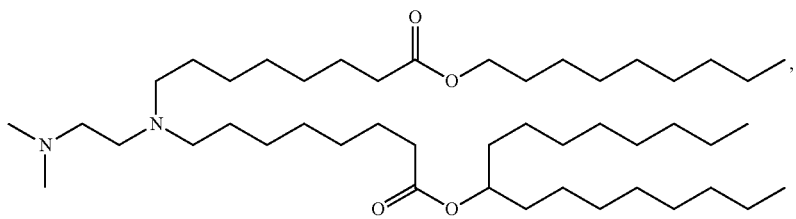
(Compound 15)
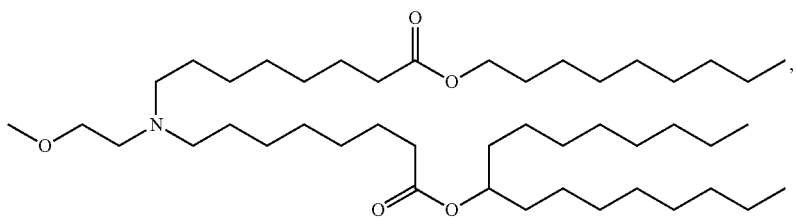
(Compound 16)
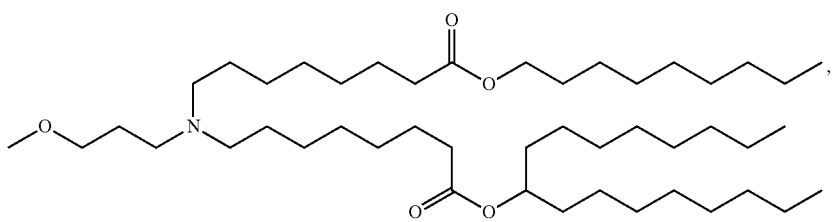
(Compound 17)
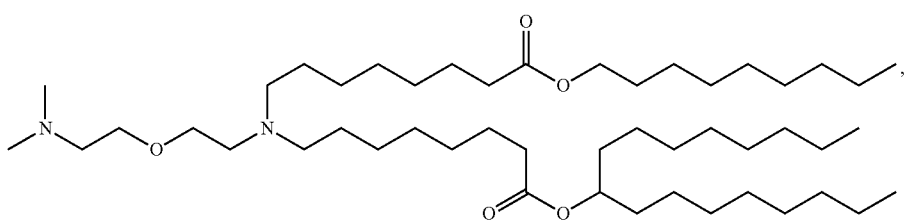
(Compound 18)
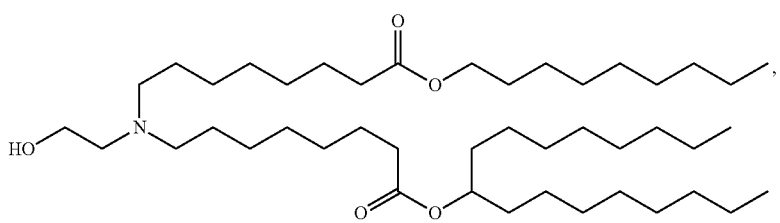

(Compound 19)
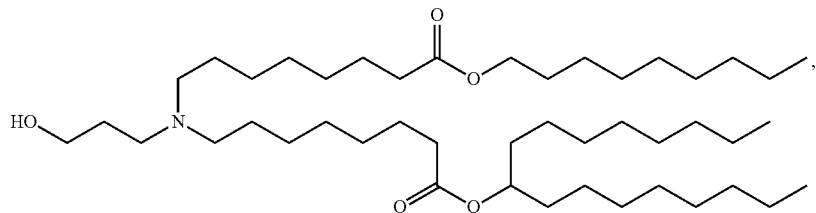
(Compound 20)
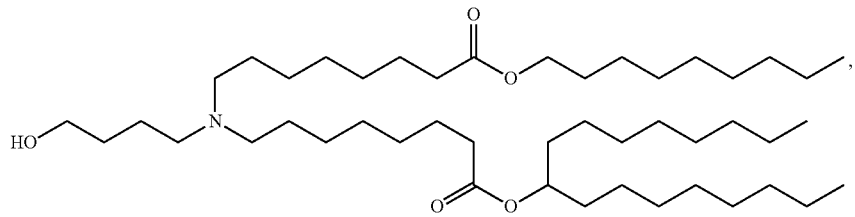
(Compound 21)
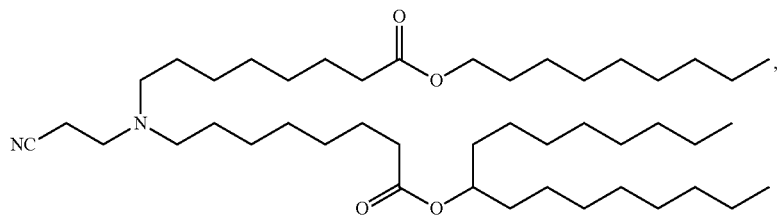
(Compound 22)
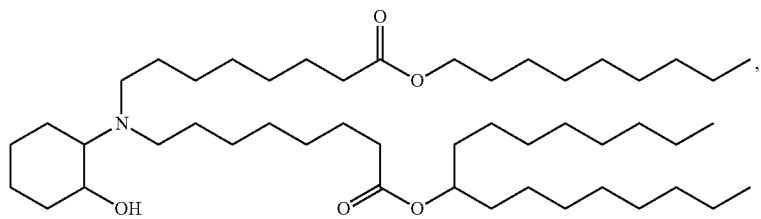
(Compound 23)
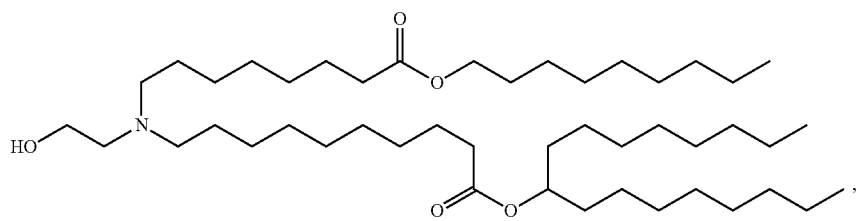
(Compound 24)
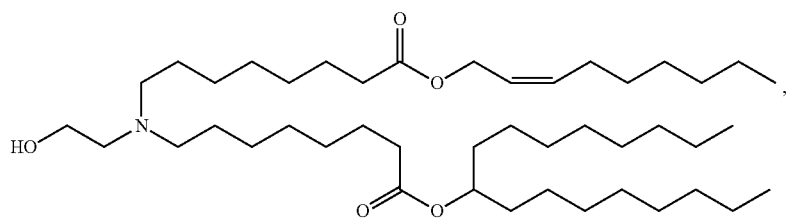
(Compound 25)
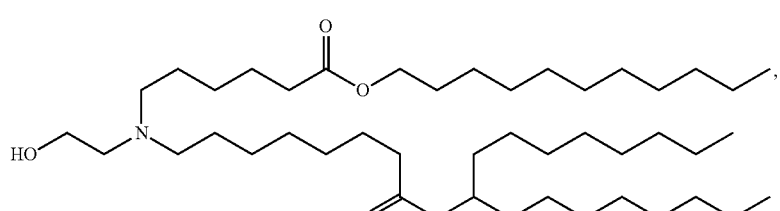

-continued
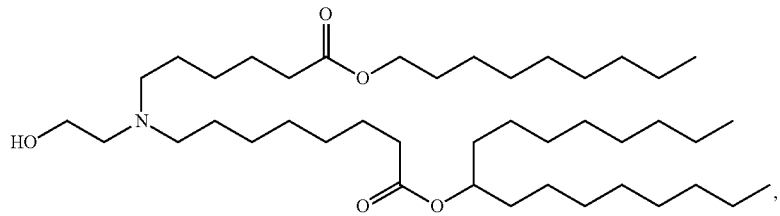
(Compound 26)
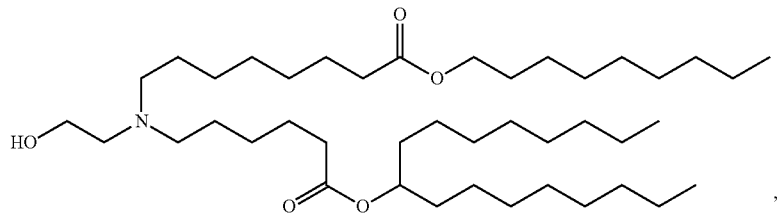
(Compound 27)
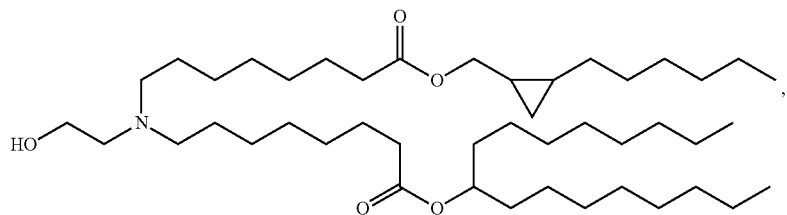
(Compound 28)
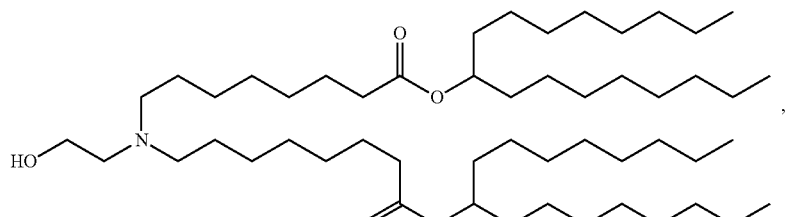
(Compound 29)
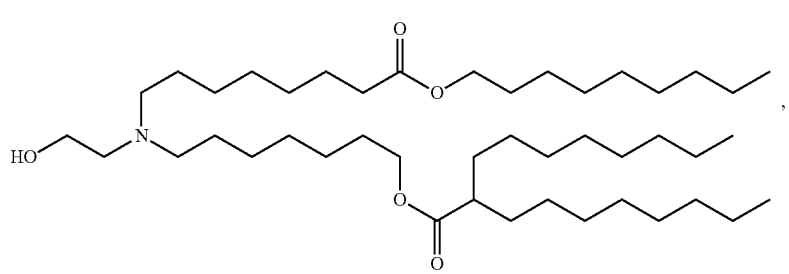
(Compound 30)
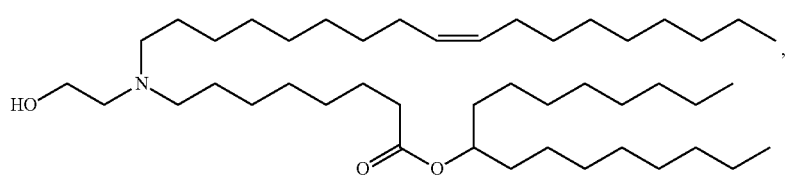
(Compound 31)
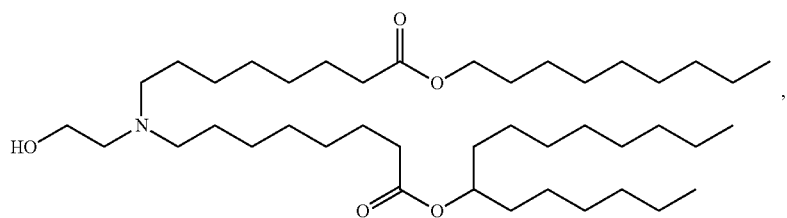
(Compound 32)

-continued
(Compound 33)
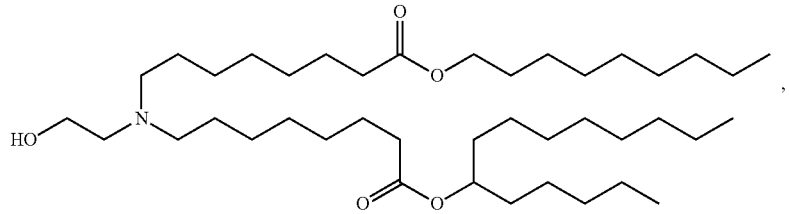
(Compound 34)
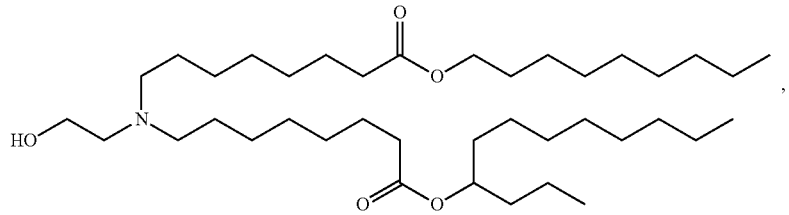
(Compound 35)
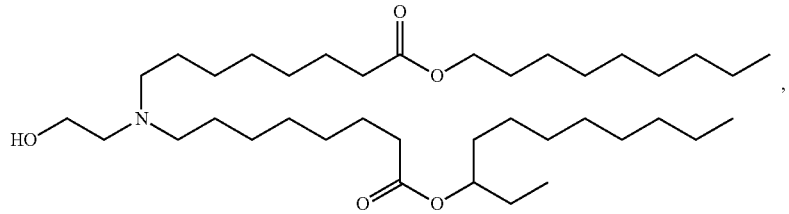
(Compound 36)
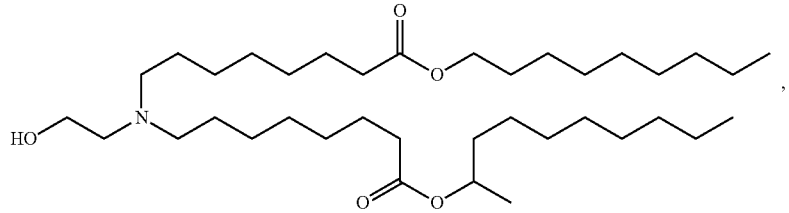
(Compound 37)
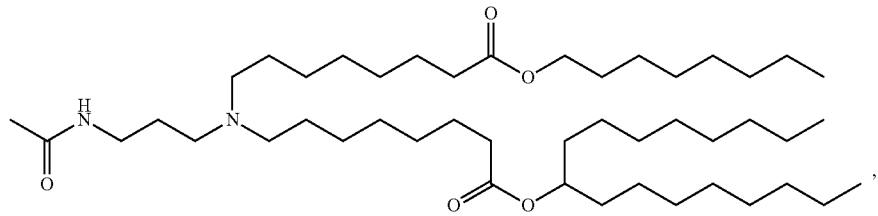
(Compound 38)
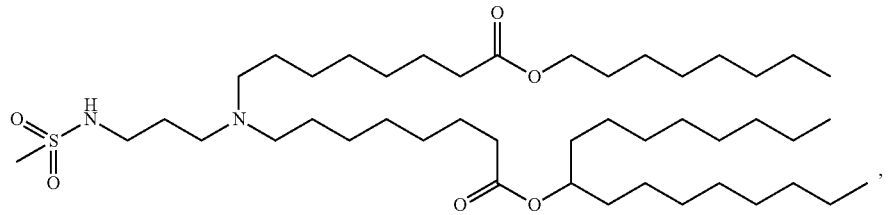
(Compound 39)
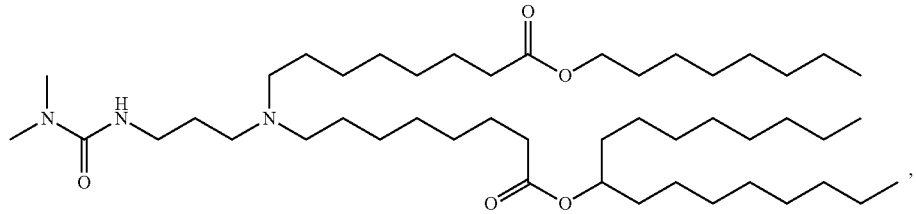

(Compound 40)
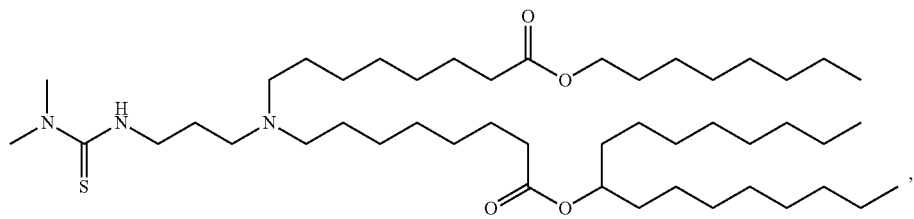
(Compound 41)
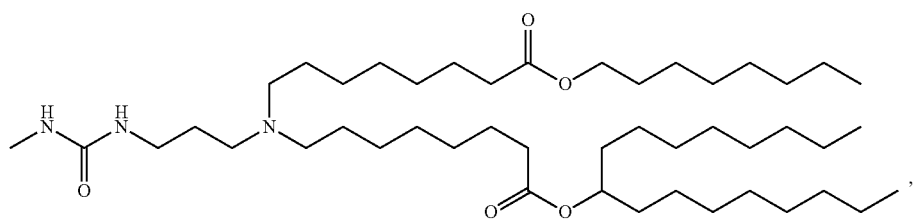
(Compound 42)
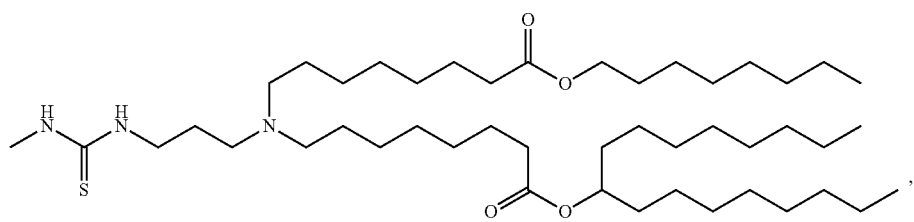
(Compound 43)
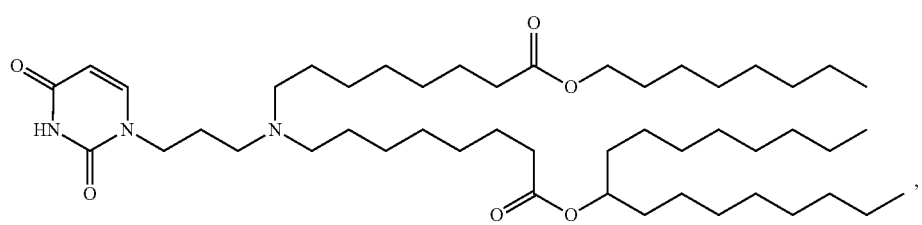
(Compound 44)
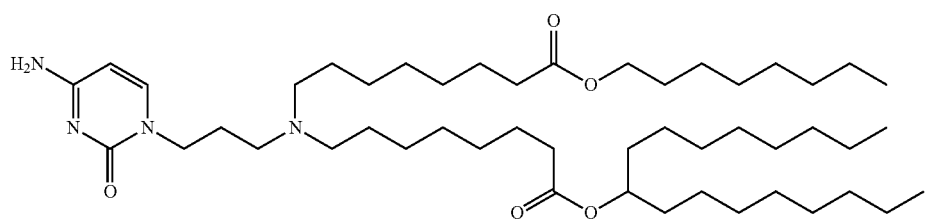
(Compound 45)
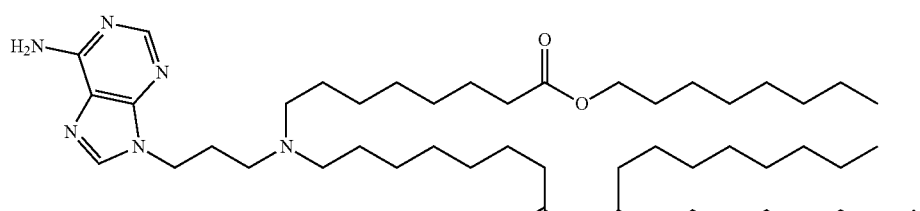
(Compound 46)
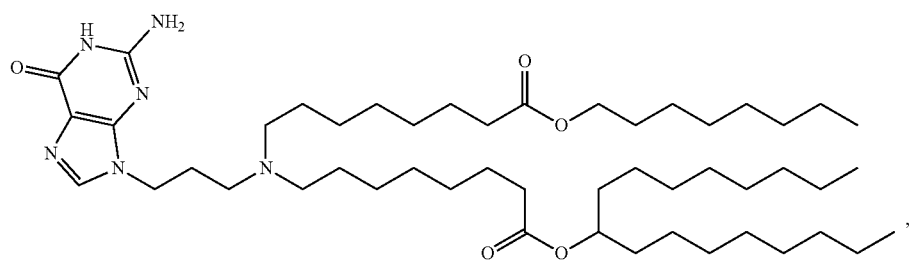

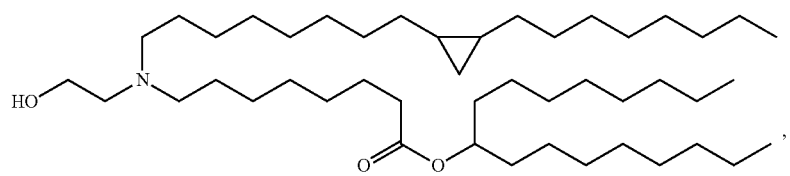
(Compound 47)
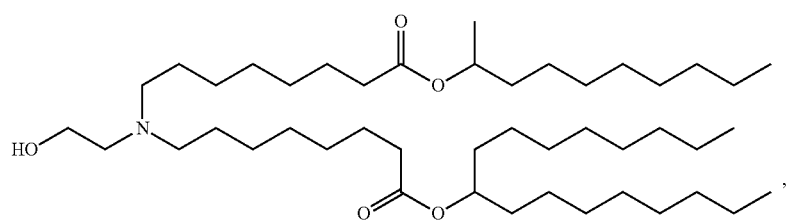
(Compound 48)
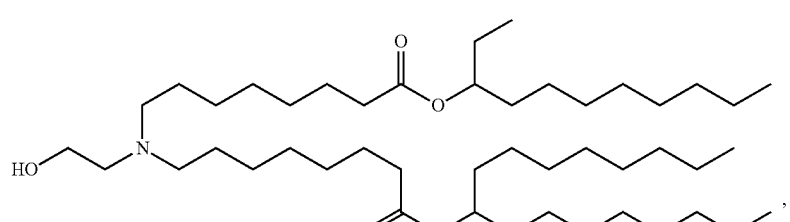
(Compound 49)
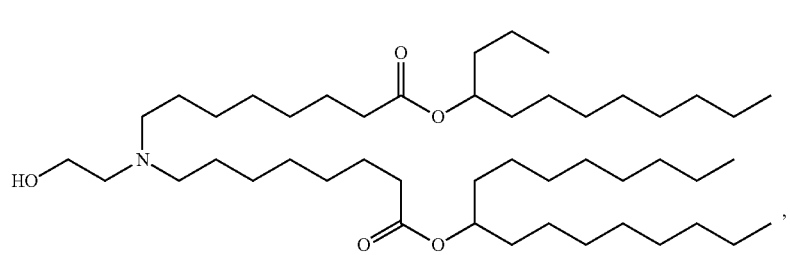
(Compound 50)
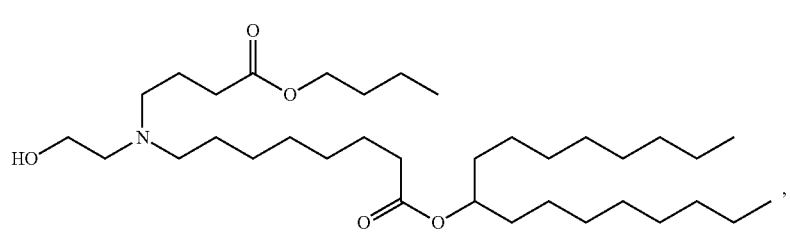
(Compound 51)
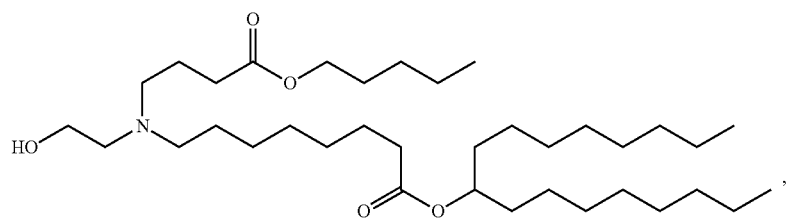
(Compound 52)
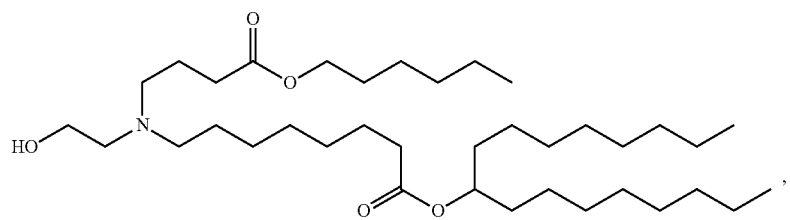
(Compound 53)

(Compound 54)
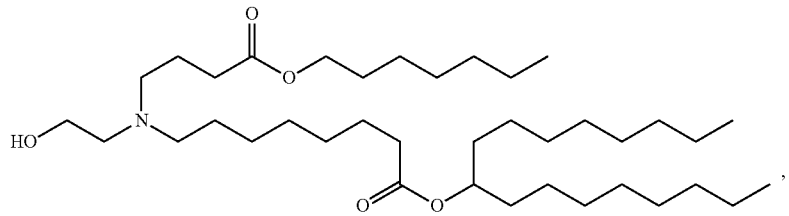
(Compound 55)
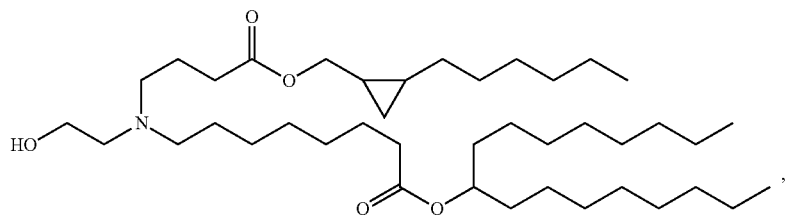
(Compound 56)
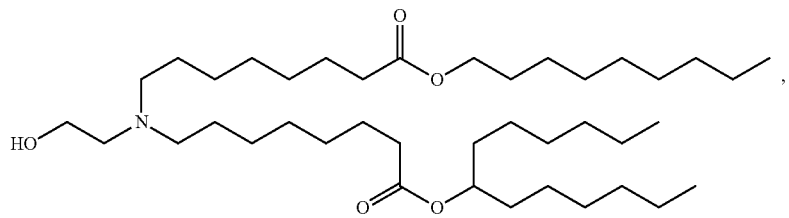
(Compound 57)
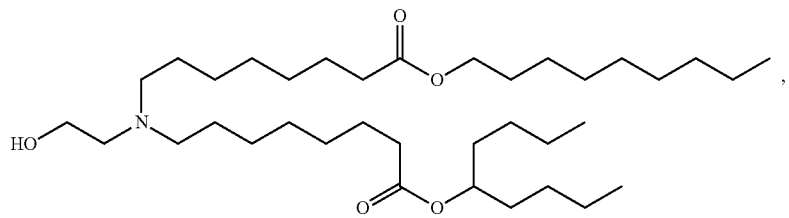
(Compound 58)
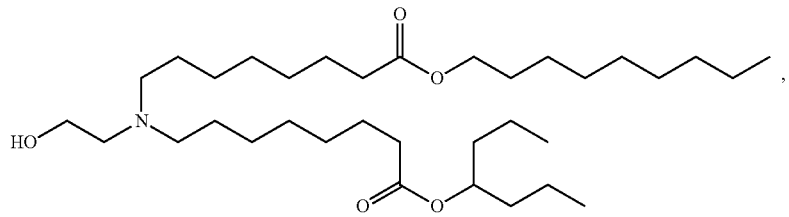
(Compound 59)
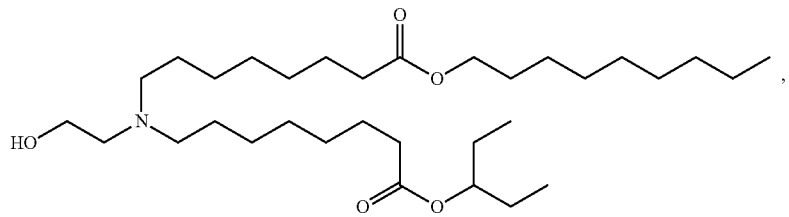
(Compound 60)
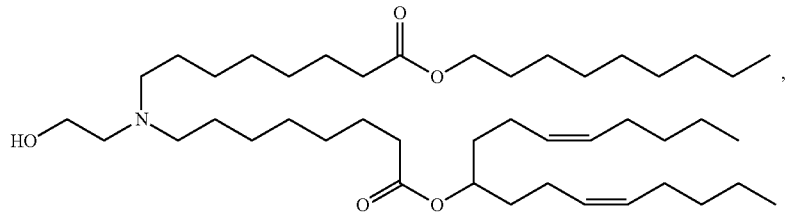

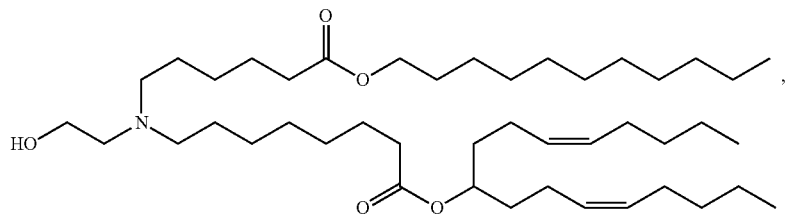
(Compound 61)
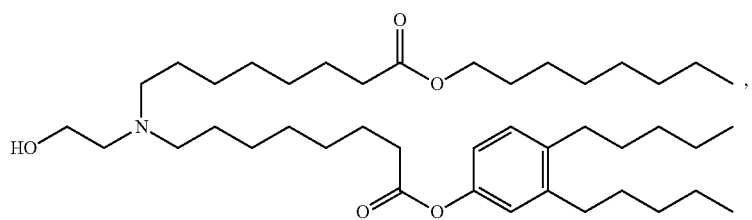
(Compound 62)
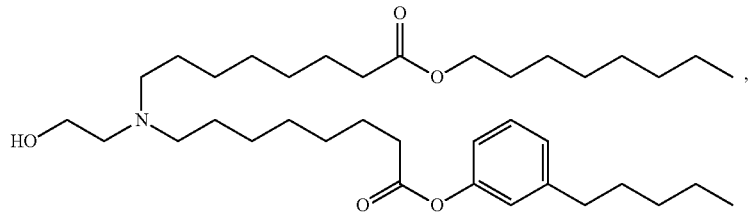
(Compound 63)
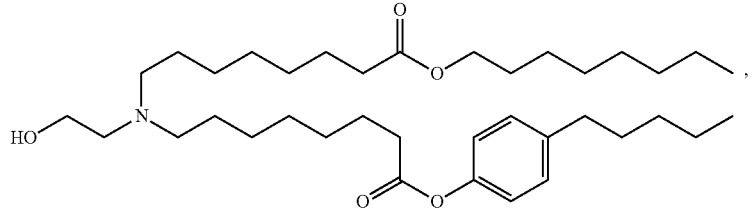
(Compound 64)
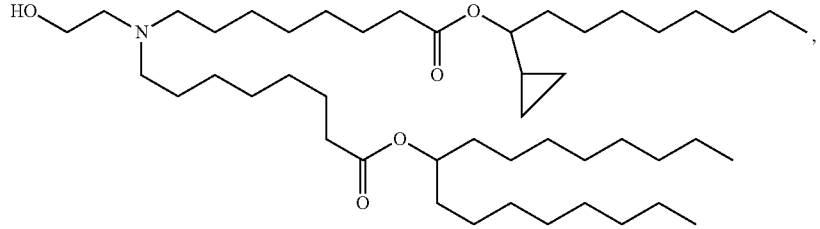
(Compound 65)
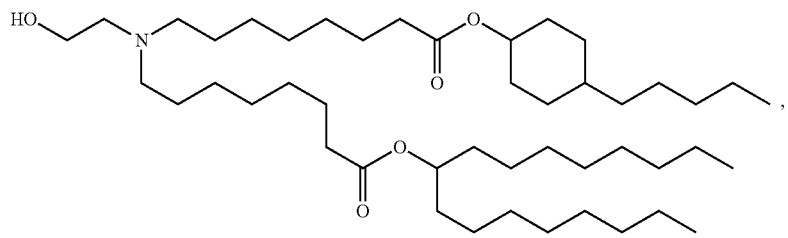
(Compound 66)
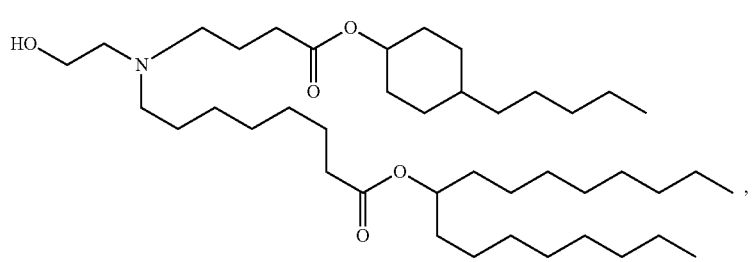
(Compound 67)

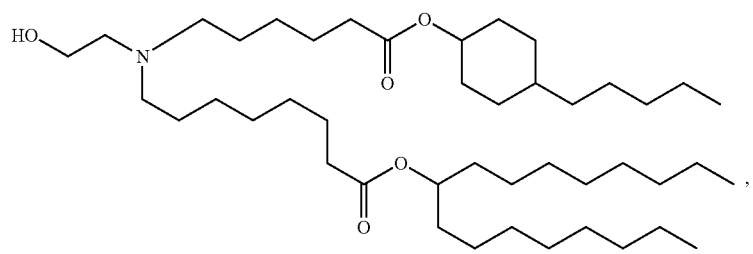
(Compound 68)
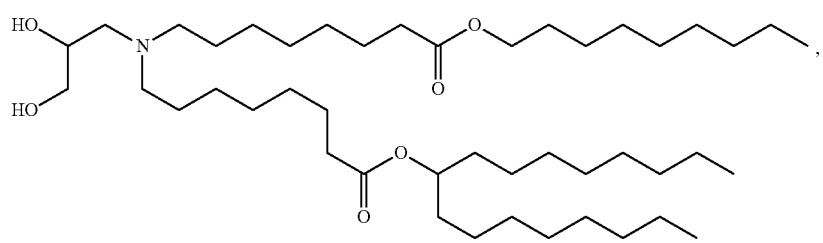
(Compound 69)
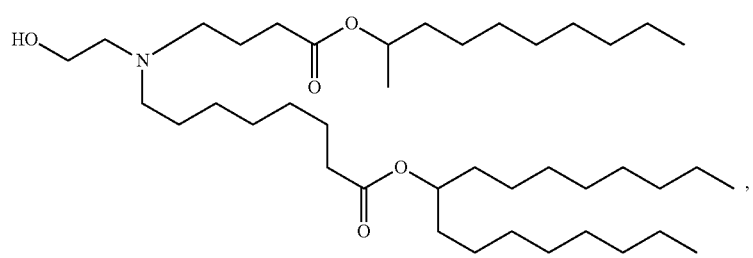
(Compound 70)
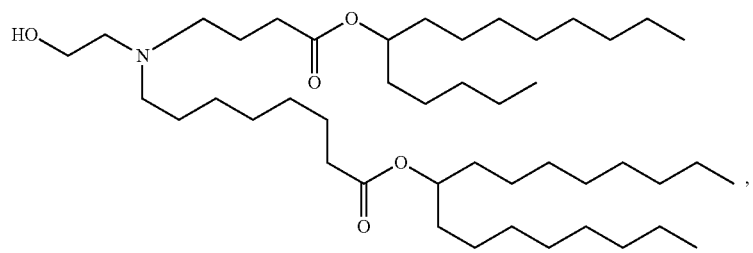
(Compound 71)
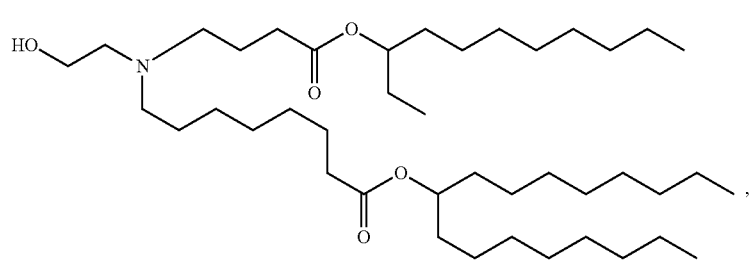
(Compound 72)
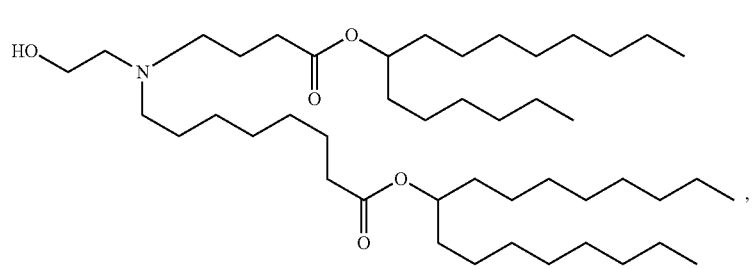
(Compound 73)

-continued
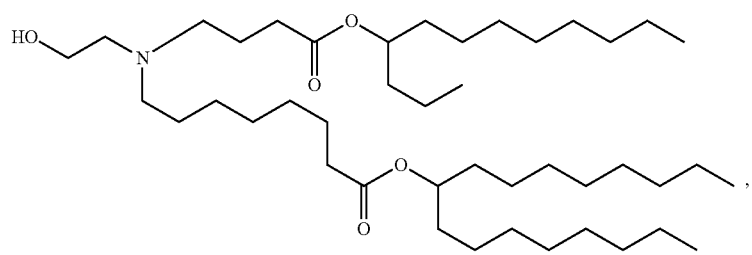
(Compound 74)
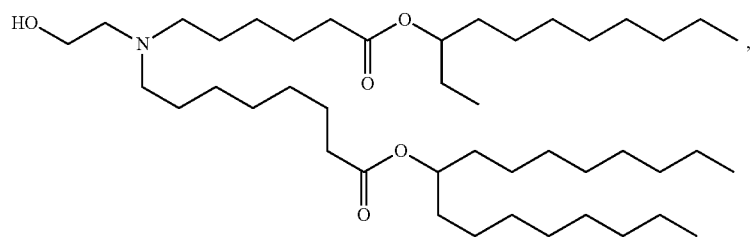
(Compound 75)
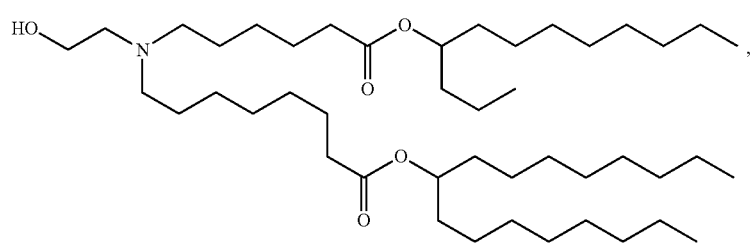
(Compound 76)
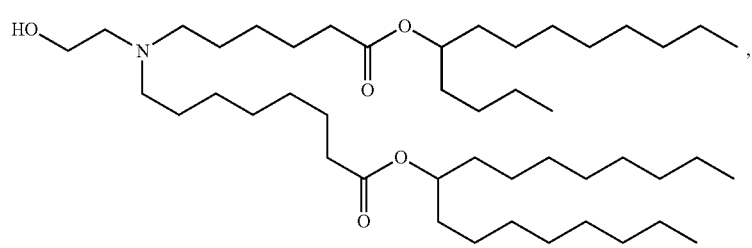
(Compound 77)
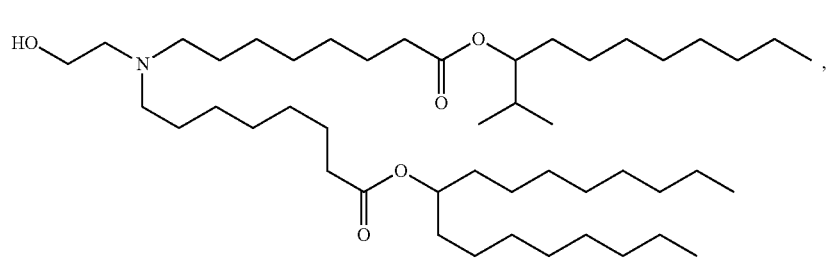
(Compound 78)
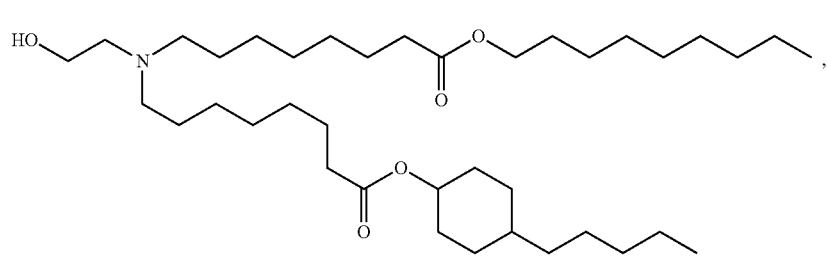
(Compound 79)

(Compound 80)
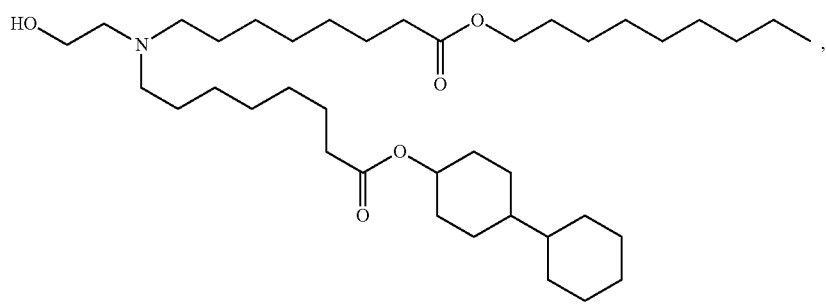
(Compound 81)
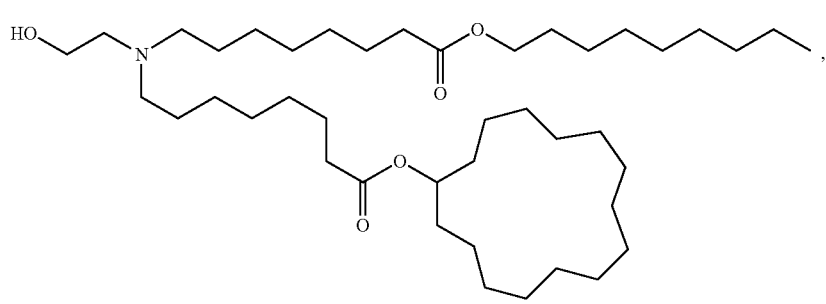
(Compound 82)
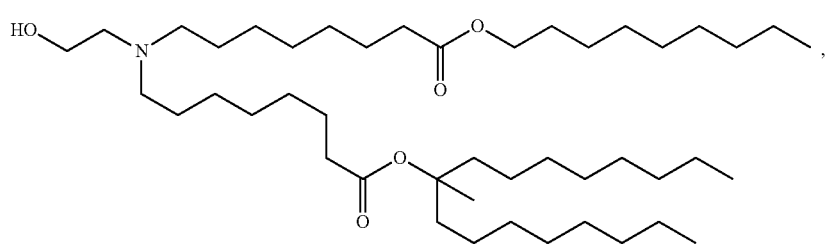
(Compound 83)
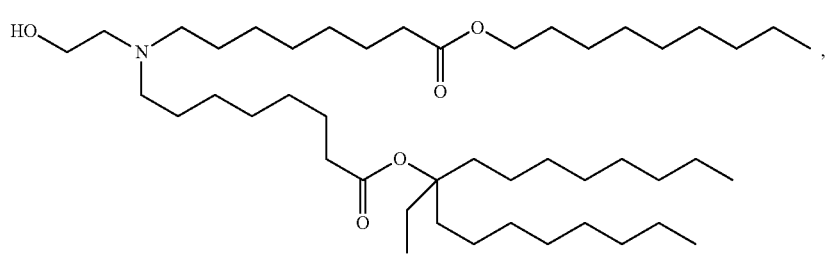
(Compound 84)
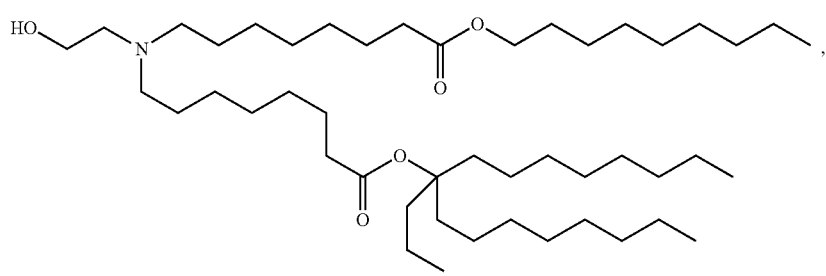
(Compound 85)
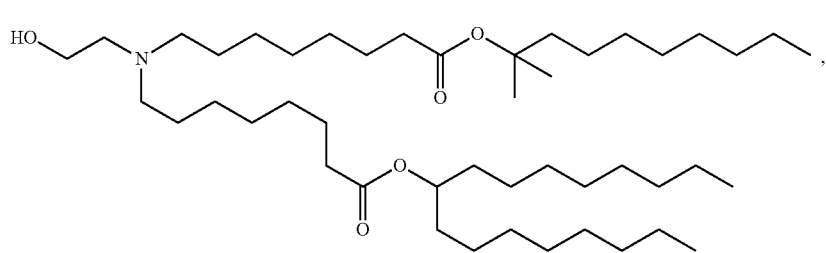

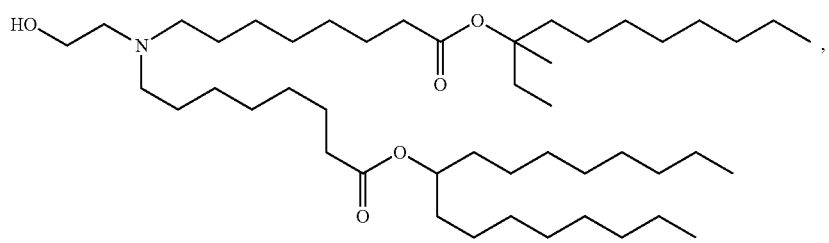
(Compound 86)
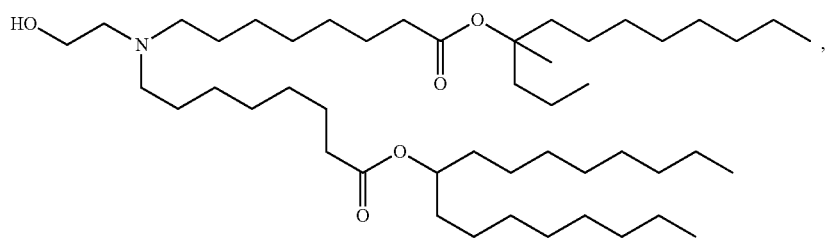
(Compound 87)
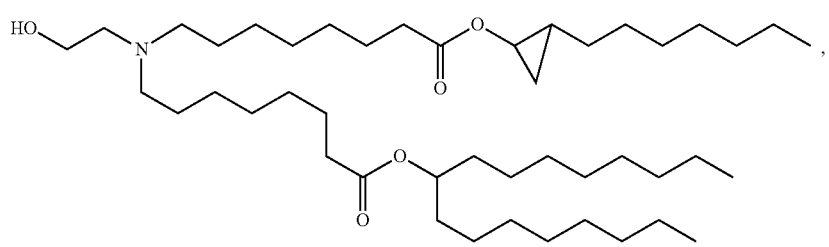
(Compound 88)
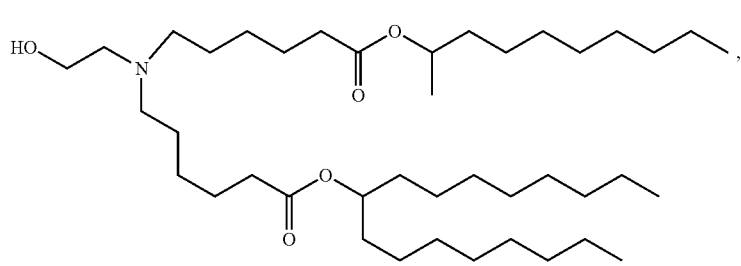
(Compound 89)
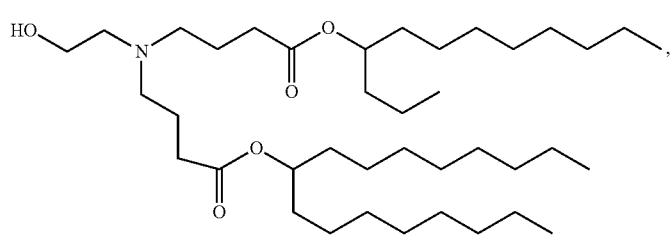
(Compound 90)
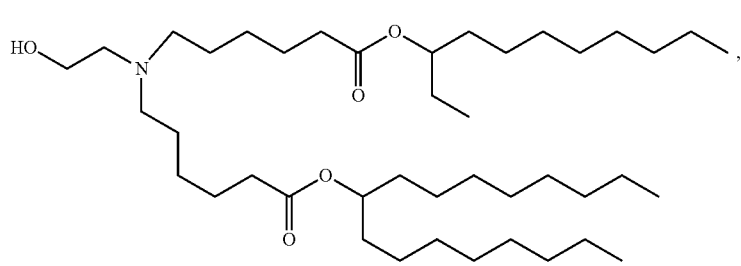
(Compound 91)

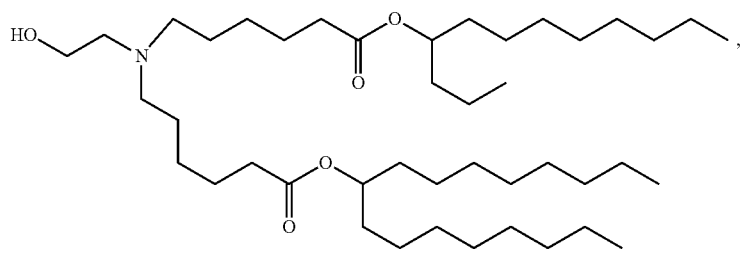
(Compound 92)
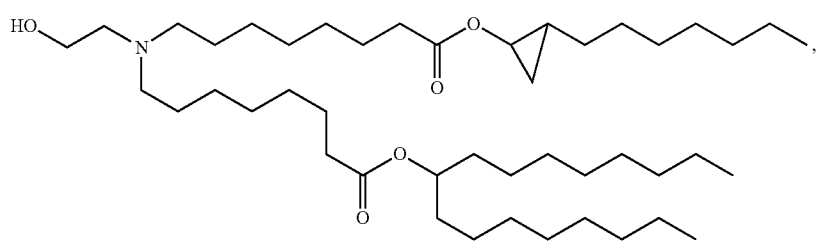
(Compound 93)
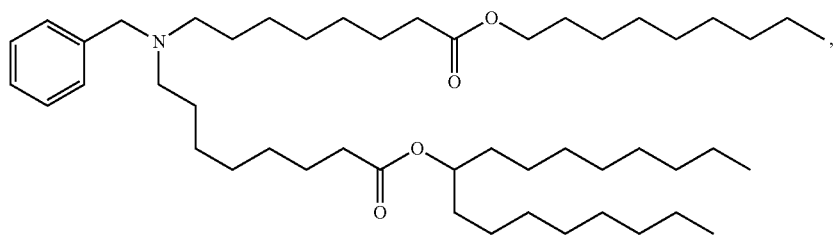
(Compound 94)
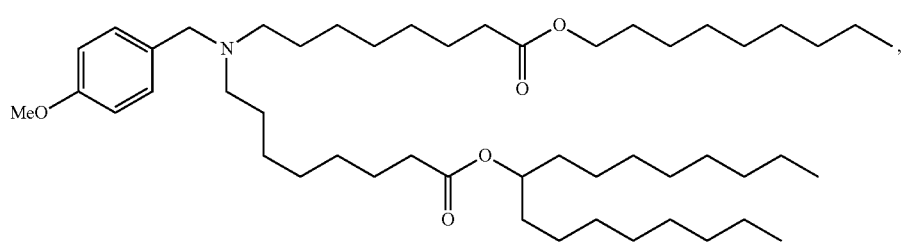
(Compound 95)
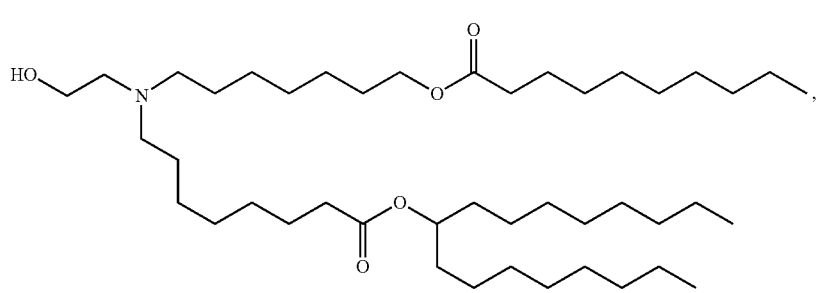
(Compound 96)
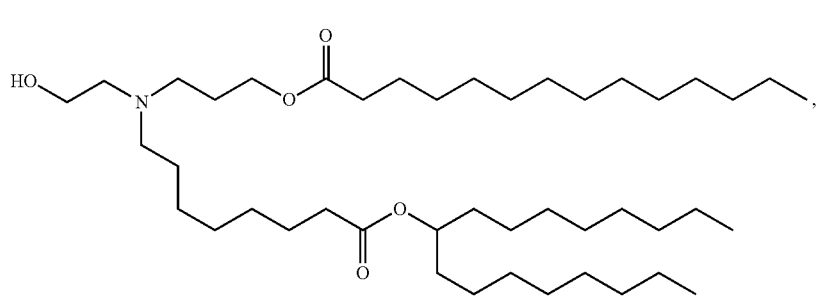
(Compound 97)

(Compound 98)
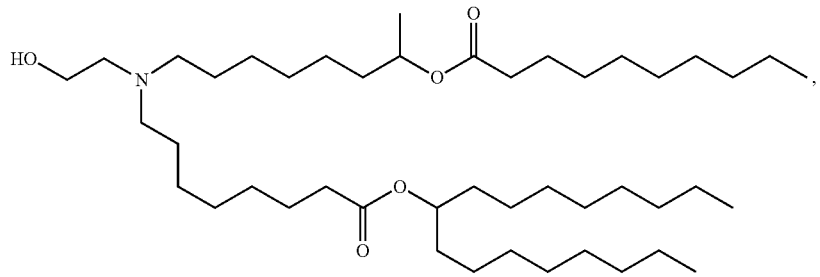
(Compound 99)
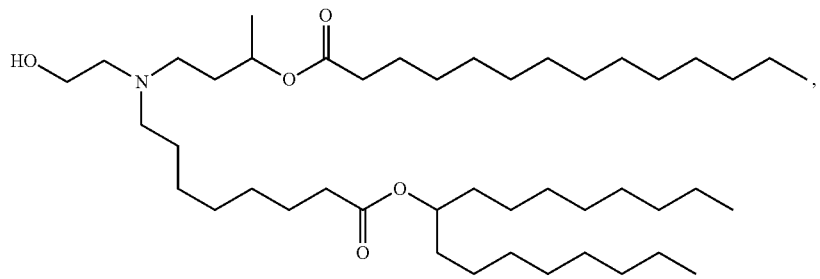
(Compound 100)
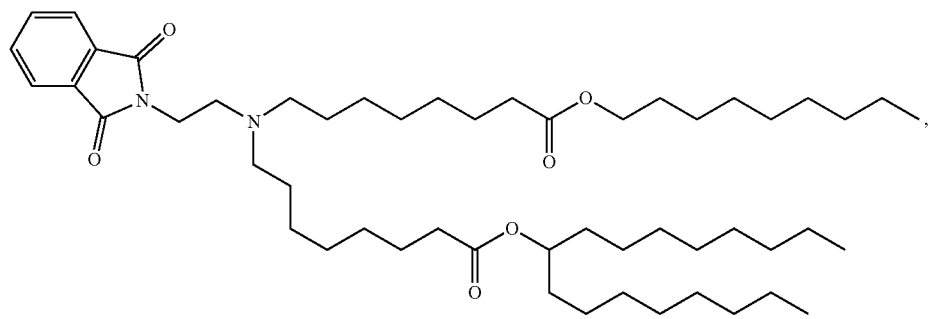
(Compound 101)
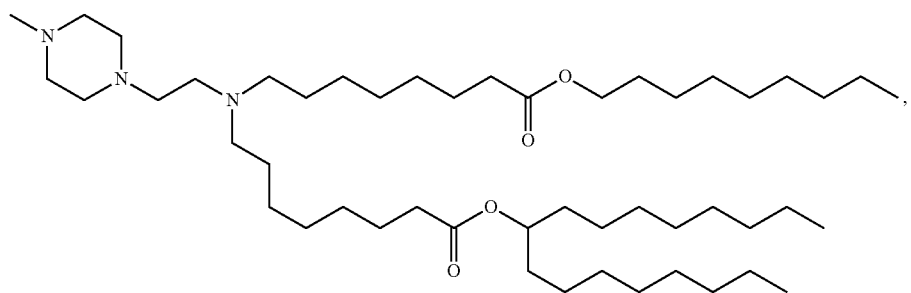
(Compound 102)
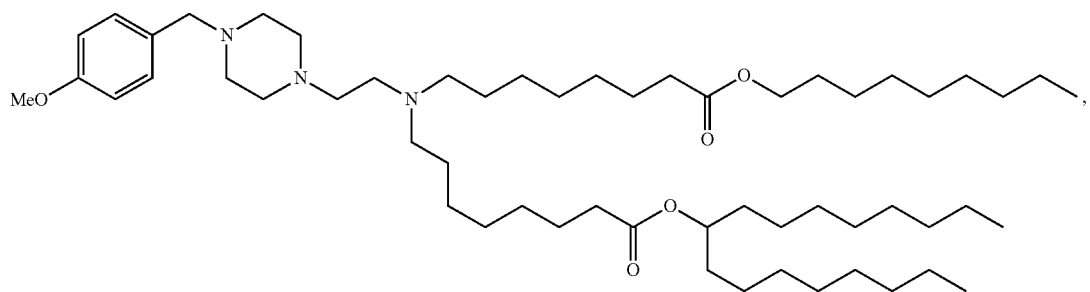

-continued
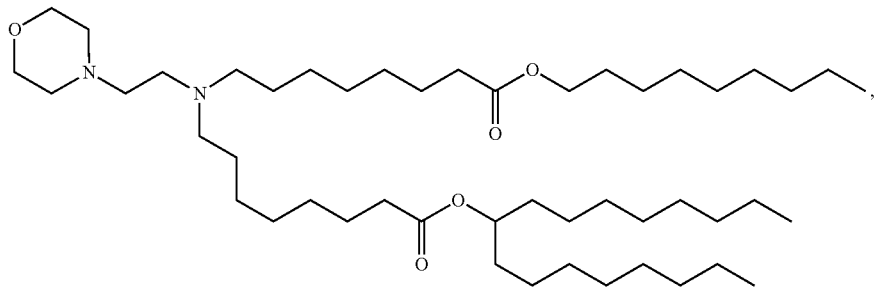
(Compound 103)
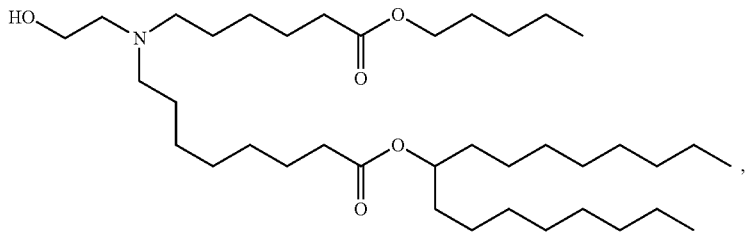
(Compound 104)
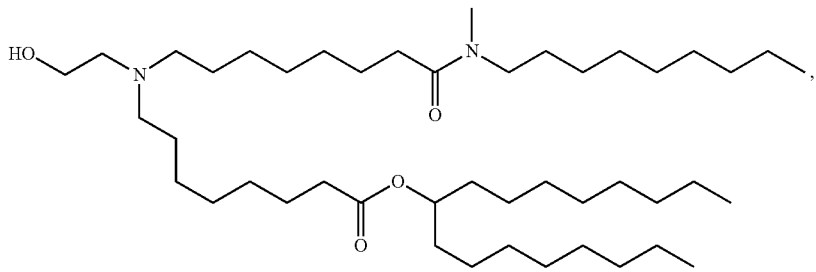
(Compound 105)
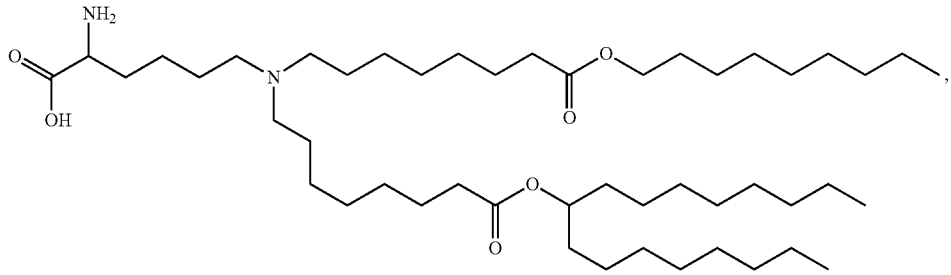
(Compound 106)
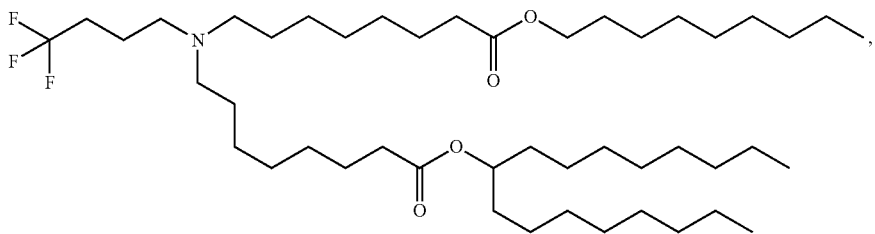
(Compound 107)
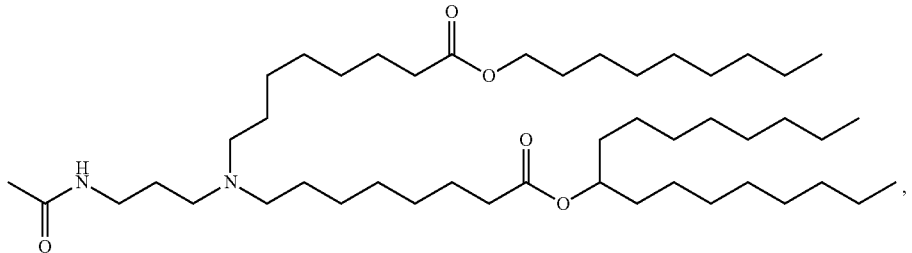
(Compound 108)

-continued
(Compound 109)
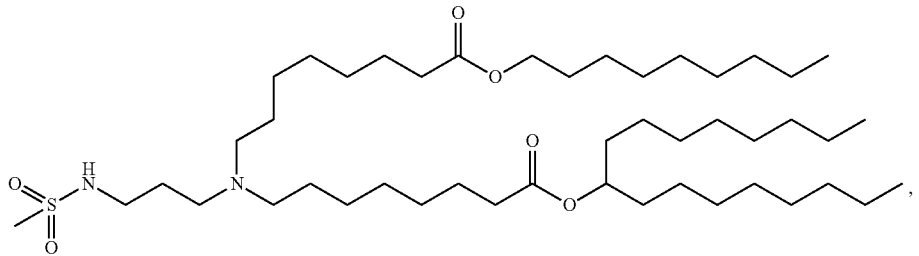
(Compound 110)
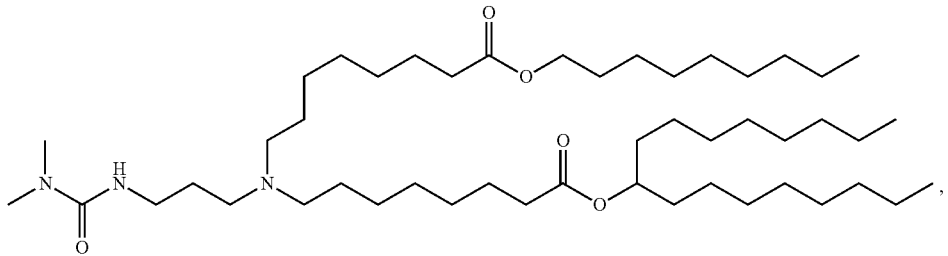
(Compound 111)
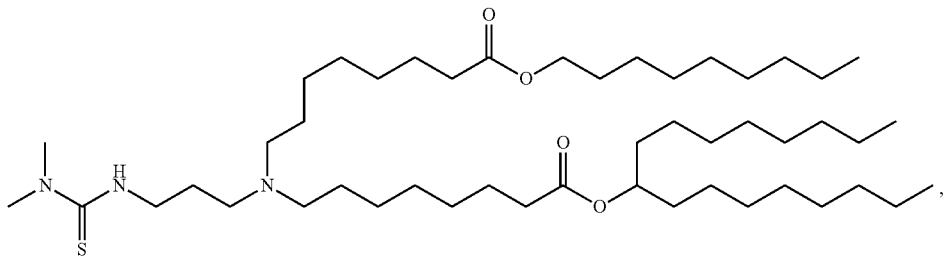
(Compound 112)
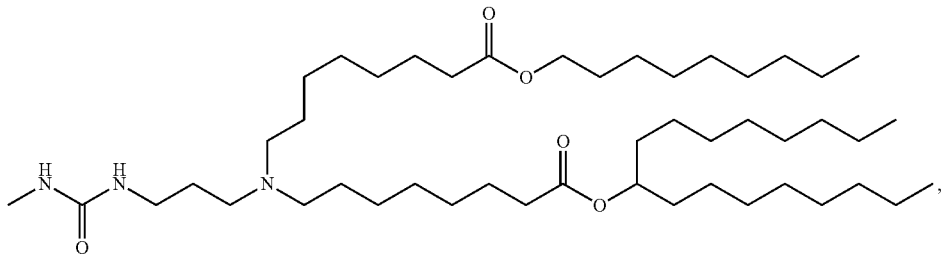
(Compound 113)
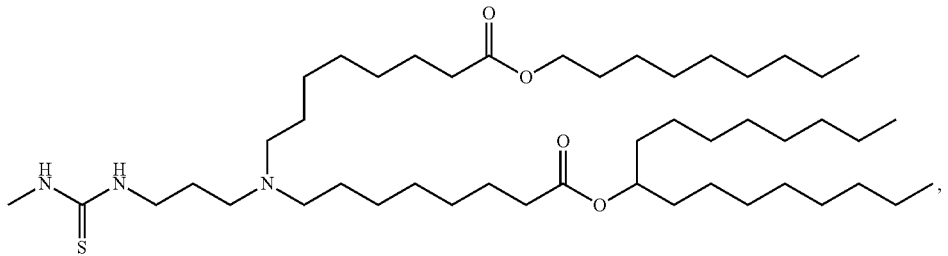
(Compound 114)
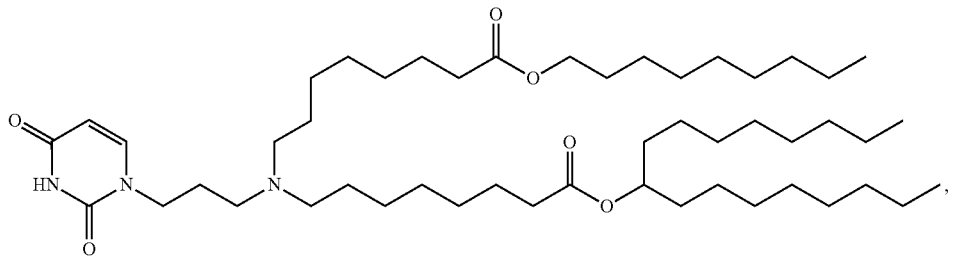

(Compound 115)
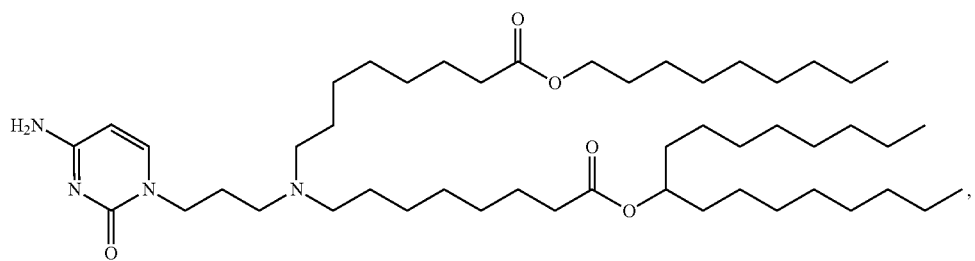
(Compound 116)
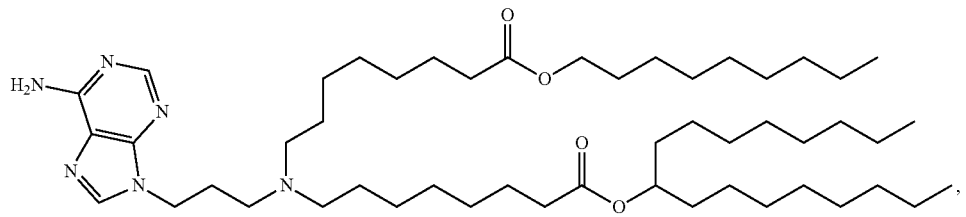
(Compound 117)
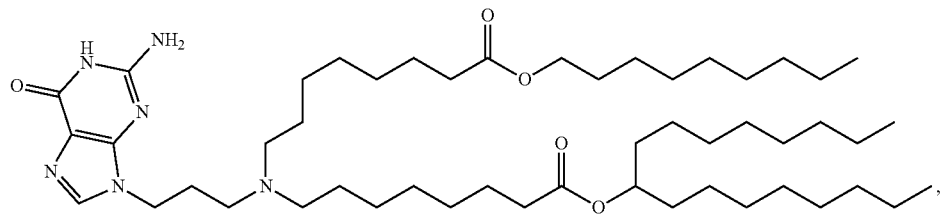
(Compound 118)
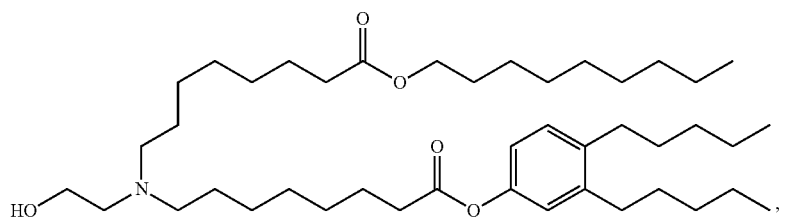
(Compound 119)
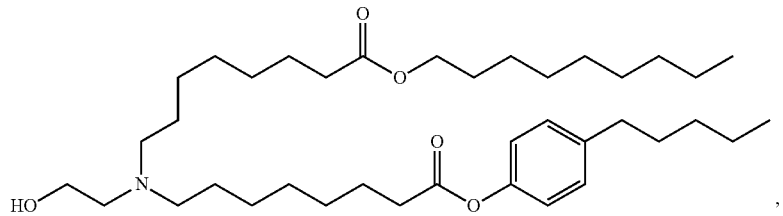
(Compound 120)
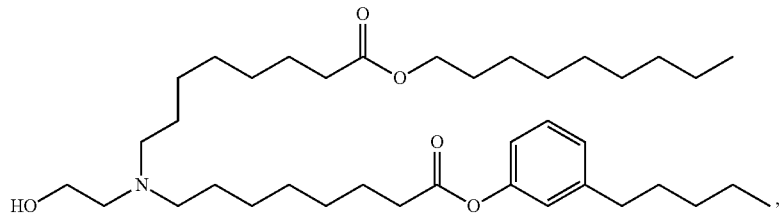
(Compound 121)
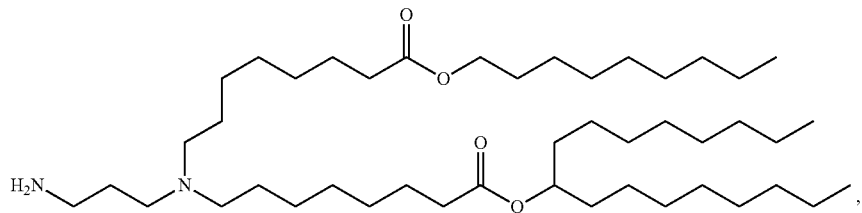

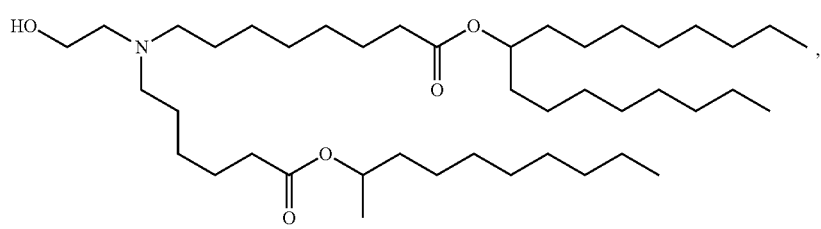
(Compound 122)
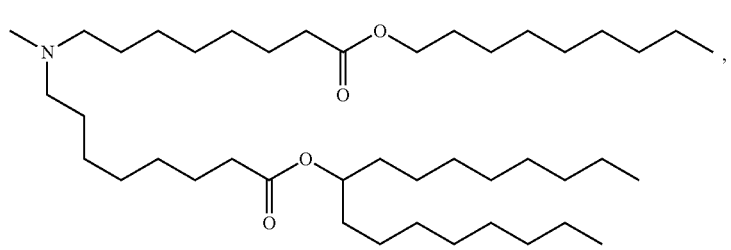
(Compound 123)
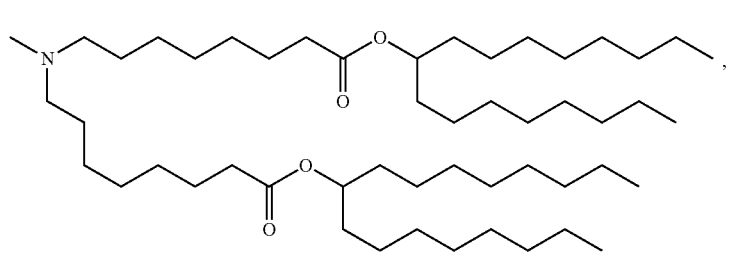
(Compound 124)
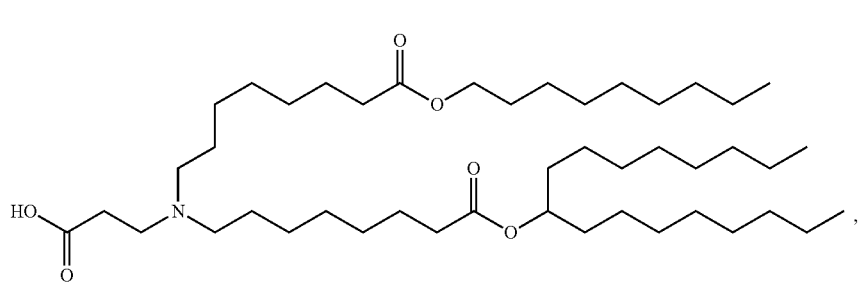
(Compound 125)
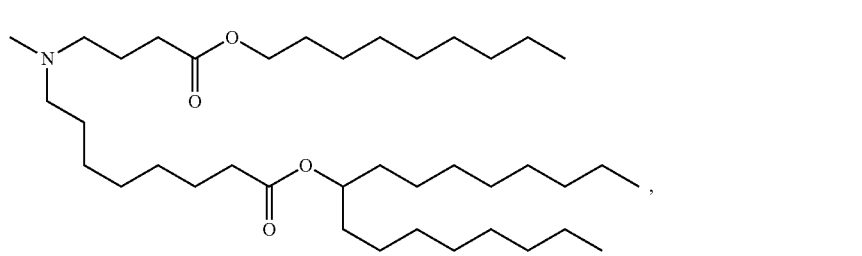
(Compound 126)
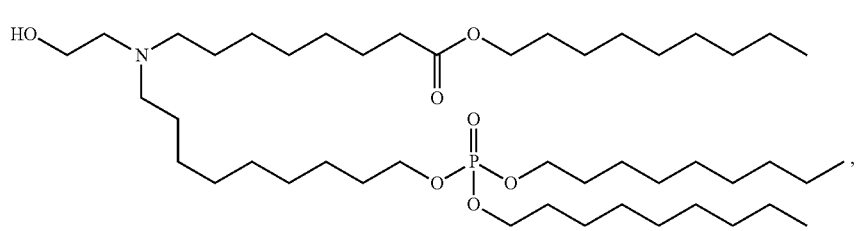
(Compound 127)

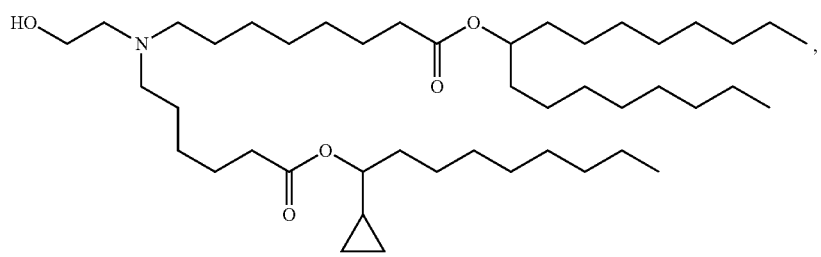
(Compound 128)
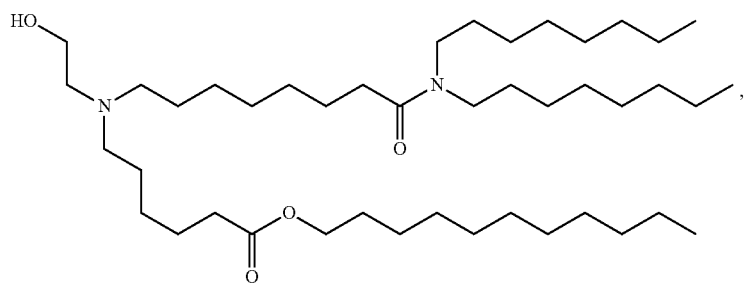
(Compound 129)
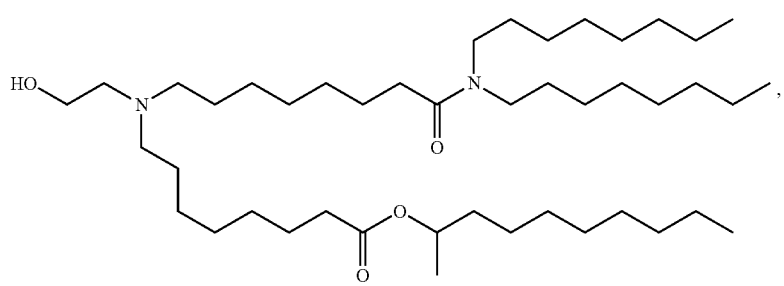
(Compound 130)
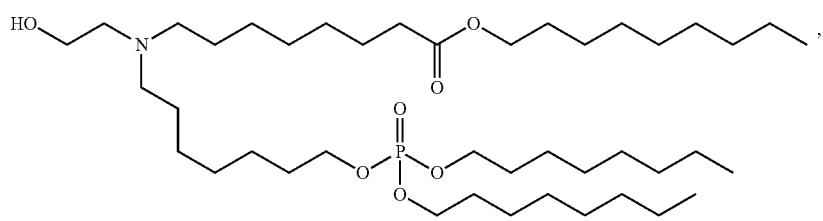
(Compound 131)
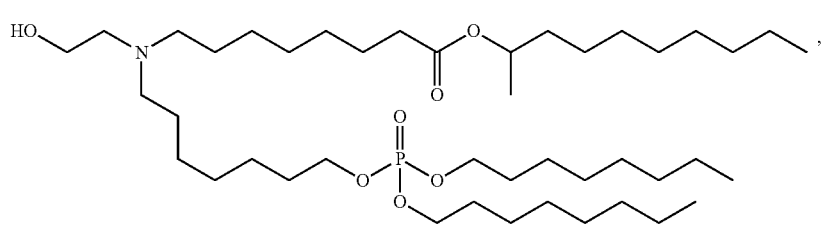
(Compound 132)
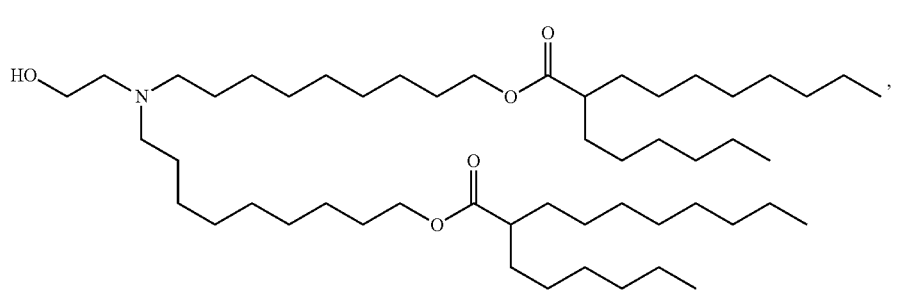
(Compound 133)

-continued
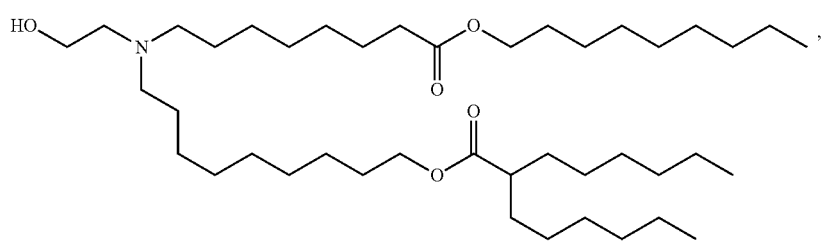
(Compound 134)
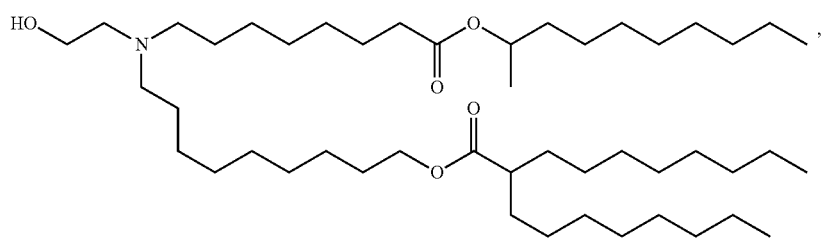
(Compound 135)
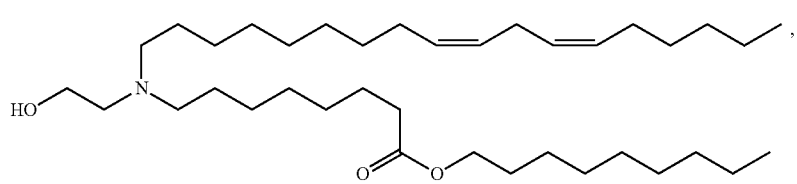
(Compound 136)
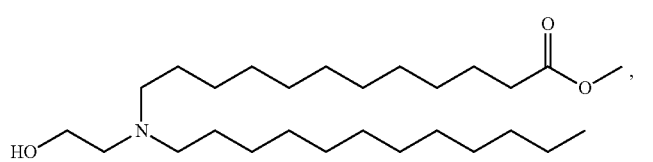
(Compound 137)
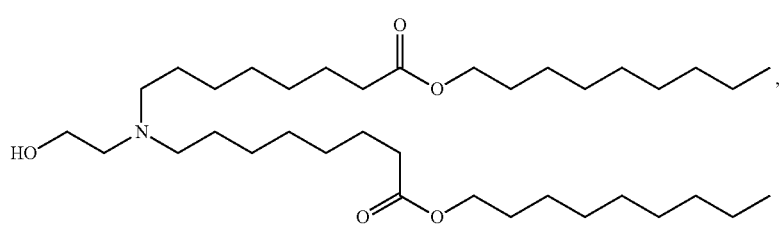
(Compound 138)
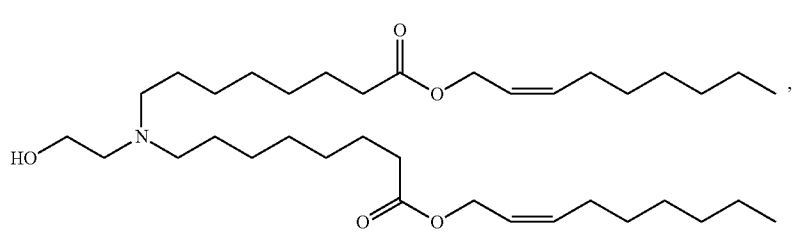
(Compound 139)
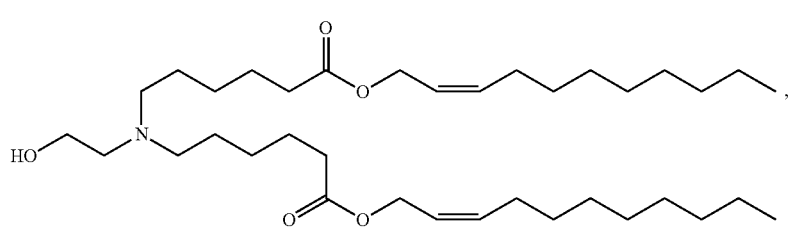
(Compound 140)

-continued
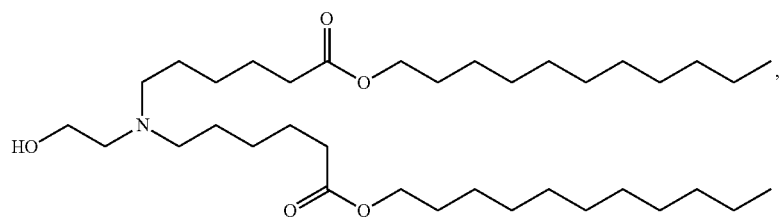
(Compound 141)
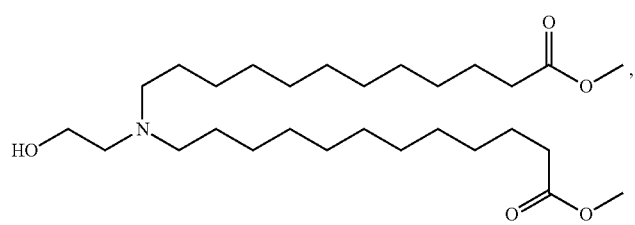
(Compound 142)
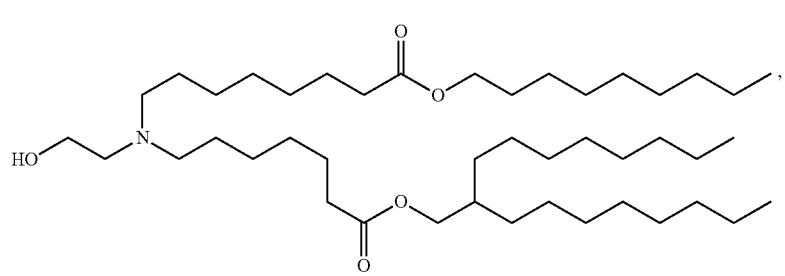
(Compound 143)
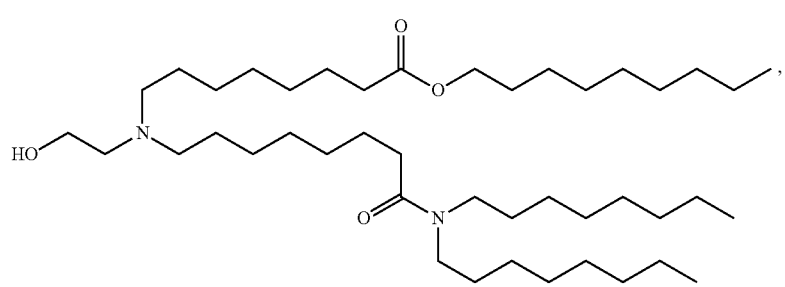
(Compound 144)
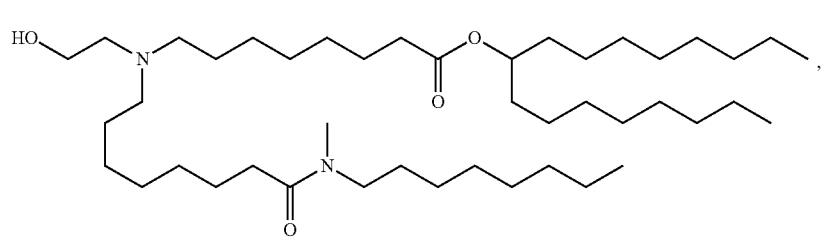
(Compound 145)
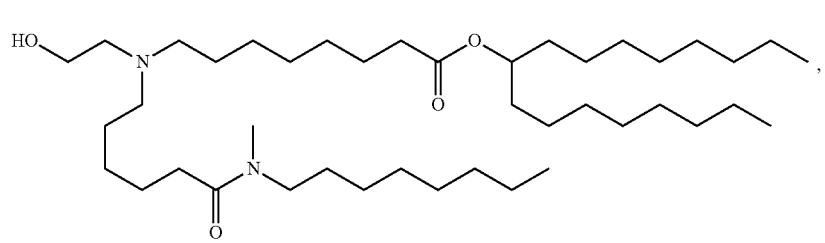
(Compound 146)

-continued
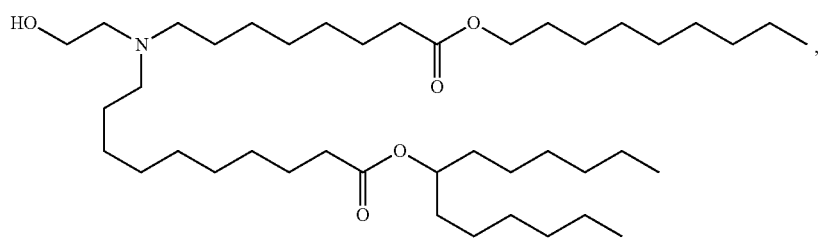
(Compound 147)
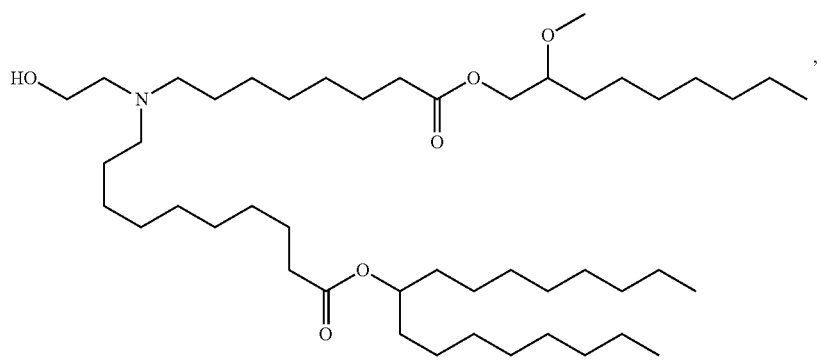
(Compound 148)
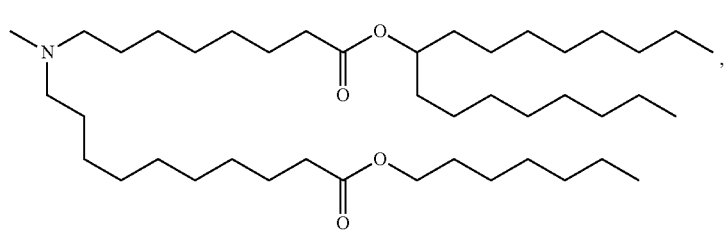
(Compound 149)
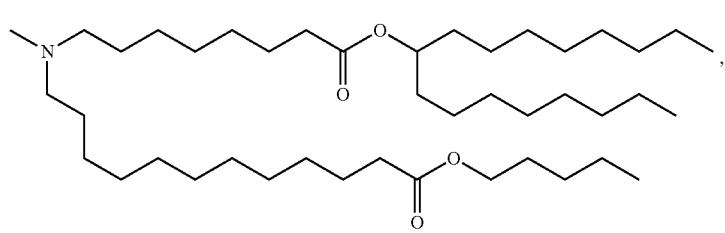
(Compound 150)
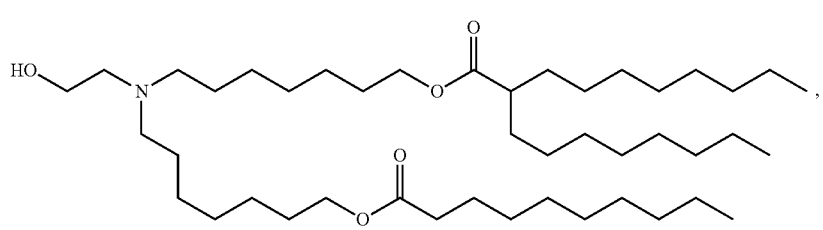
(Compound 151)
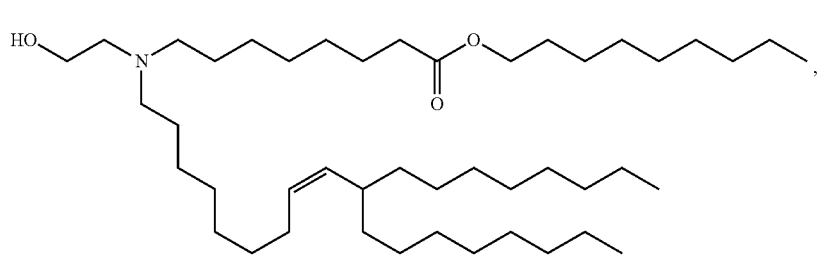
(Compound 152)

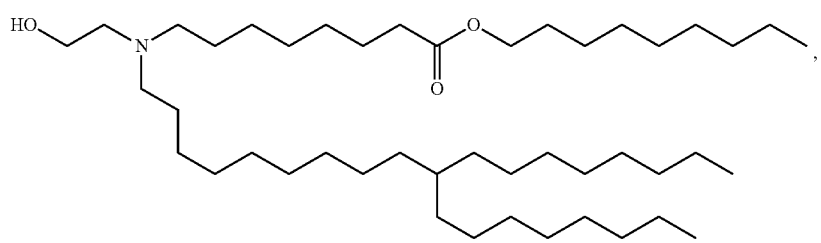
(Compound 153)
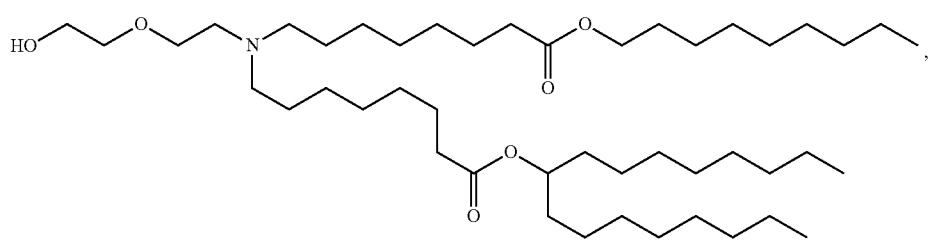
(Compound 154)
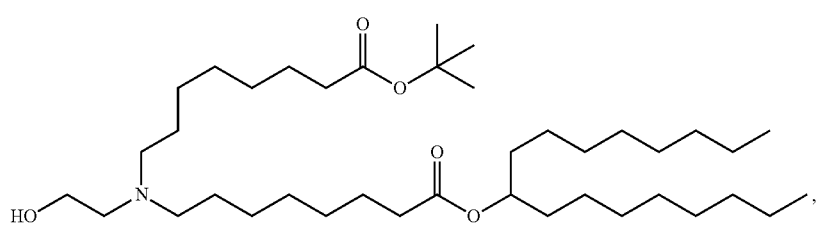
(Compound 155)
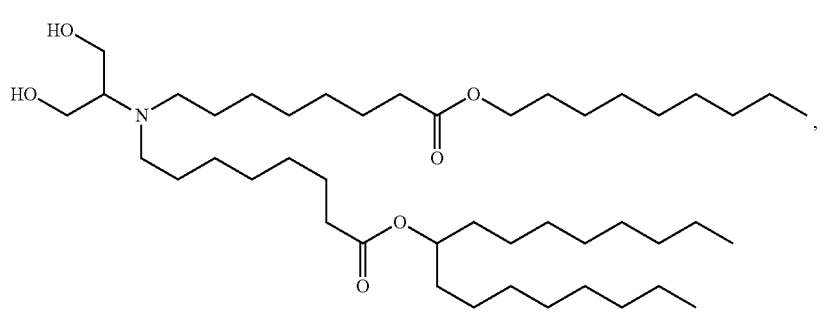
(Compound 156)
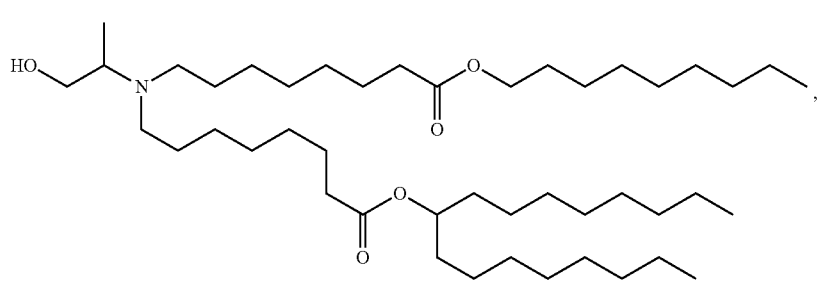
(Compound 157)
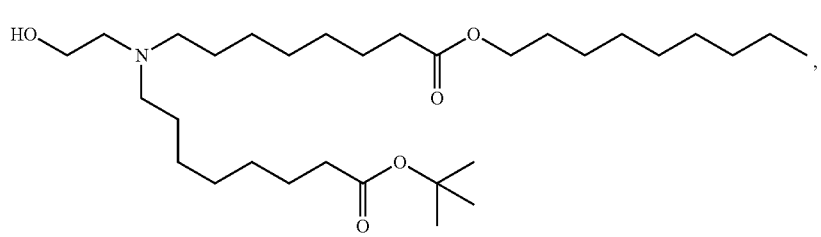
(Compound 158)

-continued
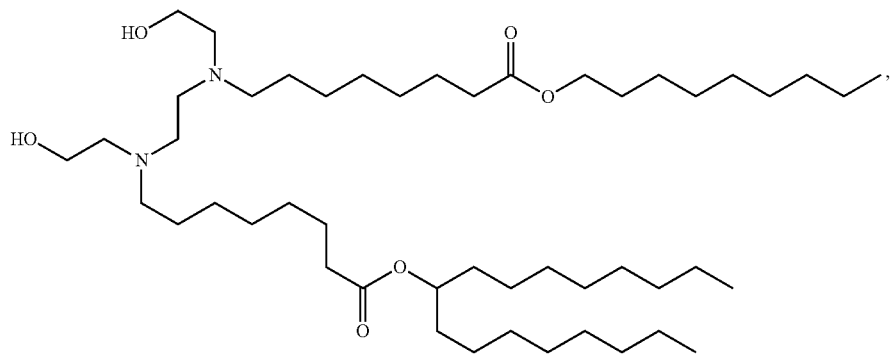
(Compound 159)
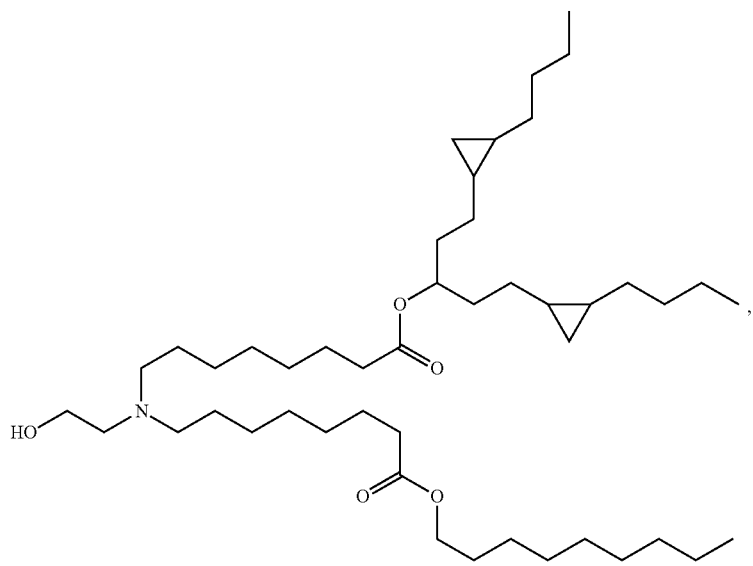
(Compound 160)
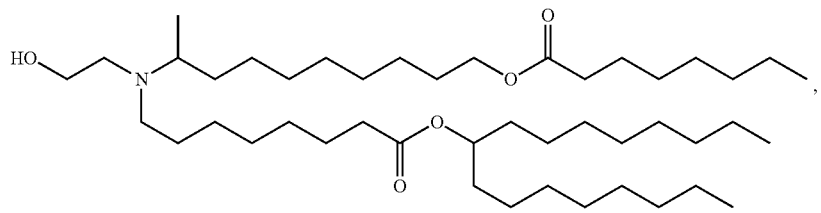
(Compound 161)
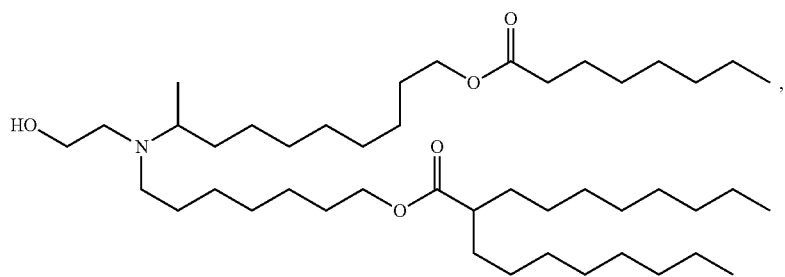
(Compound 162)

-continued
(Compound 163)
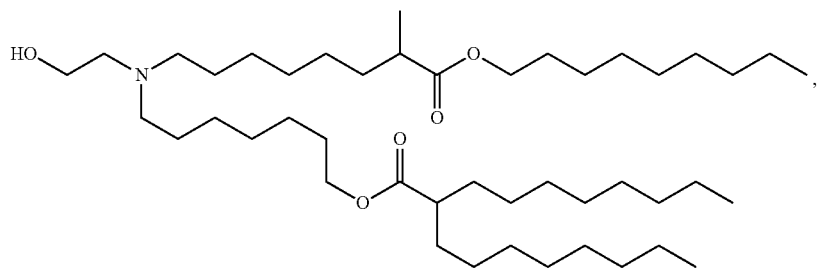
(Compound 164)
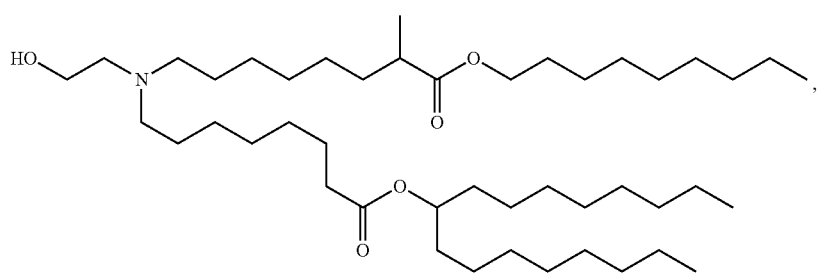
(Compound 165)
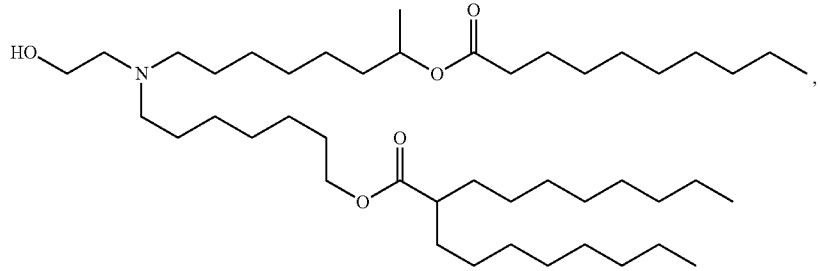
(Compound 166)
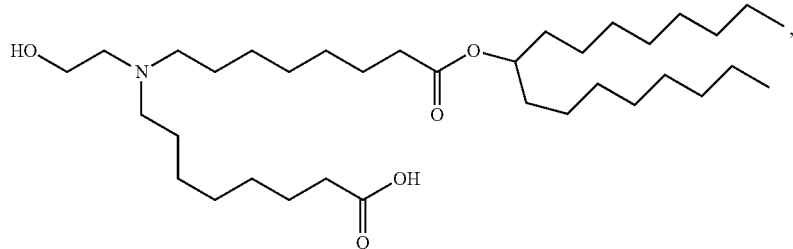
(Compound 167)
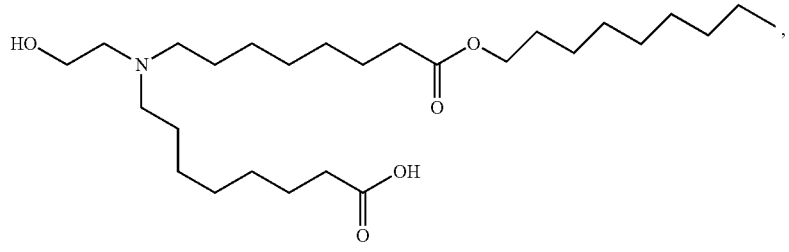
(Compound 168)
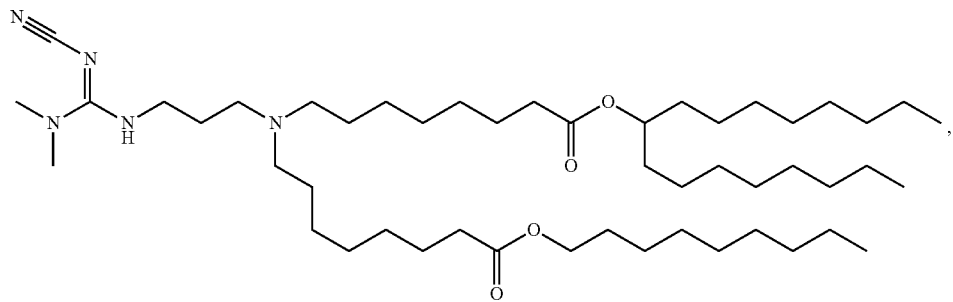

(Compound 169)
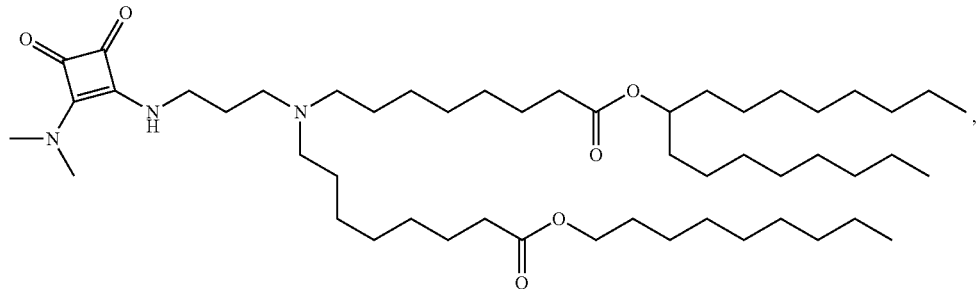
(Compound 170)
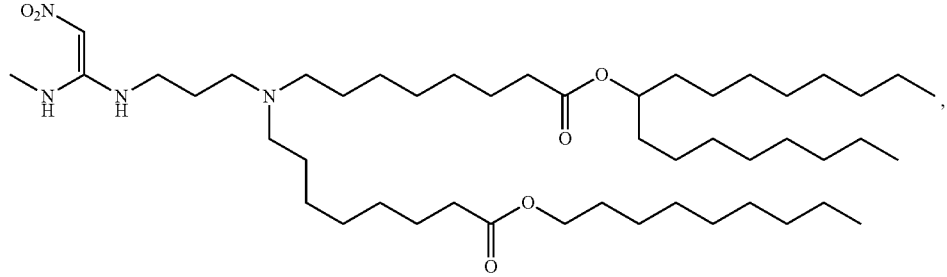
(Compound 171)
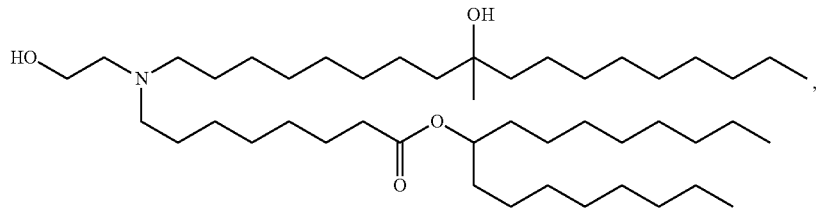
(Compound 172)
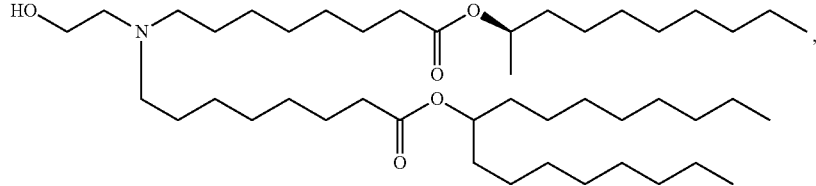
(Compound 173)
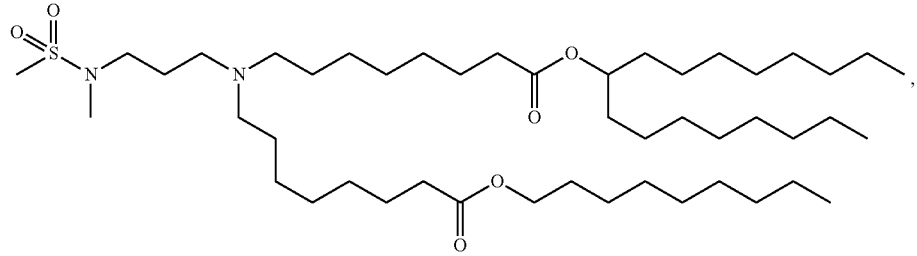
(Compound 174)
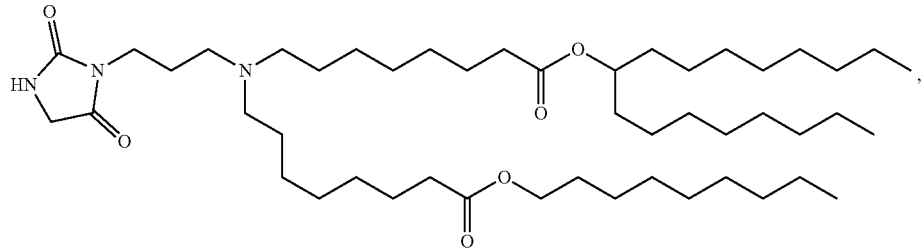

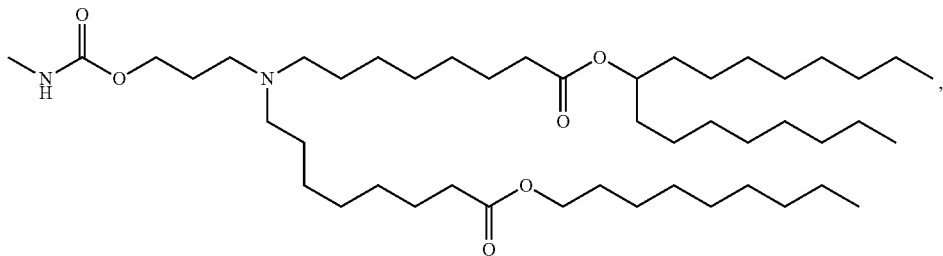
(Compound 175)
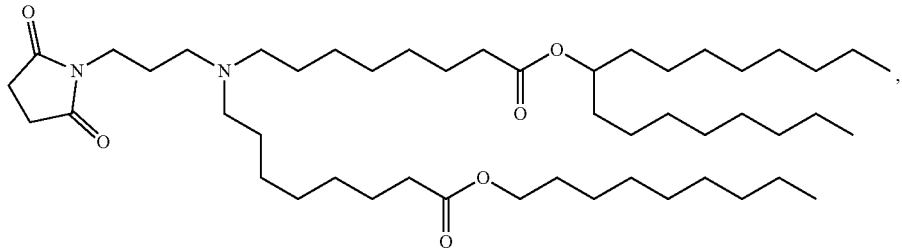
(Compound 176)
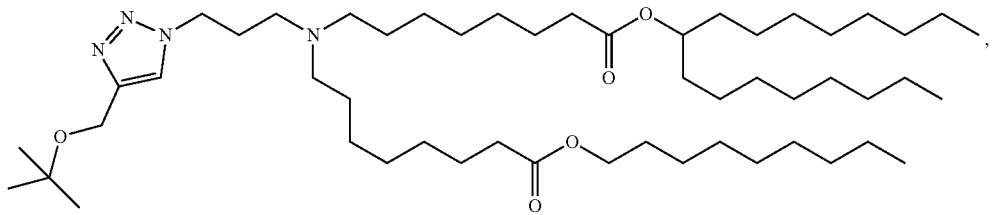
(Compound 177)
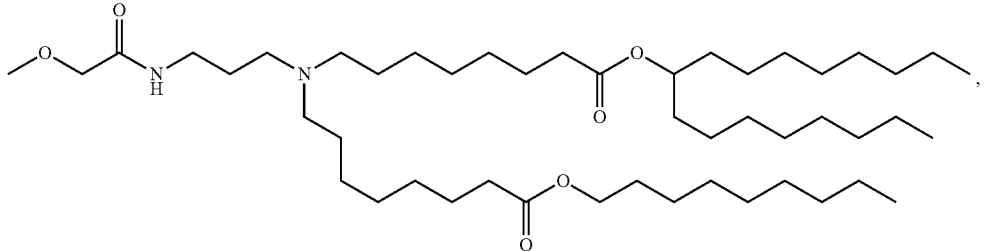
(Compound 178)
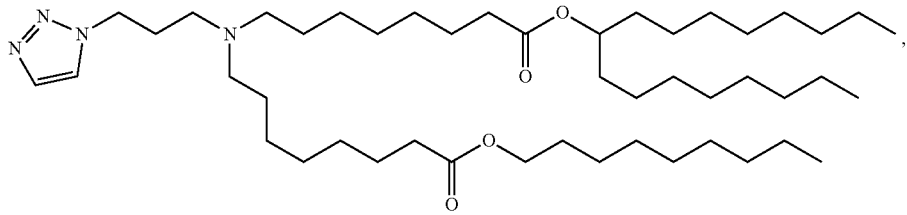
(Compound 179)
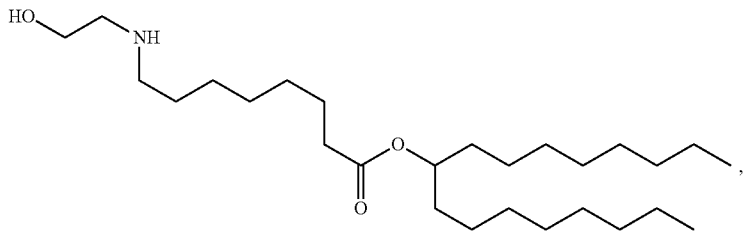
(Compound 180)

(Compound 181)
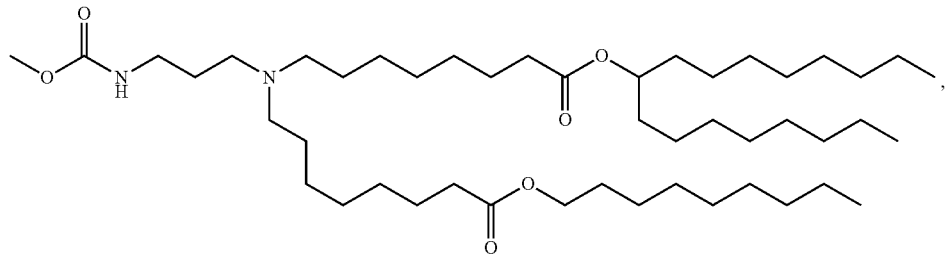
(Compound 182)
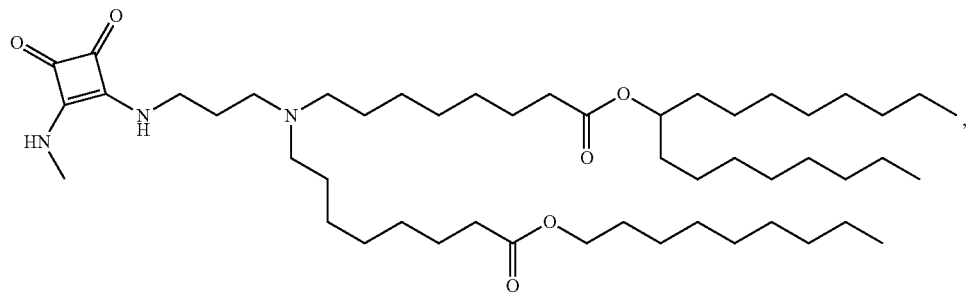
(Compound 183)
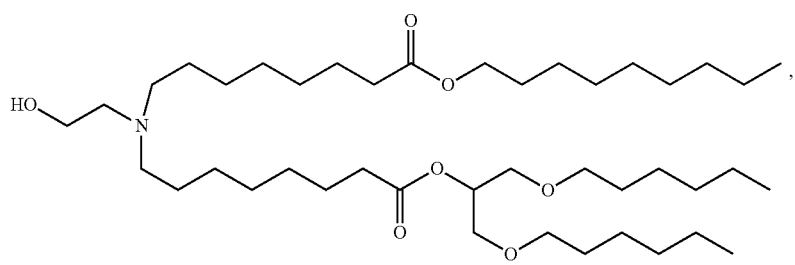
(Compound 184)
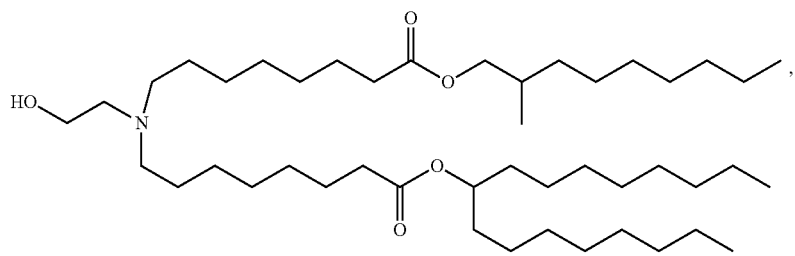
(Compound 185)
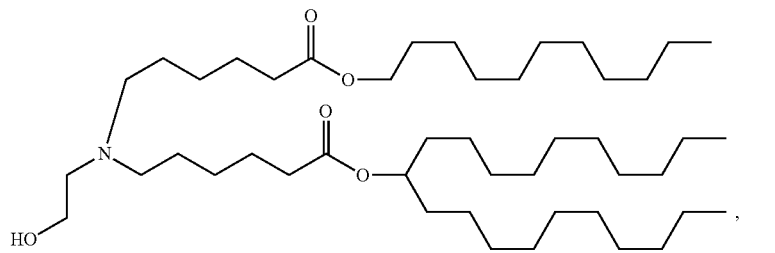
(Compound 186)
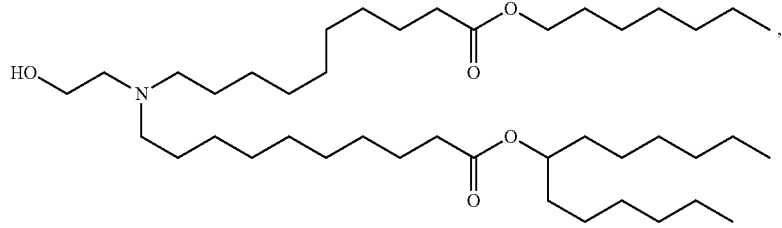

-continued
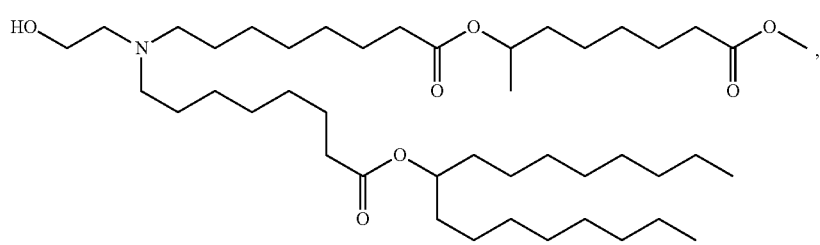
(Compound 187)
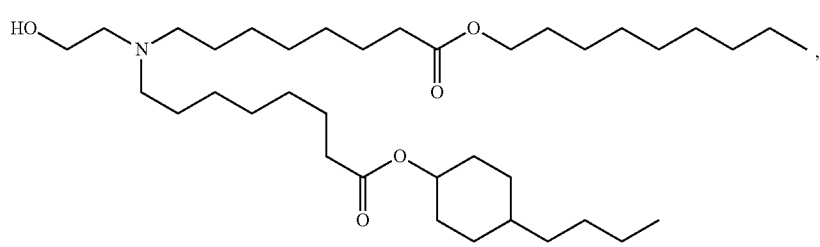
(Compound 188)
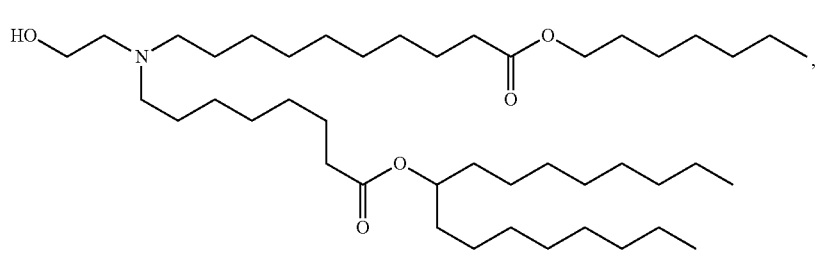
(Compound 189)
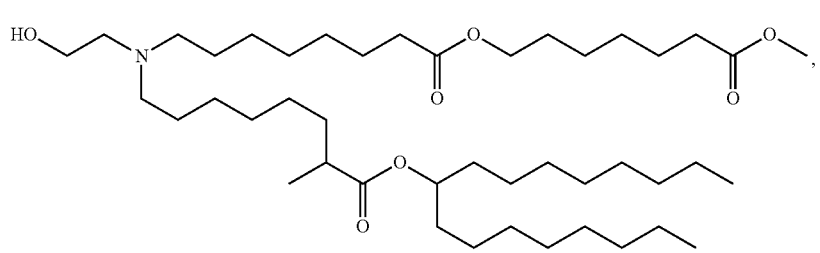
(Compound 190)
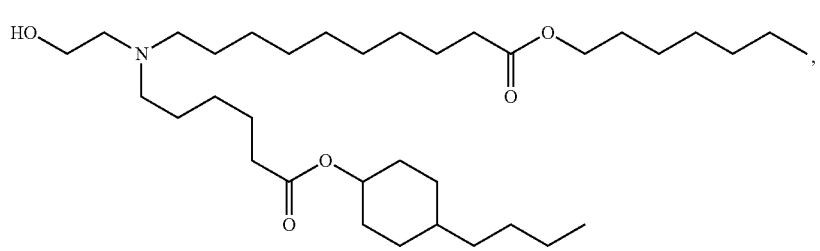
(Compound 191)
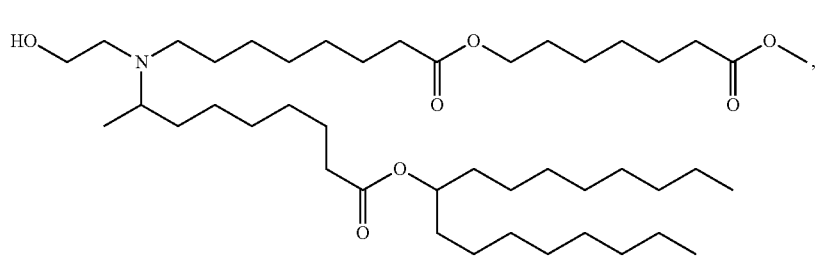
(Compound 192)

-continued
(Compoune 193)
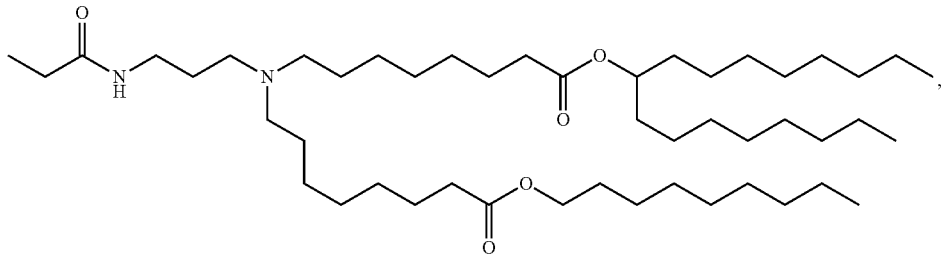
(Compound 194)
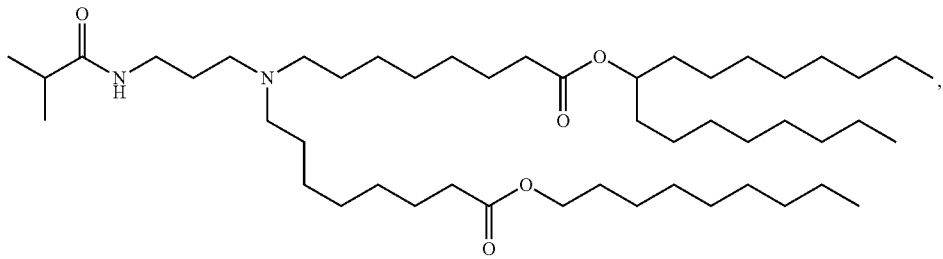
(Compound 195)
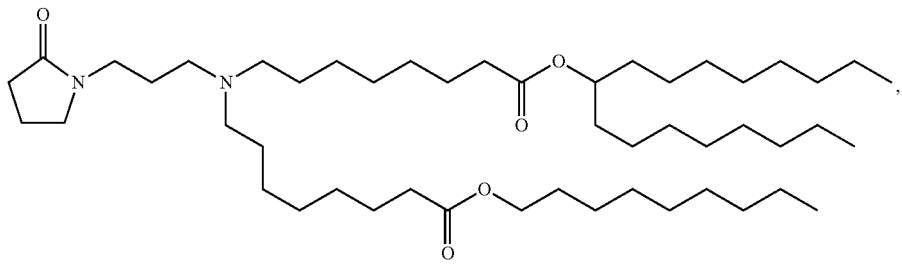
(Compound 196)
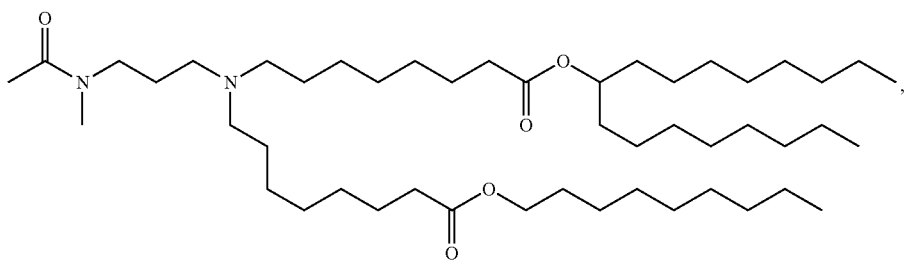
(Compound 197)
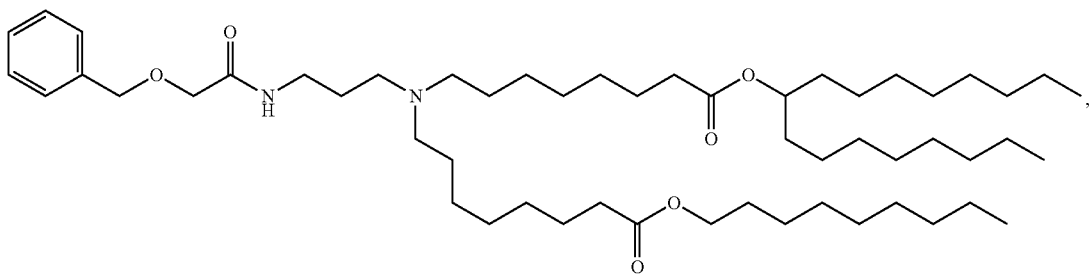
(Compound 198)
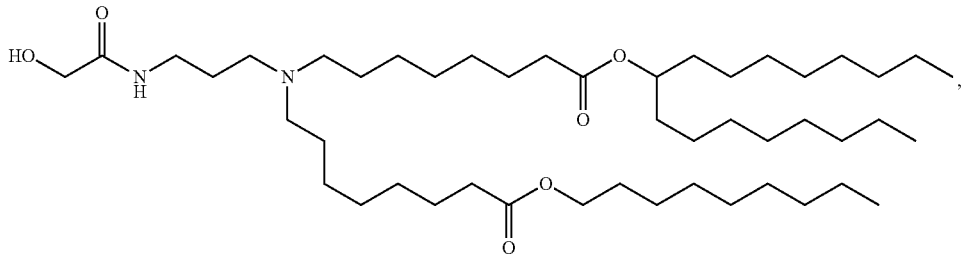

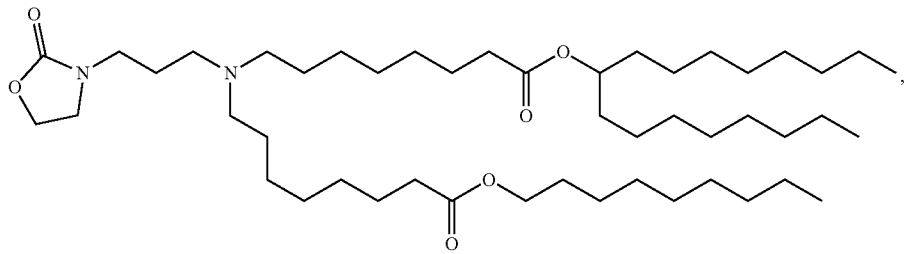
(Compound 199)
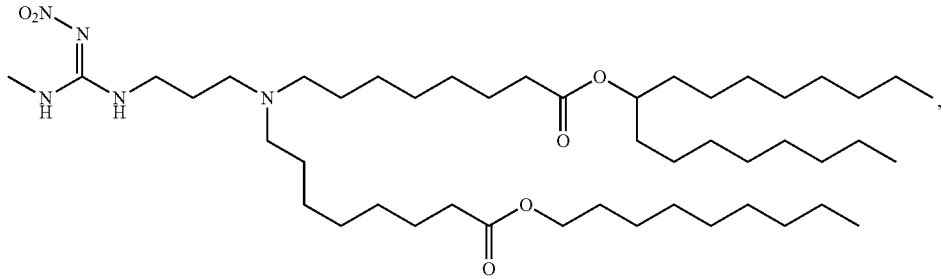
(Compound 200)
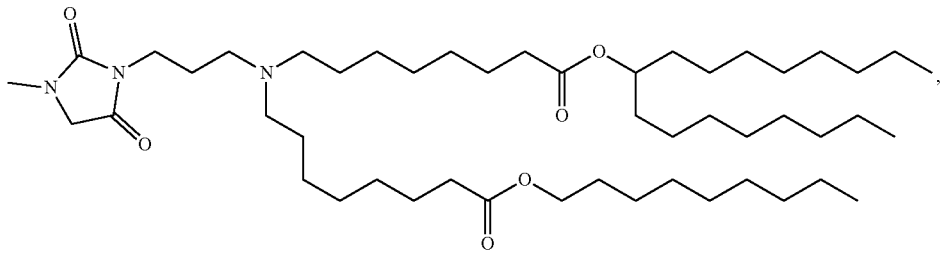
(Compound 201)
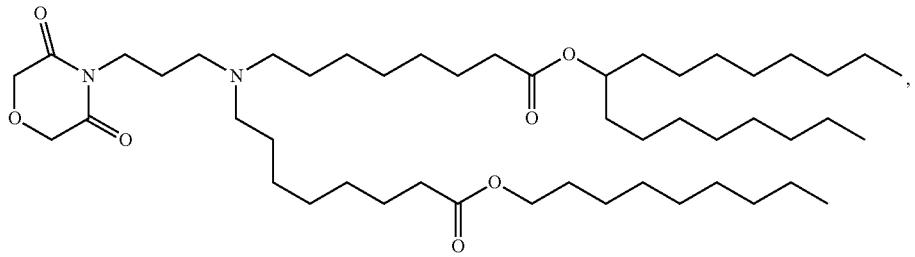
(Compound 202)
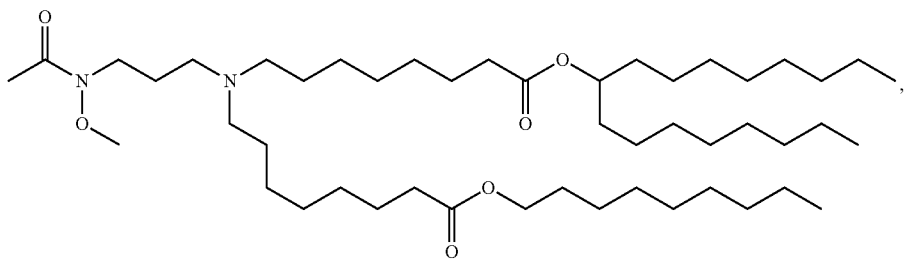
(Compound 203)
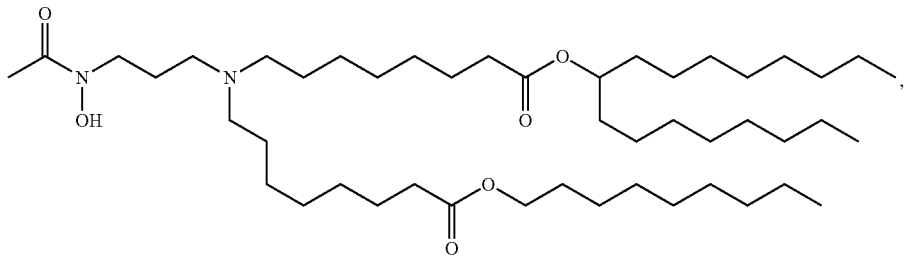
(Compound 204)

-continued
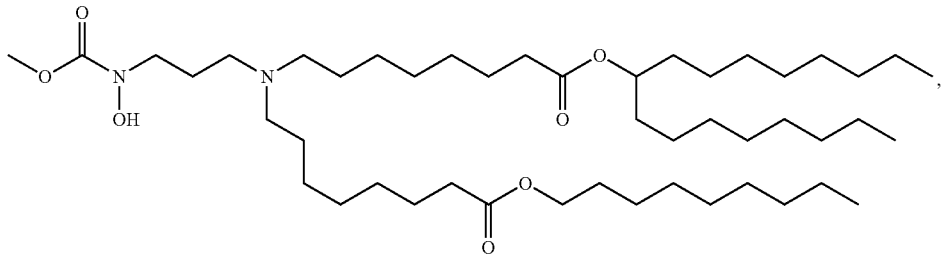
(Compound 205)
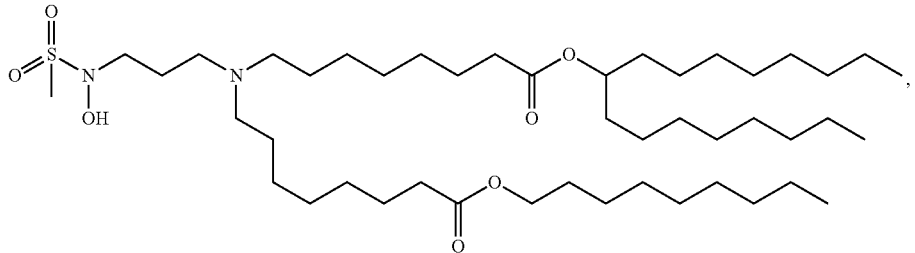
(Compound 206)
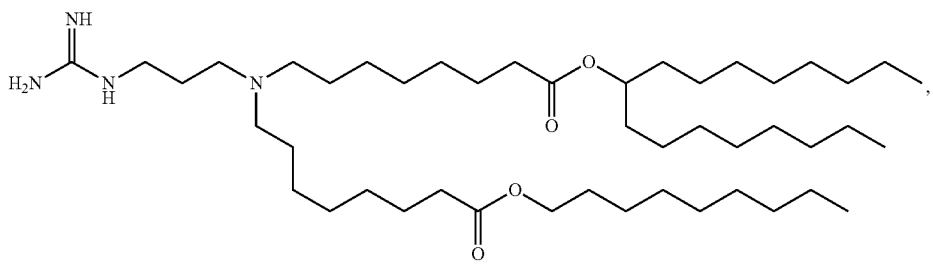
(Compound 207)
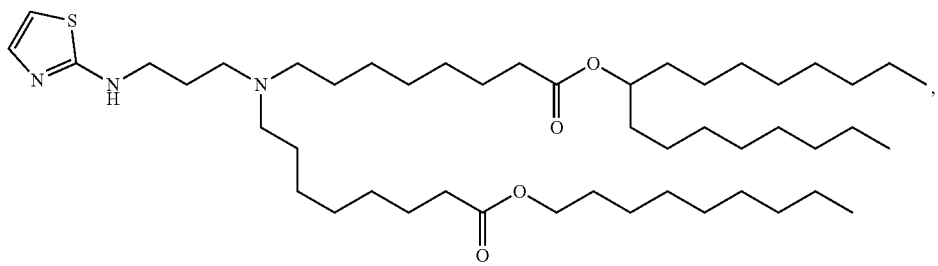
(Compound 208)
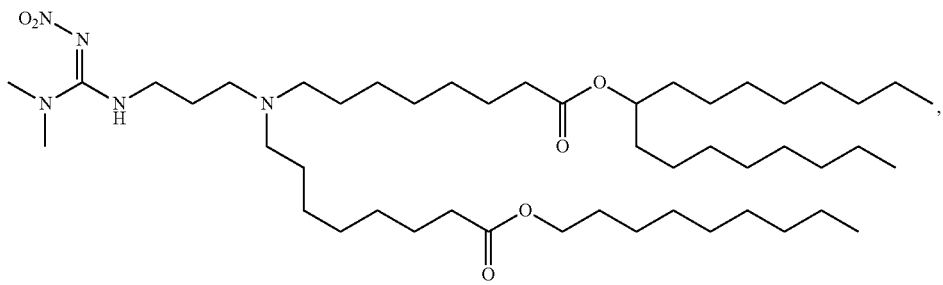
(Compound 209)

(Compound 210)
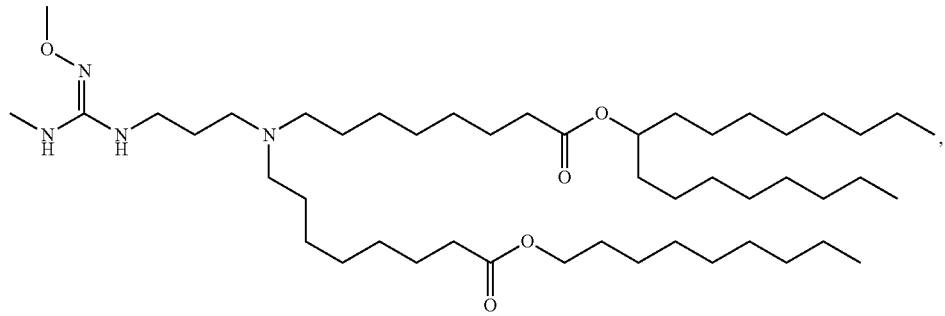
(Compound 211)
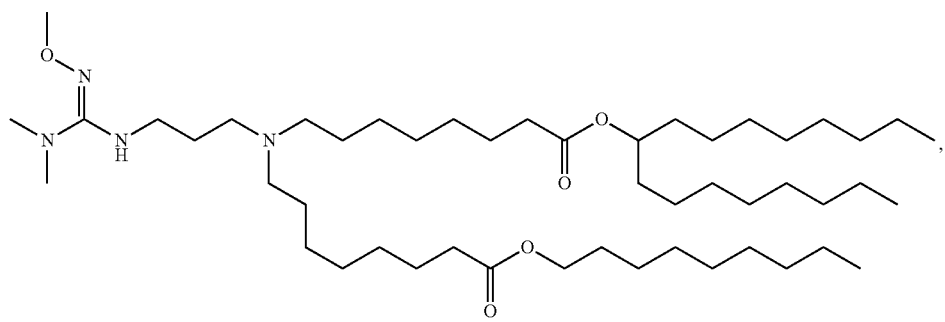
(Compound 212)
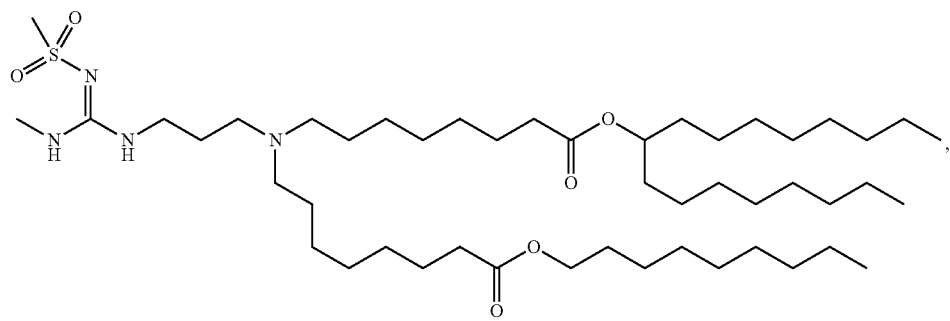
(Compound 213)
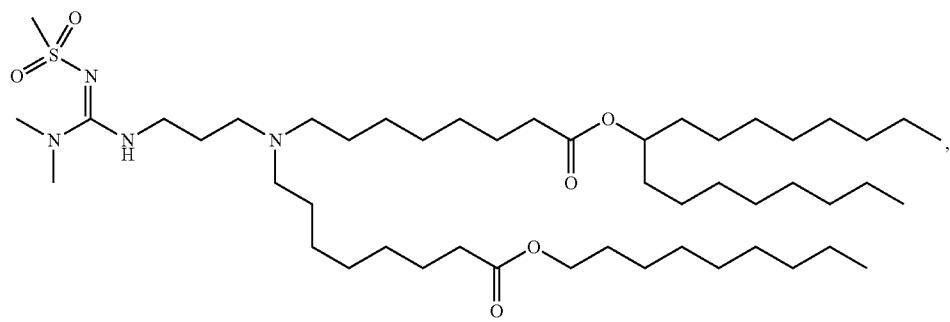
(Compound 214)
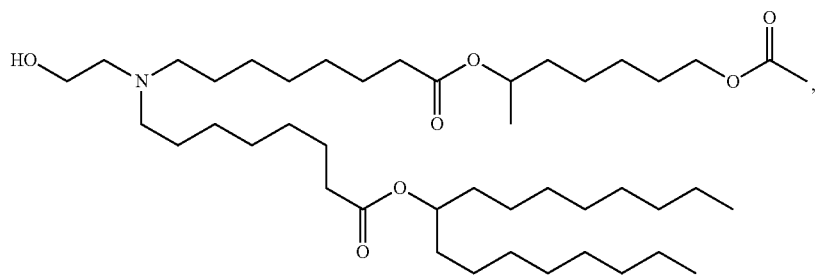

(Compound 215)
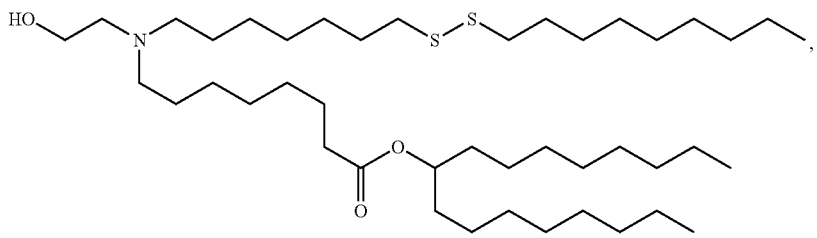
(Compound 216)
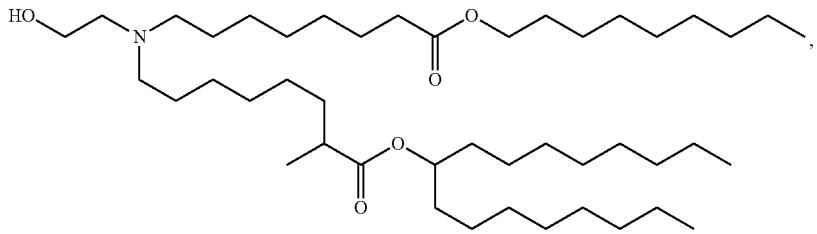
(Compound 217)
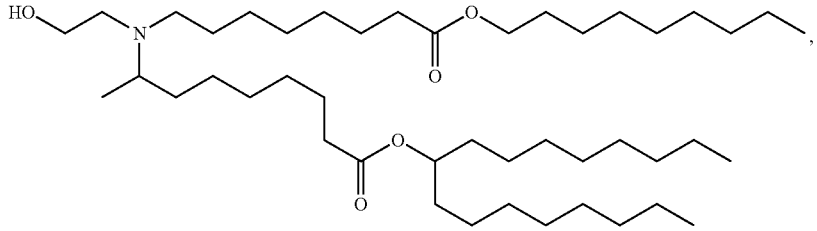
(Compound 218)
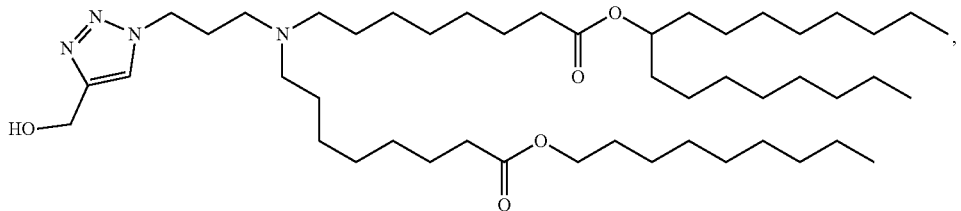
(Compound 219)
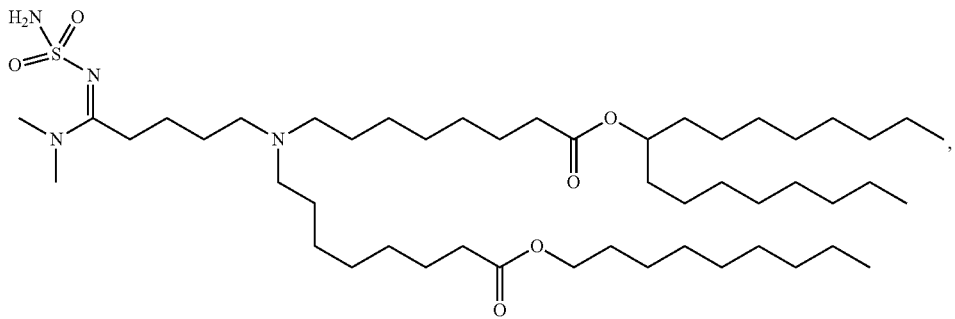
(Compound 220)
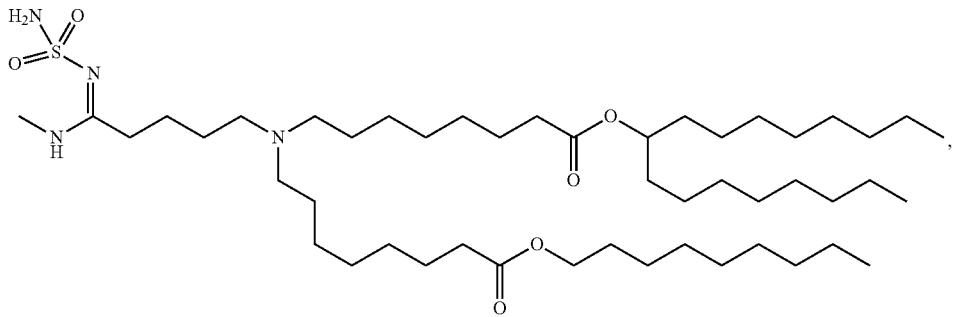

(Compound 221)
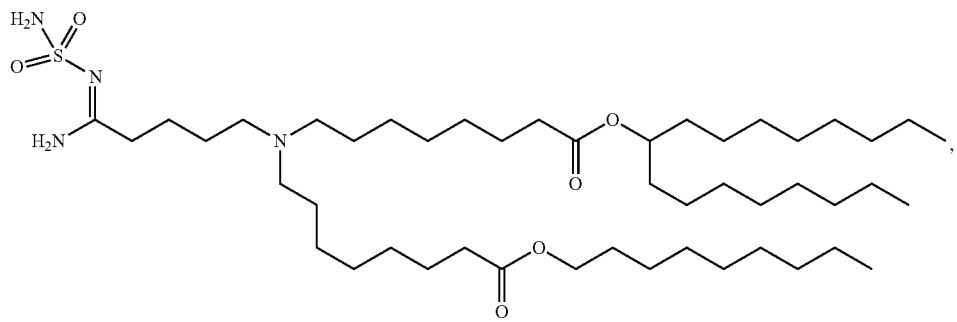
(Compound 222)
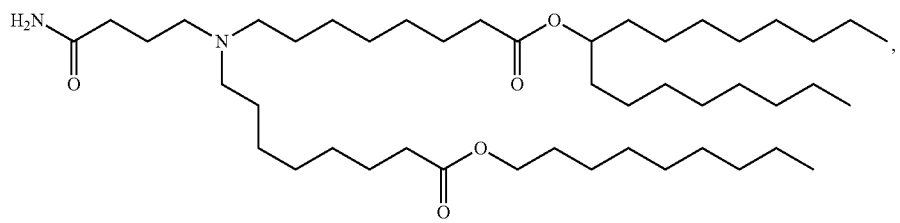
(Compound 223)
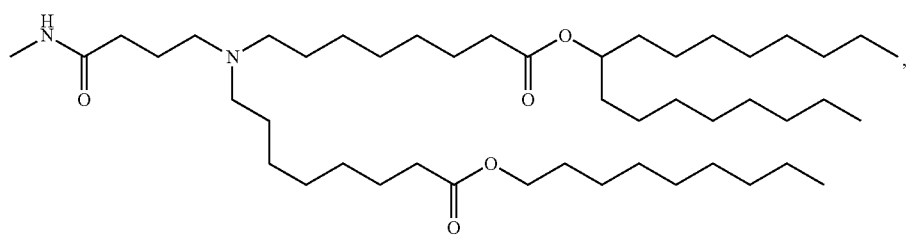
(Compound 224)
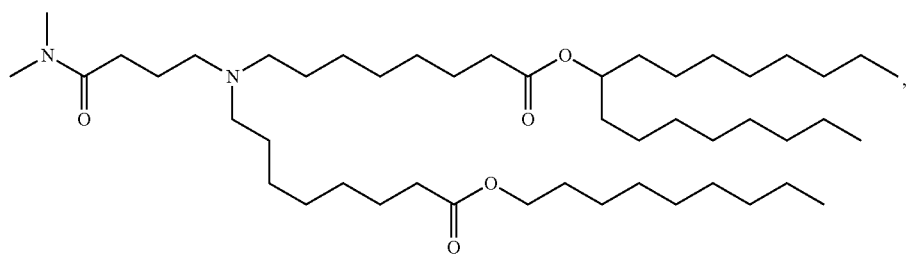
(Compound 225)
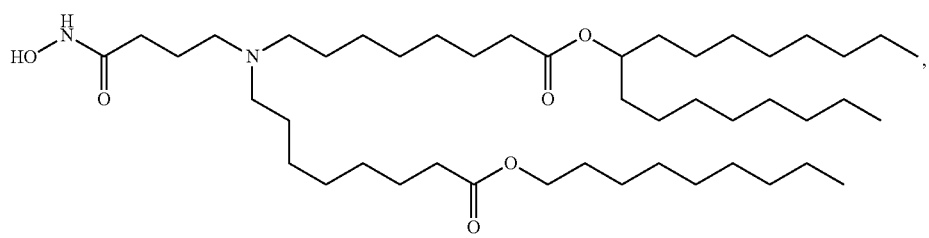
(Compound 226)
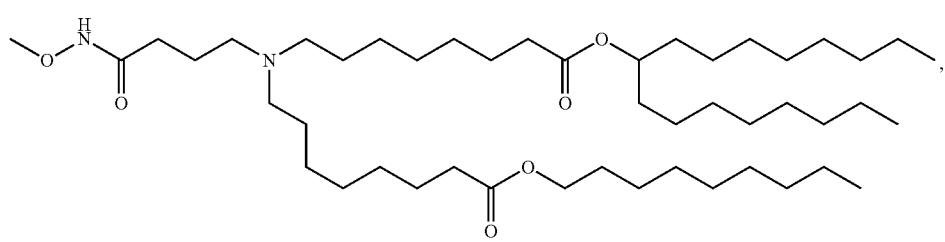

(Compound 227)
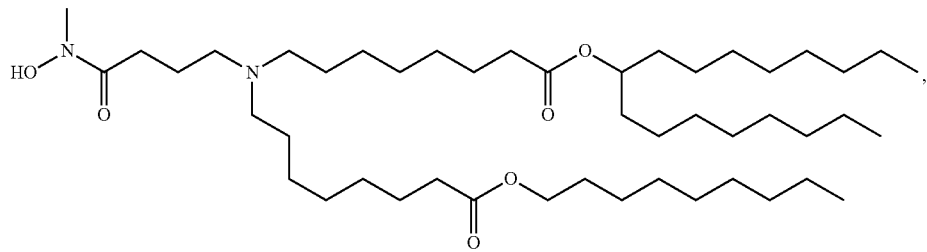
(Compound 228)
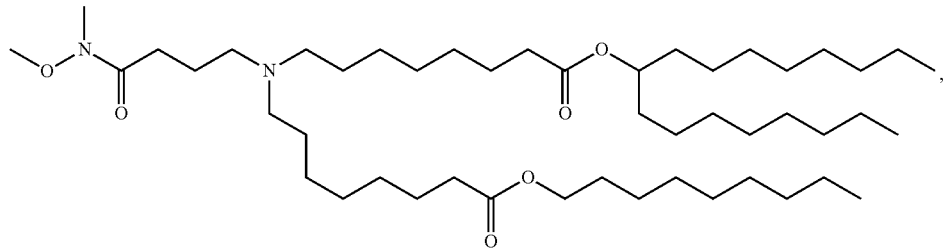
(Compound 229)
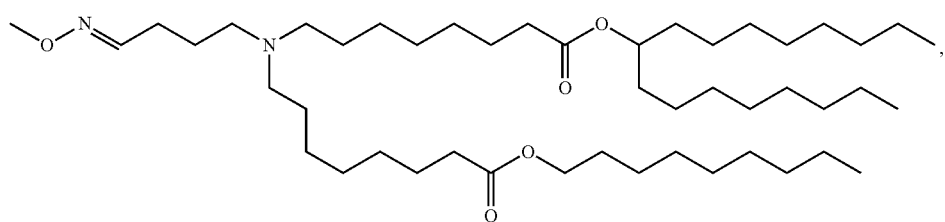
(Compound 230)
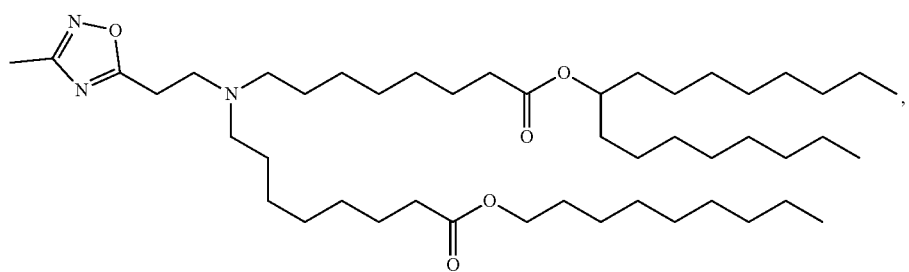
(Compound 231)
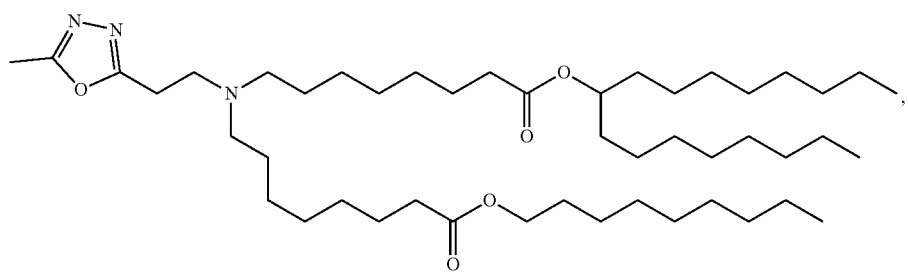

(Compound 232)

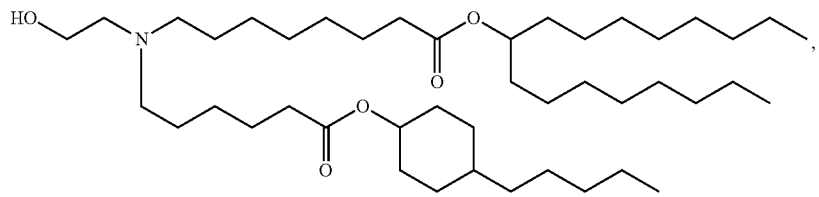

and salts or stereoisomers thereof.

In other embodiments, the compound of Formula (I) is selected from the group consisting of Compound 1-Compound 147, or salt or stereoisomers thereof.

In some embodiments ionizable lipids including a central piperazine moiety are provided. The lipids described herein may be advantageously used in lipid nanoparticle compositions for the delivery of therapeutic and/or prophylactic agents to mammalian cells or organs. For example, the lipids described herein have little or no immunogenicity. For example, the lipid compounds disclosed hereinhave a lower immunogenicity as compared to a reference amino lipid (e.g., MC3, KC2, or DLinDMA). For example, a formulation comprising a lipid disclosed herein and a therapeutic or prophylactic agent has an increased therapeutic index as compared to a corresponding formulation which comprises a reference amino lipid (e.g., MC3, KC2, or DLinDMA) and the same therapeutic or prophylactic agent.

In some embodiments, the delivery agent comprises a lipid compound having the formula (III)

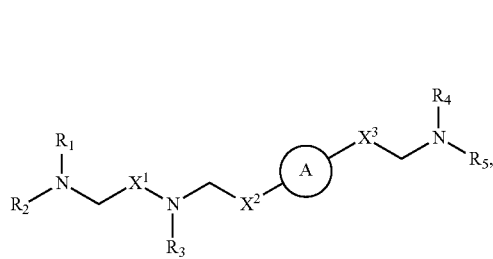

(III)

or salts or stereoisomers thereof, wherein ring A is

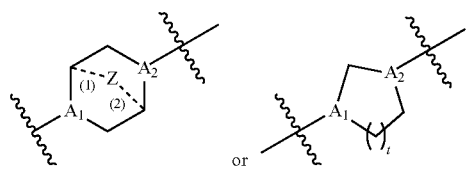

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$X^1$, $X^2$, and $X^3$ are independently selected from the group consisting of a bond, —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl, wherein when ring A is

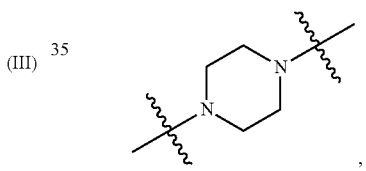

then i) at least one of $X^1$, $X^2$, and $X^3$ is not —CH$_2$—; and/or ii) at least one of $R_1$, $R_2$, $R_3$, $R_4$, and $R_5$ is —R"MR'.

In some embodiments, the compound is of any of formulae (IIIa1)-(IIIa6):

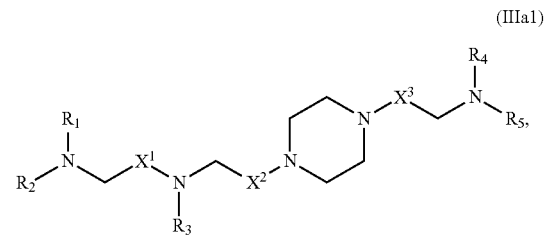

(IIIa1)

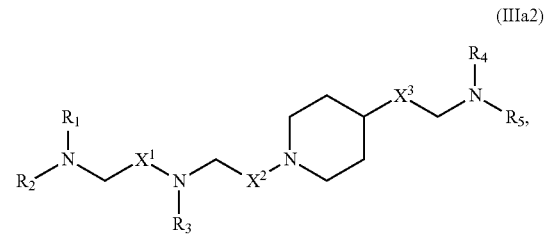

(IIIa2)

-continued (IIIa3)
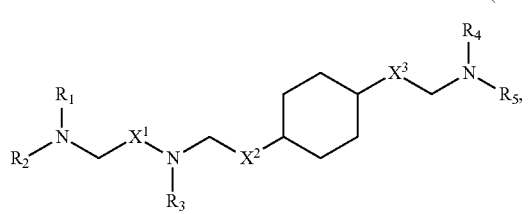

(IIIa4)
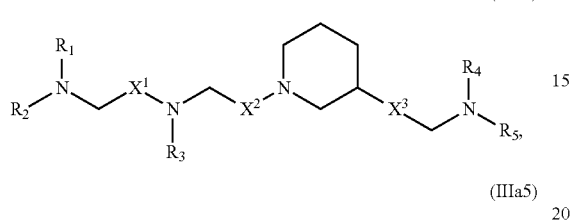

(IIIa5)

(IIIa6)
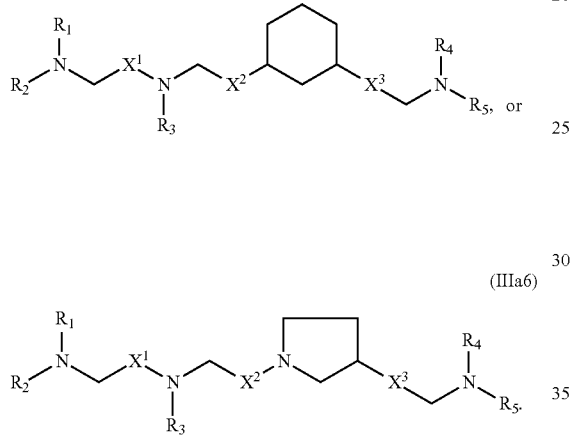

The compounds of Formula (III) or any of (IIIa1)-(IIIa6) include one or more of the following features when applicable.

In some embodiments, ring A is

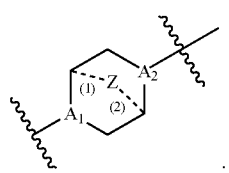

In some embodiments, ring A is

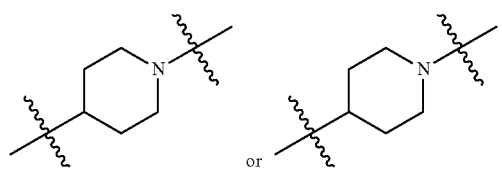

In some embodiments, ring A is

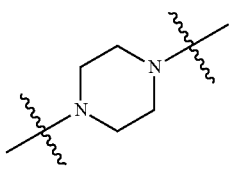

In some embodiments, ring A is

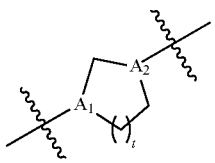

In some embodiments, ring A is

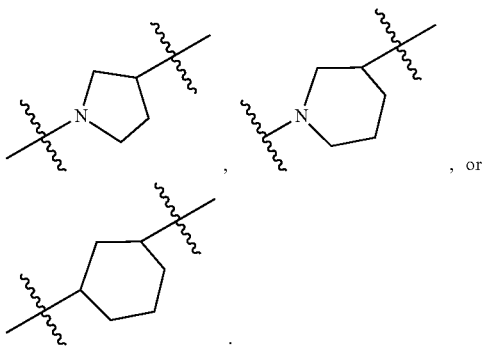

In some embodiments, ring A is

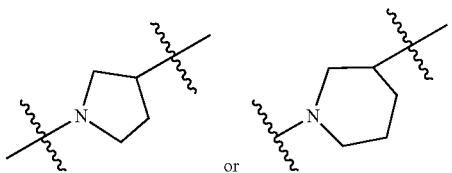 [SMILES: *C1CCN(*)C1 ; *C1CCCN(*)C1]

wherein ring, in which the N atom is connected with $X^2$.

In some embodiments, Z is $CH_2$.
In some embodiments, Z is absent.
In some embodiments, at least one of $A_1$ and $A_2$ is N.
In some embodiments, each of $A_1$ and $A_2$ is N.
In some embodiments, each of $A_1$ and $A_2$ is CH.
In some embodiments, $A_1$ is N and $A_2$ is CH.
In some embodiments, $A_1$ is CH and $A_2$ is N.
In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $X^3$ is —C(O)—, —C(O)O—, —OC(O)—, —C(O)—$CH_2$—, —$CH_2$—C(O)—, —C(O)

O—CH$_2$—, —OC(O)—CH$_2$—, —CH$_2$—C(O)O—, or —CH$_2$—OC(O)—. In other embodiments, X$^3$ is —CH$_2$—.

In some embodiments, X$^3$ is a bond or —(CH$_2$)$_2$.

In some embodiments, R$_1$ and R$_2$ are the same. In certain embodiments, R$_1$, R$_2$, and R$_3$ are the same. In some embodiments, R$_4$ and R$_5$ are the same. In certain embodiments, R$_1$, R$_2$, R$_3$, R$_4$, and R$_5$ are the same.

In some embodiments, at least one of R$_1$, R$_2$, R$_3$, R$_4$, and R$_5$ is —R"MR'. In some embodiments, at most one of R$_1$, R$_2$, R$_3$, R$_4$, and R$_5$ is —R"MR'. For example, at least one of R$_1$, R$_2$, and R$_3$ may be —R"MR', and/or at least one of R$_4$ and R$_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is C$_3$ alkyl. In certain embodiments, each R" is C$_3$ alkyl. In some embodiments, at least one R" is C$_5$ alkyl. In certain embodiments, each R" is C$_5$ alkyl. In some embodiments, at least one R" is C$_6$ alkyl. In certain embodiments, each R" is C$_6$ alkyl. In some embodiments, at least one R" is C$_7$ alkyl. In certain embodiments, each R" is C$_7$ alkyl. In some embodiments, at least one R' is C$_5$ alkyl. In certain embodiments, each R' is C$_5$ alkyl. In other embodiments, at least one R' is C$_1$ alkyl. In certain embodiments, each R' is C$_1$ alkyl. In some embodiments, at least one R' is C$_2$ alkyl. In certain embodiments, each R' is C$_2$ alkyl.

In some embodiments, at least one of R$_1$, R$_2$, R$_3$, R$_4$, and R$_5$ is C$_{12}$ alkyl. In certain embodiments, each of R$_1$, R$_2$, R$_3$, R$_4$, and R$_5$ are C$_{12}$ alkyl.

In certain embodiments, the compound is selected from the group consisting of:

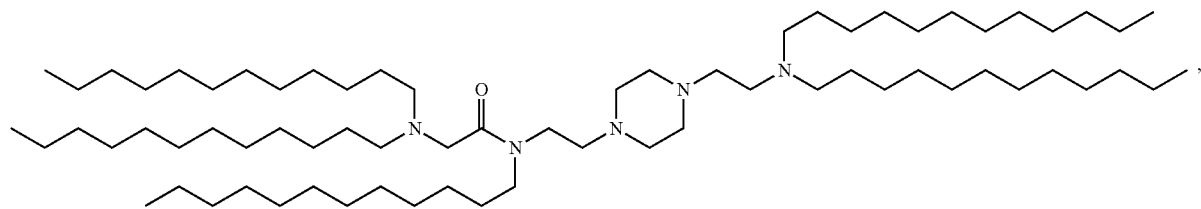
(Compound 233)

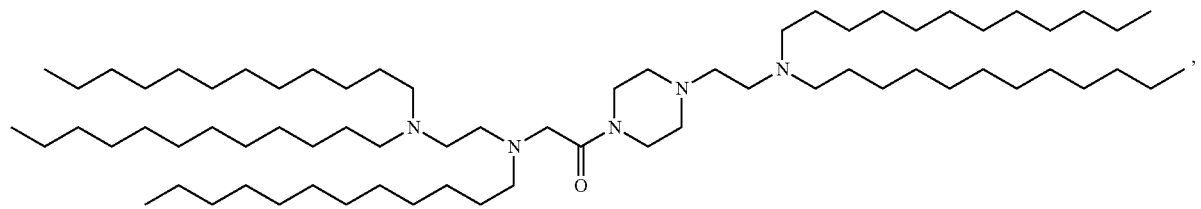
(Compound 234)

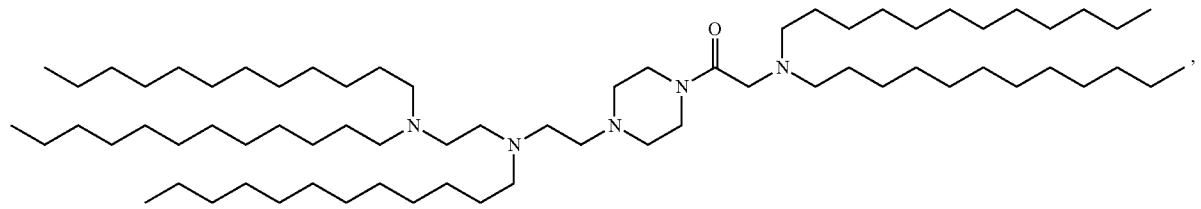
(Compound 235)

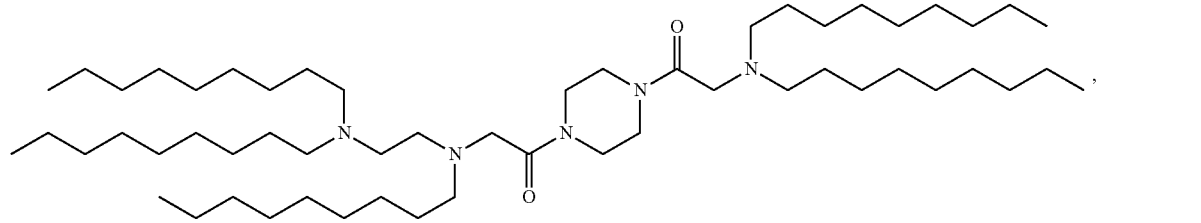
(Compound 236)

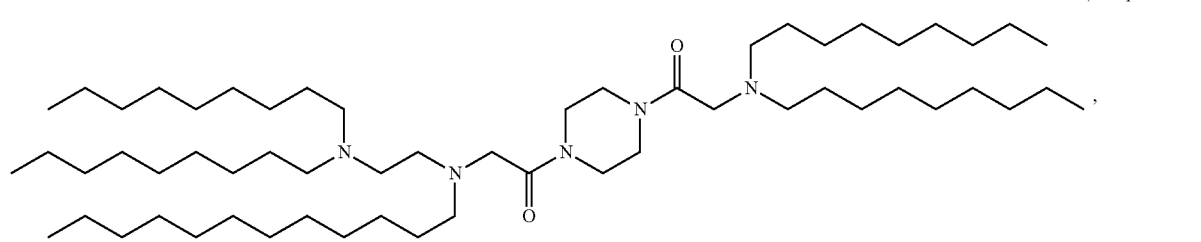
(Compound 237)

(Compound 238)
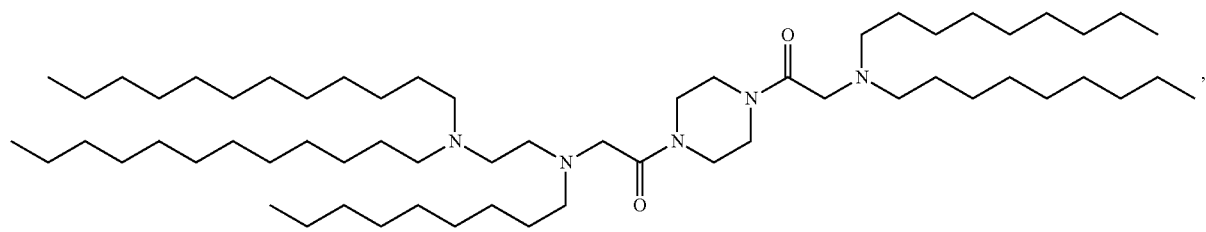
(Compound 239)
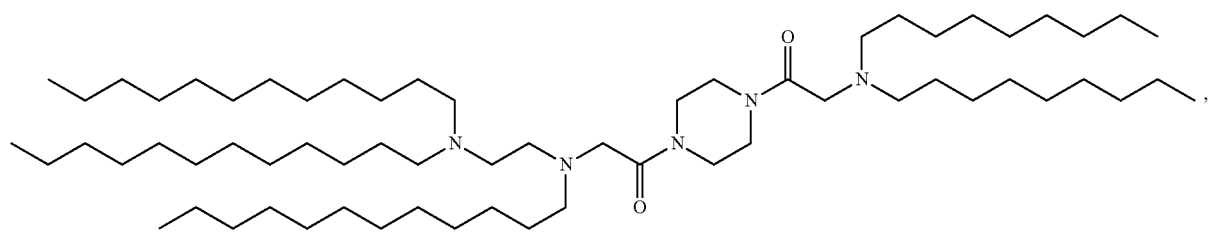
(Compound 240)
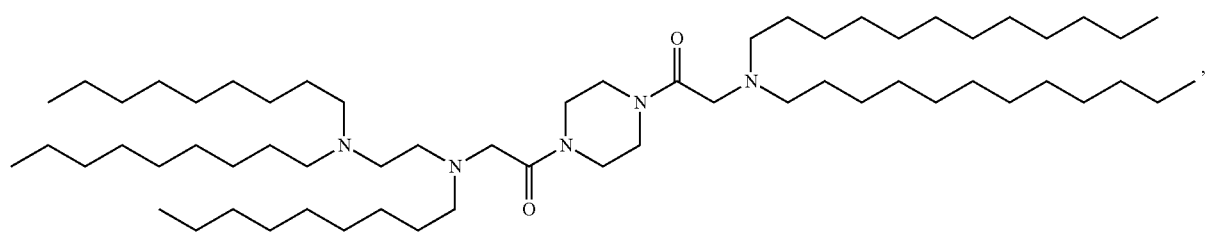
(Compound 241)
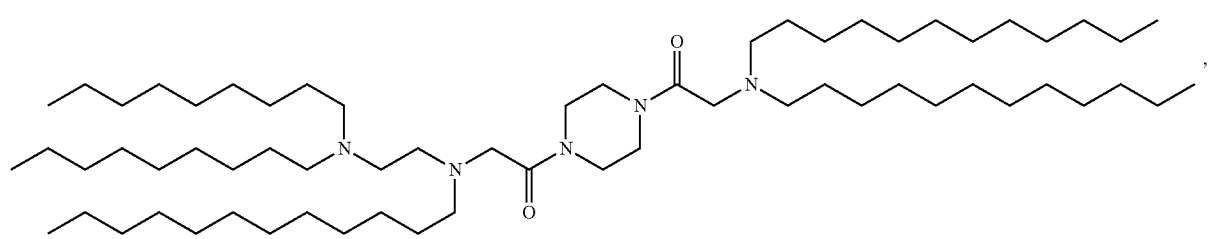
(Compound 242)
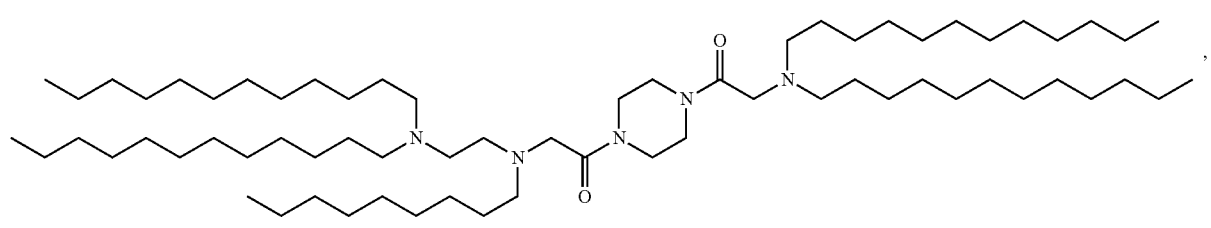
(Compound 243)
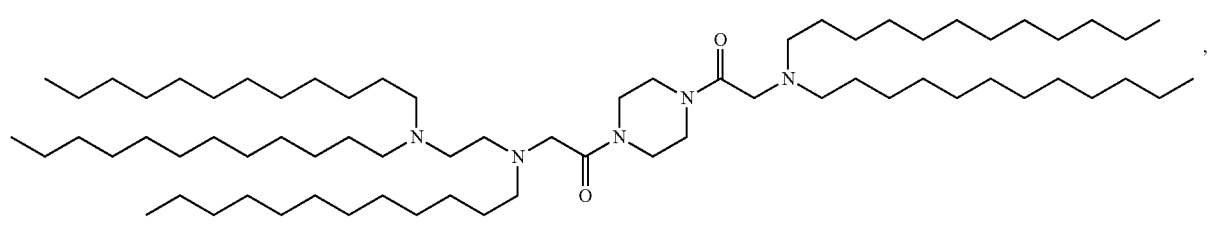

-continued
(Compound 244)
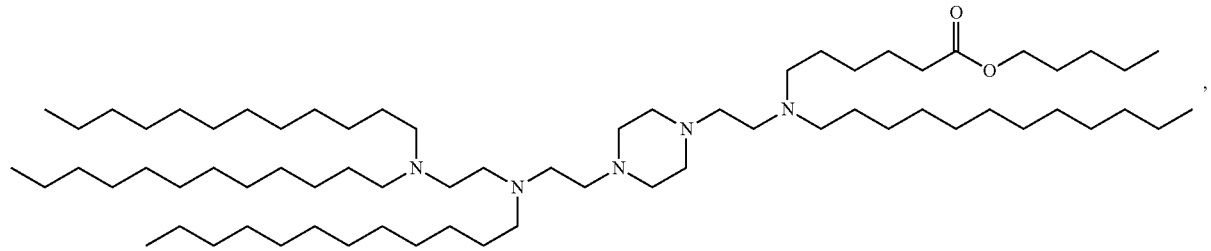
(Compound 245)
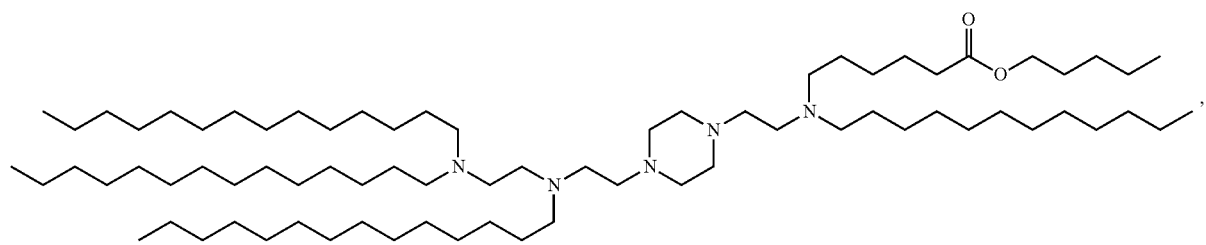
(Compound 246)
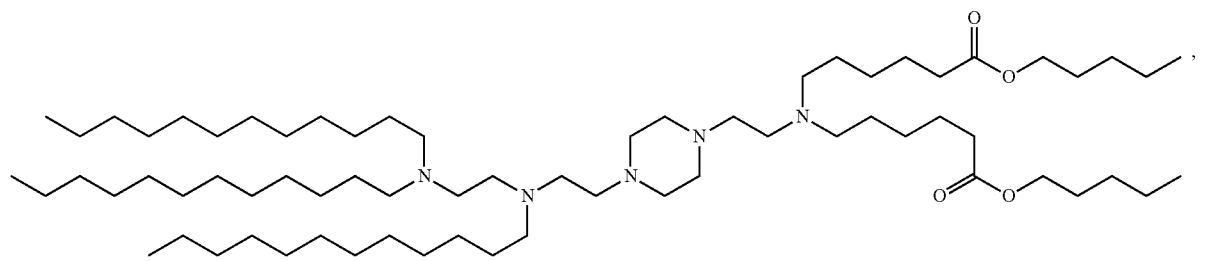
(Compound 247)
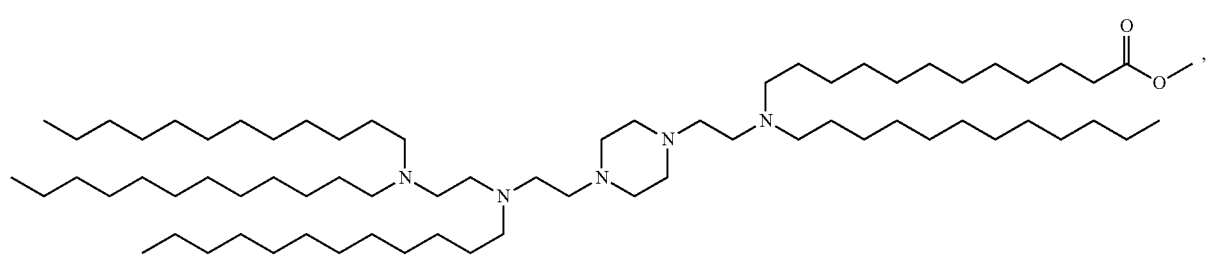
(Compound 248)
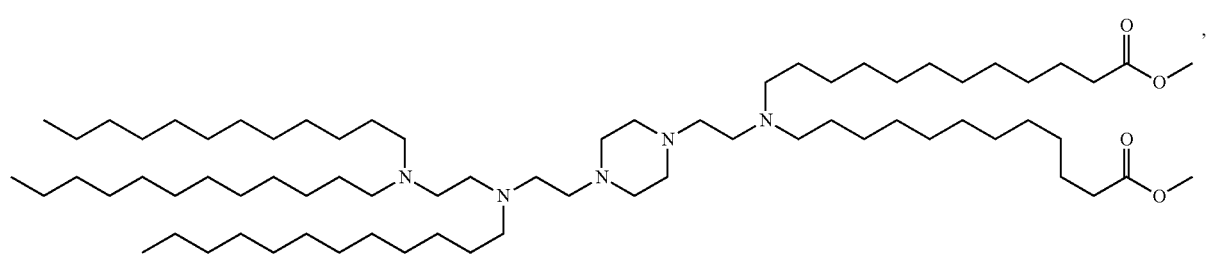
(Compound 274)
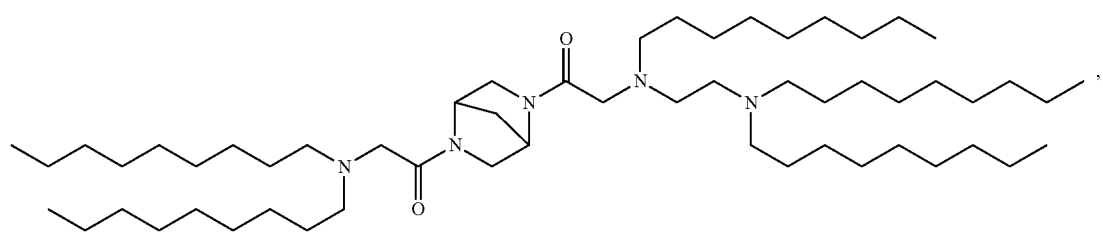

-continued
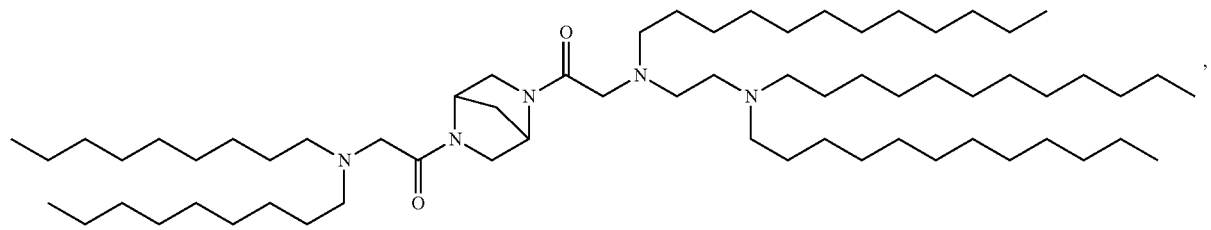
(Compound 275)
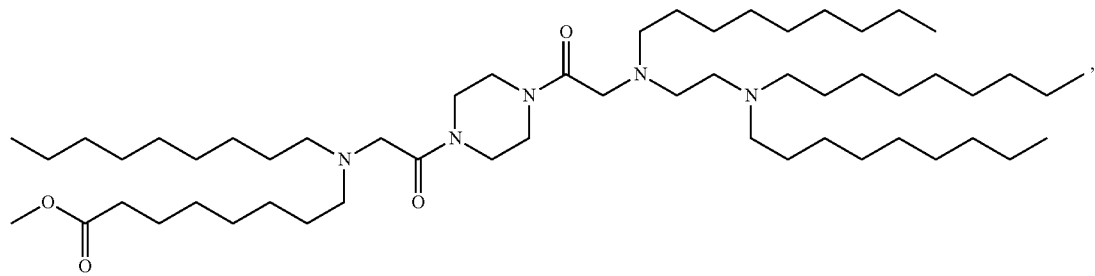
(Compound 276)
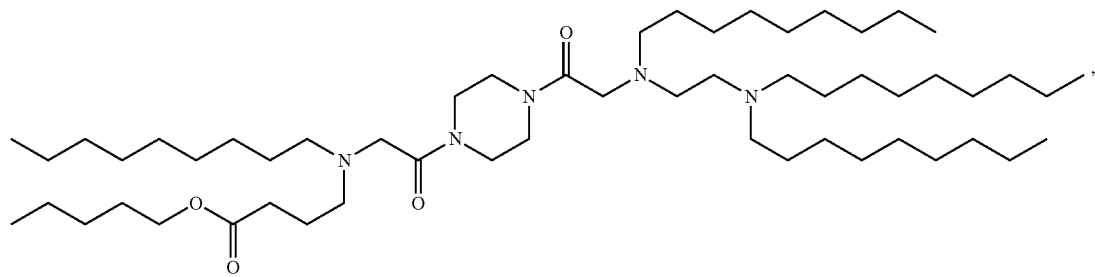
(Compound 277)
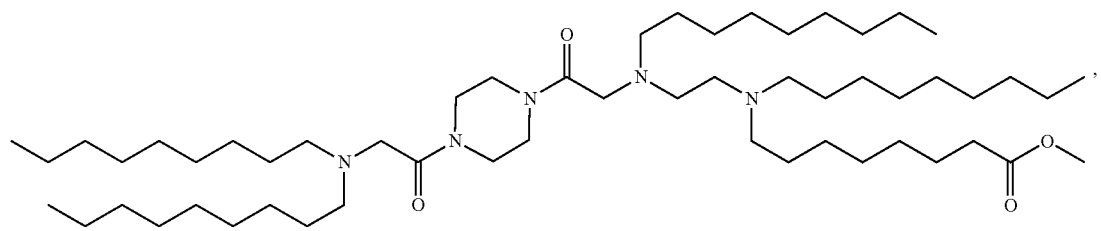
(Compound 278)
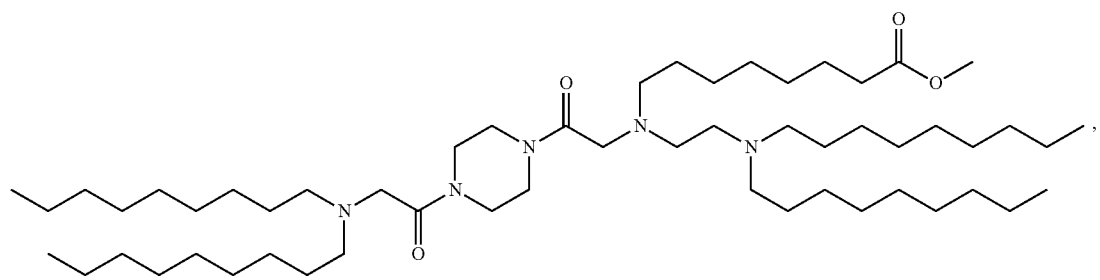
(Compound 279)

(Compound 280)
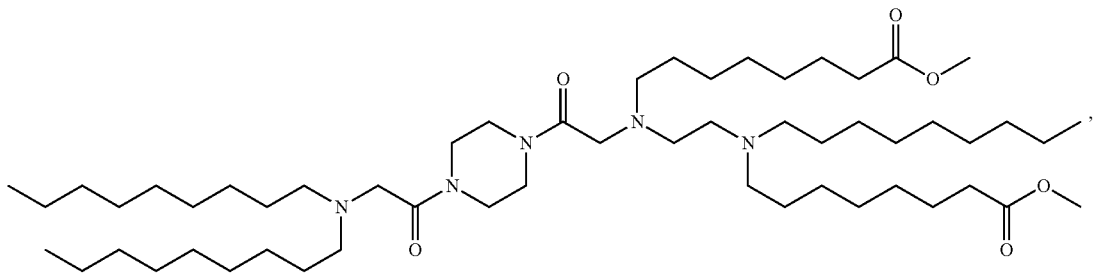
(Compound 281)
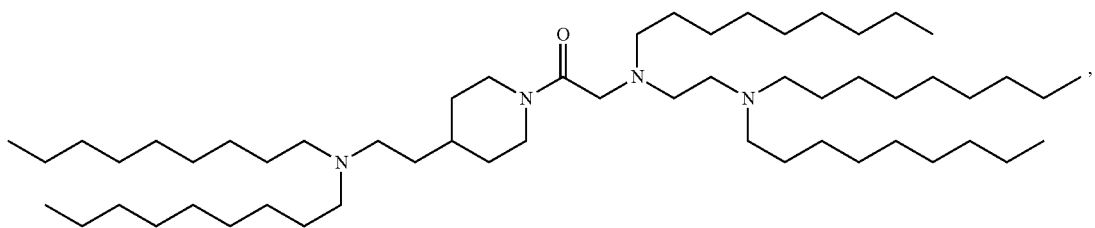
(Compound 282)
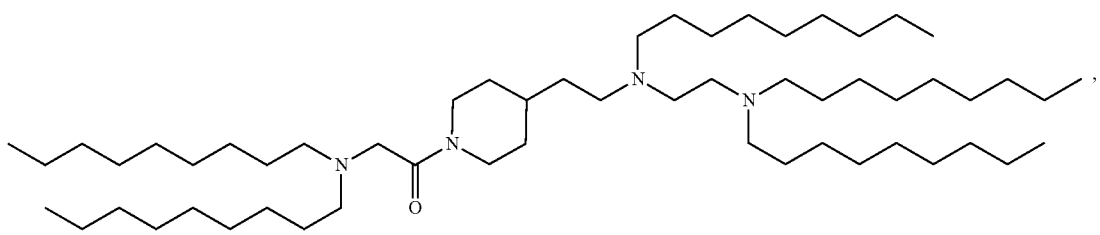
(Compound 283)
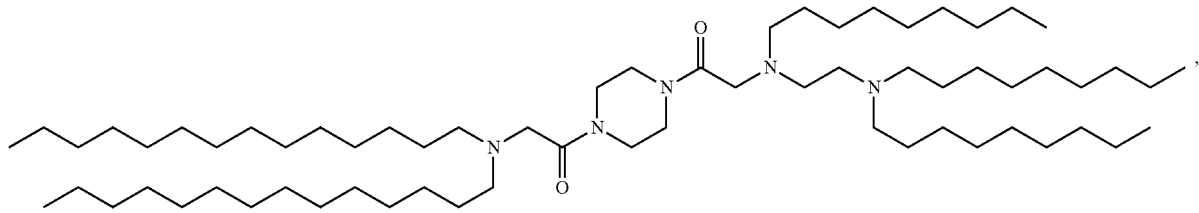
(Compound 284)
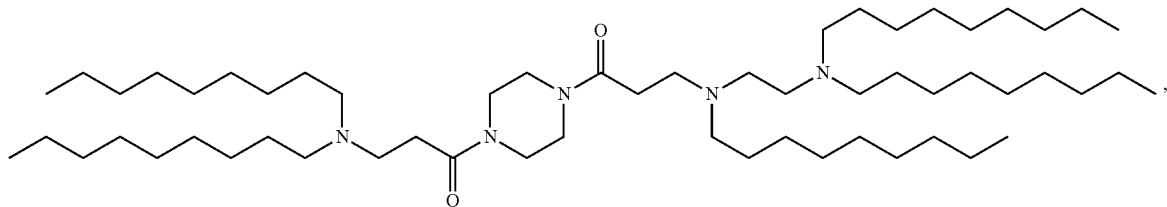
(Compound 285)
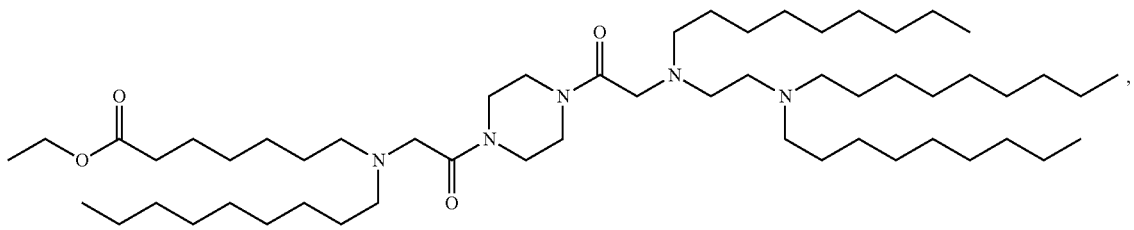

-continued
(Compound 286)
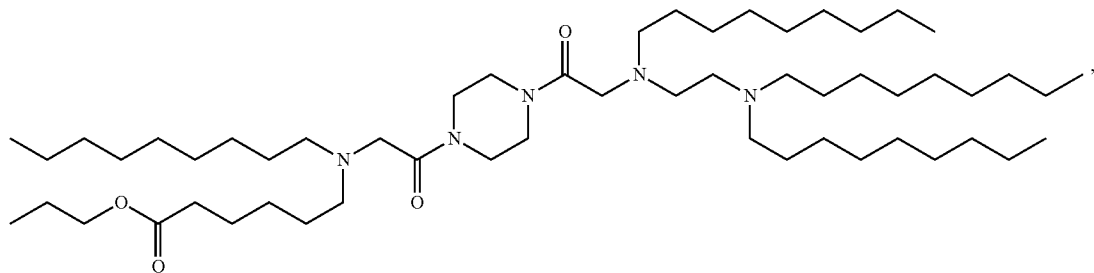
(Compound 287)
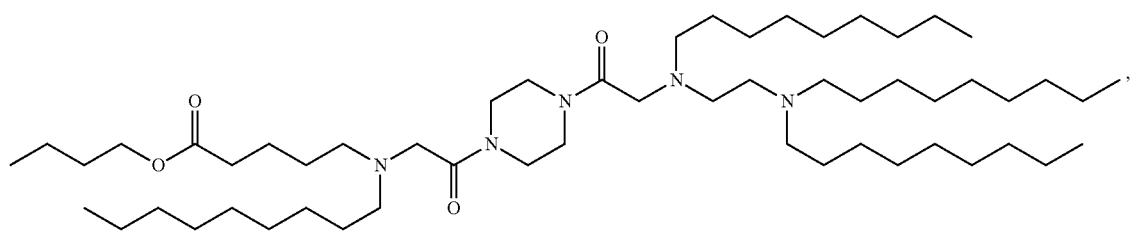
(Compound 288)
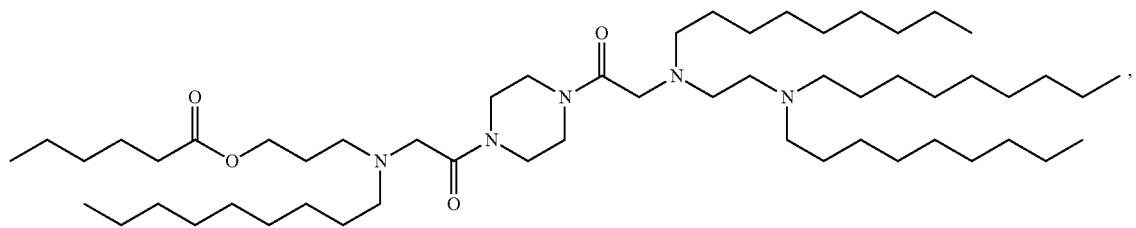
(Compound 289)
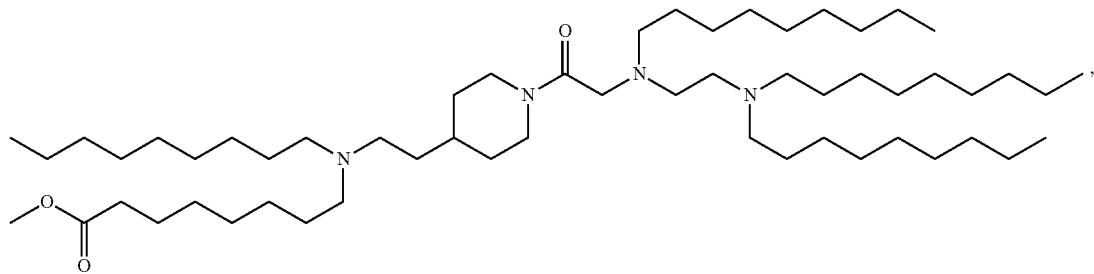
(Compound 290)
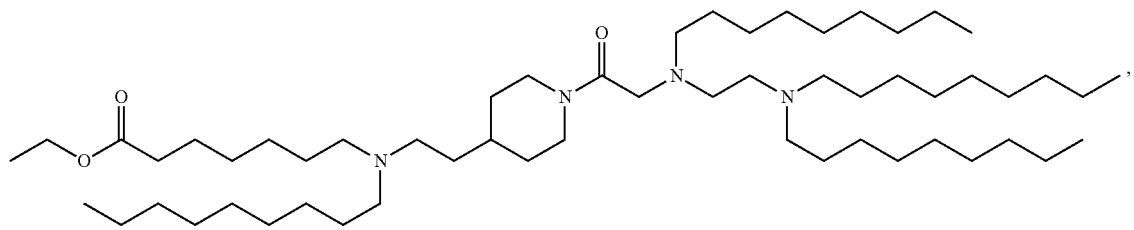

-continued
(Compound 291)
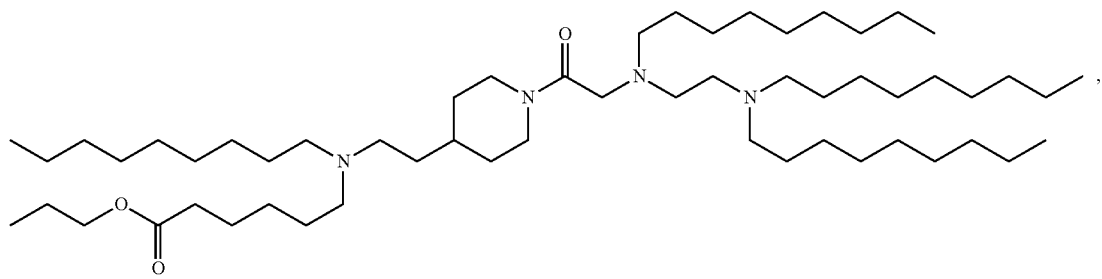
(Compound 292)
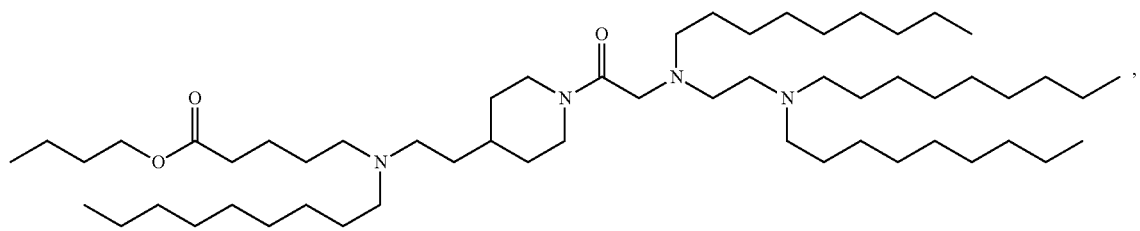
(Compound 293)
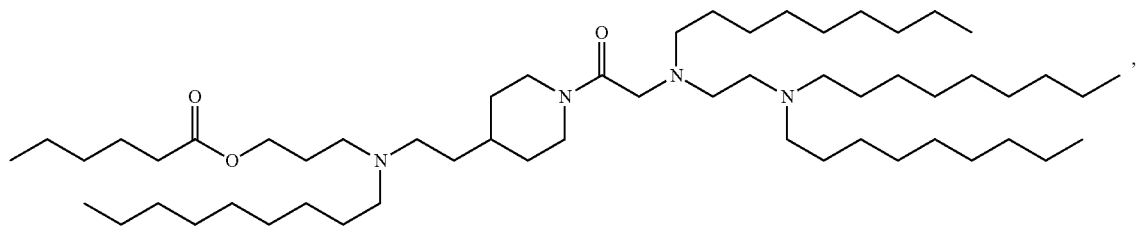
(Compound 294)
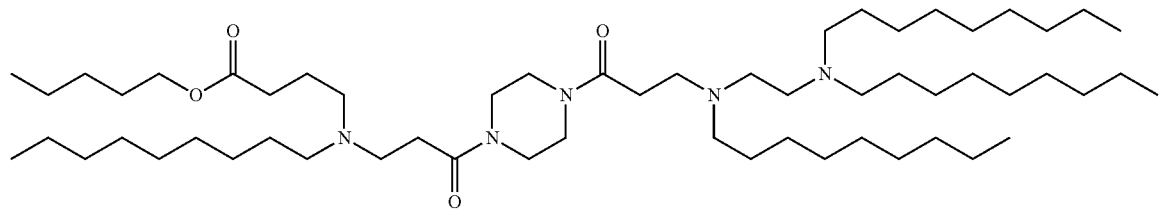
(Compound 295)
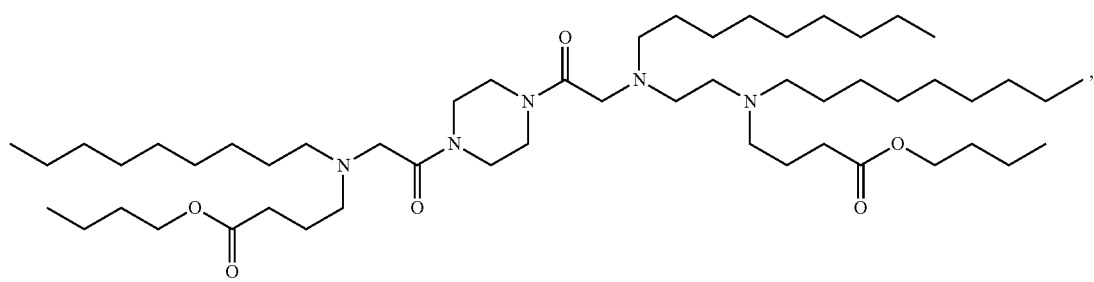
(Compound 296)
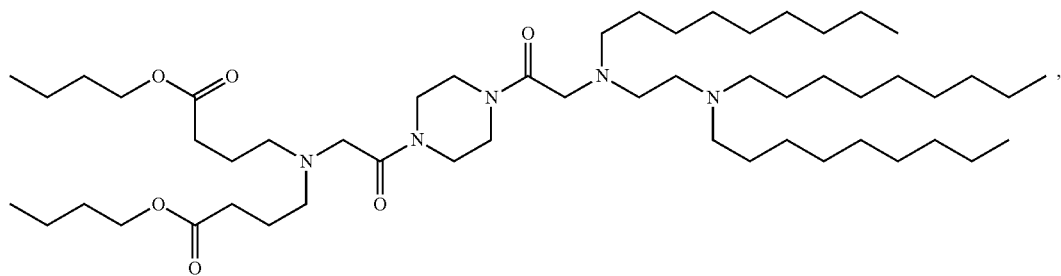

(Compound 297)
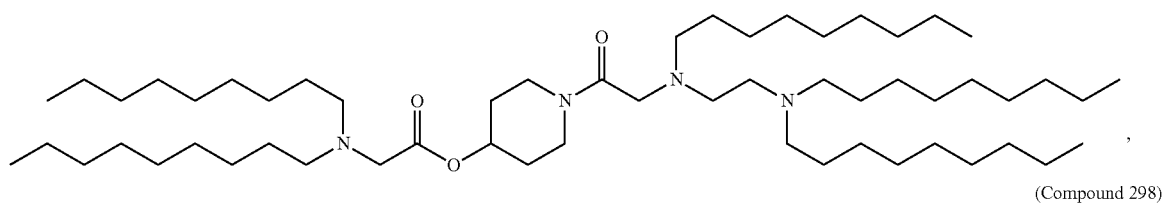
(Compound 298)
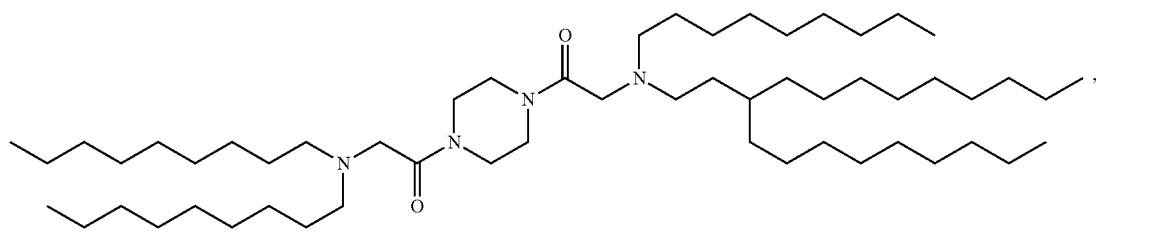
(Compound 300)
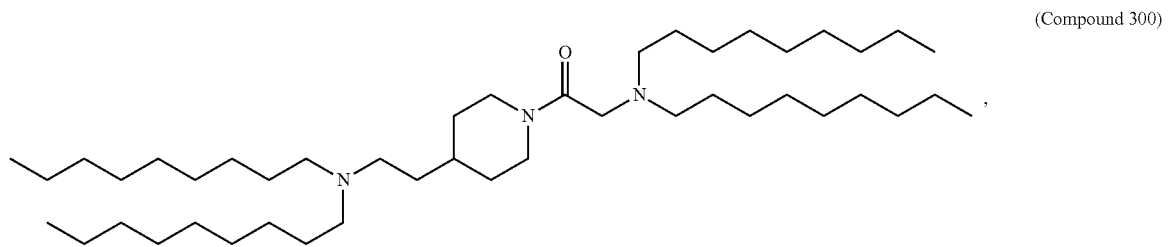
(Compound 301)
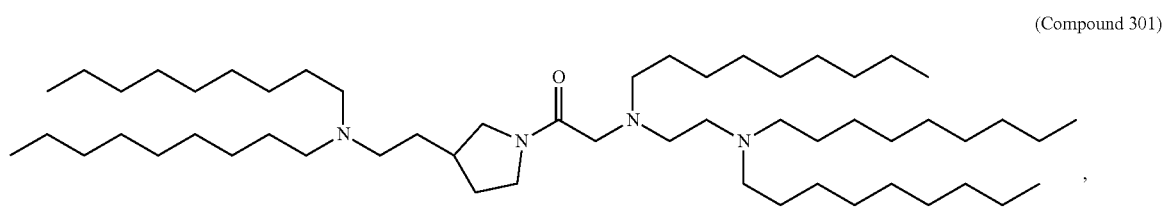
(Compound 302)
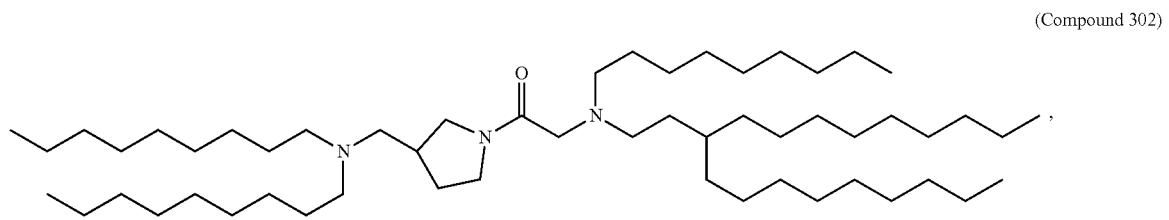
(Compound 303)
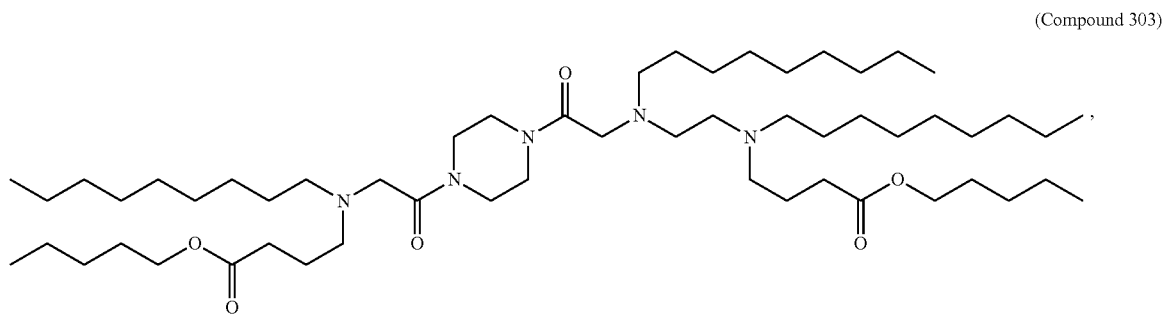

(Compound 304)
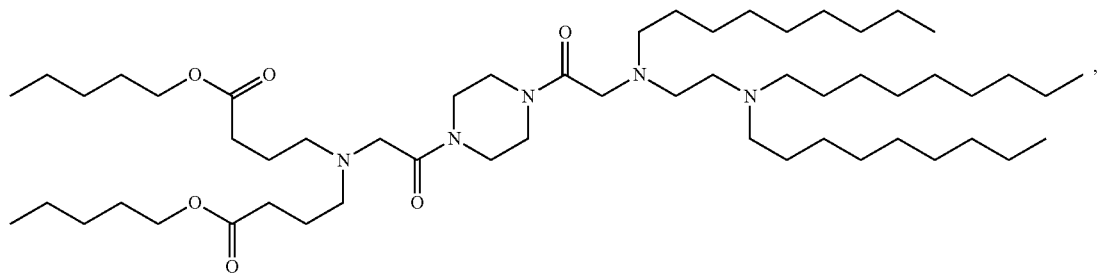
(Compound 305)
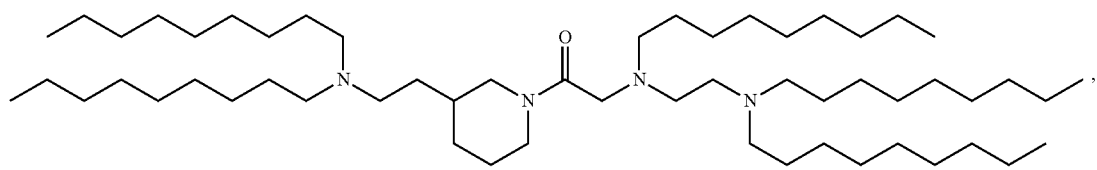
(Compound 306)
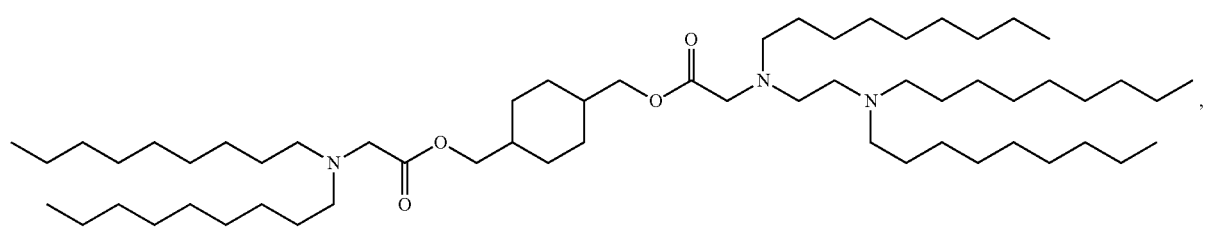
(Compound 307)
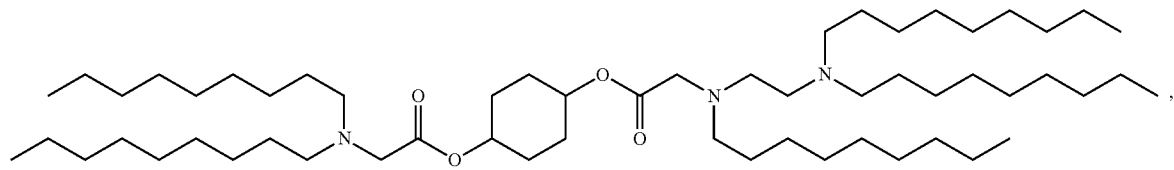
(Compound 308)
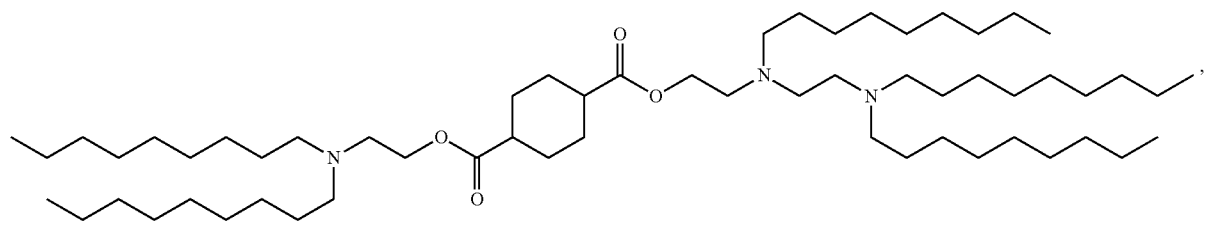
(Compound 310)
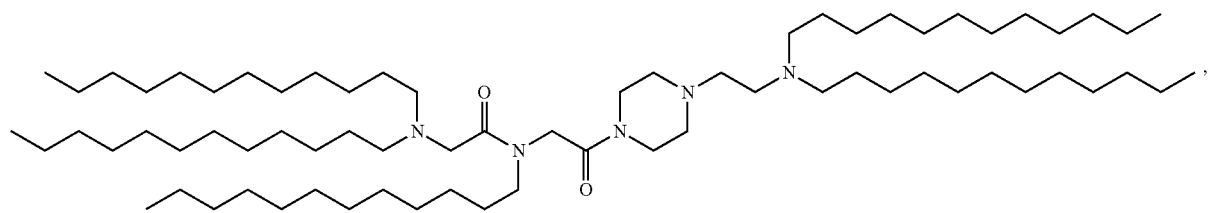

-continued
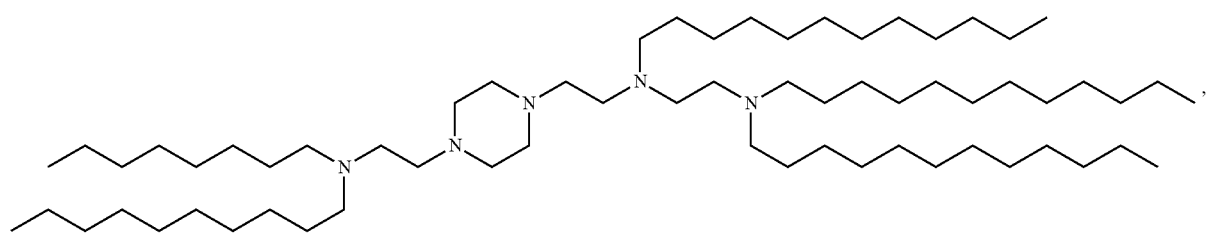
(Compound 311)
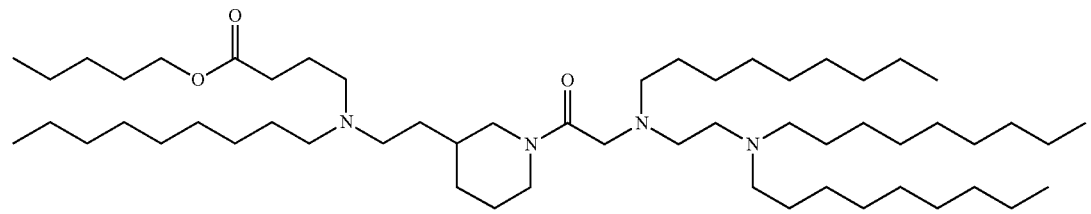
(Compound 312)
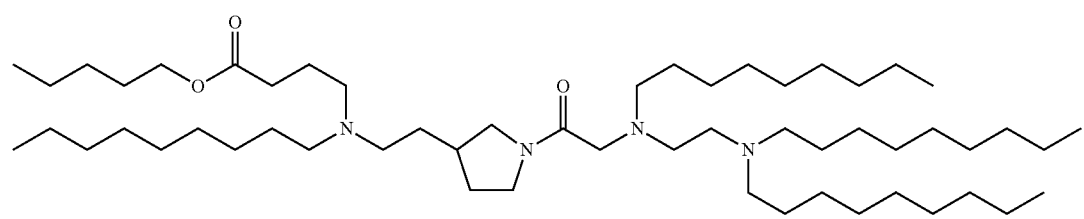
(Compound 313)
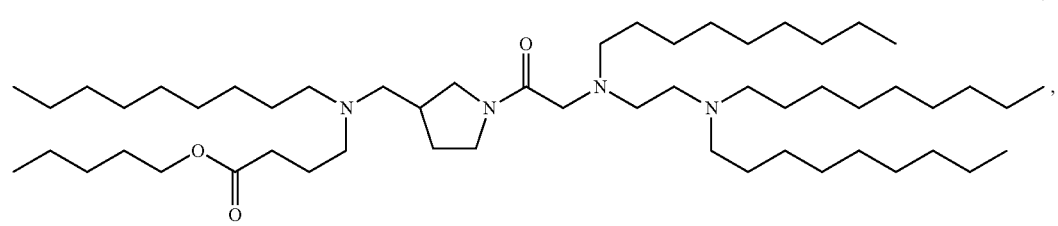
(Compound 314)
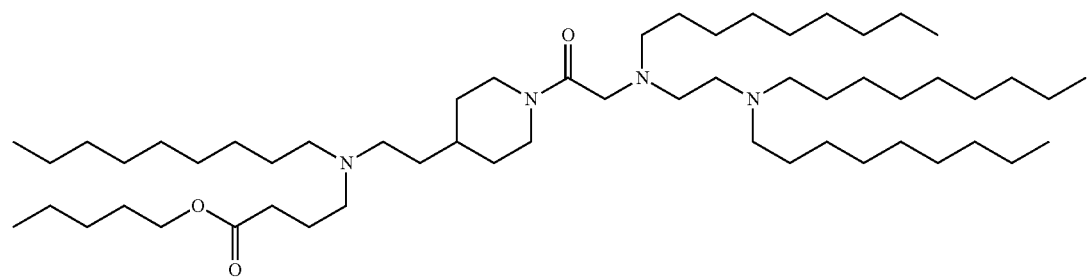
(Compound 315)
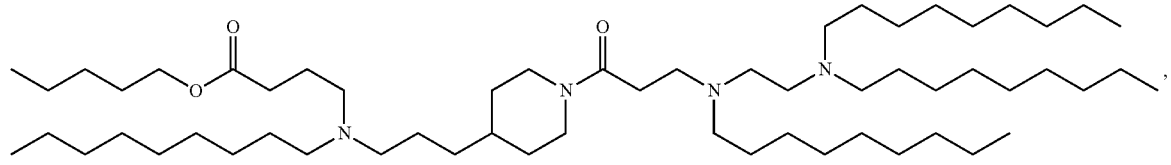
(Compound 316)
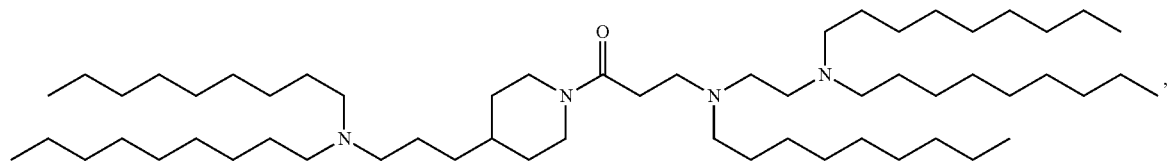
(Compound 317)

(Compound 318)
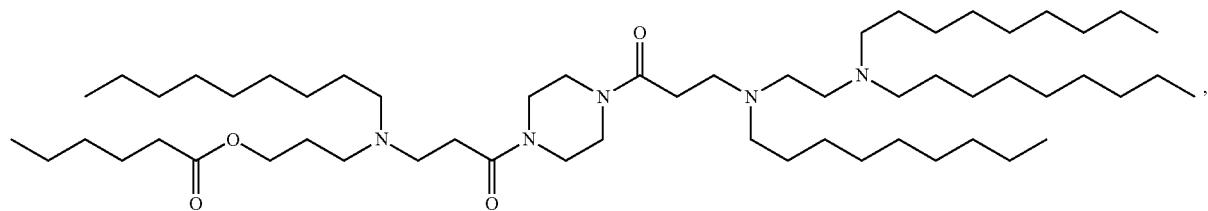
(Compound 319)
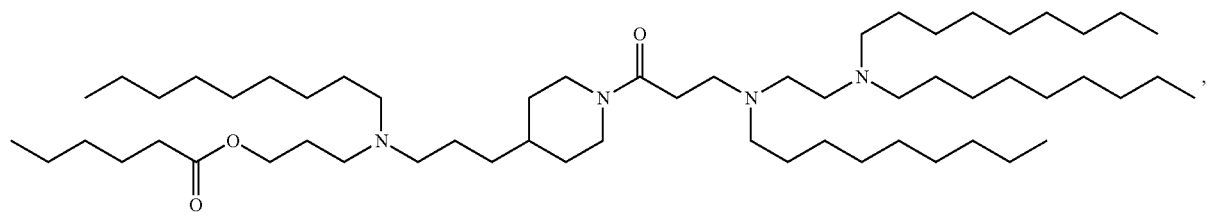
(Compound 320)
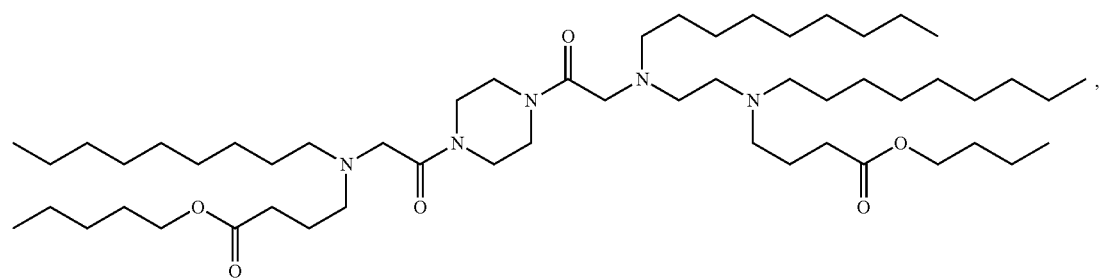
(Compound 321)
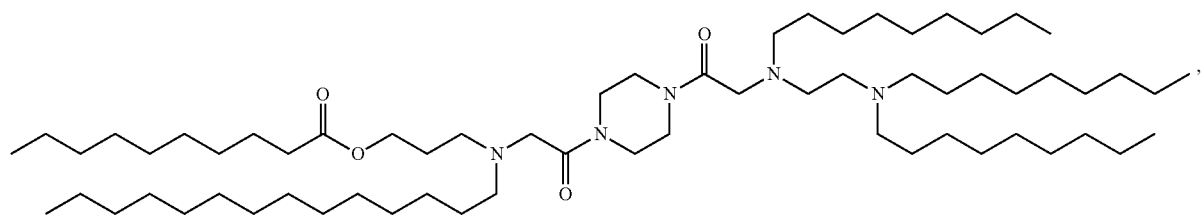
(Compound 322)
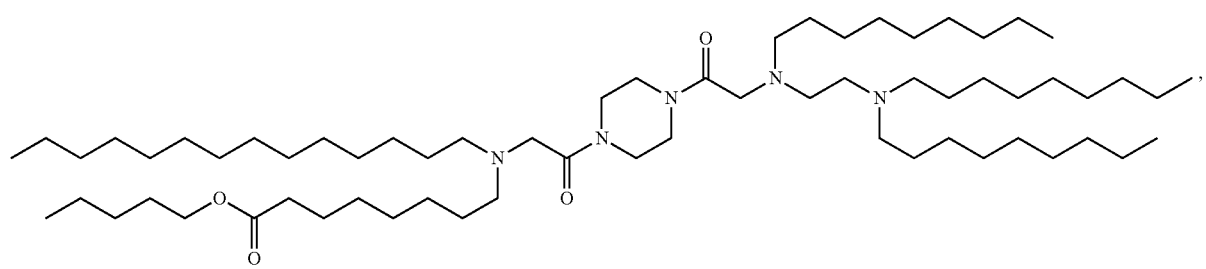
(Compound 323)
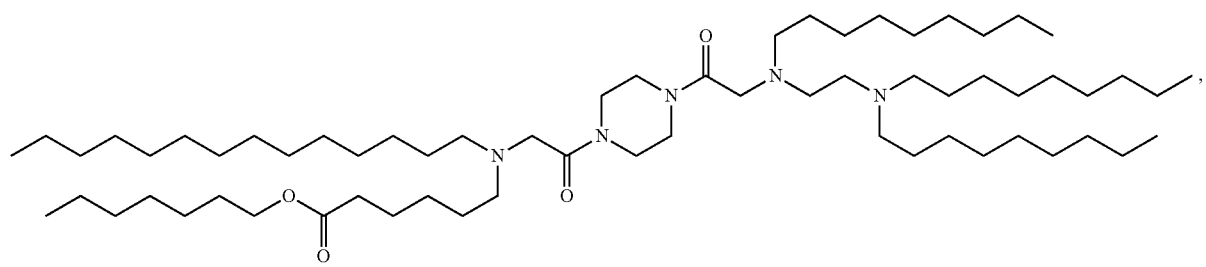

-continued
(Compound 324)
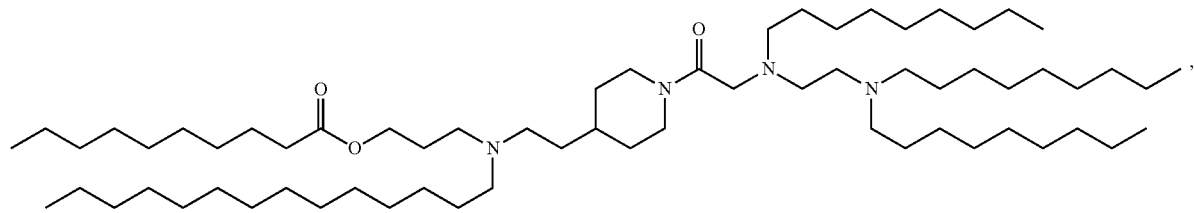
(Compound 325)
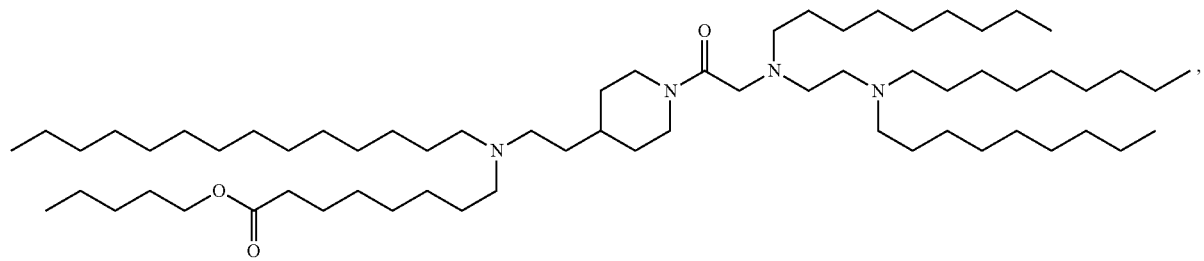
(Compound 326)
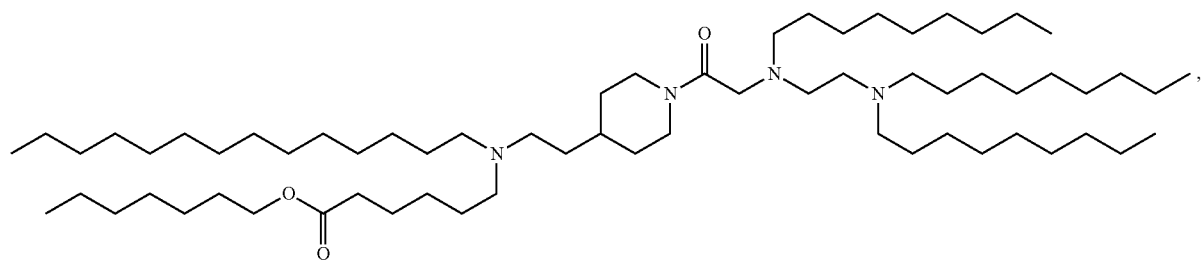
(Compound 327)
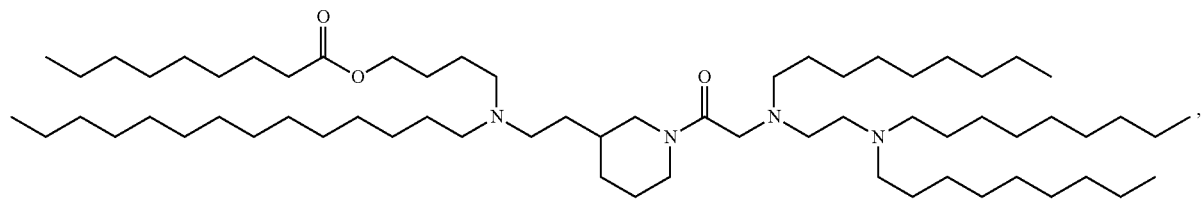
(Compound 328)
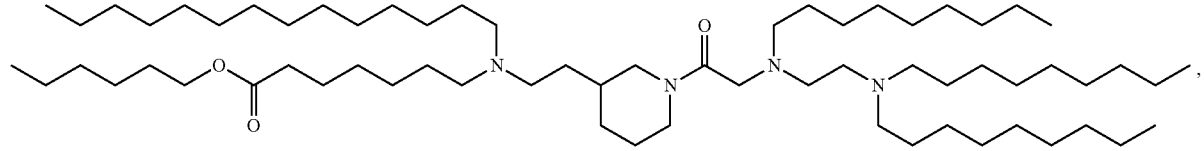
(Compound 329)
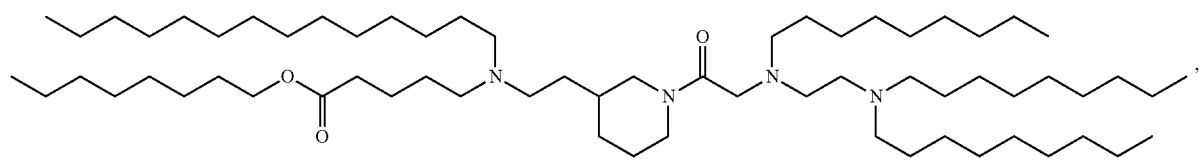
(Compound 330)
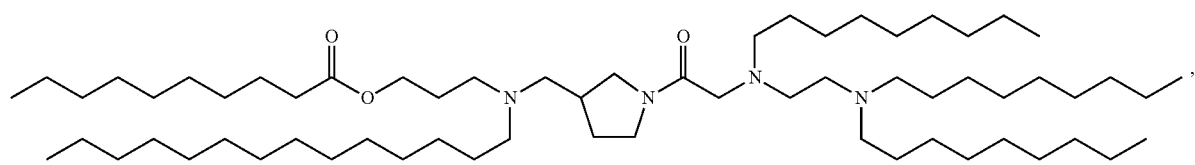

-continued
(Compound 331)
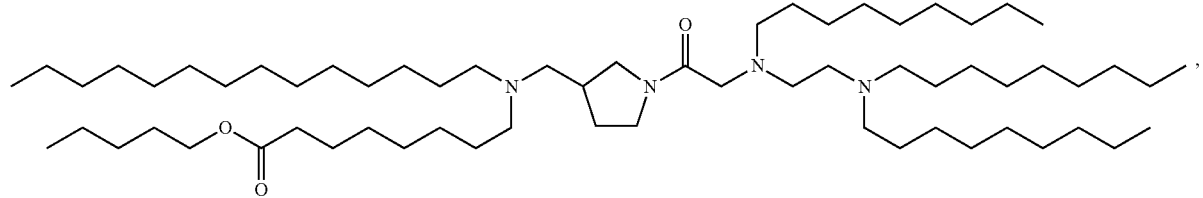
(Compound 332)
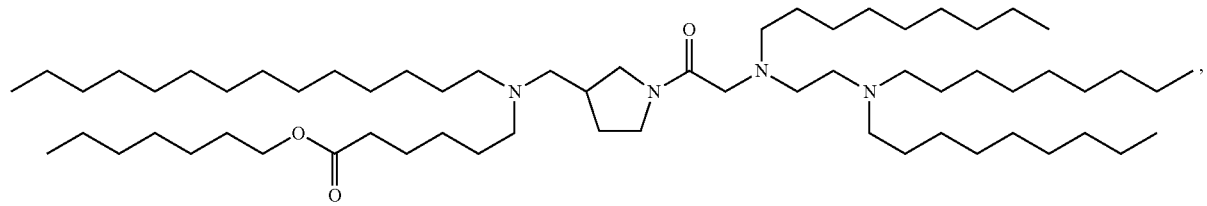
(Compound 333)
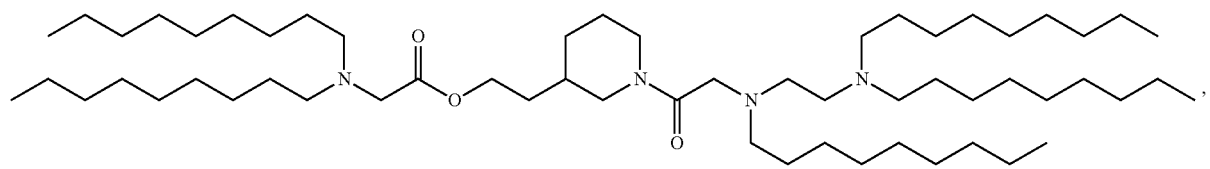
(Compound 334)
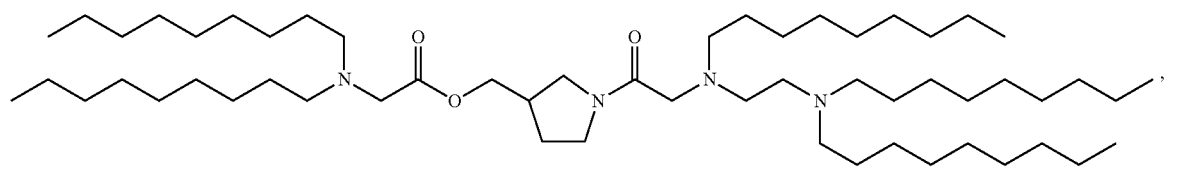
(Compound 335)
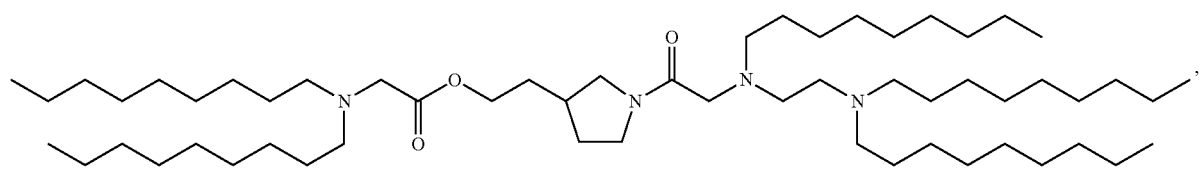
(Compound 336)
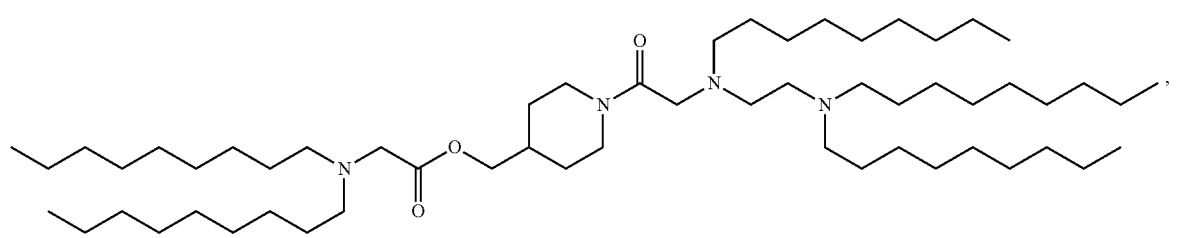
(Compound 337)
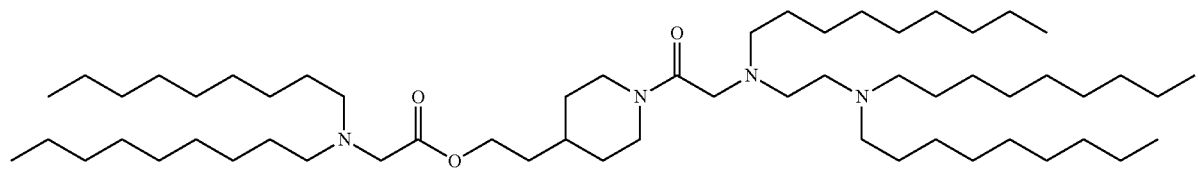

-continued (Compound 338)
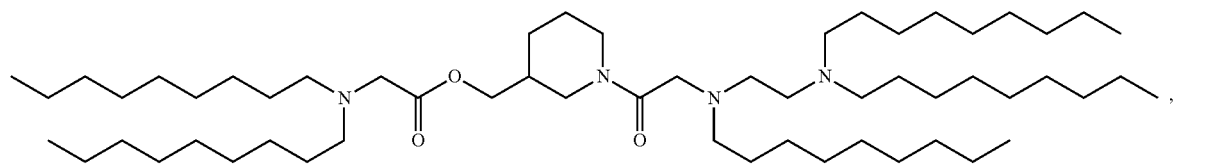

(Compound 339)
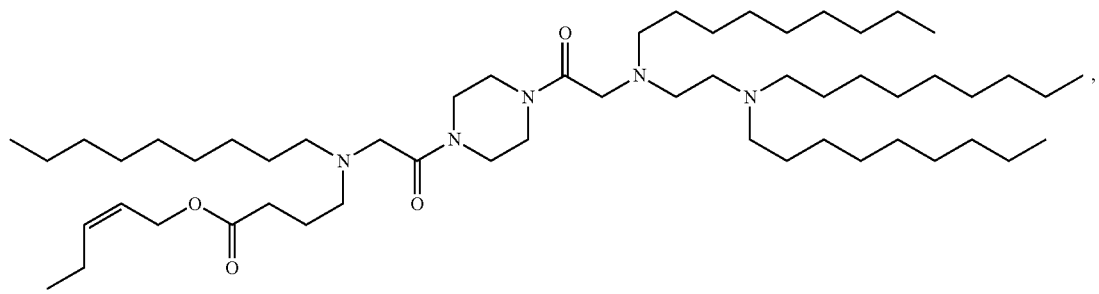

(Compound 340)
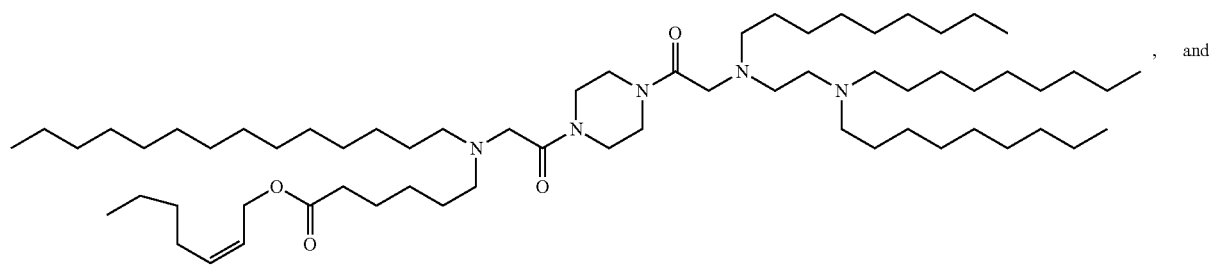
, and (Compound 341)
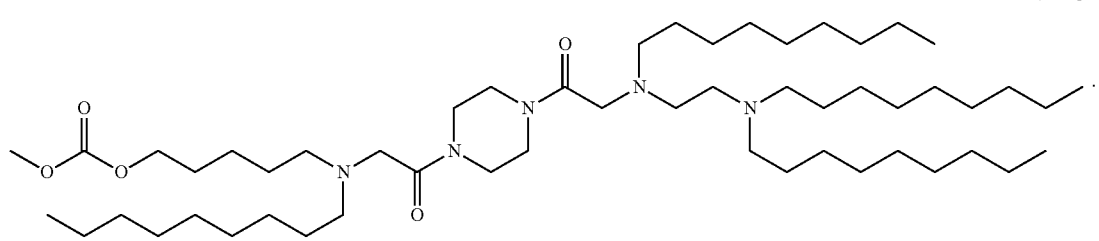

In some embodiments, the delivery agent comprises Compound 236.

In some embodiments, the delivery agent comprises a compound having the formula (IV)

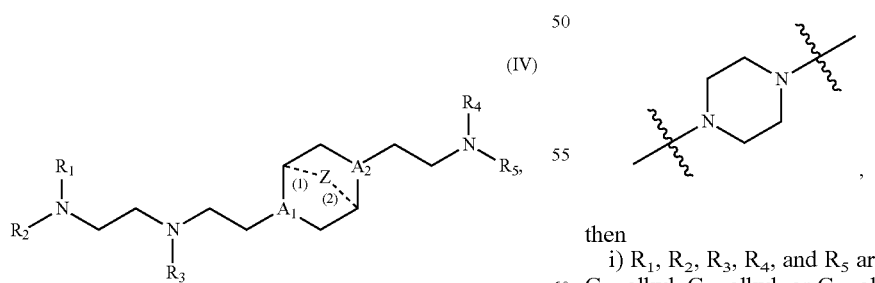

(IV)

or salts or stereoisomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{6-20}$ alkyl and $C_{6-20}$ alkenyl;

wherein when ring A is then i) $R_1$, $R_2$, $R_3$, $R_4$, and $R_5$ are the same, wherein $R_1$ is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of formula (IVa):

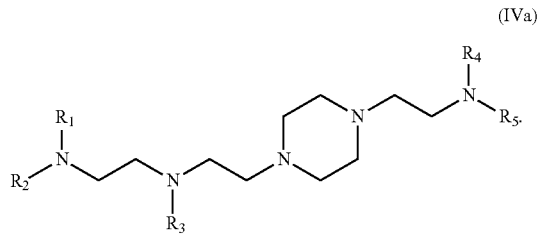

(IVa)

The compounds of Formula (IV) or (IVa) include one or more of the following features when applicable.

In some embodiments, Z is $CH_2$
In some embodiments, Z is absent.
In some embodiments, at least one of $A_1$ and $A_2$ is N.
In some embodiments, each of $A_1$ and $A_2$ is N.
In some embodiments, each of $A_1$ and $A_2$ is CH.
In some embodiments, $A_1$ is N and $A_2$ is CH.
In some embodiments, $A_1$ is CH and $A_2$ is N.
In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl. In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are $C_{18}$ alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In some embodiments, the compound is selected from the group consisting of:

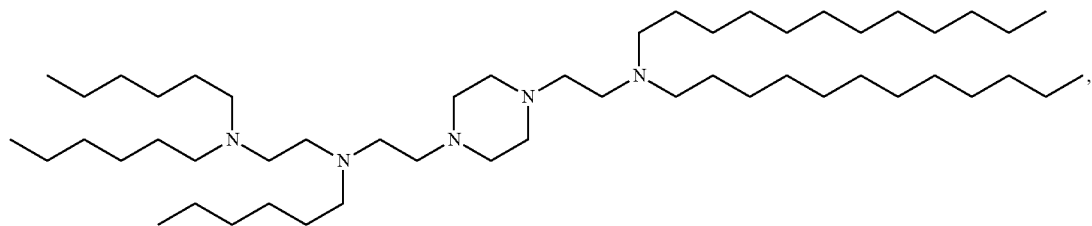

(Compound 249)

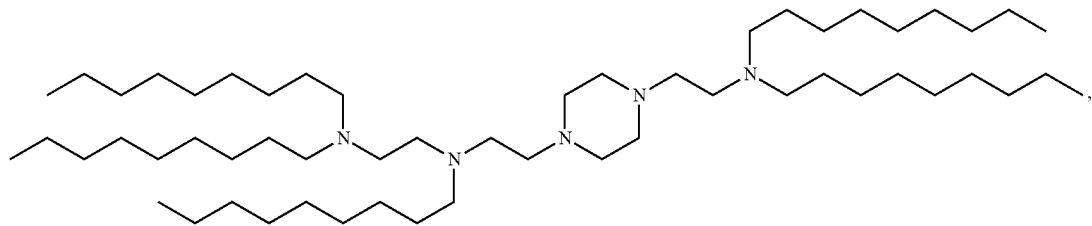

(Compound 250)

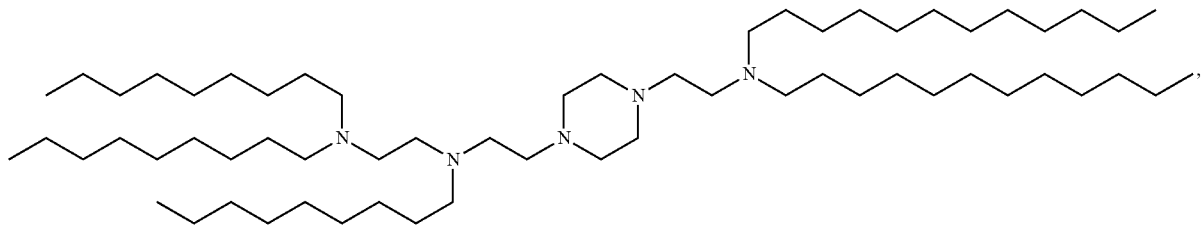

(Compound 251)

(Compound 252)
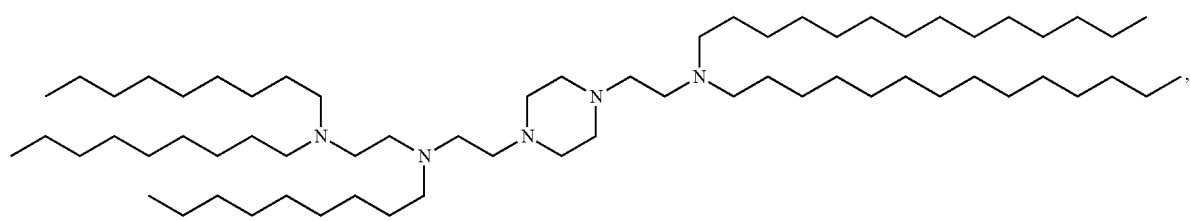
(Compound 253)
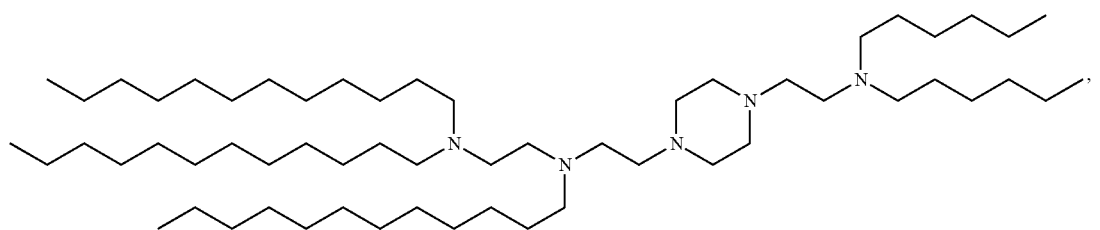
(Compound 254)
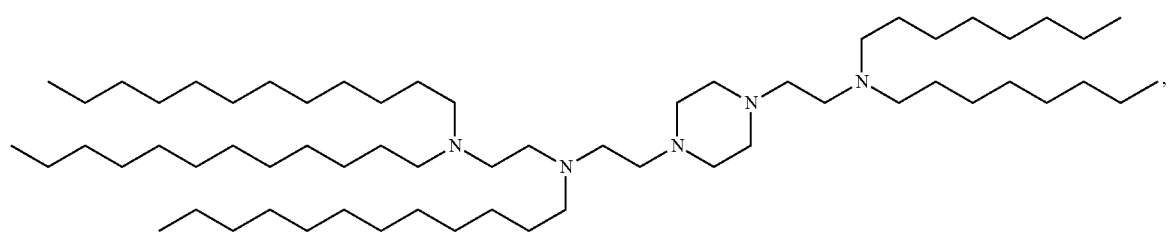
(Compound 255)
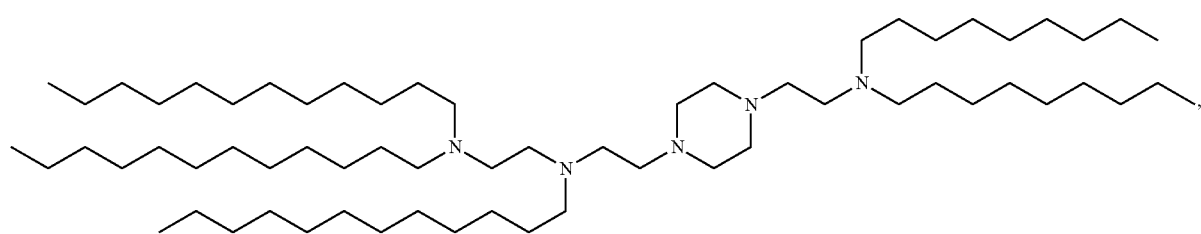
(Compound 256)
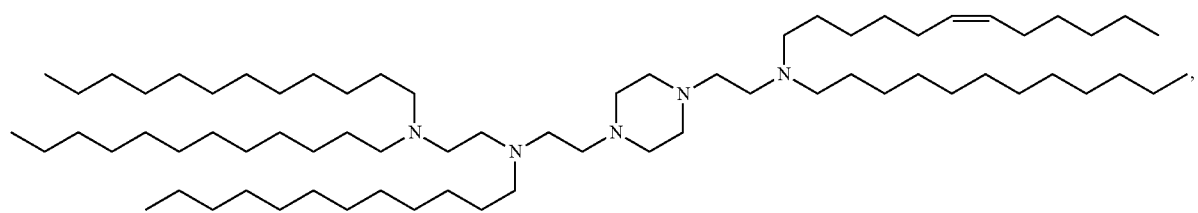
(Compound 257)
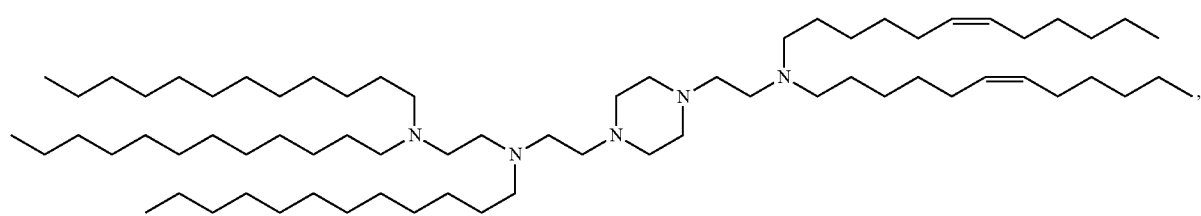

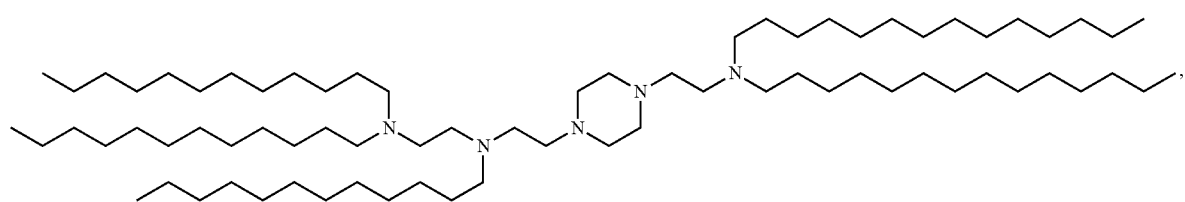
(Compound 258)
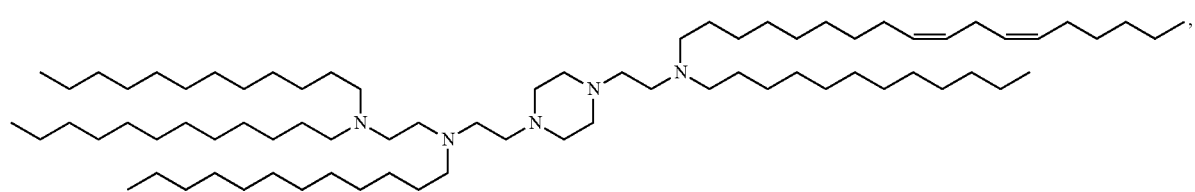
(Compound 259)
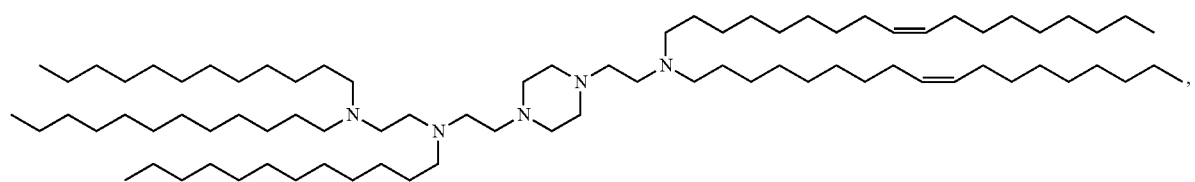
(Compound 260)
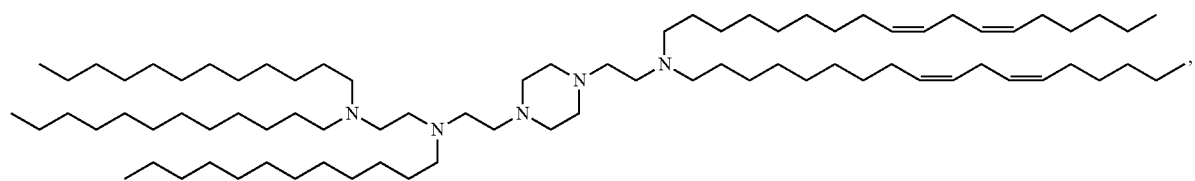
(Compound 261)
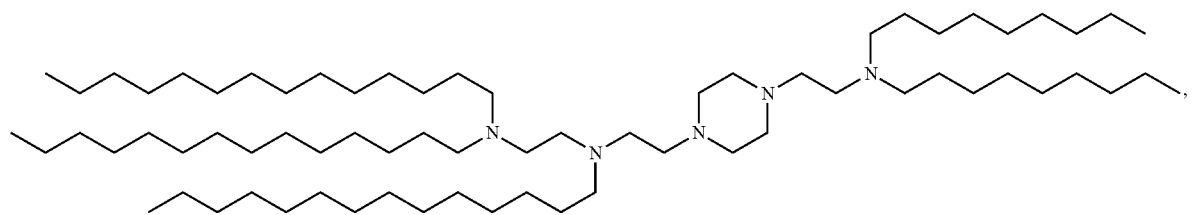
(Compound 262)
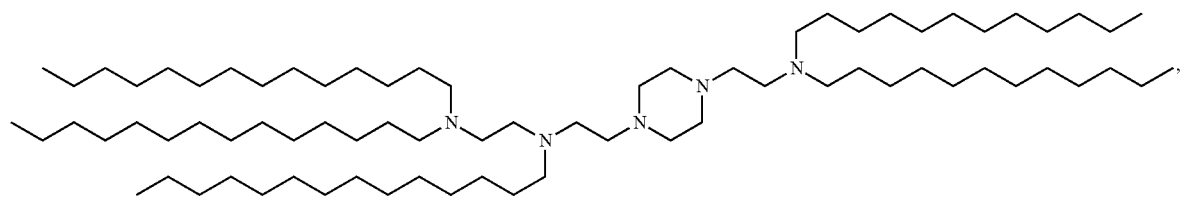
(Compound 263)
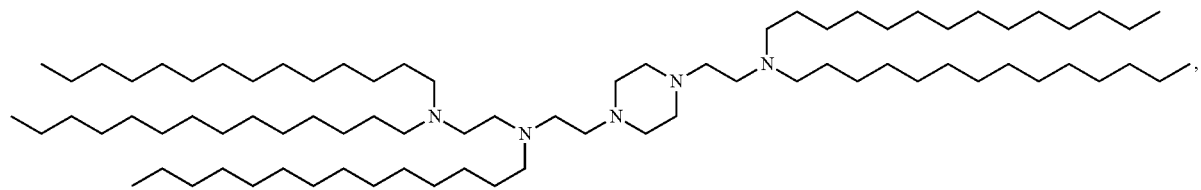
(Compound 264)

(Compound 265)

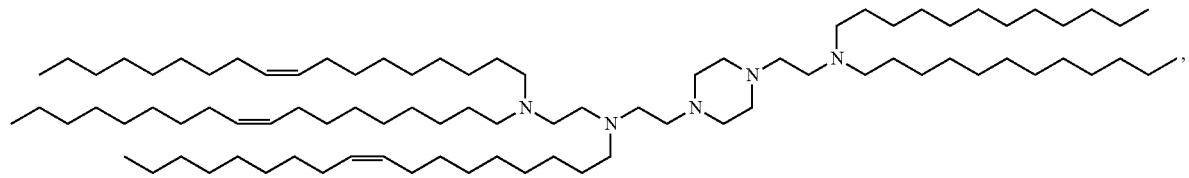

and (Compound 266)

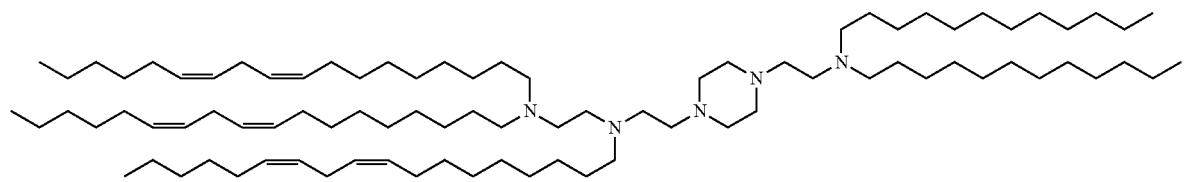

In other embodiments, the delivery agent comprises a compound having the formula (V)

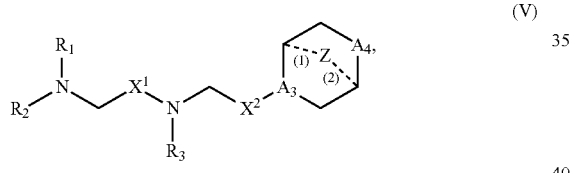

or salts or stereoisomers thereof, in which $A_3$ is CH or N;

$A_4$ is $CH_2$ or NH; and at least one of $A_3$ and $A_4$ is N or NH;

Z is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$X^1$ and $X^2$ are independently selected from the group consisting of —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, the compound is of formula (Va):

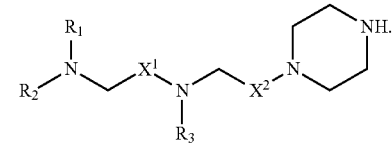

The compounds of Formula (V) or (Va) include one or more of the following features when applicable.

In some embodiments, Z is $CH_2$

In some embodiments, Z is absent.

In some embodiments, at least one of $A_3$ and $A_4$ is N or NH.

In some embodiments, $A_3$ is N and $A_4$ is NH.

In some embodiments, $A_3$ is N and $A_4$ is $CH_2$.

In some embodiments, $A_3$ is CH and $A_4$ is NH.

In some embodiments, at least one of $X^1$ and $X^2$ is not —CH$_2$—. For example, in certain embodiments, $X^1$ is not —CH$_2$—. In some embodiments, at least one of $X^1$ and $X^2$ is —C(O)—.

In some embodiments, $X^2$ is —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, or —CH$_2$—OC(O)—.

In some embodiments, $R_1$, $R_2$, and $R_3$ are independently selected from the group consisting of $C_{5-20}$ alkyl and $C_{5-20}$ alkenyl. In some embodiments, $R_1$, $R_2$, and $R_3$ are the same. In certain embodiments, $R_1$, $R_2$, and $R_3$ are $C_6$, $C_9$, $C_{12}$, or $C_{14}$ alkyl. In other embodiments, $R_1$, $R_2$, and $R_3$ are $C_{18}$ alkenyl. For example, $R_1$, $R_2$, and $R_3$ may be linoleyl.

In some embodiments, the compound is selected from the group consisting of:

(Compound 267)

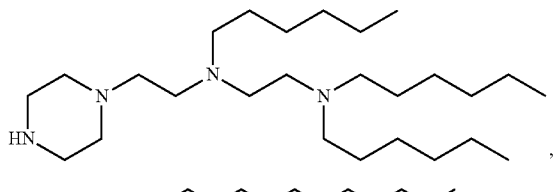

(Compound 268)

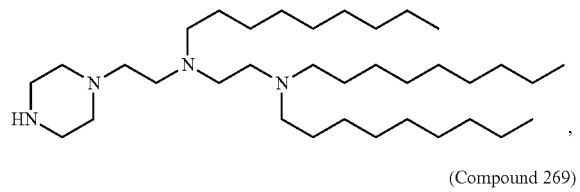

(Compound 269)

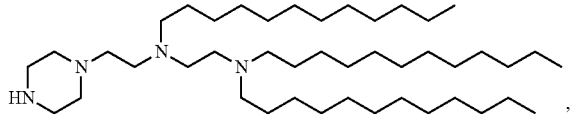

(Compound 270)

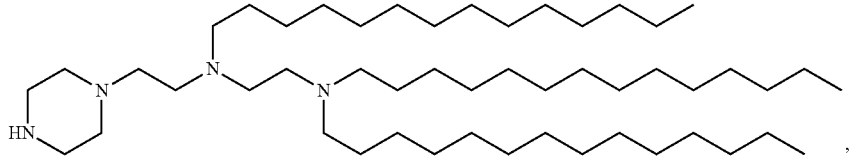

(Compound 271)

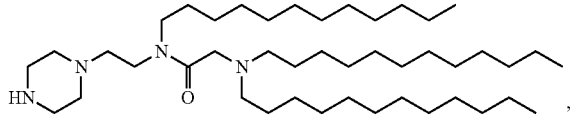

(Compound 272)

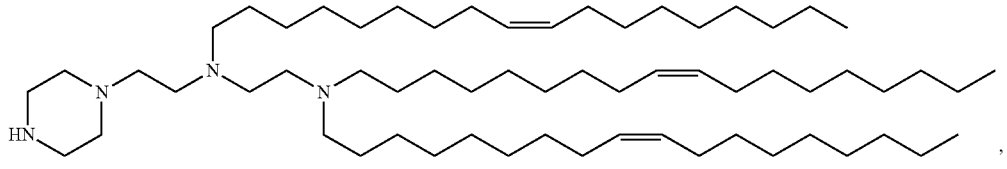

(Compound 273)

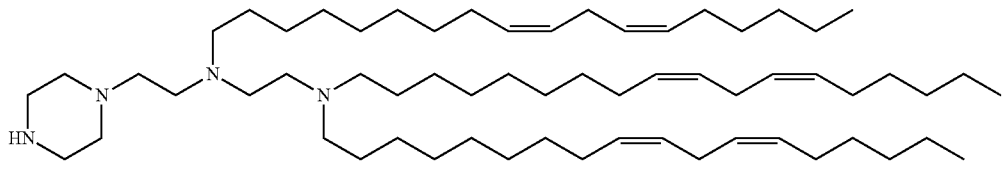

, and (Compound 309)

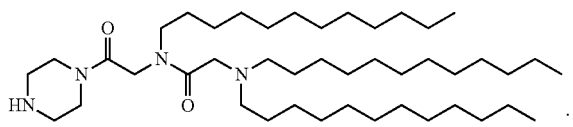

.

In other embodiments, the delivery agent comprises a compound having the formula (VI):

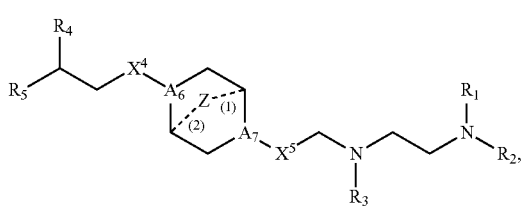

(VI)

or salts or stereoisomers thereof, in which $A_6$ and $A_7$ are each independently selected from CH or N, wherein at least one of $A_6$ and $A_7$ is N;

Z is $CH_2$ or absent wherein when Z is $CH_2$, the dashed lines (1) and (2) each represent a single bond; and when Z is absent, the dashed lines (1) and (2) are both absent;

$X^4$ and $X^5$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

$R_1$, $R_2$, $R_3$, $R_4$, and $R_5$ each are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$— an aryl group, and a heteroaryl group;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, $R_1$, $R_2$, $R_3$, $R_4$, and $R_5$ each are independently selected from the group consisting of $C_{6-20}$ alkyl and $C_{6-20}$ alkenyl.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is $C_{9-12}$ alkyl. In certain embodiments, each of $R_1$, $R_2$, $R_3$, $R_4$, and $R_5$ independently is $C_9$, $C_{12}$ or $C_{14}$ alkyl. In certain embodiments, each of $R_1$, $R_2$, $R_3$, $R_4$, and $R_5$ is $C_9$ alkyl.

In some embodiments, $A_6$ is N and $A_7$ is N. In some embodiments, $A_6$ is CH and $A_7$ is N.

In some embodiments, $X^4$ is —$CH_2$— and $X^5$ is —C(O)—. In some embodiments, $X^4$ and $X^5$ are —C(O)—.

In some embodiments, when $A_6$ is N and $A_7$ is N, at least one of $X^4$ and $X^5$ is not —$CH_2$—, e.g., at least one of $X^4$ and $X^5$ is —C(O)—. In some embodiments, when $A_6$ is N and $A_7$ is N, at least one of $R_1$, $R_2$, $R_3$, $R_4$, and $R_5$ is —R"MR'.

In some embodiments, at least one of $R_1$, $R_2$, $R_3$, $R_4$, and $R_5$ is not —R"MR'.

In some embodiments, the compound is

In some embodiments, the amount the ionizable amino lipid, e.g., compound of formula (I) ranges from about 1 mol % to 99 mol % in the lipid composition.

In one embodiment, the amount of the ionizable amino lipid, e.g., compound of formula (I) is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 mol % in the lipid composition.

In one embodiment, the amount of the ionizable amino lipid, e.g., the compound of formula (I) ranges from about 30 mol % to about 70 mol %, from about 35 mol % to about 65 mol %, from about 40 mol % to about 60 mol %, and from about 45 mol % to about 55 mol % in the lipid composition.

In one specific embodiment, the amount of the ionizable amino lipid, e.g., compound of formula (I) is about 50 mol % in the lipid composition.

In addition to the ionizable amino lipid disclosed herein, e.g., compound of formula (I), the lipid composition of the pharmaceutical compositions disclosed herein can comprise additional components such as phospholipids, structural lipids, PEG-lipids, and any combination thereof.

b. Phospholipids

The lipid composition of the pharmaceutical composition disclosed herein can comprise one or more phospholipids, (Compound 299)

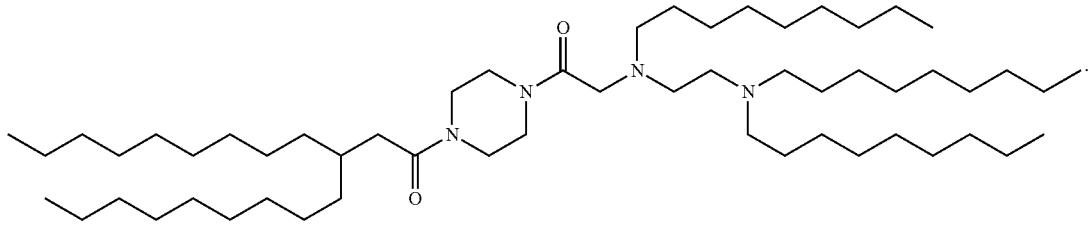

In other embodiments, the delivery agent comprises a compound having the formula:

for example, one or more saturated or (poly)unsaturated phospholipids or a combination thereof. In general, phos- (Compound 342)

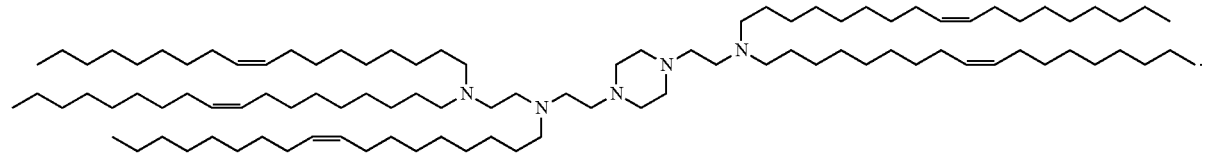

Amine moieties of the lipid compounds disclosed herein can be protonated under certain conditions. For example, the central amine moiety of a lipid according to formula (I) is typically protonated (i.e., positively charged) at a pH below the pKa of the amino moiety and is substantially not charged at a pH above the pKa. Such lipids can be referred to ionizable amino lipids.

In one specific embodiment, the ionizable amino lipid is Compound 18. In another embodiment, the ionizable amino lipid is Compound 236.

pholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

Examples of phospholipids include, but are not limited to, the following:

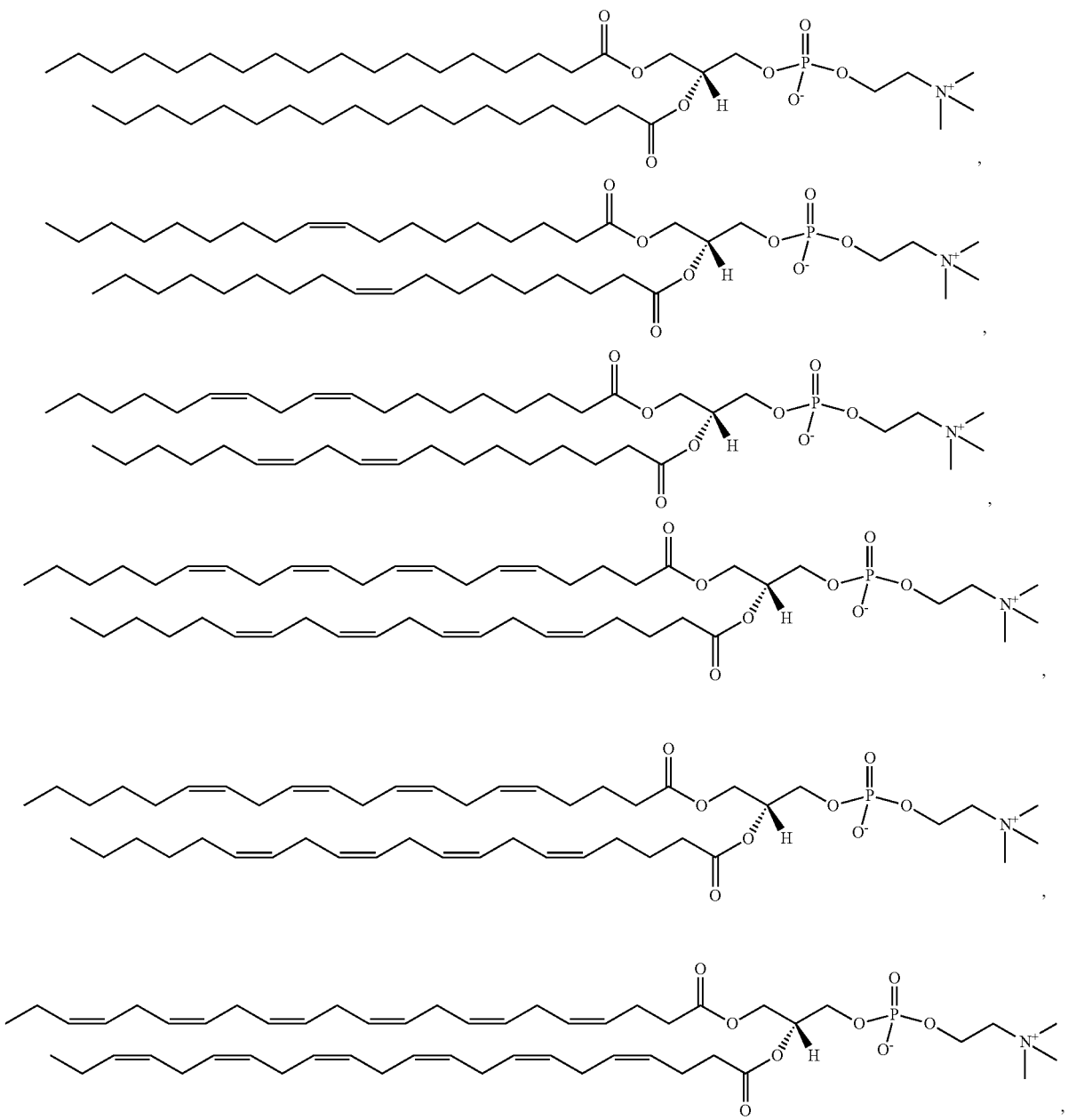

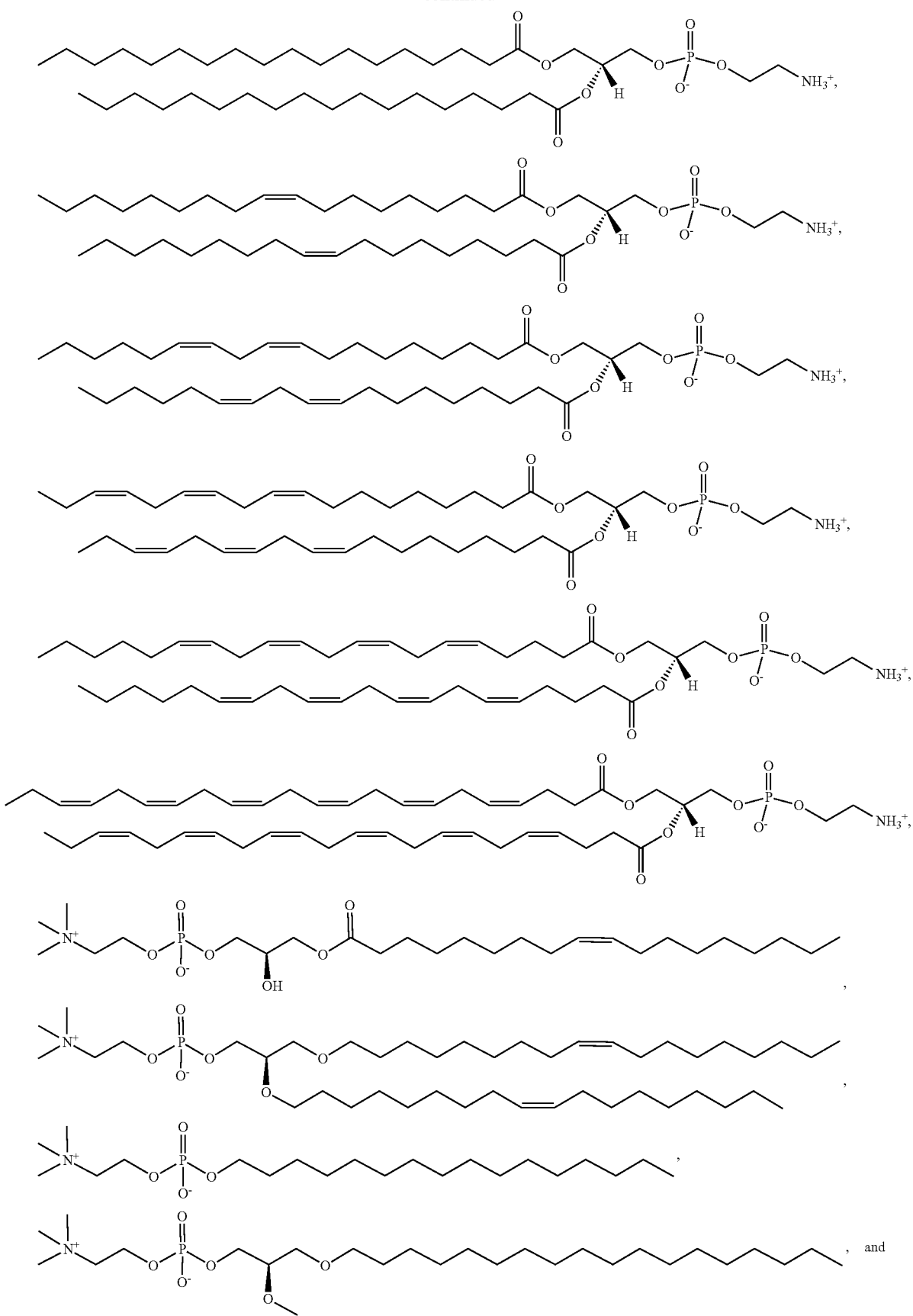

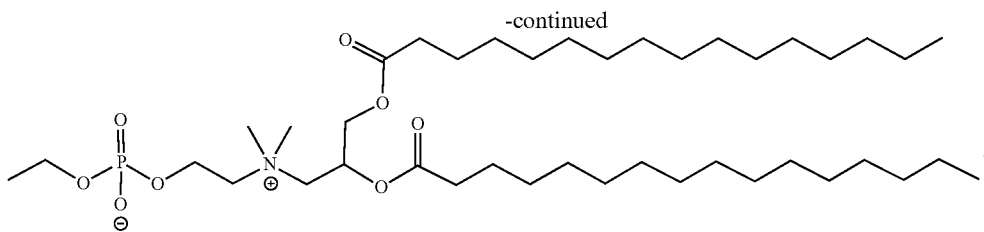

In certain embodiments, a phospholipid useful or potentially useful in the present invention is an analog or variant of DSPC. In certain embodiments, a phospholipid useful or potentially useful in the present invention is a compound of Formula (IX):

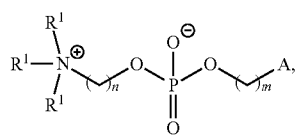

(or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;
m is 0, 1, 2, 3, 4, 5, 6, 7, 8, 9, or 10;
A is of the formula:

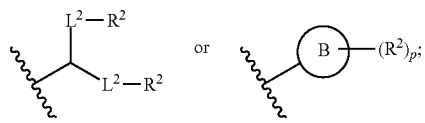

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, O, S, C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

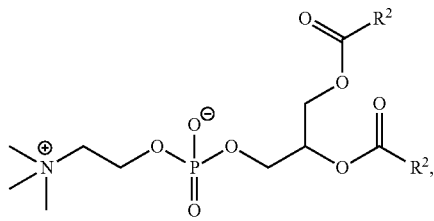

wherein each instance of $R^2$ is independently unsubstituted alkyl, unsubstituted alkenyl, or unsubstituted alkynyl.

i) Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IX), at least one of $R^1$ is not methyl. In certain embodiments, at least one of $R^1$ is not hydrogen or methyl. In certain embodiments, the compound of Formula (IX) is of one of the following formulae:

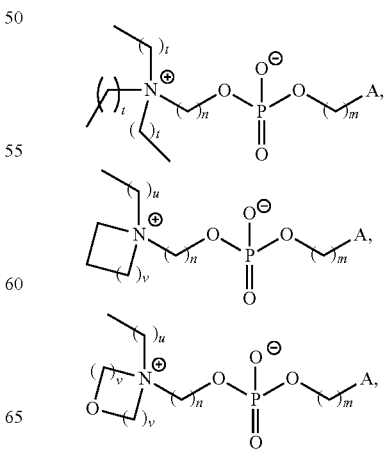

-continued
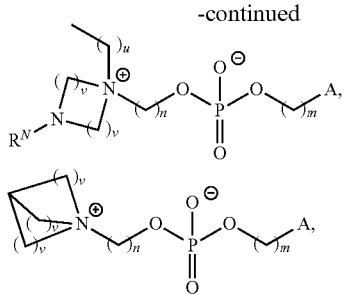
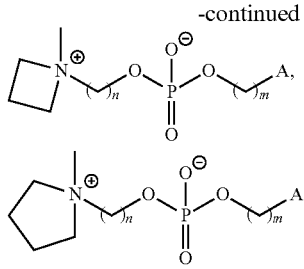
or a salt thereof, wherein:
each t is independently 1, 2, 3, 4, 5, 6, 7, 8, 9, or 10;
each u is independently 0, 1, 2, 3, 4, 5, 6, 7, 8, 9, or 10; and
each v is independently 1, 2, or 3.
In certain embodiments, the compound of Formula (IX) is of one of the following formulae:
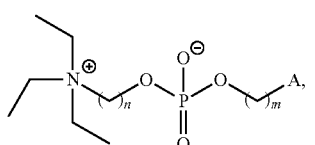
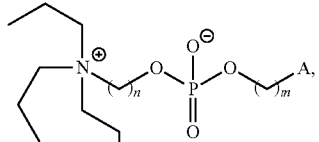
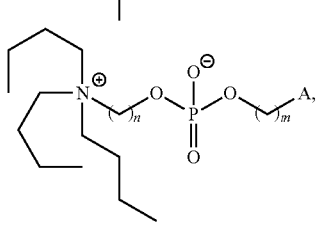
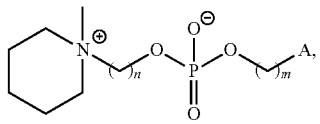
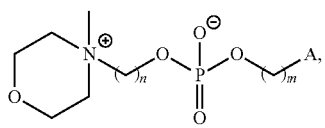
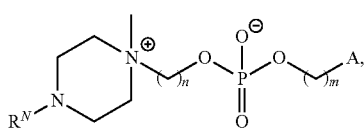
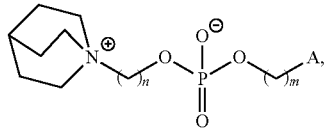
or a salt thereof.
In certain embodiments, a compound of Formula (IX) is one of the following:
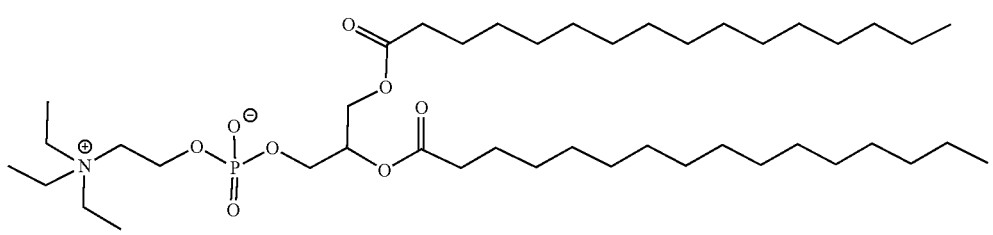
(Compound 400)
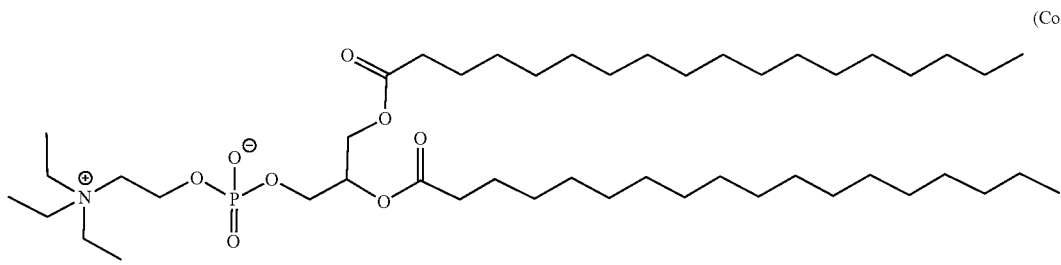
(Compound 401)

(Compound 402)
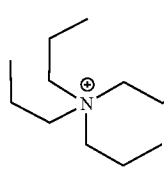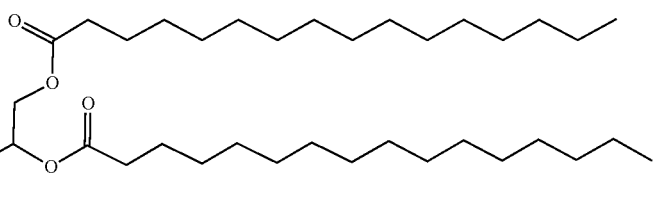
(Compound 403)
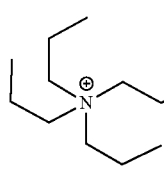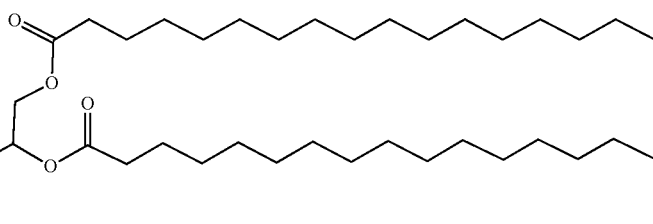
(Compound 404)
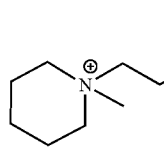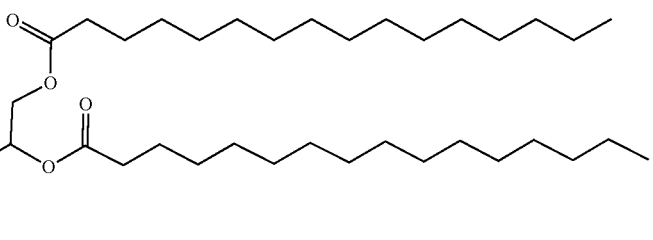
(Compound 405)
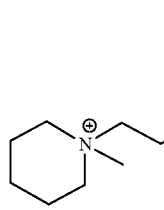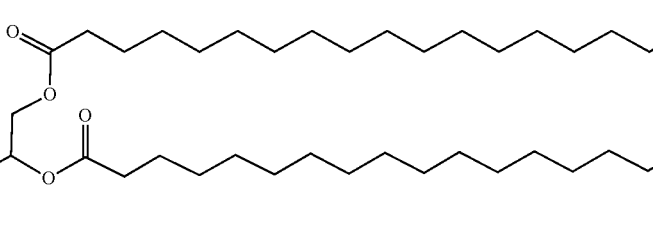
(Compound 406)
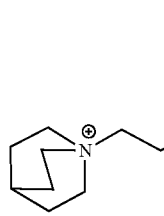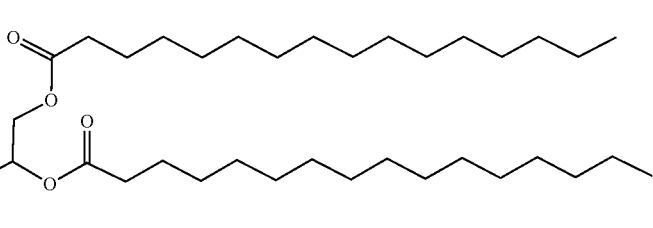
(Compound 407)
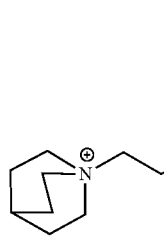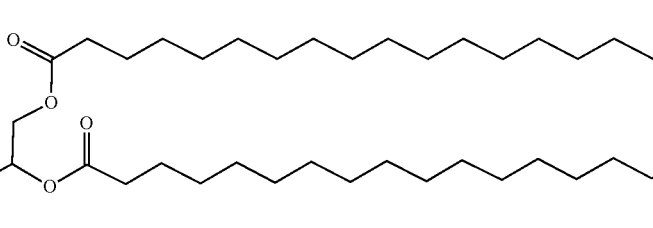

(Compound 408)

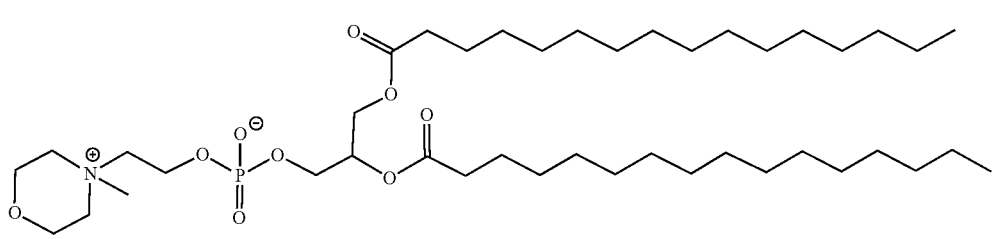

(Compound 409)

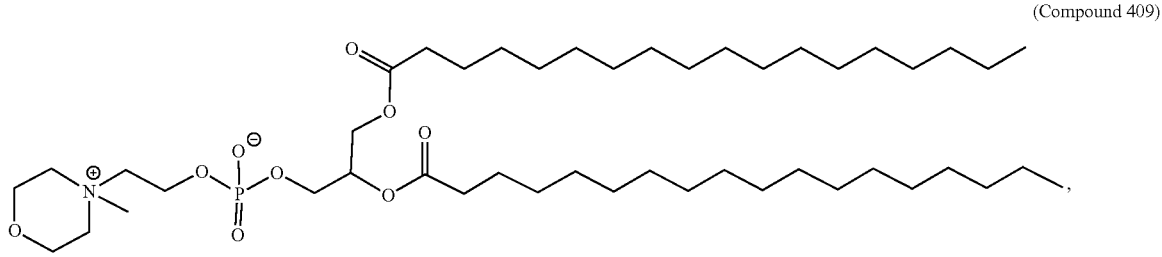

or a salt thereof.

In certain embodiments, a compound of Formula (IX) is of Formula (IX-a):

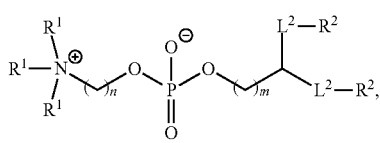

(IX-a)

or a salt thereof.

In certain embodiments, phospholipids useful or potentially useful in the present invention comprise a modified core. In certain embodiments, a phospholipid with a modified core described herein is DSPC, or analog thereof, with a modified core structure. For example, in certain embodiments of Formula (IX-a), group A is not of the following formula:

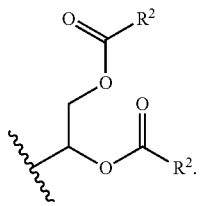

In certain embodiments, the compound of Formula (IX-a) is of one of the following formulae:

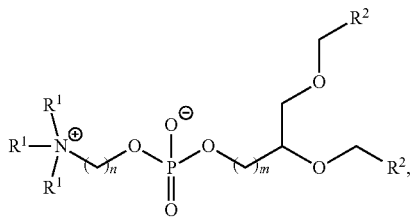

-continued

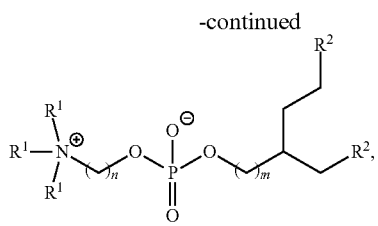

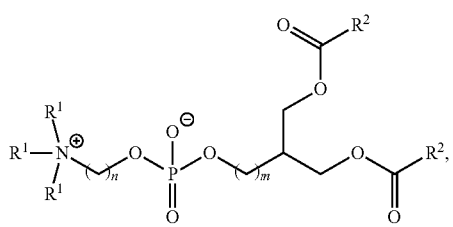

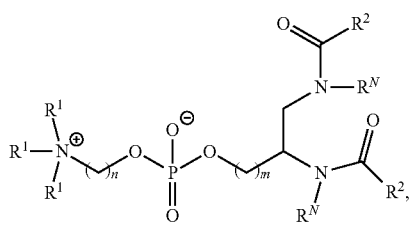

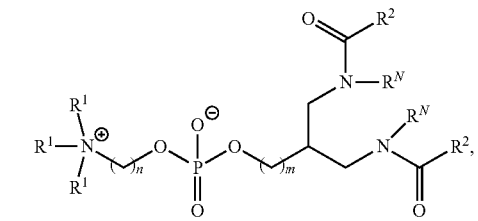

or a salt thereof.

In certain embodiments, a compound of Formula (IX) is one of the following:

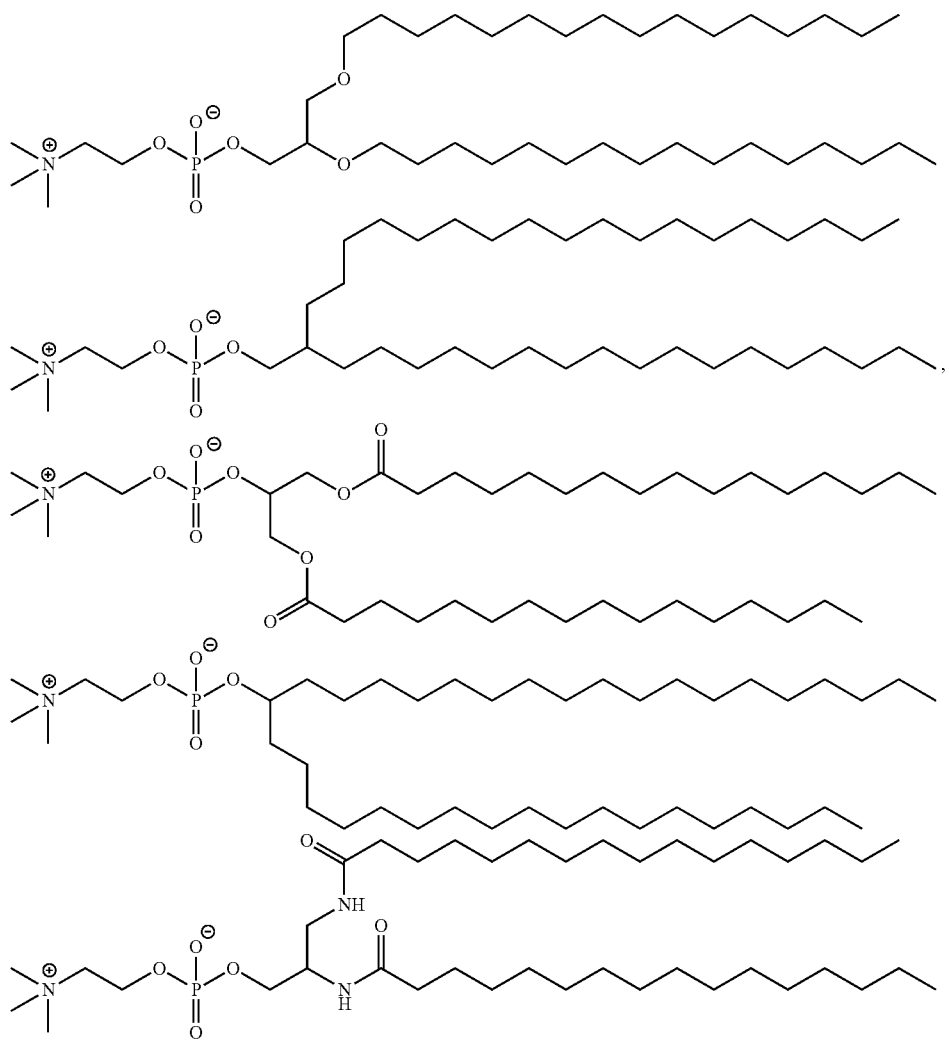

or salts thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IX) is of Formula (IX-b):

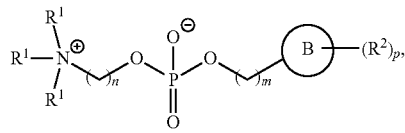

(IX-b)

or a salt thereof.

In certain embodiments, the compound of Formula (IX-b) is of Formula (IX-b-1):

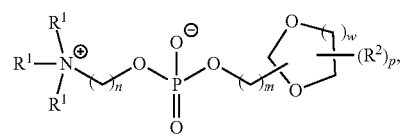

(IX-b-1)

or a salt thereof, wherein:
w is 0, 1, 2, or 3.

In certain embodiments, the compound of Formula (IX-b) is of Formula (IX-b-2):

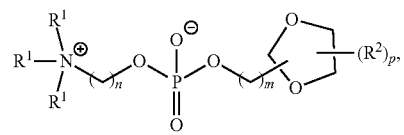

(IX-b-2)

or a salt thereof.

In certain embodiments, the compound of Formula (IX-b) is of Formula (IX-b-3):

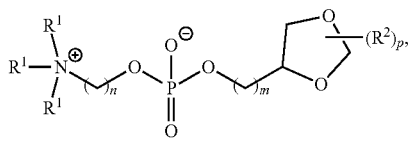

(IX-b-3)

or a salt thereof.

In certain embodiments, the compound of Formula (IX-b) is of Formula (IX-b-4):

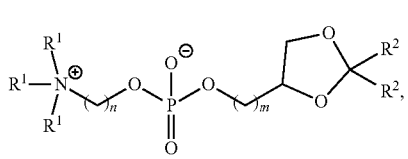

(IX-b-4)

or a salt thereof.

In certain embodiments, the compound of Formula (IX-b) is one of the following:

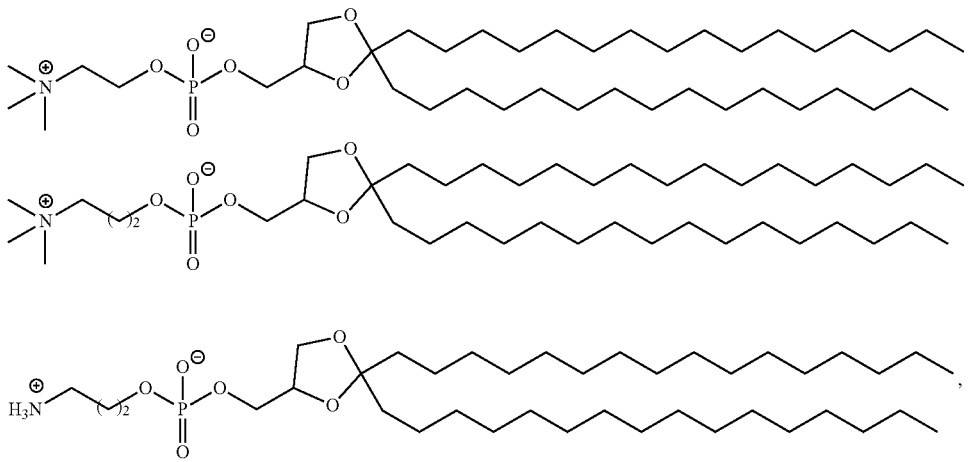

or salts thereof.

(ii) Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IX) is of Formula (IX-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—.

In certain embodiments, the compound of Formula (IX) is of Formula (IX-c):

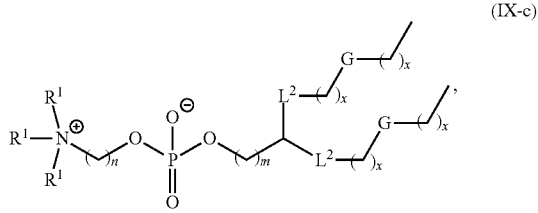

(IX-c)

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, —N($R^N$)—, O, S, C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—. Each possibility represents a separate embodiment of the present invention.

In certain embodiments, the compound of Formula (IX-c) is of Formula (IX-c-1):
or salt thereof, wherein:

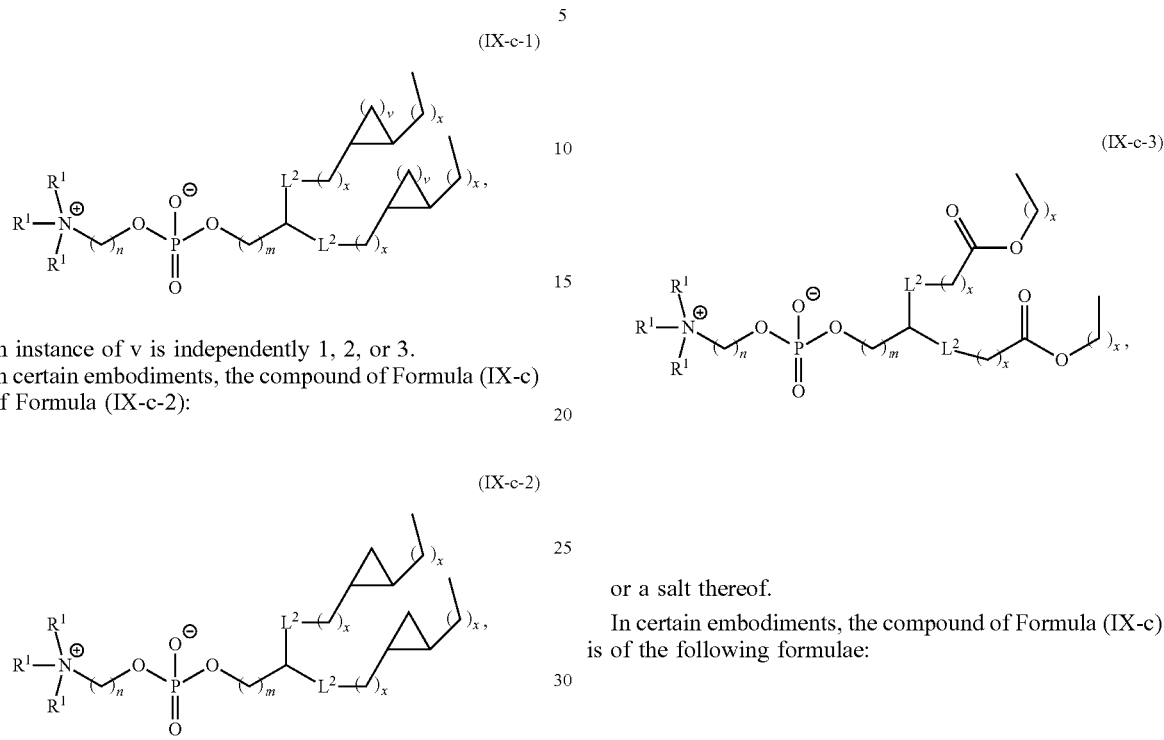

each instance of v is independently 1, 2, or 3.

In certain embodiments, the compound of Formula (IX-c) is of Formula (IX-c-2):

or a salt thereof.

In certain embodiments, the compound of Formula (IX-c) is of the following formula:

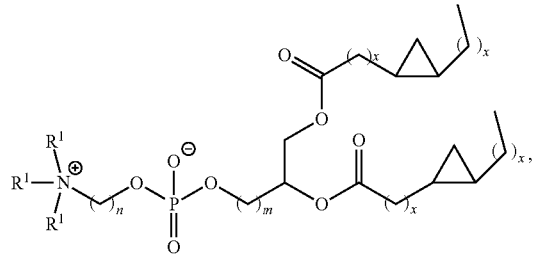

or a salt thereof.

In certain embodiments, the compound of Formula (IX-c) is the following:

In certain embodiments, the compound of Formula (IX-c) is of Formula (IX-c-3):

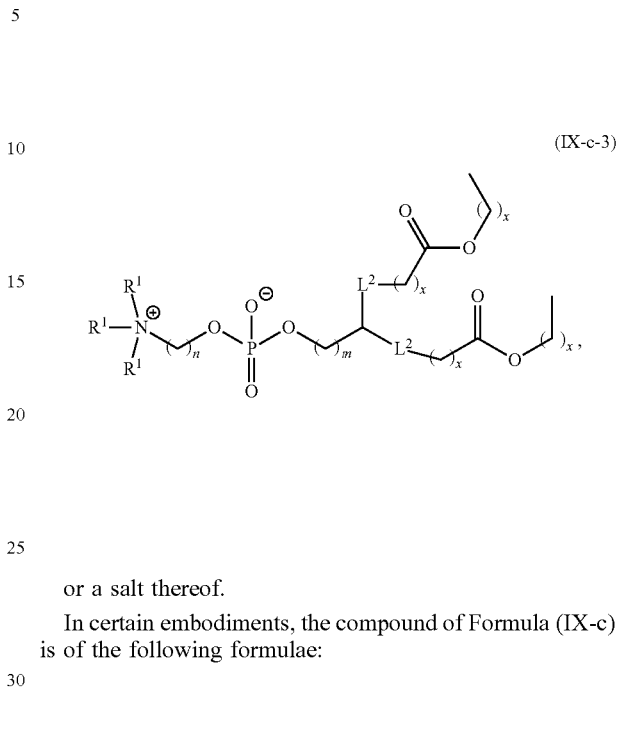

or a salt thereof.

In certain embodiments, the compound of Formula (IX-c) is of the following formulae:

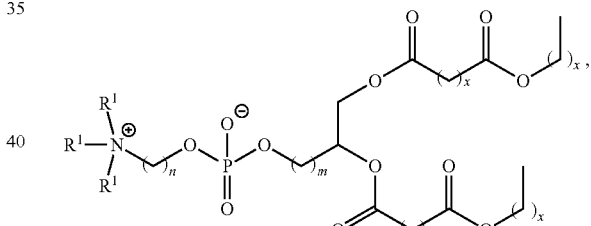

or a salt thereof.

In certain embodiments, the compound of Formula (IX-c) is the following:

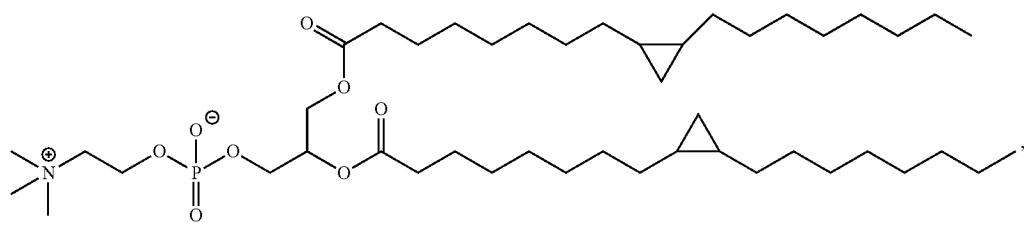 [SMILES: CCCCCCCCC1CC1CCCCCCCC(=O)OCC(COP(=O)([O-])OCC[N+](C)(C)C)OC(=O)CCCCCCCC1CC1CCCCCCCC]

or a salt thereof.

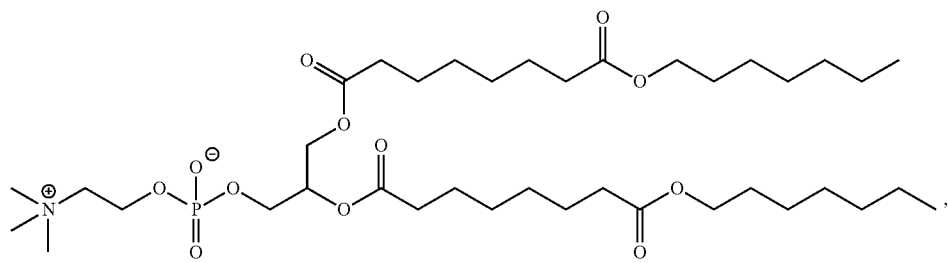 [SMILES: CCCCCCCOC(=O)CCCCCCC(=O)OCC(COP(=O)([O-])OCC[N+](C)(C)C)OC(=O)CCCCCCC(=O)OCCCCCCC]

or a salt thereof.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IX), wherein n is 1, 3, 4, 5, 6, 7, 8, 9, or 10. For example, in certain embodiments, a compound of Formula (IX) is of one of the following formulae:

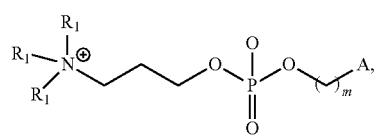

-continued

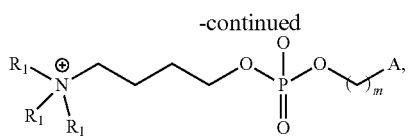

or a salt thereof.

In certain embodiments, a compound of Formula (IX) is one of the following:

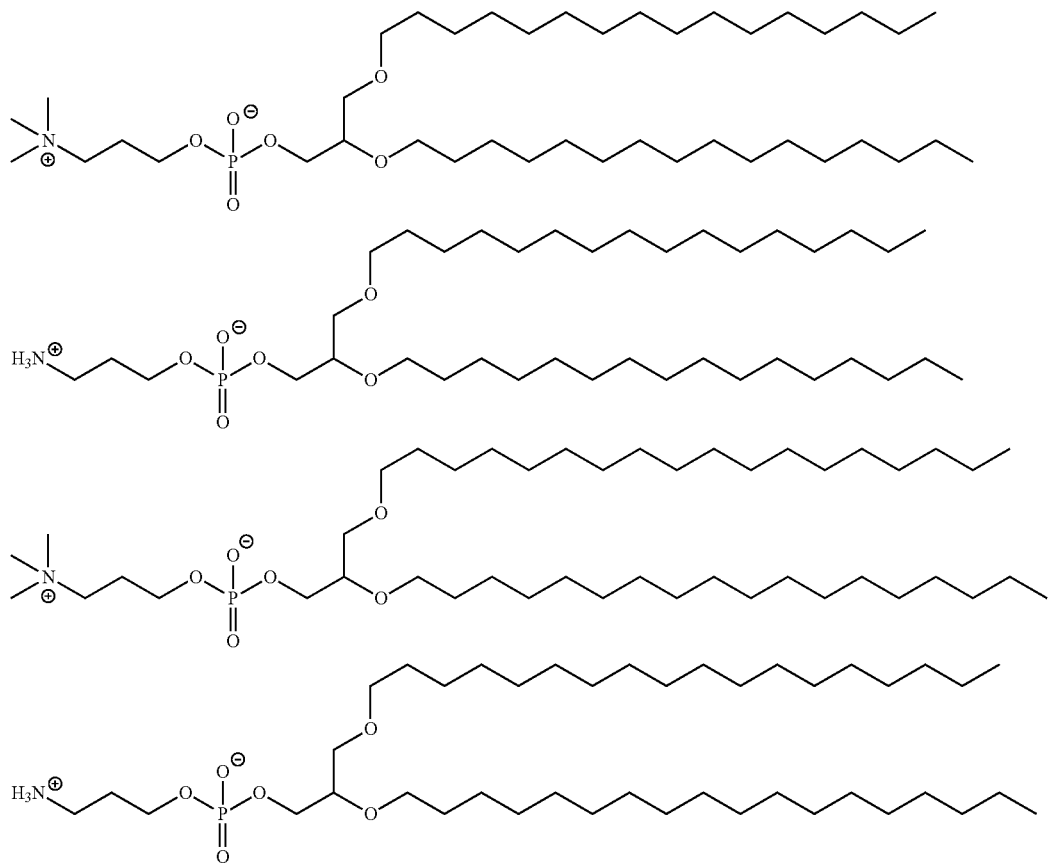

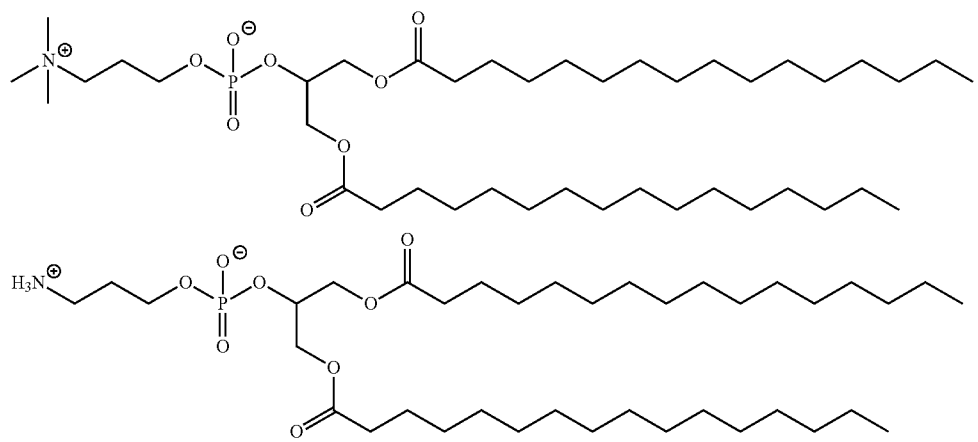
(Compound 411)
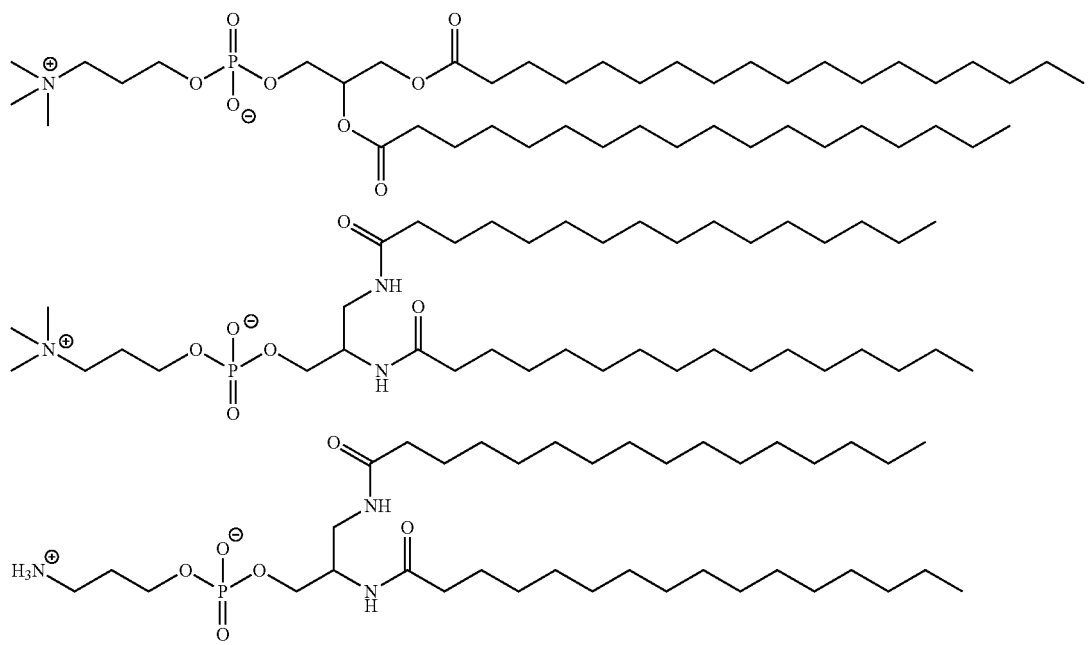
(Compound 412)
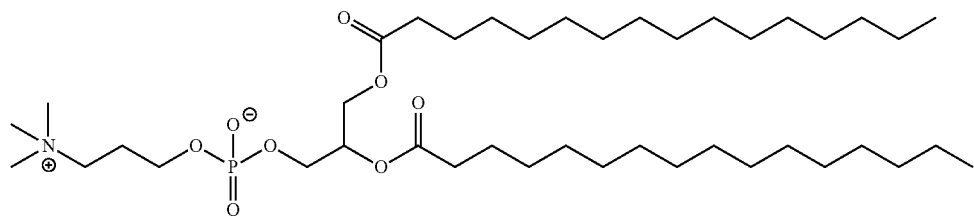
(Compound 413)
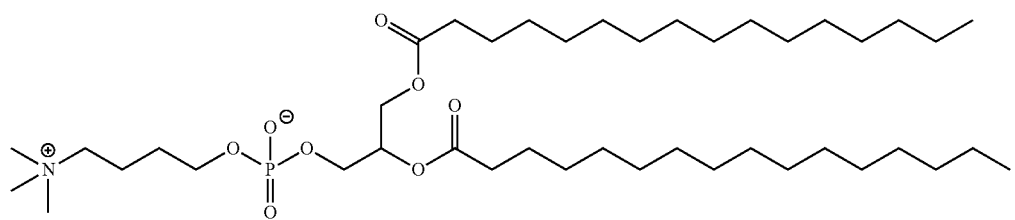

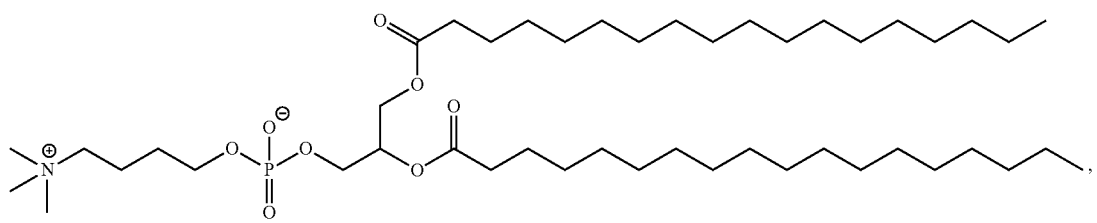
(Compound 414)
or salts thereof.
c. Alternative Lipids
In certain embodiments, an alternative lipid is used in place of a phospholipid of the invention. Non-limiting examples of such alternative lipids include the following:
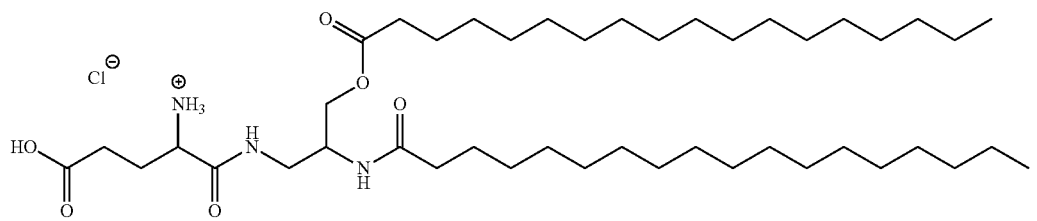
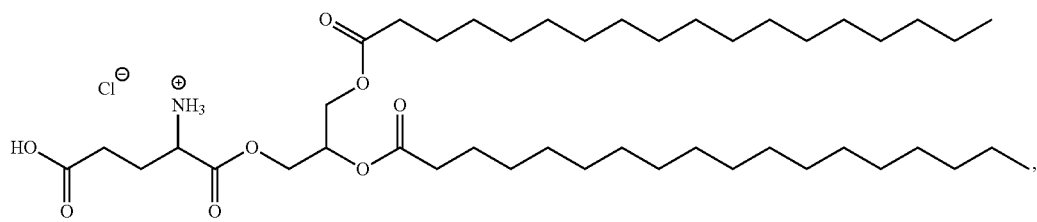
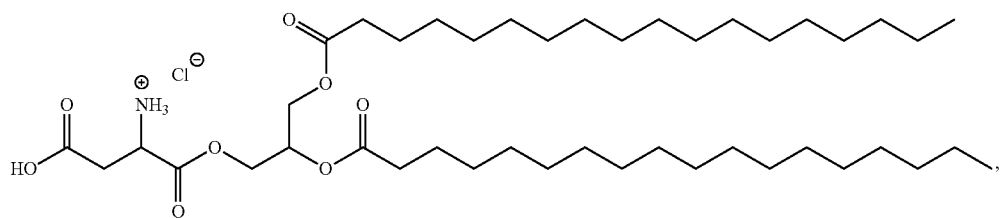
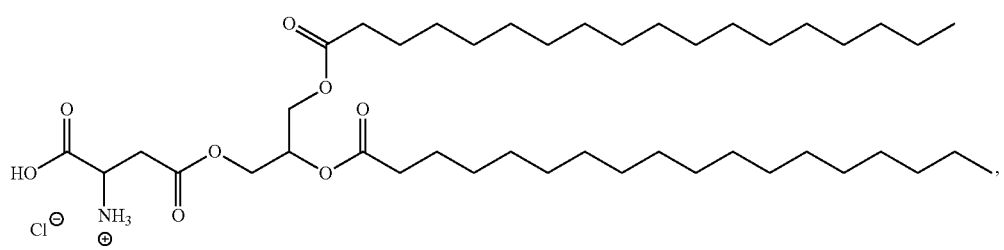
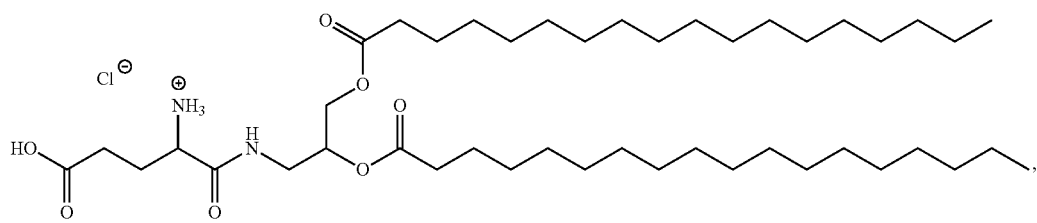

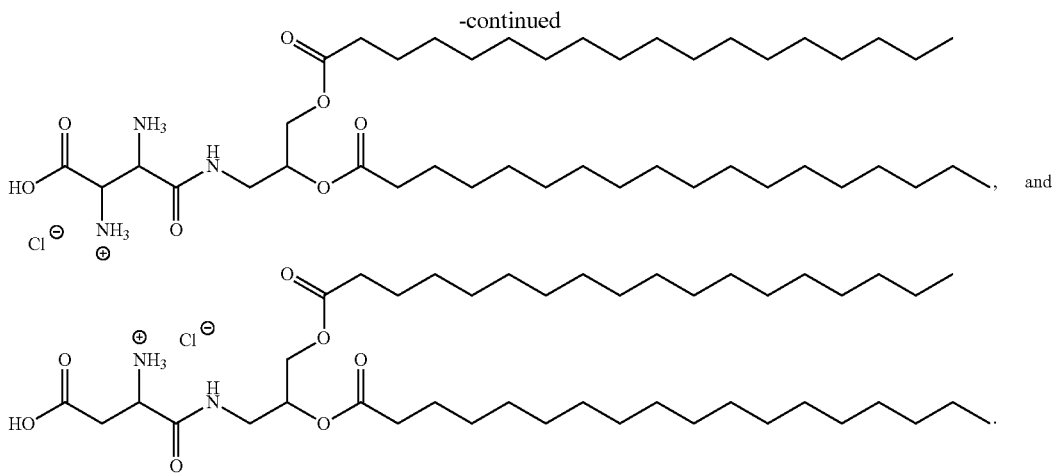
, and
.

d. Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol. Examples of structural lipids include, but are not limited to, the following:

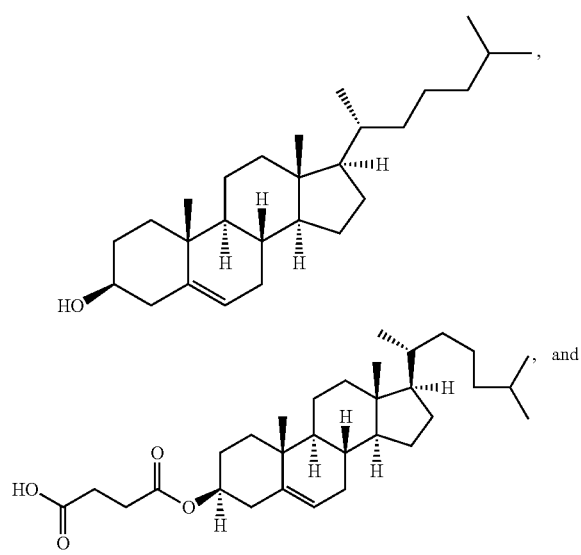

In one embodiment, the amount of the structural lipid (e.g., a sterol such as cholesterol) in the lipid composition of a pharmaceutical composition disclosed herein ranges from about 20 mol % to about 60 mol %, from about 25 mol % to about 55 mol %, from about 30 mol % to about 50 mol %, or from about 35 mol % to about 45 mol %.

In one embodiment, the amount of the structural lipid (e.g., a sterol such as cholesterol) in the lipid composition disclosed herein ranges from about 25 mol % to about 30 mol %, from about 30 mol % to about 35 mol %, or from about 35 mol % to about 40 mol %.

In one embodiment, the amount of the structural lipid (e.g., a sterol such as cholesterol) in the lipid composition disclosed herein is about 24 mol %, about 29 mol %, about 34 mol %, or about 39 mol %.

In some embodiments, the amount of the structural lipid (e.g., a sterol such as cholesterol) in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol %.

e. Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEG lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N4amino(polyethylene glycol)] (PEG- DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristoyloxypropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons. In one embodiment, the PEG-lipid is PEG$_{2k}$-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEG lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

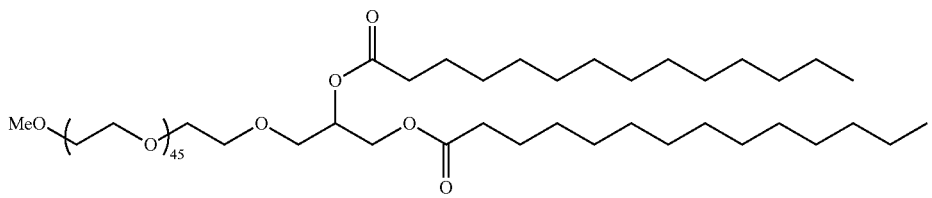

In one embodiment, PEG lipids useful in the present invention can be PEG lipids described in International Publication No. WO2012/099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEG lipid") is a PEG lipid having one or more hydroxyl (—OH) groups on the lipid. In certain embodiments, the PEG-OH lipid includes one or more hydroxyl groups on the PEG chain. In certain embodiments, a PEG-OH or hydroxy-PEG lipid comprises an —OH group at the terminus of the PEG chain. Each possibility represents a separate embodiment of the present invention.

In certain embodiments, a PEG lipid useful in the present invention is a compound of Formula (VII). Provided herein are compounds of Formula (VII):

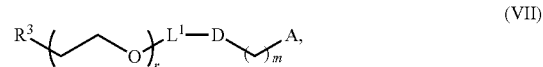

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, N($R^N$), S, C(O), C(O)N($R^N$), $NR^NC$(O), C(O)O, —OC(O), OC(O)O, OC(O)N($R^N$), $NR^NC$(O)O, or $NR^NC$(O)N($R^N$);

D is a moiety obtained by click chemistry or a moiety cleavable under physiological conditions;

m is 0, 1, 2, 3, 4, 5, 6, 7, 8, 9, or 10;

A is of the formula:

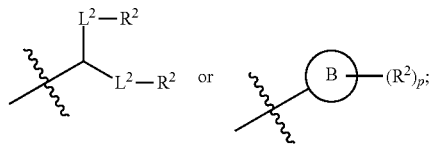

each instance of $L^2$ is independently a bond or optionally substituted $C_{1-6}$ alkylene, wherein one methylene unit of the optionally substituted $C_{1-6}$ alkylene is optionally replaced with O, N($R^N$), S, C(O), C(O)N($R^N$), $NR^NC$(O), C(O)O, OC(O), OC(O)O, OC(O)N($R^N$), $NR^NC$(O)O, or $NR^NC$(O)N($R^N$);

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, N($R^N$), O, S, C(O), C(O)N($R^N$), $NR^NC$(O), $NR^NC$(O)N($R^N$), C(O)O, OC(O), OC(O)O, OC(O)N($R^N$), N$R^N$C(O)O, C(O)S, SC(O), C(=N$R^N$), C(=N$R^N$)N($R^N$), N$R^N$C(=N$R^N$), N$R^N$C(=N$R^N$)N($R^N$), C(S), C(S)N($R^N$), N$R^N$C(S), N$R^N$C(S)N($R^N$), S(O), OS(O), S(O)O, OS(O)O, OS(O)$_2$, S(O)$_2$O, OS(O)$_2$O, N($R^N$)S(O), S(O)N($R^N$), N($R^N$)S(O)N($R^N$), OS(O)N($R^N$), N($R^N$)S(O)O, S(O)$_2$, N($R^N$)S(O)$_2$, S(O)$_2$N($R^N$), N($R^N$)S(O)$_2$N($R^N$), OS(O)$_2$N($R^N$), or N($R^N$)S(O)$_2$O;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (VII) is a PEG-OH lipid (i.e., $R^3$ is —$OR^O$, and $R^O$ is hydrogen). In certain embodiments, the compound of Formula (VII) is of Formula (VII-OH):

(VII-OH)

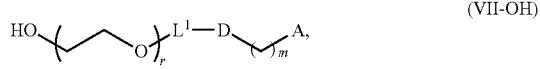

or a salt thereof.

In certain embodiments, D is a moiety obtained by click chemistry (e.g., triazole). In certain embodiments, the compound of Formula (VII) is of Formula (VII-a-1) or (VII-a-2):

(VII-a-1)

(VII-a-2)

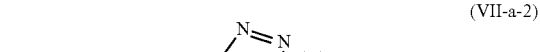

or a salt thereof.

In certain embodiments, the compound of Formula (VII) is of one of the following formulae:

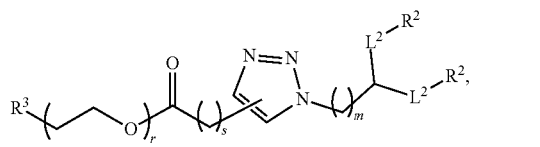

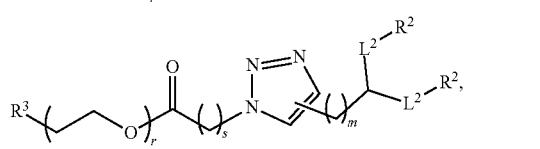

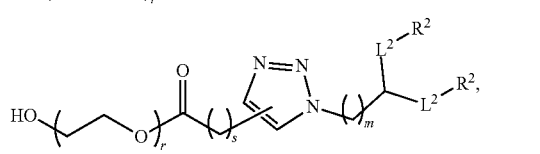

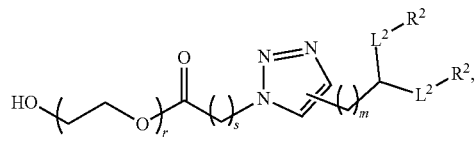

or a salt thereof, wherein s is 0, 1, 2, 3, 4, 5, 6, 7, 8, 9, or 10.

In certain embodiments, the compound of Formula (VII) is of one of the following formulae:

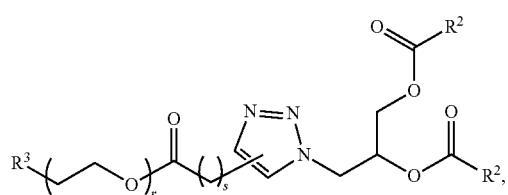

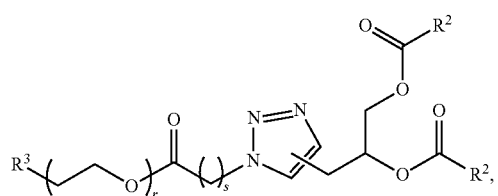

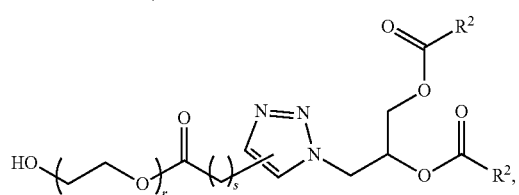

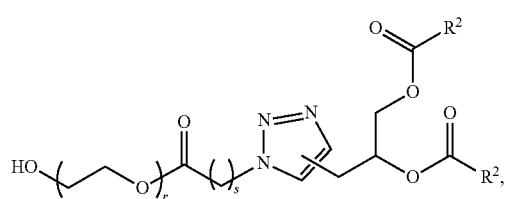

or a salt thereof.

In certain embodiments, a compound of Formula (VII) is of one of the following formulae:

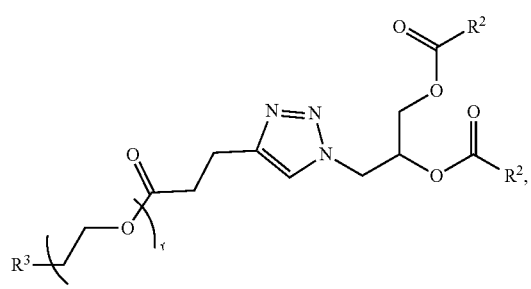

207
-continued
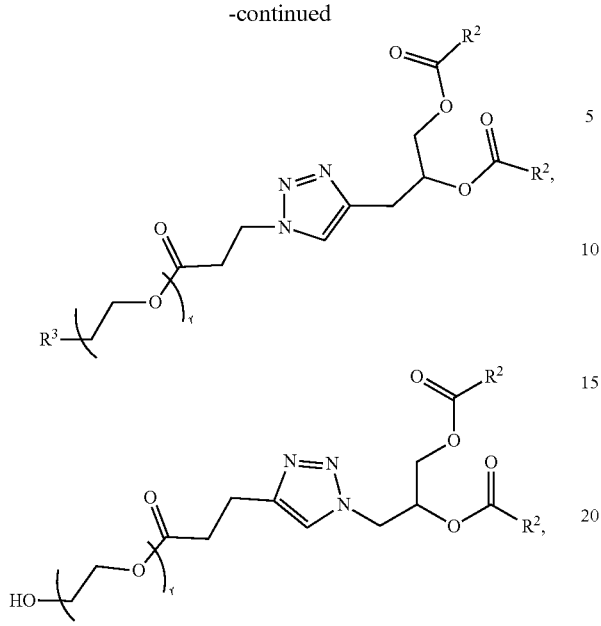
208
-continued
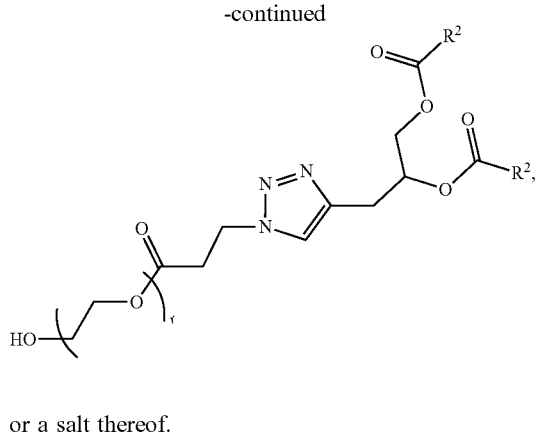
or a salt thereof.
In certain embodiments, a compound of Formula (VII) is of one of the following formulae:
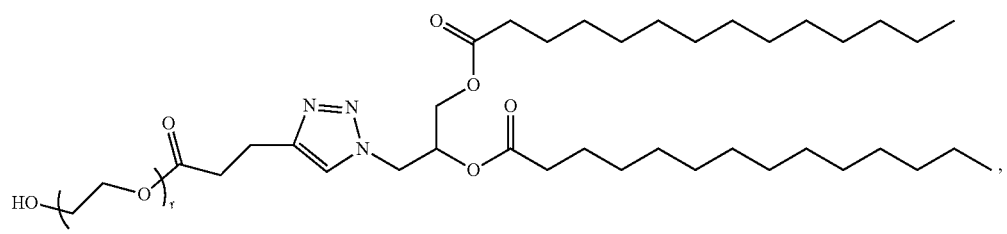
(Compound 415)
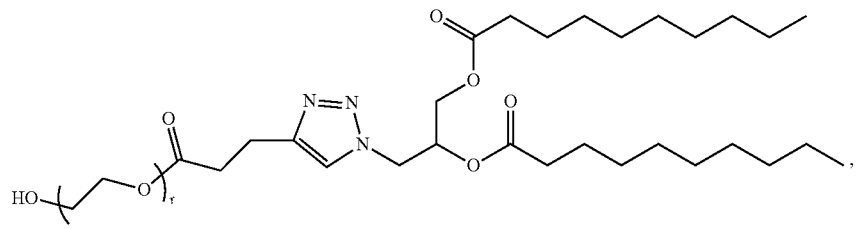
(Compound 416)
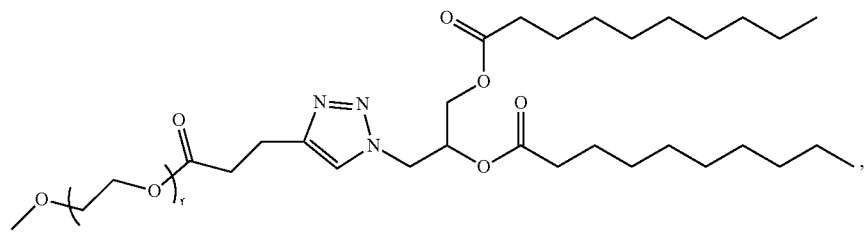
(Compound 417)

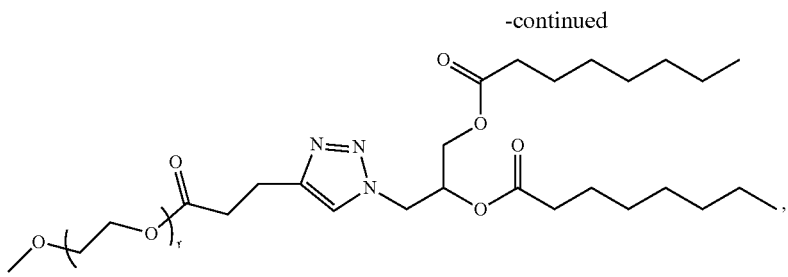
(Compound 418)

or a salt thereof.

In certain embodiments, D is a moiety cleavable under physiological conditions (e.g., ester, amide, carbonate, carbamate, urea). In certain embodiments, a compound of Formula (VII) is of Formula (VII-b-1) or (VII-b-2):

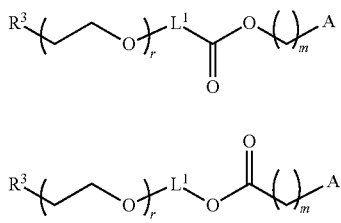

or a salt thereof.

In certain embodiments, a compound of Formula (VII) is of Formula (VII-b-1-OH) or (VII-b-2-OH):

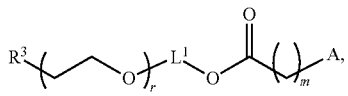

or a salt thereof.

In certain embodiments, the compound of Formula (VII) is of one of the following formulae:

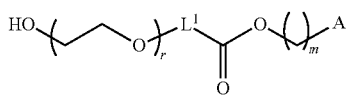

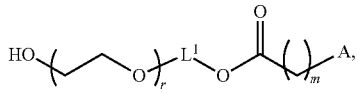

or a salt thereof.

In certain embodiments, a compound of Formula (VII) is of one of the following formulae:

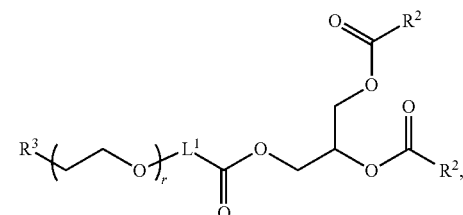

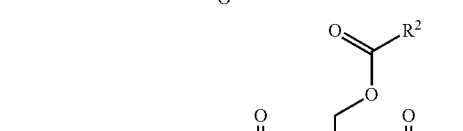

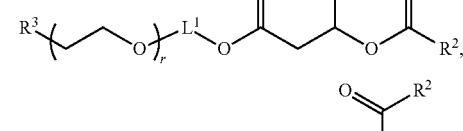

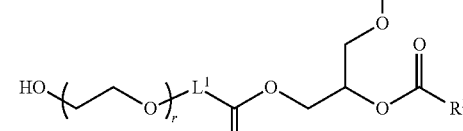

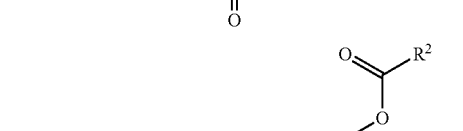

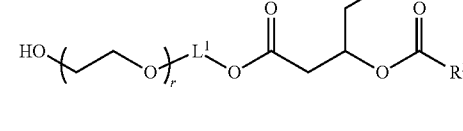

or a salt thereof.

In certain embodiments, a compound of Formula (VII) is of one of the following formulae:

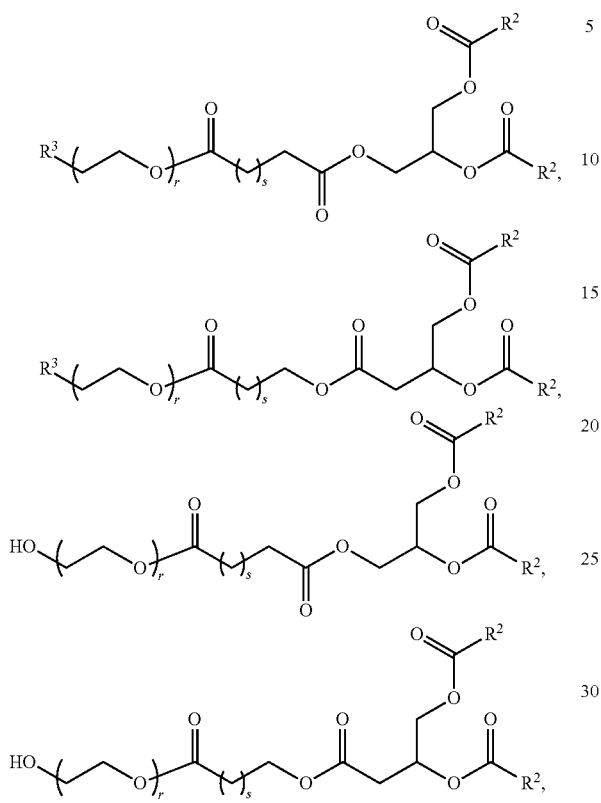

or a salt thereof.

In certain embodiments, a compound of Formula (VII) is of one of the following formulae:

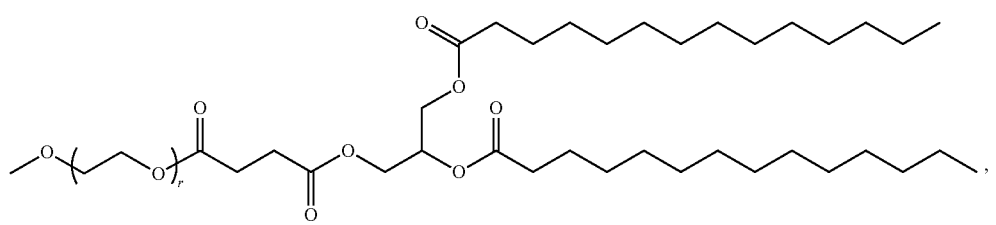

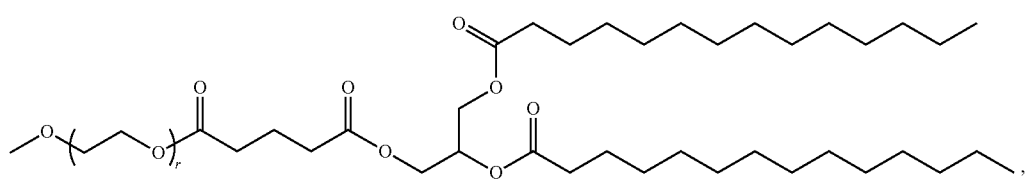

or salts thereof.

In certain embodiments, a PEG lipid useful in the present invention is a PEG fatty acid. In certain embodiments, a PEG lipid useful in the present invention is a compound of Formula (VIII). Provided herein are compounds of Formula (VIII):

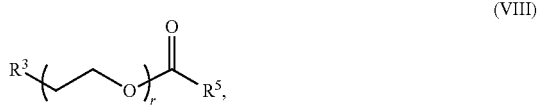

or a salt thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), —C(O)N($R^N$), $NR^NC(O)$, $NR^NC(O)N(R^N)$, C(O)O, OC(O), OC(O)O, OC(O)N($R^N$), —$NR^NC(O)O$, C(O)S, SC(O), C(=$NR^N$), C(=$NR^N$)N($R^N$), $NR^NC$(=$NR^N$), $NR^NC$(=$NR^N$)N($R^N$), C(S), C(S)N($R^N$), $NR^NC(S)$, $NR^NC(S)N(R^N)$, S(O), OS(O), S(O)O, OS(O)O, OS(O)$_2$, —S(O)$_2$O, OS(O)$_2$O, N($R^N$)S(O), S(O)N($R^N$), N($R^N$)S(O)N($R^N$), OS(O)N($R^N$), N($R^N$)S(O)O, —S(O)$_2$, N($R^N$)S(O)$_2$, S(O)$_2$N($R^N$), N($R^N$)S(O)$_2$N($R^N$), OS(O)$_2$N($R^N$), or N($R^N$)S(O)$_2$O; and each instance of $R^N$ is independently hydrogen, optionally substituted alkyl, or a nitrogen protecting group.

In certain embodiments, the compound of Formula (VIII) is of Formula (VIII-0111:

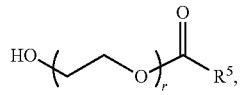
(VIII-OH)

or a salt thereof. In some embodiments, r is 45.

In certain embodiments, a compound of Formula (VIII) is of one of the following formulae:

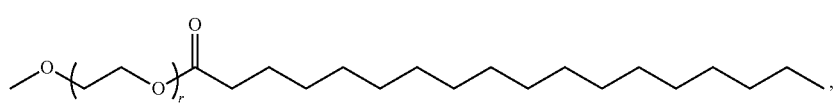
(Compound 419)

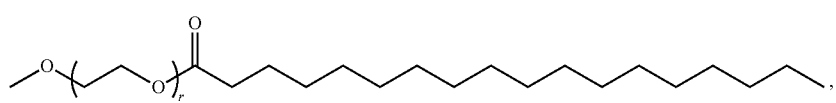
(Compound 420)

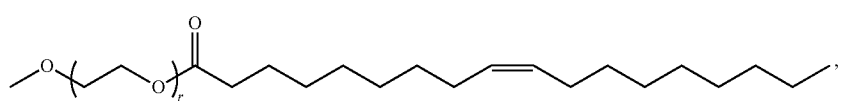
(Compound 421)

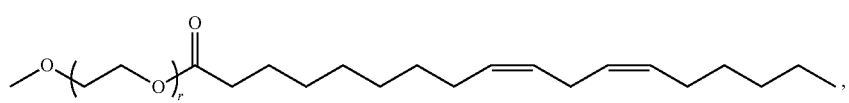
(Compound 422)

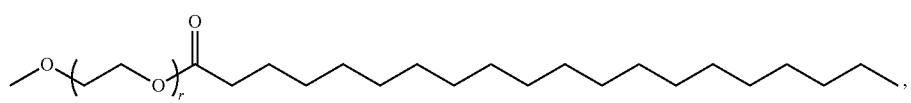
(Compound 423)

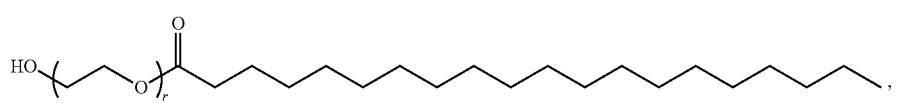
(Compound 424)

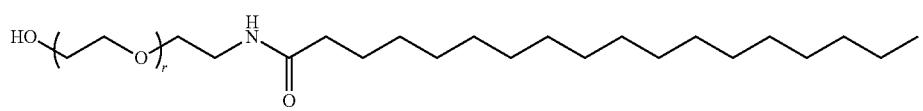
(Compound 425)

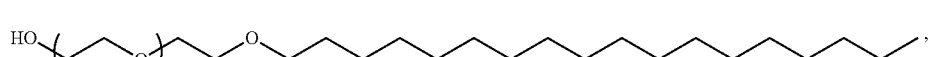
(Compound 426)

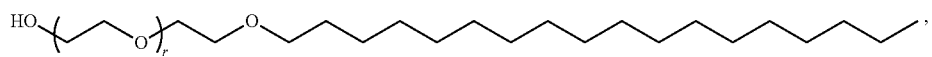

or a salt thereof. In some embodiments, r is 45.

In yet other embodiments the compound of Formula (VIII) is:

(Compound 427)

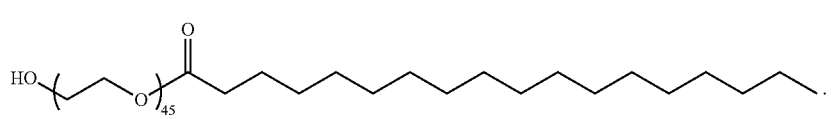

or a salt thereof.

In one embodiment, the compound of Formula (VIII) is (Compound 428)

In one embodiment, the amount of PEG-lipid in the lipid composition of a pharmaceutical composition disclosed herein ranges from about 0.1 mol % to about 5 mol %, from about 0.5 mol % to about 5 mol %, from about 1 mol % to about 5 mol %, from about 1.5 mol % to about 5 mol %, from about 2 mol % to about 5 mol % mol %, from about 0.1 mol % to about 4 mol %, from about 0.5 mol % to about 4 mol %, from about 1 mol % to about 4 mol %, from about 1.5 mol % to about 4 mol %, from about 2 mol % to about 4 mol %, from about 0.1 mol % to about 3 mol %, from about 0.5 mol % to about 3 mol %, from about 1 mol % to about 3 mol %, from about 1.5 mol % to about 3 mol %, from about 2 mol % to about 3 mol %, from about 0.1 mol % to about 2 mol %, from about 0.5 mol % to about 2 mol %, from about 1 mol % to about 2 mol %, from about 1.5 mol % to about 2 mol %, from about 0.1 mol % to about 1.5 mol %, from about 0.5 mol % to about 1.5 mol %, or from about 1 mol % to about 1.5 mol %.

In one embodiment, the amount of PEG-lipid in the lipid composition disclosed herein is about 2 mol %. In one embodiment, the amount of PEG-lipid in the lipid composition disclosed herein is about 1.5 mol %.

In one embodiment, the amount of PEG-lipid in the lipid composition disclosed herein is at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mol %.

In some aspects, the lipid composition of the pharmaceutical compositions disclosed herein does not comprise a PEG-lipid.

f. Other Ionizable Amino Lipids

The lipid composition of the pharmaceutical composition disclosed herein can comprise one or more ionizable amino lipids in addition to or instead of a lipid according to Formula (I), (II), (III), (IV), (V), or (VI).

Ionizable lipids can be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraazaoctatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z, 16SZ)-N,N-dimethyl-3-nonydocosa-13-16-dien-1-amine (L608), 2-({8-[(3(3)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, an ionizable amino lipid can also be a lipid including a cyclic amine group.

Ionizable lipids can also be the compounds disclosed in International Publication No. WO 2017/075531 A1, hereby incorporated by reference in its entirety. For example, the ionizable amino lipids include but not limited to:

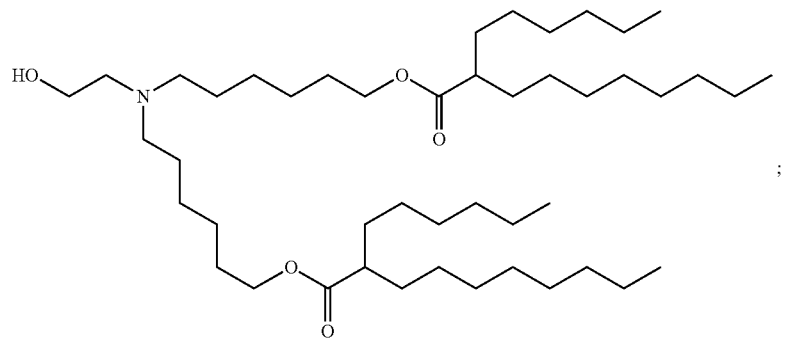

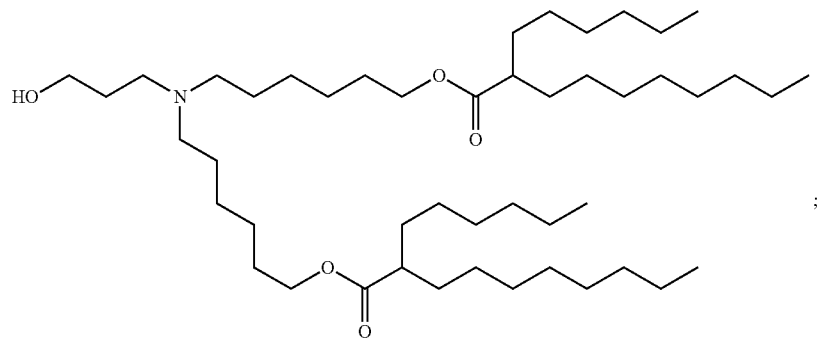

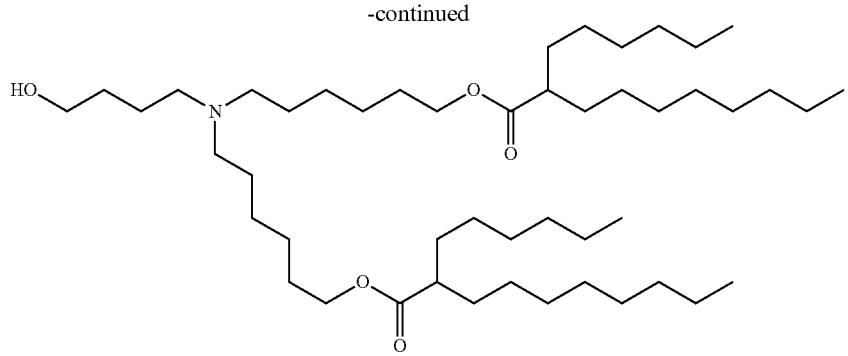
and any combination thereof.
Ionizable lipids can also be the compounds disclosed in International Publication No. WO 2015/199952 A1, hereby incorporated by reference in its entirety. For example, the ionizable amino lipids include, but not limited to:
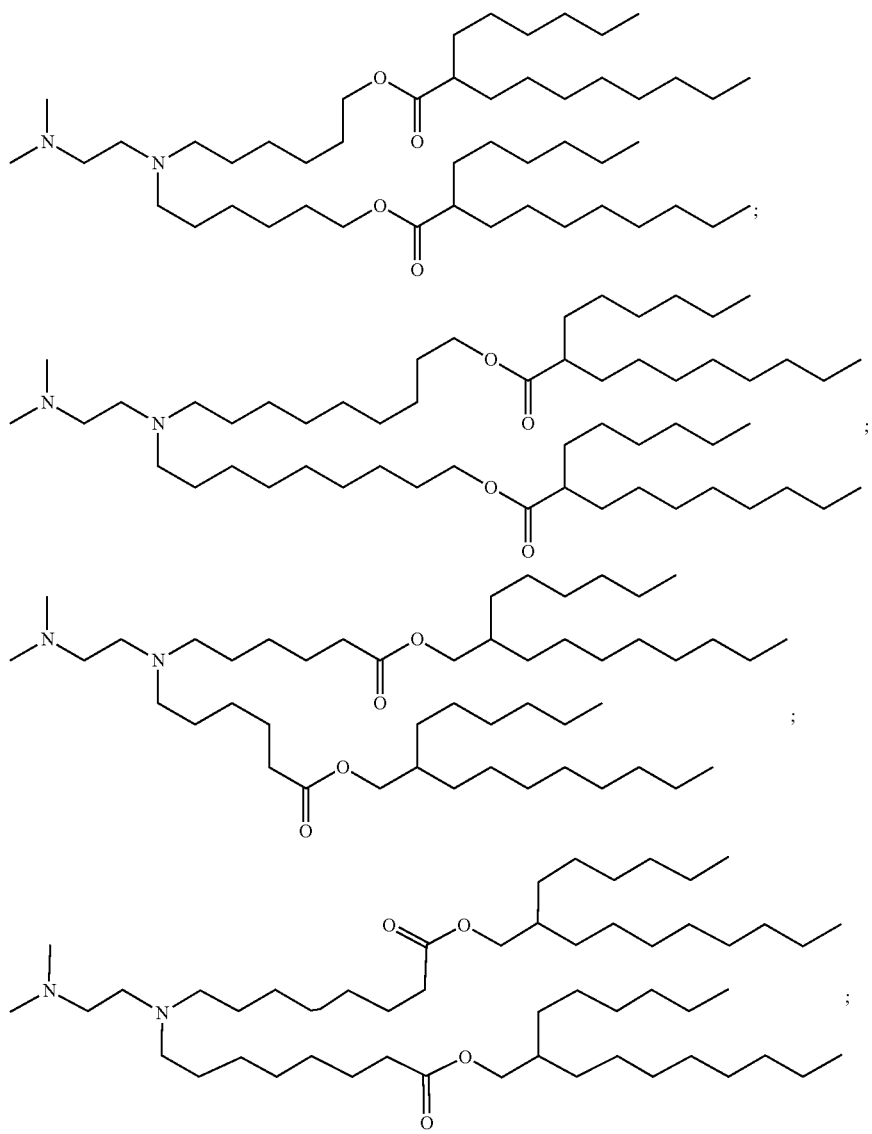

-continued
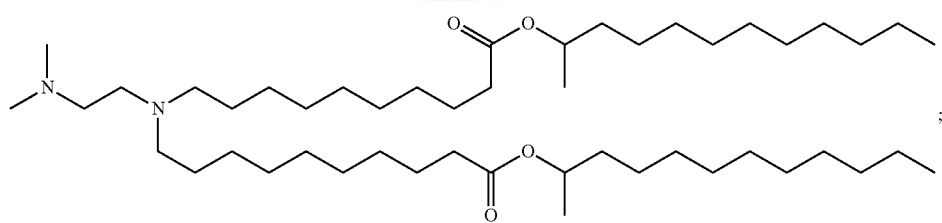
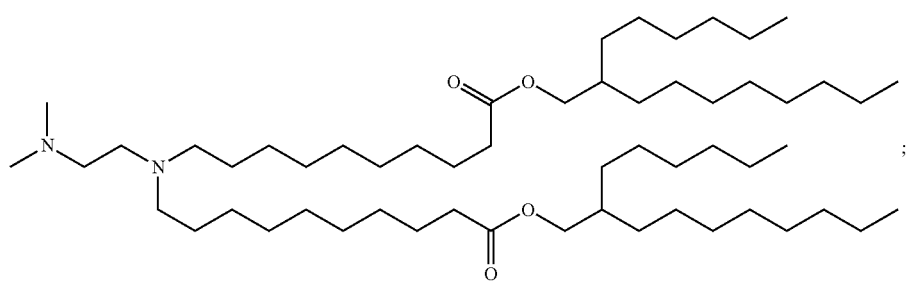
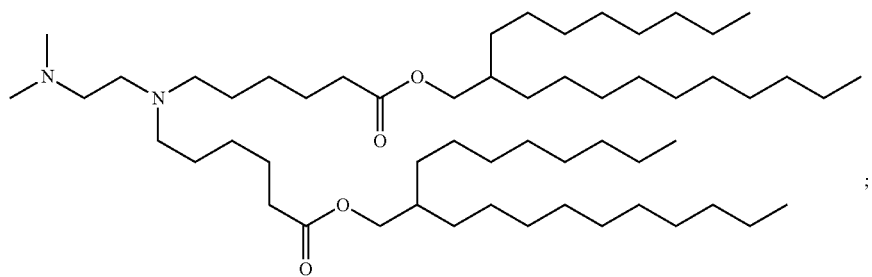
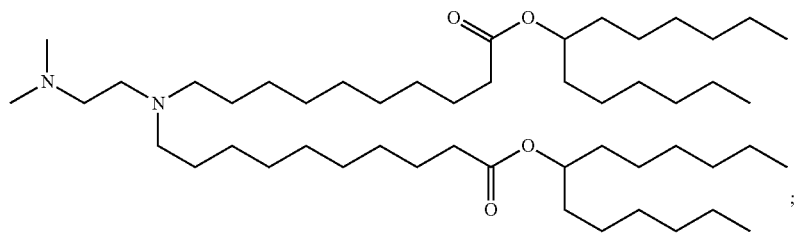
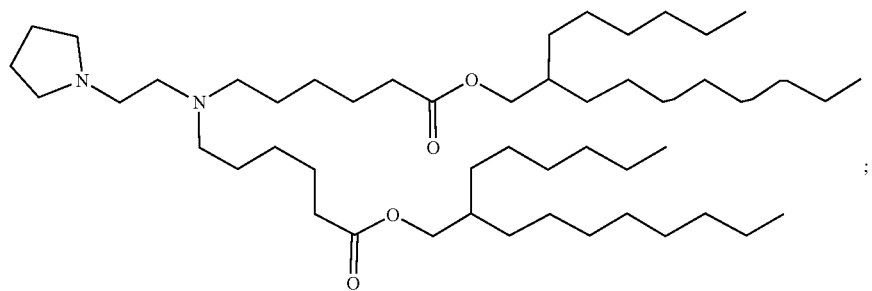

-continued

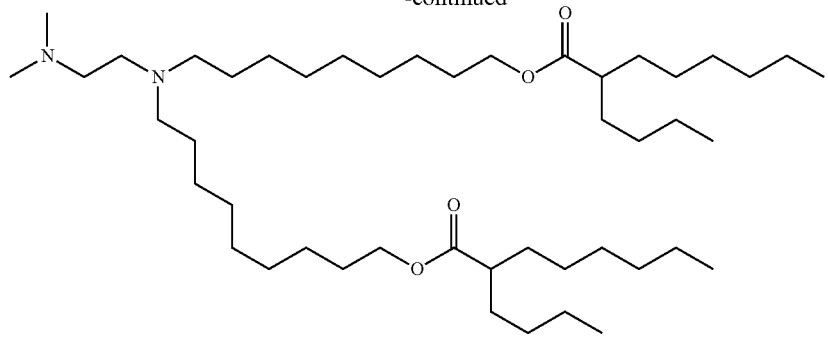

and any combination thereof.

g. Nanoparticle Compositions

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1,from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as a compound of Formula (I) or (III) as described herein, and (ii) a polynucleotide encoding a target polypeptide. In such nanoparticle composition, the lipid composition disclosed herein can encapsulate the polynucleotide encoding a target polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In some embodiments, the nanoparticle compositions of the present disclosure comprise at least one compound according to Formula (I), (III), (IV), (V), or (VI). For example, the nanoparticle composition can include one or more of Compounds 1-147, or one or more of Compounds 1-342. Nanoparticle compositions can also include a variety of other components. For example, the nanoparticle composition may include one or more other lipids in addition to a lipid according to Formula (I), (II), (III), (IV), (V), or (VI), such as (i) at least one phospholipid, (ii) at least one structural lipid, (iii) at least one PEG-lipid, or (iv) any combination thereof. Inclusion of structural lipid can be optional, for example when lipids according to formula III are used in the lipid nanoparticle compositions of the invention.

In some embodiments, the nanoparticle composition comprises a compound of Formula (I), (e.g., Compounds 18, 25, 26 or 48). In some embodiments, the nanoparticle composition comprises a compound of Formula (I) (e.g., Compounds 18, 25, 26 or 48) and a phospholipid (e.g., DSPC).

In some embodiments, the nanoparticle composition comprises a compound of Formula (III) (e.g., Compound 236). In some embodiments, the nanoparticle composition comprises a compound of Formula (III) (e.g., Compound 236) and a phospholipid (e.g., DOPE or DSPC).

In some embodiments, the nanoparticle composition comprises a lipid composition consisting or consisting essentially of compound of Formula (I) (e.g., Compounds 18, 25, 26 or 48). In some embodiments, the nanoparticle composition comprises a lipid composition consisting or consisting essentially of a compound of Formula (I) (e.g., Compounds 18, 25, 26 or 48) and a phospholipid (e.g., DSPC).

In some embodiments, the nanoparticle composition comprises a lipid composition consisting or consisting essentially of compound of Formula (III) (e.g., Compound 236). In some embodiments, the nanoparticle composition comprises a lipid composition consisting or consisting essentially of a compound of Formula (III) (e.g., Compound 236) and a phospholipid (e.g., DOPE or DSPC).

In one embodiment, a lipid nanoparticle comprises an ionizable lipid, a structural lipid, a phospholipid, and mRNA. In some embodiments, the LNP comprises an ionizable lipid, a PEG-modified lipid, a phospholipid and a structural lipid. In some embodiments, the LNP has a molar ratio of about 20-60% ionizable lipid:about 5-25% phospholipid:about 25-55% structural lipid; and about 0.5-15% PEG-modified lipid. In some embodiments, the LNP comprises a molar ratio of about 50% ionizable lipid, about 1.5% PEG-modified lipid, about 38.5% structural lipid and about 10% phospholipid. In some embodiments, the LNP comprises a molar ratio of about 55% ionizable lipid, about 2.5% PEG lipid, about 32.5% structural lipid and about 10% phospholipid. In some embodiments, the ionizable lipid is an ionizable amino lipid and the phospholipid is a neutral lipid, and the structural lipid is a cholesterol. In some embodiments, the LNP has a molar ratio of 50:38.5:10:1.5 of ionizable lipid:cholesterol:DSPC:PEG lipid. In some embodiments, the ionizable lipid is Compound 18 or Compound 236, and the PEG lipid is Compound 428.

In some embodiments, the LNP has a molar ratio of 50:38.5:10:1.5 of Compound 18:Cholesterol:Phospholipid:Compound 428. In some embodiments, the LNP has a molar ratio of 50:38.5:10:1.5 of Compound 18:Cholesterol:DSPC:Compound 428.

In some embodiments, the LNP has a molar ratio of 50:38.5:10:1.5 of Compound 236:Cholesterol:Phospholipid:Compound 428. In some embodiments, the LNP has a molar ratio of 50:38.5:10:1.5 of Compound 236:Cholesterol:DSPC:Compound 428.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids lead them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipids. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013/086354 and WO2013/116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012/170889, herein incorporated by reference in its entirety. In one embodiment, the lipid may be synthesized by methods known in the art and/or as described in International Publication Nos. WO2013/086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

In some embodiments, the nanoparticle composition comprises a lipid composition consisting or consisting essentially of compound of Formula (I) (e.g., Compounds 18, 25, 26 or 48). In some embodiments, the nanoparticle composition comprises a lipid composition consisting or consisting essentially of a compound of Formula (I) (e.g., Compounds 18, 25, 26 or 48) and a phospholipid (e.g., DSPC or MSPC).

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a target polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 µm or shorter (e.g., 1 µm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

Biologically Active Agents

This disclosure contemplates that the LNPs provided herein and/or the various combination therapies provided herein may be used to deliver a variety of agents to a subject. Such agents typically will be biologically active agents. Biologically active agents are agents that have an effect in vivo, and preferably a beneficial effect, such as desirable immune modulation, immune stimulation, immune inhibition, cell killing, cell preservation, modified gene expression, protein replacement, and the like. Biologically active agents include but are not limited to prophylactic agents, therapeutic agents, and diagnostic agents. Biologically active agents include immunomodulatory agents such as immunostimulatory or immunoinhibitory agents, antigens, antibodies and antibody fragments such as antigen-binding antibody fragments, adjuvants, cytokines such as interleukins, anti-bacterial agents, anti-viral agents, anti-fungal agents, anti-parasitic agents, anti-cancer agents, anti-inflammatory agents, and the like.

Such agents may be, without limitation, nucleic acids, proteins or peptide, small organic compounds, carbohydrates and/or polysaccharides, and the like. They may be used to express nucleic acids and/or proteins in cells, particularly in cells that are deficient in such nucleic acids or proteins or have mutated versions of such nucleic acids or proteins. They may be used to introduce and express nucleic acids or proteins that are not native to the cell or organism, as may be done for example in the context of an immunization or vaccination protocol. In this respect, the nucleic acid or protein may be foreign to the subject to whom it is administered (e.g., not naturally occurring in such subject, or not naturally occurring at all), and it is administered to the subject to induce and/or boost an immune response to such nucleic acid or protein. The nucleic acids provided herein may be used for such a purpose.

Other biologically active agents may be used alone or together with such nucleic acids or proteins, including formulated together with such nucleic acids or proteins, including formulated in the LNPs of this disclosure.

Nucleic Acids

As used herein, the term "nucleic acid" refers to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. A nucleic acid sequence is presented in the 5' to 3' direction unless otherwise indicated.

Nucleic acids include any compound and/or substance that comprises a polymer of nucleotides. These polymers are referred to as polynucleotides. Nucleic acids may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

Nucleic acids may be naturally occurring, for example, in the context of a genome, a transcript, an mRNA, tRNA, rRNA, siRNA, snRNA, plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Nucleic acids can be purified from natural sources, produced using recombinant expression systems and optionally purified, chemically synthesized, etc.

Furthermore, the terms "nucleic acid," "DNA," "RNA," and/or similar terms include nucleic acid analogs, i.e., analogs having other than a phosphodiester backbone.

Where appropriate, e.g., in the case of chemically synthesized molecules, nucleic acids can comprise nucleoside analogs such as analogs having chemically modified bases or sugars, and backbone modifications. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphdioester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s.

Modifications of polynucleotides (e.g., RNA polynucleotides, such as mRNA polynucleotides) that are useful in the compositions, methods and synthetic processes of the present disclosure include, but are not limited to the following nucleotides, nucleosides, and nucleobases: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladeno sine; 2-methylthio-N6-isopentenyladenosine; 7-deaza-adenosine; N1-methyladenosine; N6, N6 (dimethyl)adenine; N6-cis-hydroxyisopentenyl-adenosine; α-thio-adenosine; 2 (amino)adenine; 2 (aminopropyl)adenine; 2 (methylthio) N6 (isopentenyl) adenine; 2-(alkyl)adenine; 2-(aminoalkyl)adenine; 2-(aminopropyl)adenine; 2-(halo)adenine; 2-(halo)adenine; 2-(propyl)adenine; 2'-Amino-2'-deoxy-ATP; 2'-Azido-2'-deoxy-ATP; 2'-Deoxy-2'-α-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl) adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytidine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo) cytosine; 5 (methyl)cytosine; 5 (propynyl)cytosine; 5 (trifluoromethyl)cytosine; 5-(alkyl)cytosine; 5-(alkynyl) cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl)cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl) cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methylguanosine; 7 (alkyl)guanine; 7 (deaza)guanine; 7 (methyl) guanine; 7-(alkyl)guanine; 7-(deaza)guanine; 7-(methyl) guanine; 8 (alkyl)guanine; 8 (alkynyl)guanine; 8 (halo) guanine; 8 (thioalkyl)guanine; 8-(alkenyl)guanine; 8-(alkyl) guanine; 8-(alkynyl)guanine; 8-(amino)guanine; 8-(halo) guanine; 8-(hydroxyl)guanine; 8-(thioalkyl)guanine; 8-(thiol)guanine; aza guanine; deaza guanine; N (methyl) guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homoguanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl) pseudouridine; 1-methylpseduouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methylpseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 1-Ethyl-pseudo-UTP; 2 (thio)pseudouracil; 2' deoxy uridine; 2' fluorouridine; 2-(thio)uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio)pseudouracil; 4-(thio)pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil; 5-(methoxy)uracil; 5-(methoxycarbonylmethyl)-2-(thio) uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio) uracil; 5-(methyl-aminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; P seudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±) 1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-prop yl)pseudo-UTP; 1-(3-Cyclopropyl-prop-2-ynyl)pseudouridine TP; 1-(4-Amino-4-carboxybutyl)pseudo-UTP; 1-(4-Amino-benzyl)pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl)pseudouridine TP; 1-(4-Fluorobenzyl) pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl) pseudo-UTP; 1-(4-Methoxy-phenyl)pseudo-UTP; 1-(4-Methylbenzyl)pseudouridine TP; 1-(4-Methyl-benzyl) pseudo-UTP; 1-(4-Nitrobenzyl)pseudouridine TP; 1-(4-Nitro-benzyl)pseudo-UTP; 1(4-Nitro-phenyl)pseudo-UTP; 1-(4-Thiomethoxybenzyl)pseudouridine TP; 1-(4-Trifluoromethoxybenzyl)pseudouridine TP; 1-(4-Trifluoromethyl-benzyl)pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy}]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluoro-cytidine; 2' methyl, 2'amino, 2'azido, 2'fluoro-adenine; 2'methyl, 2'amino, 2'azido, 2'fluoro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl)isocarbostyrilyl; 3-(methyl)isocarbostyrilyl; 4-(fluoro)-6-(methyl)benzimidazole; 4-(methyl) benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thiozebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, the mRNA comprises at least one chemically modified nucleoside. In some embodiments, the at least one chemically modified nucleoside is selected from the group consisting of pseudouridine (ψ), 2-thiouridine (s2U), 4'-thiouridine, 5-methylcytosine, 2-thio-1-methyl-1- deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (miI), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyl-adenosine, 2-geranylthiouridine, 2-lysidine, 2-selenouridine, 3-(3-amino-3-carboxypropyl)-5,6-dihydrouridine, 3-(3-amino-3-carboxypropyl)pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQObase, preQ1base, and two or more combinations thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, the mRNA is a uracil-modified sequence comprising an ORF encoding a target polypeptide, wherein the mRNA comprises a chemically modified nucleobase, e.g., 5-methoxyuracil. In certain aspects of the invention, when the 5-methoxyuracil base is connected to a ribose sugar, as it is in polynucleotides, the resulting modified nucleoside or nucleotide is referred to as 5-methoxyuridine. In some embodiments, uracil in the polynucleotide is at least about 25%, at least about 30%, at least about 40%, at least about 50%, at least about 60%, at least about 70%, at least about 80%, at least 90%, at least 95%, at least 99%, or about 100% 5-methoxyuracil. In one embodiment, uracil in the polynucleotide is at least 95% 5-methoxyuracil. In another embodiment, uracil in the polynucleotide is 100% 5-methoxyuracil.

In embodiments where uracil in the polynucleotide is at least 95% 5-methoxyuracil, overall uracil content can be adjusted such that an mRNA provides suitable protein expression levels while inducing little to no immune response. In some embodiments, the uracil content of the ORF is between about 105% and about 145%, about 105% and about 140%, about 110% and about 140%, about 110% and about 145%, about 115% and about 135%, about 105% and about 135%, about 110% and about 135%, about 115% and about 145%, or about 115% and about 140% of the theoretical minimum uracil content in the corresponding wild-type ORF (% Utm). In other embodiments, the uracil content of the ORF is between about 117% and about 134% or between 118% and 132% of the % UTM. In some embodiments, the uracil content of the ORF encoding a target polypeptide is about 115%, about 120%, about 125%, about 130%, about 135%, about 140%, about 145%, or about 150% of the % Utm. In this context, the term "uracil" can refer to 5-methoxyuracil and/or naturally occurring uracil.

In some embodiments, the uracil content in the ORF of the mRNA encoding a target polypeptide of the invention is less than about 50%, about 40%, about 30%, about 20%, about 15%, or about 12% of the total nucleobase content in the ORF. In some embodiments, the uracil content in the ORF is between about 12% and about 25% of the total nucleobase content in the ORF. In other embodiments, the uracil content in the ORF is between about 15% and about 17% of the total nucleobase content in the ORF. In one embodiment, the uracil content in the ORF of the mRNA encoding a target polypeptide is less than about 20% of the total nucleobase content in the open reading frame. In this context, the term "uracil" can refer to 5-methoxyuracil and/or naturally occurring uracil.

In further embodiments, the ORF of the mRNA encoding a target polypeptide of the invention comprises 5-methoxyuracil and has an adjusted uracil content containing less uracil pairs (UU) and/or uracil triplets (UUU) and/or uracil quadruplets (UUUU) than the corresponding wild-type nucleotide sequence encoding the target polypeptide. In some embodiments, the ORF of the mRNA encoding a target polypeptide of the invention contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the target polypeptide. In a particular embodiment, the ORF of the mRNA encoding the target polypeptide of the invention contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the the ORF of the mRNA encoding the target polypeptide contains no non-phenylalanine uracil pairs and/or triplets.

In further embodiments, the ORF of the mRNA encoding a target polypeptide of the invention comprises 5-methoxyuracil and has an adjusted uracil content containing less uracil-rich clusters than the corresponding wild-type nucleotide sequence encoding the target polypeptide. In some embodiments, the ORF of the mRNA encoding the target polypeptide of the invention contains uracil-rich clusters that are shorter in length than corresponding uracil-rich clusters in the corresponding wild-type nucleotide sequence encoding the target polypeptide.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the target polypeptide-encoding ORF of the 5-methoxyuracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the target polypeptide is substituted with an alternative codon having a codon frequency lower than the codon frequency of the substituted codon in the synonymous codon set.

In some embodiments, the adjusted uracil content, of the target polypeptide-encoding ORF of the 5-methoxyuracil-comprising mRNA exhibits expression levels of the target protein when administered to a mammalian cell that are higher than expression levels of the target protein from the corresponding wild-type mRNA. In other embodiments, the expression levels of the target protein when administered to a mammalian cell are increased relative to a corresponding mRNA containing at least 95% 5-methoxyuracil and having a uracil content of about 160%, about 170%, about 180%, about 190%, or about 200% of the theoretical minimum. In yet other embodiments, the expression levels of the target protein when administered to a mammalian cell are increased relative to a corresponding mRNA, wherein at least about 50%, at least about 60%, at least about 70%, at least about 80%, at least about 90%, or about 100% of uracils are 1-methylpseudouracil or pseudouracils. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, a target protein is expressed when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or about 0.15 mg/kg. In some embodiments, the mRNA is administered intravenously or intramuscularly. In other embodiments, the target polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, a target polypeptide-encoding ORF of the 5-methoxyuracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present invention induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for a target polypeptide but does not comprise 5-methoxyuracil under the same conditions, or relative to the immune response induced by an mRNA that encodes for a target polypeptide and that comprises 5-methoxyuracil but that does not have adjusted uracil content under the same conditions. The innate immune response can be manifested by increased expression of pro-inflammatory cytokines, activation of intracellular PRRs (RIG-I, MDA5, etc), cell death, and/or termination or reduction in protein translation. In some embodiments, a reduction in the innate immune response can be measured by expression or activity level of Type 1 interferons (e.g., IFN-$\alpha$, IFN-$\beta$, IFN-$\kappa$, IFN-$\delta$, IFN-$\epsilon$, IFN-$\tau$, IFN-$\omega$, and IFN-$\zeta$) or the expression of interferon-regulated genes such as the toll-like receptors (e.g., TLR7 and TLR8), and/or by decreased cell death following one or more administrations of the mRNA of the invention into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes a target polypeptide but does not comprise 5-methoxyuracil, or to an mRNA that encodes a target polypeptide and that comprises 5-methoxyuracil but that does not have adjusted uracil content. In some embodiments, the interferon is IFN-$\beta$. In some embodiments, cell death frequency cased by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for a target polypeptide but does not comprise 5-methoxyuracil, or an mRNA that encodes for a target polypeptide and that comprises 5-methoxyuracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

In some embodiments, the polynucleotide is an mRNA that comprises an ORF that encodes a target polypeptide, wherein uracil in the mRNA is at least about 95% 5-methoxyuracil, wherein the uracil content of the ORF is between about 115% and about 135% of the theoretical minimum uracil content in the corresponding wild-type ORF, and wherein the uracil content in the ORF encoding the target polypeptide is less than about 23% of the total nucleobase content in the ORF. In some embodiments, the ORF that encodes the target polypeptide is further modified to decrease G/C content of the ORF (absolute or relative) by at least about 40%, as compared to the corresponding wild-type ORF. In yet other embodiments, the ORF encoding the target polypeptide contains less than 20 non-phenylalanine uracil pairs and/or triplets. In some embodiments, at least one codon in the ORF of the mRNA encoding the target polypeptide is further substituted with an alternative codon having a codon frequency lower than the codon frequency of the substituted codon in the synonymous codon set. In some embodiments, the expression of the target polypeptide encoded by an mRNA comprising an ORF wherein uracil in the mRNA is at least about 95% 5-methoxyuracil, and wherein the uracil content of the ORF is between about 115% and about 135% of the theoretical minimum uracil content in the corresponding wild-type ORF, is increased by at least about 10-fold when compared to expression of the target polypeptide from the corresponding wild-type mRNA. In some embodiments, the mRNA comprises an open ORF wherein uracil in the mRNA is at least about 95% 5-methoxyuracil, and wherein the uracil content of the ORF is between about 115% and about 135% of the theoretical minimum uracil content in the corresponding wild-type ORF, and wherein the mRNA does not substantially induce an innate immune response of a mammalian cell into which the mRNA is introduced.

In certain embodiments, the chemical modification is at nucleobases in the polynucleotides (e.g., RNA polynucleotide, such as mRNA polynucleotide). In some embodiments, modified nucleobases in the polynucleotide (e.g., RNA polynucleotide, such as mRNA polynucleotide) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide (e.g., RNA polynucleotide, such as mRNA polynucleotide) comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide (e.g., RNA polynucleotide, such as mRNA polynucleotide) comprises 1-ethyl-pseudouridine (e1ψ). In some embodiments, the polynucleotide (e.g., RNA polynucleotide, such as mRNA polynucleotide) comprises 1-methyl-pseudouridine (m1ψ) and 5-methyl-cytidine (m5C). In some embodiments, the polynucleotide (e.g., RNA polynucleotide, such as mRNA polynucleotide) comprises 1-ethyl-pseudouridine (e1ψ) and 5-methyl-cytidine (m5C). In some embodiments, the polynucleotide (e.g., RNA polynucleotide, such as mRNA polynucleotide) comprises 2-thiouridine (s2U). In some embodiments, the polynucleotide (e.g., RNA polynucleotide, such as mRNA polynucleotide) comprises 2-thiouridine and 5-methyl-cytidine (m5C). In some embodiments, the polynucleotide (e.g., RNA polynucleotide, such as mRNA polynucleotide) comprises methoxy-uridine (mo5U). In some embodiments, the polynucleotide (e.g., RNA polynucleotide, such as mRNA polynucleotide) comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide (e.g., RNA polynucleotide, such as mRNA polynucleotide) comprises 2'-O-methyl uridine and 5-methyl-cytidine (m5C). In some embodiments, the polynucleotide (e.g., RNA polynucleotide, such as mRNA polynucleotide) comprises N6-methyl-adenosine (m6A). In some embodiments, the polynucleotide (e.g., RNA polynucleotide, such as mRNA polynucleotide) comprises N6-methyl-adenosine (m6A) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the chemically modified nucleosides in the open reading frame are selected from the group consisting of uridine, adenine, cytosine, guanine, and any combination thereof.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenine (m6A), and 2,6-Diaminopurine.

In some embodiments, a modified nucleobase is a modified guanine. Example nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the nucleobase modified nucleotides in the polynucleotide (e.g., RNA polynucleotide, such as mRNA polynucleotide) are 5-methoxyuridine.

In some embodiments, the polynucleotide (e.g., RNA polynucleotide, such as mRNA polynucleotide) includes a combination of at least two (e.g., 2, 3, 4 or more) of modified nucleobases.

In some embodiments, the polynucleotide (e.g., RNA polynucleotide, such as mRNA polynucleotide) comprises 5-methoxyuridine (5mo5U) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methoxyuridine, meaning that substantially all uridine residues in the mRNA sequence are replaced with 5-methoxyuridine. Similarly, a polynucleotide can be uniformly modified for any type of nucleoside residue present in the sequence by replacement with a modified residue such as any of those set forth above.

In some embodiments, the modified nucleobase is a modified cytosine.

In some embodiments, a modified nucleobase is a modified uracil. Example nucleobases and nucleosides having a modified uracil include 5-methoxyuracil.

In some embodiments, a modified nucleobase is a modified adenine.

In some embodiments, a modified nucleobase is a modified guanine.

In some embodiments, the polynucleotides can include any useful linker between the nucleosides. Such linkers, including backbone modifications, that are useful in the composition of the present disclosure include, but are not limited to the following: 3'-alkylene phosphonates, 3'-amino phosphoramidate, alkene containing backbones, aminoalkylphosphoramidates, aminoalkylphosphotriesters, boranophosphates, —$CH_2$—O—N($CH_3$)—$CH_2$—, —$CH_2$—N($CH_3$)—N($CH_3$)—$CH_2$—, —$CH_2$—NH—$CH_2$—, chiral phosphonates, chiral phosphorothioates, formacetyl and thioformacetyl backbones, methylene (methylimino), methylene formacetyl and thioformacetyl backbones, methyleneimino and methylenehydrazino backbones, morpholino linkages, —N($CH_3$)—$CH_2$—$CH_2$—, oligonucleosides with heteroatom internucleoside linkage, phosphinates, phosphoramidates, phosphorodithioates, phosphorothioate internucleoside linkages, phosphorothioates, phosphotriesters, PNA, siloxane backbones, sulfamate backbones, sulfide sulfoxide and sulfone backbones, sulfonate and sulfonamide backbones, thionoalkylphosphonates, thionoalkylphosphotriesters, and thionophosphoramidates.

The modified nucleosides and nucleotides (e.g., building block molecules), which can be incorporated into a polynucleotide (e.g., RNA or mRNA, as described herein), can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), —O($CH_2CH_2O$).$CH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threo-furanosyl-(3'→2)), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar. Such sugar modifications are taught International Patent Publication Nos. WO2013/052523 and WO2014/093924, the contents of each of which are incorporated herein by reference in their entireties.

The polynucleotides of the invention (e.g., a polynucleotide comprising a nucleotide sequence encoding a target polypeptide or a functional fragment or variant thereof) can include a combination of modifications to the sugar, the nucleobase, and/or the internucleoside linkage. These combinations can include any one or more modifications described herein.

In some embodiments, polynucleotides function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. The basic components of an mRNA molecule typically include at least one coding region, a 5' untranslated region (UTR), a 3' UTR, a 5' cap and a poly-A tail. Polynucleotides may function as mRNA but can be distinguished from wild-type mRNA in their functional and/or structural design features which serve to overcome existing problems of effective polypeptide expression using nucleic-acid based therapeutics.

The mRNA, as provided herein, comprises at least one (one or more) ribonucleic acid (RNA) polynucleotide having an open reading frame encoding at least one polypeptide of interest. In some embodiments, a RNA polynucleotide of an mRNA encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 polypeptides. In some embodiments, a RNA polynucleotide of an mRNA encodes at least 10, 20, 30, 40, 50, 60, 70, 80, 90 or 100 polypeptides. In some embodiments, a RNA polynucleotide of an mRNA encodes at least 100 or at least 200 polypeptides.

Untranslated regions (UTRs) are nucleic acid sections of a polynucleotide before a start codon (5'UTR) and after a stop codon (3'UTR) that are not translated. In some embodiments, a polynucleotide (e.g., a ribonucleic acid (RNA), e.g., a messenger RNA (mRNA)) of the invention comprising an open reading frame (ORF) encoding a target polypeptide further comprises UTR (e.g., a 5'UTR or functional fragment thereof, a 3'UTR or functional fragment thereof, or a combination thereof).

A UTR can be homologous or heterologous to the coding region in a polynucleotide. In some embodiments, the UTR is homologous to the ORF encoding the target polypeptide. In some embodiments, the UTR is heterologous to the ORF encoding the target polypeptide. In some embodiments, the polynucleotide comprises two or more 5'UTRs or functional fragments thereof, each of which have the same or different nucleotide sequences. In some embodiments, the polynucleotide comprises two or more 3'UTRs or functional fragments thereof, each of which have the same or different nucleotide sequences.

In some embodiments, the 5'UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5'UTR or 3'UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG, where R is a purine (adenine or guanine) three bases upstream of the start codon (AUG), which is followed by another 'G'. 5'UTRs also have been known to form secondary structures that are involved in elongation factor binding.

By engineering the features typically found in abundantly expressed genes of specific target organs, one can enhance the stability and protein production of a polynucleotide. For example, introduction of 5'UTR of liver-expressed mRNA, such as albumin, serum amyloid A, Apolipoprotein A/B/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5'UTR and the 3'UTR can be heterologous. In some embodiments, the 5'UTR can be derived from a different species than the 3'UTR. In some embodiments, the 3'UTR can be derived from a different species than the 5'UTR.

Co-owned International Patent Application No. PCT/US2014/021522 (Publ. No. WO2014/164253, incorporated herein by reference in its entirety) provides a listing of exemplary UTRs that can be utilized in the polynucleotide of the present invention as flanking regions to an ORF.

Exemplary UTRs of the application include, but are not limited to, one or more 5'UTR and/or 3'UTR derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., eIF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial H$^+$-ATP synthase); a growth hormone e (e.g., bovine (bGH) or human (hGH)); an elongation factor (e.g., elongation factor 1 α1 (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nntl); calreticulin (Calr); a procollagen-lysine, 2-oxoglutarate 5-dioxygenase 1 (Plod1); and a nucleobindin (e.g., Nucb1).

In some embodiments, the 5'UTR is selected from the group consisting of a β-globin 5'UTR; a 5'UTR containing a strong Kozak translational initiation signal; a cytochrome b-245 α polypeptide (CYBA) 5'UTR; a hydroxysteroid (1743) dehydrogenase (HSD17B4) 5'UTR; a Tobacco etch virus (TEV) 5'UTR; a Venezuelen equine encephalitis virus (TEEV) 5'UTR; a 5' proximal open reading frame of rubella virus (RV) RNA encoding nonstructural proteins; a Dengue virus (DEN) 5'UTR; a heat shock protein 70 (Hsp70) 5'UTR; a eIF4G 5'UTR; a GLUT1 5'UTR; functional fragments thereof and any combination thereof.

In some embodiments, the 3'UTR is selected from the group consisting of a β-globin 3'UTR; a CYBA 3'UTR; an albumin 3'UTR; a growth hormone (GH) 3'UTR; a VEEV 3'UTR; a hepatitis B virus (HBV) 3'UTR; α-globin 3'UTR; a DEN 3'UTR; a PAV barley yellow dwarf virus (BYDV-PAV) 3'UTR; an elongation factor 1 α1 (EEF1A1) 3'UTR; a manganese superoxide dismutase (MnSOD) 3'UTR; a β subunit of mitochondrial H(+)-ATP synthase (β-mRNA) 3'UTR; a GLUT1 3'UTR; a MEF2A 3'UTR; a β-F1-ATPase 3'UTR; functional fragments thereof and combinations thereof.

Wild-type UTRs derived from any gene or mRNA can be incorporated into the polynucleotides of the invention. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, and sequences available at www.addgene.org/Derrick_Rossi/, the contents of each are incorporated herein by reference in their entirety. UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5'UTR or 3'UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the invention comprise a 5'UTR and/or a 3'UTR selected from any of the UTRs disclosed herein. In some embodiments, the 5'UTR and/or the 3' UTR comprise:

| Name: | SEQ ID NO: |
|---|---|
| 5'UTR-001 (Upstream UTR)<br>GGGAAAUAAGAGAGAAAAGAAGAGUAAGAAGAAAUAUAAGAGCCACC | 1 |
| 5'UTR-002 (Upstream UTR)<br>GGGAGAUCAGAGAGAAAAGAAGAGUAAGAAGAAAUAUAAGAGCCACC | 2 |
| 5'UTR-003 (Upstream UTR) GGAAUAAAAGUCUCAACACAACAUAUACAAA<br>ACAAACGAAUCUCAAGCAAUCAAGCAUUCUACUUCUAUUGCAGCAAUUU<br>AAAUCAUUUCUUUUAAAGCAAAAGCAAUUUUCUGAAAAUUUUCACCAUUU<br>ACGAACGAUAGCAAC | 3 |
| 5'UTR-004 (Upstream UTR)<br>GGGAGACAAGCUUGGCAUUCCGGUACUGUUGGUAAAGCCACC | 4 |
| 5'UTR-005 (Upstream UTR)<br>GGGAGAUCAGAGAGAAAAGAAGAGUAAGAAGAAAUAUAAGAGCCACC | 5 |
| 5'UTR-006 (Upstream UTR)<br>GGAAUAAAAGUCUCAACACAACAUAUACAAAACAAACGAAUCUCAAGC<br>AAUCAAGCAUUCUACUUCUAUUGCAGCAAUUUAAAUCAUUUCUUUUAAA<br>GCAAAAGCAAUUUUCUGAAAAUUUUCACCAUUUACGAACGAUAGCAAC | 6 |
| 5'UTR-007 (Upstream UTR)<br>GGGAGACAAGCUUGGCAUUCCGGUACUGUUGGUAAAGCCACC | 7 |
| 5'UTR-008 (Upstream UTR)<br>GGGAAUUAACAGAGAAAAGAAGAGUAAGAAGAAAUAUAAGAGCCACC | 8 |
| 5'UTR-009 (Upstream UTR)<br>GGGAAAUUAGACAGAAAAGAAGAGUAAGAAGAAAUAUAAGAGCCACC | 9 |
| 5'UTR-010 (Upstream UTR)<br>GGGAAAUAAGAGAGUAAAGAACAGUAAGAAGAAAUAUAAGAGCCACC | 10 |
| 5'UTR-011 (Upstream UTR)<br>GGGAAAAAGAGAGAAAAGAAGACUAAGAAGAAAUAUAAGAGCCACC | 11 |
| 5'UTR-012 (Upstream UTR)<br>GGGAAAUAAGAGAGAAAAGAAGAGUAAGAAGAUAUAUAAGAGCCACC | 12 |
| 5'UTR-013 (Upstream UTR)<br>GGGAAAUAAGAGACAAAACAAGAGUAAGAAGAAAUAUAAGAGCCACC | 13 |
| 5'UTR-014 (Upstream UTR)<br>GGGAAAUUAGAGAGUAAAGAACAGUAAGUAGAAUUAAAGAGCCACC | 14 |
| 5'UTR-015 (Upstream UTR)<br>GGGAAAUAAGAGAGAAUAGAAGAGUAAGAAGAAAUAUAAGAGCCACC | 15 |
| 5'UTR-016 (Upstream UTR)<br>GGGAAAUAAGAGAGAAAAGAAGAGUAAGAAGAAAAUUAAGAGCCACC | 16 |
| 5'UTR-017 (Upstream UTR)<br>GGGAAAUAAGAGAGAAAAGAAGAGUAAGAAGAAAUUUAAGAGCCACC | 17 |
| 5'UTR-018 (Upstream UTR)<br>UCAAGCUUUUGGACCCUCGUACAGAAGCUAAUACGACUCACUAUAGGG<br>AAAUAAGAGAGAAAAGAAGAGUAAGAAGAAAUAUAAGAGCCACC | 18 |
| 142-3p 5'UTR-001 (Upstream UTR including miR142-3p binding site)<br>UGAUAAUAGUCCAUAAAGUAGGAAACACUACAGCUGGAGCCUCGG<br>UGGCCAUGCUUCUUGCCCCUUGGGCCUCCCCCCAGCCCCUCCUCCCC<br>UUCCUGCACCCGUACCCCCGUGGUCUUUGAAUAAAGUCUGAGUGGGCGGC | 19 |
| 142-3p 5'UTR-002 (Upstream UTR including miR142-3p binding site)<br>UGAUAAUAGGCUGGAGCCUCGGUGGCUCCAUAAAGUAGGAAACACU<br>ACACAUGCUUCUUGCCCCUUGGGCCUCCCCCCAGCCCCUCCUCCCCUU<br>CCUGCACCCGUACCCCCGUGGUCUUUGAAUAAAGUCUGAGUGGGCGGC | 20 |

| Name: | SEQ ID NO: |
|---|---|
| 142-3p 5'UTR-003 (Upstream UTR including miR142-3p binding site)<br>UGAUAAUAGGCUGGAGCCUCGGUGGCCAUGCUUCUUGCCCCUUCCAU<br>AAAGUAGGAAACACUACAUGGGCCUCCCCCCAGCCCCUCCUCCCCUUC<br>CUGCACCCGUACCCCCGUGGUCUUUGAAUAAAGUCUGAGUGGGCGGC | 21 |
| 142-3p 5'UTR-004 (Upstream UTR including miR142-3p binding site)<br>UGAUAAUAGGCUGGAGCCUCGGUGGCCAUGCUUCUUGCCCCUUGGGC<br>CUCCCCCCAGUCCAUAAAGUAGGAAACACUACACCCCUCCUCCCCUUC<br>CUGCACCCGUACCCCCGUGGUCUUUGAAUAAAGUCUGAGUGGGCGGC | 22 |
| 142-3p 5'UTR-005 (Upstream UTR including miR142-3p binding site)<br>UGAUAAUAGGCUGGAGCCUCGGUGGCCAUGCUUCUUGCCCCUUGGGCC<br>UCCCCCCAGCCCCUCCUCCCCUUCUCCAUAAAGUAGGAAACACUACACU<br>GCACCCGUACCCCCGUGGUCUUUGAAUAAAGUCUGAGUGGGCGGC | 23 |
| 142-3p 5'UTR-006 (Upstream UTR including miR142-3p binding site)<br>UGAUAAUAGGCUGGAGCCUCGGUGGCCAUGCUUCUUGCCCCUUGGGCC<br>UCCCCCCAGCCCCUCCUCCCCUUCCUGCACCCGUACCCCCUCCAUAAAGU<br>AGGAAACACUACAGUGGUCUUUGAAUAAAGUCUGAGUGGGCGGC | 24 |
| 142-3p 5'UTR-007 (Upstream UTR including miR142-3p binding site)<br>UGAUAAUAGGCUGGAGCCUCGGUGGCCAUGCUUCUUGCCCCUUGGGCCU<br>CCCCCCAGCCCCUCCUCCCCUUCCUGCACCCGUACCCCCGUGGUCUUUGAA<br>UAAAGUUCCAUAAAGUAGGAAACACUACACUGAGUGGGCGGC | 25 |
| 3'UTR comprises: 3'UTR-001 (Creatine Kinase UTR)<br>GCGCCUGCCCACCUGCCACCGACUGCUGGAACCCAGCCAGUGGGAGGGCCU<br>GGCCCACCAGAGUCCUGCUCCCUCACUCCUCGCCCCGCCCCUGUCCCAGAG<br>UCCCACCUGGGGUCUCUCCACCCUUCUCAGAGUUCCAGUUUCAACCAGAG<br>UUCCAACCAAUGGGCUCCAUCCUCUGGAUUCUGGCCAAUGAAUAUCUCCCU<br>GGCAGGGUCCUCUUCUUUUCCCAGAGCUCCACCCCAACCAGGAGCUCUAGUU<br>AAUGGAGAGCUCCCAGCACACUCGGAGCUUGUGCUUUGUCUCCACGCAAAGC<br>GAUAAAUAAAAGCAUUGGUGGCCUUUGGUCUUUGAAUAAAGCCUGAGUAGG<br>AAGUCUAGA | 26 |
| 3'UTR-002 (Myoglobin UTR)<br>GCCCUGCCGCUCCCACCCCCACCCAUCUGGGCCCCGGGUUCAAGAGAGAG<br>CGGGGUCUGAUCUCGUGUAGCCAUAUAGAGUUUGCUUCUGAGUGUCUGCU<br>UUGUUUAGUAGAGGUGGGCAGGAGGAGCUGAGGGGCUGGGGUGU<br>UGAAGUUGGCUUUGCAUGCCCAGCGAUGCGCCUCCCUGUGGGAUGUCAUCA<br>CCCUGGGAACCGGGAGUGGCCCUUGGCUCACUGUGUUCUGCAUGGUUUGGA<br>UCUGAAUUAAUUGUCCUUUCUUCUAAAUCCCAACCGAACUUCUUCCAACCU<br>CCAAACUGGCUGUAACCCCAAAUCCAAGCCAUUAACUACACCUGACAGUAG<br>CAAUUGUCUGAUUAAUCACUGGCCCCUUGAAGACAGCAGAAUGUCCCUUUG<br>CAAUGAGGAGGAGAUCUGGGCUGGGCGGGCCAGCUGGGGAAGCAUUUGACU<br>AUCUGGAACUUGUGUGUGCCUCCUCAGGUAUGGCAGUGACUCACCUGGUUU<br>UAAUAAAACAACCUGCAACAUCUCAUGGUCUUUGAAUAAAGCCUGAGUAGG<br>AAGUCUAGA | 27 |
| 3'UTR-003 (α-actin UTR)<br>ACACACUCCACCUCCAGCACGCGACUUCUCAGGACGACGAAUCUUCUCAAUG<br>GGGGGCGGCUGAGCUCCAGCCACCCCGCAGUCACUUUCUUUGUAACAACUU<br>CCGUUGCUGCCAUCGUAAACUGACACAGUGUUUAUAACGUGUACAUACAUUA<br>ACUUAUUACCUCAUUUUGUUAUUUUUCGAAACAAAGCCCUGUGGAAGAAAAU<br>GGAAAACUUGAAGAAGCAUUAAAGUCAUUCUGUUAAGCUGCGUAAAUGGUCU<br>UUGAAUAAAGCCUGAGUAGGAAGUCUAGA | 28 |
| 3'UTR-004 (Albumin UTR)<br>CAUCACAUUUAAAAGCAUCUCAGCCUACCAUGAGAAUAAGAGAAAGAAAAUG<br>AAGAUCAAAAGCUUAUUCAUCUGUUUUUCUUUUUCGUUGGUGUAAAGCCAAC<br>ACCCUGUCUAAAAAACAUAAAUUUCUUUAAUCAUUUUGCCUCUUUUCUCUGU<br>GCUUCAAUUAAUAAAAAAUGGAAAGAAUCUAAUAGAGUGGUACAGCACUGUU<br>AUUUUUCAAAGAUGUGUUGCUAUCCUGAAAAUUCUGUAGGUUCUGUGGAAGU<br>UCCAGUGUUCUCUCUUAUUCCACUUCGGUAGAGGAUUUCUAGUUUCUUGUGGG<br>CUAAUUAAAAAUCAUUAAUACUCUUCUAAUGGUCUUUGAAUAAAGCCUGA<br>GUAGGAAGUCUAGA | 29 |

| Name: | SEQ ID NO: |
|---|---|
| 3'UTR-005 (α-globin UTR)<br>GCUGCCUUCUGCGGGGCUUGCCUUCUGGCCAUGCCCUUCUUCUCUCCCUUGCA<br>CCUGUACCUCUUGGUCUUUGAAUAAAGCCUGAGUAGGAAGGCGGCCGCUCGA<br>GCAUGCAUCUAGA | 30 |
| 3'UTR-006 (G-CSF UTR)<br>GCCAAGCCCUCCCCAUCCCAUGUAUUUAUCUCUAUUUAAUAUUUAUGUCUAU<br>UUAAGCCUCAUAUUUAAAGACAGGGAAGAGCAGAACGGAGCCCCAGGCCUCU<br>GUGUCCUUCCCUGCAUUUCUGAGUUUCAUUCUCCUGCCUGUAGCAGUGAGAA<br>AAAGCUCCUGUCCUCCCAUCCCCUGGACUGGGAGGUAGAUAGGUAAAUACCA<br>AGUAUUUAUUACUAUGACUGCUCCCCAGCCCUGGCUCUGCAAUGGGCACUGG<br>GAUGAGCCGCUGUGAGCCCCUGGUCCUGAGGGUCCCCACCUGGGACCCUUGA<br>GAGUAUCAGGUCUCCCACGUGGGAGACAAGAAAUCCCUGUUUAAUAUUUAAA<br>CAGCAGUGUUCCCCAUCUGGGUCCUUGCACCCCUCACUCUGGCCUCAGCCGAC<br>UGCACAGCGGCCCCUGCAUCCCCUUGGCUGUGAGGCCCCUGGACAAGCAGAGG<br>UGGCCAGAGCUGGGAGGCAUGGCCCUGGGGUCCCACGAAUUUGCUGGGGAAU<br>CUCGUUUUUCUUCUUAAGACUUUUGGGACAUGGUUUGACUCCCGAACAUCAC<br>CGACGCGUCUCCUGUUUUUCUGGGUGGCCUCGGGACACCUGCCCUGCCCCCAC<br>GAGGGUCAGGACUGUGACUCUUUUUAGGGCCAGGCAGGUGCCUGGACAUUUG<br>CCUUGCUGGACGGGACUGGGGAUGUGGGAGGGAGCAGACAGGAGGAAUCAU<br>GUCAGGCCUGUGUGUGAAAGGAAGCUCCACUGUCACCCUCCACCUCUUCACCC<br>CCCACUCACCAGUGUCCCCUCCACUGUCACAUUGUAACUGAACUUCAGGAUAA<br>UAAAGUGUUUGCCUCCAUGGUCUUUGAAUAAAGCCUGAGUAGGAAGGCGGCC<br>GCUCGAGCAUGCAUCUAGA | 31 |
| 3'UTR-007 (Col1a2; collagen, type I, alpha 2 UTR)<br>ACUCAAUCUAAAUUAAAAAGAAAGAAAUUUGAAAAAACUUUCUCUUUGCC<br>AUUUCUUCUUCUUCUUUUUUAACUGAAAGCUGAAUCCUUCCAUUUCUUCUGCA<br>CAUCUACUUGCUUAAAUUGUGGGCAAAAGAGAAAAAGAAGGAUUGAUCAGAG<br>CAUUGUGCAAUACAGUUUCAUUAACUCCUUCCCCCGCUCCCCCAAAAAUUUGA<br>AUUUUUUUUCAACACUCUUACACCUGUUAUGGAAAAUGUCAACCUUUGUAA<br>GAAAACCAAAAUAAAAAUUGAAAAAUAAAAACCAUAAAACAUUUGCACCACUU<br>GUGGCUUUUGAAUAUCUUCCACAGAGGGAAGUUUAAAACCCAAACUUCCAAA<br>GGUUUAAACUACCUCAAAACACUUUCCCAUGAGUGUGAUCCACAUUGUUAGG<br>UGCUGACCUAGACAGAUGAACUGAGGUCCUUGUUUUGUUUUGUUCAUAAU<br>ACAAAGGUGCUAAUUAAUAGUAUUUCAGAUACUUGAAGAAUGUUGAUGGUGC<br>UAGAAGAAUUUGAGAAGAAAACUCCUGUAUUGAGUUGUAUCGUGUGGUGUA<br>UUUUUAAAAAAUUUGAUUUAGCAUUCAUAUUUUCCAUCUUAUUCCAAUUA<br>AAAGUAUGCAGAUUAUUGCCCAAAUCUUCUUCAGAUUCAGCAUUUGUUCUU<br>UGCCAGUCUCAUUUCAUCUUCUUCCAUGGUUCCACAGAAGCUUUGUUUCUUG<br>GGCAAGCAGAAAAUUAAAUUGUACCUAUUUUGUAUAUGUGAGAUGUUUAAA<br>UAAAUUGUGAAAAAAAUGAAAUAAAGCAUGUUUGGUUUUCCAAAAGAACAUAU | 32 |
| 3'UTR-008 (Col6a2; collagen, type VI, alpha 2 UTR)<br>CGCCGCCGCCCGGGCCCCGCAGUCGAGGGUCGUGAGCCCACCCCGUCCAUGGUG<br>CUAAGCGGGCCCGGGUCCCACACGGCCAGCACCGCUGCUCACUCGGACGACGCC<br>CUGGGCCUGCACCUCUCCAGCUCCUCCCACGGGGUCCCCGUAGCCCCGGCCCCC<br>GCCCAGCCCCAGGUCUCCCCAGGCCCUCCGCAGGCUGCCCGGCCUCCCUCCCCC<br>UGCAGCCAUCCCAAGGCUCCUGACCUACCUGGCCCCUGAGCUCUGGAGCAAGC<br>CCUGACCCAAUAAAGGCUUUGAACCCAU | 33 |
| 3'UTR-009 (RPN1; ribophorin I UTR)<br>GGGGCUAGAGCCCUCUCCGCACAGCGUGGAGACGGGGCAAGGAGGGGGGUUA<br>UUAGGAUUGUGGUUUUGUUUUGCUUUGUUUAAAGCCGUGGGAAAAUGGCAC<br>AACUUUACCUCUGUGGGAGAUGCAACACUGAGAGCCAAGGGGUGGGAGUUGG<br>GAUAAUUUUUAUAUAAAAGAAGUUUUUCCACUUUGAAUUGCUAAAAGUGGCA<br>UUUUUCCUAUGUGCAGUCACUCCUCUCAUUUCUAAAAUAGGGACGUGGCCAGG<br>CACGGUGGCUCAUGCCUGUAAUCCCAGCACUUUGGGAGGCCGAGGCAGGCGG<br>UCACGAGGUCAGGAGAUCGAGACUAUCCUGGCUAACACGGUAAAACCCUGUCU<br>CUACUAAAAGUACAAAAAAUUAGCUGGGCGUGGUGGGCACCUGUAGUCCC<br>AGCUACUCGGGAGGCUGAGGCAGGAGAAAGGCAUGAAUCCAAGAGGCAGAGCU<br>UGCAGUGAGCUGAGAUCACGCCAUUGCACUCCAGCCUGGGCAACAGUGUUAAG<br>ACUCUGUCUCAAAUAUAAAAUAAAUAAAUAAAUAAAUAAAUAAAUAAAA<br>AUAAAGCGAGAUGUUGCCCUCAAA | 34 |
| 3'UTR-010 (LRP1; low density lipoprotein receptor-related protein 1 UTR)<br>GGCCCUGCCCCGUCGGACUGCCCCAGAAAGCCUCCUGCCCCCUGCCAGUGAAG<br>UCCUUCAGUGAGCCCCUCCCCAGCCAGCCCUUCCCUGGCCCCGCCGGAUGUAUA<br>AAUGUAAAAAUGAAGGAAUUACAUUUUAUAUGUGAGCGAGCAAGCCGGCAAGC<br>GAGCACAGUAUUAUUUCUCCAUCCCCUCCCUGCCUGCUCCUUGGCACCCCCAUG<br>CUGCCUUCAGGGAGACAGGCAGGGAGGGCUUGGGGCUGCACCUCCUACCCUCCC<br>ACCAGAACGCACCCCACUGGGAGAGCUGGUGGUGCAGCCUUCCCCUCCCUGUAU<br>AAGACACUUUGCCAAGGCUCUCCCCCUCUCGCCCCAUCCCUGCUUGCCCGCUCCCA | 35 |

| Name: | SEQ ID NO: |
|---|---|
| CAGCUUCCUGAGGGCUAAUUCUGGGAAGGGAGAGUUCUUUGCUGCCCCUGUCU<br>GGAAGACGUGGCUCUGGGUGAGGUAGGCGGGAAAGGAUGGAGUGUUUUAGUU<br>CUUGGGGGAGGCCACCCCAAACCCCAGCCCCAACUCCAGGGGCACCUAUGAGAU<br>GGCCAUGCUCAACCCCCCUCCCAGACAGGCCCUCCCUGUCUCCAGGGCCCCCAC<br>CGAGGGUUCCCAGGGCUGGAGACUUCCUCUGGUAAACAUUCCUCCAGCCUCCCC<br>UCCCCUGGGGACGCCAAGGAGGUGGGCCACACCCAGGAAGGGAAAGCGGGCAG<br>CCCCGUUUGGGGACGUGAACGUUUUAAUAAUUUUUGCUGAAUUCCUUUACAA<br>CUAAAUAACACAGAUAUUGUUAUAAAUAAAAUUGU | |
| 3'UTR-011 (Nnt1; cardiotrophin-like cytokine factor 1 UTR)<br>AUAUUAAGGAUCAAGCUGUUAGCUAAUAAUGCCACCUCUGCAGUUUUGGGAA<br>CAGGCAAAUAAAGUAUCAGUAUACAUGGUGAUGUACAUCUGUAGCAAAGCUC<br>UUGGAGAAAAUGAAGACUGAAGAAAGCAAAGCAAAAACUGUAUAGAGAGAUU<br>UUUCAAAAGCAGUAAUCCCUCAAUUUUAAAAAAGGAUUGAAAAUUCUAAAUG<br>UCUUUCUGUGCAUAUUUUUGUGUUAGGAAUCAAAAGUAUUUUAUAAAAGGA<br>GAAAGAACAGCCUCAUUUUAGAUGUAGUCCUGUUGGAUUUUUAUGCCUCCUC<br>AGUAACCAGAAAUGUUUUAAAAAACUAAGUGUUUAGGAUUUCAAGACAACAUU<br>AUACAUGGCUCUGAAAUAUCUGACACAAUGUAAACAUUGCAGGCACCUGCAU<br>UUAUGUUUUUUUUUCAACAAAUGUGACUAAUUUGAAACUUUUAUGAACUUCU<br>GAGCUGUCCCCUUGCAAUUCAACCGCAGUUUGAAUUAAUCAUAUCAAAUCAGU<br>UUUAAUUUUUAAAUUGUACUUCAGAGUCUAUAUUUCAAGGGCACAUUUUCU<br>CACUACUAUUUUAAUACAUUAAAGGACUAAAUAAUCUUUCAGAGAUGCUGGA<br>AACAAAUCAUUUGCUUUAUAUGUUUCAUUAGAAUACCAAUGAAACAUACAAC<br>UUGAAAAUUAGUAAUAGUAUUUUUGAAGAUCCCAUUUCUAAUUGGAGAUCUC<br>UUUAAUUUCGAUCAACUUAUAAUGUGUAGUACUAUAUUAAGUGCACUUGAGU<br>GGAAUUCAACAUUUGACUAAUAAAAAUGAGUUCAUCAUGUUGGCAAGUGAUGU<br>GGCAAUUAUCUCUGGUGACAAAAGAGUAAAAUCAAAUAUUUCUGCCUGUUACA<br>AAUAUCAAGGAAGACCUGCUACUAUGAAAUAGAUGACAUUAAUCUGUCUUCAC<br>UGUUUAUAAUACGGAUGGAUUUUUUUUCAAACAGUGUGUGUUUUGAGGUCU<br>UAUGUAAUUGAUGACAUUUGAGAGAAAUGGUGGCUUUUUUUAGCUACCUCUU<br>UGUUCAUUUAAGCACCAGUAAAGAUCAUGUCUUUUUAUAGAAGUGUAGAUUU<br>UCUUUGUGACUUUGCUAUCGUGCCUAAAGCUCUAAAUAUAGGUGAAUGUGUGA<br>UGAAUACUCAGAUUAUUUGUCUCUCUAUAUAAUUAGUUUGGUACUAAGUUUC<br>UCAAAAAAUUAUUAACACAUGAAAGACAAUCUCUAAACCAGAAAAAGAAGUA<br>GUACAAAUUUUGUUACUGUAAUGCUCGCGUUUAGUGAGUUUAAAACACACAG<br>UAUCUUUUGGUUUUAUAAUCAGUUUCUAUUUUGCUGUGCCUGAGAUUAAGAU<br>CUGUGUAUGUGUGUGUGUGUGUGCGUUUGUGUGUUAAAGCAGAAAAGA<br>CUUUUUUAAAAGUUUUAAGUGAUAAAUGCAAUUUGUUAAUUGAUCUUAGAUC<br>ACUAGUAAACUCAGGGCUGAAUUAUACCAUGUAUAUUCUAUUAGAAGAAAGU<br>AAACACCAUCUUUAUUCCUGCCCUUUUUCUUCUCUCAAAGUAGUUGUAGUUA<br>UAUCUAGAAAGAAGCAAUUUUGAUUUCUUGAAAAGGUAGUUCCUGCACUCAG<br>UUUAAACUAAAAAUAAUCAUACUUGGAUUUUAUUUAUUUUUGUCAUAGUAAA<br>AAUUUUAAUUUAUAUAAUUUUUAUUUAGUAUUAUCUUAUUCUUUUGCUAUUU<br>GCCAAUCCUUUGUCAUCAAUUGUGUUAAAUGAAUUGAAAAUUCAUGCCCUGUU<br>CAUUUUAUUUUACUUUAUUGGUUAGGAUAUUUAAAGGAUUUUUGUAUAUAUA<br>AUUUCUUAAAUUAAUAUUCCAAAAGGUUAGUGGACUUAGAUUAUAAAUUAUG<br>GCAAAAAUCUAAAAACAACAAAAAUGAUUUUUAUACAUUCUAUUUCAUUAUU<br>CCUCUUUUUCCAAUAAGUCAUACAAUUGGUAGAUAUGACUUAUUUUAUUUUUG<br>UAUUAUUCACUAUAUCUUUAUGAUAUUUAAGUAUAAAUAAUUAAAAAAUUU<br>AUUGUACCUUAUAGUCUGUCACCAAAAAAAAAAAAUUAUCUGUAGGUAGUGAA<br>AUGCUAAAUGUUGAUUUGUCUUUAAGGGCUUGUUAACUAUCCUUUAUUUUCUCA<br>UUUGUCUUAAAUUAGGAGUUUGUGUUUAAAUUACUCAUCUAAGCAAAAAAUGU<br>AUAUAAAUCCCAUUACUGGGUAUAUACCCAAAGGAUUAUAAAUCAUGCUGCUA<br>UAAAGACACAUGCACACGUAUGUUUAUUGCAGCACUAUUCACAAUAGCAAAGA<br>CUUGGAACCAACCCAAAUGUCCAUCAAUGAUAGACUUGAUUAUGAAAAAUGUGC<br>ACAUAUACACCAUGGAAUACUAUGCAGCCAUAAAAAAGGAUGAGUUCAUGUCC<br>UUUGUAGGGACAUGGAUAAAGCUGGAAACCAUCAUUCUGAGCAAACUAUUGCA<br>AGGACAGAAAACCAAACACUGCAUGUUCUCACUCAUAGGUGGGAAUUGAACAA<br>UGAGAACACUUGGACACAAGGUGGGGAACACCACACACCAGGGCCUGUCAUGG<br>GGUGGGGGGAGUGGGGAGGGAUAGCAUUAGGAGAUAUACCUAAUGUAAAUGA<br>UGAGUUAAUGGGUGCAGCACACCAACAUGGCACAUGUAUACAUAUGUAGCAAA<br>CCUGCACGUUGUGCACAUGUACCCUAGAACUUAAAGUAUAAUUAAAAAAAAAA<br>AGAAAACAGAAGCUAUUUAUAAAGAAGUUAUUUGCUGAAAUAAAUGUGAUCU<br>UUCCCAUUUAAAAAAAAGAAAUUUUGGGGUAAAAAACACAAUAUUAUUGU<br>AUUCUUGAAAAAUUCUAAGAGAGUGGAUGUGAAGUGUUCUCACCACAAAAGUG<br>AUAACUAAUUGAGGUAAUGCACAUAUUAAUUAGAAAGAUUUUGUCAUUCCACA<br>AUGUAUAUACUUAAAAAUAUGUUAUACACAAUAAAUACAUACAUUAAAAA<br>AUAAGUAAAUGUA | 36 |
| 3'UTR-012 (Col6a1; collagen, type VI, alpha 1 UTR)<br>CCCACCCUGCACGCCGGCACCAAACCCUGUCCUCCCACCCCUCCCCACUCAUCA<br>CUAAACAGAGUAAAAUGUGAUGCGAAUUUCCCGACCAACCUGAUUCGCUAGA<br>UUUUUUUUAAGGAAAAGCUUGGAAAGCCAGGACACAACGCUGCUGCCUGCUUU<br>GUGCAGGGUCCUCCGGGGCUCAGCCCUGAGUUGGCAUCACCUGCGCAGGGCCC<br>UCUGGGGCUCAGCCCUGAGCUAGUGUCACCUGCACAGGGCCCUCUGAGGCUCA | 37 |

| Name: | SEQ ID NO: |
|---|---|
| GCCCUGAGCUGGCGUCACCUGUGCAGGGCCCUCUGGGGCUCAGCCCUGAGCUG<br>GCCUCACCUGGGUUCCCCACCCCGGGCUCUCCUGCCCUGCCCUCCUGCCCGCCC<br>UCCCUCCUGCCUGCGCAGCUCCUUCCCUAGGCACCUCUGUGCUGCAUCCCACCA<br>GCCUGAGCAAGACGCCCUCUCGGGCCUGUGCCGCACUAGCCUCCCUCUCCUCU<br>GUCCCCAUAGCUGGUUUUUCCCACCAAUCCUCACCUAACAGUUACUUUACAAUU<br>AAACUCAAAGCAAGCUCUUCUCCUCAGCUUGGGGCAGCCAUUGGCCUCUGUCUC<br>GUUUUGGGAAACCAAGGUCAGGAGGCCGUUGCAGACAUAAAUCUCGGCGACUC<br>GGCCCCGUCUCCUGAGGGUCCUGCUGGUGACCGGCCUGGACCUUGGCCCUACAG<br>CCCUGGAGGCCGCUGCUGACCAGCACUGACCCCGACCUCAGAGAGUACUCGCAG<br>GGGCGCUGGCUGCACUCAAGACCCUCGAGAUUAACGGUGCUAACCCCGUCUGCU<br>CCUCCCUCCCGCAGAGACUGGGGCCUGGACUGGACAUGAGAGCCCCUUGGUGCC<br>ACAGAGGGCUGUGUCUUACUAGAAACAACGCAAACCUCUCCUUCCUCAGAAUAG<br>UGAUGUGUUCGACGUUUUAUCAAAGGCCCCCUUUCUAUGUUCAUGUUAGUUUU<br>GCUCCUUCUGUGUUUUUUCUGAACCAUAUCCAUGUUGCUGACUUUUCCAAAU<br>AAAGGUUUUCACUCCUCUC | |
| 3'UTR-013 (Calr; calreticulin UTR)<br>AGAGGCCUGCCUCCAGGGCUGGACUGAGGCCUGAGCGCUCCUGCCGCAGAGCU<br>GGCCGCGCCAAAUAAUGUCUCUGUGAGACUCGAGAACUUUCAUUUUUUUCCAG<br>GCUGGUUCGGAUUUGGGUGGAUUUUGGUUUUGUUCCCCUCCCUCCACUCUCCC<br>CCACCCCCUCCCCGCCCUUUUUUUUUUUUUUUAAACUGGUAUUUUAUCUU<br>UGAUUCUCCUUCAGCCCUCACCCCUGGUUCUCAUCUUUCUUGAUCAACAUCUU<br>UUCUUGCCUCUGUCCCCUUCUCUCAUCUCUUAGCUCCCCUCCAACCUGGGGGG<br>CAGUGGUGUGGAGAAGCCACAGGCCUGAGAUUUCAUCUGCUCUCCUUCCUGGA<br>GCCCAGAGGAGGGCAGCAGAAGGGGGUGGUGUCUCCAACCCCCAGCACUGAG<br>GAAGAACGGGGCUCUUCUCAUUUCACCCCUCCCUUUCUCCCCUGCCCCCAGGAC<br>UGGGCCACUUCUGGGUGGGCAGUGGGUCCCAGAUUGGCUCACACUGAGAAUG<br>UAAGAACUACAAACAAAAUUUCUAUUAAAUUAAAUUUUGUGUCUCC | 38 |
| 3'UTR-014 (Col1a1; collagen, type I, alpha 1 UTR)<br>CUCCCUCCAUCCCAACCUGGCUCCCUCCCACCCAACCAACUUUCCCCCCAACCCG<br>GAAACAGACAAGCAACCCAAACUGAACCCCCUCAAAAGCCAAAAAAUGGGAGA<br>CAAUUUCACAUGGACUUUGGAAAAUAUUUUUUUCCUUUGCAUUCAUCUCUCAA<br>ACUUAGUUUUUAUCUUUGACCAACCGAACAUGACCAAAAACCAAAAGUGCAUU<br>CAACCUUACCAAAAAAAAAAAAAAAAAAAGAAUAAAUAAAUAACUUUUUAAAA<br>AAGGAAGCUUGGUCCACUUGCUUGAAGACCCAUGCGGGGGUAAGUCCCUUUCU<br>GCCCGUUGGGCUUAUGAAACCCCAAUGCUGCCCUUUCUGCUCCUUUCUCCACAC<br>CCCCCUUGGGGCCUCCCCUCCACUCCUUCCCAAAUCUGUCUCCCCAGAAGACAC<br>AGGAAACAAUGUAUUGUCUGCCCAGCAAUCAAAGGCAAUGCUCAAACACCCAA<br>GUGGCCCCCACCCUCAGCCCGCUCCUGCCCGCCCAGCACCCCCAGGCCCUGGGG<br>GACCUGGGGUUCUCAGACUGCAAAGAAGCCUUGCCAUCUGGCGCUCCCAUGG<br>CUCUUGCAACAUCUCCCCUUCGUUUUUGAGGGGGUCAUGCCGGGGGAGCCACC<br>AGCCCCUCACUGGGUUCGGAGGAGAGUCAGGAAGGGCCACGACAAAGCAGAAA<br>CAUCGGAUUUGGGGAACGCGUGUCAAUCCCUUGUGCCGCAGGGCUGGGCGGGA<br>GAGACUGUUCUGUUCCUUGUGUAACUGUGUUGCUGAAAGACUACCUCGUUCUU<br>GUCUUGAUGUGUCACCGGGGCAACUGCCUGGGGGCGGGGAUGGGGGCAGGGUG<br>GAAGCGGCUCCCCAUUUUAUACCAAAGGUGCUACAUCUAUGUGAUGGGUGGGG<br>UGGGGAGGGAAUCACUGGUGCUAUAGAAAUUGAGAUGCCCCCCCAGGCCAGCA<br>AAUGUUCCUUUUUGUUCAAAGUCUAUUUUUAUUCCUUGAUAUUUUCUUUUUU<br>UUUUUUUUUUUUGUGGAUGGGGACUUGUGAAUUUUUCUAAAGGUGCUAUUUA<br>ACAUGGGAGGAGAGCGUGUGCGGCUCCAGCCCAGCCGCUGCUCACUUUCCACC<br>CUCUCUCCACCUGCCUCUGGCUUCUCAGGCCUCUGCUCUCCGACCUCUCUCCUCU<br>GAAACCUCCUCCACAGCUGCAGCCCAUCCUCCCGGCUCCCUCCUAGUCUGUCCU<br>GCGUCCUCUGUCCCCGGGUUUCAGAGACAACUUCCCAAAGCACAAAGCAGUUUU<br>UCCCCCUAGGGGUGGGAGGAAGCAAAAGACUCUGUACCUAUUUUGUAUGUGUA<br>UAAUAAUUUGAGAUGUUUUUAAUUAUUUUGAUUGCUGGAAUAAAGCAUGUGG<br>AAAUGACCCAAACAUAAUCCGCAGUGGCCUCCUAAUUUCCUUCUUUGGAGUUG<br>GGGGAGGGGUAGACAUGGGAAGGGGCUUUGGGGUGAUGGGCUUGCCUUCCAU<br>UCCUGCCCUUUCCUCCCCACUAUUCUCUUCUAGAUCCCUCCAUAACCCCACUC<br>CCCCUUUCUCUCACCCUUCUUAUACCGCAAACCUUUCUACUUCCUCUUUCAUUUU<br>CUAUUCUUGCAAUUUCCUUGCACCUUUUUCAAAUCCUCUUCCCCUGCAAUAC<br>CAUACAGGCAAUCCACGUGCACAACACACACACACUCUUCACAUCUGGGGUU<br>GUCCAAACCUCAUACCCACUCCCCUUCAAGCCCAUCCACUCUCCACCCCCUGGA<br>UGCCCUGCACUGGUGGCGGUGGGAUGCUCAUGGAUACUGGGAGGGUGAGGGG<br>AGUGGAACCCGUGAGGAGGACCUGGGGGCCUCUCCUUGAACUGACAUGAAGGG<br>UCAUCUGGCCUCUGCUCCCUUCUCACCCACGCUGACCUCCUGCCGAAGGAGCAA<br>CGCAACAGGAGAGGGGUCUGCUGAGCCUGGCGAGGGUCUGGGAGGGACCAGGA<br>GGAAGGCGUGCUCCCUGCUCGCUGUCCUGGCCCUGGGGGAGUGAGGGAGACAG<br>ACACCUGGGAGAGCUGUGGGGAAGGCACUCGCACCGUGCUCUUGGGAAGGAAG<br>GAGACCUGGCCCUGCUCACCACGGACUGGGUGCCUCGACCUCCUGAAUCCCCAG<br>AACACAACCCCCUGGGCUGGGGUGGUCUGGGGAACCAUCGUGCCCCCGCCUCC<br>CGCCUACUCCUUUUUAAGCUU | 39 |

| Name: | SEQ ID NO: |
|---|---|
| 3'UTR-015 (Plod1; procollagen-lysine, 2-oxoglutarate 5-dioxygenase 1 UTR)<br>UUGGCCAGGCCUGACCCUCUUGGACCUUUCUUCUUUGCCGACAACCACUGCCCA<br>GCAGCCUCUGGGACCUCGGGGUCCCAGGGAACCCAGUCCAGCCUCCUGGCUGUU<br>GACUUCCCAUUGCUCUUGGAGCCACCAAUCAAAGAGAUUCAAAGAGAUUCCUGC<br>AGGCCAGAGGCGGAACACACCUUUAUGGCUGGGGCUCUCCGUGGUGUUCUGGAC<br>CCAGCCCCUGGAGACACCAUUCACUUUUACUGCUUUGUAGUGACUCGUGCUCUC<br>CAACCUGUCUUCCUGAAAAACCAAGGCCCCCUUCCCCCACCUCUUCCAUGGGGU<br>GAGACUUGAGCAGAACAGGGGCUUCCCCAAGUUGCCCAGAAAGACUGUCUGGG<br>UGAGAAGCCAUGGCCAGAGCUUCUCCCAGGCACAGGUGUUGCACCAGGGACUU<br>CUGCUUCAAGUUUUGGGGUAAAGACACCUGGAUCAGACUCCAAGGGCUGCCCU<br>GAGUCUGGGACUUCUGCCUCCAUGGCUGGUCAUGAGAGCAAACCGUAGUCCCC<br>UGGAGACAGCGACUCCAGAGAACCUCUUGGGAGACAGAAGAGGCAUCUGUGCA<br>CAGCUCGAUCUUCUACUUGCCUGUGGGGAGGGGAGUGACAGGUCCACACACCA<br>CACUGGGUCACCCUGUCCUGGAUGCCUCUGAAGAGAGGGACAGACCGUCAGAA<br>ACUGGAGAGUUUCUAUUAAAGGUCAUUUAAACCA | 40 |
| 3'UTR-016 (Nucb1; nucleobindin 1 UTR)<br>UCCUCCGGGACCCCAGCCCUCAGGAUUCCUGAUGCUCCAAGGCGACUGAUGGGC<br>GCUGGAUGAAGUGGCACAGUCAGCUUCCCUGGGGGCUGGUGUCAUGUUGGGCU<br>CCUGGGGCGGGGGCACGGCCUGGCAUUUCACGCAUUGCUGCCACCCCAGGUCCA<br>CCUGUCUCCACUUUCACAGCCUCCAAGUCUGUGGCUCUUCCCUUCUGUCCUCCG<br>AGGGGCUUGCCUUCUCUCGUGUCCAGUGAGGUGCUCAGUGAUCGGCUUAACUU<br>AGAGAAGCCCGCCCCCUCCCCUUCUCCGUCUGUCCCAAGAGGGUCUGCUCUGAG<br>CCUGCGUUCCUAGGUGGCUCGGCCUCAGCUGCCUGGGUUGUGGCCGCCCUAGCA<br>UCCUGUAUGCCCACAGCUACUGGAAUCCCCGCUGCUGCUCCGGGCCAAGCUUCU<br>GGUUGAUUAAUGAGGGCAUGGGGUGGUCCCUCAAGACCUUCCCCUACCUUUUG<br>UGGAACCAGUGAUGCCUCAAAGACAGUGUCCCCUCCACAGCUGGGGUGCCAGGG<br>GCAGGGGAUCCUCAGUAUAGCCGGUGAACCCUGAUACCAGGAGCCUGGGCCUC<br>CCUGAACCCCUGGCUUCCAGCCAUCUCAUCGCCAGCCUCCUCCUGGACCUCUUG<br>GCCCCCAGCCCCUUCCCCACACAGCCCCAGAAGGGUCCCAGAGCUGACCCCACU<br>CCAGGACCUAGGCCCAGCCCCUCAGCCUCAUCUGGAGCCCCUGAAGACCAGUCC<br>CACCCACCUUUCUGGCCUCAUCUGACACUGCUCCGCAUCCUGCUGUGUGUCCUG<br>UUCCAUGUUCCGGUUCCAUCCAAAUACACUUUCUGGAACAAA | 41 |
| 3'UTR-017 (α-globin)<br>GCUGGAGCCUCGGUGGCCAUGCUUCUUGCCCCUUGGGCCUCCCCCAGCCCCUC<br>CUCCCCUUCCUGCACCCGUACCCCGUGGUCUUUGAAUAAAGUCUGAGUGGGC<br>GGC | 42 |
| 3'UTR-018<br>UGAUAAUAGGCUGGAGCCUCGGUGGCCUAGCUUCUUGCCCCUUGGGCCUCCCC<br>CCAGCCCCUCCUCCCCUUCCUGCACCCGUACCCCGUGGUCUUUGAAUAAAGUC<br>UGAGUGGGCGGC | 43 |
| 3'UTR with miR 142-3p binding site<br>UGAUAAUAGGCUGGAGCCUCGGUGGCCUAGCUUCUUGCCCCUUGGGCCUCCCC<br>CCAGCCCCUCCUCCCCUUCCUGCACCCGUACCCCUCCAUAAAGUAGGAAACAC<br>UACAGUGGUCUUUGAAUAAAGUCUGAGUGGGCGGC | 44 |
| 3'UTR with miR 126-3p binding site<br>UGAUAAUAGGCUGGAGCCUCGGUGGCCUAGCUUCUUGCCCCUUGGGCCUCCCC<br>CCAGCCCCUCCUCCCCUUCCUGCACCCGUACCCCCGCAUUAUUACUCACGGUA<br>CGAGUGGUCUUUGAAUAAAGUCUGAGUGGGCGGC | 45 |
| 3'UTR with miR 142-3p and miR 126-3p binding sites<br>UGAUAAUAGUCCAUAAAGUAGGAAACACUACAGCUGGAGCCUCGGUGGCCUAG<br>CUUCUUGCCCCUUGGGCCUCCCCCAGCCCCUCCUCCCCUUCCUGCACCCGUAC<br>CCCCCGCAUUAUUACUCACGGUACGAGUGGUCUUUGAAUAAAGUCUGAGUGGG<br>CGGC | 46 |
| 3'UTR with 3 miR 142-3p binding sites<br>UGAUAAUAGUCCAUAAAGUAGGAAACACUACAGCUGGAGCCUCGGUGGCCUAG<br>CUUCUUGCCCCUUGGGCCUCCAUAAAGUAGGAAACACUACAUCCCCCAGCCCC<br>UCCUCCCCUUCCUGCACCCGUACCCCUCCAUAAAGUAGGAAACACUACAGUGG<br>UCUUUGAAUAAAGUCUGAGUGGGCGGC | 47 |
| 3'UTR with miR 142-5p binding site<br>UGAUAAUAGGCUGGAGCCUCGGUGGCCAUGCUUCUUGCCCCUUGGGCCUCCCCC<br>CAGCCCCUCCUCCCCUUCCUGCACCCGUACCCCCAGUAGUGCUUUCUACUUUAU<br>GGUGGUCUUUGAAUAAAGUCUGAGUGGGCGGC | 48 |

| Name: | SEQ ID NO: |
|---|---|
| 3'UTR with 3 miR 142-5p binding sites<br>UGAUAAUAGAGUAGUGCUUUCUACUUUAUGGCUGGAGCCUCGGUGGCCAUGCU<br>UCUUGCCCCUUGGGCCAGUAGUGCUUUCUACUUUAUGUCCCCCCAGCCCCUCUC<br>CCCUUCCUGCACCCGUACCCCCAGUAGUGCUUUCUACUUUAUGGUGGUCUUUGA<br>AUAAAGUCUGAGUGGGCGGC | 49 |
| 3'UTR with 2 miR 142-5p binding sites and 1 miR 142-3p binding site<br>UGAUAAUAGAGUAGUGCUUUCUACUUUAUGGCUGGAGCCUCGGUGGCCAUGCU<br>UCUUGCCCCUUGGGCCUCCAUAAAGUAGGAAACACUACAUCCCCCCAGCCCCU<br>CCUCCCCUUCCUGCACCCGUACCCCCAGUAGUGCUUUCUACUUUAUGGUGGUC<br>UUUGAAUAAAGUCUGAGUGGGCGGC | 50 |
| 3'UTR with miR 142-3p binding site, P1 insertion<br>UGAUAAUAGUCCAUAAAGUAGGAAACACUACAGCUGGAGCCUCGGUGGCCUAG<br>CUUCUUGCCCCUUGGGCCUCCCCCCAGCCCCUCCUCCCCUUCCUGCACCCGUACC<br>CCCGUGGUCUUUGAAUAAAGUCUGAGUGGGCGGC | 51 |
| 3'UTR with miR 142-3p binding site, P2 insertion<br>UGAUAAUAGGCUGGAGCCUCGGUGGCUCCAUAAAGUAGGAAACACUACACUAG<br>CUUCUUGCCCCUUGGGCCUCCCCCAGCCCCUCCUCCCCUUCCUGCACCCGUACC<br>CCCGUGGUCUUUGAAUAAAGUCUGAGUGGGCGGC | 52 |
| 3'UTR with miR 142-3p binding site, P3 insertion<br>UGAUAAUAGGCUGGAGCCUCGGUGGCCUAGCUUCUUGCCCCUUGGGCCUCCAU<br>AAAGUAGGAAACACUACAUCCCCCCAGCCCCUCCUCCCCUUCCUGCACCCGUAC<br>CCCCGUGGUCUUUGAAUAAAGUCUGAGUGGGCGGC | 53 |
| 3'UTR with miR 155-5p binding site<br>UGAUAAUAGGCUGGAGCCUCGGUGGCCUAGCUUCUUGCCCCUUGGGCCUCCCC<br>CCAGCCCCUCCUCCCCUUCCUGCACCCGUACCCCCACCCCUAUCACAAUUAGCA<br>UUAAGUGGUCUUUGAAUAAAGUCUGAGUGGGCGGC | 54 |
| 3'UTR with 3 miR 155-5p binding sites<br>UGAUAAUAGACCCCUAUCACAAUUAGCAUUAAGCUGGAGCCUCGGUGGCCUAG<br>CUUCUUGCCCCUUGGGCCACCCCUAUCACAAUUAGCAUUAAUCCCCCCAGCCCC<br>UCCUCCCCUUCCUGCACCCGUACCCCCACCCCUAUCACAAUUAGCAUUAAGUGG<br>UCUUUGAAUAAAGUCUGAGUGGGCGGC | 55 |
| 3'UTR with 2 miR 155-5p binding sites and 1 miR 142-3p binding site<br>UGAUAAUAGACCCCUAUCACAAUUAGCAUUAAGCUGGAGCCUCGGUGGCCUAG<br>CUUCUUGCCCCUUGGGCCUCCAUAAAGUAGGAAACACUACAUCCCCCCAGCCCC<br>UCCUCCCCUUCCUGCACCCGUACCCCCACCCCUAUCACAAUUAGCAUUAAGUGG<br>UCUUUGAAUAAAGUCUGAGUGGGCGGC | 56 |

In certain embodiments, the 5'UTR and/or 3'UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5'UTR sequences comprising any of SEQ ID NOs in the table and/or 3'UTR sequences comprises any of SEQ ID NOs in the table, and any combination thereof.

The polynucleotides of the invention can comprise combinations of features. For example, the ORF can be flanked by a 5'UTR that comprises a strong Kozak translational initiation signal and/or a 3'UTR comprising an oligo(dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the invention. For example, introns or portions of intron sequences can be incorporated into the polynucleotides of the invention. Incorporation of intronic sequences can increase protein production as well as polynucleotide expression levels. In some embodiments, the polynucleotide of the invention comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide comprises an IRES instead of a 5'UTR sequence. In some embodiments, the polynucleotide comprises an ORF and a viral capsid sequence. In some embodiments, the polynucleotide comprises a synthetic 5'UTR in combination with a non-synthetic 3'UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can include those described in US2009/0226470, incorporated herein by reference in its entirety, and others known in the art. As a non-limiting example, the TEE can be located between the transcription promoter and the start codon. In some embodiments, the 5'UTR comprises a TEE.

In one aspect, a TEE is a conserved element in a UTR that can promote translational activity of a nucleic acid such as, but not limited to, cap-dependent or cap-independent translation.

In one non-limiting example, the TEE comprises the TEE sequence in the 5'-leader of the Gtx homeodomain protein. See Chappell et al., PNAS 2004 101:9590-9594, incorporated herein by reference in its entirety.

"Translational enhancer polynucleotide" or "translation enhancer polynucleotide sequence" refer to a polynucleotide that includes one or more of the TEE provided herein and/or known in the art (see. e.g., U.S. Pat. Nos. 6,310,197, 6,849,405, 7,456,273, 7,183,395, US2009/0226470, US2007/0048776, US2011/0124100, U52009/0093049, US2013/0177581, WO2009/075886, WO2007/025008, WO2012/009644, WO2001/055371, WO1999/024595, EP2610341A1, and EP2610340A1; the contents of each of which are incorporated herein by reference in their entirety), or their variants, homologs, or functional derivatives. In some embodiments, the polynucleotide of the invention comprises one or multiple copies of a TEE. The TEE in a translational enhancer polynucleotide can be organized in one or more sequence segments. A sequence segment can harbor one or more of the TEEs provided herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the TEE provided herein, identical or different number of copies of each of the TEE, and/or identical or different organization of the TEE within each sequence segment. In one embodiment, the polynucleotide of the invention comprises a translational enhancer polynucleotide sequence.

In some embodiments, a 5'UTR and/or 3'UTR comprising at least one TEE described herein can be incorporated in a monocistronic sequence such as, but not limited to, a vector system or a nucleic acid vector.

In some embodiments, a 5'UTR and/or 3'UTR of a polynucleotide of the invention comprises a TEE or portion thereof described herein. In some embodiments, the TEEs in the 3'UTR can be the same and/or different from the TEE located in the 5'UTR.

In some embodiments, a 5'UTR and/or 3'UTR of a polynucleotide of the invention can include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. In one embodiment, the 5'UTR of a polynucleotide of the invention can include 1-60, 1-55, 1-50, 1-45, 1-40, 1-35, 1-30, 1-25, 1-20, 1-15, 1-10, 9, 8, 7, 6, 5, 4, 3, 2, or 1 TEE sequences. The TEE sequences in the 5'UTR of the polynucleotide of the invention can be the same or different TEE sequences. A combination of different TEE sequences in the 5'UTR of the polynucleotide of the invention can include combinations in which more than one copy of any of the different TEE sequences are incorporated.

In some embodiments, the 5'UTR and/or 3'UTR comprises a spacer to separate two TEE sequences. As a non-limiting example, the spacer can be a 15 nucleotide spacer and/or other spacers known in the art. As another non-limiting example, the 5'UTR and/or 3'UTR comprises a TEE sequence-spacer module repeated at least once, at least twice, at least 3 times, at least 4 times, at least 5 times, at least 6 times, at least 7 times, at least 8 times, at least 9 times, at least 10 times, or more than 10 times in the 5'UTR and/or 3'UTR, respectively. In some embodiments, the 5'UTR and/or 3'UTR comprises a TEE sequence-spacer module repeated 1, 2, 3, 4, 5, 6, 7, 8, 9, or 10 times.

In some embodiments, the spacer separating two TEE sequences can include other sequences known in the art that can regulate the translation of the polynucleotide of the invention, e.g., miR sequences described herein (e.g., miR binding sites and miR seeds). As a non-limiting example, each spacer used to separate two TEE sequences can include a different miR sequence or component of a miR sequence (e.g., miR seed sequence).

In some embodiments, a polynucleotide of the invention comprises a miR and/or TEE sequence. In some embodiments, the incorporation of a miR sequence and/or a TEE sequence into a polynucleotide of the invention can change the shape of the stem loop region, which can increase and/or decrease translation. See e.g., Kedde et al., Nature Cell Biology 2010 12(10):1014-20, herein incorporated by reference in its entirety).

GC-rich: As used herein, the term "GC-rich" refers to the nucleobase composition of a polynucleotide (e.g., mRNA), or any portion thereof (e.g., an RNA element), comprising guanine (G) and/or cytosine (C) nucleobases, or derivatives or analogs thereof, wherein the GC-content is greater than about 50%. The term "GC-rich" refers to all, or to a portion, of a polynucleotide, including, but not limited to, a gene, a non-coding region, a 5' UTR, a 3' UTR, an open reading frame, an RNA element, a sequence motif, or any discrete sequence, fragment, or segment thereof which comprises about 50% GC-content. In some embodiments of the disclosure, GC-rich polynucleotides, or any portions thereof, are exclusively comprised of guanine (G) and/or cytosine (C) nucleobases.

GC-content: As used herein, the term "GC-content" refers to the percentage of nucleobases in a polynucleotide (e.g., mRNA), or a portion thereof (e.g., an RNA element), that are either guanine (G) and cytosine (C) nucleobases, or derivatives or analogs thereof, (from a total number of possible nucleobases, including adenine (A) and thymine (T) or uracil (U), and derivatives or analogs thereof, in DNA and in RNA). The term "GC-content" refers to all, or to a portion, of a polynucleotide, including, but not limited to, a gene, a non-coding region, a 5' or 3' UTR, an open reading frame, an RNA element, a sequence motif, or any discrete sequence, fragment, or segment thereof.

Initiation Codon: As used herein, the term "initiation codon", used interchangeably with the term "start codon", refers to the first codon of an open reading frame that is translated by the ribosome and is comprised of a triplet of linked adenine-uracil-guanine nucleobases. The initiation codon is depicted by the first letter codes of adenine (A), uracil (U), and guanine (G) and is often written simply as "AUG". Although natural mRNAs may use codons other than AUG as the initiation codon, which are referred to herein as "alternative initiation codons", the initiation codons of polynucleotides described herein use the AUG codon. During the process of translation initiation, the sequence comprising the initiation codon is recognized via complementary base-pairing to the anticodon of an initiator tRNA (Met-tRNA$_i^{Met}$) bound by the ribosome. Open reading frames may contain more than one AUG initiation codon, which are referred to herein as "alternate initiation codons".

The initiation codon plays a critical role in translation initiation. The initiation codon is the first codon of an open reading frame that is translated by the ribosome. Typically, the initiation codon comprises the nucleotide triplet AUG, however, in some instances translation initiation can occur at other codons comprised of distinct nucleotides. The initiation of translation in eukaryotes is a multistep biochemical process that involves numerous protein-protein, protein-RNA, and RNA-RNA interactions between messenger RNA molecules (mRNAs), the 40S ribosomal subunit, other components of the translation machinery (e.g., eukaryotic initiation factors; eIFs). The current model of mRNA translation initiation postulates that the pre-initiation complex (alternatively "43 S pre-initiation complex"; abbreviated as "PIC") translocates from the site of recruitment on the mRNA (typically the 5' cap) to the initiation codon by scanning nucleotides in a 5' to 3' direction until the first AUG codon that resides within a specific translation-promotive nucleotide context (the Kozak sequence) is encountered (Kozak (1989) J Cell Biol 108:229-241). Scanning by the PIC ends upon complementary base-pairing between nucleotides comprising the anticodon of the initiator Met-tRNA$_i^{Met}$ transfer RNA and nucleotides comprising the initiation codon of the mRNA. Productive base-pairing between the AUG codon and the Met-tRNA$_i^{Met}$ anticodon elicits a series of structural and biochemical events that culminate in the joining of the large 60S ribosomal subunit to the PIC to form an active ribosome that is competent for translation elongation.

Kozak Sequence: The term "Kozak sequence" (also referred to as "Kozak consensus sequence") refers to a translation initiation enhancer element to enhance expression of a gene or open reading frame, and which in eukaryotes, is located in the 5' UTR. The Kozak consensus sequence was originally defined as the sequence GCCRCC, where R=a purine, following an analysis of the effects of single mutations surrounding the initiation codon (AUG) on translation of the preproinsulin gene (Kozak (1986) Cell 44:283-292). Polynucleotides disclosed herein comprise a Kozak consensus sequence, or a derivative or modification thereof. (Examples of translational enhancer compositions and methods of use thereof, see U.S. Pat. No. 5,807,707 to Andrews et al., incorporated herein by reference in its entirety; U.S. Pat. No. 5,723,332 to Chernajovsky, incorporated herein by reference in its entirety; U.S. Pat. No. 5,891,665 to Wilson, incorporated herein by reference in its entirety.)

Leaky scanning: A phenomenon known as "leaky scanning" can occur whereby the PIC bypasses the initiation codon and instead continues scanning downstream until an alternate or alternative initiation codon is recognized. Depending on the frequency of occurrence, the bypass of the initiation codon by the PIC can result in a decrease in translation efficiency. Furthermore, translation from this downstream AUG codon can occur, which will result in the production of an undesired, aberrant translation product that may not be capable of eliciting the desired therapeutic response. In some cases, the aberrant translation product may in fact cause a deleterious response (Kracht et al., (2017) Nat Med 23(4):501-507).

Modified: As used herein "modified" or "modification" refers to a changed state or a change in composition or structure of a polynucleotide (e.g., mRNA). Polynucleotides may be modified in various ways including chemically, structurally, and/or functionally. For example, polynucleotides may be structurally modified by the incorporation of one or more RNA elements, wherein the RNA element comprises a sequence and/or an RNA secondary structure(s) that provides one or more functions (e.g., translational regulatory activity). Accordingly, polynucleotides of the disclosure may be comprised of one or more modifications (e.g., may include one or more chemical, structural, or functional modifications, including any combination thereof).

Nucleobase: As used herein, the term "nucleobase" (alternatively "nucleotide base" or "nitrogenous base") refers to a purine or pyrimidine heterocyclic compound found in nucleic acids, including any derivatives or analogs of the naturally occurring purines and pyrimidines that confer improved properties (e.g., binding affinity, nuclease resistance, chemical stability) to a nucleic acid or a portion or segment thereof. Adenine, cytosine, guanine, thymine, and uracil are the nucleobases predominately found in natural nucleic acids. Other natural, non-natural, and/or synthetic nucleobases, as known in the art and/or described herein, can be incorporated into nucleic acids.

Nucleoside/Nucleotide: As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof (also referred to herein as "nucleobase"), but lacking an internucleoside linking group (e.g., a phosphate group). As used herein, the term "nucleotide" refers to a nucleoside covalently bonded to an internucleoside linking group (e.g., a phosphate group), or any derivative, analog, or modification thereof that confers improved chemical and/or functional properties (e.g., binding affinity, nuclease resistance, chemical stability) to a nucleic acid or a portion or segment thereof.

Nucleic acid: As used herein, the term "nucleic acid" is used in its broadest sense and encompasses any compound and/or substance that includes a polymer of nucleotides, or derivatives or analogs thereof. These polymers are often referred to as "polynucleotides". Accordingly, as used herein the terms "nucleic acid" and "polynucleotide" are equivalent and are used interchangeably. Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, mRNAs, modified mRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an a-L-ribo configuration (a diastereomer of LNA), 2'-amino-LNA having a 2'-amino functionalization, and 2'-amino-α-LNA having a 2'-amino functionalization) or hybrids thereof.

Nucleic Acid Structure: As used herein, the term "nucleic acid structure" (used interchangeably with "polynucleotide structure") refers to the arrangement or organization of atoms, chemical constituents, elements, motifs, and/or sequence of linked nucleotides, or derivatives or analogs thereof, that comprise a nucleic acid (e.g., an mRNA). The term also refers to the two-dimensional or three-dimensional state of a nucleic acid. Accordingly, the term "RNA structure" refers to the arrangement or organization of atoms, chemical constituents, elements, motifs, and/or sequence of linked nucleotides, or derivatives or analogs thereof, comprising an RNA molecule (e.g., an mRNA) and/or refers to a two-dimensional and/or three-dimensional state of an RNA molecule. Nucleic acid structure can be further demarcated into four organizational categories referred to herein as "molecular structure", "primary structure", "secondary structure", and "tertiary structure" based on increasing organizational complexity.

Open Reading Frame: As used herein, the term "open reading frame", abbreviated as "ORF", refers to a segment or region of an mRNA molecule that encodes a polypeptide. The ORF comprises a continuous stretch of non-overlapping, in-frame codons, beginning with the initiation codon and ending with a stop codon, and is translated by the ribosome.

Pre-Initiation Complex (PIC): As used herein, the term "pre-initiation complex" (alternatively "43 S pre-initiation complex"; abbreviated as "PIC") refers to a ribonucleoprotein complex comprising a 40S ribosomal subunit, eukaryotic initiation factors (eIF1, eIF1A, eIF3, eIF5), and the eIF2-GTP-Met-tRNA$_i^{Met}$ ternary complex, that is intrinsically capable of attachment to the 5' cap of an mRNA molecule and, after attachment, of performing ribosome scanning of the 5' UTR.

RNA element: As used herein, the term "RNA element" refers to a portion, fragment, or segment of an RNA molecule that provides a biological function and/or has biological activity (e.g., translational regulatory activity). Modification of a polynucleotide by the incorporation of one or more RNA elements, such as those described herein, provides one or more desirable functional properties to the modified polynucleotide. RNA elements, as described herein, can be naturally-occurring, non-naturally occurring, synthetic, engineered, or any combination thereof. For example, naturally-occurring RNA elements that provide a regulatory activity include elements found throughout the transcriptomes of viruses, prokaryotic and eukaryotic organisms (e.g., humans). RNA elements in particular eukaryotic mRNAs and translated viral RNAs have been shown to be involved in mediating many functions in cells. Exemplary natural RNA elements include, but are not limited to, translation initiation elements (e.g., internal ribosome entry site (IRES), see Kieft et al., (2001) RNA 7(2):194-206), translation enhancer elements (e.g., the APP mRNA translation enhancer element, see Rogers et al., (1999) J Biol Chem 274(10):6421-6431), mRNA stability elements (e.g., AU-rich elements (AREs), see Garneau et al., (2007) Nat Rev Mol Cell Biol 8(2):113-126), translational repression element (see e.g., Blumer et al., (2002) Mech Dev 110(1-2):97-112), protein-binding RNA elements (e.g., iron-responsive element, see Selezneva et al., (2013) J Mol Biol 425(18):3301-3310), cytoplasmic polyadenylation elements (Villalba et al., (2011) Curr Opin Genet Dev 21(4):452-457), and catalytic RNA elements (e.g., ribozymes, see Scott et al., (2009) Biochim Biophys Acta 1789(9-10):634-641).

Residence time: As used herein, the term "residence time" refers to the time of occupancy of a pre-initiation complex (PIC) or a ribosome at a discrete position or location along an mRNA molecule.

Translational Regulatory Activity: As used herein, the term "translational regulatory activity" (used interchangeably with "translational regulatory function") refers to a biological function, mechanism, or process that modulates (e.g., regulates, influences, controls, varies) the activity of the translational apparatus, including the activity of the PIC and/or ribosome. In some aspects, the desired translation regulatory activity promotes and/or enhances the translational fidelity of mRNA translation. In some aspects, the desired translational regulatory activity reduces and/or inhibits leaky scanning.

Translation of a polynucleotide comprising an open reading frame encoding a polypeptide can be controlled and regulated by a variety of mechanisms that are provided by various cis-acting nucleic acid structures. For example, naturally-occurring, cis-acting RNA elements that form hairpins or other higher-order (e.g., pseudoknot) intramolecular mRNA secondary structures can provide a translational regulatory activity to a polynucleotide, wherein the RNA element influences or modulates the initiation of polynucleotide translation, particularly when the RNA element is positioned in the 5' UTR close to the 5'-cap structure (Pelletier and Sonenberg (1985) Cell 40(3):515-526; Kozak (1986) Proc Natl Acad Sci 83:2850-2854). Cis-acting RNA elements can also affect translation elongation, being involved in numerous frameshifting events (Namy et al., (2004) Mol Cell 13(2):157-168). Internal ribosome entry sequences (IRES) represent another type of cis-acting RNA element that are typically located in 5' UTRs, but have also been reported to be found within the coding region of naturally-occurring mRNAs (Holcik et al. (2000) Trends Genet 16(10):469-473). In cellular mRNAs, IRES often coexist with the 5'-cap structure and provide mRNAs with the functional capacity to be translated under conditions in which cap-dependent translation is compromised (Gebauer et al., (2012) Cold Spring Harb Perspect Biol 4(7):a012245). Another type of naturally-occurring cis-acting RNA element comprises upstream open reading frames (uORFs). Naturally-occurring uORFs occur singularly or multiply within the 5' UTRs of numerous mRNAs and influence the translation of the downstream major ORF, usually negatively (with the notable exception of GCN4 mRNA in yeast and ATF4 mRNA in mammals, where uORFs serve to promote the translation of the downstream major ORF under conditions of increased eIF2 phosphorylation (Hinnebusch (2005) Annu Rev Microbiol 59:407-450)). Additional exemplary translational regulatory activities provided by components, structures, elements, motifs, and/or specific sequences comprising polynucleotides (e.g., mRNA) include, but are not limited to, mRNA stabilization or destabilization (Baker & Parker (2004) Curr Opin Cell Biol 16(3):293-299), translational activation (Villalba et al., (2011) Curr Opin Genet Dev 21(4):452-457), and translational repression (Blumer et al., (2002) Mech Dev 110(1-2):97-112). Studies have shown that naturally-occurring, cis-acting RNA elements can confer their respective functions when used to modify, by incorporation into, heterologous polynucleotides (Goldberg-Cohen et al., (2002) J Biol Chem 277(16):13635-13640).

Modified Polynucleotides Comprising Functional RNA Elements

The present disclosure provides synthetic polynucleotides comprising a modification (e.g., an RNA element), wherein the modification provides a desired translational regulatory activity. In some embodiments, the disclosure provides a polynucleotide comprising a 5' untranslated region (UTR), an initiation codon, a full open reading frame encoding a polypeptide, a 3' UTR, and at least one modification, wherein the at least one modification provides a desired translational regulatory activity, for example, a modification that promotes and/or enhances the translational fidelity of mRNA translation. In some embodiments, the desired translational regulatory activity is a cis-acting regulatory activity. In some embodiments, the desired translational regulatory activity is an increase in the residence time of the 43S pre-initiation complex (PIC) or ribosome at, or proximal to, the initiation codon. In some embodiments, the desired translational regulatory activity is an increase in the initiation of polypeptide synthesis at or from the initiation codon. In some embodiments, the desired translational regulatory activity is an increase in the amount of polypeptide translated from the full open reading frame. In some embodiments, the desired translational regulatory activity is an increase in the fidelity of initiation codon decoding by the PIC or ribosome. In some embodiments, the desired translational regulatory activity is inhibition or reduction of leaky scanning by the PIC or ribosome. In some embodiments, the desired translational regulatory activity is a decrease in the rate of decoding the initiation codon by the PIC or ribosome. In some embodiments, the desired translational regulatory activity is inhibition or reduction in the initiation of polypeptide synthesis at any codon within the mRNA other than the initiation codon. In some embodiments, the desired translational regulatory activity is inhibition or reduction of the amount of polypeptide translated from any open reading frame within the mRNA other than the full open reading frame. In some embodiments, the desired translational regulatory activity is inhibition or reduction in the production of aberrant translation products. In some embodiments, the desired translational regulatory activity is a combination of one or more of the foregoing translational regulatory activities.

Accordingly, the present disclosure provides a polynucleotide, e.g., an mRNA, comprising an RNA element that comprises a sequence and/or an RNA secondary structure(s) that provides a desired translational regulatory activity as described herein. In some aspects, the mRNA comprises an RNA element that comprises a sequence and/or an RNA secondary structure(s) that promotes and/or enhances the translational fidelity of mRNA translation. In some aspects, the mRNA comprises an RNA element that comprises a sequence and/or an RNA secondary structure(s) that provides a desired translational regulatory activity, such as inhibiting and/or reducing leaky scanning. In some aspects, the disclosure provides an mRNA that comprises an RNA element that comprises a sequence and/or an RNA secondary structure(s) that inhibits and/or reduces leaky scanning thereby promoting the translational fidelity of the mRNA.

In some embodiments, the RNA element comprises natural and/or modified nucleotides. In some embodiments, the RNA element comprises of a sequence of linked nucleotides, or derivatives or analogs thereof, that provides a desired translational regulatory activity as described herein. In some embodiments, the RNA element comprises a sequence of linked nucleotides, or derivatives or analogs thereof, that forms or folds into a stable RNA secondary structure, wherein the RNA secondary structure provides a desired translational regulatory activity as described herein. RNA elements can be identified and/or characterized based on the primary sequence of the element (e.g., GC-rich element), by RNA secondary structure formed by the element (e.g. stem-loop), by the location of the element within the RNA molecule (e.g., located within the 5' UTR of an mRNA), by the biological function and/or activity of the element (e.g., "translational enhancer element"), and any combination thereof.

In some aspects, the disclosure provides an mRNA having one or more structural modifications that inhibits leaky scanning and/or promotes the translational fidelity of mRNA translation, wherein at least one of the structural modifications is a GC-rich RNA element. In some aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is 70-80% cytosine, 60-70% cytosine, 50%-60% cytosine, 40-50% cytosine, 30-40% cytosine bases. In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is about 80% cytosine, about 70% cytosine, about 60% cytosine, about 50% cytosine, about 40% cytosine, or about 30% cytosine.

In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is 70-80% cytosine, 60-70% cytosine, 50%-60% cytosine, 40-50% cytosine, or 30-40% cytosine. In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is about 80% cytosine, about 70% cytosine, about 60% cytosine, about 50% cytosine, about 40% cytosine, or about 30% cytosine.

In some embodiments, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of 3, 4, 5, 6, 7, 8, 9, 10, 11, 12, 13, 14, 15, 16, 17, 18, 19, or 20 nucleotides, or derivatives or analogs thereof, linked in any order, wherein the sequence composition is >50% cytosine. In some embodiments, the sequence composition is >55% cytosine, >60% cytosine, >65% cytosine, >70% cytosine, >75% cytosine, >80% cytosine, >85% cytosine, or >90% cytosine.

In other aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of about 3-30, 5-25, 10-20, 15-20 or about 20, about 15, about 12, about 10, about 6 or about 3 nucleotides, or derivatives or analogues thereof, wherein the sequence comprises a repeating GC-motif, wherein the repeating GC-motif is [CCG]n (SEQ ID NO: 62), wherein n=1 to 10, n=2 to 8, n=3 to 6, or n=4 to 5. In some embodiments, the sequence comprises a repeating GC-motif [CCG]n (SEQ ID NO: 64), wherein n=1, 2, 3, 4 or 5. In some embodiments, the sequence comprises a repeating GC-motif [CCG]n, wherein n=1, 2, or 3. In some embodiments, the sequence comprises a repeating GC-motif [CCG]n, wherein n=1. In some embodiments, the sequence comprises a repeating GC-motif [CCG]n, wherein n=2. In some embodiments, the sequence comprises a repeating GC-motif [CCG]n, wherein n=3. In some embodiments, the sequence comprises a repeating GC-motif [CCG]n (SEQ ID NO: 65), wherein n=4. In some embodiments, the sequence comprises a repeating GC-motif [CCG]n, wherein n=5 (SEQ ID NO: 66).

In another aspect, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element comprises any one of the sequences set forth in Table 1. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located about 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In other aspects, the disclosure provides a modified mRNA comprising at least one modification, wherein at least one modification is a GC-rich RNA element comprising the sequence V1 [CCCCGGCGCC (SEQ ID NO: 57)] as set forth in Table 1, or derivatives or analogs thereof, preceding a Kozak consensus sequence in the 5' UTR of the mRNA. In some embodiments, the GC-rich element comprises the sequence V1 as set forth in Table 1 located immediately adjacent to and upstream of the Kozak consensus sequence in the 5' UTR of the mRNA. In some embodiments, the GC-rich element comprises the sequence V1 as set forth in Table 1 located 1, 2, 3, 4, 5, 6, 7, 8, 9 or 10 bases upstream of the Kozak consensus sequence in the 5' UTR of the mRNA. In other embodiments, the GC-rich element comprises the sequence V1 as set forth in Table 1 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence V2 [CCCCGGC] as set forth in Table 1, or derivatives or analogs thereof, preceding a Kozak consensus sequence in the 5' UTR of the mRNA. In some embodiments, the GC-rich element comprises the sequence V2 as set forth in Table 1 located immediately adjacent to and upstream of the Kozak consensus sequence in the 5' UTR of the mRNA. In some embodiments, the GC-rich element comprises the sequence V2 as set forth in Table 1 located 1, 2, 3, 4, 5, 6, 7, 8, 9 or 10 bases upstream of the Kozak consensus sequence in the 5' UTR of the mRNA. In other embodiments, the GC-rich element comprises the sequence V2 as set forth in Table 1 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence EK [GCCGCC] as set forth in Table 1, or derivatives or analogs thereof, preceding a Kozak consensus sequence in the 5' UTR of the mRNA. In some embodiments, the GC-rich element comprises the sequence EK as set forth in Table 1 located immediately adjacent to and upstream of the Kozak consensus sequence in the 5' UTR of the mRNA. In some embodiments, the GC-rich element comprises the sequence EK as set forth in Table 1 located 1, 2, 3, 4, 5, 6, 7, 8, 9 or 10 bases upstream of the Kozak consensus sequence in the 5' UTR of the mRNA. In other embodiments, the GC-rich element comprises the sequence EK as set forth in Table 1 located 1-3, 3-5, 5-7, 7-9, 9-12, or 12-15 bases upstream of the Kozak consensus sequence in the 5' UTR of the mRNA.

In yet other aspects, the disclosure provides a modified mRNA comprising at least one modification, wherein at least one modification is a GC-rich RNA element comprising the sequence V1 [CCCCGGCGCC (SEQ ID NO: 57)] as set forth in Table 1, or derivatives or analogs thereof, preceding a Kozak consensus sequence in the 5' UTR of the mRNA, wherein the 5' UTR comprises the following sequence shown in Table 1:

(SEQ ID NO: 58)
GGGAAATAAGAGAGAAAAGAAGAGTAAGAAGAAATATAAGA.

In some embodiments, the GC-rich element comprises the sequence V1 as set forth in Table 1 located immediately adjacent to and upstream of the Kozak consensus sequence in the 5' UTR sequence shown in Table 1. In some embodiments, the GC-rich element comprises the sequence V1 as set forth in Table 1 located 1, 2, 3, 4, 5, 6, 7, 8, 9 or 10 bases upstream of the Kozak consensus sequence in the 5' UTR of the mRNA, wherein the 5' UTR comprises the following sequence shown in Table 1:

(SEQ ID NO: 58)
GGGAAATAAGAGAGAAAAGAAGAGTAAGAAGAAATATAAGA.

In other embodiments, the GC-rich element comprises the sequence V1 as set forth in Table 1 located 1-3, 3-5, 5-7, 7-9, 9-12, or 12-15 bases upstream of the Kozak consensus sequence in the 5' UTR of the mRNA, wherein the 5' UTR comprises the following sequence shown in Table 1:

(SEQ ID NO: 58)
GGGAAATAAGAGAGAAAAGAAGAGTAAGAAGAAATATAAGA.

In some embodiments, the 5' UTR comprises the following sequence set forth in Table 1:

(SEQ ID NO: 59)
GGGAAATAAGAGAGAAAAGAAGAGTAAGAAGAAATATAAGACCCCGGCGC
CGCCACC

TABLE 1

| 5'UTRs | 5'UTR Sequence |
|---|---|
| Standard | GGGAAATAAGAGAGAAAAGAAGAGTAAGAAGAAATATAAGAGCCACC (SEQ ID NO: 60) |
| V1-UTR | GGGAAATAAGAGAGAAAAGAAGAGTAAGAAGAAATATAAGACCCCGGCGCCGCCACC (SEQ ID NO: 59) |
| V2-UTR | GGGAAATAAGAGAGAAAAGAAGAGTAAGAAGAAATATAAGACCCCGGCGCCACC (SEQ ID NO: 61) |

| GC-Rich RNA Elements | Sequence |
|---|---|
| K0 (Traditional Kozak consensus) | [GCCA/GCC] |
| EK | [GCCGCC] |
| V1 | [CCCCGGCGCC] (SEQ ID NO: 57) |
| V2 | [CCCCGGC] |
| (CCG)$_n$, where n = 1-10 | [CCG]$_n$ (SEQ ID NO: 62) |
| (GCC)$_n$, where n = 1-10 | [GCC]$_n$ (SEQ ID NO: 63) |

In another aspect, the disclosure provides a modified mRNA comprising at least one modification, wherein at least one modification is a GC-rich RNA element comprising a stable RNA secondary structure comprising a sequence of nucleotides, or derivatives or analogs thereof, linked in an order which forms a hairpin or a stem-loop. In one embodiment, the stable RNA secondary structure is upstream of the Kozak consensus sequence. In another embodiment, the stable RNA secondary structure is located about 30, about 25, about 20, about 15, about 10, or about 5 nucleotides upstream of the Kozak consensus sequence. In another embodiment, the stable RNA secondary structure is located about 20, about 15, about 10 or about 5 nucleotides upstream of the Kozak consensus sequence. In another embodiment, the stable RNA secondary structure is located about 5, about 4, about 3, about 2, about 1 nucleotides upstream of the Kozak consensus sequence. In another embodiment, the stable RNA secondary structure is located about 15-30, about 15-20, about 15-25, about 10-15, or about 5-10 nucleotides upstream of the Kozak consensus sequence. In another embodiment, the stable RNA secondary structure is located 12-15 nucleotides upstream of the Kozak consensus sequence. In another embodiment, the stable RNA secondary structure has a deltaG of about −30 kcal/mol, about −20 to −30 kcal/mol, about −20 kcal/mol, about −10 to −20 kcal/mol, about −10 kcal/mol, about −5 to −10 kcal/mol.

In another embodiment, the modification is operably linked to an open reading frame encoding a polypeptide and wherein the modification and the open reading frame are heterologous.

In another embodiment, the sequence of the GC-rich RNA element is comprised exclusively of guanine (G) and cytosine (C) nucleobases.

RNA elements that provide a desired translational regulatory activity as described herein can be identified and characterized using known techniques, such as ribosome profiling. Ribosome profiling is a technique that allows the determination of the positions of PICs and/or ribosomes bound to mRNAs (see e.g., Ingolia et al., (2009) Science 324(5924):218-23, incorporated herein by reference). The technique is based on protecting a region or segment of mRNA, by the PIC and/or ribosome, from nuclease digestion. Protection results in the generation of a 30-bp fragment of RNA termed a 'footprint'. The sequence and frequency of RNA footprints can be analyzed by methods known in the art (e.g., RNA-seq). The footprint is roughly centered on the A-site of the ribosome. If the PIC or ribosome dwells at a particular position or location along an mRNA, footprints generated at these positions would be relatively common. Studies have shown that more footprints are generated at positions where the PIC and/or ribosome exhibits decreased processivity and fewer footprints where the PIC and/or ribosome exhibits increased processivity (Gardin et al., (2014) eLife 3:e03735). In some embodiments, residence time or the time of occupancy of the PIC or ribosome at a discrete position or location along a polynucleotide comprising any one or more of the RNA elements described herein is determined by ribosome profiling.

Polynucleotides of the invention can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences". Non-limiting examples of sensor sequences are described in U.S. Publication 2014/0200261, the contents of which are incorporated herein by reference in their entirety.

In some embodiments, a polynucleotide (e.g., a ribonucleic acid (RNA), e.g., a messenger RNA (mRNA)) of the invention comprises an open reading frame (ORF) encoding a polypeptide of interest and further comprises one or more miRNA binding site(s). Inclusion or incorporation of miRNA binding site(s) provides for regulation of polynucleotides of the invention, and in turn, of the polypeptides encoded therefrom, based on tissue-specific and/or cell-type specific expression of naturally-occurring miRNAs.

A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol Cell. 2007 Jul. 6; 27(1):91-105. miRNA profiling of the target cells or tissues can be conducted to determine the presence or absence of miRNA in the cells or tissues. In some embodiments, a polynucleotide (e.g., a ribonucleic acid (RNA), e.g., a messenger RNA (mRNA)) of the invention comprises one or more microRNA binding sites, microRNA target sequences, microRNA complementary sequences, or microRNA seed complementary sequences. Such sequences can correspond to, e.g., have complementarity to, any known microRNA such as those taught in US Publication US2005/0261218 and US Publication US2005/0059005, the contents of each of which are incorporated herein by reference in their entirety.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the invention comprising an ORF encoding a polypeptide of interest and further comprises one or more miRNA binding site(s). In exemplary embodiments, a 5'UTR and/or 3'UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the invention, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide miRNA sequence, to a 19-23 nucleotide miRNA sequence, or to a 22 nucleotide miRNA sequence. A miRNA binding site can be complementary to only a portion of a miRNA, e.g., to a portion less than 1, 2, 3, or 4 nucleotides of the full length of a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the invention, the polynucleotide can be targeted for degradation or reduced translation, provided the miRNA in question is available. This can reduce off-target effects upon delivery of the polynucleotide. For example, if a polynucleotide of the invention is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polynucleotide of the invention can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the invention to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5'UTR and/or 3'UTR of a polynucleotide of the invention.

To further drive the selective degradation and suppression in APCs and macrophage, a polynucleotide of the invention can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. MiRNA binding sites from any liver specific miRNA can be introduced to or removed from a polynucleotide of the invention to regulate expression of the polynucleotide in the liver. Liver specific miRNA binding sites can be engineered alone or further in combination with immune cell (e.g., APC) miRNA binding sites in a polynucleotide of the invention.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the invention to regulate expression of the polynucleotide in the lung. Lung specific miRNA binding sites can be engineered alone or further in combination with immune cell (e.g., APC) miRNA binding sites in a polynucleotide of the invention.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-

3p, miR-499b-5p, miR-744-3p, miR-744-5p, miR-92b-3p, and miR-92b-5p. mMiRNA binding sites from any heart specific microRNA can be introduced to or removed from a polynucleotide of the invention to regulate expression of the polynucleotide in the heart. Heart specific miRNA binding sites can be engineered alone or further in combination with immune cell (e.g., APC) miRNA binding sites in a polynucleotide of the invention.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the invention to regulate expression of the polynucleotide in the nervous system. Nervous system specific miRNA binding sites can be engineered alone or further in combination with immune cell (e.g., APC) miRNA binding sites in a polynucleotide of the invention.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polynucleotide of the invention to regulate expression of the polynucleotide in the pancreas. Pancreas specific miRNA binding sites can be engineered alone or further in combination with immune cell (e.g. APC) miRNA binding sites in a polynucleotide of the invention.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the invention to regulate expression of the polynucleotide in the kidney. Kidney specific miRNA binding sites can be engineered alone or further in combination with immune cell (e.g., APC) miRNA binding sites in a polynucleotide of the invention.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the invention to regulate expression of the polynucleotide in the muscle. Muscle specific miRNA binding sites can be engineered alone or further in combination with immune cell (e.g., APC) miRNA binding sites in a polynucleotide of the invention.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the invention to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the invention to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008,18, 610-621; Yoo J K et al., Stem Cells Dev. 2012, 21(11), 2049-2057, each of which is herein incorporated by reference in its entirety). MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR- 200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008,18, 610-621; Goff L A et al., PLoS One, 2009, 4:e7192; Bar M et al., Stem cells, 2008, 26, 2496-2505, the content of each of which is incorporated herein by reference in its entirety).

In some embodiments, a miRNA binding site is inserted in the polynucleotide of the invention in any position of the polynucleotide (e.g., the 5'UTR and/or 3'UTR). In some embodiments, the 5'UTR comprises a miRNA binding site. In some embodiments, the 3'UTR comprises a miRNA binding site. In some embodiments, the 5'UTR and the 3'UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the invention comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the invention. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the invention.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, herein incorporated by reference in its entirety). The polynucleotides of the invention can further include this structured 5'UTR in order to enhance microRNA mediated gene regulation.

At least one miRNA binding site can be engineered into the 3'UTR of a polynucleotide of the invention. In this context, at least two, at least three, at least four, at least five, at least six, at least seven, at least eight, at least nine, at least ten, or more miRNA binding sites can be engineered into a 3'UTR of a polynucleotide of the invention. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the invention. In one embodiment, miRNA binding sites incorporated into a polynucleotide of the invention can be the same or can be different miRNA sites. A combination of different miRNA binding sites incorporated into a polynucleotide of the invention can include combinations in which more than one copy of any of the different miRNA sites are incorporated. In another embodiment, miRNA binding sites incorporated into a polynucleotide of the invention can target the same or different tissues in the body.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the invention. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In one embodiment, a polynucleotide of the invention can be engineered to include more than one miRNA site expressed in different tissues or different cell types of a subject. As a non-limiting example, a polynucleotide of the invention can be engineered to include miR-192 and miR-122 to regulate expression of the polynucleotide in the liver and kidneys of a subject. In another embodiment, a polynucleotide of the invention can be engineered to include more than one miRNA site for the same tissue.

In some embodiments, the expression of a polynucleotide of the invention can be controlled by incorporating at least one miR binding site in the polynucleotide and formulating the polynucleotide for administration. As a non-limiting example, a polynucleotide of the invention can be targeted to a tissue or cell by incorporating a miRNA binding site and formulating the polynucleotide in a lipid nanoparticle comprising a ionizable lipid, including any of the lipids described herein.

A polynucleotide of the invention can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the invention can be designed for optimal protein expression in a tissue or cell, or in the context of a biological condition.

In some embodiments, a polynucleotide of the invention can be designed to incorporate miRNA binding sites that either have 100% identity to known miRNA seed sequences or have less than 100% identity to miRNA seed sequences. In some embodiments, a polynucleotide of the invention can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment, a translation enhancer element (TEE) can be incorporated on the 5'end of the stem of a stem loop and a miRNA seed can be incorporated into the stem of the stem loop. In another embodiment, a TEE can be incorporated on the 5' end of the stem of a stem loop, a miRNA seed can be incorporated into the stem of the stem loop and a miRNA binding site can be incorporated into the 3' end of the stem or the sequence after the stem loop. The miRNA seed and the miRNA binding site can be for the same and/or different miRNA sequences.

In one embodiment, the incorporation of a miRNA sequence and/or a TEE sequence changes the shape of the stem loop region which can increase and/or decrease translation. (see e.g, Kedde et al., "A Pumilio-induced RNA structure switch in p27-3'UTR controls miR-221 and miR-22 accessibility." Nature Cell Biology. 2010, incorporated herein by reference in its entirety).

In one embodiment, the 5'-UTR of a polynucleotide of the invention can comprise at least one miRNA sequence. The miRNA sequence can be, but is not limited to, a 19 or 22 nucleotide sequence and/or a miRNA sequence without the seed.

In one embodiment, the miRNA sequence in the 5'UTR can be used to stabilize a polynucleotide of the invention described herein.

In another embodiment, a miRNA sequence in the 5'UTR of a polynucleotide of the invention can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the invention can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site. As another non-limiting example, the site of translation initiation can be located within a miR-122 sequence such as the seed sequence or the mir-122 binding site.

In some embodiments, a polynucleotide of the invention can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the invention can be specific to the hematopoietic system. As another non-limiting example, a miRNA incorporated into a polynucleotide of the invention to dampen antigen presentation is miR-142-3p.

In some embodiments, a polynucleotide of the invention can include at least one miRNA in order to dampen expression of the encoded polypeptide in a tissue or cell of interest. As a non-limiting example, a polynucleotide of the invention can include at least one miR-122 binding site in order to dampen expression of an encoded polypeptide of interest in the liver. As another non-limiting example, a polynucleotide of the invention can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the invention can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the invention more unstable in antigen presenting cells. Non-limiting examples of these miRNAs include mir-142-5p, mir-142-3p, mir-146a-5p, and mir-146-3p.

In one embodiment, a polynucleotide of the invention comprises at least one miRNA sequence in a region of the polynucleotide that can interact with a RNA binding protein.

In some embodiments, the nucleic acids are therapeutic mRNAs. As used herein, the term "therapeutic mRNA" refers to an mRNA that encodes a therapeutic protein. Therapeutic proteins mediate a variety of effects in a host cell or a subject in order to treat a disease or ameliorate the signs and symptoms of a disease. For example, a therapeutic protein can replace a protein that is deficient or abnormal, augment the function of an endogenous protein, provide a novel function to a cell (e.g., inhibit or activate an endogenous cellular activity, or act as a delivery agent for another therapeutic compound (e.g., an antibody-drug conjugate). Therapeutic mRNA may be useful for the treatment of the following diseases and conditions: bacterial infections, viral infections, parasitic infections, cell proliferation disorders, genetic disorders, and autoimmune disorders.

Thus, the structures of the invention can be used as therapeutic or prophylactic agents. They are provided for use in medicine. For example, the mRNA of the structures described herein can be administered to a subject, wherein the polynucleotides are translated in vivo to produce a therapeutic peptide. Provided are compositions, methods, kits, and reagents for diagnosis, treatment or prevention of a disease or condition in humans and other mammals. The active therapeutic agents of the invention include the structures, cells containing structures or polypeptides translated from the polynucleotides contained in the structures.

The structures may be induced for translation in a cell, tissue or organism. Such translation can be in vivo, ex vivo, in culture, or in vitro. The cell, tissue or organism is contacted with an effective amount of a composition containing a structure which contains the mRNA polynucleotides each of which has at least one translatable region encoding a peptide.

An "effective amount" of the structures are provided based, at least in part, on the target tissue, target cell type, means of administration, physical characteristics of the polynucleotide (e.g., size, and extent of modified nucleosides) and other components of the nucleic acids, and other determinants. In general, an effective amount of the nucleic acids provides an induced or boosted peptide production in the cell.

The mRNA of the present invention may be designed to encode polypeptides of interest selected from any of several target categories including, but not limited to, biologics, antibodies, vaccines, therapeutic proteins or peptides, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome for which no therapeutic indication has been identified but which nonetheless have utility in areas of research and discovery. "Therapeutic protein" refers to a protein that, when administered to a cell has a therapeutic, diagnostic, and/or prophylactic effect and/or elicits a desired biological and/or pharmacological effect.

The mRNA disclosed herein, may encode one or more biologics. As used herein, a "biologic" is a polypeptide-based molecule produced by the methods provided herein and which may be used to treat, cure, mitigate, prevent, or diagnose a serious or life-threatening disease or medical condition. Biologics, according to the present invention include, but are not limited to, allergenic extracts (e.g. for allergy shots and tests), blood components, gene therapy products, human tissue or cellular products used in transplantation, vaccines, monoclonal antibodies, cytokines, growth factors, enzymes, thrombolytics, and immunomodulators, among others.

According to the present invention, one or more biologics currently being marketed or in development may be encoded by the mRNA of the present invention. While not wishing to be bound by theory, it is believed that incorporation of the encoding polynucleotides of a known biologic into the mRNA of the invention will result in improved therapeutic efficacy due at least in part to the specificity, purity and/or selectivity of the construct designs.

The mRNA disclosed herein, may encode one or more antibodies or fragments thereof. The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments. The term "immunoglobulin" (Ig) is used interchangeably with "antibody" herein. As used herein, the term "monoclonal antibody" refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include, but are not limited to, "primatized" antibodies comprising variable domain antigen-binding sequences derived from a non-human primate (e.g., Old World Monkey, Ape etc.) and human constant region sequences.

An "antibody fragment" comprises a portion of an intact antibody, preferably the antigen binding and/or the variable region of the intact antibody. Examples of antibody fragments include Fab, Fab', F(ab')2 and Fv fragments; diabodies; linear antibodies; nanobodies; single-chain antibody molecules and multispecific antibodies formed from antibody fragments.

Any of the five classes of immunoglobulins, IgA, IgD, IgE, IgG and IgM, may be encoded by the mRNA of the invention, including the heavy chains designated alpha, delta, epsilon, gamma and mu, respectively. Also included are polynucleotide sequences encoding the subclasses, gamma and mu. Hence any of the subclasses of antibodies may be encoded in part or in whole and include the following subclasses: IgG1, IgG2, IgG3, IgG4, IgA1 and IgA2. According to the present invention, one or more antibodies or fragments currently being marketed or in development may be encoded by the mRNA of the present invention.

Antibodies encoded in the mRNA of the invention may be utilized to treat conditions or diseases in many therapeutic areas such as, but not limited to, blood, cardiovascular, CNS, poisoning (including antivenoms), dermatology, endocrinology, gastrointestinal, medical imaging, musculoskeletal, oncology, immunology, respiratory, sensory and anti-infective.

In one embodiment, mRNA disclosed herein may encode monoclonal antibodies and/or variants thereof. Variants of antibodies may also include, but are not limited to, substitutional variants, conservative amino acid substitution, insertional variants, deletional variants and/or covalent derivatives. In one embodiment, the mRNA disclosed herein may encode an immunoglobulin Fc region. In another embodiment, the mRNA may encode a variant immunoglobulin Fc region.

The mRNA disclosed herein, may encode one or more vaccine antigens. As used herein, a "vaccine antigen" is a biological preparation that improves immunity to a particular disease or infectious agent. According to the present invention, one or more vaccine antigens currently being marketed or in development may be encoded by the mRNA of the present invention. Vaccine antigens encoded in the mRNA of the invention may be utilized to treat conditions or diseases in many therapeutic areas such as, but not limited to, cancer, allergy and infectious disease.

The mRNA of the present invention may be designed to encode on or more antimicrobial peptides (AMP) or antiviral peptides (AVP). AMPs and AVPs have been isolated and described from a wide range of animals such as, but not limited to, microorganisms, invertebrates, plants, amphibians, birds, fish, and mammals. The anti-microbial polypeptides described herein may block cell fusion and/or viral entry by one or more enveloped viruses (e.g., HIV, HCV). For example, the anti-microbial polypeptide can comprise or consist of a synthetic peptide corresponding to a region, e.g., a consecutive sequence of at least about 5, 10, 15, 20, 25, 30, 35, 40, 45, 50, 55, or 60 amino acids of the transmembrane subunit of a viral envelope protein, e.g., HIV-1 gp120 or gp41. The amino acid and nucleotide sequences of HIV-1 gp120 or gp41 are described in, e.g., Kuiken et al., (2008). "HIV Sequence Compendium," Los Alamos National Laboratory.

In some embodiments, the anti-microbial polypeptide may have at least about 75%, 80%, 85%, 90%, 95%, 100% sequence homology to the corresponding viral protein sequence. In some embodiments, the anti-microbial polypeptide may have at least about 75%, 80%, 85%, 90%, 95%, or 100% sequence homology to the corresponding viral protein sequence.

In other embodiments, the anti-microbial polypeptide may comprise or consist of a synthetic peptide corresponding to a region, e.g., a consecutive sequence of at least about 5, 10, 15, 20, 25, 30, 35, 40, 45, 50, 55, or 60 amino acids of the binding domain of a capsid binding protein. In some embodiments, the anti-microbial polypeptide may have at least about 75%, 80%, 85%, 90%, 95%, or 100% sequence homology to the corresponding sequence of the capsid binding protein.

The anti-microbial polypeptides described herein may block protease dimerization and inhibit cleavage of viral proproteins (e.g., HIV Gag-pol processing) into functional proteins thereby preventing release of one or more enveloped viruses (e.g., HIV, HCV). In some embodiments, the anti-microbial polypeptide may have at least about 75%, 80%, 85%, 90%, 95%, 100% sequence homology to the corresponding viral protein sequence.

In other embodiments, the anti-microbial polypeptide can comprise or consist of a synthetic peptide corresponding to a region, e.g., a consecutive sequence of at least about 5, 10, 15, 20, 25, 30, 35, 40, 45, 50, 55, or 60 amino acids of the binding domain of a protease binding protein. In some embodiments, the anti-microbial polypeptide may have at least about 75%, 80%, 85%, 90%, 95%, 100% sequence homology to the corresponding sequence of the protease binding protein.

A non-limiting list of infectious diseases that the mRNA vaccine antigens or anti-microbial peptides may treat is presented below: human immunodeficiency virus (HIV), HIV resulting in mycobacterial infection, AIDS related Cacheixa, AIDS related Cytomegalovirus infection, HIV-associated nephropathy, Lipodystrophy, AID related cryptococcal meningitis, AIDS related neutropaenia, Pneumocysitis jiroveci (*Pneumocystis carinii*) infections, AID related toxoplasmosis, hepatitis A, B, C, D or E, herpes, herpes zoster (chicken pox), German measles (rubella virus), yellow fever, dengue fever etc. (flavi viruses), flu (influenza viruses), haemorrhagic infectious diseases (Marburg or Ebola viruses), bacterial infectious diseases such as Legionnaires' disease (*Legionella*), gastric ulcer (*Helicobacter*), cholera (*Vibrio*), *E. coli* infections, staphylococcal infections, *salmonella* infections or streptococcal infections, tetanus (*Clostridium tetani*), protozoan infectious diseases (malaria, sleeping sickness, leishmaniasis, toxoplasmosis, i.e. infections caused by *plasmodium*, trypanosomes, *leishmania* and *toxoplasma*), diphtheria, leprosy, measles, pertussis, rabies, tetanus, tuberculosis, typhoid, varicella, diarrheal infections such as Amoebiasis, *Clostridium difficile*-associated diarrhea (CDAD), Cryptosporidiosis, Giardiasis, Cyclosporiasis and Rotaviral gastroenteritis, encephalitis such as Japanese encephalitis, Wester equine encephalitis and Tick-borne encephalitis (TBE), fungal skin diseases such as candidiasis, onychomycosis, Tinea captis/scal ringworm, Tinea corporis/body ringworm, Tinea cruris/jock itch, sporotrichosis and Tinea pedis/Athlete's foot, Meningitis such as *Haemophilus* influenza type b (Hib), Meningitis, viral, meningococcal infections and pneumococcal infection, neglected tropical diseases such as Argentine haemorrhagic fever, Leishmaniasis, Nematode/roundworm infections, Ross river virus infection and West Nile virus (WNV) disease, Non-HIV STDs such as Trichomoniasis, Human papillomavirus (HPV) infections, sexually transmitted chlamydial diseases, Chancroid and Syphilis, Non-septic bacterial infections such as cellulitis, lyme disease, MRSA infection, *pseudomonas*, staphylococcal infections, Boutonneuse fever, Leptospirosis, Rheumatic fever, Botulism, Rickettsial disease and Mastoiditis, parasitic infections such as Cysticercosis, Echinococcosis, Trematode/Fluke infections, Trichinellosis, Babesiosis, Hypodermyiasis, Diphyllobothriasis and Trypanosomiasis, respiratory infections such as adenovirus infection, aspergillosis infections, avian (H5N1) influenza, influenza, RSV infections, severe acute respiratory syndrome (SARS), sinusitis, Legionellosis, Coccidioidomycosis and swine (H1N1) influenza, sepsis such as bacteraemia, sepsis/septic shock, sepsis in premature infants, urinary tract infection such as vaginal infections (bacterial), vaginal infections (fungal) and gonococcal infection, viral skin diseases such as B19 parvovirus infections, warts, genital herpes, orofacial herpes, shingles, inner ear infections, fetal cytomegalovirus syndrome, foodborn illnesses such as brucellosis (*Brucella* species), *Clostridium perfringens* (Epsilon toxin), *E. Coli* O157:H7 (*Escherichia coli*), Salmonellosis (*Salmonella* species), Shingellosis (Shingella), Vibriosis and Listeriosis, bioterrorism and potential epidemic diseases such as Ebola haemorrhagic fever, Lassa fever, Marburg haemorrhagic fever, plague, Anthrax Nipah virus disease, Hanta virus, Smallpox, Glanders (*Burkholderia mallei*), Melioidosis (*Burkholderia pseudomallei*), Psittacosis (*Chlamydia psittaci*), Q fever (*Coxiella burnetii*), Tularemia (*Fancisella tularensis*), rubella, mumps and polio.

The mRNA disclosed herein, may encode one or more validated or "in testing" therapeutic proteins or peptides. According to the present invention, one or more therapeutic proteins or peptides currently being marketed or in development may be encoded by the mRNA of the present invention. Therapeutic proteins and peptides encoded in the mRNA of the invention may be utilized to treat conditions or diseases in many therapeutic areas such as, but not limited to, blood, cardiovascular, CNS, poisoning (including antivenoms), dermatology, endocrinology, genetic, genitourinary, gastrointestinal, musculoskeletal, oncology, and immunology, respiratory, sensory and anti-infective.

The mRNA disclosed herein, may encode one or more cell-penetrating polypeptides. As used herein, "cell-penetrating polypeptide" or CPP refers to a polypeptide which may facilitate the cellular uptake of molecules. A cell-penetrating polypeptide of the present invention may contain one or more detectable labels. The polypeptides may be partially labeled or completely labeled throughout. The mRNA may encode the detectable label completely, partially or not at all. The cell-penetrating peptide may also include a signal sequence. As used herein, a "signal sequence" refers to a sequence of amino acid residues bound at the amino terminus of a nascent protein during protein translation. The signal sequence may be used to signal the secretion of the cell-penetrating polypeptide.

In one embodiment, the mRNA may also encode a fusion protein. The fusion protein may be created by operably linking a charged protein to a therapeutic protein. As used herein, "operably linked" refers to the therapeutic protein and the charged protein being connected in such a way to permit the expression of the complex when introduced into the cell. As used herein, "charged protein" refers to a protein that carries a positive, negative or overall neutral electrical charge. Preferably, the therapeutic protein may be covalently linked to the charged protein in the formation of the fusion protein. The ratio of surface charge to total or surface amino acids may be approximately 0.1, 0.2, 0.3, 0.4, 0.5, 0.6, 0.7, 0.8 or 0.9.

The cell-penetrating polypeptide encoded by the mRNA may form a complex after being translated. The complex may comprise a charged protein linked, e.g. covalently linked, to the cell-penetrating polypeptide.

In one embodiment, the cell-penetrating polypeptide may comprise a first domain and a second domain. The first domain may comprise a supercharged polypeptide. The second domain may comprise a protein-binding partner. As used herein, "protein-binding partner" includes, but is not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where the mRNA may be introduced. The cell-penetrating polypeptide may also be capable of penetrating the first cell.

In one embodiment, the mRNA may encode a cell-penetrating polypeptide which may comprise a protein-binding partner. The protein binding partner may include, but is not limited to, an antibody, a supercharged antibody or a functional fragment. The mRNA may be introduced into the cell where a cell-penetrating polypeptide comprising the protein-binding partner is introduced.

Some embodiments of the present disclosure provide a therapeutic mRNA that includes at least one ribonucleic acid (RNA) polynucleotide having an open reading frame encoding at least one antigenic polypeptide, in which the RNA polynucleotide of the RNA includes at least one chemical modification. In some embodiments, the chemical modification is selected from pseudouridine, N1-methylpseudouridine, N1-ethylpseudouridine, 2-thi ouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine), 5-methoxyuridine, and 2'-O-methyl uridine. Each possibility represents a separate embodiment of the present invention.

Any of the foregoing polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., an antigenic protein or polypeptide.

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares between 65% and 75 or about 80% sequence identity to a naturally-occurring or wild-type sequence (e.g., a naturally-occurring or wild-type mRNA sequence encoding a polypeptide or protein of interest (e.g., an antigenic protein or polypeptide.

In some embodiments, a codon optimized RNA may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

As used herein, when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide or polynucleotide based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids which are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% or 60% identical to any of the sequences described herein can be utilized in accordance with the disclosure.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and FASTA Altschul, S. F. et al., J. Molec. Biol., 215, 403 (1990)).

ABC is a threshold phenomenon, which means that the dose of an agent such as LNPs must reach a threshold to induce clinically signicant ABC (substantial). Accordingly, it is contemplated that using a dose lower than the threshold could reduce ABC or prevent its occurrence. Alternatively, the LNPs described herein can lower B1a and/or B1b and/or natural IgM stimulating activity and thus increase the dosing threshold.

In some embodiments, a method for reducing ABC of lipid LNPs encapsulating an mRNA can be performed by at least (i) administering to a subject in need thereof a first dose of the LNPs, and (ii) administering to the subject a second dose of the LNPs; wherein the first dose, the second dose, or both are equal to or less than about 0.3 mg/kg. For example, the first dose, the second dose, or both can be equal to or less than 0.2 mg/kg or 0.1 mg/kg. In some examples, the first dose, the second dose, or both, can range from about 0.1-0.3 mg/kg. The interval between the first dose and the second dose can be less than 2 weeks, e.g, less than 10 days, less than 1 week, less than 4 days, or less than 2 days. When subsequent doses are required, the same low doses described herein may be used. The interval between two consecutive doses may be less than 2 weeks, for example, less than 10 days, less than 1 week, less than 4 days, or less than 2 days.

Dose-limiting toxicity, such as CARPA, refers to side effects of a drug or other treatment that are serious enough to prevent an increase in dose or level of treatment. It is contemplated that using treatment regimens that could maintain the serum level of LNPs below the threshold for triggering clinically significant dose-limiting toxicity would reduce such toxicity or prevent its occurrence.

Accordingly, provided herein is a method for delivering lipid nanoparticles (LNPs) encapsulating an mRNA to a subject without promoting LNP-related toxicity. Such a method comprises administering an amount of the LNPs to a subject during a period, wherein the serum level of the LNPs in the subject during the administration period is not sufficient to induce LNP-related toxicity. The LNP-related toxicity may be coagulopathy, disseminated intravascular coagulation (DIC), vascular thrombosis, activation-related pseudoallergy (CARPA), acute phase response (APR), or a combination thereof.

It is within the knowledge of those skilled in the art to select suitable doses of the mRNA-encapsulating LNPs and the duration of the administration (e.g., infusion) so as to maintain the serum level of the LNPs below the threshold. For example, when a large dose is needed to reach the intended therapeutic effects, a longer administration period can be used. Occurrence of any of the dose-limiting toxicity can be monitored via conventional approaches in medical practice. The dose and administration period can be adjusted upon showing of any symptom associated with the toxicity. In some examples, the dose of the LNPs may be lower than 1 mg/kg, e.g., 0.5 mg/kg, 0.3 mg/kg, 0.2 mg/kg, or 0.1 mg/kg. In other examples, the LNP dose may range from 0.5 to 1 mg/kg (e.g., 0.3 to 0.5 mg/kg). The administration period may range from 30 minutes to 3 hours, for example 1-2 hours. In some instances, the administration period is no less than 1 hour, for example, no less than 1.5 hours, no less than 2 hours, no less than 2.5 hours, or no less than 3 hours.

In any of the methods described herein, the mRNA encapsulated in LNPs can be a therapeutic mRNA, which may code for a therapeutic protein. The mRNA encapsulated in LNPs may also be a mRNA encoding a vaccine antigen. In some instances, the mRNA encapsulated in LNPs may encode multiple proteins. In some embodiments, the LNPs used in this method can be any of the LNPs described herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Exemplary Assay Methods:
1. Bead Assays by Flow Cytometry:

Streptavidin CML latex beads (Polysciences Inc) were coupled with biotinylated DSPC (6 μm beads) or biotinylated PEG (10 μm beads) following manufacturer's recommendations. Coupled Beads (DSPC coupled and PEG coupled) were incubated with diluted serum from mice injected with different LNPs for 30 minutes at room temperature. After washing, beads were then incubated with a rat anti-mouse IgM IgG (BD biosciences) for 15 minutes at room temperature. After washing, cells were resuspended in PBS+2% BSA and analyzed by flow cytometry with a BD Fortesssa (BD Biosciences). Titers of anti LNP IgM were calculated based on standard curve obtained with an anti-PEG IgM monoclonal antibody. Analysis was performed with FlowJo and Prism Software.

2. In Vitro Platelet Activation Assay with LNPs or LNPs Components

Blood samples were collected in 6 mL BD Vacutainer containing 1 mL anticoagulant citrate dextrose (BD biosciences) and centrifuged with no acceleration and no brake at 200×g, 22° C., for 20 minutes. The top, transparent layer of platelet rich plasma (PRP) was transferred into a 15 mL conical tube and washed in PBS+2% fetal calf serum. After counting, $10^5$ cells were incubated at room temperature for different time points with different LNPs or LPS or different LNP components and stained with anti-CD41, CD31 and CD62P fluorescently labeled for 20 min on ice. After washing cells were fixed and analyzed by flow cytometry with a BD Fortessa (BD Biosciences). Analysis was performed with FlowJo and Prism Software.

3. In Vitro Platelet Aggregation with Macrophages, B Cells

Blood sample were collected in 6 mL BD Vacutainer containing 1 mL anticoagulant citrate dextrose (BD biosciences). 10-25 ml of blood were incubated at room temperature for different time points at room temperature with different LNPs or LPS and stained with anti-CD41, CD11b, CD19 and F4/80 fluorescently labeled for 20 min on ice. After washing cells were fixed and analyzed by flow cytometry with a BD Fortessa (BD Biosciences). Analysis was performed with FlowJo and Prism Software.

4. In Vivo Platelet Activation Assay

Mice were injected intravenously with different LNPs. After different time points, Blood sample were collected in 6 mL BD Vacutainer containing 1 mL anticoagulant citrate dextrose (BD biosciences) and centrifuged with no acceleration and no brake at 200×g, 22° C., for 20 minutes. The top, transparent layer of platelet rich plasma (PRP) was transferred into a 15 mL conical tube and washed in PBS+2% fetal calf serum. After counting, $10^5$ cells were stained with anti-CD41, CD31 and CD62P fluorescently labeled for 20 min on ice. After washing cells were fixed and analyzed by flow cytometry with a BD Fortessa (BD Biosciences). Analysis was performed with FlowJo and Prism Software.

5. In Vivo Platelet Aggregation with Macrophages, B Cells

Mice were injected intravenously with different LNPs. After different time points, Blood sample were collected in 6 mL BD Vacutainer containing 1 mL anticoagulant citrate dextrose (BD biosciences). 10-25 ml of blood were the stained with anti-CD41, CD11b, CD19 and F4/80 fluorescently labeled for 20 min on ice. After washing cells were fixed and analyzed by flow cytometry with a BD Fortessa (BD Biosciences). Analysis was performed with FlowJo and Prism Software.

6. In Vivo Splenic B Cell Activation Assay:

Spleen of injected animals with fluorescent LNPs were collected in saline buffer. Splenocytes cell suspension were prepared by gently pressing the spleen through a 70-μM mesh cell strainer (Fisher Scientific). After washing, red blood cells was lysed and cells were resuspended in PBS+2% fetal calf serum. After washing and counting, $10^5$ cells were stained with anti-CD19, CD86 and CD69 fluorescently labeled for 20 min on ice. After washing cells were fixed and analyzed by flow cytometry with a BD Fortessa (BD Biosciences). Analysis was performed with FlowJo and Prism Software.

7. In Vivo LNP Interaction with B Cells:

Spleen of injected animals with fluorescent LNPs were collected in saline buffer. Splenocytes cell suspension were prepared by gently pressing the spleen through a 70-μM mesh cell strainer (Fisher Scientific). After washing, red blood cells was lysed and cells were resuspended in PBS+2% fetal calf serum. After washing and counting, $10^5$ cells were stained with anti-CD19 and CD5 fluorescently labeled for 20 min on ice. After washing cells were fixed and analyzed by flow cytometry with a BD Fortessa (BD Biosciences). Analysis was performed with FlowJo and Prism Software.

8. In Vitro Splenic B Cell Activation Assay:

Spleen of injected animals with fluorescent LNPs were collected in saline buffer. Splenocytes cell suspension were prepared by gently pressing the spleen through a 70-μM mesh cell strainer (Fisher Scientific). After washing, red blood cells was lysed and cells were resuspended in PBS+2% Fetal calf serum. After counting, $10^5$ cells were incubated at 37 C for the indicated time points with different LNPs or medium. After incubation, cells were stained anti-CD19, CD86 and CD69 fluorescently labeled for 20 min on ice. After washing cells were fixed and analyzed by flow cytometry with a BD Fortessa (BD Biosciences). Analysis was performed with FlowJo and Prism Software.

9. In Vitro LNP Interaction with B Cells:

Spleen of injected animals with fluorescent LNPs were collected in saline buffer. Splenocytes cell suspension were prepared by gently pressing the spleen through a 70-μM mesh cell strainer (Fisher Scientific). After washing, red blood cells was lysed and cells were resuspended in PBS+2% Fetal calf serum. After counting, $10^5$ cells were incubated at 37 C for the indicated time points with different LNPs or medium. After incubation, cells were stained anti-CD19 and CD5 fluorescently labeled for 20 min on ice. After washing cells were fixed and analyzed by flow cytometry with a BD Fortessa (BD Biosciences). Analysis was performed with FlowJo and Prism Software.

10. Human B Cell Activation Assay:

Human PBMC were isolated post-Ficoll gradient separation. After counting, $10^5$ cells were incubated at 37 C for the indicated time points with different LNPs or medium. After incubation, cells were washed and stained with anti-CD19, CD86 and CD69 fluorescently labeled for 20 min on ice. After washing cells were fixed and analyzed by flow cytometry with a BD Fortessa (BD Biosciences). Analysis was performed with FlowJo and Prism Software.

Anti-PEG IgM: In several of the figures the terminology anti-PEG IgM is used generally to refer to IgM. If the IgM is detected at a time point earlier than 96 hours following delivery of the LNP, the IgM is natural IgM. If the IgM is measured after 96 hours, the IgM may be anti-PEG IgM and/or natural IgM. Natural IgM bind phosphocholine motif rather than PEG.

Ion Exchange (IEX) Chromatography to Determine Encapsulation Efficiency

An ion exchange (IEX) chromatography method was developed to accurately determine encapsulation efficiency for mRNAs encapsulated in ionizable-lipid-based LNPs, produced according to routine T mixer methodologies (Example 1). IEX chromatography can be used to separate bound versus free mRNA. IEX Screening method separates free mRNA from LNP's when there is a gradient change from low to high salt concentration. LNP elutes in the void (peak 1) and mRNA elutes when gradient changes from low to high salt concentration (peak 2, termed "accessible mRNA").

Without being bound in theory, it is believed that within a population of LNPs (e.g., LNPs encapsulating mRNA), mRNA can exist in a variety of different encapsulation states, including, for example, fully encapsulated, surface-associated, loosely encapsulated (or other physical states). Art-recognized methods for determining nucleic acid encapsulation efficiency, in particular, the routinely-used Ribogreen assay, fails to differentiate between such physical states (e.g., does not discern important differences in structural characteristics and contexts). To exemplify the utility of the IEX method of the invention, a LNP sample population can be subjected to an art-recognized separation technique, for example, size-exclusion chromatography (SEC). This fractionates particles based on size. Fractions can be subjected, for example, to a biological assay, e.g., in vitro protein expression assay. Fractions can likewise be subjected to determination of encapsulation efficiency according to the IEX methods of the invention. It is shown in Examples 2 and 3 that % mRNA accessible or retention on IEX column correlates (inversely) with in vitro protein expression.

Physiochemical Characterization of LNPs

Lipid nanoparticles can be assessed for a variety of physiochemical properties using a variety of analytical techniques known to the skilled artisan.

In exemplary aspects, particles characterized and/or fractionated can be determine Size Exclusion Chromatography (SEC). SEC is a chromatographic separation technique where molecules are separated based on their size (large molecules are eluted first, followed by small molecules) It is a good analytical tool to characterize the polydispersity in LNP's and assess the heterogeneity in physiochemical properties and their possible impact on biological activity. Exemplary methods are set forth in Zhang et al (2012) Mol. Pharmaceutics, 2013, 10 (1), pp 397-405

In certain embodiments, LNP preparations (e.g., populations) are fractionated and fractions (or pools thereof) are analyzed for polydispersity in size (e.g., particle size) and/or composition (e.g., ionizable cationic lipid amount or concentration, phospholipid amount or concentration, cholesterol amount or concentration, PEG-lipid amount or concentration, mRNA amount (e.g., mass) or concentration) and, optionally, further assayed for in-vitro and/or in vivo activity. Fractions or pools thereof can also be analyzed for accessible mRNA and/or purity (e.g., purity as determined by reverse-phase (RP) chromatography.)

Particle size can be determined by Dynamic Light Scattering (DLS). DLS measures a hydrodynamic radius. Smaller particles diffuse more quickly, leading to faster fluctuations in the scattering intensity and shorter decay times for the autocorrelation function. Larger particles diffuse more slowly, leading to slower fluctuations in the scattering intensity and longer decay times in the autocorrelation function.

mRNA quantification can be determined by by Anion-Exchange Chromatography (AEX). AEX is a chromatographic separation technique based on charge using a positively charged groups. Detergent, e.g., 2% Triton and/or salt, e.g., 150 mM salt can be used as a diluent to break up the nanoparticles. The concentration of mRNA is calculated using external standard.

% Mass of mRNA=Concentration of Fraction*Volume of Fraction collected/Yield

Total Lipids can be quantitated by Reverse Phase HPLC with CAD detection. LNPs are diluted in Ammonium salt, centrifuged to separate lipids from mRNA and supernatant was used for quantification. The concentration of lipids is calculated using external standard.

mRNA purity can be determined by Reverse Phase HPLC:Size based separation. This method can be used to assess mRNA integrity by a length-based gradient RP separation and UV detection at 260 nm.

The above methods can further be used to determine lipid:mRNA ratio across fractions.

DOSY NMR can be used to determine the amount of surface accessible polyethylene glycol molecules, amount of residual polyethylene glycol molecules, and/or half-life time of polyethylene glycol molecules in a composition as describe herein. Briefly, the surface accessible, residual, and/or half-life time of molecules comprising polyethylene glycol may be determined by monitoring shedding of the molecule comprising polyethylene glycol in the presence of serum. For example, in certain embodiments, the lipid nanoparticles and mouse serum are added in a 1:1 ratio. The total volume was 400 μL with 180 μL of mouse serum, 180 μL of sample at a concentration of 0.5 mg/mL of mRNA, and 40 μL of $D_2O$ at 25° C. Diffusion-ordered spectroscopy (DOSY) NMR experiments are recorded at about 30 minute time intervals over a 24 hour period. The percent of the molecule comprising polyethylene glycol within (e.g., bound) to the lipid nanoparticle (i.e., % PEG bound) is determined at each time point as described above, generating a % PEG bound vs time plot, where the time to reach 50% shedding can be extrapolated using the experimental diffusion coefficient (e.g., $Diffusion_{experimental}$) of the molecule comprising polyethylene glycol. To determine the diffusion coefficient of a given proton, the Bruker Diffusion Ordered Spectroscopy (DOSY) NMR pulse program ledbpgp2s* is utilized to generate a 2D plot of chemical shift vs Log (diffusion coefficient). The diffusion coefficient of the peak (chemical shift) corresponding to the polyethylene glycol (i.e., PEG) particle is extrapolated, which is converted to % PEG bound to the lipid nanoparticle by the formula:

$$\text{Diffusion}_{experimental} = (\% \text{ PEG}_{free})*(\text{Diffusion}_{free}) + (\% \text{ PEG}_{bound})*(\text{Diffusion}_{bound})$$

wherein $\text{Diffusion}_{free}$ is the diffusion coefficient of free polyethylene glycol (e.g., $10^{-9.6}$), and $\text{Diffusion}_{bound}$ is the diffusion coefficient of lipid nanoparticle-bound PEG (e.g., $10^{-11.2}$), $\text{Diffusion}_{experimental}$ is the measured diffusion coefficient under after serum addition. Parameters for ledbgp2s NMR experiment are gradient pulse length (δ) of 10 ms, diffusion time (Δ) of 100 ms, recycle delay (d1) of 2 seconds, and acquisition time of 1.5 seconds. The gradient strength is incremented from 2% to 95% in steps of 16. The total experiment time is 31 minutes. The DOZY NMR is further described in Kerssebaum, R. (2002). DOSY and Diffusion by NMR. Rheinstetten, Germany: Bruker BioSpin GmbH, which is incorporated by reference in its entirety. The PEG shedding is further described in Wilson, S. C.; Baryza, J. L.; Reynolds, A. J.; Bowman, K.; Rajan, S.; et al. (2015). Real Time Measurement of PEG Shedding from Lipid Nanoparticles in Serum via NMR Spectroscopy. Molecular Pharmaceutics, 12(2):386-92, which is incorporated by reference in its entirety.

Normalized general polarization can be used to determine the surface polarity, as described herein.

Bloody escape of encapsulation by fluorescent intercalation (BEEFI) can be used to determine the endosomal release characteristics of lipid nanoparticles and compositions. Briefly, the lipid nanoparticles and mouse serum are added in a 1:1 ratio. The total volume was 40 μL with 20 μL of mouse serum and 20 μL of LNPs at a concentration of 0.5 mg/mL of mRNA. The lipid nanoparticles and mouse serum were incubated at 25° C. for 20 minutes. Then, the mixture of LNPs and serum was aliquoted into two tubes, such that each tube contained 6 One tube was designated as the control tube. 14 μL of PBS was added to the control tube. The other tube was designated as the assay tube. 12 μL of the endosome mix (ENDO) and 2 μL of pH 6 buffer was added to the assay tube. The control tube and assay tube were then incubated at 37° C. for 15 minutes. Then, 4 μL of each sample was pipetted into a 96 well plate. Specifically, the control tube was pipetted twice, into A1 and B1. The assay tube was pipetted twice, into C1 and D1. Then, TE or Triton was added into each well accordingly to the following A1 add 46 uL TE (mix), then and 50 μL Triton
B1 add 96 uL TE (mix)
C1 add 96 uL TE (mix)
D1 add 96 uL TE (mix).

Then, 100 μL of Ribogreen was added into each well and the fluorescence of the wells were read. The in vitro release was calculated using the following equations. The duplicates were averaged.

$$\text{First duplicate} = \frac{[C1] - [B1]}{[A1]}$$

$$\text{Second duplicate} = \frac{[D1] - [B1]}{[A1]}$$

To make the endosome mix (ENDO), three stock solutions of DOPE, DOPC, and DOPS in chloroform at a concentration of 25 mg/mL were made. The stock solutions were added together at a ratio of 2:1:1 (DOPE:DOPC:DOPS), making note of the total mass (mg). The chloroform was then envaporated with a Roto-Evaporator. The lipids were then dissolved in PBS so that final concentration was 20 mg/mL lipid. The lipids were then sonicated until the size was 400-600 nm by Malvern. The BEEFI assay is further described in Zhang, et al. (2014), The development of an in vitro assay to screen lipid based nanoparticles for siRNA delivery," J. Control. Release 2014, 174, pp. 7-14.

Example 1: Ion-Exchange Chromatography for Determining Encapsulation Efficiency

Figure 1B:
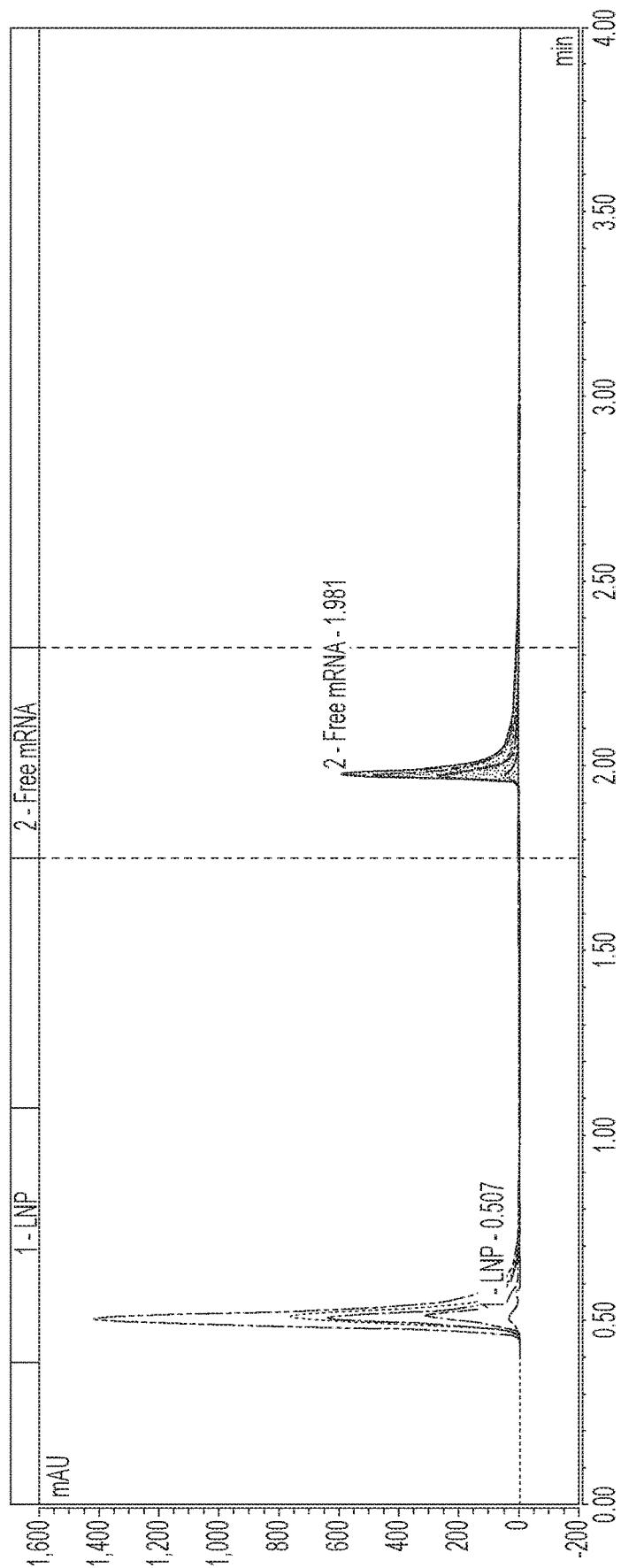

IEX methodology was developed to separate free mRNA versus LNP-encapsulated mRNA. A schematic representation of LNP-encapsulated mRNA is shown in FIG. 1. Using an exemplary process, LNP elutes in the void and mRNA elutes when gradient changes from low to high salt concentration. Representative separation is depicted in FIGS. 1A-B. FIG. 1A depicts varying encapsulation efficiency based on mRNA formulation buffer conditions. FIG. 1B depicts varying encapsulation efficiency based on mRNA formulation salt concentrations.

The method conditions below were used to separate encapsulated from free mRNA encoding an infectious disease antigen.

| Buffer A | 25 mM NaOH/Glycine |
| Buffer B | 25 mM NaOH/Glycine with 750 mM NaCl |
| Column | Proswift WAX-1S |
| Flow rate | 0.7 mL/min |
| Run time | 4 minutes |

Gradient was as follows:

| No | Time | Flow mL/min | % B | Curve |
| --- | --- | --- | --- | --- |
| 1 | 0.0 | 0.7 | 7 | 5 |
| 2 | 0.8 | 0.7 | 7 | 5 |
| 3 | 1.6 | 0.7 | 100 | 5 |
| 4 | 2.9 | 0.7 | 100 | 5 |
| 5 | 3.0 | 0.7 | 7 | 5 |
| 6 | 4.0 | 0.7 | 7 | 5 |

Example 2: Encapsulation Efficiency, as Determined by IEX Correlates with In Vitro Activity mRNA encoding a cytokine was encapsulated in Compound 18-based LNPs and formulation process and formulation buffers were varied. The IEX method described above was used to characterize various samples to determine if in vitro activity correlated with % mRNA retained on the column.

Six formulations were characterized and the data obtained from the characterization of the samples was as shown below:

| Sample | % mRNA retained on the column | In-vitro value (125 ng) |
|---|---|---|
| 1 | 10.85 | 95080 |
| 2 | 38.27 | 4533 |
| 3 | 49.22 | 5477 |
| 4 | 22.76 | 26286 |
| 5 | 25.74 | 48128 |
| 6 | 9.56 | 84906 |

Example 3: Correlation of Encapsulation Efficiency as Determined by IEX with Biological Activity LNPs encapsulating an mRNA vaccine composition were fractionated according to SEC then subjected to second dimensional analysis (physiochemical analysis of the SEC fractions). Particle size was determined according to dynamic light scattering. % mass of mRNA across the peak on SEC was determined according to the following:

% Mass of mRNA=Concentration of Fraction*Volume of Fraction collected/Yield.

Figure 2:
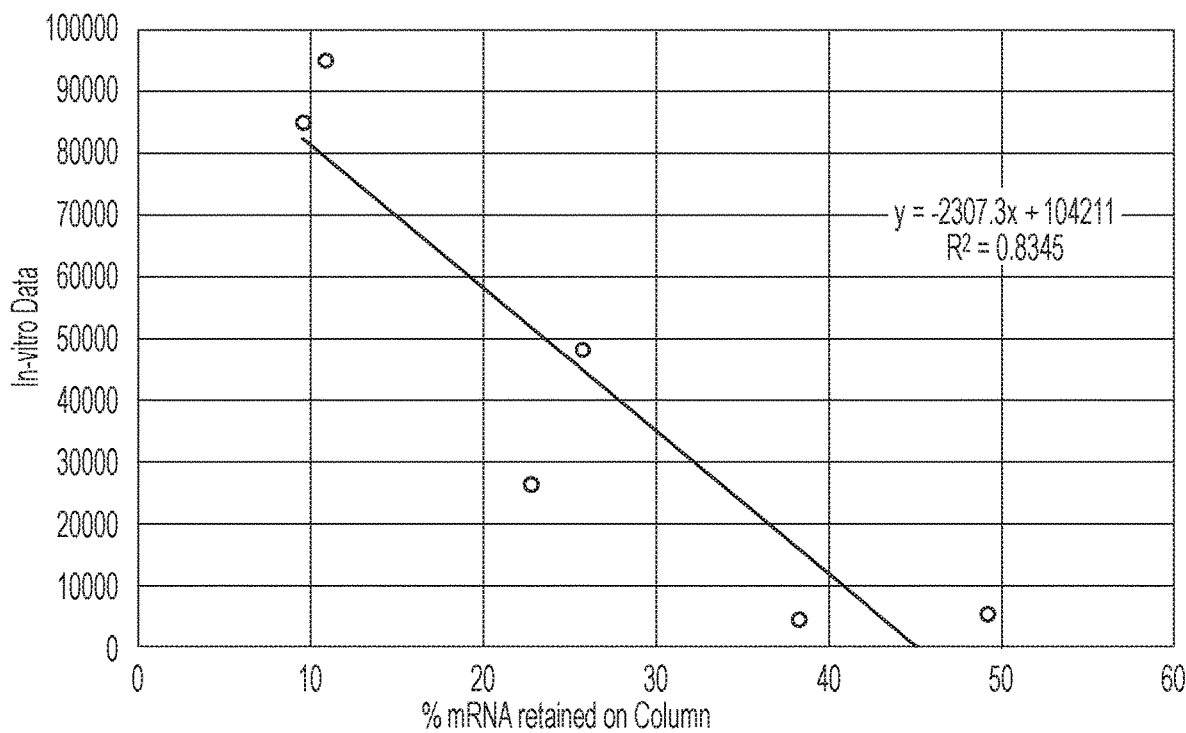
FIG. 2 is a graph showing correlation between the % mRNA retained on the column and In vitro expression of samples.

Fractions were subjected to both in vitro expression assay and encapsulation efficiency assay. the data in FIG. 2C show that % mRNA accessible or retention on IEX column correlates (inversely) with in vitro protein expression.

Example 4: Percent Encapsulation of mRNA

The encapsulation % of the mRNA in lipid nanoparticles is determined using a 4.6×50 mm Proswift WAX-1S weak anion exchange column in 25 mM Sodium Hydroxide and Glycine buffer with elution of accessible RNA using a sodium chloride salt gradient. Samples are diluted to a target concentration of 0.1 mg/mL RNA using 10 mM TRIS-HCL 1 mM EDTA buffer and the accessible RNA peaks is quantitated with an external reference standard. The methods are shown in the table.

| | |
|---|---|
| Instrument: | Thermofisher Vanquish UHPLC, Agilent 1260, or equivalent (Biocompatible System recommended by not required) |
| Column: | Thermofisher PROswift WAX-1S 4.6 × 50 mm Monolithic column |
| Mobile Phase A: | 25 mM NaOH/Glycine pH 10.09 |
| Mobile Phase B: | 25 mM NaOH/Glycine pH 10.09, 750 mM Sodium Chloride |
| Needle Wash: | 50% Ethanol: 50% Water |
| Seal Wash: | 0.1% Formic Acid in 25% Water: 75% IPA |
| Column Wash: | 80% 0.25N NaOH in water and 20% Ethanol |
| Acquisition/Run Time: | 4 minutes |
| Flow Rate: | 0.7 mL/ min |
| Detection: | UV at 260 nm |
| Injection Volume: | 10 µL (except for standard curve in R&D analysis) |
| Column Temperature: | 25° C. |
| Auto sampler Temperature: | 20° C. |
| Injection/Needle Wash: | After Draw or Both-20 seconds, 30 µL/sec (or wash vial for Agilent) |
| Sample Concentration: | Target 0.1 mg/mL |

| Time (min) | Mobile Phase A % | Mobile Phase B % |
|---|---|---|
| 0.0 | 93.0 | 7.0 |
| 0.8 | 93.0 | 7.0 |
| 1.6 | 0.0 | 100.0 |
| 2.9 | 0.0 | 100.0 |
| 3.0 | 93.0 | 7.0 |
| 4.0 | 93.0 | 7.0 |

Calculations $$\text{Accessible } RNA_{Conc} = \frac{(Sample_{Peak\ Area} * Standard_{Conc})}{Mean\ Standard_{peak\ area}} * \text{Dilution Factor}$$

Encapsulation % from Accessible RNA =

$$\left(\left[\frac{\text{Total } mRNA\ Conc - \text{Accessible } RNA_{Conc}}{\text{Total } mRNA\ Conc}\right] * 100\right)$$

Accessible RNA—This is the concentration of RNA that can be quantitated when the formulations is diluted in non-denaturing conditions and assayed according to the method conditions. This RNA represents a combination of mRNA that is free or loosely associated with lipids.

Total RNA—This is the concentration of RNA that can be quantitated when the formulations is diluted in denaturing conditions. This RNA represents encapsulated, loosely associated, and free RNA.

Un-retained LNP—This is the un-retained material that elutes in the void of the column. Likely consists of mRNA in an encapsulation state that is strongly associated and lacks significant surface charge for retention.

Figure 3:
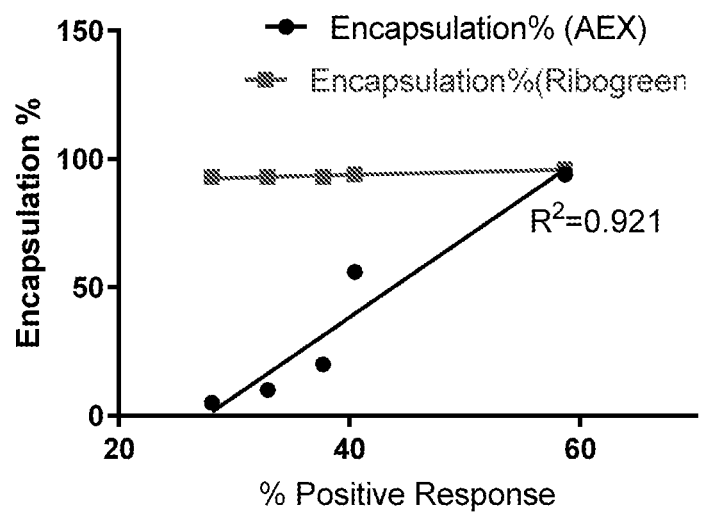
FIG. 3 is a graph of mRNA encapsulation percent as determined by Ribogreen and anion exchange chromatography versus in vitro expression.
Figure 4:
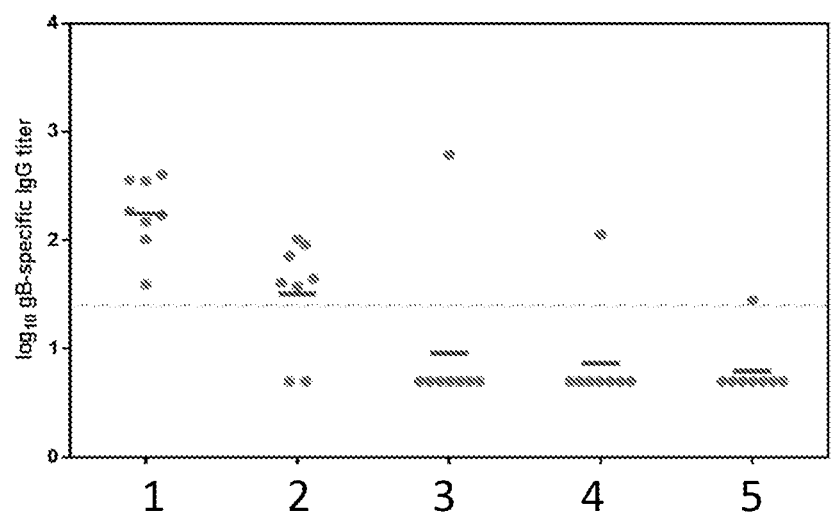
FIG. 4 is a graph of in vivo immunogenicity for the lipid nanoparticles in FIG. 3 having different encapsulation percentage as determined by anion exchange chromatography.

The Ribogreen assay cannot discriminate between the prototype formulations and shows them to be in the same encapsulation state, as illustrated by the graphs of in vitro expression in FIG. 3 and in vivo immunogenicity in FIG. 4. It is likely, that Ribogreen can only detect truly free RNA and does not discriminate between loose or poorly structured encapsulations states. Encapsulation by weak anion exchange chromatography can discriminate between the formulations and correlates reasonably well to the in-vitro expression data shown below. The table, below, shows the percent encapsulation using Ribogreen and using AEX for the compositions in FIGS. 3 and 4.

| Prototype | Description | Encapsulation by Ribogreen (%) | Encapsulation by AEX (%) |
|---|---|---|---|
| 1 | 20 mM Tris 0 mM NaCl 8% Sucrose | 96 | 94 |
| 2 | 20 mM Tris 30 mM NaCl 8% Sucrose | 94 | 56 |
| 3 | 20 mM Tris 60 mM NaCl 8% Sucrose | 93 | 20 |
| 4 | 20 mM Tris 140 mM NaCl 8% Sucrose | 93 | 10 |
| 5 | 20 mM Tris 300 mM NaCl 8% Sucrose | 93 | 5 |

Figure 5:
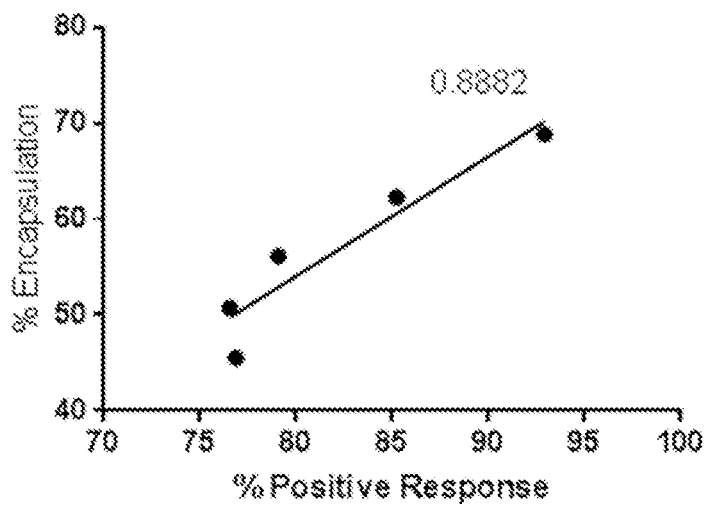
FIG. 5 is a graph of mRNA encapsulation percent as determined by anion exchange chromatography versus in vitro expression.
Figure 6:
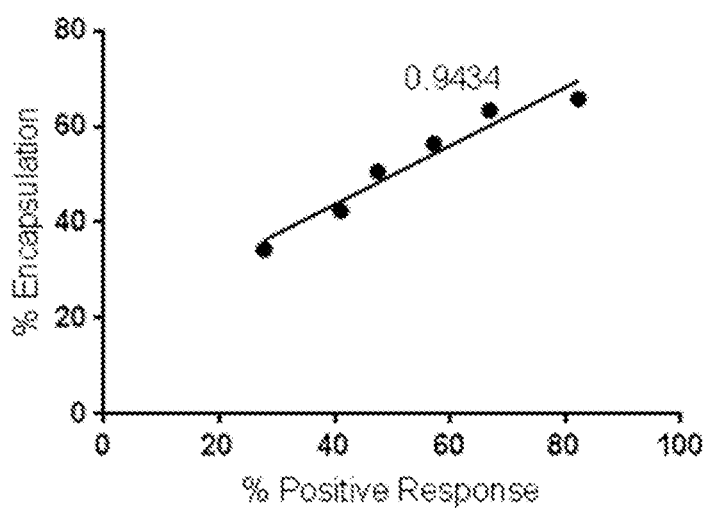
FIG. 6 is a graph of mRNA encapsulation percent as determined by anion exchange chromatography versus in vitro expression.

Examplary Formulation SEC Fractions were assessed with varied encapsulation by anion exchange chromatography and in-vitro expression. Two batches were fractionated using size exclusion chromatography and characterized for physio-chemical characteristics and biological activity. SEC fractions varied in encapsulation state by weak ion exchange chromatography and correlated well with in-vitro expression as shown in FIGS. 5 and 6.

Figure 7:
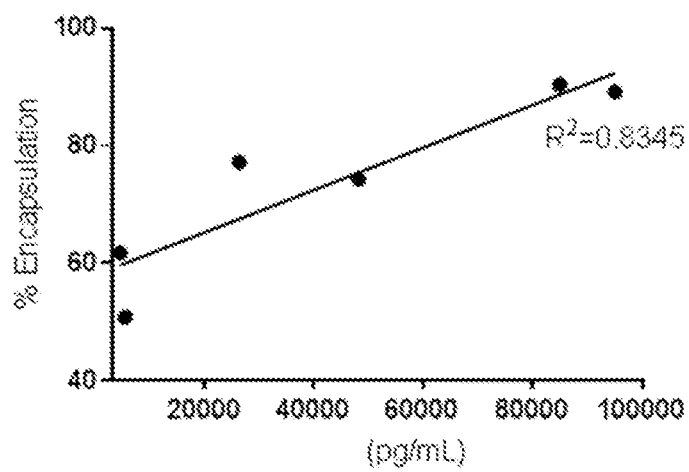
FIG. 7 is a graph of mRNA encapsulation percent as determined by anion exchange chromatography versus in vitro expression.

An examplary cytokine prototype formulation was assessed with varied encapsulation by anion exchange chromatography and in-vitro expression. The data is shown in FIG. 7 (x-axis=cytokine expression in pg/ml).

Examplary cytokine encoding RNA formulation—SEC Fractions with varied encapsulation by anion exchange chromatography and in-vitro expression.

Figure 8:
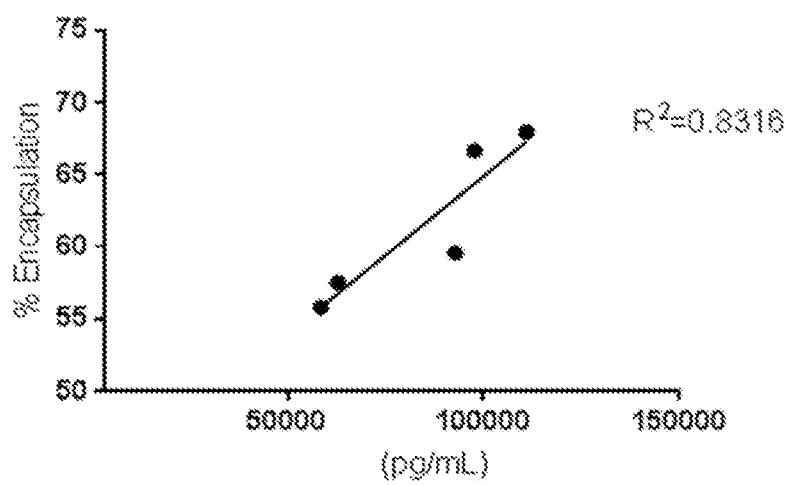
FIG. 8 is a graph of mRNA encapsulation percent as determined by anion exchange chromatography versus in vitro expression.

A cyotkine RNA batch was fractionated using size exclusion chromatography and characterized for physio-chemical characteristics and biological activity. SEC fractions varied in encapsulation state by weak ion exchange chromatography and correlated well with in-vitro expression. The data is shown in FIG. 8 (x-axis=cytokine expression in pg/ml).

Example 5

In this example, the effect of the formulation process on encapsulation, half-life time of a PEG lipid, surface polarity, in vitro expression, and in vivo expression are described. In general, LNPs formed by a process including a step in which additional PEG lipid was added to the LNPs after the nanoprecipitation reaction had a higher percent encapsulation, lower surface polarity, shorter half-life time of the PEG lipid, higher in vitro expression, and higher in vivo expression than LNPs formed by process in which PEG lipid was added only during the nanoprecipitation reaction.

LNPs formed via three different methods were investigated. The LNPs only differed significantly in the particle formation process. In this example, the LNPs comprised 50 mol % cationic lipid, 10 mol % DSPC, 38.5 mol % cholesterol, and 1.5 mol % PEG-DMG. All LNPs were formed via a nanoprecipitation reaction using a T-mixer. However, three different procedures (i.e., standard, post-insertion, final addition) were used after the nanoprecipitation reaction. The standard procedure comprised (i) a nanoprecipitation reaction between the lipids dissolved in ethanol and the mRNA in aqueous solution, (ii) tangential flow filtration, and (iii) a final filtration step. The mol % of PEG-DMG used in the nanoprecipitation reaction was 1.5 mol % for the standard procedure.

The post-insertion procedure comprised (i) a nanoprecipitation reaction between the lipids dissolved in ethanol and the mRNA in aqueous solution, (ii) exposure of the resulting particles to a solution comprising a certain weight percentage of PEG-DMG, (iii) tangential flow filtration, and (iv) a final filtration step. The mol % of PEG-DMG used in the nanoprecipitation reaction varied depending on the amount of PEG-DMG used in the post-particle formation exposure step. 0.5 mol % of PEG-DMG was used when the resulting particles were exposed to 1.0 mol % PEG-DMG. The mol % of PEG-DMG used in the nanoprecipitation reaction was 1.0 mol % when the resulting particles were exposed to 0.5 mol % PEG-DMG.

The final addition procedure comprised (i) a nanoprecipitation reaction between the lipids dissolved in ethanol and the mRNA in aqueous solution, (ii) tangential flow filtration, (iii) exposure of the filtered particles to a solution comprising a certain weight percentage of PEG-DMG, and (iv) a final filtration step. The mol % of PEG-DMG used in the nanoprecipitation reaction varied depending on the amount of PEG-DMG used in the post-filtration exposure step. When the filtered particles were exposed to 1.0 mol % PEG-DMG, the mol % of PEG-DMG used in the nanoprecipitation reaction was 0.5 mol %. The mol % of PEG-DMG used in the nanoprecipitation reaction was 1.0 mol % when the filtered particles were exposed to 0.5 mol % PEG-DMG. The amount of PEG added for each procedure is shown in the table below.

| Batch No. | Batch Description | Core PEG (mol%) | Post Inserted PEG (mol %) | Final PEG Spike (mol %) | Total PEG (mol %) |
|---|---|---|---|---|---|
| 17129-1 | Standard | 1.5 | 0.00 | 0.00 | 1.5 |
| 17129-2 | Post Insertion-1.0 to 1.5 | 1.0 | 0.50 | 0.00 | 1.5 |
| 17129-3 | Final Addition-1.0 to 1.5 | 1.0 | 0.00 | 0.50 | 1.5 |
| 17129-4 | Post Insertion-0.5 to 1.5 | 0.5 | 1.00 | 0.00 | 1.5 |
| 17129-5 | Final Addition-0.5 to 1.5 | 0.5 | 0.00 | 1.00 | 1.5 |

The table below shows the mole percentage of components in the LNPs formed by different formulation processes. As shown in the table, the final composition of the LNPs formed by different formulation process did not vary significantly.

| Batch | mRNA (mg/mL) | Total lipids (mg/ML) | Lipid: RNA | Cationic Lipid (Mol %) | DSPC (Mol %) | Chol (Mol %) | PEG (Mol %) |
|---|---|---|---|---|---|---|---|
| 17129-1 | 0.507 | 9.53 | 18.8 | 50.37 | 9.66 | 38.51 | 1.45 |
| 17129-2 | 0.459 | 8.69 | 18.9 | 49.68 | 10.04 | 38.85 | 1.41 |
| 17129-3 | 0.544 | 10.21 | 18.8 | 50.32 | 9.90 | 38.52 | 1.25 |
| 17129-4 | 0.493 | 9.07 | 18.4 | 49.85 | 10.26 | 38.44 | 1.44 |
| 17129-5 | 0.485 | 9.52 | 19.6 | 49.96 | 10.18 | 38.48 | 1.38 |

Figure 9:
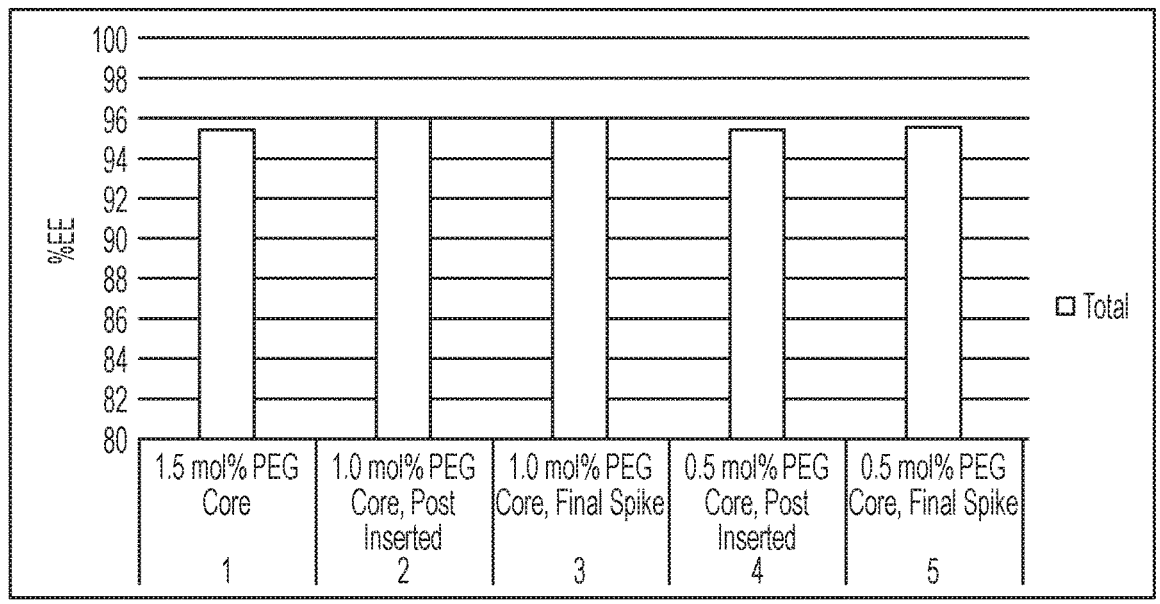
FIG. 9 is a histogram of mRNA encapsulation percent as determined by Ribogreen for lipid nanoparticles formed via various processes.
Figure 10:
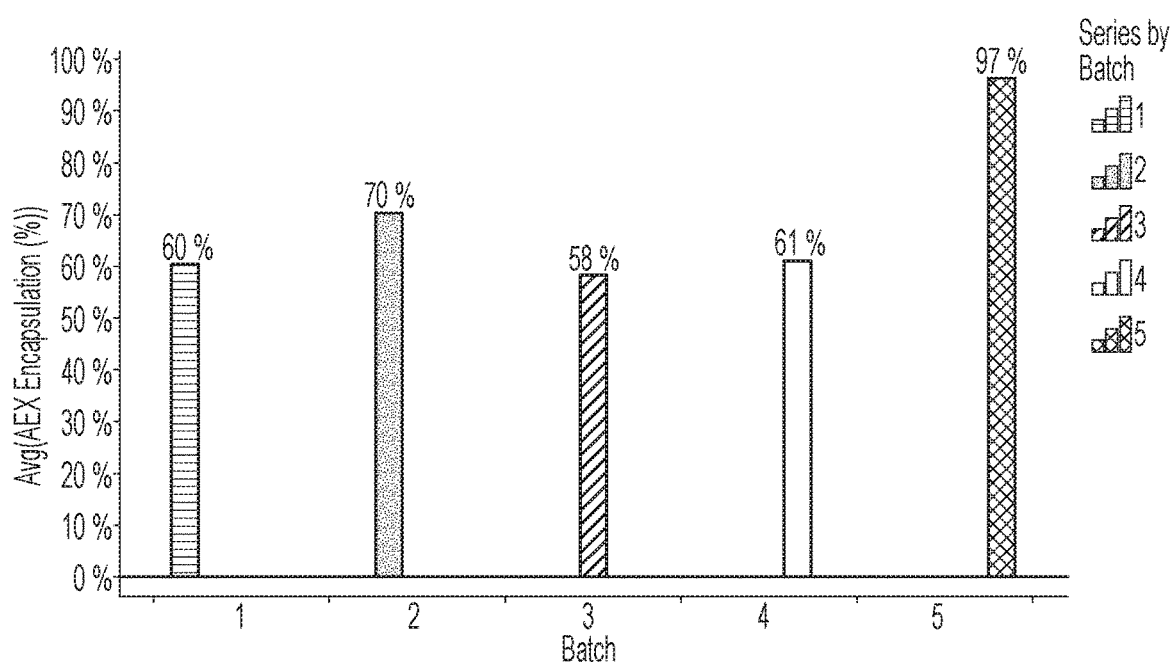
FIG. 10 is a histogram of mRNA encapsulation percent as determined by anion exchange chromatography for lipid nanoparticles formed via various processes.

Though no significant difference in mRNA encapsulation was found using Ribogreen as shown in FIG. 9, AEX showed a clear difference in mRNA encapsulation for the different procedures as shown in FIG. 10.

Figure 11:
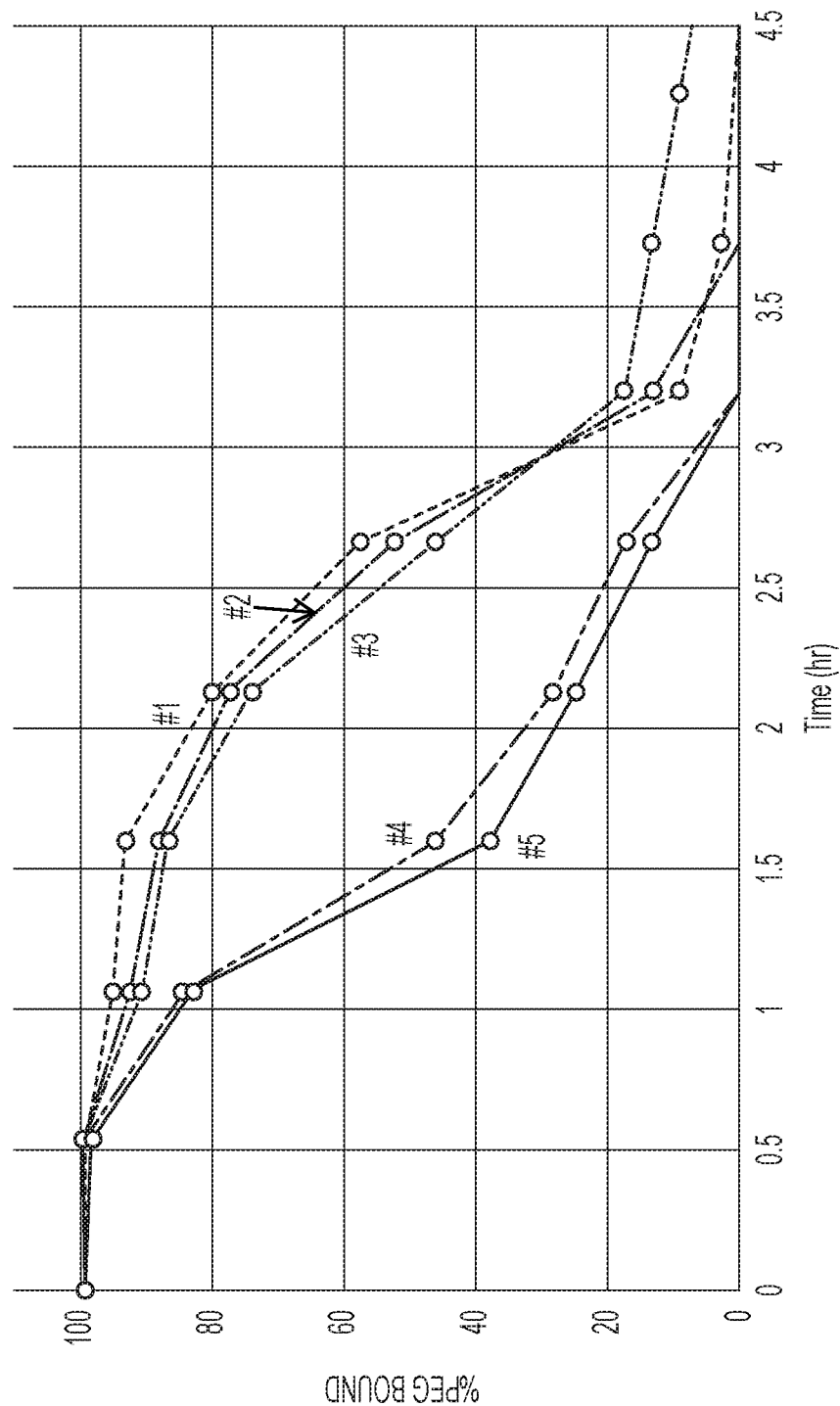
FIG. 11 is a graph of percent bound polyethylene glycol (PEG) versus time

As shown in FIG. 11, LNPs formed via the post-insertion procedure and final addition procedure had shorter PEG-DMG half-lives than LNPs formed via the standard procedure.

Figure 12:
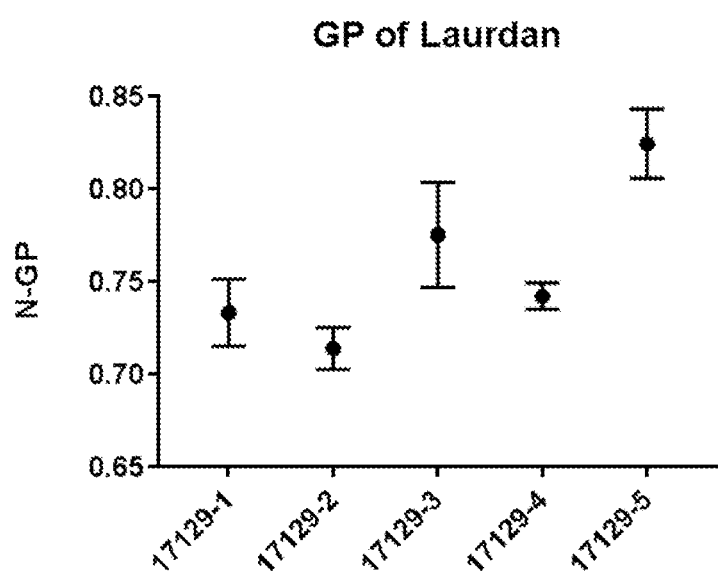
FIG. 12 is a graph of normalized general polarization using laurdan for lipid nanoparticles formed via various processes.

In general, the LNPs formed via the post-insertion and final addition procedures had lower surface polarity (i.e., higher normalized general polarization) than LNPs formed via the standard process as shown in FIG. 12. The surface polarity of the LNP surfaces from lowest surface polarity to highest was: 17129-5<17129-3<17129-4<19129-1<17129-2. In general, LNPs with higher polarity (e.g., lower rigidity or hydrophobicity) had lower in vitro expression as shown in FIGS. 13 and 14.

Figure 13:
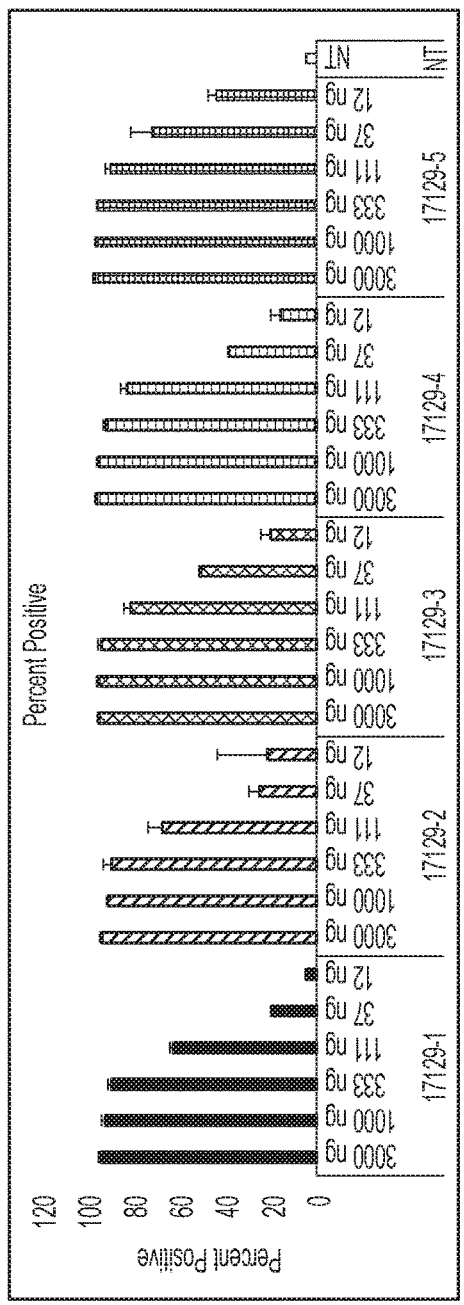
FIG. 13 is a histogram of in vitro protein expression for lipid nanoparticles formed via various processes.
Figure 14:
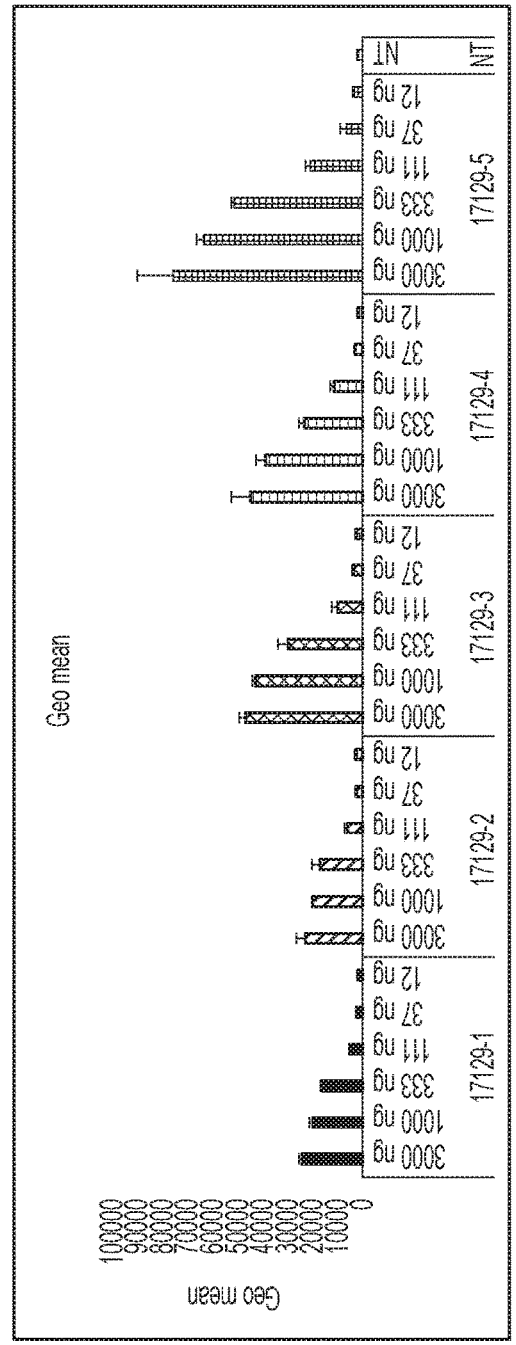
FIG. 14 is a histogram of geo mean for lipid nanoparticles formed via various processes.

The in vitro protein expression of the LNPs formed from the different procedures is shown in FIGS. 13 and 14. As illustrated in FIGS. 13 and 14, the post-insertion and final addition procedures produced LNPs having a higher in vitro protein expression than the standard procedure. The final addition procedure resulted in the highest in vitro expression. The in vitro protein expression of the post-insertion and final addition procedure was higher when less PEG-DMG was added during the nanoprecipitation reaction.

Figure 15:
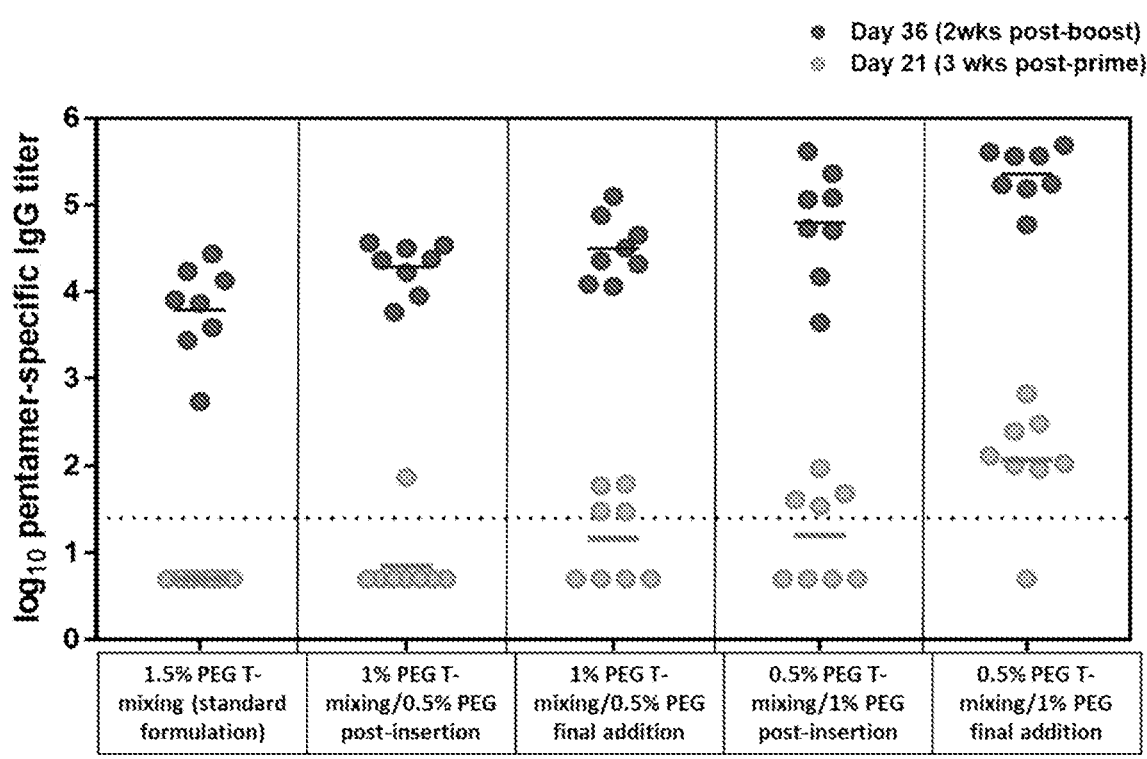
FIG. 15 is a graph of in vivo immunogenicity for lipid nanoparticles formed via various processes.
Figure 16:
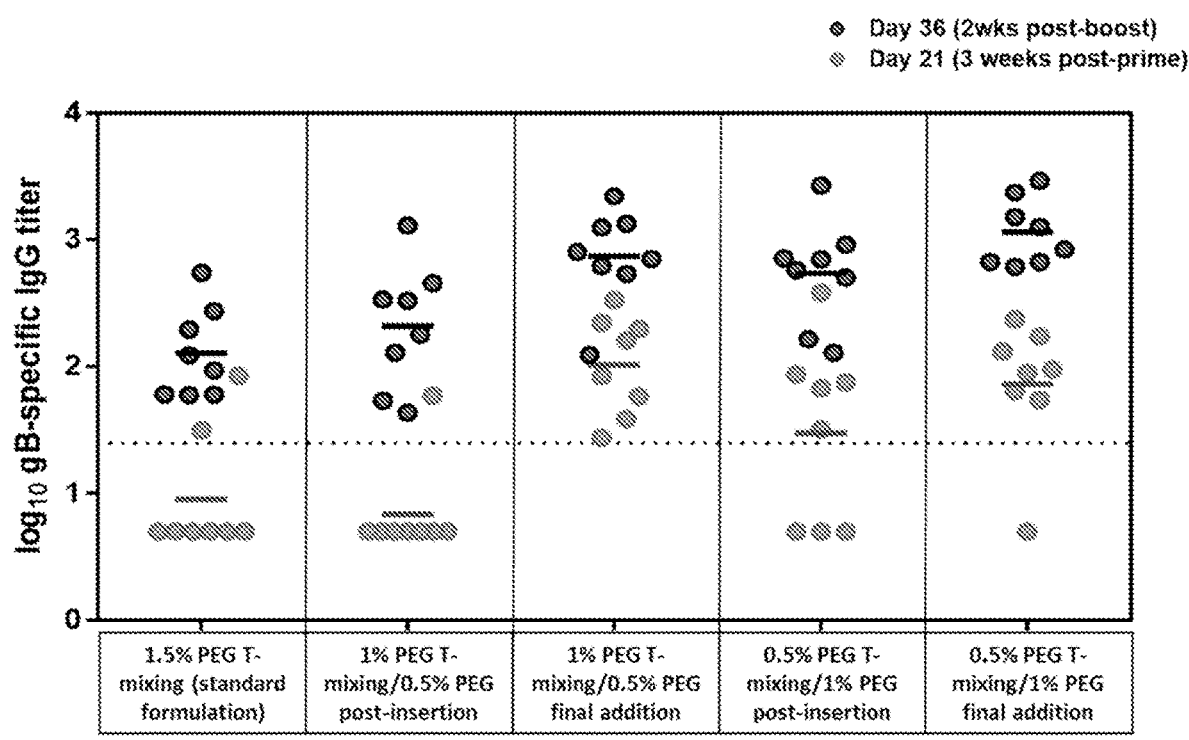
FIG. 16 is a graph of in vivo immunogenicity for lipid nanoparticles formed via various processes.

The LNPs formed via the standard mixing, post-insertion, and final addition procedures were evaluated in an in vivo immunogenicity model in mice. As shown in FIGS. 15 and 16, the LNPs formed via the post-insertion and final addition procedures produced higher antibody titers. The final addition procedure using 0.5 mol % in the nanoprecipitation reaction had over a log increase in antibody titers compared to the standard procedure.

Example 6

This example describes the in vivo protein expression in rats of LNPs formed via the standard procedure, the post-insertion procedure, and the final addition procedure, which is referred to as the final spike process in this example, described in Example 5. LNPs formed using the post-insertion and final spike process had higher in vivo protein expression than LNPs formed via the standard process. The most protein expression occurred in the LNPs formed via the final spike process.

In general, the LNPs were formed as described in Example 5, except 2 mol % of PEG-lipid was used. The mol % of PEG-lipid added during the nanoprecipitation reaction for the standard procedure, post-insertion procedure, and final spike procedure are shown in the table below.

| PEG in Mix ("Core") | PEG Post-Inserted | PEG in Final Product Spike | Description |
|---|---|---|---|
| 2.0% | 0.0% | 0.0% | Standard Condition |
| 0.0% | 2.0% | 0.0% | Post-Insertion Series |
| 0.5% | 1.5% | 0.0% | |
| 1.0% | 1.0% | 0.0% | |
| 1.5% | 0.5% | 0.0% | |
| 0.0% | 0.0% | 2.0% | Final Spike Series |
| 0.5% | 0.0% | 1.5% | |
| 1.0% | 0.0% | 1.0% | |
| 1.5% | 0.0% | 0.5% | |

The final composition of the resulting LNPs are shown in the table below. In general, the final composition of the LNPs formed by different formulation process did not vary significantly.

| Group # | Process | PEG (mol %) | Cationic Lipid (mol %) | Cholesterol (mol %) | DSPC (mol %) |
|---|---|---|---|---|---|
| 1 | Standard | 1.8% | 50.4% | 38.7% | 9.1% |
| 2 | 2.0 mol % Post-Insertion | 1.4% | 49.8% | 39.1% | 9.7% |
| 3 | 1.5 mol % Post-Insertion | 1.7% | 49.5% | 39.1% | 9.7% |
| 4 | 1.0 mol % Post-Insertion | 1.7% | 50.1% | 38.9% | 9.3% |
| 5 | 0.5 mol % Post-Insertion | 1.9% | 50.1% | 38.6% | 9.5% |
| 6 | 2.0 mol % Final Spike | 1.9% | 49.2% | 38.6% | 10.5% |
| 7 | 1.5 mol % Final Spike | 1.9% | 49.2% | 38.8% | 10.1% |
| 8 | 1.0 mol % Final Spike | 1.9% | 49.6% | 39.0% | 9.6% |
| 9 | 0.5 mol % Final Spike | 1.9% | 49.8% | 38.5% | 9.9% |

Figure 17:
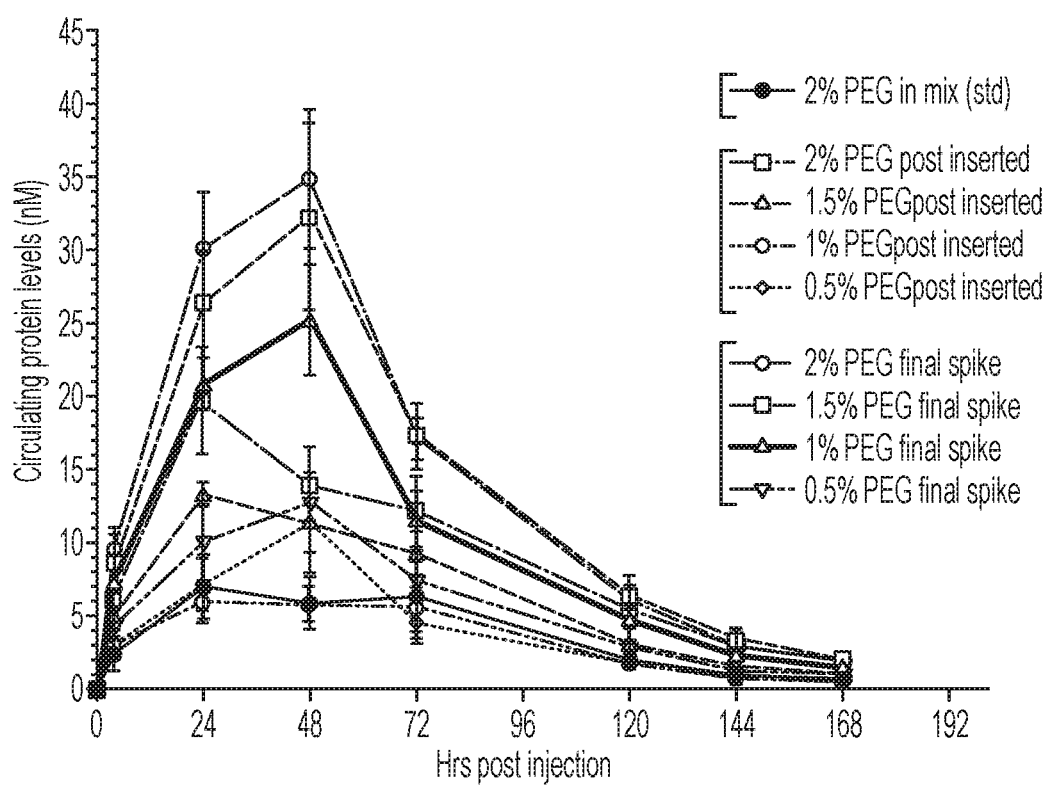
FIG. 17 is a graph of in vivo protein expression for lipid nanoparticles formed via various processes.

As illustrated in FIG. 17, LNPs formed using the post-insertion and final spike process had significantly higher in vivo protein expression than LNPs formed via the standard process. The most protein expression occurred in the LNPs formed via the final spike process.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including mRNA accessibilityrfac represents a separate embodiment of the present invention.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A composition comprising an enriched population of lipid nanoparticles (LNPs), wherein the LNPs have an outer shell and an inner core and comprise an ionizable lipid, a phospholipid, a poly(ethylene glycol) (PEG) lipid, wherein at least 50% of the LNPs comprise mRNA encapsulated within the inner core and wherein the outer shell comprises at least 95% of the total PEG lipid in the LNP, and wherein the LNP's are formed by a nanoprecipitation process including a step in which additional PEG lipid was added to the LNP's after an initial nanoprecipitation reaction.

2. The composition of claim 1, further comprising a structural lipid.

3. The composition of claim 2, wherein at least 50% of the LNPs have a ratio of ionizable lipid:phospholipid:structural lipid of 35-50:30-40: 20-30.

4. The composition of claim 2, wherein:
(a) the LNP is insensitive to accelerated blood clearance upon repeated administration in vivo within 10 days;
(b) at least 50% of the LNPs have 1-5 inner shells;
(c) the structural lipid is cholesterol;
(d) 10-30% of the LNP, exclusive of mRNA, is the structural lipid; and/or
(e) the outer shell is comprised of 10-30% of the structural lipid.

5. The composition of claim 1, wherein at least 50% of the LNPs have an outer shell fluidity value of greater than a threshold polarization level.

6. The composition of claim 1, wherein a quantitative value of the amount of mRNA encapsulated in the LNP is generated using an ion-exchange (IEX) chromatography assay.

7. The composition of claim 1, wherein:
(a) at least about 50% of the LNPs in the population have mRNA encapsulated therein, as determined by ion-exchange chromatography (IEX); and/or
(b) the LNPs have an encapsulation efficiency of at least about 50% as determined by ion-exchange chromatography (IEX).

8. The composition of claim 1, wherein the phospholipid is DSPC.

9. A composition comprising a population of lipid nanoparticles (LNPs), the LNPs comprise an ionizable amino lipid, a poly(ethylene glycol) (PEG) lipid, a phospholipid, wherein:
(a) at least about 50% of the LNPs in the population have mRNA encapsulated therein, as determined by ion-exchange chromatography (IEX), and wherein the LNP's are formed by a nanoprecipitation process including a step in which additional PEG lipid was added to the LNP's after an initial nanoprecipitation reaction; and/or
(b) the LNPs have an encapsulation efficiency of at least about 50% as determined by ion-exchange chromatography (IEX).

10. The composition of claim 9, further comprising a structural lipid.

11. The composition of claim 10, wherein the structural lipid is cholesterol or a cholesterol derivative.

12. The composition of claim 9, wherein the composition is enriched for LNPs:
(a) lacking B1a cell-stimulating phospholipid epitopes, and/or
(b) lacking scavenger receptor ligands.

13. The composition of claim 12, wherein at least about 50% of the LNPs:
(a) lack B1a cell-stimulating phospholipid epitopes, and/or
(b) lack scavenger receptor ligands.

14. The composition of claim 9, wherein the composition is enriched for LNPs having a majority of the total phospholipid present in the outer LNP shell.

15. The composition of claim 14, wherein at least about 50% of the LNPs have the majority of the total phospholipid present in the outer LNP shell.

16. The composition of claim 9, wherein the composition is enriched for LNPs having more than 50% of the total phospholipid present on the surface.

17. The composition of claim 16, wherein at least about 50% of the LNPs have more than 50% of the total phospholipid present on the surface.

18. The composition of claim 9, wherein the composition is enriched for LNPs having a majority of the total PEG lipid present in the outer LNP shell.

19. The composition of claim 18, wherein at least about 50% of the LNPs have the majority of the total PEG lipid present in the outer LNP shell.

20. The composition of claim 9, wherein the composition is enriched for LNPs having more than 50% of the total PEG lipid present on the surface.

21. The composition of claim 20, wherein at least about 50% of the LNPs have more than 50% of the total PEG lipid present on the surface.

22. The composition of claim 13, wherein the phospholipid is DSPC.

* * * * *

UNITED STATES PATENT AND TRADEMARK OFFICE
CERTIFICATE OF CORRECTION

PATENT NO. : 11,786,607 B2  
APPLICATION NO. : 16/623069  
DATED : October 17, 2023  
INVENTOR(S) : Stephen Hoge et al.

Page 1 of 1

It is certified that error appears in the above-identified patent and that said Letters Patent is hereby corrected as shown below:

In the Claims

At Column 342, Line 42:  
"The composition of claim 13"  
Should read:  
--The composition of claim 9--

Signed and Sealed this  
Twenty-sixth Day of December, 2023

Katherine Kelly Vidal  
*Director of the United States Patent and Trademark Office*